US010022376B2

(12) United States Patent
Coe et al.

(10) Patent No.: US 10,022,376 B2
(45) Date of Patent: Jul. 17, 2018

(54) PYRAZOLOPYRIDINES AND PYRAZOLOPYRIMIDINES

(71) Applicant: Pfizer Inc., New York, NY (US)

(72) Inventors: Jotham Wadsworth Coe, Niantic, CT (US); Christoph Martin Dehnhardt, Burnaby (CA); Peter Jones, Arlington, MA (US); Yogesh Anil Sabnis, Brussels (BE); Joseph Walter Strohbach, Wentzville, MO (US); Florian Michel Wakenhut, Melsungen (DE); Gavin Alistair Whitlock, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/342,601

(22) Filed: Nov. 3, 2016

(65) Prior Publication Data
US 2017/0071946 A1    Mar. 16, 2017

Related U.S. Application Data

(62) Division of application No. 14/710,631, filed on May 13, 2015, now Pat. No. 9,518,052.

(60) Provisional application No. 61/993,138, filed on May 14, 2014.

(51) Int. Cl.
| C07D 471/04 | (2006.01) |
| C07D 487/04 | (2006.01) |
| A61K 31/519 | (2006.01) |
| A61K 31/437 | (2006.01) |
| A61K 31/4725 | (2006.01) |

(52) U.S. Cl.
CPC .......... *A61K 31/519* (2013.01); *A61K 31/437* (2013.01); *A61K 31/4725* (2013.01); *C07D 471/04* (2013.01); *C07D 487/04* (2013.01)

(58) Field of Classification Search
CPC ..... C07D 471/04; C07D 487/04; A61P 35/00; A61K 31/4162
USPC .................................................. 514/210.21
See application file for complete search history.

(56) References Cited

U.S. PATENT DOCUMENTS

| 6,106,864 A | 8/2000 | Dolan et al. |
| 8,129,371 B2 | 3/2012 | Zask et al. |
| 2003/0139427 A1 | 7/2003 | Castelhano et al. |
| 2009/0149458 A1 | 6/2009 | Chen et al. |
| 2009/0181963 A1 | 7/2009 | Dehnhardt et al. |
| 2010/0317646 A1 | 12/2010 | McIver et al. |
| 2010/0331297 A1* | 12/2010 | Bulawa ................ C07D 487/04 514/210.18 |
| 2011/0172216 A1 | 7/2011 | Dotson et al. |
| 2011/0230467 A1 | 9/2011 | Shirakami et al. |
| 2015/0329542 A1 | 11/2015 | Coe et al. |

FOREIGN PATENT DOCUMENTS

| WO | 91/11172 A1 | 8/1991 |
| WO | 94/02518 A1 | 6/1994 |
| WO | 98/55148 A1 | 12/1998 |
| WO | 00/35298 A1 | 6/2000 |
| WO | 2004/046107 A1 | 6/2004 |
| WO | 2008/115974 A1 | 9/2008 |
| WO | 2008/129380 A1 | 10/2008 |
| WO | 2009/147187 A1 | 12/2009 |

(Continued)

OTHER PUBLICATIONS

OShea; "Janus kinase Inhibitors in autoimmune diseases"; Ann Rheum Dis. 2013, 72 ii111-ii115.*
Patterson; "Protein kinase inhibitors in the treatment of inflammatory and autoimmune diseases"; Clinical and Experimental Immunology, 2014, 176, 1-10.*
Pesu; "Therapeutic targeting of Janus kinases"; Immunological Reviews 2008, 223, 132-142.*
Vallath; "Targeting EGFR signalling in chronic lung disease: therapeutic challenges and opportunities"; Eur Respir J. 2014, 44, 513-522.*
Clark; "Discovery and Development of Janus Kinase (JAK) Inhibitors for Inflammatory Diseases"; J. Med. Chem. 2014, 57, 5023-5038.*
Furumoto; "The Arrival of JAK Inhibitors: Advancing the Treatment of Immune and Hematologic Disorders"; BioDrugs 2013, 27, 431-438.*

(Continued)

*Primary Examiner* — Daniel R Carcanague
(74) *Attorney, Agent, or Firm* — A. David Joran

(57) ABSTRACT

A compound having the structure:

(I)

or a pharmaceutically acceptable salt or solvate thereof, wherein A and A' are C or N, where C may be substituted by halo or $C_1$-$C_6$ alkyl; R and $R^0$ are selected from the group consisting of H, $C_1$-$C_6$ alkyl, —$(CH_2)_n$—W, etc., where W is 5- or 6-membered heteroaryl or heterocyclic containing N, S and/or O atoms, —NR"$SO_2$—R', etc., where R' and R" are $C_1$-$C_6$ alkyl, etc.; wherein each alkyl, etc., may be substituted; or, R and Ro and the N atom to which they are bonded together to form a monocyclic or bicyclic heterocyclic ring, etc.; $R^1$ is H, halo or cyano; $R^2$ and $R^{2'}$ are H, $C_1$-$C_6$ alkyl, etc.; X is a bond, etc.; $R^3$ is H, $C_1$-$C_4$ alkyl, etc.; Y is a bond, —$(CH_2)_m$—, etc. The invention also relates to compositions and uses in the treatment of various diseases.

9 Claims, No Drawings

(56) References Cited

FOREIGN PATENT DOCUMENTS

| WO | 2009/153261 A1 | 12/2009 |
|----|----------------|---------|
| WO | 2010/058846 A1 | 5/2010  |
| WO | 2012/045195 A1 | 4/2012  |
| WO | 2013/014567 A1 | 1/2013  |

OTHER PUBLICATIONS

Kontzias; "Jakinibs: a new class of kinase inhibitors in cancer and autoimmune disease"; Current Opinion in Pharmacology 2012, 12, 464-470.*
Laurence; "JAK Kinases in Health and Disease: An Update"; The Open Rheumatology Journal, 2012, 6, (Suppl 2, M4), 232-244.*
Almarsson, O., et al., "Crystal engineering of the composition of pharmaceutical phases. Do pharmaceutical co-crystals represent a new path to improved medicines?", Chem. Commun., 17:1889-1896 (2004).
Baker et al, "Irreversible Enzyme Inhibitors, CXXV. Active-Site-Directed Irreversible Inhibitors of Xanthine Oxidase Derived from Arylpurines and Pyrazolo[3,4-d]pyrimidines Bearing a Terminal Sulfonyl Fluoride", Journal of Medicinal Chemistry 11:656-661 (1968).
Bianucci et al, "Bioisosterism, Enantioselectivity, and Molecular Modeling of New Effective N6- and/or N(9)-Substituted 2-Phenyl Adenines and 8-Aza Analogs: Different Binding Modes to A1 Adenosine Receptors", Drug Development Research 54:52-65 (2001).
Gilbert et al, "Novel purine and pyrazolo[3,4-d]pyrimidine inhibitors of PI3 kinase-alpha: Hit to lead studies", Bioorganic and Medicinal Chemistry Letters 20(2):636-639 (2010).
Greene, T.W., et al., "Protection for the Carboxyl Group", Greene's Protective Groups in Organic Synthesis, Chapter 5, pp. 369-453 (1999).
Greene, T.W., et al., "Protection for the Amino Group", Greene's Protective Groups in Organic Synthesis', Chapter 7, pp. 494-653 (1999).
Haleblian, J.K., et al., "Characterization of Habits and Crystalline Modification of Solids and Their Pharmaceutical Applications", Journal of Pharmaceutical Sciences, 64(8):1269-1288 (1975).
Heinrich et al, "Fragment-based discovery of new highly substituted 1H-pyrrolo[2,3-b]- and 3H-imidazolo[4,5-b]-pyridines as focal adhesion kinase inhibitors", J Med Chem 56(3):1160-1170 (2013).
Joo, J.M., et al., "C-H Bonds as Ubiquitous Functionality: A General Approach to Complex Arylated Imidazoles via Regioselective Sequential Arylation of All Three C-H Bonds and Regioselective N-Alkylation Enabled by SEM-Group Transposition", Journal of Organic Chemistry, 75(15):4911-4920 (2010).
Liang, A.C., et al., "Fast-dissolving intraoral drug delivery systems", Expert Opinion in Therapeutic Patents, 11(6):981-986 (2001).
PCT International Search Report and Written Opinion for International Application No. PCT/162015/053174 dated Jul. 15, 2015.
Sartini et al, "Structure-Based Optimization of Tyrosine Kinase Inhibitor CLM3. Design, Synthesis, Functional Evaluation, and Molecular Modeling Studies", J Med Chem 57(4):1225-1235 (2014).
Smith, R.M., "Chiral Chromatography Using Sub-and Supercritical Fluids", in Supercritical Fluid Chromatography with Packed Columns, 1998. Marcel Dekker, New York, 223-249.
Verma, R.K., et al., "Current Status of Drug Delivery Technologies and Future Directions", Pharmaceutical Technology On-Line, 25(2):1-14 (2001).

* cited by examiner

PYRAZOLOPYRIDINES AND PYRAZOLOPYRIMIDINES

CROSS REFERENCE TO RELATED APPLICATION

This application is a divisional of Ser. No. 14/710,631, filed May 13, 2015, which claimed the benefit under 35 U.S.C. 119(e) of Ser. No. 61/993,138, filed May 14, 2014.

FIELD OF THE INVENTION

The present invention relates to pyrazolopyridines and pyrazolopyrimidines, pharmaceutical compositions comprising such compounds and their use as medicaments. More particularly, the present invention provides 6-phenyl-1H-pyrazolopyridines derivatives and 6-phenyl-1H-pyrazolopyrimidines derivatives which are Janus Kinase (JAK) inhibitors and useful for the treatment of allergic and respiratory conditions, particularly chronic obstructive pulmonary disease.

BACKGROUND

Chronic obstructive pulmonary disease (COPD) is the fourth leading cause of death in the US and is characterized by airflow obstruction that is not fully reversible with bronchodilators. The airflow limitation is usually progressive and is associated with an abnormal inflammatory response of the lungs to noxious particles or gases, primarily cigarette smoke. Symptoms are typically breathing-related (e.g. chronic cough, exertional dyspnea, expectoration and wheeze). Patients experience periods of stable disease interspersed with inflammatory exacerbations resulting in acute decline in lung function and often hospitalization.

Current treatment guidelines recommend bronchodilators as the mainstay of COPD drug treatment. However, anti-inflammatory inhaled corticosteroids (ICS) and bronchodilator/inhaled corticosteroid combination products, are extensively used. Whilst inhaled corticosteroids do provide some benefits with respect to short term lung function improvements and exacerbation frequency, they do not address the corticosteroid-refractory inflammation which is characteristic of this disease and thought to play a key role in disease progression. There is a clear medical need for anti-inflammatory therapies in COPD that will address the chronic inflammatory component of the disease and ultimately provide symptomatic relief, a reduction in exacerbation frequency and an amelioration of exacerbation severity.

The Janus kinase (JAK) family of receptor associated tyrosine kinases, JAK 1, JAK 2, JAK 3 and tyrosine kinase 2 (TYK2), are involved in signal transduction associated with a variety of inflammatory cytokines. JAK kinases can function as either hetero or homo-dimers, phosphorylating STAT transcription factors which regulate inflammatory gene transcription. Oral JAK 1/JAK 3 inhibitors such as CP-690550 have shown impressive anti-inflammatory activity in inflammatory diseases such as rheumatoid arthritis and psoriasis.

Many JAK dependent cytokines are thought to play key roles in the pathology of COPD which involves the interplay of multiple inflammatory cells such as T lymphocytes, neutrophils, macrophages and lung epithelium. For example the JAK 1/JAK 3 heterodimer plays a key role in T lymphocyte survival and activation whereas JAK 2 is thought to be critical for regulation of neutrophil activation and apoptosis. JAK 1 and JAK 2 play an important role in IL-13 mediated inflammatory signaling in macrophages, which is thought to link acute inflammatory events to chronic progressive disease. Importantly JAK 1, JAK 2 and TYK 2 also play an important role in signaling mediated by IFNγ, a cytokine associated with the chronic inflammation observed in COPD, which modulates the activity of T cells, epithelium and macrophages whilst not being modulated by corticosteroids.

Macrophage phagocytosis of bacteria is impaired in the lungs of COPD patients, potentially in part due to high local IFNγ levels. In vitro studies with isolated patient cells have shown that JAK inhibitors increase phagocytic rate in the presence of IFNγ. Consequently, as well as exerting a direct anti-inflammatory effect, JAK inhibitors may also increase the ability of the lung to maintain a sterile environment.

JAK inhibitors are therefore likely to have utility in the treatment of a range of inflammatory diseases, including lung diseases such as COPD, asthma and pulmonary vascular disease. Compounds which have a broad inhibitory activity across the range of Janus kinases, in particular, are likely to have a potent anti-inflammatory effect. However, such a selectivity profile can also lead to undesirable side-effects in systemically circulating compounds, particularly anemia and neutropenia associated with JAK 2 inhibition. For the treatment of lung diseases, it is therefore particularly favorable to provide JAK inhibitors which can be administered by inhalation and which inhibit Janus kinases locally in the lung without having a significant systemic exposure.

There is thus a need to provide new JAK inhibitors that are potent, selective inhibitors of Janus kinases with appropriate metabolic stability and pharmacokinetic properties, particularly compounds which can be administered by inhalation and are active in lung tissue whilst having poor systemic penetration or high systemic lability.

SUMMARY OF THE INVENTION

The present invention provides pyrazolopyridines and pyrazolopyrimidines which are potent and selective inhibitors of Janus kinases, including a compound having the structure:

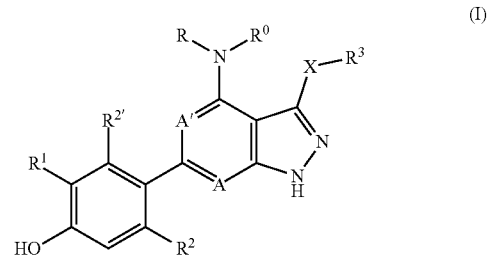

or a pharmaceutically acceptable salt thereof, or a pharmaceutically acceptable solvate of said compound or pharmaceutically acceptable salt, wherein A and A' are independently C or N, where C may be unsubstituted or substituted by halo or $C_1$-$C_6$ alkyl;

R and $R^0$ are independently selected from the group consisting of H, $C_1$-$C_6$ alkyl, hydroxy($C_1$-$C_6$ alkyl), phenyl ($C_1$-$C_6$ alkyl), and —$(CH_2)_n$—W, where W is $C_3$-$C_8$ cycloalkyl, phenyl, naphthyl, 5- or 6-membered heteroaryl or heterocyclic containing 1-3 N, S and/or O atoms, —$SO_2$—R', —$NHSO_2$—R', —$NR''SO_2$—R' and SR', where R' and R" are independently $C_1$-$C_6$ alkyl or $C_3$-$C_8$ cycloalkyl, amino, $C_1$-$C_6$ alkylamino, di($C_1$-$C_6$ alkyl)amino, phenyl, heteroaryl, or heterocyclic; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —CONR'R", NR'COR", —NR'CONR'R", —NR'CO$_2$R", —(CH$_2$)$_n$—SO$_2$—R', —NHSO$_2$—R', —NR"SO$_2$—R' or SR' where R' and R" are independently $C_1$-$C_6$ alkyl, $C_3$-$C_6$ cycloalkyl, phenyl, amino, hydroxyalkylamino, heterocyclic, or —(CH$_2$)$_n$—W', where W' is hydroxy, $C_3$-$C_8$ cycloalkyl, phenyl, naphthyl, heterocyclic, or 5- or 6-membered heteroaryl containing 1-3 N, S and/or O atoms;

or, R and R$^0$ and the N atom to which they are bonded together form a monocyclic or bicyclic heterocyclic ring which may be unsubstituted or substituted by (a) halo, hydroxy, heteroaryl, $C_1$-$C_6$ alkyl, $C_1$-$C_6$ alkoxy, ($C_1$-$C_6$ alkoxy)$C_1$-$C_6$ alkoxy, aryl($C_1$-$C_6$ alkoxy), aryloxy, amino, aminoacyl, $C_1$-$C_6$ alkylaminoacyl, arylalkylaminoacyl, di($C_1$-$C_6$ alkyl)aminoacyl, —$SO_2$—R', —$SO_2$—NR"—(CH$_2$)$_n$—W, —NHSO$_2$—R', —NR"SO$_2$—R' or SR' where R' and R" is independently amino, $C_1$-$C_6$ alkylamino, di($C_1$-$C_6$ alkyl)amino, $C_1$-$C_6$ alkyl or $C_3$-$C_8$ cycloalkyl, or (b) —(CH$_2$)$_n$—W, where W is $C_3$-$C_8$ cycloalkyl, phenyl, naphthyl, heterocyclic, 5- or 6-membered heteroaryl containing 1-3 N atoms, —$SO_2$—R', —NHSO$_2$—R', —NR"SO$_2$—R' or SR', where R' and R" is independently alkyl or cycloalkyl; wherein each of said phenyl, aryl, or heteroaryl may be unsubstituted or substituted by halo, $C_1$-$C_6$ alkyl, $C_1$-$C_6$ alkoxy, cyano, or hydroxy;

$R^1$ is H, cyano or halo; $R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

X is a bond, —CO—, —CONH—, —$SO_2$—, —SONH—, or —(CH$_2$)$_m$—;

$R^3$ is H, $C_1$-$C_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—$R^4$ and/or 1-4 substituents each independently selected from $R^5$; with the proviso that when X is —CO— or —$SO_2$—, $R^3$ is not H;

Y is a bond, —(CH$_2$)$_m$— or —O—;

$R^4$ is (a) H, $C_1$-$C_6$ alkyl, $C_3$-$C_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; (b) phenyl or naphthyl, said phenyl and naphthyl being optionally substituted with 1-5 substituents selected from $C_1$-$C_6$ alkyl, $C_3$-$C_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; or (c) a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$;

$R^5$ is $C_1$-$C_6$ alkyl, $C_3$-$C_8$ cycloalkyl, halo, cyano, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ or —NR$^6$SO$_2$NR$^7$R$^8$;

$R^6$ is H, $C_1$-$C_6$ alkyl or $C_3$-$C_8$ cycloalkyl, said $C_1$-$C_6$ alkyl is optionally substituted by —NR$^7$R$^8$ or a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, cyano, hydroxy and cyano;

$R^7$ and $R^8$ are each independently H, $C_1$-$C_6$ alkyl or $C_3$-$C_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said $C_1$-$C_6$ alkyl is optionally substituted by $C_3$-$C_8$ cycloalkyl, halo, cyano, hydroxy, amino, ($C_1$-$C_6$ alkyl)amino or di($C_1$-$C_6$ alkyl)amino and said heterocyclic ring being optionally substituted by one or more $C_1$-$C_6$ alkyl or $C_3$-$C_8$ cycloalkyl groups;

$R^9$ is $C_1$-$C_6$ alkyl or $C_3$-$C_8$ cycloalkyl; and, m and n are independently 0, 1, 2 or 3.

The invention also provides a compound of formula (Ia) having the structure:

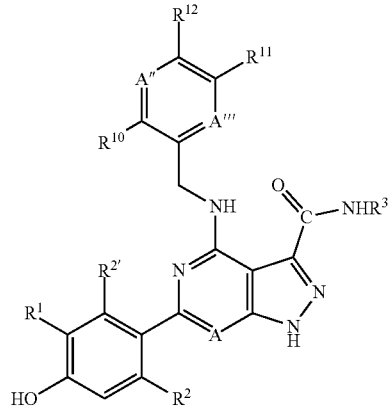

(Ia)

or a pharmaceutically acceptable salt thereof, or a pharmaceutically acceptable solvate of said compound or pharmaceutically acceptable salt, wherein:

A, A" and A'" are independently C or N, where C may be unsubstituted or substituted by halo or $C_1$-$C_6$ alkyl;

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^3$ is H, $C_1$-$C_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—$R^4$ and/or 1-4 substituents each independently selected from $R^5$;

Y is a bond, —$(CH_2)_m$— or —O—;

$R^4$ is (a) H, $C_1$-$C_6$ alkyl, $C_3$-$C_8$ cycloalkyl, halo, oxo, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$; (b) phenyl or naphthyl, said phenyl and naphthyl being optionally substituted with 1-5 substituents selected from $C_1$-$C_6$ alkyl, $C_3$-$C_8$ cycloalkyl, halo, —CN, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$; or (c) a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, oxo, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$;

$R^5$ is $C_1$-$C_6$ alkyl, $C_3$-$C_8$ cycloalkyl, halo, cyano, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ or —$NR^6SO_2NR^7R^8$;

$R^6$ is H, $C_1$-$C_6$ alkyl or $C_3$-$C_8$ cycloalkyl, said $C_1$-$C_6$ alkyl is optionally substituted by —$NR^7R^8$ or a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, hydroxy and cyano;

$R^7$ and $R^8$ are each independently H, $C_1$-$C_6$ alkyl or $C_3$-$C_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said $C_1$-$C_6$ alkyl is optionally substituted by $C_3$-$C_8$ cycloalkyl, halo, cyano, hydroxy, amino, ($C_1$-$C_6$ alkyl)amino or di($C_1$-$C_6$ alkyl)amino and said heterocyclic ring being optionally substituted by one or more $C_1$-$C_6$ alkyl or $C_3$-$C_8$ cycloalkyl groups;

$R^9$ is $C_1$-$C_6$ alkyl or $C_3$-$C_8$ cycloalkyl;

$R^{10}$ is —$NHSO_2$—R', —NR"$SO_2$—R' or SR' where R' and R" are independently hydrogen, $C_1$-$C_6$ alkyl, $C_3$-$C_8$ cycloalkyl, phenyl, amino, $C_1$-$C_6$ alkylamino, di($C_1$-$C_6$ alkyl)amino, heterocyclic, —$(CH_2)_n$—W', where W' is hydroxy, $C_3$-$C_8$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —$NHSO_2$—R', —NR"$SO_2$—R' or SR' where R' and R" are independently phenyl, $C_1$-$C_6$ alkyl or $C_3$-$C_8$ cycloalkyl;

$R^{11}$ and $R^{12}$ are each independently H, hydroxy, halo, cyano, $C_1$-$C_6$ alkyl or $C_3$-$C_8$ cycloalkyl; and, m and n are independently 0, 1, 2, or 3.

The invention further provides a compound of formula (Ib) having the structure:

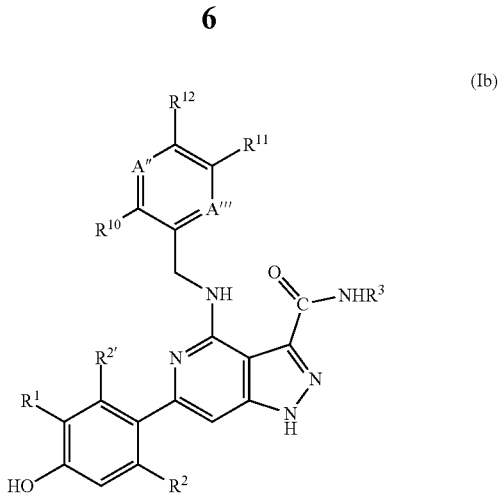

(Ib)

or a pharmaceutically acceptable salt thereof, or a pharmaceutically acceptable solvate of said compound or pharmaceutically acceptable salt, wherein:

A" and A''' are independently C or N, where C may be unsubstituted or substituted by halo or $C_1$-$C_6$ alkyl;

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^3$ is H, $C_1$-$C_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—$R^4$ and/or 1-4 substituents each independently selected from $R^5$;

Y is a bond, —$(CH_2)_m$— or —O—;

$R^4$ is (a) H, $C_1$-$C_6$ alkyl, $C_3$-$C_8$ cycloalkyl, halo, oxo, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$; (b) phenyl or naphthyl, said phenyl and naphthyl being optionally substituted with 1-5 substituents selected from $C_1$-$C_6$ alkyl, $C_3$-$C_8$ cycloalkyl, halo, —CN, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$; or (c) a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, oxo, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$;

$R^5$ is $C_1$-$C_6$ alkyl, $C_3$-$C_8$ cycloalkyl, halo, cyano, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ or —$NR^6SO_2NR^7R^8$;

$R^6$ is H, $C_1$-$C_6$ alkyl or $C_3$-$C_8$ cycloalkyl, said $C_1$-$C_6$ alkyl is optionally substituted by —$NR^7R^8$ or a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, hydroxy and cyano;

$R^7$ and $R^8$ are each independently H, $C_1$-$C_6$ alkyl or $C_3$-$C_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said $C_1$-$C_6$ alkyl is optionally substituted by $C_3$-$C_8$ cycloalkyl, halo, cyano, hydroxy, amino, ($C_1$-$C_6$ alkyl)amino or di($C_1$-$C_6$ alkyl)amino and said heterocyclic ring being optionally substituted by one or more $C_1$-$C_6$ alkyl or $C_3$-$C_8$ cycloalkyl groups;

$R^9$ is $C_1$-$C_6$ alkyl or $C_3$-$C_8$ cycloalkyl;

$R^{10}$ is —$NHSO_2$—R', —NR"$SO_2$—R' or SR' where R' and R" are independently hydrogen, $C_1$-$C_6$ alkyl, $C_3$-$C_8$ cycloalkyl, phenyl, amino, $C_1$-$C_6$ alkylamino, di($C_1$-$C_6$ alkyl)amino, heterocyclic, —$(CH_2)_n$—W', where W' is hydroxy, $C_3$-$C_6$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —$NHSO_2$—R', —NR"$SO_2$—R' or SR' where R' and R" are independently phenyl, $C_1$-$C_6$ alkyl or $C_3$-$C_8$ cycloalkyl;

$R^{11}$ and $R^{12}$ are each independently H, hydroxy, halo, cyano, $C_1$-$C_6$ alkyl or $C_3$-$C_8$ cycloalkyl; and, m and n are independently 0, 1, 2 or 3. In another embodiment, the invention provides the compound of formula Ib wherein $R^{10}$ is —NR"$SO_2$—R' and R' and R" are both $C_1$-$C_6$ alkyl.

The invention also provides a compound of formula (Ic) having the structure:

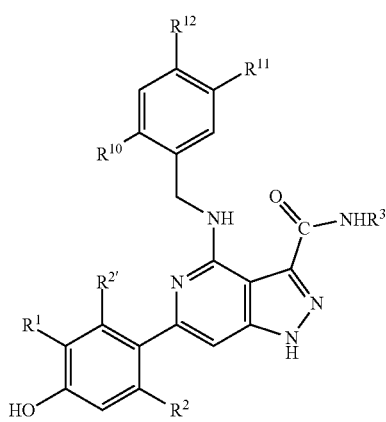

(Ic)

or a pharmaceutically acceptable salt thereof, or a pharmaceutically acceptable solvate of said compound or pharmaceutically acceptable salt, wherein:

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^3$ is H, $C_1$-$C_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—$R^4$ and/or 1-4 substituents each independently selected from $R^5$;

Y is a bond, —$(CH_2)_m$— or —O—;

$R^4$ is (a) H, $C_1$-$C_6$ alkyl, $C_3$-$C_8$ cycloalkyl, halo, oxo, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$; (b) phenyl or naphthyl, said phenyl and naphthyl being optionally substituted with 1-5 substituents selected from $C_1$-$C_6$ alkyl, $C_3$-$C_8$ cycloalkyl, halo, —CN, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$; or (c) a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, oxo, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$;

$R^5$ is $C_1$-$C_6$ alkyl, $C_3$-$C_8$ cycloalkyl, halo, cyano, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ or —$NR^6SO_2NR^7R^8$;

$R^6$ is H, $C_1$-$C_6$ alkyl or $C_3$-$C_8$ cycloalkyl, said $C_1$-$C_6$ alkyl is optionally substituted by —$NR^7R^8$ or a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, cyano, hydroxy and cyano;

$R^7$ and $R^8$ are each independently H, $C_1$-$C_6$ alkyl or $C_3$-$C_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said $C_1$-$C_6$ alkyl is optionally substituted by $C_3$-$C_8$ cycloalkyl, halo, cyano, hydroxy, amino, ($C_1$-$C_6$ alkyl)amino or di($C_1$-$C_6$ alkyl)amino and said heterocyclic ring being optionally substituted by one or more $C_1$-$C_6$ alkyl or $C_3$-$C_8$ cycloalkyl groups;

$R^9$ is $C_1$-$C_6$ alkyl or $C_3$-$C_8$ cycloalkyl;

$R^{10}$ is —$NHSO_2$—R', —NR"$SO_2$—R' or SR' where R' and R" are independently hydrogen, $C_1$-$C_6$ alkyl, $C_3$-$C_8$ cycloalkyl, phenyl, amino, $C_1$-$C_6$ alkylamino, di($C_1$-$C_6$ alkyl)amino, heterocyclic, —$(CH_2)_n$—W', where W' is hydroxy, $C_3$-$C_5$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —$NHSO_2$—R', —NR"$SO_2$—R' or SR' where R' and R" are independently phenyl, $C_1$-$C_6$ alkyl or $C_3$-$C_8$ cycloalkyl;

$R^{11}$ and $R^{12}$ are each independently H, hydroxy, halo, cyano, $C_1$-$C_6$ alkyl or $C_3$-$C_8$ cycloalkyl; and, m and n are independently 0, 1, 2 or 3. In certain embodiments, the invention provides a compound of formula Ic wherein $R^{10}$ is —NR"SO$_2$—R' and R' and R" are both $C_1$-$C_6$ alkyl.

The invention additionally provides the compound of formula (Id) having the structure:

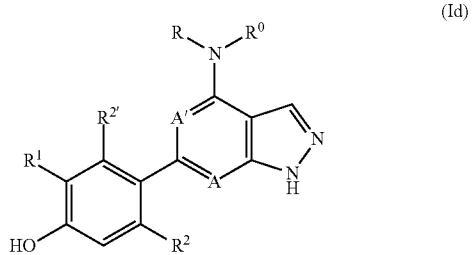

(Id)

or a pharmaceutically acceptable salt thereof, or a pharmaceutically acceptable solvate of said compound or pharmaceutically acceptable salt, wherein:

A and A' are independently C or N, where C may be unsubstituted or substituted by $C_1$-$C_6$ alkyl;

R and $R^0$ are independently selected from the group consisting of H, $C_1$-$C_6$ alkyl, hydroxy($C_1$-$C_6$ alkyl), phenyl ($C_1$-$C_6$ alkyl), and —(CH$_2$)$_n$—W, where W is $C_3$-$C_8$ cycloalkyl, phenyl, naphthyl, 5- or 6-membered heteroaryl or heterocyclic containing 1-3 N, S and/or O atoms, —SO$_2$—R', —NHSO$_2$—R', —NR"SO$_2$—R' and SR', where R' and R" are independently $C_1$-$C_6$ alkyl or $C_3$-$C_8$ cycloalkyl, amino, $C_1$-$C_6$ alkylamino, di($C_1$-$C_6$ alkyl)amino, phenyl, heteroaryl, or heterocyclic; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —SO$_2$—R', —CONR'R", NR'COR", —NR'CONR'R", —NR'CO$_2$R", —(CH$_2$)$_n$—SO$_2$—R', —NHSO$_2$—R', —NR"SO$_2$—R' or SR' where R' and R" are independently $C_1$-$C_6$ alkyl, $C_3$-$C_8$ cycloalkyl, phenyl, amino, hydroxyalkylamino, heterocyclic, or —(CH$_2$)$_n$—W', where W' is hydroxy, $C_3$-$C_8$ cycloalkyl, phenyl, naphthyl, heterocyclic, or 5- or 6-membered heteroaryl containing 1-3 N, S and/or O atoms;

or, R and $R^0$ and the N atom to which they are bonded together form a monocyclic or bicyclic heterocyclic ring which may be unsubstituted or substituted by (a) halo, hydroxy, heteroaryl, $C_1$-$C_6$ alkyl, $C_1$-$C_6$ alkoxy, ($C_1$-$C_6$ alkoxy)$C_1$-$C_6$ alkoxy, aryl($C_1$-$C_6$ alkoxy), aryloxy, amino, aminoacyl, $C_1$-$C_6$ alkylaminoacyl, arylalkylaminoacyl, di($C_1$-$C_6$ alkyl)aminoacyl, —SO$_2$—R', —SO$_2$—NR"—(CH$_2$)$_n$—W, —NHSO$_2$—R', —NR"SO$_2$—R' or SR' where R' and R" is independently amino, $C_1$-$C_6$ alkylamino, di($C_1$-$C_6$ alkyl)amino, $C_1$-$C_6$ alkyl or $C_3$-$C_8$ cycloalkyl, or (b) —(CH$_2$)$_n$—W, where W is $C_3$-$C_8$ cycloalkyl, phenyl, naphthyl, heterocyclic, 5- or 6-membered heteroaryl containing 1-3 N atoms, —SO$_2$—R', —NHSO$_2$—R', —NR"SO$_2$—R' or SR', where R' and R" is independently alkyl or cycloalkyl; wherein each of said phenyl, aryl, or heteroaryl may be unsubstituted or substituted by halo, $C_1$-$C_6$ alkyl, $C_1$-$C_6$ alkoxy, cyano, or hydroxy;

$R^1$ is H, cyano or halo; $R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms; and, n is 0, 1, 2 or 3.

The invention additionally provides the compound of formula (Ie) having the structure:

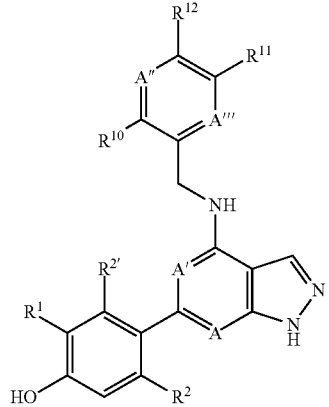

(Ie)

or a pharmaceutically acceptable salt thereof, or a pharmaceutically acceptable solvate of said compound or pharmaceutically acceptable salt, wherein:

A, A', A" and A'" are independently C or N, where C may be unsubstituted or substituted by halo or $C_1$-$C_6$ alkyl;

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^{10}$ is —NHSO$_2$—R', —NR"SO$_2$—R' or SR' where R' and R" is independently $C_1$-$C_6$ alkyl or $C_3$-$C_8$ cycloalkyl; and, $R^{11}$ and $R^{12}$ are each independently H, hydroxy, halo, cyano, $C_1$-$C_6$ alkyl or $C_3$-$C_8$ cycloalkyl. In certain embodiments, the invention provides a compound having the structure:

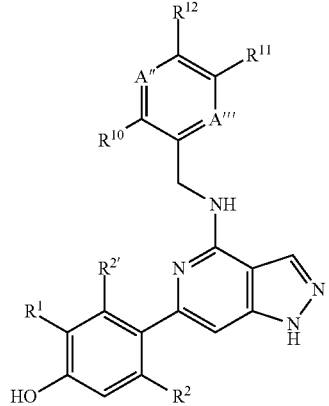

(If)

or a pharmaceutically acceptable salt thereof, or a pharmaceutically acceptable solvate of said compound or pharmaceutically acceptable salt, wherein:

A" and A'" are independently C or N, where C may be unsubstituted or substituted by halo or $C_1$-$C_6$ alkyl;

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^{10}$ is —NHSO$_2$—R', —NR"SO$_2$—R' or SR' where R' and R" are independently hydrogen, $C_1$-$C_6$ alkyl, $C_3$-$C_8$ cycloalkyl, phenyl, amino, $C_1$-$C_6$ alkylamino, di($C_1$-$C_6$ alkyl)amino, heterocyclic, —$(CH_2)_n$—W', where W' is hydroxy, $C_3$-$C_8$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —$NHSO_2$—R', —NR"$SO_2$—R' or SR' where R' and R" are independently phenyl, $C_1$-$C_6$ alkyl or $C_3$-$C_8$ cycloalkyl;

$R^{11}$ and $R^{12}$ are each independently H, hydroxy, halo, cyano, $C_1$-$C_6$ alkyl or $C_3$-$C_8$ cycloalkyl; and, m and n are independently 0, 1, 2 or 3.

The also provides the compound of formula (Ig) having the structure:

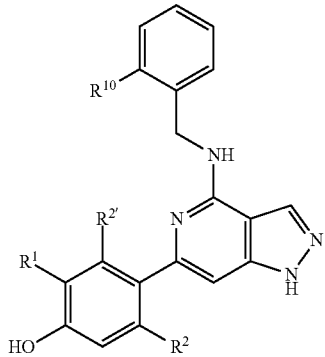

(Ig)

or a pharmaceutically acceptable salt thereof, or a pharmaceutically acceptable solvate of said compound or pharmaceutically acceptable salt, wherein:

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^{10}$ is —$NHSO_2$—R', —NR"$SO_2$—R' or SR' where R' and R" are independently hydrogen, $C_1$-$C_6$ alkyl, $C_3$-$C_8$ cycloalkyl, phenyl, amino, $C_1$-$C_6$ alkylamino, di($C_1$-$C_6$ alkyl)amino, heterocyclic, —$(CH_2)_n$—W', where W' is hydroxy, $C_3$-$C_8$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —$NHSO_2$—R', —NR"$SO_2$—R' or SR' where R' and R" are independently phenyl, $C_1$-$C_6$ alkyl or $C_3$-$C_8$ cyclo alkyl; and, n is 0, 1, 2 or 3. In certain embodiments, the invention provides the compound of formula Ig wherein $R^{10}$ is —NR"$SO_2$—R' and R' and R" are both $C_1$-$C_6$ alkyl.

The invention also provides the compound of formula (Ih) having the structure:

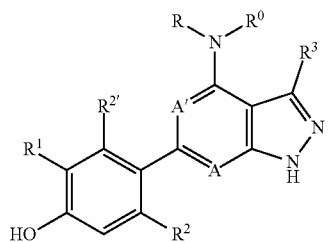

(Ih)

or a pharmaceutically acceptable salt thereof, or a pharmaceutically acceptable solvate of said compound or pharmaceutically acceptable salt, wherein:

A and A' are independently C or N, where C may be unsubstituted or substituted by halo or $C_1$-$C_6$ alkyl;

R and $R^0$ are independently selected from the group consisting of H, $C_1$-$C_6$ alkyl, hydroxy($C_1$-$C_6$ alkyl), phenyl ($C_1$-$C_6$ alkyl), and —$(CH_2)_n$—W, where W is $C_3$-$C_8$ cycloalkyl, phenyl, naphthyl, 5- or 6-membered heteroaryl or heterocyclic containing 1-3 N, S and/or O atoms, —$SO_2$—R', —$NHSO_2$—R', —NR"$SO_2$—R' and SR', where R' and R" are independently $C_1$-$C_6$ alkyl or $C_3$-$C_8$ cycloalkyl, amino, $C_1$-$C_6$ alkylamino, di($C_1$-$C_6$ alkyl)amino, phenyl, heteroaryl, or heterocyclic; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —CONR'R", NR'COR", —NR'CONR'R", —NR'$CO_2$R", —$(CH_2)_n$—$SO_2$—R', —$NHSO_2$—R', —NR"$SO_2$—R' or SR' where R' and R" are independently $C_1$-$C_6$ alkyl, $C_3$-$C_8$ cycloalkyl, phenyl, amino, hydroxyalkylamino, heterocyclic, or —$(CH_2)_n$—W, where W is hydroxy, $C_3$-$C_8$ cycloalkyl, phenyl, naphthyl, heterocyclic, or 5- or 6-membered heteroaryl containing 1-3 N, S and/or O atoms;

or, R and $R^0$ and the N atom to which they are bonded together form a monocyclic or bicyclic heterocyclic ring which may be unsubstituted or substituted by (a) halo, hydroxy, heteroaryl, $C_1$-$C_6$ alkyl, $C_1$-$C_6$ alkoxy, ($C_1$-$C_6$ alkoxy)$C_1$-$C_6$ alkoxy, aryl($C_1$-$C_6$ alkoxy), aryloxy, amino, aminoacyl, $C_1$-$C_6$ alkylaminoacyl, arylalkylaminoacyl, di($C_1$-$C_6$ alkyl)aminoacyl, —$SO_2$—R', —$SO_2$—NR"—$(CH_2)_n$—W, —$NHSO_2$—R', —NR"$SO_2$—R' or SR' where R' and R" is independently amino, $C_1$-$C_6$ alkylamino, di($C_1$-$C_6$ alkyl)amino, $C_1$-$C_6$ alkyl or $C_3$-$C_8$ cycloalkyl, or (b) —$(CH_2)_n$—W, where W is $C_3$-$C_8$ cycloalkyl, phenyl, naphthyl, heterocyclic, 5- or 6-membered heteroaryl containing 1-3 N atoms, —$SO_2$—R', —$NHSO_2$—R', —NR"$SO_2$—R' or SR', where R' and R" is independently alkyl or cycloalkyl; wherein each of said phenyl, aryl, or heteroaryl may be unsubstituted or substituted by halo, $C_1$-$C_6$ alkyl, $C_1$-$C_6$ alkoxy, cyano, or hydroxy;

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^3$ is H, $C_1$-$C_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—R$^4$ and/or 1-4 substituents each independently selected from R$^5$; with the proviso that when X is —CO— or —SO$_2$—, R$^3$ is not H;

Y is a bond, —(CH$_2$)$_m$— or —O—;

R$^4$ is (a) H, C$_1$-C$_6$ alkyl, C$_3$-C$_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; (b) phenyl or naphthyl, said phenyl and naphthyl being optionally substituted with 1-5 substituents selected from C$_1$-C$_6$ alkyl, C$_3$-C$_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; or (c) a 3 to 8-membered saturated or partially unsaturated monocyclic heteroaryl, containing 1 or 2 heteroatoms selected from O and N, said heteroaryl being optionally substituted by 1-5 substituents selected from C$_1$-C$_6$ alkyl, C$_3$-C$_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$;

R$^5$ is C$_1$-C$_6$ alkyl, C$_3$-C$_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ or —NR$^6$SO$_2$NR$^7$R$^8$;

R$^6$ is H, C$_1$-C$_6$ alkyl or C$_3$-C$_8$ cycloalkyl, said C$_1$-C$_6$ alkyl is optionally substituted by —NR$^7$R$^8$ or a 3 to 8-membered saturated or partially unsaturated monocyclic heteroaryl, containing 1 or 2 heteroatoms selected from O and N, said heteroaryl being optionally substituted by 1-5 substituents selected from C$_1$-C$_6$ alkyl, C$_3$-C$_8$ cycloalkyl, halo, hydroxy and cyano;

R$^7$ and R$^8$ are each independently H, C$_1$-C$_6$ alkyl or C$_3$-C$_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said C$_1$-C$_6$ alkyl is optionally substituted by C$_3$-C$_8$ cycloalkyl, halo, cyano, hydroxy, amino, (C$_1$-C$_6$ alkyl)amino or di(C$_1$-C$_6$ alkyl)amino and said heterocyclic ring being optionally substituted by one or more C$_1$-C$_6$ alkyl or C$_3$-C$_8$ cycloalkyl groups;

R$^9$ is C$_1$-C$_6$ alkyl or C$_3$-C$_8$ cycloalkyl; and, m and n are independently 0, 1, 2 or 3. In certain embodiments, the invention provides the compound of formula Ih wherein R$^{10}$ is —NR"SO$_2$—R' and R' and R" are both C$_1$-C$_6$ alkyl.

The invention also provides the compound of formula (Ii) having the structure:

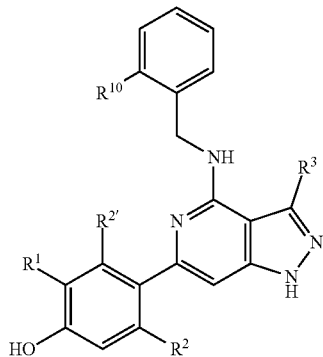

(Ii)

or a pharmaceutically acceptable salt thereof, or a pharmaceutically acceptable solvate of said compound or pharmaceutically acceptable salt, wherein:

R$^1$ is H, cyano or halo;

R$^2$ and R$^{2'}$ are independently H, C$_1$-C$_6$ alkyl, cyano, C$_1$-C$_6$ alkoxy, C$_1$-C$_6$ alkylthio, or C$_3$-C$_8$ cycloalkyl where alkyl, alkoxy, or cycloalkyl is optionally substituted by one or more fluorine atoms;

R$^3$ is H, C$_1$-C$_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—R$^4$ and/or 1-4 substituents each independently selected from R$^5$;

Y is a bond, —(CH$_2$)$_m$— or —O—;

R$^4$ is (a) H, C$_1$-C$_6$ alkyl, C$_3$-C$_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; (b) phenyl or naphthyl, said phenyl and naphthyl being optionally substituted with 1-5 substituents selected from C$_1$-C$_6$ alkyl, C$_3$-C$_8$ cycloalkyl, halo, cyano, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; or (c) a 3 to 8-membered saturated or partially unsaturated monocyclic heteroaryl, containing 1 or 2 heteroatoms selected from O and N, said heteroaryl being optionally substituted by 1-5 substituents selected from C$_1$-C$_6$ alkyl, C$_3$-C$_8$ cycloalkyl, halo, cyano, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$;

R$^5$ is C$_1$-C$_6$ alkyl, C$_3$-C$_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ or —NR$^6$SO$_2$NR$^7$R$^8$;

R$^6$ is H, C$_1$-C$_6$ alkyl or C$_3$-C$_8$ cycloalkyl, said C$_1$-C$_6$ alkyl is optionally substituted by —NR$^7$R$^8$ or a 3 to 8-membered saturated or partially unsaturated monocyclic heteroaryl, containing 1 or 2 heteroatoms selected from O and N, said heteroaryl being optionally substituted by 1-5 substituents selected from C$_1$-C$_6$ alkyl, C$_3$-C$_8$ cycloalkyl, halo, hydroxy and cyano;

R$^7$ and R$^8$ are each independently H, C$_1$-C$_6$ alkyl or C$_3$-C$_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said C$_1$-C$_6$ alkyl is optionally substituted by C$_3$-C$_8$ cycloalkyl, halo, cyano, hydroxy, amino, (C$_1$-C$_6$ alkyl)amino or di(C$_1$-C$_6$ alkyl)amino and said heterocyclic ring being optionally substituted by one or more C$_1$-C$_6$ alkyl or C$_3$-C$_8$ cycloalkyl groups; R$^9$ is C$_1$-C$_6$ alkyl or C$_3$-C$_8$ cycloalkyl;

R$^{10}$ is —NHSO$_2$—R', —NR"SO$_2$—R' or SR' where R' and R" are independently hydrogen, C$_1$-C$_6$ alkyl, C$_3$-C$_8$ cycloalkyl, phenyl, amino, C$_1$-C$_6$ alkylamino, di(C$_1$-C$_6$ alkyl)amino, heterocyclic, —(CH$_2$)$_n$—W', where W' is hydroxy, $C_3$-$C_8$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —$NHSO_2$—R', —NR"$SO_2$—R' or SR' where R' and R" are independently phenyl, $C_1$-$C_6$ alkyl or $C_3$-$C_8$ cycloalkyl; and, m and n are independently 0, 1, 2 or 3.

In certain embodiments, the invention provides a compound of formula Ig wherein $R^{10}$ is —NR"$SO_2$—R' and R' and R" are both $C_1$-$C_6$ alkyl.

In specific embodiments, the invention provides a compound selected from the group consisting of:

4-({2-[ethyl(ethylsulfonyl)amino]benzyl}amino)-6-[5-fluoro-4-hydroxy-2-(2,2,2-trifluoroethyl)-phenyl]-N-methyl-1H-pyrazolo[4,3-c]pyridine-3-carboxamide;

4-({2-[ethyl(ethylsulfonyl)amino]benzyl}amino)-6-(2-ethyl-5-fluoro-4-hydroxyphenyl)-N-methyl-1H-pyrazolo[4,3-c]pyridine-3-carboxamide;

6-(2-ethyl-5-fluoro-4-hydroxyphenyl)-4-({2-[(ethylsulfonyl)(methyl)amino]benzyl}amino)-N-methyl-1H-pyrazolo[4,3-c]pyridine-3-carboxamide;

6-(2-ethyl 5-fluoro-4-hydroxyphenyl)-4-{[2-(4-hydroxyphenyl)ethyl]amino}-N-methyl-1H-pyrazolo[4,3-c]pyridine-3-carboxamide;

6-(2-ethyl-5-fluoro-4-hydroxyphenyl)-N-methyl-4-[(2-methylpropyl)amino]-1H-pyrazolo[4,3-c]pyridine-3-carboxamide;

4-({5-chloro-2-[methyl(methylsulfonyl)amino]benzyl}amino)-6-(2-ethyl-5-fluoro-4-hydroxyphenyl)-N-methyl-1H-pyrazolo[4,3-c]pyridine-3-carboxamide;

6-(2-ethyl-5-fluoro-4-hydroxyphenyl)-4-({5-fluoro-2-[methyl(methylsulfonyl)amino]benzyl}amino)-N-methyl-1H-pyrazolo[4,3-c]pyridine-3-carboxamide;

6-(2-ethyl-5-fluoro-4-hydroxyphenyl)-4-({2-fluoro-6-[methyl(methylsulfonyl)amino]benzyl}amino)-N-methyl-1H-pyrazolo[4,3-c]pyridine-3-carboxamide;

6-(2-ethyl-5-fluoro-4-hydroxyphenyl)-4-({2-[ethyl(methylsulfonyl)amino]benzyl}amino)-N-methyl-1H-pyrazolo[4,3-c]pyridine-3-carboxamide;

4-[(cyclopentylmethyl)amino]-6-(2-ethyl-5-fluoro-4-hydroxyphenyl)-N-methyl-1H-pyrazolo[4,3-c]pyridine-3-carboxamide;

6-[5-fluoro-4-hydroxy-2-(2,2,2-trifluoroethyl)phenyl]-N-methyl-4-({5-methyl-2-[methyl(methylsul-fonyl)amino]benzyl}amino)-1H-pyrazolo[4,3-c]pyridine-3-carboxamide;

4-({2-[ethyl(methylsulfonyl)amino]benzyl}amino)-6-[5-fluoro-4-hydroxy-2-(2,2,2-trifluoro-ethyl)phenyl]-N-methyl-1H-pyrazolo[4,3-c]pyridine-3-carboxamide;

4-({2-[(ethylsulfonyl)(methyl)amino]benzyl}amino)-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-4-({5-fluoro-2-[methyl(methylsulfonyl)amino]benzyl}amino)-N-methyl-1H-pyrazolo[4,3-c]pyridine-3-carboxamide;

4-({5-chloro-2-[methyl(methylsulfonyl)amino]benzyl}amino)-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-N-methyl-4-[(2-methylpropyl)amino]-1H-pyrazolo[4,3-c]pyridine-3-carboxamide;

4-[(cyclopentylmethyl)amino]-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-4-({2-fluoro-6-[methyl(methylsulfonyl)-amino]benzyl}amino)-N-methyl-1H-pyrazolo[4,3-c]pyridine-3-carboxamide;

6-(2-ethyl-5-fluoro-4-hydroxyphenyl)-N-methyl-4-({2-[methyl(methylsulfonyl)amino]benzyl}-amino)-1H-pyrazolo[4,3-c]pyridine-3-carboxamide;

6-[5-fluoro-4-hydroxy-2-(2,2,2-trifluoroethyl)phenyl]-N-methyl-4-({2-[methyl(methylsulfonyl)-amino]benzyl}amino)-1H-pyrazolo[4,3-c]pyridine-3-carboxamide;

6-(2-ethyl-5-fluoro-4-hydroxyphenyl)-N-methyl-4-({5-methyl-2-[methyl(methylsulfonyl)amino]-benzyl}amino)-1H-pyrazolo[4,3-c]pyridine-3-carboxamide;

6-(2-ethyl-5-fluoro-4-hydroxyphenyl)-N-methyl-4-({2-[methyl(phenylsulfonyl)-amino]benzyl}amino)-1H-pyrazolo[4,3-c]pyridine-3-carboxamide;

6-(2-ethyl-5-fluoro-4-hydroxyphenyl)-N-methyl-4-[(2-{4-[(phenylsulfonyl)amino]-phenyl}ethyl)-amino]-1H-pyrazolo[4,3-c]pyridine-3-carboxamide;

6-[5-fluoro-4-hydroxy-2-(2,2,2-trifluoroethyl)phenyl]-4-({2-[(2-hydroxyethyl)(methylsulfonyl)-amino]benzyl}amino)-N-methyl-1H-pyrazolo[4,3-c]pyridine-3-carboxamide;

6-[5-fluoro-4-hydroxy-2-(2,2,2-trifluoroethyl)phenyl]-4-({2-[methyl(phenylsulfonyl)amino]benzyl}-amino)-1H-pyrazolo[4,3-c]pyridine-3-carboxamide;

6-[5-fluoro-4-hydroxy-2-(2,2,2-trifluoroethyl)phenyl]-4-({2-[(2-hydroxyethyl)(methylsulfonyl)-amino]benzyl}amino)-1H-pyrazolo[4,3-c]pyridine-3-carboxamide;

6-(2-ethyl-5-fluoro-4-hydroxyphenyl)-4-({4-hydroxy-2-[methyl(methylsulfonyl)amino]benzyl}-amino)-N-methyl-1H-pyrazolo[4,3-c]pyridine-3-carboxamide;

6-(2-ethyl-5-fluoro-4-hydroxyphenyl)-4-({4-hydroxy-2-[methyl(methylsulfonyl)amino]benzyl}-amino)-1H-pyrazolo[4,3-c]pyridine-3-carboxamide;

6-(2-ethyl-5-fluoro-4-hydroxyphenyl)-4-({5-hydroxy-2-[methyl(methylsulfonyl)amino]benzyl}-amino)-N-methyl-1H-pyrazolo[4,3-c]pyridine-3-carboxamide;

6-[5-fluoro-4-hydroxy-2-(2,2,2-trifluoroethyl)phenyl]-4-[(2-{[(3-hydroxyphenyl)sulfonyl](methyl)-amino}benzyl)amino]-N-methyl-1H-pyrazolo[4,3-c]pyridine-3-carboxamide;

6-[5-fluoro-4-hydroxy-2-(2,2,2-trifluoroethyl)phenyl]-4-({4-hydroxy-2-[methyl(methylsulfonyl)-amino]benzyl}amino)-N-methyl-1H-pyrazolo[4,3-c]pyridine-3-carboxamide;

4-({2-[ethyl(methylsulfonyl)amino]-5-hydroxybenzyl}amino)-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-4-({5-hydroxy-2-[methyl(phenylsulfonyl)-amino]benzyl}amino)-N-methyl-1H-pyrazolo[4,3-c]pyridine-3-carboxamide;

4-({2-[ethyl(phenylsulfonyl)amino]-5-hydroxybenzyl}amino)-6-[5-fluoro-4-hydroxy-2-(2,2,2-trifluoroethyl)phenyl]-N-methyl-1H-pyrazolo[4,3-c]pyridine-3-carboxamide;

6-(2-cyclopropyl-5-fluoro-4-hydroxyphenyl)-N-methyl-4-({2-[methyl(methylsulfonyl)amino]-benzyl}amino)-1H-pyrazolo[4,3-c]pyridine-3-carboxamide;

6-(2-ethyl-5-fluoro-4-hydroxyphenyl)-N-methyl-4-{[(1R)-1-(2-[methyl(methylsulfonyl)amino]-phenyl)ethyl]amino}-1H-pyrazolo[4,3-c]pyridine-3-carboxamide;

6-(2-ethyl-5-fluoro-4-hydroxyphenyl)-N-methyl-4-{[((1S)-1-{2-[methyl(methylsulfonyl)-amino]phenyl}ethyl]amino}-1H-pyrazolo[4,3-c]pyridine-3-carboxamide;

6-(2-ethyl-5-fluoro-4-hydroxyphenyl)-4-({2-[methyl(phenylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-4-({4-hydroxy-2-[methyl(methylsulfonyl)-amino]benzyl}amino)-1H-pyrazolo[4,3-c]pyridine-3-carboxamide;

6-[5-fluoro-4-hydroxy-2-(2,2,2-trifluoroethyl)phenyl]-4-({5-hydroxy-2-[methyl(phenylsulfonyl)-amino]benzyl}amino)-1H-pyrazolo[4,3-c]pyridine-3-carboxamide;

4-({2-[ethyl(phenylsulfonyl)amino]-5-hydroxybenzyl}amino)-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-N-methyl-4-[({3-[methyl(phenylsulfonyl)-amino]pyrazin-2-yl}methyl)amino]-1H-pyrazolo[4,3-c]pyridine-3-carboxamide;

4-[({3-[ethyl(methylsulfonyl)amino]pyrazin-2-yl}methyl)amino]-6-[5-fluoro-4-hydroxy-2-(2,2,2-trifluoroethyl)phenyl]-N-methyl-1H-pyrazolo[4,3-c]pyridine-3-carboxamide;

N-ethyl-4-[({3-[ethyl(methylsulfonyl)amino]pyrazin-2-yl}methyl)amino]-6-[5-fluoro-4-hydroxy-2-(2,2,2-trifluoroethyl)phenyl]-1H-pyrazolo[4,3-c]pyridine-3-carboxamide;

6-(2-cyclopropyl-5-fluoro-4-hydroxyphenyl)-4-({2-[methyl(methylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-N-methyl-4-[({4-[methyl(methylsulfonyl)-amino]pyridin-3-yl}methyl)amino]-1H-pyrazolo[4,3-c]pyridine-3-carboxamide;

6-(2-cyclopropyl-5-fluoro-4-hydroxyphenyl)-N-methyl-4-[({2-[methyl(methylsulfonyl)amino]-pyridin-3-yl}methyl)amino]-1H-pyrazolo[4,3-c]pyridine-3-carboxamide;

6-[5-fluoro-4-hydroxy-2-(2,2,2-trifluoroethyl)phenyl]-4-({5-methoxy-2-[methyl(methylsulfonyl)-amino]benzyl}amino)-N-methyl-1H-pyrazolo[4,3-c]pyridine-3-carboxamide;

6-[5-fluoro-4-hydroxy-2-(2,2,2-trifluoroethyl)phenyl]-N-methyl-4-[({3-[methyl(methylsulfonyl)amino]pyrazin-2-yl}methyl)amino]-1H-pyrazolo[4,3-c]pyridine-3-carboxamide;

4-[({2-[ethyl(methylsulfonyl)amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-N-methyl-4-[({2-[methyl(methylsulfonyl)-amino]pyridin-3-yl}methyl)amino]-1H-pyrazolo[4,3-c]pyridine-3-carboxamide;

6-[5-fluoro-4-hydroxy-2-(2,2,2-trifluoroethyl)phenyl]-4-({5-hydroxy-2-[methyl(pyridin-3-ylsulfonyl)amino]benzyl}amino)-N-methyl-1H-pyrazolo[4,3-c]pyridine-3-carboxamide;

6-[5-fluoro-4-hydroxy-2-(2,2,2-trifluoroethyl)phenyl]-N-methyl-4-[({3-[methyl(methylsulfonyl)-amino]pyridin-2-yl}methyl)amino]-1H-pyrazolo[4,3-c]pyridine-3-carboxamide;

6-(2-ethyl-5-fluoro-4-hydroxyphenyl)-4-({2-[methyl(methylsulfonyl)amino]benzyl}amino)-N-(6-methylpyridin-3-yl)-1H-pyrazolo[4,3-c]pyridine-3-carboxamide;

6-(5-fluoro-hydroxy-2-(2,2,2-trifluoroethyl)phenyl)-N-methyl-4-((1,3,3-trimethylureido)benzyl)-amino)-1H-pyrazolo[4,3-c]pyridine-3-carboxamide;

6-(5-fluoro-4-hydroxy-2-(2,2,2-trifluoroethyl)phenyl)-N-methyl-4-((2-(N-methyl-1H-pyrazole-4-sulfonamido)benzyl)amino)-1H-pyrazolo[4,3-c]pyridine-3-carboxamide;

4-((2-N,1-dimethyl-1H-imidazole-4-sulfonamido)benzyl)amido)-6-(5-fluoro-4-hydroxy-2-(2,2,2-trifluoroethyl)phenyl)-N-methyl-1H-pyrazolo[4,3-c]pyridine-3-carboxamide;

6-[5-fluoro-4-hydroxy-2-(2,2,2-trifluoroethyl)phenyl]-4-[(2-{[(2-methoxyethyl)sulfonyl]-(methyl)amino}benzyl)amino]-N-methyl-1H-pyrazolo[4,3-c]pyridine-3-carboxamide;

6-[5-fluoro-4-hydroxy-2-(2,2,2-trifluoroethyl)phenyl]-4-({2-[methyl(pyridin-3-ylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-4-[({2-[methyl(methylsulfonyl)amino]pyridin-3-yl}methyl)amino]-1H-pyrazolo[4,3-c]pyridine-3-carboxamide;

4-[({2-[ethyl(methylsulfonyl)amino]pyridin-3-yl}methyl)amino]-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-N-methyl-4-{[2-(sulfamoylmethyl)benzyl]-amino}-1H-pyrazolo[4,3-c]pyridine-3-carboxamide;

6-[5-fluoro-4-hydroxy-2-(2,2,2-trifluoroethyl)phenyl]-4-{[2-(methyl{[6-(morpholin-4-yl)pyridin-3-yl]sulfonyl}amino)benzyl]amino}-1H-pyrazolo[4,3-c]pyridine-3-carboxamide;

6-[5-fluoro-4-hydroxy-2-(2,2,2-trifluoroethyl)phenyl]-4-{[2-(methyl{[3-(morpholin-4-yl)propyl]sulfonyl}amino)benzyl]amino}-1H-pyrazolo[4,3-c]pyridine-3-carboxamide;

6-[5-fluoro-4-hydroxy-2-(2,2,2-trifluoroethyl)phenyl]-N-methyl-4-[({5-methyl-2-[methyl(methyl-sulfonyl)amino]pyridin-3-yl}methyl)amino]-1H-pyrazolo[4,3-c]pyridine-3-carboxamide;

6-[5-fluoro-4-hydroxy-2-(2,2,2-trifluoroethyl)phenyl]-N-methyl-4-({2-[methyl(pyridin-3-ylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-N-methyl-4-[2-{methyl[(6-methylpyridin-3-yl)sulfonyl]amino}benzyl)amino]-1H-pyrazolo[4,3-c]pyridine-3-carboxamide;

6-[5-fluoro-4-hydroxy-2-(2,2,2-trifluoroethyl)phenyl]-4-[2-{methyl[(6-methylpyridin-3-yl)sulfonyl]amino}benzyl)amino]-1H-pyrazolo[4,3-c]pyridine-3-carboxamide;

4-[({5-chloro-2-[ethyl(methylsulfonyl)amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide;

4-[({5-chloro-2-[methyl(methylsulfonyl)amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide;

6-(2-ethyl-5-fluoro-4-hydroxyphenyl)-N-methyl-4-({2-[methyl(sulfamoyl)amino]benzyl}amino)-1H-pyrazolo[4,3-c]pyridine-3-carboxamide;

6-(5-fluoro-4-hydroxy-2-(2,2,2-trifluoroethyl)phenyl)-4-((N-(2-hydroxyethyl)sulfamoyl)(methyl)-aminobenzyl)amino)-N-methyl-1H-pyrazolo[4,3-c]pyridine-3-carboxamide;

6-[5-fluoro-4-hydroxy-2-(2,2,2-trifluoroethyl)phenyl]-N-{6-[(2-hydroxyethyl)amino]pyridin-3-yl}-4-({5-hydroxy-2-[methyl(methylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-4-({2-[methyl(methylsulfonyl)amino]benzyl}amino)-N-(6-methylpyridin-3-yl)-1H-pyrazolo[4,3-c]pyridine-3-carboxamide;

6-[5-fluoro-4-hydroxy-2-(2,2,2-trifluoroethyl)phenyl]-4-({2-[methyl(methylsulfonyl)-amino]benzyl}amino)-1H-pyrazolo[4,3-c]pyridine-3-carboxamide;

6-[5-fluoro-4-hydroxy-2-(2,2,2-trifluoroethyl)phenyl]-4-[({5-fluoro-2-[methyl(methylsulfonyl)-amino]pyridin-3-yl}methyl)amino]-1H-pyrazolo[4,3-c]pyridine-3-carboxamide;

4-[({2-[ethyl(methylsulfonyl)amino]-5-fluoropyridin-3-yl}methyl)amino]-6-[5-fluoro-4-hydroxy-2-(2,2,2-trifluoroethyl)phenyl]-1H-pyrazolo[4,3-c]pyridine-3-carboxamide;

4-[({3-[ethyl(methylsulfonyl)amino]pyrazin-2-yl}methyl)amino]-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-4-({5-methyl-2-[methyl(methylsulfonyl)-amino]benzyl}amino)-1H-pyrazolo[4,3-c]pyridine-3-carboxamide;

4-((2-(N-ethylethylsulfonamido)benzyl)amino)-6-(5-fluoro-hydroxy-2-(2,2,2-trifluoroethyl)phenyl)-1H-pyrazolo[4,3-c]pyridine-3-carboxamide;

4-((2-(N-ethylmethylsulfonamido)-5-fluorobenzyl)amino)-6-(5-fluoro-4-hydroxy-2-(2,2,2-trifluoro-ethyl)phenyl)-1H-pyrazolo[4,3-c]pyridine-3-carboxamide;

4-((5-chloro-2-(N-ethylmethylsulfonamido)benzyl)amino)-6-(5-fluoro-4-hydroxy-2-(2,2,2-trifluoro-ethyl)phenyl)-1H-pyrazolo[4,3-c]pyridine-3-carboxamide;

6-(5-fluoro-hydroxy-2-(2,2,2-trifluoroethyl)phenyl)-4-((2-(N-methylethyl-sulfonamido)benzyl)-amino)-1H-pyrazolo[4,3-c]pyridine-3-carboxamide;

6-(5-fluoro-4-hydroxy-2-(2,2,2-trifluoroethyl)phenyl)-4-(((5-methyl-2-(N-methylmethylsulfonamido)pyridin-3-yl)methyl)amino)-1H-pyrazolo[4,3-c]pyridine-3-carboxamide;

4-[({2-[ethyl(methylsulfonyl)amino]-5-methylpyridin-3-yl}methyl)amino]-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-4-({5-fluoro-2-[methyl(methylsulfonyl)-amino]benzyl}amino)-1H-pyrazolo[4,3-c]pyridine-3-carboxamide;

4-({5-chloro-2-[methyl(methylsulfonyl)amino]benzyl}amino)-6-[5-fluoro-4-hydroxy-2-(2,2,2-trifluoro-ethyl)phenyl]-1H-pyrazolo[4,3-c]pyridine-3-carboxamide;

4-({2-[ethyl(methylsulfonyl)amino]benzyl}amino)-6-[5-fluoro-4-hydroxy-2-(2,2,2-trifluoroethyl)-phenyl]-1H-pyrazolo[4,3-c]pyridine-3-carboxamide;

4-({2-[ethyl(methylsulfonyl)amino]-5-methylbenzyl}amino)-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-4-({5-hydroxy-2-[methyl(methylsulfonyl)-amino]benzyl}amino)-1H-pyrazolo[4,3-c]pyridine-3-carboxamide;

6-(2-ethyl-5-fluoro-4-hydroxyphenyl)-N-methyl-4-((2-(N-methylmethylsulfonamido)benzyl)-amino)-1H-pyrazolo[3,4-d]pyrimidine-3-carboxamide;

6-(5-fluoro-4-hydroxy-2-(2,2,2-trifluoroethyl)phenyl)-N-methyl-4-((2-(N-methylmethylsulfonamido)benzyl)amino)-1H-pyrazolo[3,4-d]pyrimidine-3-carboxamide;

6-(2-ethyl-5-fluoro-4-hydroxyphenyl)-4-((2-(N-methylphenylsulfonamido)benzyl)amino)-1H-pyrazolo[3,4-d]pyrimidine-3-carboxamide;

6-(5-fluoro-4-hydroxy-2-(2,2,2-trifluoroethyl)phenyl)-4-((2-(N-methylphenylsulfonamido)-benzyl)amino)-1H-pyrazolo[3,4-d]pyrimidine-3-carboxamide;

6-(5-fluoro-4-hydroxy-2-(2,2,2-trifluoroethyl)phenyl)-4-((5-hydroxy-2-(N-methylmethylsulfonamido)benzyl)amino)-1H-pyrazolo[3,4-d]pyrimidine-3-carboxamide;

6-(5-fluoro-4-hydroxy-2-(2,2,2-trifluoroethyl)phenyl)-4-((2-(N-methylmethylsulfonamido)benzyl)amino)-1H-pyrazolo[3,4-d]pyrimidine-3-carboxamide;

6-(5-fluoro-4-hydroxy-2-(2,2,2-trifluoroethyl)phenyl)-4-((5-hydroxy-2-(N-methylmethylsulfonamido)benzyl)amino)-N-(6-((2-hydroxyethyl)amino)pyridin-3-yl)-1H-pyrazolo[3,4-d]pyrimidine-3-carboxamide;

6-(5-fluoro-4-hydroxy-2-(2,2,2-trifluoroethyl)phenyl)-N-methyl-4-(((3-(N-methylmethylsulfonamido)pyrazin-2-yl)methyl)amino)-1H-pyrazolo[3,4-d]pyrimidine-3-carboxamide;

6-(5-fluoro-4-hydroxy-2-(2,2,2-trifluoroethyl)phenyl)-4-((2-(N-(2-hydroxyethyl)methyl-sulfonamido)benzyl)amino)-1H-pyrazolo[3,4-d]pyrimidine-3-carboxamide;

6-(5-fluoro-4-hydroxy-2-(2,2,2-trifluoroethyl)phenyl)-4-((2-(N-(2-hydroxyethyl)methylsulfonamido)benzyl)amino)-N-methyl-1H-pyrazolo[3,4-d]pyrimidine-3-carboxamide;

4-((2-(N-ethylmethylsulfonamido)benzyl)amino)-6-(5-fluoro-4-hydroxy-2-(2,2,2-trifluoroethyl)-phenyl)-N-methyl-1H-pyrazolo[3,4-d]pyrimidine-3-carboxamide;

4-((5-fluoro-2-(N-methylmethylsulfonamido)benzyl)amino)-6-(5-fluoro-4-hydroxy-2-(2,2,2-trifluoroethyl)phenyl)-N-methyl-1H-pyrazolo[3,4-d]pyrimidine-3-carboxamide;

4-((2-(N-ethylphenylsulfonamido)-5-hydroxybenzyl)amino)-6-(5-fluoro-4-hydroxy-2-(2,2,2-trifluoroethyl)phenyl)-N-methyl-1H-pyrazolo[3,4-d]pyrimidine-3-carboxamide;

4-((2-(N-methylphenylsulfonamido)-5-hydroxybenzyl)amino)-6-(5-fluoro-4-hydroxy-2-(2,2,2-trifluoroethyl)phenyl)-N-methyl-1H-pyrazolo[3,4-d]pyrimidine-3-carboxamide;

4-((2-(N-ethylphenylsulfonamido)-5-hydroxybenzyl)amino)-6-(5-fluoro-4-hydroxy-2-(2,2,2-trifluoroethyl)phenyl)-1H-pyrazolo[3,4-d]pyrimidine-3-carboxamide;

4-((2-(N-methylphenylsulfonamido)-5-hydroxybenzyl)amino)-6-(5-fluoro-4-hydroxy-2-(2,2,2-trifluoroethyl)phenyl)-1H-pyrazolo[3,4-d]pyrimidine-3-carboxamide;

6-(5-fluoro-4-hydroxy-2-(2,2,2-trifluoroethyl)phenyl)-N-methyl-4-((2-(methyl(sulfamoyl)amino)-benzyl)amino)-1H-pyrazolo[3,4-d]pyrimidine-3-carboxamide;

6-(5-fluoro-4-hydroxy-2-(2,2,2-trifluoroethyl)phenyl)-N-methyl-4-((2-(methyl(N-methylsulfamoyl)amino)benzyl)amino)-1H-pyrazolo[3,4-d]pyrimidine-3-carboxamide;

4-[4-(7,8-dimethoxy-3,4-dihydroisoquinolin-2(1H)-yl)-1H-pyrazolo[4,3-c]pyridin-6-yl]-3-ethylphenol formate;

3-ethyl-4-[4-(3-phenoxyazetidin-1-yl)-1H-pyrazolo[4,3-c]pyridin-6-yl]phenol formate;
3-ethyl-4-{4-[6-(4-methyl-1H-imidazol-1-yl)-3,4-dihydroisoquinolin-2(1H)-yl]-1H-pyrazolo[4,3-c]pyridin-6-yl}phenol formate;
3-ethyl-4-{4-[6-(2-methoxyethoxy)-3,4-dihydroisoquinolin-2(1H)-yl]-1H-pyrazolo[4,3-c]pyridin-6-yl}phenol formate;
1-[6-(2-ethyl-4-hydroxyphenyl)-1H-pyrazolo[4,3-c]pyridin-4-yl]-3-methylazetidin-3-ol formate;
2-[6-(2-ethyl-4-hydroxyphenyl)-1H-pyrazolo[4,3-c]pyridin-4-yl]-N-[2-(pyrrolidin-1-yl)ethyl]-1,2,3,4-tetrahydroisoquinoline-7-sulfonamide formate;
N-benzyl-2-[6-(2-ethyl-4-hydroxyphenyl)-1H-pyrazolo[4,3-c]pyridin-4-yl]-1,2,3,4-tetrahydroisoquinoline-5-carboxamide formate;
4-{4-[7-(benzyloxy)-6-methoxy-3,4-dihydroisoquinolin-2(1H)-yl]-1H-pyrazolo[4,3-c]pyridin-6-yl}-3-ethylphenol formate;
4-[4-(5-chloro-3,4-dihydroisoquinolin-2(1H)-yl)-1H-pyrazolo[4,3-c]pyridin-6-yl]-3-ethylphenol formate;
4-chloro-3-({1-[6-(2-ethyl-4-hydroxyphenyl)-1H-pyrazolo[4,3-c]pyridin-4-yl]azetidin-3-yl}oxy)benzonitrile formate;
3-ethyl-4-[4-(6-fluoro-3,4-dihydroisoquinolin-2(1H)-yl)-1H-pyrazolo[4,3-c]pyridin-6-yl]phenol formate;
3-ethyl-A-[4-(8-methoxy-3,4-dihydroisoquinolin-2(1H)-yl)-1H-pyrazolo[4,3-c]pyridin-6-yl]phenol formate;
N-{2-[6-(2-ethyl-4-hydroxyphenyl)-1H-pyrazolo[4,3-c]pyridin-4-yl]-1,2,3,4-tetrahydroisoquinolin-5-yl}methanesulfonamide formate;
4-(4-{[2-(biphenyl-4-yl)ethyl]amino}-1H-pyrazolo[4,3-c]pyridin-6-yl)-3-ethylphenol formate;
N-[2-({[6-(2-ethyl-4-hydroxyphenyl)-1H-pyrazolo[4,3-c]pyridin-4-yl]amino}methyl)phenyl]-N-methylmethanesulfonamide hydrochloride;
1-[6-(2-ethyl-4-hydroxyphenyl)-1H-pyrazolo[4,3-c]pyridin-4-yl]-N, N-dimethylpyrrolidine-3-sulfonamide (racemic);
N-[2-({[6-(2-ethyl-4-hydroxyphenyl)-1H-pyrazolo[4,3-c]pyridin-4-yl]amino}methyl)-3-methylphenyl]-N-methylmethanesulfonamide diethylamine salt;
3-ethyl-4-[4-(4-methoxypiperidin-1-yl)-1H-pyrazolo[4,3-c]pyridin-6-yl]phenol diethylamine salt;
N-[2-({[2-(3,4-dimethoxyphenyl)ethyl][6-(2-ethyl-5-fluoro-4-hydroxyphenyl)-1H-pyrazolo[4,3-c]pyridin-4-yl]amino}methyl)phenyl]-N-methylmethanesulfonamide hydrochloride;
N-[2-({[6-(2-ethyl-5-fluoro-4-hydroxyphenyl)-1H-pyrazolo[4,3-c]pyridin-4-yl](2-{4-[(methylsulfonyl)amino]phenyl}ethyl)amino}methyl)phenyl]-N-methylmethanesulfonamide hydrochloride;
N-[2-({[6-(2-ethyl-5-fluoro-4-hydroxyphenyl)-1H-pyrazolo[4,3-c]pyridin-4-yl]amino}methyl)-phenyl]-N-methyl-methanesulfonamide;
N-[2-({[6-(2-ethyl-5-fluoro-4-hydroxyphenyl)-1H-pyrazolo[4,3-c]pyridin-4-yl]amino}methyl)-4-methylphenyl]-N-methylmethanesulfonamide hydrochloride;
N-[4-chloro-2-({[6-(2-ethyl-5-fluoro-4-hydroxyphenyl)-1H-pyrazolo[4,3-c]pyridin-4-yl]amino}methyl)phenyl]-N-methylmethanesulfonamide hydrochloride;
N-[2-({[6-(2-ethyl-5-fluoro-4-hydroxyphenyl)-1H-pyrazolo[4,3-c]pyridin-4-yl]amino}methyl)-3-fluorophenyl]-N-methylmethanesulfonamide hydrochloride;
N-[2-({[6-(2-ethyl-5-fluoro-4-hydroxyphenyl)-1H-pyrazolo[4,3-c]pyridin-4-yl]amino}methyl)-phenyl]-N-methyl-ethanesulfonamide hydrochloride;
N-ethyl-N-[2-({[6-(2-ethyl-5-fluoro-4-hydroxyphenyl)-1H-pyrazolo[4,3-c]pyridin-4-yl]amino}-methyl)phenyl]ethanesulfonamide hydrochloride;
N-[2-({[6-(2-ethyl-5-fluoro-4-hydroxyphenyl)-1H-pyrazolo[4,3-c]pyridin-4-yl]amino}methyl)phenyl]-N-propyl-methanesulfonamide;
N-ethyl-N-[2-({[6-(2-ethyl-5-fluoro-4-hydroxyphenyl)-1H-pyrazolo[4,3-c]pyridin-4-yl]amino}-methyl)phenyl]methanesulfonamide;
N-butyl-N-[2-({[6-(2-ethyl-5-fluoro-4-hydroxyphenyl)-1H-pyrazolo[4,3-c]pyridin-4-yl]amino}-methyl)phenyl]methanesulfonamide;
N-[2-({[6-(2-ethyl-5-fluoro-4-hydroxyphenyl)-1H-pyrazolo[4,3-c]pyridin-4-yl][2-(morpholin-4-yl)ethyl]amino}methyl)phenyl]-N-methylmethanesulfonamide;
N-[2-({[6-(2-ethyl-5-fluoro-4-hydroxyphenyl)-1H-pyrazolo[4,3-c]pyridin-4-yl][2-(morpholin-4-yl)ethyl]amino}methyl)phenyl]-N-methylmethanesulfonamide;
N-ethyl-N-[2-({[6-(2-ethyl-5-fluoro-4-hydroxyphenyl)-1H-pyrazolo[4,3-c]pyridin-4-yl](methyl)-amino}methyl)-4-methylphenyl]methanesulfonamide;
N-[2-({ethyl[6-(2-ethyl-5-fluoro-4-hydroxyphenyl)-1H-pyrazolo[4,3-c]pyridin-4-yl]amino}methyl)-4-methylphenyl]-N-methylmethanesulfonamide;
N-[2-({[6-(2-ethyl-5-fluoro-4-hydroxyphenyl)-1H-pyrazolo[4,3-c]pyridin-4-yl](propyl)amino}-methyl)-4-methylphenyl]-N-methylmethanesulfonamide;
N-ethyl-N-[2-({[6-(2-ethyl-5-fluoro-4-hydroxyphenyl)-1H-pyrazolo[4,3-c]pyridin-4-yl](methyl)amino}methyl)phenyl]methanesulfonamide hydrochloride;
N-[2-({[6-(2-ethyl-5-fluoro-4-hydroxyphenyl)-1H-pyrazolo[4,3-c]pyridin-4-yl](methyl)amino}-methyl)phenyl]-N-methylmethanesulfonamide hydrochloride;
N-[2-({[6-(2-ethyl-5-fluoro-4-hydroxyphenyl)-1H-pyrazolo[4,3-c]pyridin-4-yl]amino}methyl)phenyl]-N-(2-hydroxyethyl)methanesulfonamide;
N-{2-[({6-[5-fluoro-4-hydroxy-2-(2,2,2-trifluoroethyl)phenyl]-1H-pyrazolo[4,3-c]pyridin-4-yl}amino)methyl]phenyl}-N-methylmethanesulfonamide;
N-(2-{[({6-[5-fluoro-4-hydroxy-2-(2,2,2-trifluoroethyl)phenyl]-1H-pyrazolo[4,3-c]pyridin-4-yl}(methyl)amino]methyl}phenyl)-N-methylmethanesulfonamide;
N-{2-[({6-[5-fluoro-4-hydroxy-2-(2,2,2-trifluoroethyl)phenyl]-1H-pyrazolo[4,3-c]pyridin-4-yl}amino)methyl]-4-methylphenyl}-N-methylmethanesulfonamide;
4-{4-[(cyclopropylmethyl)amino]-1H-pyrazolo[3,4-d]pyrimidin-6-yl}-2-fluoro-5-(2,2,2-trifluoroethyl)phenol;
4-{4-[(2-cyclopropylethyl)amino]-1H-pyrazolo[3,4-d]pyrimidin-6-yl}-2-fluoro-5-(2,2,2-trifluoroethyl)phenol;
2-fluoro-4-{4-[(2-methylpropyl)amino]-1H-pyrazolo[3,4-d]pyrimidin-6-yl}-5-(2,2,2-trifluoro-ethyl)phenol;
4-[4-(butylamino)-1H-pyrazolo[3,4-d]pyrimidin-6-yl]-2-fluoro-5-(2,2,2-trifluoroethyl)phenol;
N-[2-({[6-(2-ethyl-5-fluoro-4-hydroxyphenyl)-1H-pyrazolo[3,4-d]pyrimidin-4-yl]amino}methyl)-phenyl]-N-methyl-methanesulfonamide hydrochloride;
N-(2-(((6-(2-ethyl-4-hydroxy-6-methylphenyl)-1H-pyrazolo[4,3-c]pyridin-4-yl)amino)methyl)-phenyl)-N-methylmethanesulfonamide;
N-[2-({[6-(2-ethyl-5-fluoro-4-hydroxyphenyl)-3-(1H-imidazol-2-yl)-1H-pyrazolo[4,3-c]pyridin-4-yl]amino}methyl)phenyl]-N-methylmethanesulfonamide;
N-[2-({[3-(4,5-dimethyl-1H-imidazol-2-yl)-6-(2-ethyl-5-fluoro-4-hydroxyphenyl)-1H-pyrazolo[4,3-c]pyridin-4-yl]amino}methyl)phenyl]-N-methylmethanesulfonamide;

N-[2-({[6-(2-ethyl-5-fluoro-4-hydroxyphenyl)-3-(4-methyl-1H-imidazol-2-yl)-1H-pyrazolo[4,3-c]pyridin-4-yl]amino}methyl)phenyl]-N-methylmethanesulfonamide;

4-[3-(5-benzyl-4,5,6,7-tetrahydro-1H-imidazo[4,5-c]pyridin-2-yl)-4-{[2-(methylsulfanyl)ethyl]-amino}-1H-pyrazolo[4,3-c]pyridin-6-yl]-2-fluoro-5-(2,2,2-trifluoroethyl)phenol;

N-[2-({[6-(2-ethyl-5-fluoro-4-hydroxyphenyl)-3-(1H-pyrazol-1-yl)-1H-pyrazolo[4,3-c]pyridin-4-yl]amino}methyl)phenyl]-N-methylmethanesulfonamide;

N-{2-[({6-[5-fluoro-4-hydroxy-2-(2,2,2-trifluoroethyl)phenyl]-3-(1H-pyrazol-1-yl)-1H-pyrazolo[4,3-c]pyridin-4-yl}amino)methyl]phenyl}-N-methylmethanesulfonamide;

N-{2-[({6-[5-fluoro-4-hydroxy-2-(2,2,2-trifluoroethyl)phenyl]-3-(5-methyl-4H-1,2,4-triazol-3-yl)-1H-pyrazolo[4,3-c]pyridin-4-yl}amino)methyl]phenyl}-N-methylmethanesulfonamide;

N-[2-({[6-(2-ethyl-5-fluoro-4-hydroxyphenyl)-3-(5-methyl-4H-1,2,4-triazol-3-yl)-1H-pyrazolo[4,3-c]pyridin-4-yl]amino}methyl)phenyl]-N-methylmethanesulfonamide;

N-{2-[({6-[5-fluoro-4-hydroxy-2-(2,2,2-trifluoroethyl)phenyl]-3-[5-(6-methylpyridin-3-yl)-4H-1,2,4-triazol-3-yl]-1H-pyrazolo[4,3-c]pyridin-4-yl}amino)methyl]phenyl}-N-methylmethanesulfonamide;

4-(5-{6-[5-fluoro-4-hydroxy-2-(2,2,2-trifluoroethyl)phenyl]-4-({5-hydroxy-2-[methyl(methyl-sulfonyl)amino]benzyl}amino)-1H-pyrazolo[3,4-d]pyrimidin-3-yl)-4H-1,2,4-triazol-3-yl)piperidine-1-carboxamide;

N-(2-[(6-[5-fluoro-4-hydroxy-2-(2,2,2-trifluoroethyl)phenyl]-3-{5-[1-(pyrrolidin-1-ylacetyl)piperidin-4-yl]-4H-1,2,4-triazol-3-yl}-1H-pyrazolo[3,4-d]pyrimidin-4-yl)amino]methyl}phenyl)-N-methyl-methanesulfonamide;

N-{2-[({6-[5-fluoro-4-hydroxy-2-(2,2,2-trifluoroethyl)phenyl]-3-(4,5,6,7-tetrahydro-1H-imidazo[4,5-c]pyridin-2-yl)-1H-pyrazolo[3,4-d]pyrimidin-4-yl}amino)methyl]-4-hydroxyphenyl}-N-methylmethanesulfonamide;

N-{2-[({3-(5-acetyl-4,5,6,7-tetrahydro-1H-imidazo[4,5-c]pyridin-2-yl)-6-[5-fluoro-4-hydroxy-2-(2,2,2-trifluoroethyl)phenyl]-1H-pyrazolo[3,4-d]pyrimidin-4-yl}amino)methyl]-4-hydroxyphenyl}-N-methylmethanesulfonamide;

N-[2-(dimethylamino)ethyl]-2-{6-[5-fluoro-4-hydroxy-2-(2,2,2-trifluoroethyl)phenyl]-4-({5-hydroxy-2-[methyl(methylsulfonyl)amino]benzyl}amino)-1H-pyrazolo[3,4-d]pyrimidin-3-yl}-1,4,6,7-tetrahydro-5H-imidazo[4,5-c]pyridine-5-carboxamide; and, 4-(3-(5-benzyl-4,5,6,7-tetrahydro-1H-imidazo[4,5-c]pyridin-2-yl)-4-((3-hydroxy-2-methylpropyl)-amino)-1H-pyrazolo[3,4-d]pyrimidin-6-yl)-2-fluoro-5-(2,2,2-trifluoroethyl)phenol.

Preferred embodiments of the invention include:

4-({2-[(ethylsulfonyl)(methyl)amino]benzyl}amino)-6-[5-fluoro-4-hydroxy-2-(2,2,2-trifluoroethyl)phenyl]-1H-pyrazolo[4,3-c]pyridine-3-carboxamide;

4-({2-[ethyl(ethylsulfonyl)amino]benzyl}amino)-6-[5-fluoro-4-hydroxy-2-(2,2,2-trifluoroethyl)phenyl]-1H-pyrazolo[4,3-c]pyridine-3-carboxamide;

4-({2-[ethyl(methylsulfonyl)amino]-5-methylbenzyl}amino)-6-[5-fluoro-4-hydroxy-2-(2,2,2-trifluoroethyl)phenyl]-1H-pyrazolo[4,3-c]pyridine-3-carboxamide;

4-({2-[ethyl(methylsulfonyl)amino]-5-fluorobenzyl}amino)-6-[5-fluoro-4-hydroxy-2-(2,2,2-trifluoroethyl)phenyl]-1H-pyrazolo[4,3-c]pyridine-3-carboxamide;

4-({2-[ethyl(methylsulfonyl)amino]benzyl}amino)-6-[5-fluoro-4-hydroxy-2-(2,2,2-trifluoroethyl)phenyl]-1H-pyrazolo[4,3-c]pyridine-3-carboxamide;

4-({5-chloro-2-[ethyl(methylsulfonyl)amino]benzyl}amino)-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-N-methyl-4-({2-[methyl(methylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-4-({5-fluoro-2-[methyl(methylsulfonyl)amino]benzyl}amino)-N-methyl-1H-pyrazolo[4,3-c]pyridine-3-carboxamide;

6-[5-fluoro-4-hydroxy-2-(2,2,2-trifluoroethyl)phenyl]-4-({5-fluoro-2-[methyl(methylsulfonyl)amino]benzyl}amino)-1H-pyrazolo[4,3-c]pyridine-3-carboxamide; and, 6-[5-fluoro-4-hydroxy-2-(2,2,2-trifluoroethyl)phenyl]-4-({2-[methyl(methylsulfonyl)amino]benzyl}amino)-1H-pyrazolo[4,3-c]pyridine-3-carboxamide;

or, a pharmaceutically acceptable salt thereof.

More preferred embodiments of the invention include 4-({2-[(ethylsulfonyl)-(methyl)amino]benzyl}amino)-6-[5-fluoro-4-hydroxy-2-(2,2,2-trifluoroethyl)phenyl]-1H-pyrazolo[4,3-c]pyridine-3-carboxamide, 4-({2-[ethyl(ethylsulfonyl)amino]benzyl}amino)-6-[5-fluoro-4-hydroxy-2-(2,2,2-trifluoroethyl)phenyl]-1H-pyrazolo[4,3-c]pyridine-3-carboxamide, 6-[5-fluoro-4-hydroxy-2-(2,2,2-trifluoroethyl)phenyl]-4-({2-[methyl(methylsulfonyl)amino]benzyl}amino)-1H-pyrazolo[4,3-c]pyridine-3-carboxamide, 4-({2-[ethyl(methylsulfonyl)amino]-5-fluorobenzyl}amino)-6-[5-fluoro-4-hydroxy-2-(2,2,2-trifluoro-ethyl)phenyl]-1H-pyrazolo[4,3-c]pyridine-3-carboxamide, 4-({2-[ethyl(methylsulfonyl)amino]benzyl}amino)-6-[5-fluoro-4-hydroxy-2-(2,2,2-trifluoroethyl)phenyl]-1H-pyrazolo[4,3-c]pyridine-3-carboxamide, or a pharmaceutically acceptable salt thereof.

In other aspects, the invention provides a pharmaceutical composition comprising any pyrazolopyridine and pyrazolopyrimidine compound set forth herein, or a pharmaceutically acceptable salt thereof, or a pharmaceutically acceptable solvate of said compound or salt, and a pharmaceutically acceptable excipient.

The present invention also provides a method of treating a disease or condition for which a JAK inhibitor is indicated, in a subject in need of such treatment, comprising administering to the subject a therapeutically effective amount of any compound set forth herein, or a pharmaceutically acceptable salt thereof, or a pharmaceutically acceptable solvate of said compound or salt.

The present invention further provides a method of treating a disease or condition selected from allergic rhinitis, nasal congestion, rhinorrhea, perennial rhinitis, nasal inflammation, asthma of all types, chronic obstructive pulmonary disease, chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, pulmonary vascular disease, pulmonary arterial hypertension, acute lung injury, bronchiectasis, sinusitis, allergic conjunctivitis, idiopathic pulmonary fibrosis or atopic dermatitis, comprising administering to the subject a therapeutically effective amount of any compound set forth herein, or a pharmaceutically acceptable salt thereof, or a pharmaceutically acceptable solvate of said compound or salt.

The present invention also provides a method of treating chronic obstructive pulmonary disease, comprising administering to the subject a therapeutically effective amount of any compound set forth herein, or a pharmaceutically acceptable salt thereof, or a pharmaceutically acceptable solvate of said compound or salt.

The present invention also provides a method of treating a disease or condition selected from inflammation, neuroinflammation, arthritis, rheumatoid arthritis, spondyloarthropathies, systemic lupus erythematous arthritis, osteoarthritis, gouty arthritis, pain, fever, pulmonary sarcoisosis, silicosis, cardiovascular disease, atherosclerosis, myocardial infarction, thrombosis, congestive heart failure and cardiac reperfusion injury, cardiomyopathy, stroke, ischaemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, autoimmune disease, osteoporosis, multiple sclerosis, endometriosis, menstrual cramps, vaginitis, candidiasis, cancer, fibrosis, obesity, muscular dystrophy, polymyositis, Alzheimer's disease, skin flushing, eczema, psoriasis, atopic dermatitis and sunburn, comprising administering to the subject a therapeutically effective amount of any compound set forth herein, or a pharmaceutically acceptable salt thereof, or a pharmaceutically acceptable solvate of said compound or salt.

The disease or condition for which a JAK inhibitor is indicated is preferably an allergic or respiratory condition such as allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, pulmonary vascular disease (including pulmonary arterial hypertension), acute lung injury, bronchiectasis, sinusitis, allergic conjunctivitis, idiopathic pulmonary fibrosis or atopic dermatitis, particularly asthma or chronic obstructive pulmonary disease, most particularly chronic obstructive pulmonary disease.

Other diseases and conditions of interest are inflammation (including neuroinflammation), arthritis (including rheumatoid arthritis, spondyloarthropathies, systemic lupus erythematous arthritis, osteoarthritis and gouty arthritis), pain, fever, pulmonary sarcoisosis, silicosis, cardiovascular disease (including atherosclerosis, myocardial infarction, thrombosis, congestive heart failure and cardiac reperfusion injury), cardiomyopathy, stroke, ischaemia, reperfusion injury, brain edema, brain trauma, neurodegeneration, liver disease, inflammatory bowel disease (including Crohn's disease and ulcerative colitis), nephritis, retinitis, retinopathy, macular degeneration, glaucoma, diabetes (including type 1 and type 2 diabetes), diabetic neuropathy, viral and bacterial infection, myalgia, endotoxic shock, toxic shock syndrome, autoimmune disease, osteoporosis, multiple sclerosis, endometriosis, menstrual cramps, vaginitis, candidiasis, cancer, fibrosis, obesity, muscular dystrophy, polymyositis, Alzheimer's disease, skin flushing, eczema, psoriasis, atopic dermatitis and sunburn.

Types of asthma include atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

The treatment of asthma includes palliative treatment for the symptoms and conditions of asthma such as wheezing, coughing, shortness of breath, tightness in the chest, shallow or fast breathing, nasal flaring (nostril size increases with breathing), retractions (neck area and between or below the ribs moves inward with breathing), cyanosis (gray or bluish tint to skin, beginning around the mouth), runny or stuffy nose, and headache.

The present invention also provides any of the uses, methods or compositions as defined above wherein the compound of formula (I)-(Ii), or pharmaceutically acceptable salt thereof, or pharmaceutically acceptable solvate of said compound or salt, is used in combination with another pharmacologically active compound, particularly one of the functionally-defined classes or specific compounds listed below. Generally, the compounds of the combination will be administered together as a formulation in association with one or more pharmaceutically acceptable excipients.

Suitable agents for use in combination therapy with a compound of formula (I)-(Ii), or pharmaceutically acceptable salt thereof, or pharmaceutically acceptable solvate of said compound or salt, particularly in the treatment of respiratory disease, include: a 5-lipoxygenase activating protein (FLAP) antagonist; a leukotriene antagonist (LTRA) such as an antagonist of $LTB_4$, $LTC_4$, $LTD_4$, $LTE_4$, $CysLT_1$ or $CysLT_2$, e.g. montelukast or zafirlukast; a histamine receptor antagonist, such as a histamine type 1 receptor antagonist or a histamine type 2 receptor antagonist, e.g. loratidine, fexofenadine, desloratidine, levocetirizine, methapyrilene or cetirizine; an al-adrenoceptor agonist or an α2-adrenoceptor agonist, e.g. phenylephrine, methoxamine, oxymetazoline or methylnorephrine; a muscarinic M3 receptor antagonist, e.g. tiotropium or ipratropium; a dual muscarinic M3 receptor antagononist/132 agonist; a PDE inhibitor, such as a PDE3 inhibitor, a PDE4 inhibitor or a PDE5 inhibitor, e.g. theophylline, sildenafil, vardenafil, tadalafil, ibudilast, cilomilast or roflumilast; sodium cromoglycate or sodium nedocromil; a cyclooxygenase (COX) inhibitor, such as a non-selective inhibitor (e.g. aspirin or ibuprofen) or a selective inhibitor (e.g. celecoxib or valdecoxib); a glucocorticosteroid, e.g. fluticasone, mometasone, dexamethasone, prednisolone, budesonide, ciclesonide or beclamethasone; an anti-inflammatory monoclonal antibody, e.g. infliximab, adalimumab, tanezumab, ranibizumab, bevacizumab or mepolizumab; a 02 agonist, e.g. salmeterol, albuterol, salbutamol, fenoterol or formoterol, particularly a long-acting β2 agonist; an intigrin antagonist, e.g. natalizumab; an adhesion molecule inhibitor, such as a VLA-4 antagonist; a kinin $B_1$ or $B_2$ receptor antagonist; an immunosuppressive agent, such as an inhibitor of the IgE pathway (e.g. omalizumab) or cyclosporine; a matrix metalloprotease (MMP) inhibitor, such as an inhibitor of MMP-9 or MMP-12; a tachykinin $NK_1$, $NK_2$ or $NK_3$ receptor antagonist; a protease inhibitor, such as an inhibitor of elastase, chymase or catheopsin G; an adenosine A28 receptor agonist; an adenosine A2b receptor antagonist; a urokinase inhibitor; a dopamine receptor agonist (e.g. ropinirole), particularly a dopamine D2 receptor agonist (e.g., bromocriptine); a modulator of the NFκB pathway, such as an IKK inhibitor; a further modulator of a cytokine signalling pathway such as an inhibitor of JAK kinase, syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g. Zileuton; an adhesion factor, such as VLAM, ICAM or ELAM; a CRTH2 receptor ($DP_2$) antagonist; a prostaglandin $D_2$ receptor ($DP_1$) antagonist; a haematopoietic prostaglandin D2 synthase (HPGDS) inhibitor; interferon-β; a soluble human TNF receptor, e.g. Etanercept; a HDAC inhibitor; a phosphoinositotide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; and, a TLR-4 or TLR-9 inhibitor, including the pharmaceutically acceptable salts of the specifically named compounds and the pharmaceutically acceptable solvates of said specifically named compounds and salts.

Besides being useful for human treatment, compounds of formula (I)-(Ii) are also useful for veterinary treatment of companion animals, exotic animals and farm animals.

DETAILED DESCRIPTION OF THE INVENTION

Unless otherwise defined herein, scientific and technical terms used in connection with the present invention have the meanings that are commonly understood by those of ordinary skill in the art.

The phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect palliative, supportive, restorative or curative treatment. The term treatment encompasses any objective or subjective improvement in a subject with respect to a relevant condition or disease.

The term "palliative treatment," as used herein to describe the present invention, means that the compound, pharmaceutical composition or combination is administered to a subject to remedy signs and/or symptoms of a condition, without necessarily modifying the progression of, or underlying etiology of, the relevant condition.

The term "supportive treatment," as used herein to describe the present invention, means that the compound, pharmaceutical composition or combination is administered to a subject as a part of a regimen of therapy, but that such therapy is not limited to administration of the compound, pharmaceutical composition or combination. Unless otherwise expressly stated, supportive treatment may embrace preventive, palliative, restorative or curative treatment, particularly when the compounds or pharmaceutical compositions are combined with another component of supportive therapy.

The term "restorative treatment," as used herein to describe the present invention, means that the compound, pharmaceutical composition or combination is administered to a subject to modify the underlying progression or etiology of a condition. Non-limiting examples include an increase in forced expiratory volume in one second (FEV 1) for lung disorders, decreased rate of a decline in lung function over time, inhibition of progressive nerve destruction, reduction of biomarkers associated and correlated with diseases or disorders, a reduction in relapses, improvement in quality of life, reduced time spent in hospital during an acute exacerbation event and the like.

The term "curative treatment," as used herein to describe the present invention, means that compound, pharmaceutical composition or combination is administered to a subject for the purpose of bringing the disease or disorder into complete remission, or that the disease or disorder is undetectable after such treatment.

The term "selective", when used to describe a functionally-defined receptor ligand or enzyme inhibitor means selective for the defined receptor or enzyme subtype as compared with other receptor or enzyme subtypes in the same family. For instance, a selective PDE5 inhibitor is a compound which inhibits the PDE5 enzyme subtype more potently than any other PDE enzyme subtype. Such selectivity is preferably at least 2 fold (as measured using conventional binding assays), more preferably at least 10 fold, most preferably at least 100 fold.

The term "alkyl", alone or in combination, means an acyclic, saturated hydrocarbon group of the formula $C_nH_{2+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms.

The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH radical.

$Het^3$ is a saturated or partially saturated (i.e. non aromatic) heterocycle and may be attached via a ring nitrogen atom (when the heterocycle is attached to a carbon atom) or a ring carbon atom (in all cases). Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

$Het^3$ may be fully saturated or partially unsaturated, i.e. may have one or more degrees of unsaturation but may not be fully aromatic.

$Het^1$ is an aromatic heterocycle and may be attached via a ring carbon atom (in all cases) or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). Specific examples include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl.

$Het^2$ is an aromatic heterocycle and may be attached via a ring carbon atom (in all cases) or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). $Het^2$ is aromatic and is therefore necessarily a fused bicycle. Specific examples include imidazo[2,1-b][1,3]thiazolyl, benzofuranyl, benzothienyl, indolyl, benzimidazolyl, indazolyl, benzotriazolyl, pyrrolo[2,3-b]pyridyl, pyrrolo[2,3-c]pyridyl, pyrrolo[3,2-c]pyridyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridyl, pyrazolo[3,4-b]pyridyl, isoindolyl, indazolyl, purinyl, indolizinyl, imidazo[1,2-a]pyridyl, imidazo[1,5-a]pyridyl, pyrazolo[1,5-a]pyridyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-d]pyrazinyl, pyrido[3,4-b]pyrazinyl, pyrimido[5,4-d]pyrimidinyl, pyrazino[2,3-b]pyrazinyl and pyrimido[4,5-d]pyrimidine.

The term "cycloalkyl" means a means a monocyclic, saturated hydrocarbon group of the formula $C_nH_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The term "oxo" means a doubly bonded oxygen. The term "alkoxy" means a radical comprising an alkyl radical that is bonded to an oxygen atom, such as a methoxy radical. Examples of such radicals include methoxy, ethoxy, propoxy, isopropoxy, butoxy and tert-butoxy. The term "halo" means, fluoro, chloro, bromo or iodo.

As used herein, the terms "co-administration", "co-administered" and "in combination with", referring to a combination of a compound of formula (I)-(Ii) and one or more other therapeutic agents, includes the following:
  simultaneous administration of such a combination of a compound of formula (I)-(Ii) and a further therapeutic agent to a patient in need of treatment, when such components are formulated together into a single dosage form which releases said components at substantially the same time to said patient,
  substantially simultaneous administration of such a combination of a compound of formula (I)-(Ii) and a further therapeutic agent to a patient in need of treatment, when such components are formulated apart from each other into separate dosage forms which are taken at substantially the same time by said patient, whereupon said components are released at substantially the same time to said patient,
  sequential administration of such a combination of a compound of formula (I)-(Ii) and a further therapeutic agent to a patient in need of treatment, when such components are formulated apart from each other into separate dosage forms which are taken at consecutive times by said patient with a significant time interval between each administration, whereupon said components are released at substantially different times to said patient; and
  sequential administration of such a combination of a compound of formula (I)-(Ii) and a further therapeutic agent to a patient in need of treatment, when such components are formulated together into a single dosage form which releases said components in a controlled manner.

The term 'excipient' is used herein to describe any ingredient other than a compound of formula (I)-(Ii). The choice of excipient will to a large extent depend on factors such as the particular mode of administration, the effect of the excipient on solubility and stability, and the nature of the dosage form. The term "excipient" encompasses diluent, carrier or adjuvant.

One way of carrying out the invention is to administer a compound of formula (I)-(Ii) in the form of a prodrug. Thus, certain derivatives of a compound of formula (I)-(Ii) which may have little or no pharmacological activity themselves can, when administered into or onto the body, be converted into a compound of formula (I)-(Ii) having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Pro-drugs as Novel Delivery Systems', Vol. 14, ACS Symposium Series (T. Higuchi and W. Stella) and 'Bioreversible Carriers in Drug Design', Pergamon Press, 1987 (Ed. E. B. Roche, American Pharmaceutical Association). Reference can also be made to Nature Reviews/Drug Discovery, 2008, 7, 355 and Current Opinion in Drug Discovery and Development, 2007, 10, 550.

Prodrugs in accordance with the invention can, for example, be produced by replacing appropriate functionalities present in the compounds of formula (I)-(Ii) with certain moieties known to those skilled in the art as 'promoieties' as described, for example, in 'Design of Prodrugs' by H. Bundgaard (Elsevier, 1985).

Thus, a prodrug in accordance with the invention is (a) an ester or amide derivative of a carboxylic acid in a compound of formula (I)-(Ii); (b) an ester, carbonate, carbamate, phosphate or ether derivative of a hydroxyl group in a compound of formula (I)-(Ii); (c) an amide, imine, carbamate or amine derivative of an amino group in a compound form formula (I)-(Ii); (d) a thioester, thiocarbonate, thiocarbamate or sulphide derivatives of a thiol group in a compound of formula (I)-(Ii); or (e) an oxime or imine derivative of a carbonyl group in a compound of formula (I)-(Ii).

Some specific examples of prodrugs in accordance with the invention include:
  (i) where a compound of formula (I)-(Ii) contains a carboxylic acid functionality
  (—COOH), an ester thereof, such as a compound wherein the hydrogen of the carboxylic acid functionality of the compound of formula (I)-(Ii) is replaced by $C_1$-$C_8$ alkyl (e.g. ethyl) or ($C_1$-$C_8$ alkyl)C(=O)OCH$_2$— (e.g. $^tBuC$(=O)OCH$_2$—);
  (ii) where a compound of formula (I)-(Ii) contains an alcohol functionality (—OH), an ester thereof, such as a compound wherein the hydrogen of the alcohol functionality of the compound of formula (I)-(Ii) is replaced by —CO($C_1$-$C_8$ alkyl) (e.g. methylcarbonyl) or the alcohol is esterified with an amino acid;
  (iii) where a compound of formula (I)-(Ii) contains an alcohol functionality (—OH), an ether thereof, such as a compound wherein the hydrogen of the alcohol functionality of the compound of formula (I)-(Ii) is replaced by ($C_1$-$C_8$ alkyl)C(=O)OCH$_2$— or —CH$_2$OP(=O)(OH)$_2$;
  (iv) where a compound of formula (I)-(Ii) contains an alcohol functionality (—OH), a phosphate thereof, such as a compound wherein the hydrogen of the alcohol functionality of the compound of formula (I)-(Ii) is replaced by —P(=O)(OH)$_2$ or —P(=O)(ONa)$_2$ or —P(=O)(O)$_2$Ca$^{2+}$;
  (v) where a compound of formula (I)-(Ii) contains a primary or secondary amino functionality (—NH$_2$ or —NHR where R≠H), an amide thereof, for example, a compound wherein, as the case may be, one or both hydrogens of the amino functionality of the compound of formula (I)-(Ii) is/are replaced by $(C_1-C_{10})$alkanoyl, —$COCH_2NH_2$ or the amino group is derivatised with an amino acid;

(vi) where a compound of formula (I)-(Ii) contains a primary or secondary amino functionality (—$NH_2$ or —NHR where R≠H), an amine thereof, for example, a compound wherein, as the case may be, one or both hydrogens of the amino functionality of the compound of formula (I)-(Ii) is/are replaced by —$CH_2OP(=O)(OH)_2$.

Certain compounds of formula (I)-(Ii) may themselves act as prodrugs of other compounds of formula (I)-(Ii). It is also possible for two compounds of formula (I)-(Ii) to be joined together in the form of a prodrug. In certain circumstances, a prodrug of a compound of formula (I)-(Ii) may be created by internally linking two functional groups in a compound of formula (I)-(Ii), for instance by forming a lactone.

References below to compounds of formula (I)-(Ii) are taken to include the compounds themselves and prodrugs thereof. The invention includes such compounds of formula (I)-(Ii) as well as pharmaceutically acceptable salts of such compounds and pharmaceutically acceptable solvates of said compounds and salts. Pharmaceutically acceptable salts of the compounds of formula (I)-(Ii) include acid addition and base salts.

Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, naphatlene-1,5-disulfonic acid and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of formula (I)-(Ii) may be prepared by one or more of three methods:

(i) by reacting a compound of formula (I)-(Ii) with the desired acid or base;

(ii) by removing an acid- or base-labile protecting group from a suitable precursor of a compound of formula (I)-(Ii) or by ring-opening a suitable cyclic precursor, for example, a lactone or lactam, using the desired acid or base; or (iii) by converting one salt of the compound of formula (I)-(Ii) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I)-(Ii), and pharmaceutically acceptable salts thereof, may exist in unsolvated and solvated forms. The term 'solvate' is used herein to describe a molecular complex comprising the compound of formula (I)-(Ii), or a pharmaceutically acceptable salt thereof, and one or more pharmaceutically acceptable solvent molecules, for example, ethanol. The term 'hydrate' may be employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. Cf. Chem. Commun., 17, 1889-1896, by O. Almarsson and M. J. Zaworotko (2004). For a general review of multi-component complexes, see J. Pharm. Sci., 64 (8), 1269-1288, by Haleblian (1975).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of formula (I)-(Ii) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$N$^+$) or non-ionic (such as —N$^-$N$^+$(CH$_3$)$_3$) polar head group. For more information, see *Crystals and the Polarizina Microscope* by N. H. Hartshome and A. Stuart, 4$^{th}$ Edition (Edward Arnold, 1970).

Hereinafter all references to compounds of formula (I)-(Ii) include references to pharmaceutically acceptable salts, solvates, multi-component complexes and liquid crystals thereof and to solvates, multi-component complexes and liquid crystals of pharmaceutically acceptable salts thereof.

The compounds of formula (I)-(Ii) may exhibit polymorphism and/or one or more kinds of isomerism (e.g. optical, geometric or tautomeric isomerism). The compounds of formula (I)-(Ii) may also be isotopically labelled. Such variation is implicit to the compounds of formula (I)-(Ii) defined as they are by reference to their structural features and therefore within the scope of the invention.

Compounds of formula (I)-(Ii) containing one or more asymmetric carbon atoms can exist as two or more stereoisomers. Where a compound of formula (I)-(Ii) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I)-(Ii) containing, for example, an imino, keto, or oxime group, or so-called valence tautomerism in compounds which contain an aromatic moiety. It follows that a single compound may exhibit more than one type of isomerism.

The pharmaceutically acceptable salts of compounds of formula (I)-(Ii) may also contain a counterion which is optically active (e.g. d-lactate or l-lysine) or racemic (e.g. dl-tartrate or dl-arginine).

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of formula (I)-(Ii) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of formula (I)-(Ii) (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). In some relevant examples herein, columns were obtained from Chiral Technologies, Inc, West Chester, Pa., USA, a subsidiary of Daicel® Chemical Industries, Ltd., Tokyo, Japan.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art. See, for example, *Stereochemistry of Organic Compounds* by E. L. Eliel and S. H. Wilen (Wiley, 1994).

The present invention includes all pharmaceutically acceptable isotopically-labelled compounds of formula (I)-(Ii) wherein one or more atoms are replaced by atoms having the same atomic number, but an atomic mass or mass number different from the atomic mass or mass number which predominates in nature. Isotopically-labelled compounds of formula (I)-(Ii) can generally be prepared by conventional techniques known to those skilled in the art or by processes analogous to those described in the accompanying Examples and Preparations using an appropriate isotopically-labelled reagent in place of the non-labelled reagent previously employed. In particular, hydrogen atoms may be replaced by deuterium atoms since such deuterated compounds are sometimes more resistant to metabolism.

Also included within the scope of the invention are active metabolites of compounds of formula (I)-(Ii), that is, compounds formed in vivo upon administration of the drug, often by oxidation or dealkylation. Some examples of metabolites in accordance with the invention include (i) where a compound of formula (I)-(Ii) contains a methyl group, an hydroxymethyl derivative thereof (—CH$_3$→—CH$_2$OH):

(ii) where a compound of formula (I)-(Ii) contains an alkoxy group, an hydroxy derivative thereof (—OR→—OH);

(iii) where a compound of formula (I)-(Ii) contains a tertiary amino group, a secondary amino derivative thereof (—NRR'→—NHR or —NHR');

(iv) where a compound of formula (I)-(Ii) contains a secondary amino group, a primary derivative thereof (—NHR→—NH$_2$);

(v) where a compound of formula (I)-(Ii) contains a phenyl moiety, a phenol derivative thereof (-Ph→-PhOH); and (vi) where a compound of formula (I)-(Ii) contains an amide group, a carboxylic acid derivative thereof (—CONH$_2$→COOH).

For administration to human patients, the total daily dose of a compound of formula (I)-(Ii) is typically in the range of 0.01 mg to 500 mg depending, of course, on the mode of administration. In another embodiment of the present invention, the total daily dose of a compound of formula (I)-(Ii) is typically in the range of 0.1 mg to 300 mg. In yet another embodiment of the present invention, the total daily dose of a compound of formula (I)-(Ii) is typically in the range of 1 mg to 30 mg. The total daily dose may be administered in single or divided doses and may, at the physician's discretion, fall outside of the typical range given herein. These dosages are based on an average human subject having a weight of about 65 kg to 70 kg. The physician will readily be able to determine doses for subjects whose weight falls outside this range, such as infants and the elderly.

In the case of dry powder inhalers and aerosols, the dosage unit is determined by means of a prefilled capsule, blister or pocket or by a system that utilises a gravimetrically fed dosing chamber. Units in accordance with the invention are typically arranged to administer a metered dose or "puff" containing from 1 to 5000 µg of drug. The overall daily dose will typically be in the range 1 µg to 20 mg which may be administered in a single dose or, more usually, as divided doses throughout the day.

A compound of formula (I)-(Ii) can be administered per se, or in the form of a pharmaceutical composition, which, as active constituent contains an efficacious dose of at least one compound of the invention, in addition to customary pharmaceutically innocuous excipients and/or additives.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Compounds of formula (I)-(Ii) may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of formula (I)-(Ii) may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %. In one embodiment of the present invention, lubricants comprise from 0.5 weight % to 3 weight % of the tablet. Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I)-(Ii), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO-A-00/35298.

Compounds of formula (I)-(Ii) may also be administered directly into the blood stream, into muscle, or into an internal organ. Such parenteral administration includes intravenous, intraarterial, intraperitoneal, intrathecal, intraventricular, intraurethral, intrasternal, intracranial, intramuscular, intra-articular and subcutaneous administration. Suitable devices for parenteral administration include needle (including microneedle) injectors, needle-free injectors and infusion techniques.

Compounds of the invention may also be administered topically to the skin or mucosa, that is, dermally or transdermally.

The compounds of formula (I)-(Ii) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin. Delivery by inhalation is the preferred route of administration for the compounds of the present invention.

The pressurised container, pump, spray, atomizer, or nebuliser contains a solution or suspension of the compound of formula (I)-(Ii) comprising, for example, ethanol, aqueous ethanol, or a suitable alternative agent for dispersing, solubilising, or extending release of the compound, a propellant as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 1001 µl. A typical formulation may comprise a compound of formula (I)-(Ii), propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of formula (I)-(Ii) may also be administered directly to the eye or ear, typically in the form of drops of a micronised suspension or solution in isotonic, pH-adjusted, sterile saline.

Compounds of formula (I)-(Ii) may be combined with soluble macromolecular entities, such as cyclodextrin and suitable derivatives thereof or polyethylene glycol-containing polymers, in order to improve their solubility, dissolution rate, taste, bioavailability and/or stability when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in international patent publications WO91/11172, WO94/02518 and WO98/55148.

Inasmuch as it may desirable to administer a combination of active compounds, for example, for the purpose of treating a particular disease or condition, it is within the scope of the present invention that two or more pharmaceutical compositions, at least one of which contains a compound of formula (I)-(Ii), may conveniently be combined in the form of a kit suitable for coadministration of the compositions. Thus, a kit of the invention comprises two or more separate pharmaceutical compositions, at least one of which contains a compound of formula (I)-(Ii), and means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by processes similar to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I)-(Ii). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the derivatives of the formula (I)-(Ii) can be prepared by the procedures described in the general methods presented below or by routine modifications thereof. The present invention also encompasses any one or more of these processes for preparing the derivatives of formula (I)-(Ii), in addition to any novel intermediates used therein. The person skilled in the art will appreciate that the following reactions may be heated thermally or under microwave irradiation.

According to a first process, compounds of formula (I) may be prepared from compounds of formula (IX) and (VIII), as illustrated by Scheme 1.

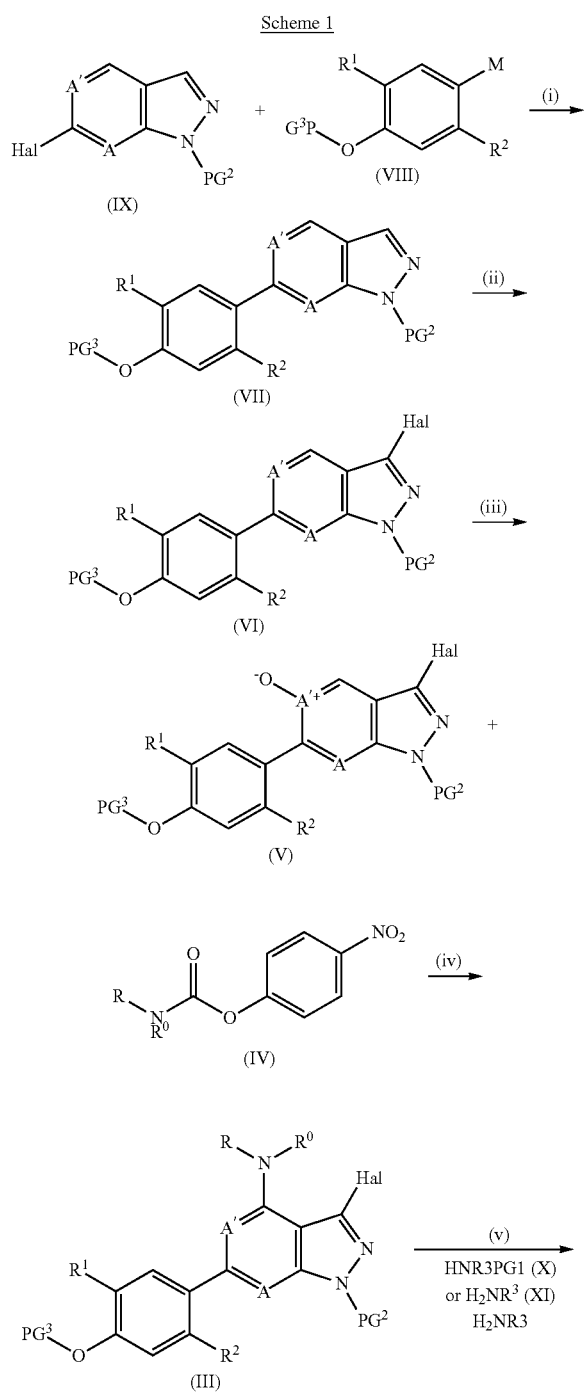

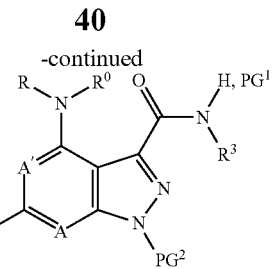

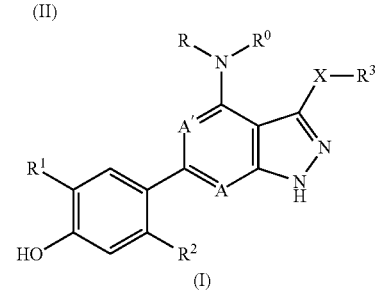

Wherein X is —CONH—; Hal is Cl, Br or iodo; M is boronic acid or boranate ester; PG¹ is tert-butyl, 2,4-dimethoxybenzyl; PG² is silylethoxymethyl, tetrahydropyranyl; PG³ is silylethoxymethyl, benzyl, or methyl.

It may be necessary or desirable to interchange the protecting groups in this Scheme to provide the highest yielding transformations.

Compounds of formulae (X), (IX), (VIII) and (IV) are commercially available or may be synthesized by those skilled in the art according to the literature or preparations described herein.

Compounds of formula (I)-(II) may be prepared from compounds of formula (II) according to process step (vi), a deprotection step mediated by either an organic acid, a Lewis acid or hydrogenation, or a sequential combination of each required. Preferred conditions comprise TFA and/or boron tribromide in a suitable organic solvent such as DCM or neat, at room or elevated temperatures and/or hydrogenation using a suitable catalyst such as 10% Pd/C in an organic solvent such as EtOH at room temperature.

Wherein compounds of formula (I)-(II) are racemic, chiral separation may be employed to afford the two enantiomers. Wherein compounds of formula (I) include an R group that contains oxooxazolidine, this may be reacted with a suitable organic base to effect an open chain R group. Preferred conditions comprise sodium hydroxide at from 0° C. to room temperature for 18 hours.

Compounds of formula (II) may be prepared from compounds of formula (III) according to process step (v), a carbonylation step in the presence of a suitable amine of formula (X) or (XI), a suitable palladium catalyst, and an organic base and a suitable solvent heated either in a sealed tube or under microwave irradiation. Typical conditions comprise molybdenum hexacarbonyl with DBU and palladium acetate heated to 100° C. either thermally for 45 minutes or under microwave irradiation for 10 minutes in the presence of a compound of formula (X) or (XI), such as methylamine or 88% ammonia in a suitable organic solvent such as THF. Alternatively carbon monoxide gas (typically at 1-100 atmospheres) can be used in place of molybdenum hexacarbonyl in the carbonylation step.

Compounds of formula (III) may be prepared from compounds of formula (IV) and (V) according to process step (iv), an N-oxide rearrangement step with compounds of formula (IV) and an organic base in a suitable organic solvent at elevated temperatures. Preferred conditions comprise triethylamine in DMF at elevated temperatures of between 80-100° C. for 18 hours.

Compounds of formula (V) may be prepared from compounds of formula (VI) according to process step (iii), an oxidation reaction. Preferred conditions comprise mCPBA in DCM at 0° C. for 18 hours. Compounds of formula (VI) may be prepared from compounds of formula (VII) according to process step (ii), an electrophilic halogenation reaction. Typically, compounds (VII) have the PG² protecting group removed by methods known to those skilled in the art prior to electrophilic halogenation. Preferred conditions comprise N-iodosuccinimide in DMF at from 0° C. to room temperature for 18 hours followed by subsequent reprotection with PG².

Compounds of formula (VII) may be prepared from compounds of formula (IX) and (VIII) according to process step (i), a Suzuki cross-coupling reaction with compounds of formula (V). Suzuki cross-coupling is conveniently effected in the presence of a suitable catalyst, e.g., palladium or nickel and a base. Typical conditions comprise a boronic acid or ester, a palladium catalyst with phosphine ligands in an organic solvent at elevated temperatures. Preferred Suzuki conditions comprise palladium acetate with phosphine ligand S-Phos, and potassium phosphate in ethanol at 80° C. for 18 hours.

According to a second process, compounds of formula (I) may be prepared from compounds of formula (VI) as illustrated by Scheme 2.

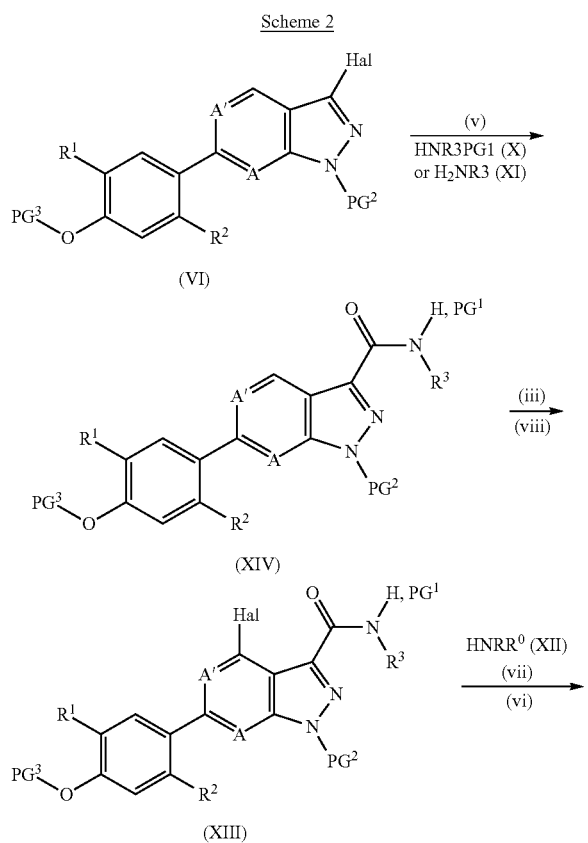

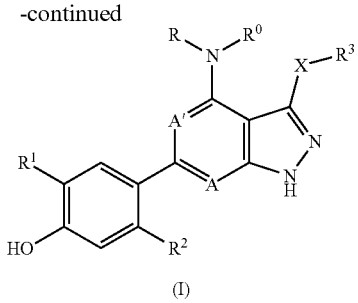

Wherein X is —CONH—; Hal is Cl, Br or I, PG¹ is tert-butyl, 2,4-dimethoxybenzyl; PG² is silylethoxymethyl, tetrahydropyranyl; PG³ is silylethoxymethyl, benzyl, or methyl.

Compounds of formulae (XII) are commercially available or may be synthesized by those skilled in the art according to the literature or preparations described herein. Compounds of formula (VI) are described in Scheme 1.

Compounds of formula (I) may be prepared from compounds of formula (XIII) according to process steps (vii) and (vi), a nucleophilic aromatic substitution reaction with compounds of formula (XII) followed by a deprotection step. Typical conditions comprise heating to 90° C. with compounds of formula (XII) in a suitable organic solvent with a suitable organic base, followed by deprotection as described in Scheme 1. Preferred conditions comprise DIPEA in n-butanol at 90° C. for 18 hours or triethylamine in DMF at 80-100° C. for 6 hours followed by TFA in DCM followed by boron tribromide in DCM. Alternatively compounds of formula (I) may be prepared from compounds of formula (XIII) and formula (XII) using a cross coupling reaction followed by deprotection if required. Typical conditions comprise a suitable metal catalyst in the presence of an inorganic base with an organic ligand. Preferred conditions comprise Pd₂(dba)₃ with BINAP and cesium carbonate in toluene at elevated temperatures of 80-140° C. either thermally or under microwave irradiation.

Compounds of formula (XIII) may be prepared from compounds of formula (XIV) according to process steps (iii) and (viii), an oxidation reaction followed by an N-oxide rearrangement-halogenation reaction. Typical conditions comprise oxidation as described in Scheme 1 process step (iii) followed by stirring the N-oxide in a suitable organic solvent at temperatures of 0-10° C. with electrophilic halogenating reagents. Preferred conditions comprise mCPBA in DCM followed by either POCl₃ or oxalyl chloride in DCM. Compounds of formula (XIV) may be prepared from compounds of formula (VI) and either (X) or (XI) according to process step (v) as described in Scheme 1.

According to a third process, compounds of formula (I) may be prepared from compounds of formula (III) as illustrated by Scheme 3.

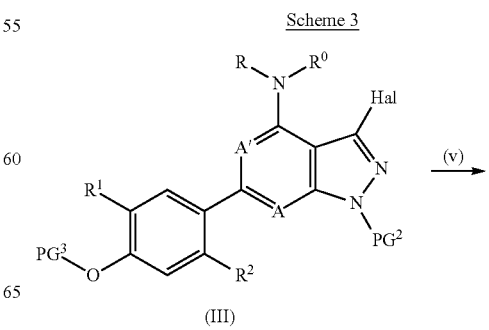

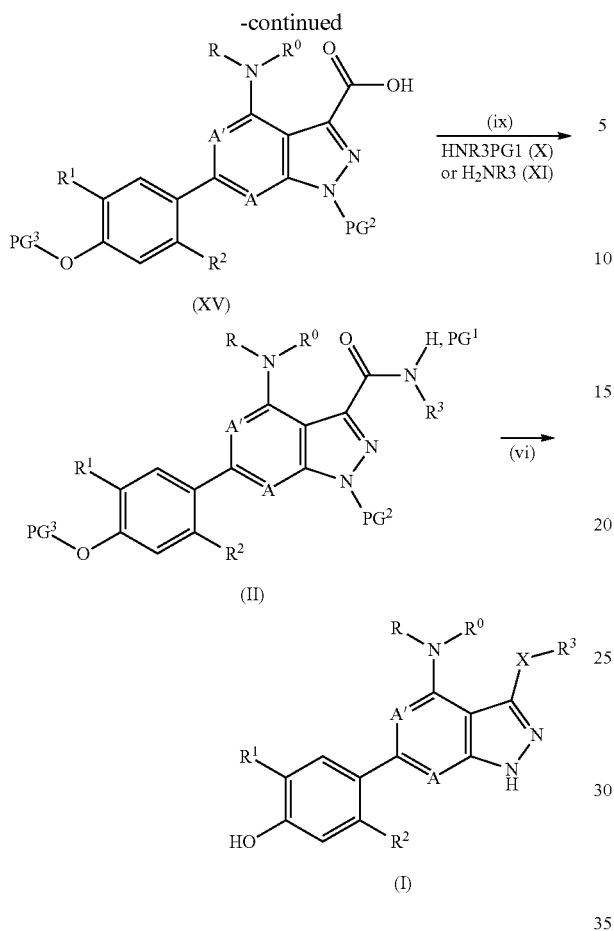

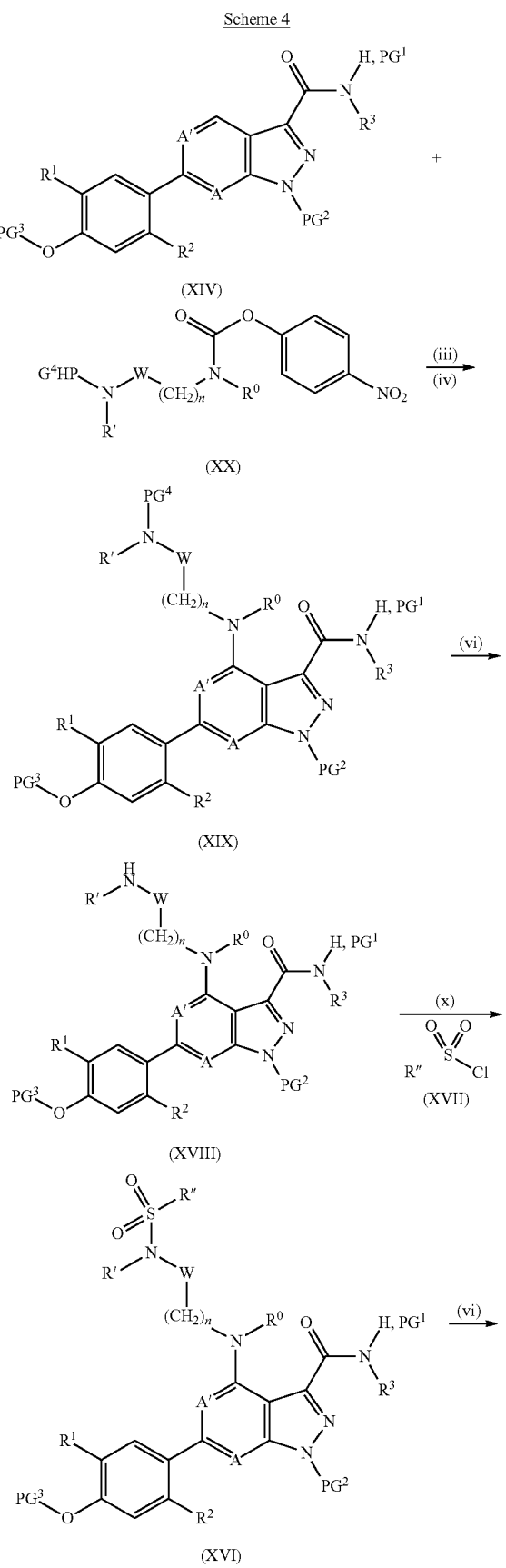

Scheme 4

Wherein X is —CONH—; Hal is Cl, Br or I; PG$^1$ is tert-butyl, 2,4-dimethoxybenzyl; PG$^2$ is silylethoxymethyl, tetrahydropyranyl; PG$^3$ is silylethoxymethyl, benzyl, or methyl.

Compounds of formulae (XI) and (XI) are commercially available or may be synthesized by those skilled in the art according to the literature or preparations described herein. Compounds of formula (III) are described in Scheme 1. Compounds of formula (I) may be prepared from compounds of formula (II) according to process step (vi) as described in Scheme 1. Compounds of formula (II) may be prepared from compounds of formula (XV) according to process step (ix), an amide bond formation reaction with compounds of formula (X) or (XI) with activation of the carboxylic acid via a mixed anhydride or using a suitable base such as DIPEA and a suitable coupling agent such as HATU, BOP. Preferred conditions comprise isobutyl chloroformate in THF with NMM or BOP or HATU in DMF with DIPEA as base.

Process step (vi) may be performed before process step (ix) to obtain compounds of formula (I) in Scheme 3.

Compounds of formula (XV) may be prepared from compounds of formula (III) according to process step (v) as described in Scheme 1 but in the absence of compounds of formula (X) and (XI) in a solvent such as methanol with water added if necessary.

According to a fourth process, compounds of formula (I) may be prepared from compounds of formula (XX) and (XIV) as illustrated by Scheme 4.

-continued

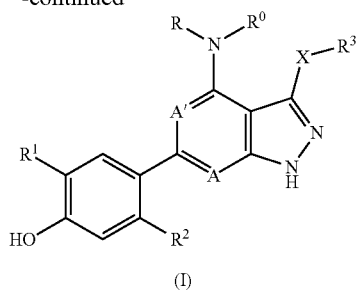

(I)

Wherein X is —CONH—; Hal is Cl, Br or I; PG¹ is tert-butyl, 2,4-dimethoxybenzyl; PG² is silylethoxymethyl, tetrahydropyranyl; PG³ is silylethoxymethyl, benzyl, or methyl; PG⁴ is carboxybenzyl.

Compounds of formulae (XVII), (X) and (XI) are commercially available or may be synthesized by those skilled in the art according to the literature or preparations described herein. Compounds of formula (XIV) are described in Scheme 2. Compounds of formula (XXI) are described in Scheme 5. Compounds of formula (I) may be prepared from compounds of formula (XVI) according to process step (vi) as described in Scheme 1.

Compounds of formula (XVI) may be prepared from compounds of formula (XVII) and (XVIII) according to process step (ix), a sulfonamide formation step. Preferred conditions comprise reacting compounds of formula (XVII) with compounds of formula (XVIII) in a suitable organic solvent such as THF at from 0° C. to room temperature for 18 hours. Alternatively a base may be added to facilitate the reaction such as sodium hydride. Compounds of formula (XVIII) may be prepared from compounds of formula (XIX) according to process step (vi) a deprotection reaction as described in Scheme 1. Preferred conditions comprise palladium on carbon in ethanol at room temperature under hydrogenation at 30 psi for 1 hour.

Compounds of formula (XIX) may be prepared from compounds of formula (XIV) according to process steps (iii) and (iv), an oxidation of compounds of formula (XIV) followed by a rearrangement step with compounds of formula (XX) as described in Scheme 1.

According to a fifth process, compounds of formula (IV) may be prepared from compounds of formula (XXIV) as illustrated by Scheme 5.

Compounds of formulae (XXIV), (XVII) and (XXVI) are commercially available or may be synthesized by those skilled in the art according to the literature or preparations described herein. Compounds of formula (IV) may be prepared from compounds of formula (XXI) according to process step (xv), a reaction to form a carbamate activating group in the presence of an inorganic base. Preferred conditions comprise sodium carbonate in DCM with 4-nitrophenylchloroformate.

Compounds of formula (XXI) may be prepared from compounds of formula (XXII) according to process step (xiv), a reduction step in the presence of a metal catalyst and an inorganic hydrogen donor or under an atmosphere of hydrogen. Preferred conditions comprise NiCl₂.6H₂O with sodium borohydride and di-tert butyl dicarbonate in methanol followed by 4M HCl in dioxane or 10% palladium on carbon in acetic acid or Raney Nickel in methanolic ammonia under an atmosphere of 40 psi of hydrogen at room temperature for 18 hours.

Compounds of formula (XXII) may be prepared from compounds of formula (XXV) according to process step (xiii), an alkylation reaction with compounds of formula (XXVI) in the presence of a quaternary ammonium salt. Preferred conditions comprise benzyltriethylammonium chloride and 40% aqueous sodium hydroxide solution in THF with compounds of formula (XXVI). Compounds of formula (XXII) may also be prepared from compounds of formula (XXIII) according to process step (xii), an alkylation reaction in the presence of an inorganic base. Preferred conditions comprise potassium carbonate in acetone with compounds of formula (XXVI) or Mitsunobu conditions with compounds of formula (XVIII) using DEAD in THF.

Compounds of formulae (XXV) and (XXIII) may be prepared from compounds of formula (XXIV) and (XVII) according to process step (xi) a sulfonamide formation reaction. Preferred conditions comprise stirring in pyridine at from 0° C. to room temperature or in the presence of LiHMDS in THF. Compounds of formula (XXIII) may also be prepared from sulfonamides reacting with halo-substituted heterocycles in the presence of a base such as cesium carbonate in acetonitrile.

Scheme 5

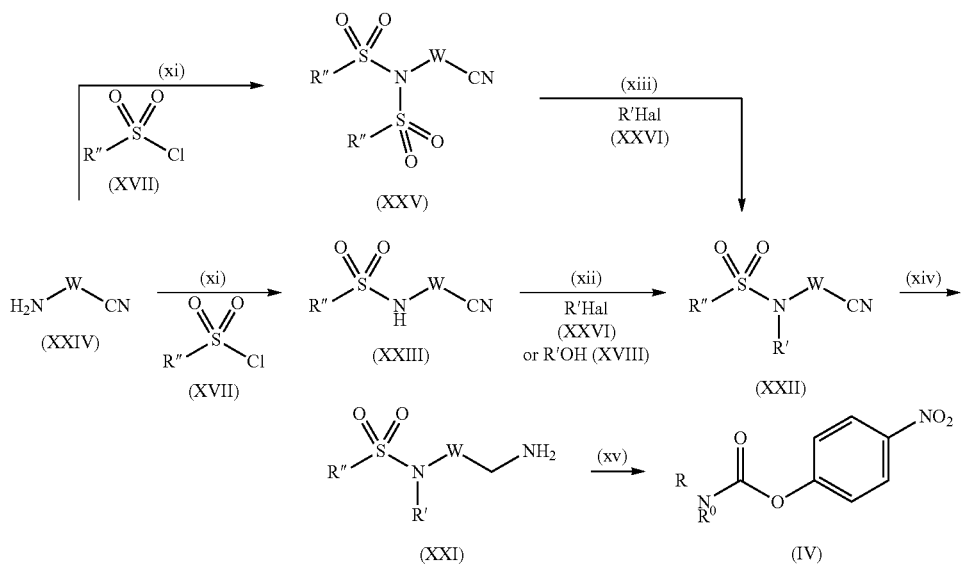

According to a sixth process, compounds of formula (II) may be prepared from compounds of formula (VII) as illustrated by Scheme 6.

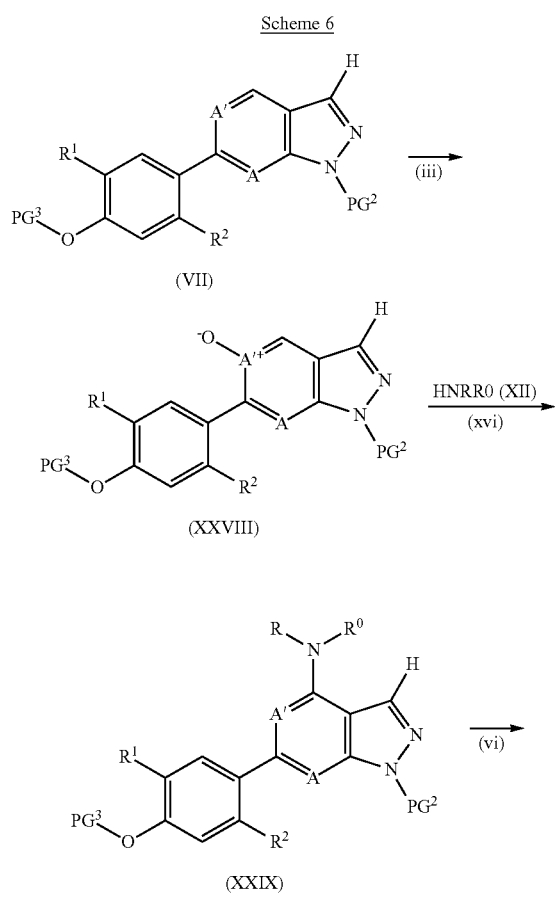

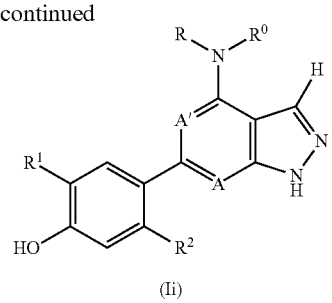

Compounds of formula (VII) may be prepared as described in Scheme 1. Compounds of formulae (XII) are commercially available or may be synthesized by those skilled in the art according to the literature or preparations described herein. Compounds of formula (I) may be prepared from compounds of formula (XXIX) according to reaction step (vi), a deprotection step as described in Scheme 1.

Compounds of formula (XXIX) may be prepared according to reaction step (xvi), an N-oxide rearrangement step effected by employment of a dehydrating agent such as PyBrop with amines of formula (XII). Preferred conditions comprise PyBrop with DIPEA in a suitable organic solvent such as DCM at room temperature. Alternatively the N-oxide rearrangement step may employ acetic anhydride to afford the hydroxy intermediate followed by interconversion to triflate. The triflate may then be converted to compounds of formula (XXIX) by heating with amines of formula (XII). Typical conditions comprise heating the N-oxide with triethylamine and acetic anhydride, followed by triflic anhydride with pyridine in DCM at room temperature, and finally heating with compounds of formula (XII) with triethylamine in DMF.

Compounds of formula (XXVIII) may be prepared from compounds of formula (VII) according to process step (iii) as described in Scheme 1.

According to a seventh process, compounds of formula (I) may be prepared from compounds of formula (VII) as illustrated by Scheme 7.

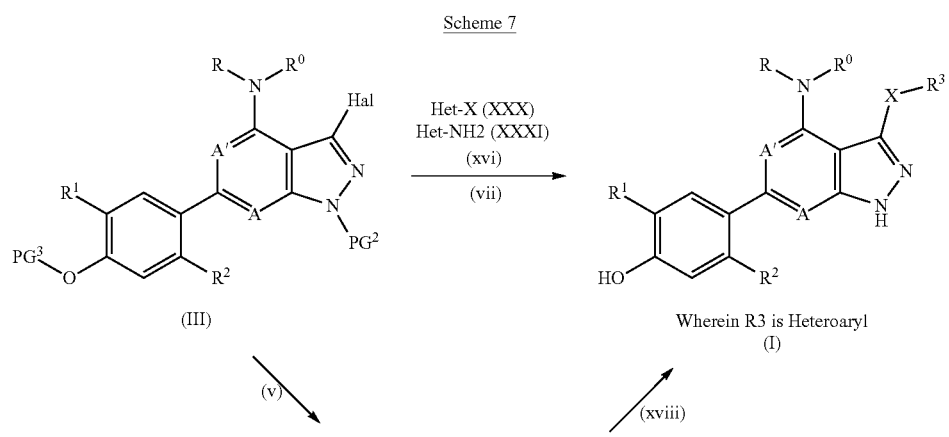

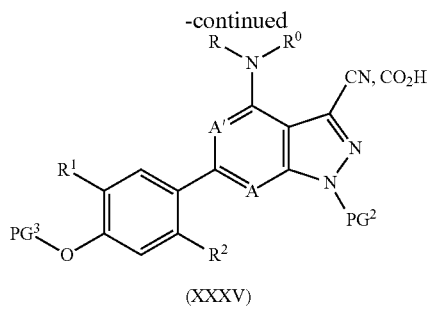

(XXXV)

Compounds of formula (III) may be prepared as described in Scheme 1. Compounds of formulae (XXX) or (XXXI) are commercially available or may be synthesized by those skilled in the art according to the literature or preparations described herein.

Compounds of formula (I)-(II) may be prepared from compounds of formula (III) according to process steps (xvii) and (vi), a cross coupling reaction, such as a Stille reaction or a Buchwald reaction followed by a deprotection step if required. Typical conditions for a Stille cross coupling reaction comprise a suitable tin reagent in the presence of one or two metal catalysts in a suitable organic solvent at elevated temperatures with compounds of formula (XXX). Preferred conditions comprise bis(tributyltin) and copper(I) iodide with tetrakis(triphenylphosphine)palladium in toluene at 100° C. Typical conditions for a Buchwald reaction comprise a copper catalyst and a suitable organic ligand in the presence of an inorganic base at elevated temperatures. Preferred conditions comprise cuprous oxide and 4.7-dimethoxy-1,10-phenanthroline with cesium carbonate and PEG in DMSO at 110° C.

Compounds of formula (I) may also be prepared from compounds of formula (XXXV) according to process step (xviii) a heterocyclic cyclization reaction, either directly from the nitrile or the carboxylic acid, or via an acyl hydrazone from the carboxylic acid. Preferred conditions comprise heating with the required nitrile or hydrazone in butanol at elevated temperatures under microwave irradiation. Compounds of formula (XXXV) may be prepared from compounds of formula (III) according to process step (v) as described in Scheme 3 to afford the carboxylic acid, or using zinc cyanide and tetrakis(triphenylphosphine)palladium in DMF at elevated temperatures under microwave irradiation to afford the nitrile.

According to an eighth process, compounds of formula (I)-(II) may be prepared from compounds of formula (XXXIII) as illustrated by Scheme 8.

Scheme 8

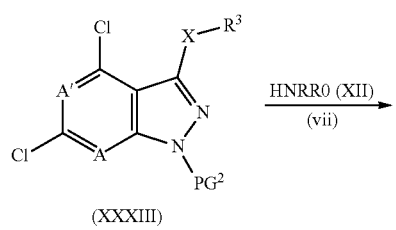

(XXXIII)

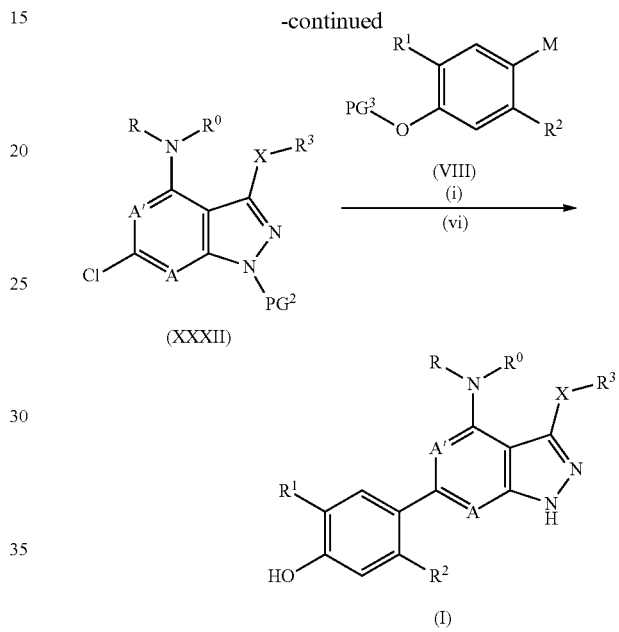

Wherein M is boronic acid or ester.

Compounds of formula (XXXIII) are either commercially available or prepared as described herein. Compounds of formula (I)-(Ii) may be prepared from compounds of formula (XXXII) and (VIII) according to process steps (i) and (vi), a Suzuki cross-coupling reaction followed by deprotection as described in Scheme 1. Preferred conditions for the Suzuki step comprise PEPPSI-IPr catalyst with potassium carbonate in toluene at elevated temperatures. Compounds of formula (XXXII) may be prepared from compounds of formula (XXXIII) and (XII) according to process step (vii), a nucleophilic aromatic substitution reaction as described in Scheme 2.

The skilled person will further appreciate that compounds of formula (I)-(II) may be interconverted to other compounds of formula (I)-(II) by functional group manipulation, or suitably protected compounds of formula (I)-(II) may be interconverted to other suitably protected compounds of formula (I)-(II) followed by a deprotection step to afford compounds of formula (I)-(II)

Typical interconversions include:

Wherein R or $R^0$ contains a ketone or aldehyde functionality, these may be reduced using a suitable reducing agent such as sodium borohydride;

Wherein R or $R^0$ contain an amine, these may be interconverted to a urea, an amide, a sulfonamide or a sulfamide followed by suitable deprotection as required.

Wherein compounds of formula (XVI) contain an R'" group that has a leaving group such as halo, an alkylation may occur with amines such as morpholine.

In the non-limiting Examples and Preparations that are set out later in the description, and in the aforementioned Schemes, the following the abbreviations, definitions and analytical procedures may be referred to:

ACE-Cl is 1-chloroethylchloroformate;
$BBr_3$ is boron tribromide;
BINAP is 2,2'-bis(diphenylphosphino)-1,1'binapthalene;
BOP is (benzotriazol-1-yloxy)tris(dimethylamino)phosphonium hexafluorophosphate;
Cbz is benzyloxycarbonyl;
$Cs_2CO_3$ is cesium carbonate;
DBU is diazabicyclo[5.4.0]undec-7-ene;
DCM is dichloromethane;
DEAD is diethylazodicarboxylate;
DIPEA is N-ethyldiisopropylamine, N,N-diisopropylethylamine;
DMAP is dimethylaminopyridine;
DMF is dimethyl formamide;
EDCl.HCl is 1-(3-dimethylaminopropyl)-3-ethylcarbodiimide hydrochloride;
EtOAc is ethylacetate;
HATU is 1-[Bis(dimethylamino)methylene]-1H-1,2,3-triazolo[4,5-b]pyridinium 3-oxid hexafluorophosphate;
HBTU is N,N,N',N'-Tetramethyl-O-(1H-benzotriazol-1-yl)uronium hexafluorophosphate;
HCl is hydrochloric acid;
HOBt is 1-hydroxybenzotriazole;
IPA is isopropanol;
KOAc is potassium acetate;
LiHMDS is lithium (bistrimethylsilyl)amide
m-CPBA is meta chloroperoxy benzoic acid
MeCN is acetonitrile;
MeOH is methanol;
$NaBH_4$ is sodium borohydride;
$NaHCO_3$ is sodium hydrogen carbonate;
NaH is sodium hydride;
NaOH is sodium hydroxide;
NBS is N-bromosuccinimide;
$NiCl_2.6H_2O$ is nickel dichloride hydrate;
NMM is N-methylmorpholine;
NMP is N-methyl-2-pyrrolidone;
Peppsi™-IPr is [1,3-Bis(2,6-Diisopropylphenyl)imidazol-2-ylidene](3-chloropyridyl)palladium(II) dichloride;
Pd/C is palladium on carbon;
$Pd_2(dba)_3$ is tris(dibenzylideneacetone)dipalladium;
Pd(dppf)2Cl2 is 1,1'-bis(diphenylphosphino)ferrocenepalladium(II)dichloride;
$Pd(OAc)_2$ is palladium acetate;
$Pd(PPh_3)_4$ is tetrakis(triphenylphosphine)palladium (0)
PEG is polyethylene glycol;
$POCl_3$ is phosphorus oxychloride;
PTSA is paratoluenesulfonic acid;
PyBrop is (benzotriazol-1-yloxy)tripyrrolidinophosphonium hexafluorophosphate;
SEM is silylethoxymethyl;
SPhos is 2-dicyclohexylphosphino-2',6'-dimethoxybiphenyl;
TBDMS is tertbutyldimethylsilyl;
TBME is tert-butyl dimethyl ether;
t-BuOK is potassium tert-butoxide;
TEA is triethylamine;
TES is triethylsilyl;
Tf is triflate which is trifluoromethanesulfonate;
TFA is trifluoroacetic acid;
THF is tetrahydrofuran;
THP is tetrahydropyran; and,
TLC is thin layer chromatography.

$^1H$ and $^{19}F$ Nuclear magnetic resonance (NMR) spectra were in all cases consistent with the proposed structures. Characteristic chemical shifts (δ) are given in parts-per-million downfield from tetramethylsilane (for $^1H$-NMR) and upfield from trichloro-fluoro-methane (for $^{19}F$ NMR) using conventional abbreviations for designation of major peaks: e.g. s, singlet; d, doublet; t, triplet; q, quartet; m, multiplet; br, broad. The following abbreviations have been used for common solvents: $CDCl_3$, deuterochloroform; $d_6$-DMSO, deuterodimethylsulphoxide; and $CD_3OD$, deuteromethanol. Where appropriate, tautomers may be recorded within the NMR data; and some exchangeable protons may not be visible. Mass spectra, MS (m/z), were recorded using either electrospray ionisation (ESI) or atmospheric pressure chemical ionisation (APCI). Where relevant and unless otherwise stated the m/z data provided are for isotopes $^{19}F$, $^{35}Cl$, $^{79}Br$ and $^{127}I$. Wherein preparative TLC or silica gel chromatography has been used, one skilled in the art may choose any combination of solvents to purify the desired compound.

Either IUPAC or ACD Labs naming packages have been used, and are interchangeably employed throughout the Examples and Preparations.

Preparative HPLC:

Where singleton compounds are purified by preparative HPLC, these are two methods used, shown below:

Detection for Both Analytical and Preparative QC:

Detectors: ELSD; Polymer Labs PL-ELS 2100, UV; Waters 2487 detector at 225 and 255 nm Mass Spectrometer; Waters ZQ using electrospray ionization.

Preparative Method 1 Acidic Conditions

Column: Gemini NX C18, 5 μm 21.2×100 mm; Temperature: Ambient; Detection: ELSD-MS; Mobile Phase A: 0.1% formic acid in water; Mobile Phase B:

0.1% formic acid in acetonitrile; Gradient: initial 0% B, 1 min—5% B; 7 mins—95% B; 9 mins—95% B; 9.1 mins—5% B; 10 mins—5% B; Flow rate: 18 mL/min; Injection volume: 1000 μL Preparative Method 2 Basic Conditions Column: Gemini NX C18, 5 μm 21.2×100 mm; Temperature: Ambient; Detection:

ELSD-MS; Mobile Phase A: 0.1% diethylamine in water; Mobile Phase B: 0.1% diethylamine in acetonitrile; Gradient: initial 0% B, 1 min—5% B; 7 mins—95% B; 9 mins—95% B; 9.1 mins—5% B; 10 mins—5% B; Flow rate: 18 mL/min; Injection volume: 1000 μL Analytical LCMS QC:

Column: Gemini C18 50×4.6 mm, 3 micron; 5 minutes run.

Gradient initial—95% A, 5% B; 3 mins—95% B; hold to 4 mins then back to 5% B at 4.1-5 mins. Flow rate 1.5 mL/min Acidic conditions: Mobile Phase A: 0.1% Formic acid in Water. Mobile Phase B: 0.1% Formic acid in acetonitrile Basic conditions: Mobile Phase A: 0.1% ammonia in water; Mobile Phase B: 0.1% Ammonia in acetonitrile.

Example 1

4-({2-[Ethyl(ethylsulfonyl)amino]benzyl}amino)-6-[5-fluoro-4-hydroxy-2-(2,2,2-trifluoroethyl)phenyl]-N-methyl-1H-pyrazolo[4,3-c]pyridine-3-carboxamide To a solution of N-ethyl-N-(2-{[(6-[5-fluoro-2-(2,2,2-trifluoroethyl)-4-{[2-(trimethyl-silyl)ethoxy]methoxy}phenyl]-3-iodo-1-{[2-(trimethylsilyl)ethoxy]methyl}-1H-pyrazolo[4,3-c]pyridin-4-yl)amino]methyl}phenyl)ethanesulfonamide (Preparation 62, 170 mg, 0.18 mmol) in 2M methylamine in THF (2.6 mL) was added molybdenum hexacarbonyl (48.18 mg, 0.181 mmol), DBU (82.77 ml, 0.544 mmol) and palladium acetate (2.85 mg, 0.01 mmol). The reaction was heated at 100° C. under microwave irradiation for 10 minutes. The reaction was cooled, concentrated in vacuo and purified using silica gel column chromatography eluting with 30% EtOAc in hexanes. The residue was dissolved in TFA (3 mL) and stirred at room temperature for 30 minutes. The reaction was concentrated in vacuo, dissolved in MeOH, cooled in ice and treated with ethylene diamine. The reaction was stirred at room temperature for 2 hours before concentrating in vacuo. The residue was purified using silica gel column chromatography eluting with EtOAc to afford the title compound (60 mg, 58% over 2 steps).

$^1$H NMR (400 MHz, DMSO-d$_6$): δ ppm 0.90 (t, 3H), 1.15 (t, 3H), 2.85 (d, 3H), 3.21 (m, 2H), 3.44-3.63 (m, 4H), 4.72-4.74 (m, 1H), 4.86-4.88 (m, 1H), 6.69 (s, 1H), 6.92 (d, 1H), 7.19 (d, 1H), 7.31 (m, 2H), 7.40 (m, 2H), 8.85 (m, 1H), 9.77 (m, 1H), 10.07 (s, 1H), 13.71 (s, 1H).

MS m/z 609 [M+H]$^+$

The following Examples (Examples 2-25) were prepared according to the method described for Example 1 using the appropriate pyrazolo-pyridine and Purification Method (PM) below if different from the method described:

Purification Method A: Silica gel column chromatography eluting with between 40-60% EtOAc in hexanes.

Purification Method B: Silica gel column chromatography or Preparative TLC eluting with 4% MeOH in DCM.

Purification Method C: Silica gel column chromatography followed by Preparative TLC eluting both with up to 30% MeOH in DCM.

Purification Method D: Silica gel column chromatography eluting with EtOAc.

| Ex | Name | Data |
| --- | --- | --- |
| 2 | 4-({2-[ethyl(ethylsulfonyl)-amino]benzyl}amino)-6-(2-ethyl-5-fluoro-4-hydroxyphenyl)-N-methyl-1H-pyrazolo[4,3-c]pyridine-3-carboxamide | MS m/z 555 [M + H]$^+$<br>$^1$H NMR (400 MHz, DMSO-d$_6$): δ ppm 0.85 (t, 3H), 0.93 (t, 3H), 1.20 (t, 3H), 2.84 (d, 3H), 3.15-3.31 (m, 2H), 3.50-3.70 (m, 2H), 4.69-4.71 (m, 1H), 4.95-4.98 (m, 1H), 6.62 (s, 1H), 6.74 (d, 1H), 6.97 (s, 1H), 7.31 (m, 2H), 7.41 (m, 2H), 8.79 (m, 1H), 9.64 (m, 1H).<br>Using N-ethyl-N-[2-({[6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-yl]amino}-methyl)phenyl]ethanesulfonamide (Preparation 63) and PM A. |
| 3 | 6-(2-ethyl-5-fluoro-4-hydroxy-phenyl)-4-({2-[(ethylsulfonyl)-(methyl)amino]ben-zyl}amino)-N-methyl-1H-pyrazolo[4,3-c]pyridine-3-carboxamide | MS m/z 541 [M + H]$^+$<br>$^1$H NMR (400 MHz, DMSO-d$_6$): δ ppm 0.86 (t, 3H), 1.22 (t, 3H), 2.49 (m, 2H), 2.84 (d, 3H), 3.35 (m, 2H), 4.70-5.00 (br m, 2H), 6.63 (s, 1H), 6.78 (d, 1H), 7.03 (d, 1H), 7.32 (m, 2H), 7.41 (m, 2H), 8.80 (t, 1H), 9.66 (t, 1H), 9.76 (s, 1H), 13.63 (s, 1H).<br>Using N-[2-({[6-(2-ethyl-5-fluoro-4-{[2-)trimethyl-silyl)ethoxy]-methoxy}phenyl)-3-iodo-1-{[2-(trimethyl-silyl)ethoxy]methyl}-1H-pyrazolo[4,3-c]pyridin-4-yl]amino}methyl)phenyl]-N-methylethanesulfonamide (Preparation 64) and PM A. |
| 4 | 6-(2-ethyl-5-fluoro-4-hydroxyphenyl)-4-{[2-(4-hydroxyphenyl)eth-yl]amino}-N-methyl-1H-pyrazolo[4,3-c]pyridine-3-carboxamide | MS m/z 450 [M + H]$^+$<br>$^1$H NMR (400 MHz, DMSO-d$_6$): δ ppm 1.06 (t, 3H), 2.66-2.84 (m, 7H), 3.62 (m, 2H), 6.61 (s, 1H), 6.65 (m, 2H), 6.86 (m, 1H), 7.05 (m, 2H), 7.15 (m, 1H), 8.73 (m, 1H), 9.28 (m, 1H).<br>Using 4-(2-{[6-(2-ethyl-5-fluoro-4-{[2-(trimethyl-silyl)ethoxy]-methoxy}phenyl)-3-iodo-1-{[2-(trimethyl-silyl)ethoxy]methyl}-1H-pyrazolo[4,3-c]pyridin-4-yl]amino}ethyl)phenol (Preparation 65) and PM B. |
| 5 | 6-(2-ethyl-5-fluoro-4-hydroxyphenyl)-N-methyl-4-[(2-methylpropyl)amino]-1H-pyrazolo[4,3-c]pyridine-3-carboxamide | MS m/z 386 [M + H]$^+$<br>$^1$H NMR (400 MHz, DMSO-d$_6$): δ ppm 0.97 (d, 6H), 1.08 (t, 3H), 1.89 (m, 1H), 2.69 (m, 2H), 2.84 (d, 3H), 3.35 (m, 2H), 6.58 (s, 1H), 6.85 (d, 1H), 7.09 (d, 1H), 8.74 (m, 1H), 9.31 (m, 1H), 9.79 (s, 1H), 13.50 (s, 1H).<br>N-ethyl-N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridin-4-yl)amino]methyl}phenyl)ethanesulfonamide (Preparation 66) and PM A. |
| 6 | 4-({5-chloro-2-[methyl(methyl-sulfonyl)amino]benzyl}amino)-6-(2-ethyl-5-fluoro-4-hydroxyphenyl)-N-methyl-1H-pyrazolo[4,3-c]pyridine-3-carboxamide | MS m/z 561 [M + H]$^+$<br>$^1$H NMR (400 MHz, DMSO-d$_6$): δ ppm 0.83 (t, 3H), 2.44 (m, 2H), 2.86 (d, 3H), 3.05 (s, 3H), 3.08 (s, 3H), 4.69-4.87 (br m, 2H), 6.66 (s, 1H), 6.78 (d, 1H), 7.03 (d, 1H), 7.36-7.39 (m, 2H), 7.54 (d, 1H), 8.83 (m, 1H), 9.69 (m, 1H), 9.77 (s, 1H), 13.67 (s, 1H).<br>N-[4-chloro-2-({[6-(2-ethyl-5-fluoro-4-{[2-(trimethylsilyl)ethoxy]-methoxy}phenyl)-3-iodo-1-{[2- |

-continued

| Ex | Name | Data |
|---|---|---|
| 7 | 6-(2-ethyl-5-fluoro-4-hydroxyphenyl)-4-({5-fluoro-2-[methyl(methylsulfonyl)amino]benzyl}amino)-N-methyl-1H-pyrazolo[4,3-c]pyridine-3-carboxamide | (trimethylsilyl)ethoxy]methyl}-1H-pyrazolo[4,3-c]pyridin-4-yl]amino}methyl)phenyl]-N-methylmethanesulfonamide (Preparation 67) and PM A.<br>MS m/z 545 [M + H]$^+$<br>$^1$H NMR (400 MHz, DMSO-d$_6$): δ ppm 0.85 (t, 3H), 2.45 (br m, 2H), 2.85 (d, 3H), 3.05 (s, 3H), 3.08 (s, 3H), 4.69 (br m, 1H), 4.90 (br m, 1H), 6.65 (s, 1H), 6.78 (d, 1H), 7.02 (d, 1H), 7.10-7.18 (m, 2H), 7.55 (m, 1H), 8.83 (m, 1H), 9.68 (m, 1H), 9.77 (s, 1H), 13.66 (s, 1H).<br>N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)-4-fluorophenyl]-N-methylmethanesulfonamide (Preparation 68) and PM A. |
| 8 | 6-(2-ethyl-5-fluoro-4-hydroxyphenyl)-4-({2-fluoro-6-[methyl(methylsulfonyl)amino]benzyl}amino)-N-methyl-1H-pyrazolo[4,3-c]pyridine-3-carboxamide | MS m/z 545 [M + H]$^+$<br>$^1$H NMR (400 MHz, DMSO-d$_6$): δ ppm 1.02 (t, 3H), 2.66 (m, 2H), 3.02 (s, 6H), 4.57-5.00 (br m, 2H), 6.61 (s, 1H), 6.85 (d, 1H), 7.06 (d, 1H), 7.25 (m, 1H), 7.36-7.45 (m, 2H), 8.71 (m, 1H), 9.44 (m, 1H), 9.79 (s, 1H), 13.58 (s, 1H).<br>N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)-3-fluorophenyl]-N-methylmethanesulfonamide (Preparation 69) and PM A. |
| 9 | 6-(2-ethyl-5-fluoro-4-hydroxyphenyl)-4-({2-[ethyl(methylsulfonyl)amino]benzyl}amino)-N-methyl-1H-pyrazolo[4,3-c]pyridine-3-carboxamide | MS m/z 541 [M + H]$^+$<br>$^1$H NMR (400 MHz, DMSO-d$_6$): δ ppm 0.85 (t, 3H), 0.93 (t, 3H), 2.45 (m, 2H), 2.84 (d, 3H), 3.02 (s, 3H), 3.49 (m, 1H), 3.68 (m, 1H), 4.70 (m, 1H), 4.97 (m, 1H), 6.62 (s, 1H), 6.77 (d, 1H), 6.98 (d, 1H), 7.31 (m, 2H(, 7.44 (m, 2H), 8.79 (m, 1H), 9.63 (m, 1H), 9.73 (br s, 1H), 13.62 (br s, 1H).<br>N-ethyl-N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)-phenyl]methanesulfonamide (Preparation 70) and PM A. |
| 10 | 4-[(cyclopentylmethyl)amino]-6-(2-ethyl-5-fluoro-4-hydroxyphenyl)-N-methyl-1H-pyrazolo[4,3-c]pyridine-3-carboxamide | MS m/z 412 [M + H]$^+$<br>$^1$H NMR (400 MHz, DMSO-d$_6$): δ ppm 1.04 (t, 3H), 1.28 (m, 2H), 1.54-1.61 (m, 4H), 1.77 (m, 2H), 2.15 (m, 1H), 2.65 (m, 2H), 2.84 (d, 3H), 3.41 (m, 2H), 6.58 (s, 1H), 6.85 (d, 1H), 7.12 (d, 1H), 8.73 (m, 1H), 9.29 (m, 1H), 9.78 (s, 1H), 13.54 (br s, 1H).<br>N-(cyclopentylmethyl)-6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-amine (Preparation 71) and PM A. |
| 11 | 6-[5-fluoro-4-hydroxy-2-(2,2,2-trifluoroethyl)phenyl]-N-methyl-4-({5-methyl-2-[methyl(methylsulfonyl)amino]benzyl}amino)-1H-pyrazolo[4,3-c]pyridine-3-carboxamide | MS m/z 595 [M + H]$^+$<br>$^1$H NMR (400 MHz, DMSO-d$_6$): δ ppm 2.21 (s, 3H), 2.85 (d, 3H), 3.01 (s, 3H), 3.07 (s, 3H), 3.62 (m, 2H), 4.64-4.83 (m, 2H), 6.70 (s, 1H), 6.93 (d, 1H), 7.13 (m, 1H), 7.19 (m, 2H), 7.37 (d, 1H), 8.82 (m, 1H), 9.71 (m, 1H), 10.09 (s, 1H), 13.70 (s, 1H).<br>6-(5-fluoro-2-(2,2,2-trifluoroethyl)-4-((2-(trimethylsilyl)ethoxy)methoxy)phenyl)-N-methyl-4-((5-methyl-2-(N-methylmethylsulfonamido)benzyl)amino)-1-((2-(trimethylsilyl)ethoxy)methyl)-1H-pyrazolo[4,3-c]pyridine-3-carboxamide(Preparation 72) and PM C. |
| 12 | 4-({2-[ethyl(methylsulfonyl)amino]benzyl}amino)-6-[5-fluoro-4-hydroxy-2-(2,2,2-trifluoroethyl)phenyl]-N-methyl-1H-pyrazolo[4,3-c]pyridine-3-carboxamide | MS m/z 595 [M + H]$^+$<br>$^1$H NMR (400 MHz, DMSO-d$_6$): δ ppm 0.92 (t, 3H), 2.85 (s, 1H), 3.02 (s, 3H), 3.50 (m, 2H), 3.64 (m, 2H), 4.72 (m, 1H), 4.93 (m, 1H), 6.69 (s, 1H), 6.93 (d, 1H), 7.16 (d, 1H), 7.31-7.45 (m, 4H), 8.84 (m, 1H), 9.75 (m, 1H), 10.07 (s, 1H), 13.70 (br s, 1H).<br>N-ethyl-N-(2-{[(6-[5-fluoro-2-(2,2,2-trifluoroethyl)-4-{[2-(trimethylsilyl)ethoxy]methoxy}phenyl)-3-iodo-1-{[2-(trimethylsilyl)-ethoxy]methyl}-1H-pyrazolo[4,3-c]pyridin-4-yl)amino]methyl}-phenyl)methane sulphonamide (Preparation 73) and PM D. |
| 13 | 4-({2-[(ethylsulfonyl)methyl)-amino]-benzyl}amino)-6-[5-fluoro-4-hydroxy-2-(2,2,2-trifluoroethyl)phenyl]-N-methyl-1H-pyrazolo[4,3-c]pyridine-3-carboxamide | MS m/z 595 [M + H]$^+$<br>$^1$H NMR (400 MHz, DMSO-d$_6$): δ ppm 1.21 (t, 3H), 2.85 (d, 3H), 3.11 (s, 3H), 3.32 (m, 2H), 3.57 (m, 2H), 4.72-4.84 (br m, 2H), 6.70 (s, 1H), 6.94 (d, 1H), 7.18-7.47 (m, 4H), 8.84 (m, 1H), 9.78 (m, 1H), 10.08 (br s, 1H), 13.70 (br s, 1H).<br>N-(2-{[(6-[5-fluoro-2-(2,2,2-trifluoroethyl)-4-{[2- |

| Ex | Name | Data |
|---|---|---|
| | | (trimethylsilyl)-ethoxy]methoxy}phenyl]-3-iodo-1-{[2-(trimethylsilyl)ethoxy]methyl}-1H-pyrazolo[4,3-c]pyridin-4-yl)amino]-methyl}phenyl)-N-methylethane Sulphonamide (Preparation 74) and PM A. |
| 14 | 6-[5-fluoro-4-hydroxy-2-(2,2,2-trifluoroeth-yl)phenyl]-4-({5-fluoro-2-[methyl(methylsulfo-nyl)amino]benzyl}amino)-N-methyl-1H-pyrazolo[4,3-c]pyridine-3-carboxamide | MS m/z 599 [M + H]$^+$<br>$^1$H NMR (400 MHz, DMSO-d$_6$): δ ppm 2.86 (d, 3H), 3.05 (s, 3H), 3.08 (s, 3H), 3.55 (m, 2H), 4.65-4.90 (m, 2H), 6.73 (s, 1H), 7.06-7.21 (m, 4H), 8.86 (m, 1H), 9.80 (m, 1H), 10.10 (s, 1H), 13.74 (s, 1H).<br>Using N-(4-fluoro-2-{[(6-[5-fluoro-2-(2,2,2-tri-fluoroethyl)-4-{[2-(trimethylsilyl)ethoxy]meth-oxy}phenyl]-3-iodo-1-{[2-(trimethylsilyl)eth-oxy]methyl}-1H-pyrazolo[4,3-c]pyridin-4-yl)ami-no]methyl}phenyl)-N-methylmethanesulfonamide (Preparation 75) and PM D. |
| 15 | 4-({5-chloro-2-[methyl(methyl-sulfonyl)amino]benzyl}amino)-6-[5-fluoro-4-hydroxy-2-(2,2,2-trifluoroethyl)phenyl]-N-methyl-1H-pyrazolo[4,3-c]pyridine-3-carboxamide | MS m/z 613 [M − H]$^−$<br>$^1$H NMR (400 MHz, DMSO-d$_6$): δ ppm 3.05 (d, 3H), 3.05 (s, 3H), 3.07 (s, 3H), 3.52 (m, 2H), 4.75-4.90 (m, 2H), 6.73 (s, 1H), 6.94 (s, 1H), 7.21 (d, 1H), 7.33 (m, 1H), 7.39 (m, 1H), 7.54 (d, 1H), 8.86 (m, 1H), 9.79 (m, 1H), 10.08 (s, 1H), 13.74 (s, 1H).<br>Using N-(4-chloro-2-{[(6-[5-fluoro-2-(2,2,2-trifluoro-ethyl)-4-{[2-(trimethylsilyl)ethoxy]methoxy}phenyl]-3-iodo-1-{[2-(trimethylsilyl)ethoxy]-methyl}-1H-pyrazolo[4,3-c]pyridin-4-yl)amino]methyl}phenyl)-N-methylmethanesulfonamide (Preparation 61) and PM C. |
| 16 | 6-[5-fluoro-4-hydroxy-2-(2,2,2-trifluoroeth-yl)phenyl]-N-methyl-4-[(2-methylpropyl)amino]-1H-pyrazolo[4,3-c]pyridine-3-carboxamide | MS m/z 440 [M + H]$^+$<br>$^1$H NMR (400 MHz, DMSO-d$_6$): δ ppm 0.97 (s, 3H), 0.98 (s, 3H), 1.90 (m, 1H), 2.84 (d, 3H), 3.31 (m, 2H), 4.10 (m, 2H), 6.67 (s, 1H), 7.05 (d, 1H), 7.30 (d, 1H), 8.77 (m, 1H), 9.39 (m, 1H), 10.13 (s, 1H), 13.62 (s, 1H).<br>Using 6-[5-fluoro-2-(2,2,2-trifluoroethyl)-4-{[2-(trimethylsilyl)ethoxy]-methoxy}phenyl]-3-iodo-N-(2-methylpropyl)-1-{[2-(trimethylsilyl)-ethoxy]methyl}-1H-pyrazolo[4,3-c]pyridin-4-amine (Preparation 78) and PM A. |
| 17 | 4-[(cyclopentylmethyl)-amino]-6-[5-fluoro-4-hydroxy-2-(2,2,2-trifluoroethyl)phenyl]-N-methyl-1H-pyrazolo[4,3-c]pyridine-3-carboxamide | MS m/z 466 [M + H]$^+$<br>$^1$H NMR (400 MHz, DMSO-d$_6$): δ ppm 1.28 (m, 2H), 1.52-1.61 (m, 4H), 1.79 (m, 1H), 2.15 (m, 1H), 3.39 (m, 2H), 4.12 (m, 2H), 6.67 (s, 1H), 7.02 (d, 1H), 7.30 (d, 1H), 8.76 (m, 1H), 9.37 (m, 1H), 10.13 (s, 1H), 13.62 (br s, 1H).<br>N-(cyclopentylmethyl)-6-[5-fluoro-2-(2,2,2-trifluoro-ethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridin-4-amine (Preparation 77) and PM A. |
| 18 | 6-[5-fluoro-4-hydroxy-2-(2,2,2-trifluoroeth-yl)phenyl]-4-({2-fluoro-6-[methyl(methylsulfo-nyl)amino]benzyl}amino)-N-methyl-1H-pyrazolo[4,3-c]pyridine-3-carboxamide | MS m/z 599 [M + H]$^+$<br>$^1$H NMR (400 MHz, DMSO-d$_6$): δ ppm 2.80 (d, 3H), 3.01 (s, 3H), 3.02 (s, 3H), 3.80-4.25 (br m, 2H), 4.55-5.10 (br m, 1H), 6.70 (s, 1H), 7.04 (d, 1H), 7.28 (m, 2H), 7.43 (m, 2H), 8.74 (m, 1H), 9.54 (m, 1H), 10.14 (s, 1H), 13.66 (s, 1H).<br>N-(3-fluoro-2-{[(6-[5-fluoro-2-(2,2,2-trifluoroethyl)-4-{[2-(trimethylsilyl)-ethoxy]methoxy}phenyl]-3-iodo-1-{[2-(trimethylsilyl)ethoxy]methyl}-1H-pyrazolo[4,3-c]pyridin-4-yl)amino]methyl}phenyl)-N-methylmethane-sulfonamide (Preparation 76) and PM A. |
| 19 | 6-(2-ethyl-5-fluoro-4-hydroxy-phenyl)-N-methyl-4-({2-[meth-yl(methylsulfonyl)ami-no]benzyl}amino)-1H-pyrazolo[4,3-c]pyridine-3-carboxamide | MS m/z 527 [M + H]$^+$<br>$^1$H NMR (400 MHz, DMSO-d$_6$): δ ppm 0.88 (t, 3H), 2.84 (d, 3H), 3.04 (s, 3H), 3.10 (s, 3H), 3.31 (m, 2H), 4.69 (br m, 1H), 4.94 (br m, 1H), 6.63 (s, 1H), 6.79 (d, 1H), 7.04 (d, 1H), 7.30 (m, 2H), 7.42 (m, 1H), 7.49 (m, 1H), 8.80 (m, 1H), 9.63 (m, 1H), 9.75 (s, 1H), 13.61 (br s, 1H).<br>N-[2-({[6-(2-ethyl-5-fluoro-4-{[2-(trimethylsilyl)eth-oxy]methoxy}phenyl)-3-iodo-1-{[2-(trimethylsilyl)-ethoxy]methyl}-1H-pyrazolo[4,3-c]pyridin-4-yl]ami-no}methyl)phenyl]-N-methylmethanesulfonamide (Preparation 79) and PM A. |

-continued

| Ex | Name | Data |
|---|---|---|
| 20 | 6-[5-fluoro-4-hydroxy-2-(2,2,2-trifluoroethyl)phenyl]-N-methyl-4-({2-[methyl(methylsulfonyl)amino]benzyl}amino)-1H-pyrazolo[4,3-c]pyridine-3-carboxamide | MS m/z 581 [M + H]$^+$<br>$^1$H NMR (400 MHz, DMSO-d$_6$): δ ppm 2.64 (d, 3H), 3.04 (s, 3H), 3.10 (s, 3H), 3.62 (q, 2H), 4.72 (br s, 1H), 4.88 (br s, 1H), 6.54 (s, 1H), 6.95 (d, 1H), 7.21 (d, 1H), 7.30 (m, 2H), 7.37 (d, 1H), 7.45 (m, 1H), 8.82 (t, 1H), 9.75 (t, 1H), 10.09 (s, 1H), 13.70 (s, 1H).<br>N-(2-{[(6-[5-fluoro-2-(2,2,2-trifluoroethyl)-4-{[2-(trimethylsilyl)ethoxy]-methoxy}phenyl]-3-iodo-1-{[2-(trimethylsilyl)ethoxy]methyl}-1H-pyrazolo[4,3-c]pyridin-4-yl)amino]-methyl}phenyl)-N-methylmethanesulfonamide (Preparation 105) and PM A. |
| 21 | 6-(2-ethyl-5-fluoro-4-hydroxyphenyl)-N-methyl-4-({5-methyl-2-[methyl(methylsulfonyl)amino]benzyl}amino)-1H-pyrazolo[4,3-c]pyridine-3-carboxamide | MS m/z 541 [M + H]$^+$<br>$^1$H NMR (400 MHz, DMSO-d$_6$): δ ppm 0.90 (t, 3H), 2.23 (s, 3H), 2.84 (d, 3H), 3.01 (s, 3H), 3.08 (s, 3H), 3.39 (m, 2H), 4.65 (br m, 1H), 4.90 (br m, 1H), 6.63 (s, 1H), 6.80 (d, 1H), 7.06 (d, 1H), 7.14 (m, 1H), 7.23 (m, 1H), 7.37 (m, 1H), 8.80 (m, 1H), 9.60 (m, 1H), 9.76 (s, 1H), 13.61 (br s, 1H).<br>N-[2-({[6-(2-ethyl-5-fluoro-4-{[2-(trimethylsilyl)ethoxy]methoxy}phenyl)-3-iodo-1-{[2-(trimethylsilyl)ethoxy]-methyl}-1H-pyrazolo[4,3-c]pyridin-4-yl]amino}methyl)-4-methylphenyl]-N-methylmethanesulfonamide (Preparation 80) and PM A. |
| 22 | 6-(2-ethyl-5-fluoro-4-hydroxyphenyl)-N-methyl-4-({2-[methyl(phenylsulfonyl)amino]benzyl}amino)-1H-pyrazolo[4,3-c]pyridine-3-carboxamide | MS m/z 589 [M + H]$^+$<br>$^1$H NMR (400 MHz, DMSO-d$_6$): δ ppm 0.89 (t, 3H), 3.03 (s, 3H), 3.17 (d, 3H), 3.31 (m, 2H), 4.70 (br m, 1H), 5.00 (br m, 1H), 6.56 (s, 1H), 6.64 (s, 1H), 6.79 (d, 1H), 7.05 (d, 1H), 7.16 (m, 1H), 7.28 (m, 1H), 7.44 (m, 1H), 7.59-7.67 (m, 4H), 7.73 (m, 1H), 8.80 (m, 1H), 9.66 (m, 1H), 9.75 (br s, 1H), 13.62 (br s, 1H).<br>N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)phenyl]-N-methylbenzenesulfonamide (Preparation 81) and PM B. |
| 23 | 6-(2-ethyl-5-fluoro-4-hydroxyphenyl)-N-methyl-4-[(2-{4-[(phenylsulfonyl)-amino]phenyl}ethyl)amino]-1H-pyrazolo[4,3-c]pyridine-3-carboxamide | MS m/z 589 [M + H]$^+$<br>$^1$H NMR (400 MHz, DMSO-d$_6$): δ ppm 1.01 (t, 3H), 2.69 (m, 2H), 2.78-2.83 (m, 5H), 3.61 (q, 2H), 6.60 (s, 1H), 6.85 (d, 1H), 6.98 (m, 2H), 7.12 (m, 3H), 7.48-7.57 (m, 3H), 7.72 (d, 1H), 8.73 (m, 1H), 9.25 (m, 1H), 10.13 (s, 1H), 13.55 (s, 1H).<br>N-[4-(2-{[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}ethyl)phenyl]benzenesulfonamide (Preparation 82) and PM B. |
| 24 | 6-[5-fluoro-4-hydroxy-2-(2,2,2-trifluoroethyl)phenyl]-4-({2-[(2-hydroxyethyl)-(methylsulfonyl)amino]benzyl}amino)-N-methyl-1H-pyrazolo[4,3-c]pyridine-3-carboxamide | MS m/z 611 [M + H]$^+$<br>$^1$H NMR (400 MHz, DMSO-d$_6$): δ ppm 2.85 (d, 3H), 3.08 (s, 3H), 3.32 (m, 2H), 3.55-3.64 (m, 4H), 4.76-4.93 (m, 3H), 6.70 (s, 1H), 6.93 (d, 1H), 7.21 (d, 1H), 7.30-7.36 (m, 3H), 7.46 (m, 1H), 8.84 (m, 1H), 9.73 (m, 1H), 10.08 (s, 1H), 13.71 (br s, 1H).<br>N-(2-{[(6-[5-fluoro-2-(2,2,2-trifluoroethyl)-4-{[2-(trimethylsilyl)-ethoxy]methoxy}phenyl]-3-iodo-1-{[2-(trimethylsilyl)ethoxy]methyl}-1H-pyrazolo[4,3-c]pyridin-4-yl)amino]-methyl}phenyl)-N-[2-(tetrahydro-2H-pyran-2-yloxy)ethyl]methanesulfonamide (Preparation 87) and PM B. |
| 25 (Intermediate) | 6-(2-ethyl-5-fluoro-4-hydroxyphenyl)-4-({4-methoxy-2-[methyl(methylsulfonyl)amino]benzyl}amino)-N-methyl-1H-pyrazolo[4,3-c]pyridine-3-carboxamide | MS m/z 557 [M + H]$^+$<br>$^1$H NMR (400 MHz, DMSO-d$_6$): δ ppm 0.95 (t, 3H), 2.55 (m, 2H), 2.82 (d, 3H), 3.05 (s, 3H), 3.10 (s, 3H), 3.76 (s, 3H), 4.50-4.90 (m, 2H), 6.62 (s, 1H), 6.81 (d, 1H), 6.92 (dd, 1H), 7.04-7.07 (m, 2H), 7.34 (d, 1H), 8.78 (m, 1H), 9.54 (m, 1H), 9.76 (s, 1H), 13.60 (s, 1H).<br>Using N-[2-({[6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-yl]amino}methyl)-5-methoxyphenyl]-N-methyl-methanesulfonamide (Preparation 88) and PM B. |

The following Examples (Examples 26-28) were prepared according to the method described for Example 1 using ammonia in THF and the appropriate pyrazolo-pyridine and Purification Method (PM) below if different from the method described.

Purification Method E: Silica gel column chromatography or preparative TLC eluting with 4% MeOH in DCM.

was purified using Preparative HPLC to afford the title compound (32 mg, 41%). $^1$H NMR (400 MHz, DMSO-$d_6$): δ ppm 0.94 (t, 3H), 2.59 (m, 2H), 2.81 (d, 3H), 3.02 (s, 3H), 3.07 (s, 3H), 4.69 (br m, 2H), 6.61 (s, 1H), 6.73 (dd, 1H), 6.79-6.83 (m, 2H), 7.05 (d, 1H), 7.23 (d, 1H), 8.76 (m, 1H), 9.49 (m, 1H), 9.60 (br s, 1H). MS m/z 543 [M+H]$^+$

| Example | Name | Data |
|---|---|---|
| 26 | 6-[5-fluoro-4-hydroxy-2-(2,2,2-trifluoroethyl)phenyl]-4-({2-[methyl(phenylsulfonyl)amino]benzyl}amino)-1H-pyrazolo[4,3-c]pyridine-3-carboxamide | MS m/z 629 [M + H]$^+$<br>$^1$H NMR (400 MHz, DMSO-$d_6$): δ ppm 3.03 (s, 3H), 3.70 (m, 2H), 4.68 (m, 1H), 4.92 (m, 1H), 6.60 (d, 1H), 6.71 (s, 1H), 6.97 (d, 1H), 7.13-7.29 (m, 3H), 7.44 (d, 1H), 7.59-7.75 (m, 5H), 7.86 (br s, 1H), 8.21 (br s, 1H), 9.75 (m, 1H), 10.10 (s, 1H), 13.69 (s, 1H).<br>Using N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)-ethoxy]methyl}-1H-pyrazolo[4,3-c]pyridin-4-yl)amino]-methyl}phenyl)-N-methylbenzene-sulfonamide (Preparation 86). |
| 27 | 6-[5-fluoro-4-hydroxy-2-(2,2,2-trifluoroethyl)phenyl]-4-({2-[(2-hydroxyethyl)(methylsulfonyl)amino]benzyl}amino)-1H-pyrazolo[4,3-c]pyridine-3-carboxamide | MS m/z 596 [M + H]$^+$<br>$^1$H NMR (400 MHz, DMSO-$d_6$): δ ppm 3.07 (s, 3H), 3.32 (m, 2H), 3.56-3.67 (m, 4H), 4.73-4.92 (m, 3H), 6.70 9s, 1H), 6.94 (d, 1H), 7.18 (d, 1H), 7.21-7.45 (m, 4H), 7.83 (br s, 1H), 8.19 (br s, 1H), 9.74 (m, 1H), 10.10 (br s, 1H), 13.70 (br s, 1H).<br>Using N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridin-4-yl)amino]methyl}phenyl)-N-[2-(tetrahydro-2H-pyran-2-yloxy)ethyl]methanesulfonamide (Preparation 87) and PM E. |
| 28 | 6-(2-ethyl-5-fluoro-4-hydroxyphenyl)-4-({4-methoxy-2-[methyl(methylsulfonyl)amino]benzyl}amino)-1H-pyrazolo[4,3-c]pyridine-3-carboxamide | MS m/z 543 [M + H]$^+$<br>$^1$H NMR (400 MHz, DMSO-$d_6$): δ ppm 0.95 (t, 3H), 2.59 (m, 2H), 3.04 (s, 3H), 3.16 (s, 3H), 3.31 (s, 3H), 3.76 (s, 3H), 4.65 (br m, 2H), 6.62 (s, 1H), 6.79 (d, 1H), 6.91 (d, 1H), 7.04-7.07 (m, 2H), 7.34 (d, 1H), 7.78 (br s, 1H), 8.14 (br s, 1H), 9.53 (m, 1H), 9.76 (s, 1H), 13.57 (s, 1H).<br>Using N-[2-({[6-(2-ethyl-5-fluoro-4-{[2-(trimethylsilyl)ethoxy]methoxy}phenyl)-3-iodo-1-{[2-(trimethylsilyl)-ethoxy]methyl}-1H-pyrazolo[4,3-c]pyridin-4-yl]amino}methyl)-5-methoxyphenyl]-N-methylmethanesulfonamide (Preparation 88) and PM E. |

Example 29

6-(2-Ethyl-5-fluoro-4-hydroxyphenyl)-4-({4-hydroxy-2-[methyl (methylsulfonyl)amino] benzyl}amino)-N-methyl-1H-pyrazolo[4,3-c]pyridine-3-carboxamide To a solution of 6-(2-ethyl-5-fluoro-4-hydroxyphenyl)-4-({4-methoxy-2-[methyl (methyl-sulfonyl)amino] benzyl}amino)-N-methyl-1H-pyrazolo[4,3-c]pyridine-3-carboxamide (Example 28, 80 mg, 0.14 mmol) in DCM (10 mL) was added boron tribromide (0.09 mL, 1 mmol) at 0° C. The reaction was stirred at room temperature for 2 hours before the addition of further boron tribromide (0.09 mL, 1 mmol) and further stirring for 2 hours. The reaction was partitioned between DCM and saturated aqueous sodium bicarbonate solution, the organic layer was collected, dried over sodium sulfate and concentrated in vacuo. The residue

Example 30

6-(2-Ethyl-5-fluoro-4-hydroxyphenyl)-4-({4-hydroxy-2-[methyl(methylsulfonyl)amino] benzyl}amino)-1H-pyrazolo[4,3-c]pyridine-3-carboxamide The title compound was prepared according to the method described for Example 29 using 6-(2-ethyl-5-fluoro-4-hydroxyphenyl)-4-({4-methoxy-2-[methyl(methylsulfonyl) amino]-benzyl}amino)-1H-pyrazolo[4,3-c]pyridine-3-carboxamide (Example 27). $^1$H NMR (400 MHz, DMSO-$d_6$): δ ppm 0.96 (t, 3H), 2.60 (m, 2H), 3.01 (s, 3H), 3.08 (s, 3H), 4.65 (br m, 2H), 6.61 (s, 1H), 6.74 (dd, 1H), 6.80-6.83 (m, 2H), 7.09 (d, 1H), 7.25 (d, 1H), 7.77 (br s, 1H), 8.13 (br s, 1H), 9.49 (m, 1H), 9.56 (s, 1H), 9.76 (s, 1H), 13.56 (s, 1H). MS m/z 529 [M+H]$^+$

Example 31

6-(2-Ethyl-5-fluoro-4-hydroxyphenyl)-4-({5-hydroxy-2-[methyl (methylsulfonyl)amino] benzyl}amino)-N-methyl-1H-pyrazolo[4,3-c]pyridine-3-carboxamide To a solution of N-[2-({[6-(2-ethyl-5-fluoro-4-{[2-(trimethylsilyl)-ethoxy]meth-oxy}phenyl)-3-iodo-1-{[2-(trimethylsilyl)ethoxy]methyl}-1H-pyrazolo[4,3-c]-pyridin-4-yl]-amino}methyl)-4-methoxyphenyl]-N-methylmethanesulfonamide (Preparation 83, 250 mg, 0.28 mmol) in 2M methylamine in THF (3 mL) was added DBU (0.13 mL, 0.85 mmol), palladium acetate (4.43 mg, 0.02 mmol) and molybdenum hexacarbonyl (75 mg, 0.28 mmol) and the reaction was heated to 100° C. for 10 minutes under microwave irradiation. The reaction was cooled, concentrated in vacuo and purified directly using silica gel column chromatography eluting with 45% EtOAc in hexanes. The resulting oil was dissolved in DCM (15 mL) and cooled to 0° C. BBr$_3$ (0.10 mL, 1.07 mmol) was added and the reaction stirred at room temperature for 6 hours. The reaction was concentrated in vacuo and partitioned between saturated aqueous sodium bicarbonate solution and EtOAc. The organic layer was collected, dried over sodium sulfate and concentrated in vacuo. The residue was purified using preparative TLC eluting with 5% MeOH in DCM to afford the title compound as a white solid (43 mg, 27% over two steps). $^1$H NMR (400 MHz, DMSO-d$_6$): δ ppm 0.88 (t, 3H), 2.84 (d, 3H), 2.98 (s, 3H), 3.05 (s, 3H), 3.31 (m, 2H), 4.61 (m, 1H), 4.86 (m, 1H), 6.66 (m, 2H), 6.78 (m, 2H), 7.05 (d, 1H), 7.26 (d, 1H), 8.80 (m, 1H), 9.51 (s, 1H), 9.59 (m, 1H), 9.74 (s, 1H), 13.62 (s, 1H). MS m/z 543 [M+H]$^+$

Example 32

6-[5-Fluoro-4-hydroxy-2-(2,2,2-trifluoroethyl)phenyl]-4-[(2-{[(3-hydroxyphenyl) sulfonyl](methyl)amino}benzyl)amino]-N-methyl-1H-pyrazolo[4,3-c]pyridine-3-carboxamide To a solution of N-(2-{[(6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridin-4-yl)amino]methyl}-phenyl)-3-methoxy-N-methylbenzenesulfonamide (Preparation 106, 330 mg, 0.37 mmol) in 2M methylamine in THF (2 mL) was added DBU (0.16 mL, 1.19 mmol), palladium acetate (5.86 mg, 0.03 mmol) and molybdenum hexacarbonyl (99 mg, 0.37 mmol) and the reaction was heated to 100° C. for 10 minutes under microwave irradiation. The reaction was cooled, concentrated in vacuo and purified using silica gel column chromatography eluting with 35% EtOAc in hexanes. The resulting oil was treated with TFA (0.5 mL) and the solution stirred at room temperature for 30 minutes before concentrating in vacuo. Ethylene diamine (0.5 mL) was added and the reaction stirred at room temperature for 15 minutes before pouring onto ice-water and extracting into 20% IPA in DCM. The organic layer was collected, dried over sodium sulfate and concentrated in vacuo. The residue was purified using silica gel column chromatography eluting with 45% EtOAc in hexanes. The residue was dissolved in DCM (10 mL) and boron tribromide (0.18 mL, 1.89 mmol) was added dropwise at 0° C. The reaction was stirred at room temperature for 2 hours followed by quenching with saturated aqueous sodium bicarbonate solution and extracting into 20% IPA in DCM. The organic layer was collected, dried over sodium sulfate and concentrated in vacuo. The residue was purified using silica gel column chromatography followed by preparative TLC eluting both with 57% EtOAc in hexanes to afford the title compound as a yellow solid (25 mg, 10% over 3 steps).

$^1$H NMR (400 MHz, DMSO-d$_6$): δ ppm 2.85 (d, 3H), 3.01 (s, 3H), 3.59-3.65 (m, 2H), 4.71 (m, 1H), 4.95 (m, 1H), 6.63 (d, 1H), 6.71 (s, 1H), 6.96 (d, 1H), 7.02 (m, 1H), 7.09 (m, 2H), 7.14-7.29 (m, 3H), 7.41 (m, 2H), 8.86 (m, 1H), 9.78 (m, 1H), 10.10 (s, 1H), 10.15 (s, 1H), 13.71 (s, 1H). MS m/z 659 [M+H]$^+$ The following Examples (Examples 33-37) were prepared according to the method described for Example 32 using the appropriate pyrazolo-pyridine, and Purification Method (PM) below if different from the method described:
Purification Method F: Silica gel column chromatography or preparative TLC eluting with 4% MeOH in DCM.

| Ex | Name | Data |
|---|---|---|
| 33 | 6-[5-fluoro-4-hydroxy-2-(2,2,2-trifluoroethyl)phenyl]-4-({4-hydroxy-2-[methyl(methylsulfonyl)amino]benzyl}amino)-N-methyl-1H-pyrazolo[4,3-c]pyridine-3-carboxamide | MS m/z 597 [M + H]$^+$<br>$^1$H NMR (400 MHz, DMSO-d$_6$): δ ppm 2.83 (d, 3H), 3.02 (s, 3H), 3.17 (s, 3H), 3.77 (m, 2H), 4.70 (br m, 2H), 6.69-6.73 (m, 2H), 6.83 (m, 1H), 6.97 (m, 1H), 7.20-7.25 (m, 2H), 8.80 (m, 1H), 9.56 (s, 1H), 9.60 (m, 1H), 10.10 (s, 1H), 13.67 (s, 1H).<br>Using N-(2-{[(6-[5-fluoro-2-(2,2,2-trifluoroethyl)-4-{[2-(trimethylsilyl)-ethoxy]methoxy}phenyl]-3-iodo-1-{[2-(trimethylsilyl)-ethoxy]methyl}-1H-pyrazolo[4,3-c]pyridin-4-yl)amino]methyl}-5-methoxyphenyl)-N-methylmethane-sulfonamide (Preparation 89). |
| 34 | 4-({2-[ethyl(methylsulfonyl)amino]-5-hydroxybenzyl}amino)-6-[5-fluoro-4-hydroxy-2-(2,2,2-trifluoroethyl)phenyl]-N-methyl-1H-pyrazolo[4,3-c]pyridine-3-carboxamide | MS m/z 611 [M + H]$^+$<br>$^1$H NMR (400 MHz, DMSO-d$_6$): δ ppm 0.90 (t, 3H), 2.88 (d, 3H), 2.96 (s, 3H), 3.39-3.51 (m, 2H), 3.54-3.68 (m, 2H), 4.60 (m, 1H), 4.80 (m, 1H), 6.66 (m, 1H), 6.69 (s, 1H), 6.78 (s, 1H), 6.93 (d, 1H), 7.20 (m, 2H), 7.95 (br s, 1H), 8.85 (m, 1H), 9.50 (s, 1H), 9.70 (m, 1H), 10.07 (br s, 1H), 13.71 (br s, 1H).<br>Using N-ethyl-N-(2-{[(6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridin-4-yl)amino]methyl}-4-methoxyphenyl)methanesulfonamide (Preparation 107). |
| 35 | 6-[5-fluoro-4-hydroxy-2-(2,2,2-trifluoroethyl)phenyl]-4-({5-hydroxy- | MS m/z 659 [M + H]$^+$<br>$^1$H NMR (400 MHz, DMSO-d$_6$): δ ppm 2.86 (d, 3H), 2.97 (s, 3H), 3.63 (m, 2H), 4.58 (m, 1H), 4.86 (m, |

| Ex | Name | Data |
|---|---|---|
|  | 2-[methyl(phenylsulfonyl)amino]benzyl}amino)-N-methyl-1H-pyrazolo[4,3-c]pyridine-3-carboxamide | 1H), 6.34 (m, 1H), 6.47 (m, 1H), 6.71 (s, 1H), 6.77 (s, 1H), 6.93 (d, 1H), 7.23 (d, 1H), 7.58-7.73 (m, 5H), 8.85 (m, 1H), 9.51 (s, 1H), 9.71 (m, 1H), 10.07 (s, 1H), 13.70 (s, 1H).<br>Using N-(2-{[(6-[5-fluoro-4-methoxy-2-(2,2,2-trifluoroethyl)phenyl]-3-iodo-1-{[2-(trimethylsilyl)ethoxy]-methyl}-1H-pyrazolo[4,3-c]pyridin-4-yl)amino]methyl}-4-methoxy-phenyl)-N-methyl-benzene-sulfonamide (Preparation 108). |
| 36 | 4-({2-[ethyl(phenylsulfonyl)amino]-5-hydroxybenzyl}amino)-6-[5-fluoro-4-hydroxy-2-(2,2,2-trifluoroethyl)phenyl]-N-methyl-1H-pyrazolo[4,3-c]pyridine-3-carboxamide | MS m/z 673 [M + H]$^+$<br>$^1$H NMR (400 MHz, DMSO-d$_6$): δ ppm 0.85 (t, 3H), 2.86 (d, 3H), 3.22 (m, 1H), 3.53 (m, 1H), 3.68 (m, 2H), 4.52 (m, 1H), 4.81 (m, 1H), 6.41 (d, 1H), 6.48 (dd, 1H), 6.70 (s, 1H), 6.78 (d, 1H), 6.94 (d, 1H), 7.21 (d, 1H), 7.56-7.70 (m, 5H), 8.83 (m, 1H), 9.52 (s, 1H), 9.67 (m, 1H), 10.06 (s, 1H), 13.71 (s, 1H).<br>Using N-ethyl-N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]-methyl}-1H-pyrazolo[4,3-c]pyridin-4-yl)amino]methyl}-4-methoxyphenyl)benzenesulfonamide (Preparation 90). |
| 37 | 6-(2-cyclopropyl-5-fluoro-4-hydroxyphenyl)-N-methyl-4-({2-[methyl(methylsulfonyl)amino]benzyl}amino)-1H-pyrazolo[4,3-c]pyridine-3-carboxamide | MS m/z 538 [M + H]$^+$<br>$^1$H NMR (400 MHz, DMSO-d$_6$): δ ppm 0.45 (m, 2H), 0.61 (m, 2H), 2.09 (m, 1H), 2.84 (s, 3H), 3.06 (s, 3H), 3.14 (s, 3H), 4.70 (br m, 1H), 5.00 (br m, 1H), 6.46 (m, 1H), 6.79 (s, 1H), 7.70 (m, 1H), 7.31 (m, 2H), 7.41 (m, 1H), 7.50 (m, 1H), 8.78 (m, 1H), 9.62 (m, 1H), 9.73 (m, 1H), 13.61 (m, 1H).<br>Using N-[2-({[6-(2-cyclopropyl-5-fluoro-4-methoxyphenyl)-3-iodo-1-{[2-(trimethylsilyl)ethoxy]methyl}-1H-pyrazolo[4,3-c]pyridin-4-yl]amino}methyl)phenyl]-N-methylmethanesulfonamide (Preparation 109) and PM F. |

Examples 38 and 39

6-(2-Ethyl-5-fluoro-4-hydroxyphenyl)-N-methyl-4-{[(1R)-1-{2-[methyl(methylsulfonyl)amino]phenyl}ethyl]amino}-1H-pyrazolo[4,3-c]pyridine-3-carboxamide and 6-(2-Ethyl-5-fluoro-4-hydroxyphenyl)-N-methyl-4-{[(1S)-1-{2-[methyl(methylsulfonyl)amino]phenyl}ethyl]amino}-1H-pyrazolo[4,3-c]pyridine-3-carboxamide The title compounds were prepared according to the method described for Example 1 using racemic N-[2-(1-([6-(2-ethyl-5-fluoro-4-{[2-(trimethylsilyl)ethoxy]-methoxy}phenyl)-3-iodo-1-{[2-(trimethyl-silyl)ethoxy]methyl}-1H-pyrazolo[4,3-c]pyridin-4-yl]amino)ethyl)phenyl]-N-methylmethanesulfonamide (Preparation 84). The residue was purified using silica gel column chromatography eluting with 6% MeOH in DCM followed by chiral separation using chiral preparative HPLC to afford the separated enantiomers.

Fraction 1: 44 mg, 100% ee, registered as (R)—enantiomer Example 38

$^1$H NMR (400 MHz, DMSO-d$_6$): δ ppm 0.86 (t, 3H), 1.53 (d, 3H), 2.21 (m, 2H), 2.83 (s, 3H), 2.90 (d, 3H), 3.08 (s, 3H), 5.47 (m, 1H), 6.50 (s, 1H), 6.73 (m, 2H), 7.21-7.45 (m, 4H), 8.82 (m, 1H), 9.69 (br s, 1H), 9.86 (m, 1H), 13.57 (br s, 1H). MS m/z 541 [M+H]$^+$ Fraction 2: 41 mg, 87.5% ee, registered as (S)—enantiomer Example 39

$^1$H NMR (400 MHz, DMSO-d$_6$): δ ppm 0.86 (t, 3H), 1.53 (d, 3H), 2.21 (m, 2H), 2.83 (s, 3H), 2.90 (d, 3H), 3.08 (s, 3H), 5.47 (m, 1H), 6.50 (s, 1H), 6.73 (m, 2H), 7.21-7.45 (m, 4H), 8.82 (m, 1H), 9.69 (br s, 1H), 9.86 (m, 1H), 13.57 (br s, 1H). MS m/z 541 [M+H]$^+$

Example 40

6-(2-Ethyl-5-fluoro-4-hydroxyphenyl)-4-({2-[methyl(phenylsulfonyl)amino]benzyl}amino)-1H-pyrazolo[4,3-c]pyridine-3-carboxamide To a solution of N-[2-({[6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-yl]amino}methyl)phenyl]-N-methylbenzenesulfonamide (Preparation 81, 400 mg, 0.44 mmol) in MeOH (2 mL) was added DBU (0.20 mL, 1.31 mmol), palladium acetate (6.85 mg, 0.03 mmol) and molybdenum hexacarbonyl (115 mg, 0.44 mmol) and the reaction was heated to 125° C. under microwave irradiation for 20 minutes. The reaction was cooled, concentrated in vacuo and purified using silica gel column chromatography eluting with 70% EtOAc in hexanes. The residue was dissolved in THF (4 mL) and cooled to −20° C. NMM (0.021 mL, 0.19 mmol) followed by isobutylchloroformate (0.03 mL, 0.19 mmol) were added and the reaction stirred at this temperature for 2 hours. Aqueous ammonia was then added and the reaction stirred at room temperature for 1 hour. The reaction was quenched by the addition of water and extracted into EtOAc. The organic layer was collected, dried over sodium sulfate and concentrated in vacuo. The residue was purified using silica gel column chromatography eluting with 40% EtOAc in hexanes. The residue was treated with TFA (2 mL) and stirred for 2 hours before concentrating in vacuo. Ethylene diamine (0.5 mL) was added and the reaction stirred at room temperature for 1 hour before concentrating in vacuo, pouring onto ice-water and extracting into EtOAc. The organic layer was collected, dried over sodium sulfate and concentrated in vacuo. The residue was purified using Preparative TLC eluting with 60% EtOAc in hexanes to afford the title compound (23 mg, 10% over 3 steps).

¹H NMR (400 MHz, DMSO-$d_6$): δ ppm 0.92 (t, 3H), 3.04 (s, 3H), 3.40 (m, 2H), 4.70 (br m, 1H), 5.00 (br m, 1H), 6.55 (d, 1H), 6.64 (s, 1H), 6.80 (d, 1H), 7.06 (m, 1H), 7.14 (m, 1H), 7.29 (m, 1H), 7.47 (m, 1H), 7.59-7.67 (m, 4H), 7.73 (m, 1H), 7.83 (br s, 1H), 8.18 (br s, 1H), 9.65 (m, 1H), 9.77 (s, 1H), 13.60 (br s, 1H). MS m/z 575 [M+H]⁺

Example 41

6-[5-Fluoro-4-hydroxy-2-(2,2,2-trifluoroethyl)phenyl]-4-({4-hydroxy-2-[methyl(methylsulfonyl)amino]benzyl}amino)-1H-pyrazolo[4,3-c]pyridine-3-carboxamide A solution of 6-[5-fluoro-2-(2,2,2-trifluoroethyl)-4-{[2-(trimethyl-silyl)ethoxy]methoxy}phenyl]-4-({4-methoxy-2-[methyl(methylsulfonyl)amino]-benzyl}-amino)-1-{[2-(trimethylsilyl)ethoxy]-methyl}-1H-pyrazolo[4,3-c]pyridine-3-carboxamide (Preparation 21, 102 mg, 0.15 mmol) in TFA (5 mL) was stirred at room temperature for 30 minutes before concentrating in vacuo. Ethylene diamine (0.5 mL) was added and the reaction stirred at room temperature for 15 minutes before concentrating in vacuo, pouring onto ice-water and extracting into EtOAc. The organic layer was collected, dried over sodium sulfate and concentrated in vacuo. The residue was purified using preparative TLC to afford a white solid. The solid was dissolved in DCM (5 mL) and boron tribromide (0.108 mL, 1.14 mmol) was added dropwise at 0° C. and stirred at room temperature for 2 hours. The reaction was washed with saturated aqueous sodium bicarbonate solution, the organic layer collected, washed with brine, dried over sodium sulfate and concentrated in vacuo. The residue was purified using preparative TLC eluting with 5% MeOH in DCM to afford the title compound (37 mg, 54%). ¹H NMR (400 MHz, DMSO-$d_6$): δ ppm 3.02 (s, 3H), 3.08 (s, 3H), 3.79 (m, 2H), 4.65 (br m, 2H), 6.69-6.73 (m, 2H), 6.83 (m, 1H), 6.99 (d, 1H), 7.20-7.25 (m, 2H), 7.81 (s, 1H), 8.17 (s, 1H), 9.59 (m, 2H), 10.10 (br s, 1H), 13.70 (br s, 1H). MS m/z 583 [M+H]⁺

The following Examples (Examples 42-54) were prepared according to the method described for Example 41 using the appropriate pyrazolo-pyridine, and Purification Method (PM) as described below if different from the method described:

Purification Method G: Silica gel column chromatography eluting with 5-7% MeOH in DCM followed by preparative HPLC.

| Ex | Name | Data |
|---|---|---|
| 42 | 6-[5-fluoro-4-hydroxy-2-(2,2,2-trifluoroethyl)phenyl]-4-({5-hydroxy-2-[methyl(phenylsulfonyl)amino]benzyl}amino)-1H-pyrazolo[4,3-c]pyridine-3-carboxamide | MS m/z 645 [M + H]⁺<br>¹H NMR (400 MHz, DMSO-$d_6$): δ ppm 2.98 (s, 3H), 3.69 (m, 2H), 4.57 (m, 1H), 4.83 (m, 1H), 6.35 (m, 1H), 6.47 (m, 1H), 6.71 (s, 1H), 6.79 (d, 1H), 6.96 (d, 1H), 7.24 (d, 1H), 7.58-7.73 (m, 5H), 7.87 (br s, 1H), 8.22 (br s, 1H), 9.53 (s, 1H), 9.71 (m, 1H), 10.09 (s, 1H), 13.69 (s, 1H).<br>Using 6-[5-fluoro-4-methoxy-2-(2,2,2-trifluoroethyl)phenyl]-4-({5-methoxy-2-[methyl(phenylsulfonyl)amino]benzyl}amino)-1-{[2-(trimethylsilyl)ethoxy]methyl}-1H-pyrazolo[4,3-c]pyridine-3-carboxamide (Preparation 24). |
| 43 | 4-({2-[ethyl(phenylsulfonyl)amino]-5-hydroxybenzyl}amino)-6-[5-fluoro-4-hydroxy-2-(2,2,2-trifluoroethyl)phenyl]-1H-pyrazolo[4,3-c]pyridine-3-carboxamide | MS m/z 657 [M − H]⁻<br>¹H NMR (400 MHz, DMSO-$d_6$): δ ppm 0.85 (t, 3H), 3.23 (m, 1H), 3.67 (m, 1H), 3.70 (m, 2H), 4.50 (m, 1H), 4.79 (m, 1H), 6.40 (m, 1H), 6.50 (m, 1H), 6.70 (s, 1H), 6.80 (s, 1H), 6.95 (d, 1H), 7.22 (d, 1H), 7.55-7.68 (m, 5H), 7.85 (br s, 1H), 8.20 (br s, 1H), 9.52 (s, 1H), 9.68 (m, 1H), 10.05 (s, 1H), 13.67 (br s, 1H).<br>Using N-ethyl-N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)-ethoxy]methyl}-1H-pyrazolo[4,3-c]pyridin-4-yl)amino]methyl}-4-methoxyphenyl)benzenesulfonamide (Preparation 25). |
| 44 | 6-[5-fluoro-4-hydroxy-2-(2,2,2-trifluoroethyl)phenyl]-N-methyl-4-[({3-[methyl(phenylsulfonyl)amino]pyrazin-2-yl}methyl)amino]-1H-pyrazolo[4,3-c]pyridine-3-carboxamide | MS m/z 645 [M + H]⁺<br>¹H NMR (400 MHz, DMSO-$d_6$): δ ppm 2.87 (m, 6H), 3.62 (m, 2H), 5.06 (m, 2H), 6.68 (s, 1H), 6.97 (d, 1H), 7.15 (d, 1H), 7.61 (m, 4H), 7.73 (m, 1H), 8.33 (s, 1H), 8.58 (s, 1H), 8.78 (m, 1H), 9.89 (m, 1H), 10.08 (s, 1H), 13.67 (s, 1H).<br>Using 6-[5-fluoro-4-methoxy-2-(2,2,2-trifluoroethyl)phenyl]-N-methyl-4-[({3-[methyl(phenylsulfonyl)amino]pyrazin-2-yl}methyl)amino]-1-{[2-(trimethylsilyl)ethoxy]methyl}-1H-pyrazolo[4,3-c]pyridine-3-carboxamide (Preparation 39). |
| 45 | 4-[({3-[ethyl(methylsulfonyl)-amino]pyrazin-2-yl}methyl)amino]-6-[5-fluoro-4-hydroxy-2-(2,2,2-trifluoroethyl)phenyl]-N-methyl-1H-pyrazolo[4,3-c]pyridine-3-carboxamide | MS m/z 597 [M + H]⁺<br>¹H NMR (400 MHz, DMSO-$d_6$): δ ppm 0.85 (t, 3H), 2.85 (d, 3H), 3.10 (s, 3H), 3.49 (q, 2H), 3.69 (q, 2H), 4.99 (m, 2H), 6.68 (s, 1H), 6.95 (d, 1H), 7.10 (d, 1H), 8.54 (s, 1H), 8.61 (s, 1H), 8.79 (m, 1H), 9.82 (m, 1H), 10.07 (s, 1H), 13.67 (s, 1H).<br>Using 4-[({3-[ethyl(methylsulfonyl)amino]pyrazin-2-yl}methyl)amino]-6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide (Preparation 40) and PM G. |

-continued

| Ex | Name | Data |
| --- | --- | --- |
| 46 | N-ethyl-4-[({3-[ethyl(methylsulfonyl)amino]pyrazin-2-yl}methyl)amino]-6-[5-fluoro-4-hydroxy-2-(2,2,2-trifluoroethyl)phenyl]-1H-pyrazolo[4,3-c]pyridine-3-carboxamide | MS m/z 611 [M + H]$^+$<br>$^1$H NMR (400 MHz, DMSO-d$_6$): δ ppm 0.86 (t, 3H), 1.14 (t, 3H), 3.35 (m, 2H), 3.53 (m, 2H), 3.67 (m, 2H), 4.99 (m, 2H), 6.68 (s, 1H), 6.94 (d, 1H), 7.13 (d, 1H), 8.54 (s, 1H), 8.60 (s, 1H), 8.83 (m, 1H), 9.81 (m, 1H), 10.07 (s, 1H), 13.68 (s, 1H).<br>Using N-ethyl-4-[({3-[ethyl(methylsulfonyl)amino]pyrazin-2-yl}methyl)amino]-6-[5-fluoro-4-methoxy-2-(2,2,2-trifluoroethyl)phenyl]-1-{[2-(trimethylsilyl)ethoxy]methyl}-1H-pyrazolo[4,3-c]pyridine-3-carboxamide (Preparation 41). |
| 47 | 6-(2-cyclopropyl-5-fluoro-4-hydroxyphenyl)-4-({2-[methyl(methylsulfonyl)amino]benzyl}amino)-1H-pyrazolo[4,3-c]pyridine-3-carboxamide | MS m/z 525 [M + H]$^+$<br>$^1$H NMR (400 MHz, DMSO-d$_6$): δ ppm 0.46 (m, 2H), 0.65 (m, 2H), 2.09 (m, 1H), 3.05 (s, 3H), 3.14 (s, 3H), 4.70 (br m, 1H), 5.00 (br m, 1H), 6.45 (d, 1H), 6.80 (s, 1H), 7.09 (d, 1H), 7.32 (m, 2H), 7.45 (m, 2H), 7.81 (s, 1H), 8.16 (s, 1H), 9.62 (m, 1H), 9.73 (s, 1H), 13.59 (br s, 1H).<br>Using 6-(2-cyclopropyl-5-fluoro-4-methoxyphenyl)-4-({2-[methyl(methylsulfonyl)amino]benzyl}amino)-1-{[2-(trimethylsilyl)ethoxy]methyl}-1H-pyrazolo[4,3-c]pyridine-3-carboxamide (Preparation 26) and PM G. |
| 48 | 6-[5-fluoro-4-hydroxy-2-(2,2,2-trifluoroethyl)phenyl]-N-methyl-4-[({4-[methyl(methylsulfonyl)amino]pyridin-3-yl}methyl)amino]-1H-pyrazolo[4,3-c]pyridine-3-carboxamide | MS m/z 582 [M + H]$^+$<br>$^1$H NMR (400 MHz, DMSO-d$_6$): δ ppm 2.83 (s, 3H), 2.90 (s, 3H), 3.70 (s, 3H), 3.85 (m, 2H), 4.47 (m, 2H), 6.72 (s, 1H), 7.00 (d, 1H), 7.20-7.26 (m, 2H), 7.77 (s, 1H), 7.87 (m, 1H), 8.78 (m, 1H), 9.67 (m, 1H), 10.13 (s, 1H), 13.67 (s, 1H).<br>Using 6-[5-fluoro-4-methoxy-2-(2,2,2-trifluoroethyl)phenyl]-N-methyl-4-[({4-[methyl(methylsulfonyl)amino]pyridin-3-yl}methyl)amino]-1-{[2-(trimethylsilyl)ethoxy]methyl}-1H-pyrazolo[4,3-c]pyridine-3-carboxamide (Preparation 42). |
| 49 | 6-(2-cyclopropyl-5-fluoro-4-hydroxyphenyl)-N-methyl-4-[({2-[methyl(methylsulfonyl)amino]pyridin-3-yl}methyl)amino]-1H-pyrazolo[4,3-c]pyridine-3-carboxamide | MS m/z 540 [M + H]$^+$<br>$^1$H NMR (400 MHz, DMSO-d$_6$): δ ppm 0.45 (m, 2H), 0.61 (m, 2H), 2.00 (m, 1H), 2.84 (d, 3H), 3.11 (s, 6H), 4.85 (m, 2H), 6.46 (m, 2H), 6.81 (s, 1H), 7.02 (d, 1H), 7.37 (m, 1H), 7.83 (d, 1H), 8.40 (m, 1H), 8.80 (m, 1H), 9.69-9.73 (m, 2H), 13.64 (s, 1H).<br>Using 6-(2-cyclopropyl-5-fluoro-4-methoxyphenyl)-N-methyl-4-[({2-[methyl(methylsulfonyl)amino]pyridin-3-yl}methyl)amino]-1-{[2-(trimethylsilyl)ethoxy]methyl}-1H-pyrazolo[4,3-c]pyridine-3-carboxamide (Preparation 110). |
| 50 | 6-[5-fluoro-4-hydroxy-2-(2,2,2-trifluoroethyl)phenyl]-4-({5-methoxy-2-[methyl(methylsulfonyl)amino]benzyl}amino)-N-methyl-1H-pyrazolo[4,3-c]pyridine-3-carboxamide | MS m/z 597 [M + H]$^+$<br>$^1$H NMR (400 MHz, DMSO-d$_6$): δ ppm 2.86 (d, 3H), 2.98 (s, 3H), 3.04 (s, 3H), 3.64 (m, 2H), 4.61 (m, 1H), 4.82 (m, 1H), 6.63 (dd, 1H), 6.70 (s, 1H), 6.76 (m, 1H), 6.95 (d, 1H), 7.19-7.27 (m, 2H), 8.84 (m, 1H), 9.50 (s, 1H), 9.70 (m, 1H), 10.09 (s, 1H), 13.70 (s, 1H).<br>Using 6-[5-fluoro-2-(2,2,2-trifluoroethyl)-4-{[2-(trimethylsilyl)ethoxy]methoxy}phenyl]-4-({5-methoxy-2-[methyl(methylsulfonyl)amino]benzyl}amino)-N-methyl-1-{[2-(trimethylsilyl)ethoxy]methyl}-1H-pyrazolo[4,3-c]pyridine-3-carboxamide (Preparation 46). |
| 51 | 6-[5-fluoro-4-hydroxy-2-(2,2,2-trifluoroethyl)phenyl]-N-methyl-4-[({3-[methyl(methylsulfonyl)amino]pyrazin-2-yl}methyl)amino]-1H-pyrazolo[4,3-c]pyridine-3-carboxamide | MS m/z 583 [M + H]$^+$<br>$^1$H NMR (400 MHz, DMSO-d$_6$): δ ppm 2.86 (d, 3H), 3.06 (s, 3H), 3.13 (s, 3H), 3.60 (m, 2H), 4.95 (m, 2H), 6.68 (s, 1H), 6.96 (d, 1H), 7.16 (d, 1H), 8.49 (s, 1H), 8.59 (s, 1H), 8.80 (m, 1H), 9.85 (m, 1H), 10.10 (s, 1H), 13.68 (s, 1H).<br>Using 6-[5-fluoro-4-methoxy-2-(2,2,2-trifluoroethyl)phenyl]-N-methyl-4-[({3-[methyl(methylsulfonyl)amino]pyrazin-2-yl}methyl)amino]-1-{[2-(trimethylsilyl)ethoxy]methyl}-1H-pyrazolo[4,3-c]pyridine-3-carboxamide (Preparation 47). |
| 52 | 4-[({2-[ethyl(methylsulfonyl)-amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide | MS m/z 582 [M + H]$^+$<br>$^1$H NMR (400 MHz, DMSO-d$_6$): δ ppm 0.86 (t, 3H), 3.07 (s, 3H), 3.55-3.67 (m, 4H), 4.84 (m, 2H), 6.72 (s, 1H), 6.95 (d, 1H), 7.19 (d, 1H), 7.38 (m, 1H), 7.82 (d, 1H), 7.87 (br s, 1H), 8.22 (br s, 1H), 8.44 (m, 1H), 9.80 (m, 1H), 10.07 (s, 1H), 13.71 (s, 1H).<br>Using N-(2,4-dimethoxybenzyl)-4-[({2-[ethyl(methylsulfonyl)-amino]pyridin-3-yl}methyl)amino]-6-[5-fluoro-4-methoxy-2-(2,2,2-trifluoroethyl)phenyl]-1-{[2-(trimethylsilyl)ethoxy]methyl}-1H-pyrazolo[4,3-c]pyridine-3-carboxamide (Preparation 52). |
| 53 | 6-[5-fluoro-4-hydroxy-2-(2,2,2-trifluoroeth- | MS m/z 582 [M + H]$^+$<br>$^1$H NMR (400 MHz, DMSO-d$_6$): δ ppm 2.86 (d, 3H), |

| Ex | Name | Data |
|---|---|---|
| | yl)phenyl]-N-methyl-4-[({2-[methyl(methylsulfonyl)amino]pyridin-3-yl}methyl)amino]-1H-pyrazolo[4,3-c]pyridine-3-carboxamide | 3.08 (s, 3H), 3.12 (s, 3H), 3.62 (q, 2H), 4.83 (m, 2H), 6.73 (s, 1H), 6.95 (d, 1H), 7.21 (d, 1H), 7.36 (m, 1H), 7.79 (d, 1H), 8.41 (m, 1H), 8.85 (m, 1H), 9.80 (m, 1H), 10.10 (s, 1H), 13.73 (s, 1H). Using 6-[5-fluoro-4-methoxy-2-(2,2,2-trifluoroethyl)phenyl]-N-methyl-4-[({2-[methyl(methylsulfonyl)amino]pyridin-3-yl}methyl)amino]-1-{[2-(trimethylsilyl)ethoxy]methyl}-1H-pyrazolo[4,3-c]pyridine-3-carboxamide (Preparation 53). |
| 54 | 6-[5-fluoro-4-hydroxy-2-(2,2,2-trifluoroethyl)phenyl]-4-({5-hydroxy-2-[methyl(pyridin-3-ylsulfonyl)amino]benzyl}amino)-N-methyl-1H-pyrazolo[4,3-c]pyridine-3-carboxamide | MS m/z 660 [M + H]$^+$<br>$^1$H NMR (400 MHz, DMSO-d$_6$): δ ppm 2.86 (d, 3H), 3.02 (s, 3H), 3.61 (m, 2H), 4.61 (m, 1H), 4.83 (m, 1H), 6.39 (d, 1H), 6.50 (m, 1H), 6.71 (s, 1H), 6.80 (m, 1H), 6.95 (d, 1H), 7.16-7.24 (m, 2H), 7.65 (m, 1H), 8.06 (m, 1H), 8.78 (s, 1H), 8.87 (m, 1H), 9.57 (s, 1H), 9.74 (m, 1H), 10.08 (s, 1H), 13.71 (br s, 1H). Using 6-[5-fluoro-4-methoxy-2-(2,2,2-trifluoroethyl)phenyl]-4-({5-methoxy-2-[methyl(pyridin-3-ylsulfonyl)amino]benzyl}amino)-N-methyl-1-{[2-(trimethylsilyl)-ethoxy]methyl}-1H-pyrazolo[4,3-c]pyridine-3-carboxamide (Preparation 54). |

Example 55

6-[5-Fluoro-4-hydroxy-2-(2,2,2-trifluoroethyl)phenyl]-N-methyl-4-[({3-[methyl(methylsulfonyl)amino]pyridin-2-yl}methyl)amino]-1H-pyrazolo[4,3-c]pyridine-3-carboxamide A solution of 6-[5-fluoro-2-(2,2,2-trifluoroethyl)-4-{[2-(trimethylsilyl)ethoxy]methoxy}phenyl]-N-methyl-4-[({3-[methyl(methylsulfonyl)amino]pyridin-2-yl}methyl)amino]-1-{[2-(trimethylsilyl)-ethoxy]methyl}-1H-pyrazolo[4,3-c]pyridine-3-carboxamide (Preparation 43, 110 mg, 0.13 mmol) in TFA (5 mL) was stirred at room temperature for 30 minutes. The reaction was concentrated in vacuo, dissolved in MeOH and cooled in ice-water. Ethylene diamine was added dropwise and stirred for 1 hour. The reaction was quenched by the addition of water and extracted into EtOAc. The organic layer was collected, dried over sodium sulfate and concentrated in vacuo. The residue was purified using Preparative HPLC to afford the title compound (18 mg, 26%). $^1$H NMR (400 MHz, DMSO-d$_6$): δ ppm 2.84 (d, 3H), 3.07 (s, 6H), 3.61 (m, 2H), 4.70-5.20 (br m, 2H), 6.66 (s, 1H), 6.94 (d, 1H), 7.16 (d, 1H), 7.37 (m, 1H), 7.92 (m, 1H), 8.47 (m, 1H), 9.77 (m, 1H), 10.08 (br s, 1H), 13.63 (br s, 1H). MS m/z 582 [M+H]$^+$ The following Examples (Examples 56-73) were prepared according to the method described for Example 55 using the appropriate pyrazolo-pyridine and Purification Method below if different from the method described Purification Method H: Preparative TLC.
Purification Method I: Preparative HPLC.

| Ex | Name | Data |
|---|---|---|
| 56 | 6-(2-ethyl-5-fluoro-4-hydroxy-phenyl)-4-({2-[methyl(methylsulfonyl)amino]benzyl}amino)-N-(6-methylpyridin-3-yl)-1H-pyrazolo[4,3-c]pyridine-3-carboxamide | MS m/z 604 [M + H]$^+$<br>$^1$H NMR (400 MHz, DMSO-d$_6$): δ ppm 0.89 (t, 3H), 2.44 (s, 3H), 3.04 (s, 3H), 3.11 (s, 3H), 3.32 (m, 2H), 4.75 (m, 1H), 5.00 (m, 1H), 6.70 (s, 1H), 6.78 (d, 1H), 7.06 (d, 1H), 7.24-7.32 (m, 3H), 7.42-7.49 (m, 2H), 8.13 (dd, 1H), 8.87 (d, 1H), 9.25 (t, 1H), 9.79 (s, 1H), 10.83 (s, 1H), 13.89 (s, 1H). Using 6-(2-ethyl-5-fluoro-4-{[2-(trimethylsilyl)ethoxy]methoxy}phenyl)-4-({2-[methyl(methylsulfonyl)amino]benzyl}amino)-N-(6-methylpyridin-3-yl)-1-{[2-(trimethylsilyl)ethoxy]methyl}-1H-pyrazolo[4,3-c]pyridine-3-carboxamide (Preparation 20) and PM H. |
| 57 | 6-(5-fluoro-4-hydroxy-2-(2,2,2-trifluoroethyl)phenyl)-N-methyl-4-((1,3,3-trimethylureido)-benzyl)amino)-1H-pyrazolo[4,3-c]pyridine-3-carboxamide | MS m/z 610 [M + H]$^+$<br>$^1$H NMR (400 MHz, DMSO-d$_6$): δ ppm 2.83 (d, 3H), 3.00 (s, 3H), 3.64 (m, 2H), 4.84 (br m, 2H), 6.70 (s, 1H), 6.96 (d, 1H), 7.19-7.46 (m, 5H), 8.83 (m, 1H), 9.74 (m, 1H), 10.09 (s, 1H), 13.70 (s, 1H). Using 6-(5-fluoro-2-(2,2,2-trifluoro-ethyl)-4-((2-(trimethylsilyl)ethoxy)-methoxy)phenyl)-N-methyl-1-((2-(trimethylsilyl)ethoxy)methyl)-4-((2-(1,3,3-trimethylureido)benz-yl)amino)-1H-pyrazolo[4,3-c]pyridine-3-carboxamide (Preparation 13) and PM H. |
| 58 | 6-(5-fluoro-4-hydroxy-2-(2,2,2-trifluoroethyl)phenyl)-N-methyl-4-((2-(N-methyl-1H-pyrazole-4-sulfonamido)benzyl)amino)-1H-pyrazolo[4,3- | MS m/z 633 [M + H]$^+$<br>$^1$H NMR (400 MHz, DMSO-d$_6$): δ ppm 2.85 (d, 3H), 2.99 (s, 3H), 3.66 (m, 2H), 4.74 (m, 1H), 4.97 (m, 1H), 6.71 (m, 2H), 6.96 (m, 1H), 7.17-7.28 (m, 3H), 7.40 (m, 1H), 7.73 (s, 1H), 8.30 (s, 1H), 8.83 (m, 1H), 9.76 (m, 1H), 10.10 (s, 1H), 13-71 (s, 1H), 13.75 (s, 1H). |

-continued

| Ex | Name | Data |
|---|---|---|
| | c]pyridine-3-carboxamide | Using 6-(5-fluoro-2-(2,2,2-trifluoroethyl)-4-((2-trimethylsilyl)ethoxy)methoxy)phenyl)-N-methyl-4-((2-(N-methyl-1H-pyrazole-4-sulfonamido)benzyl)amino)-1-((2-(trimethylsilyl)ethoxy)methyl)-1H-pyrazolo[4,3-c]pyridine-3-carboxamide (Preparation 3) and PM H. |
| 59 | 4-((2-N,1-dimethyl-1H-imidazole-4-sulfonamido)benzyl)amido)-6-(5-fluoro-4-hydroxy-2-(2,2,2-trifluoroethyl)phenyl)-N-methyl-1H-pyrazolo[4,3-c]pyridine-3-carboxamide | MS m/z 647 [M + H]+<br>¹H NMR (400 MHz, DMSO-d₆): δ ppm 2.84 (d, 3H), 3.08 (s, 3H), 3.70 (m, 5H), 4.68 (m, 1H), 4.95 (m, 1H), 6.71 (s, 1H), 6.96 (m, 2H), 7.16-7.26 (m, 3H), 7.36 (m, 1H), 7.72 (s, 1H), 7.88 (s, 1H), 8.82 (m, 1H), 9.73 (m, 1H), 10.08 (s, 1H), 13.69 (s, 1H).<br>Using 4-((2-(N,1-dimethyl-1H-imidazole-4-sulfonamido)benzyl)amino)-6-(5-fluoro-2-(2,2,2-trifluoroethyl)-4-((2-(trimethylsilyl)ethoxy)methoxy)phenyl)-N-methyl-1-((2-(trimethylsilyl)ethoxy)methyl)-1H-pyrazolo[4,3-c]pyridine-3-carboxamide (Preparation 8) and PM H. |
| 60 | 6-[5-fluoro-4-hydroxy-2-(2,2,2-trifluoroethyl)phenyl]-4-[(2-{(2-methoxyethyl)sulfonyl](methyl)amino}benzyl)amino]-N-methyl-1H-pyrazolo[4,3-c]pyridine-3-carboxamide | MS m/z 625 [M + H]+<br>¹H NMR (400 MHz, DMSO-d₆): δ ppm 2.84 (d, 3H), 3.09 (s, 3H), 3.26 (s, 3H), 3.44-3.68 (m, 6H), 4.73-4.86 (m, 2H), 6.70 (s, 1H), 6.94 (d, 1H), 7.21 (d, 1H), 7.30 (m, 2H), 7.38 (m, 1H), 7.50 (m, 1H), 8.83 (m, 1H), 9.77 (m, 1H), 10.08 (br s, 1H), 13.70 (br s, 1H).<br>Using 6-[5-fluoro-2-(2,2,2-trifluoroethyl)-4-{[2-(trimethylsilyl)ethoxy]methoxy}phenyl]-4-[(2-{[(2-methoxyethyl)sulfonyl](methyl)amino}benzyl)amino]-N-methyl-1-{[2-(trimethylsilyl)ethoxy]methyl}-1H-pyrazolo-[4,3-c]pyridine-3-carboxamide (Preparation 9) and PM H using 50% EtOAc in hexanes. |
| 61 | 6-[5-fluoro-4-hydroxy-2-(2,2,2-trifluoroethyl)phenyl]-4-({2-[methyl(pyridin-3-ylsulfonyl)amino]benzyl}amino)-1H-pyrazolo[4,3-c]pyridine-3-carboxamide | MS m/z 630 [M + H]+<br>¹H NMR (400 MHz, DMSO-d₆): δ ppm 3.08 (s, 3H), 3.69 (m, 2H), 4.71 (m, 1H), 4.92 (m, 1H), 5.75 (d, 1H), 6.71 (s, 1H), 6.97 (m, 1H), 7.17 (m, 1H), 7.24 (d, 1H), 7.30 (t, 1H), 7.44 (d, H), 7.65-7.86 (br s, 1H), 8.07 (m, 1H), 8.21 (br s, 1H), 8.79 (m, 1H), 8.89 (m, 1H), 9.78 (t, 1H), 10.09 (s, 1H), 13.69 (s, 1H).<br>Using 6-[5-fluoro-2-(2,2,2-trifluoroethyl)-4-{[2-(trimethylsilyl)ethoxy]methoxy}phenyl]-4-({2-[methyl(pyridin-3-ylsulfonyl)amino]benzyl}amino)-1-{[2-(trimethylsilyl)ethoxy]methyl}-1H-pyrazolo[4,3-c]pyridine-3-carboxamide (Preparation 10). |
| 62 | 6-[5-fluoro-4-hydroxy-2-(2,2,2-trifluoroethyl)phenyl]-4-[({2-[methyl(methylsulfonyl)amino]pyridin-3-yl}methyl)amino]-1H-pyrazolo[4,3-c]pyridine-3-carboxamide | MS m/z 568 [M + H]+<br>¹H NMR (400 MHz, DMSO-d₆): δ ppm 3.09 (s, 3H), 3.12 (s, 3H), 3.65 (m, 2H), 4.81 (m, 2H), 6.73 (s, 1H), 6.96 (d, 1H), 7.21 (d, 1H), 7.37 (m, 1H), 7.82 (m, 1H), 7.86 (br s, 1H), 8.21 (br s, 1H), 8.41 (m, 1H), 9.81 (t, 1H), 10.09 (s, 1H), 13.69 (s, 1H).<br>Using 6-[5-fluoro-4-hydroxy-2-(2,2,2-trifluoroethyl)phenyl]-4-[({2-[methyl(methylsulfonyl)amino]pyridin-3-yl}methyl)amino]-1-(tetrahydro-2H-pyran-2-yl)-1H-pyrazolo[4,3-c]pyridine-3-carboxamide (Preparation 15). |
| 63 | 4-[({2-[ethyl(methylsulfonyl)amino]pyridin-3-yl}methyl)amino]-6-[5-fluoro-4-hydroxy-2-(2,2,2-trifluoroethyl)phenyl]-N-methyl-1H-pyrazolo[4,3-c]pyridine-3-carboxamide | MS m/z 596 [M + H]+<br>¹H NMR (400 MHz, DMSO-d₆): δ ppm 0.84 (t, 3H), 2.83 (d, 3H), 3.05 (s, 3H), 3.52-3.64 (m, 4H), 4.83 (m, 2H), 6.70 (s, 1H), 6.91 (d, 1H), 7.15 (d, 1H), 7.35 (m, 1H), 7.76 (m, 1H), 8.42 (m, 1H), 8.83 (m, 1H), 9.76 (m, 1H), 10.04 (s, 1H), 13.71 (br s, 1H).<br>Using -[({2-[ethyl(methylsulfonyl)amino]pyridin-3-yl}methyl)amino]-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 48) and PM I. |
| 64 | 6-[5-fluoro-4-hydroxy-2-(2,2,2-trifluoroethyl)phenyl]-N-methyl-4-{[2-(sulfamoylmethyl)benzyl]amino}-1H-pyrazolo[4,3-c]pyridine-3-carboxamide | MS m/z 567 [M + H]+<br>¹H NMR (400 MHz, DMSO-d₆): δ ppm 2.84 (d, 3H), 3.76 (q, 2H), 4.42 (s, 2H), 4.84 (m, 2H), 6.71 (s, 1H), 6.87 (s, 2H), 6.98 (d, 1H), 7.20-7.36 (m, 5H), 8.83 (m, 1H), 9.75 (m, 1H), 10.10 (br s, 1H), 13.70 (br s, 1H).<br>Using 6-[5-fluoro-2-(2,2,2-trifluoroethyl)-4-{[2-(trimethylsilyl)ethoxy]methoxy}phenyl]-N-methyl-4-{[2-(sulfamoylmethyl)benzyl]amino}-1-{[2-(trimethylsilyl)ethoxy]methyl}-1H-pyrazolo[4,3-c]pyridine-3-carboxamide (Preparation 49). |

| Ex | Name | Data |
|---|---|---|
| 65 | 6-[5-fluoro-4-hydroxy-2-(2,2,2-trifluoroethyl)phenyl]-4-{[2-(methyl{[6-(morpholin-4-yl)pyridin-3-yl]sulfonyl}amino)benzyl]amino}-1H-pyrazolo[4,3-c]pyridine-3-carboxamide | MS m/z 715 [M + H]$^+$<br>$^1$H NMR (400 MHz, DMSO-d$_6$): δ ppm 3.00 (s, 3H), 3.61-3.74 (m, 10H), 4.73 (m, 1H), 4.94 (m, 1H), 6.71 (s, 1H), 6.70 (d, 1H), 6.91 (d, 1H), 6.95 (d, 1H), 7.19-7.30 (m, 3H), 7.43 (m, 1H), 7.64 (m, 1H), 7.86 (br s, 1H), 8.21 (br s, 1H), 8.28 (m, 1H), 9.75 (m, 1H), 10.10 (s, 1H), 13.68 (s, 1H).<br>Using 6-[5-fluoro-2-(2,2,2-trifluoroethyl)-4-{[2-(trimethylsilyl)-ethoxy]methoxy}phenyl]-4-{[2-(methyl{[6-(morpholin-4-yl)pyridin-3-yl]sulfonyl}amino)-benzyl]amino}-1-{[2-(trimethylsilyl)-ethoxy]methyl}-1H-pyrazolo[4,3-c]pyridine-3-carboxamide (Preparation 5). |
| 66 | 6-[5-fluoro-4-hydroxy-2-(2,2,2-trifluoroethyl)phenyl]-4-{[2-(methyl{[3-(morpholin-4-yl)propyl]sulfonyl}-amino)benzyl]amino}-1H-pyrazolo[4,3-c]pyridine-3-carboxamide | MS m/z 680 [M + H]$^+$<br>$^1$H NMR (400 MHz, DMSO-d$_6$): δ ppm 1.81 (m, 2H), 2.29 (m, 6H), 3.12 (s, 3H), 3.23 (m, 2H), 3.57 (m, 4H), 3.62 (m, 2H), 4.70-5.00 (m, 2H), 6.70 (s, 1H), 6.95 (d, 1H), 7.22 (d, 1H), 7.31-7.34 (m, 2H), 7.41-7.46 (m, 2H), 7.84 (s, 1H), 8.20 (s, 1H), 9.75 (m, 1H), 10.08 (s, 1H), 13.67 (s, 1H).<br>Using 6-[5-fluoro-2-(2,2,2-trifluoroethyl)-4-{[2-(trimethylsilyl)ethoxy]methoxy}phenyl]-4-{[2-(methyl{[3-(morpholin-4-yl)propyl]sulfonyl}amino)benzyl]amino}-1-{[2-(trimethylsilyl)ethoxy]methyl}-1H-pyrazolo[4,3-c]pyridine-3-carboxamide (Preparation 2). |
| 67 | 6-[5-fluoro-4-hydroxy-2-(2,2,2-trifluoroethyl)phenyl]-N-methyl-4-[({5-methyl-2-[methyl(methylsulfonyl)amino]pyridin-3-yl}methyl)amino]-1H-pyrazolo[4,3-c]pyridine-3-carboxamide | MS m/z 596 [M + H]$^+$<br>$^1$H NMR (400 MHz, DMSO-d$_6$): δ ppm 2.21 (s, 3H), 2.86 (d, 3H), 3.05 (s, 3H), 3.09 (s, 3H), 3.54 (m, 2H), 4.77 (m, 2H), 6.72 (s, 1H), 6.95 (d, 1H), 7.19 (d, 1H), 7.59 (s, 1H), 8.23 (s, 1H), 8.83 (m, 1H), 9.78 (m, 1H), 10.09 (br s, 1H), 13.72 (br s, 1H).<br>Using 6-[5-fluoro-2-(2,2,2-trifluoroethyl)-4-{[2-(trimethylsilyl)ethoxy]methoxy}phenyl]-N-methyl-4-[({5-methyl-2-[methyl(methylsulfonyl)amino]pyridin-3-yl}methyl)amino]-1-{[2-(trimethylsilyl)ethoxy]methyl}-1H-pyrazolo[4,3-c]pyridine-3-carboxamide (Preparation 44). |
| 68 | 6-[5-fluoro-4-hydroxy-2-(2,2,2-trifluoroethyl)phenyl]-N-methyl-4-({2-[methyl(pyridin-3-ylsulfonyl)amino]-benzyl}amino)-1H-pyrazolo[4,3-c]pyridine-3-carboxamide | MS m/z 644 [M + H]$^+$<br>$^1$H NMR (400 MHz, DMSO-d$_6$): δ ppm 2.84 (d, 3H), 3.07 (s, 3H), 3.62 (m, 2H), 4.74 (m, 1H), 4.93 (m, 1H), 6.66 (d, 1H), 6.71 (s, 1H), 6.96 (d, 1H), 7.15-7.23 (m, 2H), 7.28 (t, 1H), 7.42 (m, 1H), 7.65 (m, 1H), 8.06 (m, 1H), 8.80-8.83 (m, 2H), 8.89 (m, 1H), 9.76 (m, 1H), 10.07 (s, 1H), 13.70 (s, 1H).<br>Using 6-[5-fluoro-2-(2,2,2-trifluoro-ethyl)-4-{[2-(trimethylsilyl)-ethoxy]methoxy}phenyl]-N-methyl-4-({2-[methyl(pyridin-3-ylsulfonyl)-amino]benzyl}amino)-1-{[2-(trimethylsilyl)ethoxy]methyl}-1H-pyrazolo[4,3-c]pyridine-3-carboxamide (Preparation 45) and PM H using 4% MeOH in DCM. |
| 69 | 6-[5-fluoro-4-hydroxy-2-(2,2,2-trifluoroethyl)phenyl]-N-methyl-4-[(2-{methyl[(6-methylpyridin-3-yl)sulfonyl]amino}benzyl)amino]1H-pyrazolo[4,3-c]pyridine-3-carboxamide | MS m/z 658 [M + H]$^+$<br>$^1$H NMR (400 MHz, DMSO-d$_6$): δ ppm 2.58 (s, 3H), 2.85 (d, 3H), 3.05 (s, 3H), 3.65 (m, 2H), 4.74 (m, 1H), 4.93 (m, 1H), 6.68 (d, 1H), 6.71 (s, 1H), 6.96 (d, 1H), 7.16-7.23 (m, 2H), 7.29 (t, 1H), 7.43 (d, 1H), 7.50 (d, 1H), 7.93 (m, 1H), 8.65 (m, 1H), 8.82 (m, 1H), 9.75 (m, 1H), 10.08 (s, 1H), 13.70 (s, 1H).<br>Using 6-[5-fluoro-2-(2,2,2-trifluoroethyl)-4-{[2-(trimethylsilyl)ethoxy]methoxy}phenyl]-N-methyl-4-[(2-{methyl[(6-methylpyridin-3-yl)sulfonyl]amino}-benzyl)amino]-1-{[2-(trimethylsilyl)-ethoxy]methyl}-1H-pyrazolo[4,3-c]pyridine-3-carboxamide (Preparation 6). |
| 70 | 6-[5-fluoro-4-hydroxy-2-(2,2,2-trifluoroethyl)phenyl]-4-[(2-{methyl[(6-methylpyridin-3-yl)sulfonyl]amino}benzyl)amino]-1H-pyrazolo[4,3-c]pyridine-3-carboxamide | MS m/z 644 [M + H]$^+$<br>$^1$H NMR (400 MHz, DMSO-d$_6$): δ ppm 2.58 (s, 3H), 3.06 (s, 3H), 3.67 (m, 2H), 4.71 (m, 1H), 4.92 (m, 1H), 6.69 (d, 1H), 6.71 (s, 1H), 6.97 (d, 1H), 7.16-7.24 (m, 2H), 7.30 (t, 1H), 7.46 (d, 1H), 7.50 (d, 1H), 7.91 (br s, 1H), 7.93 (dd, 1H), 8.21 (br s, 1H), 8.65 (m, 1H), 9.77 (m, 1H), 10.09 (s, 1H), 13.68 (s, 1H).<br>Using 6-[5-fluoro-2-(2,2,2-trifluoroethyl)-4-{[2-(trimethylsilyl)ethoxy]methoxy}phenyl]-4-[(2-{methyl[(6-methylpyridin-3-yl)sulfonyl]amino}benzyl)amino]-1-{[2-(trimethylsilyl)ethoxy]methyl}-1H-pyrazolo[4,3-c]pyridine-3-carboxamide (Preparation 7) and using aqueous ammonia instead of ethylene diamine. |

| Ex | Name | Data |
|---|---|---|
| 71 | 4-[({5-chloro-2-[ethyl(methylsulfonyl)amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide | MS m/z 616 [M + H]$^+$<br>$^1$H NMR (400 MHz, DMSO-d$_6$): δ ppm 0.85 (t, 3H), 3.49-3.65 (m, 4H), 4.81 (m, 2H), 6.74 (s, 1H), 6.95 (d, 1H), 7.18 (d, 1H), 7.81 (m, 1H), 7.90 (br s, 1H), 8.24 (br s, 1H), 8.51 (m, 1H), 9.80 (m, 1H), 10.08 (s, 1H), 13.74 (s, 1H).<br>Using N-tert-butyl-4-[({5-chloro-2-[ethyl(methylsulfonyl)amino]pyridin-3-yl}methyl)amino]-6-[5-fluoro-2-(2,2,2-trifluoroethyl)-4-{[2-(trimethylsilyl)ethoxy]methoxy} phenyl]-1-{[2-(trimethylsilyl)-ethoxy]methyl}-1H-pyrazolo[4,3-c]pyridine-3-carboxamide (Preparation 50). |
| 72 | 4-[({5-chloro-2-[methyl(methylsulfonyl)amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide | MS m/z 602 [M + H]$^+$<br>$^1$H NMR (400 MHz, DMSO-d$_6$): δ ppm 3.07 (s, 3H), 3.16 (s, 3H), 3.58 (q, 2H), 4.79 (m, 2H), 6.75 (s, 1H), 6.96 (d, 1H), 7.18 (d, 1H), 7.80 (d, 1H), 7.89 (br s, 1H), 8.23 (br s, 1H), 8.47 (d, 1H), 9.82 (m, 1H), 10.10 (s, 1H), 13.73 (s, 1H).<br>Using N-tert-butyl-4-[({5-chloro-2-[methyl(methylsulfonyl)amino]pyridin-3-yl}methyl)amino]-6-[5-fluoro-2-(2,2,2-trifluoroethyl)-4-{[2-(trimethylsilyl)ethoxy]methoxy} phenyl]-1-{[2-(trimethylsilyl)-ethoxy]methyl}-1H-pyrazolo[4,3-c]pyridine-3-carboxamide (Preparation 51). |
| 73 | 6-(2-ethyl-5-fluoro-4-hydroxyphenyl)-N-methyl-4-({2-[methyl(sulfamoyl)amino]benzyl}amino)-1H-pyrazolo[4,3-c]pyridine-3-carboxamide | MS m/z 528 [M + H]$^+$<br>$^1$H NMR (400 MHz, DMSO-d$_6$): δ ppm 0.87 (t, 3H), 2.53 (m, 2H), 2.84 (s, 3H), 3.01 (s, 3H), 3.39 (m, 2H), 4.70 (br s, 1H), 5.00 (br s, 1H), 6.54 (s, 1H), 6.79 (d, 1H), 7.03 (m, 2H), 7.24 (m, 1H), 7.37 (m, 1H), 7.43 (m, 1H), 8.78 (m, 1H), 9.60 (m, 1H), 9.75 (s, 1H), 13.60 (s, 1H).<br>Using 6-(2-ethyl-5-fluoro-4-{[2-(trimethylsilyl)ethoxy]methoxy}phenyl)-N-methyl-4-({2-[methyl(sulfamoyl)amino]benzyl}amino)-1-{[2-(trimethylsilyl)ethoxy]methyl}-1H-pyrazolo[4,3-c]pyridine-3-carboxamide (Preparation 1). |

Example 74

6-(5-Fluoro-4-hydroxy-2-(2,2,2-trifluoroethyl)phenyl)-4-((N-(2-hydroxyethyl)-(sulfamoyl)(methyl)aminobenzyl)amino)-N-methyl-1H-pyrazolo[4,3-c]pyridine-3-carboxamide The title compound was prepared according to the method described for Example 55 using 6-(5-fluoro-2-(2,2,2-trifluoroethyl)-4-((2-(trimethylsilyl)ethoxy)-methoxy)phenyl)-N-methyl-4-((2-(N-methyl-2-oxooxazolidine-3-sulfonamido)benzyl)-amino)-1-((2-(trimethylsilyl)-ethoxy)-methyl)-1H-pyrazolo[4,3-c]pyridine-3-carboxamide (Preparation 58). The residue was treated with 6M NaOH (0.5 mL) at 0° C. and stirred at room temperature for 18 hours. The reaction was acidified with HCl at 0° C., and the resulting precipitate was filtered, extracted into EtOAc and concentrated in vacuo. The residue was purified using preparative TLC. $^1$H NMR (400 MHz, DMSO-d$_6$): δ ppm 1.07 (m, 3H), 2.84 (s, 3H), 3.02 (s, 3H), 3.39 (m, 2H), 3.69 (m, 2H), 4.70 (m, 2H), 4.90 (br m, 2H), 6.94 (s, 1H), 6.96 (m, 1H), 7.20-7.46 (m, 5H), 8.82 (m, 1H), 9.71 (m, 1H), 10.10 (br s, 1H), 13.70 (s, 1H). MS m/z 626 [M+H]$^+$

Example 75

6-[5-Fluoro-4-hydroxy-2-(2,2,2-trifluoroethyl)phenyl]-N-{6-[(2-hydroxyethyl)amino]pyridin-3-yl}-4-({5-hydroxy-2-[methyl(methylsulfonyl)amino]benzyl}amino)-1H-pyrazolo[4,3-c]pyridine-3-carboxamide To a solution of 6-[5-fluoro-2-(2,2,2-trifluoroethyl)-4-{[2-(trimethylsilyl)ethoxy]-methoxy}phenyl]-4-({5-methoxy-2-[methyl(methylsulfonyl)amino]benzyl}amino)-1-{[2-(trimethyl-silyl)ethoxy]methyl}-1H-pyrazolo[4,3-c]pyridine-3-carboxylic acid (Preparation 11, 100 mg, 0.12 mmol) in DCM (3 mL) was added boron tribromide (0.08 mL, 0.82 mmol) and the reaction was stirred at room temperature for 30 minutes. The reaction was concentrated in vacuo and triturated with ether/pentane. The resulting solid was dissolved in DMF (2 mL) and 2-[(5-aminopyridin-2-yl)amino]ethanol (51 mg, 0.33 mmol) followed by DIPEA (0.07 mL, 0.17 mmol) were added. HATU (159 mg, 0.42 mmol) was added and the reaction stirred at room temperature for 18 hours. The reaction was partitioned between EtOAc and water, the organic layer was collected, dried over sodium sulfate and concentrated in vacuo. The residue was purified using preparative TLC to afford the title compound (15 mg, 13%). $^1$H NMR (400 MHz, DMSO-d$_6$): δ ppm 2.98 (s, 3H), 3.03 (s, 3H), 3.32 (m, 2H), 3.52 (m, 2H), 3.64 (m, 2H), 4.60 (m, 1H), 4.71 (m, 1H), 4.83 (m, 1H), 6.45 (m, 1H), 6.53 (d, 1H), 6.63 (dd, 1H), 6.75 (s, 1H), 6.78 (m, 1H), 6.96 (d, 1H), 7.21-7.26 (m, 2H), 7.78 (dd, 1H), 8.31 (s, 1H), 9.46 (m, 2H), 10.10 (s, 1H), 10.48 (s, 1H), 13.86 (s, 1H). MS m/z 719 [M+H]$^+$

Example 76

6-[5-Fluoro-4-hydroxy-2-(2,2,2-trifluoroethyl)phenyl]-4-({2-[methyl(methylsulfonyl)amino]-benzyl}amino)-N-(6-methylpyridin-3-yl)-1H-pyrazolo[4,3-c]pyridine-3-carboxamide To a solution of 6-[5-fluoro-2-(2,2,2-trifluoroethyl)-4-{[2-(trimethylsilyl)ethoxy]methoxy}-phenyl]-4-({2-

[methyl(methylsulfonyl)amino]benzyl}amino)-1-{[2-(trimethyl-silyl)ethoxy]-methyl}-1H-pyrazolo[4,3-c]pyridine-3-carboxylic acid (Preparation 12, 100 mg, 0.12 mmol) in DMF (3 mL) was added 6-methylpyridin-3-amine (65 mg, 0.60 mmol), DIPEA (0.13 mL, 0.73 mmol) and BOP (267 mg, 0.60 mmol) and the reaction was stirred at room temperature for 18 hours before concentrating in vacuo. The residue was partitioned between ice-water and EtOAc, the organic layer was collected, washed with brine, dried over sodium sulfate and concentrated in vacuo. The residue was purified using silica gel column chromatography eluting with 5% MeOH in DCM. The residue was treated with TFA (3 mL) and stirred at room temperature for 30 minutes. The reaction was concentrated in vacuo, dissolved in MeOH and cooled in ice-water. Ethylene diamine was added until the solution became basic, with stirring for 15 minutes. The solution was concentrated in vacuo and purified using preparative HPLC to afford the title compound (35 mg, 29%). $^1$H NMR (400 MHz, DMSO-$d_6$): δ ppm 2.45 (s, 3H), 3.04 (s, 3H), 3.11 (s, 3H), 3.62 (m, 2H), 4.80 (m, 1H), 4.95 (m, 1H), 6.77 (s, 1H), 6.96 (d, 1H), 7.20-7.33 (m, 4H), 7.41 (m, 1H), 7.49 (m, 1H), 8.13 (dd, 1H), 8.87 (d, 1H), 9.33 (t, 1H), 10.85 (br s, 1H). MS m/z 658 [M+H]$^+$ Example 77

6-[5-Fluoro-4-hydroxy-2-(2,2,2-trifluoroethyl)phenyl]-4-({2-[methyl(methylsulfonyl)amino]benzyl}amino)-1H-pyrazolo[4,3-c]pyridine-3-carboxamide 6-(4-(Benzyloxy)-5-fluoro-2-(2,2,2-trifluoroethyl)phenyl)-N-(tert-butyl)-4-((2-(N-methylmethylsulfonamido)benzyl)amino)-1-(tetrahydro-2H-pyran-2-yl)-1H-pyrazolo[4,3-c]pyridine-3-carboxamide (Preparation 27, 60 mg, 0.07 mmol) was treated with TFA (8 mL) and heated to reflux for 18 hours. The reaction was cooled, concentrated in vacuo, quenched by the addition of saturated aqueous sodium bicarbonate solution and extracted into EtOAc. The organic layer was collected, dried over sodium sulfate and concentrated in vacuo. The crude residue was purified using preparative TLC to afford the title compound (21 mg, 51%). $^1$H NMR (400 MHz, DMSO-$d_6$): δ ppm 3.04 (s, 3H), 3.14 (s, 3H), 3.69 (m, 2H), 4.70 (br m, 1H), 4.90 (m, 1H), 6.70 (s, 1H), 6.96 (d, 1H), 7.22 (d, 1H), 7.27-7.34 (m, 2H), 7.40 (m, 1H), 7.49 (m, 1H), 7.85 (br s, 1H), 8.20 (br s, 1H), 9.75 (m, 1H), 10.09 (s, 1H), 13.70 (s, 1H). MS m/z 567 [M+H]$^+$ Example 78

6-[5-Fluoro-4-hydroxy-2-(2,2,2-trifluoroethyl)phenyl]-4-[({5-fluoro-2-[methyl(methyl-sulfonyl)amino]pyridin-3-yl}methyl)amino]-1H-pyrazolo[4,3-c]pyridine-3-carboxamide 6-(4-Benzyloxy)-5-fluoro-2-(2,2,2-trifluoroethyl)phenyl)-N-(tert-butyl)-4-(((5-fluoro-2-(N-methylmethylsulfonamido)pyridin-3-yl)methyl)amino)-1-(tetrahydro-2H-pyran-2-yl)-1H-pyrazolo-[4,3-c]pyridine-3-carboxamide (Preparation 55, 80 mg, 0.10 mmol) was treated with TFA (10 mL) and heated to reflux for 18 hours. The reaction was cooled, concentrated in vacuo and partitioned between saturated aqueous sodium bicarbonate solution and EtOAc. The organic layer was collected, dried over sodium sulfate and concentrated in vacuo. The residue was purified using preparative TLC to afford the title compound (20 mg, 35%). $^1$H NMR (400 MHz, DMSO-$d_6$): δ ppm 3.07 (s, 3H), 3.12 (s, 3H), 3.57 (q, 2H), 4.80 (m, 2H), 6.75 (s, 1H), 6.95 (d, 1H), 7.18 (d, 1H), 7.62 (dd, 1H), 7.89 (br s, 1H), 8.24 (br s, 1H), 8.42 (m, 1H), 9.85 (m, 1H), 10.11 (br s, 1H), 13.73 (br s, 1H). MS m/z 586 [M+H]$^+$ The following Examples (Examples 79-91) were prepared according to the method described for Example 78 using the appropriate pyrazolo-pyridine.

| Example | Name | Data |
|---|---|---|
| 79 | 4-[({2-[ethyl(methyl-sulfonyl)amino]-5-fluoropyridin-3-yl}methyl)amino]-6-[5-fluoro-4-hydroxy-2-(2,2,2-trifluoroethyl)phenyl]-1H-pyrazolo[4,3-c]pyridine-3-carboxamide | MS m/z 600 [M + H]$^+$<br>$^1$H NMR (400 MHz, DMSO-$d_6$): δ ppm 0.85 (t, 3H), 3.07 (s, 3H), 3.51 (q, 2H), 3.61 (q, 2H), 4.08 (m, 1H), 6.74 (s, 1H), 6.94 (d, 1H), 7.19 (d, 1H), 7.61 (m, 1H), 7.90 (br s, 1H), 8.24 (br s, 1H), 8.45 (s, 1H), 9.84 (t, 1H), 10.08 (s, 1H), 13.74 (m, 1H). Using 6-(4-benzyloxy)-5-fluoro-2-(2,2,2-trifluoroethyl)phenyl)-N-(tert-butyl)-4-(((5-fluoro-2-(N-ethylmethylsulfonamido)pyridin-3-yl)methyl)amino)-1-(tetrahydro-2H-pyran-2-yl)-1H-pyrazolo[4,3-c]pyridine-3-carboxamide (Preparation 56). |
| 80 | 4-[({3-[ethyl(methylsulfonyl)-amino]pyrazin-2-yl}methyl)amino]-6-[5-fluoro-4-hydroxy-2-(2,2,2-trifluoroethyl)phenyl]-1H-pyrazolo[4,3-c]pyridine-3-carboxamide | MS m/z 583 [M + H]$^+$<br>$^1$H NMR (400 MHz, DMSO-$d_6$): δ ppm 0.86 (t, 3H), 3.10 (s, 3H), 3.59 (q, 2H), 3.68 (q, 2H), 4.97 (m, 2H), 6.60 (s, 1H), 6.97 (d, 1H), 7.15 (d, 1H), 7.82 (br s, 1H), 8.16 (br s, 1H), 8.56 (s, 1H), 8.61 (s, 1H), 9.85 (br s, 1H), 10.09 (s, 1H), 13.66 (s, 1H). Using 6-(4-benzyloxy)-5-fluoro-2-(2,2,2-trifluoroethyl)phenyl)-N-(tert-butyl)-4-(((3-(N-ethylmethylsulfonamido)pyrazin-2-yl)methyl)amino)-1-(tetrahydro-2H-pyran-2-yl)-1H-pyrazolo[4,3-c]pyridine-3-carboxamide (Preparation 57). |
| 81 | 6-[5-fluoro-4-hydroxy-2-(2,2,2-trifluoroethyl)phenyl]-4-({5-methyl-2-[methyl(methylsulfonyl)amino]benzyl}amino)-1H-pyrazolo[4,3-c]pyridine-3-carboxamide | MS m/z 581 [M + H]$^+$<br>$^1$H NMR (400 MHz, DMSO-$d_6$): δ ppm 2.20 (s, 3H), 3.01 (s, 3H), 3.07 (s, 3H), 3.64 (m, 2H), 4.64 (m, 1H), 4.88 (m, 1H), 6.94 (s, 1H), 6.96 (d, 1H), 7.14 (m, 2H), 7.21 (m, 2H), 7.37 (m, 1H), 7.84 (br s, 1H), 8.18 (br s, 1H), 9.69 9s, 1H), 10.09 (s, 1H), 13.67 (s, 1H). Using 6-(4-benzyloxy)-5-fluoro-2-(2,2,2-trifluoroethyl)phenyl)-N-(tert-butyl)-4-((5-methyl-2-(N-methylmethylsulfonamido)benzyl)amino)-1-(tetrahydro-2H- |

| Example | Name | Data |
|---|---|---|
| | | pyran-2-yl)-1H-pyrazolo[4,3-c]pyridine-3-carboxamide (Preparation 28). |
| 82 | 4-((2-(N-ethylethyl-sulfonamido)benzyl)amino)-6-(5-fluoro-4-hydroxy-2-(2,2,2-trifluoroethyl)phenyl)-1H-pyrazolo[4,3-c]pyridine-3-carboxamide | MS m/z 595 [M + H]$^+$<br>$^1$H NMR (400 MHz, DMSO-d$_6$): δ ppm 0.90 (t, 3H), 1.19 (t, 3H), 3.19 (m, 2H), 3.51-3.64 (m, 4H), 4.70 (m, 1H), 4.87 (m, 1H), 6.69 (s, 1H), 6.94 (d, 1H), 7.19 (d, 1H), 7.30 (m, 2H), 7.42 (m, 2H), 7.85 (br s, 1H), 8.10 (br s, 1H), 9.77 (m, 1H), 10.06 (s, 1H), 13.67 (s, 1H).<br>Using 6-(4-benzyloxy)-5-fluoro-2-(2,2,2-trifluoroethyl)phenyl)-N-(tert-butyl)-4-((2-(N-ethylethylsulfonamido)benzyl)amino)-1-(tetrahydro-2H-pyran-2-yl)-1H-pyrazolo[4,3-c]pyridine-3-carboxamide (Preparation 32). |
| 83 | 4-((2-(N-ethylmethyl-sulfonamido)-5-fluorobenzyl)amino)-6-(5-fluoro-4-hydroxy-2-(2,2,2-trifluoroethyl)phenyl)-1H-pyrazolo[4,3-c]pyridine-3-carboxamide | MS m/z 599 [M + H]$^+$<br>$^1$H NMR (400 MHz, DMSO-d$_6$): δ ppm 0.89 (t, 3H), 3.02 (s, 3H), 3.43-3.64 (m, 4H), 4.71 (m, 1H), 4.85 (m, 1H), 6.72 (s, 1H), 6.93 (d, 1H), 7.10-7.19 (m, 3H), 7.51 (m, 1H), 7.88 (br s, 1H), 8.22 (br s, 1H), 9.79 (m, 1H), 10.05 (s, 1H), 13.71 (s, 1H).<br>Using 6-(4-(benzyloxy)-5-fluoro-2-(2,2,2-trifluoroethyl)phenyl)-N-(tert-butyl)-4-((2-(N-ethylmethylsulfonamido)-5-fluorobenzyl)amino)-1-(tetrahydro-2H-pyran-2-yl)-1H-pyrazolo[4,3-c]pyridine-3-carboxamide (Preparation 34). |
| 84 | 4-((5-chloro-2-(N-ethylmethylsulfonamido)benzyl)amino)-6-(5-fluoro-4-hydroxy-2-(2,2,2-trifluoroethyl)phenyl)-1H-pyrazolo[4,3-c]pyridine-3-carboxamide | MS m/z 615 [M + H]$^+$<br>$^1$H NMR (400 MHz, DMSO-d$_6$): δ ppm 1.01 (t, 3H), 3.16 (s, 3H), 3.58-3.76 (m, 4H), 4.82 (m, 1H), 4.98 (m, 1H), 6.85 (s, 1H), 7.06 (d, 1H), 7.32 (m, 1H), 7.52 (m, 2H), 7.62 (m, 1H), 8.01 (br s, 1), 8.35 (br s, 1H), 9.91 (t, 1H), 10.18 (s, 1H), 13.85 (s, 1H).<br>Using 6-(4-(benzyloxy)-5-fluoro-2-(2,2,2-trifluoroethyl)phenyl)-N-(tert-butyl)-4-((2-(N-ethylmethylsulfonamido)-5-chlorobenzyl)amino)-1-(tetrahydro-2H-pyran-2-yl)-1H-pyrazolo[4,3-c]pyridine-3-carboxamide (Preparation 35). |
| 85 | 6-(5-fluoro-4-hydroxy-2-(2,2,2-trifluoroethyl)phenyl)-4-((2-(N-methylethylsulfonamido)benzyl)amino)-1H-pyrazolo[4,3-c]pyridine-3-carboxamide | MS m/z 581 [M + H]$^+$<br>$^1$H NMR (400 MHz, DMSO-d$_6$): δ ppm 1.19 (t, 3H), 3.11 (s, 3H), 3.23-3.31 (m, 2H), 3.58 (q, 2H), 4.60-4.90 (m, 2H), 6.70 (s, 1H), 6.95 (d, 1H), 7.21 (d, 1H), 7.26-7.34 (m, 2H), 7.40-7.47 (m, 2H), 7.86 (br s, 1H), 8.21 (br s, 1H), 9.78 (t, 1H), 10.09 (s, 1H), 13.68 (s, 1H).<br>Using 6-(4-(benzyloxy)-5-fluoro-2-(2,2,2-trifluoroethyl)phenyl)-N-(tert-butyl)-4-((2-(N-methylethylsulfonamido)benzyl)amino)-1-(tetrahydro-2H-pyran-2-yl)-1H-pyrazolo[4,3-c]pyridine-3-carboxamide (Preparation 37). |
| 86 | 6-(5-fluoro-4-hydroxy-2-(2,2,2-trifluoroethyl)phenyl)-4-(((5-methyl-2-(N-methylmethylsulfonamido)pyridin-3-yl)methyl)amino)-1H-pyrazolo[4,3-c]pyridine-3-carboxamide | MS m/z 582 [M + H]$^+$<br>$^1$H NMR (400 MHz, DMSO-d$_6$): δ ppm 2.22 (s, 3H), 3.05 (s, 3H), 3.09 (s, 3H), 3.61 (q, 2H), 4.75 (m, 2H), 6.72 (s, 1H), 6.96 (d, 1H), 7.19 (d, 1H), 7.61 (br s, 1H), 7.86 (br s, 1H), 8.23 (m, 2H), 9.77 (m, 1H), 10.09 (s, 1H), 13.70 (s, 1H).<br>Using 6-(4-(benzyloxy)-5-fluoro-2-(2,2,2-trifluoroethyl)phenyl)-N-(tert-butyl)-4-(((5-methyl-2-(N-methylmethylsulfonamido)pyridin-3-yl)methyl)amino)-1-(tetrahydro-2H-pyran-2-yl)-1H-pyrazolo[4,3-c]pyridine-3-carboxamide (Preparation 38). |
| 87 | 4-[({2-[ethyl(methylsulfonyl)amino]-5-methylpyridin-3-yl}methyl)amino]-6-[5-fluoro-4-hydroxy-2-(2,2,2-trifluoroethyl)phenyl]-1H-pyrazolo[4,3-c]pyridine-3-carboxamide | MS m/z 596 [M + H]$^+$<br>$^1$H NMR (400 MHz, DMSO-d$_6$): δ ppm 0.86 (t, 3H), 2.22 (s, 3H), 3.04 (s, 3H), 3.55-3.63 (m, 4H), 4.78 (m, 2H), 6.72 (s, 1H), 6.94 (d, 1H), 7.20 (d, 1H), 7.60 (br s, 1H), 7.87 (br s, 1H), 8.22 (s, 1H), 8.26 (s, 1H), 9.76 (t, 1H), 10.07 (br s, 1H), 13.71 (br s, 1H).<br>Using 6-(4-(benzyloxy)-5-fluoro-2-(2,2,2-trifluoroethyl)phenyl)-N-(tert-butyl)-4-(((2-(N-ethylmethylsulfonamido)-5-methylpyridin-3-yl)methyl)amino)-1-(tetrahydro-2H-pyran-2-yl)-1H-pyrazolo[4,3-c]pyridine-3-carboxamide (Preparation 33). |
| 88 | 6-[5-fluoro-4-hydroxy-2-(2,2,2-trifluoroethyl)phenyl]-4-({5-fluoro-2-[methyl(methylsulfonyl)amino]benzyl}amino)-1H-pyrazolo[4,3-c]pyridine-3-carboxamide | MS m/z 611 [M + H]$^+$<br>$^1$H NMR (400 MHz, DMSO-d$_6$): δ ppm 3.05 (s, 3H), 3.08 (s, 3H), 3.58 (m, 2H), 4.70 (m, 1H), 4.83 (m, 1H), 6.73 (s, 1H), 6.94 (d, 1H), 7.09-7.22 (m, 3H), 7.56 (m, 1H), 7.89 (s, 1H), 8.24 (s, 1H), 9.80 (m, 1H), 10.11 (br s, 1H), 13.72 (br s, 1H).<br>Using 6-(4-(benzyloxy)-5-fluoro-2-(2,2,2-trifluoroethyl)phenyl)-N-(tert-butyl)-4-((5-fluoro-2-(N-methylmethylsulfonamido)benzyl)amino)-1-(tetrahydro-2H- |

| Example | Name | Data |
|---------|------|------|
| 89 | 4-({5-chloro-2-[methyl(methylsulfonyl)amino]benzyl}amino)-6-[5-fluoro-4-hydroxy-2-(2,2,2-trifluoroethyl)phenyl]-1H-pyrazolo[4,3-c]pyridine-3-carboxamide | pyran-2-yl)-1H-pyrazolo[4,3-c]pyridine-3-carboxamide (Preparation 59).<br>MS m/z 601 [M + H]$^+$<br>$^1$H NMR (400 MHz, DMSO-d$_6$): δ ppm 3.05 (s, 3H), 3.08 (s, 3H), 3.56 (m, 2H), 4.66-4.82 (m, 2H), 6.73 (s, 1H), 6.94 (d, 1H), 7.20 (d, 1H), 7.38 (m, 2H), 7.53 (m, 1H), 7.88 (s, 1H), 8.22 (s, 1H), 9.77 (m, 1H), 10.09 (s, 1H), 13.71 (br s, 1H).<br>Using 6-(4-(benzyloxy)-5-fluoro-2-(2,2,2-trifluoroethyl)phenyl)-N-(tert-butyl)-4-((5-chloro-2-(N-methylmethylsulfonamido)benzyl)amino)-1-(tetrahydro-2H-pyran-2-yl)-1H-pyrazolo[4,3-c]pyridine-3-carboxamide (Preparation 30). |
| 90 | 4-({2-[ethyl(methylsulfonyl)amino]benzyl}amino)-6-[5-fluoro-4-hydroxy-2-(2,2,2-trifluoroethyl)phenyl]-1H-pyrazolo[4,3-c]pyridine-3-carboxamide | MS m/z 581 [M + H]$^+$<br>$^1$H NMR (400 MHz, DMSO-d$_6$): δ ppm 0.88 (t, 3H), 3.02 (s, 3H), 3.46-3.68 (m, 4H), 4.69 (m, 1H), 2.92 (m, 1H), 6.69 (s, 1H), 6.94 (d, 1H), 7.17 (d, 1H), 7.32 (m, 2H), 7.45 (m, 2H), 7.86 (br s, 1H), 8.22 (br s, 1H), 9.76 (m, 1H), 10.08 (s, 1H), 13.69 (s, 1H).<br>Using 6-(4-(benzyloxy)-5-fluoro-2-(2,2,2-trifluoroethyl)phenyl)-N-(tert-butyl)-4-((2-(N-ethylmethylsulfonamido)benzyl)amino)-1-(tetrahydro-2H-pyran-2-yl)-1H-pyrazolo[4,3-c]pyridine-3-carboxamide (Preparation 36). |
| 91 | 4-({2-[ethyl(methylsulfonyl)amino]-5-methylbenzyl}amino)-6-[5-fluoro-4-hydroxy-2-(2,2,2-trifluoroethyl)phenyl]-1H-pyrazolo[4,3-c]pyridine-3-carboxamide | MS m/z 595 [M + H]$^+$<br>$^1$H NMR (400 MHz, DMSO-d$_6$): δ ppm 0.90 (t, 3H), 2.21 (s, 3H), 2.99 (s, 3H), 3.46 (m, 1H), 3.61 (m, 1H), 4.64 (m, 1H), 4.86 (m, 1H), 6.69 (s, 1H), 6.92 (d, 1H), 7.12 (m, 1H), 7.18-7.21 (m, 2H), 7.30 (d, 1H), 7.84 (s, 1H), 8.19 (s, 1H), 9.69 (m, 1H), 10.06 (s, 1H), 13.67 (s, 1H).<br>Using 6-(4-(benzyloxy)-5-fluoro-2-(2,2,2-trifluoroethyl)phenyl)-N-(tert-butyl)-4-((2-(N-ethylmethylsulfonamido)-5-methylbenzyl)amino)-1-(tetrahydro-2H-pyran-2-yl)-1H-pyrazolo[4,3-c]pyridine-3-carboxamide (Preparation 31). |

Example 92

6-[5-Fluoro-4-hydroxy-2-(2,2,2-trifluoroethyl)phenyl]-4-({5-hydroxy-2-[methyl(methylsulfonyl)amino]benzyl}amino)-1H-pyrazolo[4,3-c]pyridine-3-carboxamide 6-(4-(Benzyloxy)-5-fluoro-2-(2,2,2-trifluoroethyl)phenyl)-N-(tert-butyl)-4-((5-methoxy-2-(N-methylmethylsulfonamido)benzyl)amino)-1-(tetrahydro-2H-pyran-2-yl)-1H-pyrazolo[4,3-c]pyridine-3-carboxamide (Preparation 29, 100 mg, 0.12 mmol) was heated to 100° C. in neat TFA (15 mL) for 18 hours. The reaction was cooled, concentrated in vacuo and partitioned between saturated aqueous sodium bicarbonate solution and EtOAc. The organic layer was collected, dried over sodium sulfate and concentrated in vacuo. The residue was purified using silica gel column chromatography eluting with 55% EtOAc in hexanes. The residue was stirred with neat boron tribromide (8 eq) at 0° C. for 4 hours. The reaction was partitioned between DCM and saturated aqueous sodium bicarbonate solution, the organic layer collected, washed with brine, dried over sodium sulfate and concentrated in vacuo. The residue was purified using preparative TLC eluting with 5% MeOH in DCM to afford the title compound (30 mg, 51%). $^1$H NMR (400 MHz, DMSO-d$_6$): δ ppm 2.98 (s, 3H), 3.04 (s, 3H), 3.66 (m, 2H), 4.58 (m, 1H), 4.79 (m, 1H), 6.63 (dd, 1H), 6.70 (s, 1H), 6.78 (m, 1H), 6.93 (d, 1H), 7.19-7.26 (m, 2H), 7.85 (br s, 1H), 8.20 (br s, 1H), 9.50 (s, 1H), 9.70 (m, 1H), 10.08 (s, 1H), 13.67 (s, 1H). MS m/z 583 [M+H]$^+$

Example 93

6-(2-Ethyl-5-fluoro-4-hydroxyphenyl)-N-methyl-4-((2-(N-methylmethylsulfonamido)benzyl)amino)-1H-pyrazolo[3,4-d]pyrimidine-3-carboxamide To a solution of N-(2-(((6-(4-(benzyloxy)-2-ethyl-5-fluorophenyl)-3-iodo-1H-pyrazolo[3,4-d]pyrimidin-4-yl)amino)methyl)phenyl)-N-methylmethanesulfonamide (Preparation 272, 249 mg, 0.36 mmol) and methylamine in THF (3 mL, 2M) was added molybdenum hexacarbonyl (96 mg, 0.36 mmol) and palladium acetate (5.7 mg, 0.025 mmol) followed by DBU (165 mg, 1.09 mmol) and the reaction was heated to 100° C. under microwave irradiation for 10 minutes. The reaction was concentrated in vacuo, diluted with EtOAc and filtered through celite. The filtrate was concentrated in vacuo and purified using silica gel column chromatography followed by Preparative TLC. The residue was dissolved in ethanol (7 mL) and hydrogenated with Pd(OH)$_2$ (15 mg) at 40 psi for 16 hours. The reaction was filtered through celite and concentrated in vacuo. The residue was triturated with pentane and ether to afford the title compound as an off white solid (42 mg, 65%). $^1$H NMR (400 MHz, DMSO-d$_6$): δ ppm 0.98 (t, 3H), 2.83 (m, 4H), 3.07 (s, 3H), 3.18 (s, 3H), 3.39 (m, 1H), 4.90 (br m, 1H), 5.05 (br m, 1H), 6.82 (m, 1H), 7.35-7.56 (m, 5H), 8.86 (m, 1H), 9.81 (t, 1H), 10.02 (br s, 1H), 13.97 (br s, 1H). MS m/z 528 [M+H]$^+$

Example 94

6-(5-Fluoro-4-hydroxy-2-(2,2,2-trifluoroethyl)phenyl-N-methyl-4-((2-(N-methylmethylsulfonamido)benzyl)amino)-1H-pyrazolo[3,4-d]pyrimidine-3-carboxamide The title compound was prepared according to the method described for Preparation 93 using N-(2-(((6-(4-(benzyloxy)-5-fluoro-2-(2,2,2-trifluoroethyl)phenyl)-3-iodo-1H-pyrazolo[3,4-d]pyrimidin-4-yl)amino)methyl)phenyl)-N-methylmethanesulfonamide (Preparation 276). The residue was purified using silica gel column chromatography eluting with 60% EtOAc in hexanes. $^1$H NMR (400 MHz, DMSO-$d_6$): δ ppm 2.82 (d, 3H), 3.07 (s, 3H), 3.17 (s, 3H), 4.27 (m, 2H), 4.91-5.01 (br m, 2H), 6.97 (m, 1H), 7.32-7.41 (m, 3H), 7.54 (m, 1H), 7.67 (m, 1H), 8.87 (t, 1H), 9.91 (t, 1H), 10.37 (br s, 1H), 14.03 (br s, 1H). MS m/z 582 [M+H]$^+$

Example 95

6-(2-Ethyl-5-fluoro-4-hydroxyphenyl)-4-((2-(N-methylphenylsulfonamido)benzyl)amino)-1H-pyrazolo[3,4-d]pyrimidine-3-carboxamide To a solution of 6-(2-ethyl-5-fluoro-4-((2-(trimethylsilyl)ethoxy)methoxy)phenyl)-4-((2-(N-methylphenylsulfonamido)benzyl)amino)-1-((2-(trimethylsilyl)ethoxy)methyl)-1H-pyrazolo-[3,4-d]pyrimidine-3-carboxylic acid (Preparation 258, 300 mg, 837.14 mmol) in anhydrous THF (10 mL) was added NMM (0.06 mL, 0.57 mmol) and isobutylchloroformate (0.07 mL, 0.57 mmol) at –20° C. and the reaction mixture was stirred at this temperature for 2 hours. Aqueous ammonia (0.6 mL) was added and the reaction stirred at room temperature for 1 hour. The reaction was quenched by the addition of water and EtOAc. The organic layer was separated, washed with water, brine, dried over sodium sulfate and concentrated in vacuo. The residue was purified by silica gel column chromatography eluting with 66% EtOAc in hexanes. The residue was dissolved in TFA and stirred at room temperature for 30 minutes. The reaction was concentrated in vacuo and dissolved in MeOH (5 mL), cooling to 0° C. Ethylene diamine was added drop-wise until the solution showed a basic pH. The reaction was extracted into 20% IPA in DCM, dried over sodium sulfate and concentrated in vacuo. The residue was purified using preparative TLC to afford the title compound (30 mg, 27%).

$^1$H NMR (400 MHz, DMSO-$d_6$): δ ppm 0.96 (t, 3H), 2.89 (q, 2H), 3.10 (s, 3H), 4.90 (br m, 1H), 5.08 (br m, 1H), 6.57 (m, 1H), 6.81 (m, 1H), 7.19 (m, 1H), 7.32 (m, 1H), 7.46 (m, 1H), 7.55-7.67 (m, 5H), 7.73 (m, 1H), 7.91 (br s, 1H), 8.26 (br s, 1H), 9.86 (t, 1H), 10.05 (br s, 1H), 13.96 (br s, 1H). MS m/z 575 [M+H]$^+$

Example 96

6-(5-Fluoro-4-hydroxy-2-(2,2,2-trifluoroethyl)phenyl)-4-((2-(N-methylphenylsulfonamido)benzyl)amino)-1H-pyrazolo[3,4-d]pyrimidine-3-carboxamide The title compound was prepared according to the method described for Example 95 using 6-(5-fluoro-2-(2,2,2-trifluoroethyl)-4-((2-(trimethylsilyl)ethoxy)meth-oxy)phenyl)-4-((2-(N-meth-ylphenylsulfonamido)benzyl)amino)-1-((2-(trimethylsilyl)ethoxy)methyl)-1H-pyrazolo[3,4-d]pyrimidine-3-carboxylic acid (Preparation 261). $^1$H NMR (400 MHz, DMSO-$d_6$): δ ppm 3.10 (s, 3H), 4.32 (m, 2H), 4.92 (m, 1H), 5.06 (m, 1H), 6.56 (m, 1H), 6.99 (m, 1H), 7.17 (m, 1H), 7.32 (m, 1H), 7.44 (m, 1H), 7.61-7.67 (m, 6H), 7.93 (br s, 1H), 8.28 (br s, 1H), 9.93 (t, 1H), 10.41 (br s, 1H), 14.04 (br s, 1H). MS m/z 630 [M+H]$^+$

Example 97

6-(5-Fluoro-4-hydroxy-2-(2,2,2-trifluoroethyl)phenyl)-4-((5-hydroxy-2-(N-methylmethylsulfonamido)benzyl)amino)-1H-pyrazolo[3,4-d]pyrimidine-3-carboxamide To a solution of 6-(5-fluoro-4-methoxy-2-(2,2,2-trifluoroethyl)phenyl)-4-((5-methoxy-2-(N-methylmethylsulfonamido)benzyl)amino)-1-((2-(trimethylsilyl)ethoxy)methyl)-1H-pyrazolo-[3,4-d]pyrimidine-3-carboxylic acid (Preparation 269, 0.1 g, 0.13 mmol), HOBT (36 mg, 0.27 mmol) and EDCl (51 mg, 0.27 mmol) in dichloromethane (6 mL) at 0° C. was added ammonium chloride (36 mg, 0.67 mmol) and DIPEA (0.12 mL, 0.67 mmol) and the reaction was stirred at room temperature for 14 hours. The reaction was concentrated in vacuo and the residue diluted with ethyl acetate. The organic solution was washed with brine, dried over sodium sulfate and concentrated in vacuo. The residue was purified using silica gel column chromatography eluting with 52% EtOAc in hexanes. The residue (62 mg, 0.084 mmol) was dissolved in DCM (5 mL) at 0° C. and boron tribromide (0.08 mL, 0.83 mmol) was added. The reaction was stirred at room temperature for 1 hour. The reaction was concentrated in vacuo, diluted with methanol (5 ml) and treated with ethylene diamine until the pH was basic, stirring for 1 hour. The solvent was removed in vacuo and the residue was partitioned between ethyl acetate and water, the organic extracts were dried over sodium sulfate and purified by Preparative TLC to afford the title compound as an off-white solid (25 mg, 51%). $^1$H NMR (400 MHz, DMSO-$d_6$): δ ppm 3.01 (s, 3H), 3.12 (s, 3H), 4.30 (m, 2H), 4.80 (m, 1H), 4.91 (m, 1H), 6.68-6.71 (m, 1H), 6.76-6.77 (m, 1H), 6.97-7.00 (m, 1H), 7.31-7.33 (m, 1H), 7.69-7.72 (m, 1H), 7.93 (br s, 1H), 8.28 (br s, 1H), 9.61 (br s, 1H), 9.87 (t, 1H), 10.40 (br s, 1H). MS m/z 584 [M+H]$^+$

Example 98

6-(5-Fluoro-4-hydroxy-2-(2,2,2-trifluoroethyl)phenyl)-4-((2-(N-methylmethylsulfonamido)benzyl)amino)-1H-pyrazolo[3,4-d]pyrimidine-3-carboxamide The title compound was prepared according to the method described by Example 97 using 6-(5-fluoro-4-methoxy-2-(2,2,2-trifluoroethyl)phenyl)-4-((2-(N-methylmethylsulfonamido)-benzyl)amino)-1-((2-(trimethylsilyl)ethoxy)methyl)-1H-pyrazolo[3,4-d]pyrimidine-3-carboxylic acid (Preparation 270). $^1$H NMR (400 MHz, DMSO-$d_6$): δ ppm 3.07 (s, 3H), 3.18 (s, 3H), 4.29 (m, 2H), 4.88-5.00 (br m, 2H), 6.98 (m, 1H), 7.32-7.43 (m, 3H), 7.54 (m, 1H), 7.68 (m, 1H), 7.92 (br s, 1H), 8.27 (br s, 1H), 9.92 (t, 1H), 10.39 (br s, 1H), 14.02 (br s, 1H). MS m/z 568 [M+H]$^+$

Example 99

6-(5-Fluoro-4-hydroxy-2-(2,2,2-trifluoroethyl)phenyl)-4-((5-hydroxy-2-(N-methylmethylsulfonamido)benzyl)amino)-N-(6-((2-hydroxyethyl)amino)pyridin-3-yl)-1H-pyrazolo[3,4-d]pyrimidine-3-carboxamide To a solution of 6-(5-fluoro-4-hydroxy-2-(2,2,2-trifluoroethyl)phenyl)-4-((5-hydroxy-2-(N-methyl methylsulfonamido)benzyl)amino)-1H-pyrazolo[3,4-d]pyrimidine-3-carboxylic acid (Example 174, 160 mg, 0.27 mmol) and 2-[(5-aminopyridin-2-yl)amino]ethanol (84 mg, 0.54 mmol) in DMF (5 mL) was added HATU (312 mg, 0.82 mmol) and DIPEA (0.12 mL, 0.68 mmol) and the reaction was stirred at room temperature for 18 hours. The reaction was purified directly by Preparative HPLC to afford the title compound (48 mg, 24%). $^1$H NMR (400 MHz, DMSO-d$_6$): δ ppm 3.02 (s, 3H), 3.12 (s, 3H), 3.32 (m, 2H), 3.51 (m, 2H), 4.30 (m, 2H), 4.81-4.93 (m, 2H), 6.44-6.52 (m, 2H), 6.68 (m, 1H), 6.76 (m, 1H), 6.97 (m, 1H), 7.33 (m, 1H), 7.69-7.77 (m, 2H), 8.31 (d, 1H), 9.63 (t, 1H), 10.53 (br s, 1H). MS m/z 720 [M+H]$^+$ Example 100

6-(5-Fluoro-4-hydroxy-2-(2,2,2-trifluoroethyl)phenyl)-N-methyl-4-(((3-(N-methylmethylsulfonamido)pyrazin-2-yl)methyl)amino)-1H-pyrazolo[3,4-d]pyrimidine-3-carboxamide To a solution of N-(3-(((6-(5-fluoro-4-methoxy-2-(2,2,2-trifluoroethyl)phenyl)-3-iodo-1H-pyrazolo[3,4-d]pyrimidin-4-yl)amino)methyl)pyrazin-2-yl)-N-methylmethanesulfonamide (Preparation 277, 220 mg, 0.33 mmol) in methylamine in THF (3 mL) was added molybdenum hexacarbonyl (87.77 mg, 0.33 mmol), Pd(OAc)$_2$ (5.18 mg, 0.07 mmol) and DBU (0.15 mL, 0.99 mmol) and the reaction was heated to 100° C. under microwave irradiation for 10 minutes. The reaction was cooled, concentrated in vacuo and purified using silica gel column chromatography followed by preparative TLC. The residue was dissolved in DCM (5 mL) and treated with boron tribromide (0.11 mL, 1.17 mmol) at 0° C. and stirred at room temperature for 18 hours. The reaction was concentrated in vacuo and partitioned between DCM and saturated aqueous sodium bicarbonate solution. The organic layer was collected, washed with brine, dried over sodium sulfate and concentrated in vacuo. The residue was purified using preparative TLC eluting with 5% MeOH in DCM to afford the title compound as a white solid (23 mg, 47%). $^1$H NMR (400 MHz, DMSO-d$_6$): δ ppm 2.84 (s, 3H), 3.15 (s, 3H), 3.19 (s, 3H), 4.21 (m, 2H), 5.13 (m, 2H), 6.97 (m, 1H), 7.58 (m, 1H), 8.53 (d, 1H), 8.63 (d, 1H), 8.86 (m, 1H), 10.06 (m, 1H), 10.37 (br s, 1H), 14.04 (br s, 1H). MS m/z 584 [M+H]$^+$ The following Examples (Examples 101-104) were prepared according to the method described for Example 1 using the appropriate pyrazolo-pyrimidine as described below:

| Ex | Name | Data |
|---|---|---|
| 101 | 6-(5-fluoro-4-hydroxy-2-(2,2,2-trifluoroethyl)phenyl)-4-((2-(N-(2-hydroxyethyl)methylsulfonamido)benzyl)amino)-1H-pyrazolo[3,4-d]pyrimidine-3-carboxamide | MS m/z 598 [M + H]$^+$ $^1$H NMR (400 MHz, DMSO-d$_6$): δ ppm 3.10 (s, 3H), 3.30-3.39 (m, 2H), 3.64 (m, 2H), 4.26 (m, 2H), 4.81 (m, 1H), 4.94 (m, 2H), 6.99 (m, 1H), 7.39 (m, 3H), 7.51 (m, 1H), 7.68 (m, 1H), 7.90 (m, 1H), 8.26 (m, 1H), 9.89 (s, 1H), 10.32 (br s, 1H), 14.01 (br s, 1H). Using N-(2-(((6-(4-((tert-butyldimethylsilyl)oxy)-5-fluoro-2-(2,2,2-trifluoroethyl)phenyl)-3-iodo-1-((2-(trimethylsilyl)ethoxy)methyl)-1H-pyrazolo[3,4-d]pyrimidin-4-yl)amino)methyl)phenyl)-N-(2-((tert-butyldimethylsilyl)oxy)ethyl)methanesulfonamide (Preparation 265) with ammonia in THF. |
| 102 | 6-(5-fluoro-4-hydroxy-2-(2,2,2-trifluoroethyl)phenyl)-4-((2-(N-(2-hydroxyethyl)methylsulfonamido)benzyl)amino)-N-methyl-1H-pyrazolo[3,4-d]pyrimidine-3-carboxamide | MS m/z 612 [M + H]$^+$ $^1$H NMR (400 MHz, DMSO-d$_6$): δ ppm 2.83 (m, 3H), 3.10 (s, 3H), 3.33-3.40 (m, 2H), 3.64 (m, 2H), 4.21-4.30 (m, 2H), 4.85 (t, 1H), 5.01 (m, 2H), 6.96 (m, 1H), 7.36-7.38 (m, 3H), 7.51 (m, 1H), 7.67 (m, 1H), 8.88 (m, 1H), 9.87 (t, 1H), 10.40 (br s, 1H). Using N-(2-(((6-(4-((tert-butyldimethylsilyl)oxy)-5-fluoro-2-(2,2,2-trifluoroethyl)phenyl)-3-iodo-1-((2-(trimethylsilyl)ethoxy)methyl)-1H-pyrazolo[3,4-d]pyrimidin-4-yl)amino)methyl)phenyl)-N-(2-((tert-butyldimethylsilyl)oxy)ethyl)methanesulfonamide (Preparation 265). |
| 103 | 4-((2-(N-ethylmethylsulfonamido)-benzyl)amino)-6-(5-fluoro-4-hydroxy-2-(2,2,2-trifluoroethyl)phenyl)-N-methyl-1H-pyrazolo[3,4-d]pyrimidine-3-carboxamide | MS m/z 594 [M − H]$^-$ $^1$H NMR (400 MHz, DMSO-d$_6$): δ ppm 1.00 (t, 3H), 2.83 (d, 3H), 3.06 (s, 3H), 3.55 (m, 1H), 3.69 (m, 1H), 4.18 (m, 2H), 4.87 (m, 1H), 4.92 (m, 1H), 6.96 (m, 1H), 7.33-7.40 (m, 3H), 7.51 (m, 1H), 7.65 (m, 1H), 8.88 (t, 1H), 9.91 (t, 1H), 10.36 (br s, 1H), 14.05 (br s, 1H). Using N-ethyl-N-(2-(((6-(5-fluoro-2-(2,2,2-trifluoroethyl)-4-((2-(trimethylsilyl)ethoxy)methoxy)phenyl)-3-iodo-1-((2-(trimethylsilyl)ethoxy)-methyl)-1H-pyrazolo[3,4-d]pyrimidin-4-yl)amino)methyl)phenyl)methanesulfonamide (Preparation 263). |
| 104 | 4-((5-fluoro-2-(N-methylmethylsulfonamido)benzyl)amino)-6-(5-fluoro-4-hydroxy-2-(2,2,2-trifluoroethyl)phenyl)-N-methyl-1H-pyrazolo[3,4-d]pyrimidine-3-carboxamide | MS m/z 600 [M + H]+ 1H NMR (400 MHz, DMSO-d6): δ ppm 2.85 (d, 3H), 3.08 (s, 3H), 3.16 (s, 3H), 4.21 (m, 2H), 4.91-4.99 (m, 2H), 6.95 (m, 1H), 7.10-7.22 (m, 2H), 7.60-7.66 (m, 2H), 8.89 (m, 1H), 9.92 (t, 1H). Using N-(4-fluoro-2-(((6-(5-fluoro-4-methoxy-2-(2,2,2-trifluoroethyl)-phenyl)-3-iodo-1-((2-(trimethylsilyl)-ethoxy)methyl)-1H-pyrazolo[3,4-d]pyrimidin-4-yl)amino)methyl)phenyl)-N-methylmethanesulfonamide (Preparation 268). |

Example 105

4-((2-(N-Ethylphenylsulfonamido)-5-hydroxybenzyl)amino)-6-(5-fluoro-4-hydroxy-2-(2,2,2-trifluoroethyl)phenyl)-N-methyl-1H-pyrazolo[3,4-d]pyrimidine-3-carboxamide The title compound was prepared according to the method described for Example 32 using N-ethyl-N-(2-((((6-(5-fluoro-4-methoxy-2-(2,2,2-trifluoroethyl)phenyl)-3-iodo-1-((2-(trimethyl-silyl)ethoxy)methyl)-1H-pyrazolo[3,4-d]pyrimidin-4-yl)amino)-methyl)-4-methoxyphenyl)-benzenesulfonamide (Preparation 266). $^1$H NMR (400 MHz, DMSO-d$_6$): δ ppm 0.93 (t, 3H), 2.85 (d, 3H), 3.24 (m, 1H), 3.77 (m, 1H), 4.29 (m, 2H), 4.85-4.93 (m, 2H), 6.36 (m, 1H), 6.54 (m, 1H), 6.76 (m, 1H), 6.98 (m, 1H), 7.58-7.72 (m, 5H), 8.89 (m, 1H), 9.62 (s, 1H), 9.85 (br s, 1H), 10.10 (br s, 1H), 14.10 (br s, 1H). MS m/z 672 [M–H]$^-$

Example 106

4-((2-(N-Methylphenylsulfonamido)-5-hydroxybenzyl)amino)-6-(5-fluoro-4-hydroxy-2-(2,2,2-trifluoroethyl)phenyl)-N-methyl-1H-pyrazolo[3,4-d]pyrimidine-3-carboxamide The title compound was prepared according to the method described for Example 32 using N-methyl-N-(2-((((6-(5-fluoro-4-methoxy-2-(2,2,2-trifluoroethyl)phenyl)-3-iodo-1-((2-(trimethyl-silyl)ethoxy)methyl)-1H-pyrazolo[3,4-d]pyrimidin-4-yl)-amino)methyl)-4-methoxyphenyl)-benzenesulfonamide (Preparation 267). $^1$H NMR (400 MHz, DMSO-dc): δ ppm 2.85 (s, 3H), 3.05 (s, 3H), 4.34 (m, 2H), 4.86 (m, 1H), 4.97 (m, 1H), 6.32 (m, 1H), 6.51 (m, 1H), 6.76 (m, 1H), 6.98 (m, 1H), 7.60-7.74 (m, 6H), 8.91 (m, 1H), 9.63 (s, 1H), 9.89 (t, 1H), 10.40 (br s, 1H), 14.10 (br s, 1H). MS m/z 660 [M+H]$^+$ The following Examples (Examples 107-108) were prepared according to the method described for Example 41 using the appropriate pyrazolo-pyrimidine as described below:

Example 109

6-(5-Fluoro-4-hydroxy-2-(2,2,2-trifluoroethyl)phenyl)-N-methyl-4-((2-(methyl(sulfamoyl)amino)benzyl)amino)-1H-pyrazolo[3,4-d]pyrimidine-3-carboxamide To a solution of tert-butyl 6-(5-fluoro-4-methoxy-2-(2,2,2-trifluoroethyl)phenyl)-4-((2-(methylamino)benzyl)amino)-3-(methylcarbamoyl)-1H-pyrazolo[3,4-d]pyrimidine-1-carboxylate (Preparation 256, 50 mg, 0.08 mmol) in anhydrous THF (5 mL) was added sodium hydride (3 mg, 0.08 mmol) at 0° C. The reaction was stirred for 10 minutes before the addition of sulfamoyl chloride (7 mg, 0.06 mmol) and further stirring at 0° C. for 2.5 hours. The reaction was quenched by the addition of ice-water and extracted into EtOAc. The organic layer was washed with brine, dried over sodium sulfate and concentrated in vacuo. The residue was purified by preparative TLC and dissolved in DCM (5 mL). The solution was treated with boron tribromide (0.08 mL, 0.8 mmol) and stirred at room temperature for 18 hours. The reaction was concentrated in vacuo and partitioned between DCM and saturated aqueous sodium bicarbonate solution. The organic layer was washed with brine, dried over sodium sulfate and concentrated in vacuo. The residue was purified by preparative TLC to afford the title compound as a white solid (11 mg, 32%). $^1$H NMR (400 MHz, DMSO-d$_6$): δ ppm 2.86 (s, 3H), 3.08 (s, 3H), 4.29 (m, 2H), 4.86-5.05 (m, 2H), 6.97 (m, 1H), 7.09 (s, 2H), 7.25-7.35 (m, 3H), 7.46 (m, 1H), 7.69-7.72 (m, 1H), 8.88 (t, 1H), 9.88 (t, 1H), 10.37 (s, 1H), 14.02 (s, 1H). MS m/z 583 [M+H]$^+$

Example 110

6-(5-Fluoro-4-hydroxy-2-(2,2,2-trifluoroethyl)phenyl)-N-methyl-4-((2-(methyl(N-methylsulfamoyl)amino)benzyl)amino)-1H-pyrazolo[3,4-d]pyrimidine-3-carboxamide To a solution of tert-butyl 6-(4-((tert-butoxycarbonyl)oxy)-5-fluoro-2-(2,2,2-trifluoroethyl)phenyl)-4-((2-(methylamino)benzyl)amino)-3-(methylcarbamoyl)-1H-pyrazolo-[3,4-d]pyrimidine-1-carboxylate (Preparation 255, 56 mg,

| Ex | Name | Data |
| --- | --- | --- |
| 107 | 4-((2-(N-ethylphenyl-sulfonamido)-5-hydroxy-benzyl)amino)-6-(5-fluoro-4-hydroxy-2-(2,2,2-trifluoroeth-yl)phenyl)-1H-pyrazolo[3,4-d]pyrimidine-3-carboxamide | MS m/z 660 [M + H]$^+$ $^1$H NMR (400 MHz, DMSO-d$_6$): δ ppm 0.94 (t, 3H), 3.20 (m, 1H), 3.78 (m, 1H), 4.24-4.30 (m, 2H), 4.81 (m, 1H), 4.97 (m, 1H), 6.35 (m, 1H), 6.53 (m, 1H), 6.79 (m, 1H), 7.00 (m, 1H), 7.57-7.72 (m, 6H), 7.95 (br s, 1H), 8.30 (br s, 1H), 9.63 (s, 1H), 9.87 (t, 1H), 10.37 (br s, 1H), 14.05 (br s, 1H). Using 4-((2-(N-ethylphenylsulfon-amido)-5-methoxy-benzyl)amino)-6-(5-fluoro-4-methoxy-2-(2,2,2-trifluoro-ethyl)phenyl)-1-((2-(trimethylsilyl)-ethoxy)methyl)-1H-pyrazolo[3,4-d]pyrimidine-3-carboxamide (Preparation 253). |
| 108 | 4-((2-(N-methylphenyl-sulfonamido)-5-hydroxy-benzyl)amino)-6-(5-fluoro-4-hydroxy-2-(2,2,2-trifluoroeth-yl)phenyl)-1H-pyrazolo[3,4-d]pyrimidine-3-carboxamide | MS m/z 646 [M + H]$^+$ $^1$H NMR (400 MHz, DMSO-d$_6$): δ ppm 3.05 (s, 3H), 4.08 (m, 2H), 4.82 (m, 1H), 4.96 (m, 1H), 6.32 (m, 1H), 6.50 (m, 1H), 6.78 (m, 1H), 7.01 (m, 1H), 7.60-7.75 (m, 6H), 7.95 (br s, 1H), 8.30 (br s, 1H), 9.63 (s, 1H), 9.89 (t, 1H), 10.38 (s, 1H), 14.05 (br s, 1H). Using 4-((2-(N-methylphenylsulfonamido)-5-methoxy-benzyl)amino)-6-(5-fluoro-4-methoxy-2-(2,2,2-trifluoro-ethyl)-phenyl)-1-((2-(trimethylsilyl)-ethoxy)methyl)-1H-pyrazolo[3,4-d]pyrimidine-3-carboxamide (Preparation 254). |

0.08 mmol) in THF (3 mL) was added sodium hydride (2 mg, 0.08 mmol) at 0° C. The reaction was stirred at room temperature for 2 minutes before the addition of methanesulfonyl chloride (10 mg, 0.08 mmol) and further stirring for 18 hours. The reaction was quenched by the addition of ice-water and extracted into EtOAc. The organic layer was washed with brine, dried over sodium sulfate and concentrated in vacuo. The residue was purified by preparative TLC and treated with 4M HCl in dioxane (0.3 mL). The reaction was stirred at room temperature for 3 hours before concentrating in vacuo and triturating with pentane-ether to afford the title compound. $^1$H NMR (400 MHz, DMSO-$d_6$): δ ppm 2.62 (d, 3H), 2.86 (d, 3H), 3.05 (s, 3H), 4.33 (m, 2H), 4.95 (m, 2H), 6.98 (m, 1H), 7.28-7.49 (m, 4H), 7.73 (m, 1H), 8.89 (t, 1H), 9.92 (t, 1H), 10.38 (s, 1H), 14.03 (s, 1H). MS m/z 595 [M−H]$^-$ Library Protocol 1

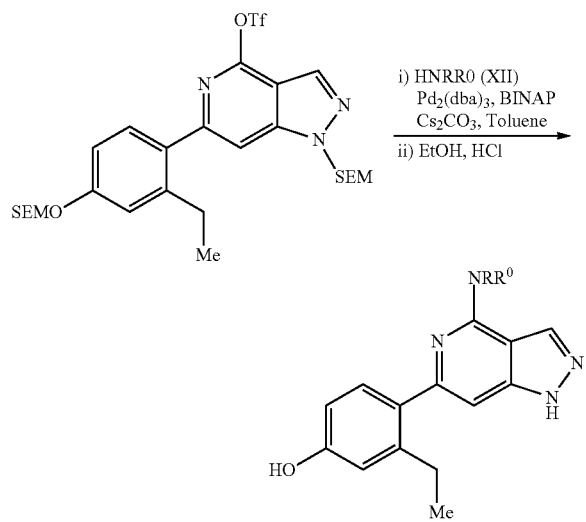

A 0.1 M solution of 6-(2-ethyl-4-((2-(trimethylsilyl)ethoxy)methoxy)phenyl)-1-((2-(trimethylsilyl)ethoxy)methyl)-1H-pyrazolo[4,3-c]pyridin-4-yl trifluoromethanesulfonate (Preparation 328, 700 μL, 70 μmol) in toluene was added to an amine of formula (XII) (200 μmol, 2.9 eq) and the solution degassed with nitrogen. Cesium carbonate (45 mg, 140 μmol) was added followed by Pd$_2$(dba)$_3$ (3.4 mg, 3.5 μmol) and BINAP (2.2 mg, 3.5 μmol) and the reaction further degassed with nitrogen. The reaction was shaken at 80° C. for 16 hours before concentrating in vacuo. Water (1 mL) was added followed by EtOAc (1 mL) and the mixture filtered. The organic layer was collected, dried over sodium sulfate and concentrated in vacuo. To the residue was added a solution of cHCl in EtOH (1 mL, v:v 1:6) and the reaction shaken at 80° C. for 2 hours. The reaction was cooled, concentrated in vacuo and purified using one of the Preparative HPLC methods described below:

Preparative HPLC

Method A: Agella Venusil ASB C18, 150×21.2 mm×5 μm; Acetonitrile-Water (0.225% formic acid); Flow rate: 35 mL/min; Gradient time 8 mins.

Method B: Boston Symmetrix ODS-H, 150×30 mm×5 μm; Acetonitrile-Water (0.225% formic acid); Flow rate: 30 mL/min; Gradient time 10 mins.

Method C: DIKMA Diamonsil(2) C18, 200×20 mm×5 μm; Acetonitrile-Water (0.225% formic acid); Flow rate: 30 mL/min; Gradient time 10 mins.

LCMS:

Method 1

A: 0.0375% TFA in water; B: 0.01875% TFA in MeCN; Column: XBridge C18, 2.1×50 mm×5 μm; Gradient: From 99% [A] and 1% [B] to 95% [A] and 5% [B] in 0.6 min, further to 100% [B] in 4.0 min and finally back to initial condition in 4.3 min, 0.8 mL/min flow rate.

Method 2

A: 0.0375% TFA in water; B: 0.01875% TFA in MeCN; Column: XBridge C18, 2.1×50 mm×5 μm; Gradient: From 90% [A] and 10% [B] to 100% [B] in 4 min and finally back to initial condition in 4.3 min, 0.8 mL/min flow rate.

Method 3

A: 0.0375% TFA in water; B: 0.01875% TFA in MeCN; Column: XBridge C18, 2.1×50 mm×5 μm; Gradient: From 75% [A] and 25% [B] to 100% [B] in 3.5 min and finally back to initial condition in 4.0 min, 0.8 mL/min flow rate.

The compounds of the Examples in the table below (Examples 111-124) were prepared and purified from 6-(2-ethyl-4-((2-(trimethylsilyl)ethoxy)methoxy)phenyl)-1-((2-(trimethylsilyl)ethoxy)methyl)-1H-pyrazolo[4,3-c]pyridin-4-yl trifluoromethanesulfonate (Preparation 328) and the appropriate amine according to Library Protocol 1. The compounds were isolated as their formate salts.

| Ex | Name | MS Data/HPLC Organic gradient/Amine |
|----|------|--------------------------------------|
| 111 | 4-[4-(7,8-dimethoxy-3,4-dihydroisoquinolin-2(1H)-yl)-1H-pyrazolo[4,3-c]pyridin-6-yl]-3-ethylphenol formate | MS m/z 431 [M + H]$^+$<br>Rt = 1.72 min<br>HPLC organic gradient: 21-51%.<br>1,2,3,4-tetrahydro-7,8-dimethoxy-isoquinoline (Chem. & Pharm. Bull. (1998), 46 (6), 918-927). |
| 112 | 3-ethyl-4-[4-(3-phenoxyazetidin-1-yl)-1H-pyrazolo[4,3-c]pyridin-6-yl]phenol formate | MS m/z 387 [M + H]$^+$<br>Rt = 1.73 min<br>HPLC organic gradient: 21-51%.<br>3-phenoxyazetidine. |
| 113 | 3-ethyl-4-{4-[6-(4-methyl-1H-imidazol-1-yl)-3,4-dihydroisoquinolin-2(1H)-yl]-1H-pyrazolo[4,3-c]pyridin-6-yl}phenol formate | MS m/z 451 [M + H]$^+$<br>Rt = 2.16 min<br>HPLC organic gradient: 3-33%.<br>6-(4-methyl-1H-imidazol-1-yl)-1,2,3,4-tetrahydroisoquinoline hydrochloride (Preparation 345). |
| 114 | 3-ethyl-4-{4-[6-(2-methoxyethoxy)-3,4-dihydroisoquinolin-2(1H)-yl]-1H-pyrazolo[4,3-c]pyridin-6-yl}phenol formate | MS m/z 445 [M + H]$^+$<br>Rt = 2.64 min<br>HPLC organic gradient: 18-48%.<br>1,2,3,4-tetrahydro-6-(2-methoxyethoxy)-isoquinoline. |

| Ex | Name | MS Data/HPLC Organic gradient/Amine |
|---|---|---|
| 115 | 1-[6-(2-ethyl-4-hydroxyphenyl)-1H-pyrazolo[4,3-c]pyridin-4-yl]-3-methylazetidin-3-ol formate | MS m/z 325 [M + H]$^+$<br>Rt = 2.11 min<br>HPLC organic gradient: 3-33%.<br>3-methyl-3-azetidinol (J. Med. Chem. (2010), 53(9), 3645-3674). |
| 116 | 2-[6-(2-ethyl-4-hydroxyphenyl)-1H-pyrazolo[4,3-c]pyridin-4-yl]-N-[2-(pyrrolidin-1-yl)ethyl]-1,2,3,4-tetrahydroisoquinoline-7-sulfonamide formate | MS m/z 547 [M + H]$^+$<br>Rt = 2.22 min<br>HPLC organic gradient: 6-36%.<br>N-(2-(pyrrolidin-1-yl)ethyl)-1,2,3,4-tetrahydroisoquinoline-7-sulfonamide (Preparation 346). |
| 117 | N-benzyl-2-[6-(2-ethyl-4-hydroxyphenyl)-1H-pyrazolo[4,3-c]pyridin-4-yl]-1,2,3,4-tetrahydroisoquinoline-5-carboxamide formate | MS m/z 504 [M + H]$^+$<br>Rt = 2.50 min<br>HPLC organic gradient: 20-50%.<br>N-benzyl-1,2,3,4-tetrahydroisoquinoline-5-carboxamide hydrochloride (Preparation 347). |
| 118 | 4-{4-[7-(benzyloxy)-6-methoxy-3,4-dihydroisoquinolin-2(1H)-yl]-1H-pyrazolo[4,3-c]pyridin-6-yl}-3-ethylphenol formate | MS m/z 507 [M + H]$^+$<br>Rt = 2.20 min<br>HPLC organic gradient: 26-56%.<br>1,2,3,4-tetrahydro-6-methoxy-7-(phenylmethoxy)-isoquinoline (Heterocycles (1989), 28(1), 295-301). |
| 119 | 4-[4-(5-chloro-3,4-dihydroisoquinolin-2(1H)-yl)-1H-pyrazolo[4,3-c]pyridin-6-yl]-3-ethylphenol formate | MS m/z 405 [M + H]$^+$<br>Rt = 2.60 min<br>HPLC organic gradient: 22-52%.<br>1,2,3,4-tetrahydro-5-chloro-isoquinoline. |
| 120 | 4-chloro-3-({1-[6-(2-ethyl-4-hydroxyphenyl)-1H-pyrazolo[4,3-c]pyridin-4-yl]azetidin-3-yl}oxy)benzonitrile formate | MS m/z 446 [M + H]$^+$<br>Rt = 2.56 min<br>HPLC organic gradient: 21-51%.<br>3-(azetidin-3-yloxy)-4-chlorobenzonitrile hydrochloride (Preparation 348). |
| 121 | 3-ethyl-4-[4-(6-fluoro-3,4-dihydroisoquinolin-2(1H)-yl)-1H-pyrazolo[4,3-c]pyridin-6-yl]phenol formate | MS m/z 389 [M + H]$^+$<br>Rt = 2.70 min<br>HPLC organic gradient: 19-49%.<br>1,2,3,4-tetrahydro-6-fluoro-isoquinoline. |
| 122 | 3-ethyl-4-[4-(8-methoxy-3,4-dihydroisoquinolin-2(1H)-yl)-1H-pyrazolo[4,3-c]pyridin-6-yl]phenol formate | MS m/z 401 [M + H]$^+$<br>Rt = 1.82 min<br>HPLC organic gradient: 14-44%.<br>1,2,3,4-tetrahydro-8-methoxyisoquinoline. |
| 123 | N-{2-[6-(2-ethyl-4-hydroxyphenyl)-1H-pyrazolo[4,3-c]pyridin-4-yl]-1,2,3,4-tetrahydroisoquinolin-5-yl}methanesulfonamide formate | MS m/z 464 [M + H]$^+$<br>Rt = 2.16 min<br>HPLC organic gradient: 13-43%.<br>N-1,2,3,4-tetrahydroisoquinolin-5-yl}methanesulfonamide hydrochloride. |
| 124 | 4-(4-{[2-(biphenyl-4-yl)ethyl]amino}-1H-pyrazolo[4,3-c]pyridin-6-yl)-3-ethylphenol formate | MS m/z 435 [M + H]$^+$<br>Rt = 2.20 min<br>HPLC organic gradient: 25-55%.<br>2-([1,1'-biphenyl]-4-yl)ethanamine. |

Example 125

N-[2-({[6-(2-Ethyl-4-hydroxyphenyl)-1H-pyrazolo[4,3-c]pyridin-4-yl]amino}methyl)phenyl]-N-methylmethanesulfonamide hydrochloride To a solution of 6-(2-ethyl-4-((2-(trimethylsilyl)ethoxy)methoxy)phenyl)-1-((2-(trimethyl-silyl)ethoxy)methyl)-1H-pyrazolo[4,3-c]pyridin-4-yl trifluoromethanesulfonate (Preparation 328, 14 mg, 0.02 mmol) in toluene (0.5 mL) was added N-[2-aminomethyl)phenyl]-N-methylmethanesulfonamide (WO20101058846A1, 9 mg, 0.03 mmol), cesium carbonate (14 mg, 0.04 mmol), Pd(OAc)$_2$ (0.9 mg, 0.004 mmol) and BINAP (3.7 mg, 0.006 mmol). The reaction was degassed with nitrogen followed by heating to 150° C. under microwave irradiation for 15 minutes. The reaction was filtered, washing through with DCM and the filtrate concentrated in vacuo. The residue was purified using silica gel column chromatography eluting with 1-5% MeOH in DCM. The residue was dissolved in MeOH (1 mL) and cHCl (0.2 mL) was added and the reaction heated to 80° C. for 3 hours. The reaction was cooled, concentrated in vacuo and triturated with DCM to afford the title compound as the hydrochloride salt (10 mg, 50%). $^1$H NMR (400 MHz, DMSO-d$_6$): δ ppm 0.75 (t, 3H), 2.40 (q, 2H), 3.00 (s, 3H), 3.03 (s, 3H), 4.55 (br m, 1H), 4.95 (br m, 1H), 6.50 (m, 3H), 7.00 (m, 1H), 7.25 (m, 2H), 7.40-7.50 (m, 2H), 7.80 (t, 1H), 8.20 (s, 1H), 9.25 (s, 1H), 12.95 (s, 1H). MS m/z 452 [M+H]$^+$ The following compounds of the Examples below (Examples 126-130) were prepared according to the method described for Example 125 above using 6-(2-ethyl-4-((2-

(trimethylsilyl)ethoxy)methoxy)phenyl)-1-((2-(trimethylsilyl)ethoxy)methyl)-1H-pyrazolo[4,3-c]pyridin-4-yl trifluoromethanesulfonate (Preparation 328) or 6-(2-ethyl-5-fluoro-4-((2-(trimethylsilyl)ethoxy)methoxy)phenyl)-1-((2-(trimethylsilyl)ethoxy)methyl)-1H-pyrazolo[4,3-c]pyridin-4-yl trifluoromethanesulfonate (Preparation 331) or 6-(2-ethyl-5-fluoro-4-((2-(trimethylsilyl)ethoxy)methoxy)phenyl)-1-(tetrahydro-2H-pyran-2-yl)-1H-pyrazolo[4,3-c]pyridin-4-yl trifluoromethanesulfonate (Preparation 330) and the appropriate amine. Purification took place according to the Purification Method (PM) described or one of the following below. Compounds were isolated as the free parent, diethylamine salt or hydrochloride salt as described below:

Purification Method J: The residue was dissolved in DMSO (0.9 mL) and triethylamine (0.1 mL) and purified using Preparative HPLC.

ration 332, 1.5 g, 3.07 mmol) and the reaction was heated to 80° C. for 15 hours. The reaction was concentrated in vacuo and partitioned between water and ethyl acetate. The organic layer was washed with brine, dried over sodium sulfate and concentrated in vacuo. The residue was purified by silica gel column chromatography eluting with 1% MeOH in DCM. The residue was dissolved in MeOH (10 mL) and cHCl (8 mL) was added. The reaction was heated at from 65-80° C. for 6 hours before cooling and concentrating in vacuo. The residue was triturated with MeCN/ether to afford the title compound as the hydrochloride salt (400 mg, 42%). $^1$H NMR (400 MHz, DMSO-$d_6$): δ ppm 0.98 (m, 3H), 2.32-2.41 (m, 2H), 3.09-3.18 (m, 6H), 5.11 (m, 2H), 6.98 (s, 2H), 7.09-7.21 (m, 2H), 7.21 (s, 2H), 7.27 (br s, 21H), 7.34-7.36 (m, 1H), 7.42-7.48 (m, 3H), 7.63 (br s, 1H), 8.70 (br s, 1H), 10.04 (br s, 1H), 10.35 (br s, 1H), 12.20 (br s, 1H), 14.17 (br s, 1H). MS m/z 470 [M+H]$^+$

| Ex | Name | MS Data/PM/Amine |
|---|---|---|
| 126 | Racemic 1-[6-(2-ethyl-4-hydroxyphenyl)-1H-pyrazolo[4,3-c]pyridin-4-yl]-N,N-dimethylpyrrolidine-3-sulfonamide (free parent). | MS m/z 416 [M + H]$^+$<br>Rt = 2.75 min<br>PM J.<br>Racemic N,N-dimethyl-3-pyrrolidinesulfonamide hydrochloride. |
| 127 | N-[2-({[6-(2-ethyl-4-hydroxyphenyl)-1H-pyrazolo[4,3-c]pyridin-4-yl]amino}methyl)-3-methylphenyl]-N-methylmethanesulfonamide diethylamine salt | MS m/z 466 [M + H]$^+$<br>Rt = 2.99 min<br>PM J.<br>N-[2-(aminomethyl)-3-methylphenyl]-N-methylmethanesulfonamide (WO2012/045195A1). |
| 128 | 3-ethyl-4-[4-(4-methoxypiperidin-1-yl)-1H-pyrazolo[4,3-c]pyridin-6-yl]phenol diethylamine salt | MS m/z 353 [M + H]$^+$<br>Rt = 2.13 min<br>PM J.<br>4-methoxypiperidine. |
| 129 | N-[2-({[2-(3,4-dimethoxyphenyl)ethyl][6-(2-ethyl-5-fluoro-4-hydroxyphenyl)-1H-pyrazolo[4,3-c]pyridin-4-yl]amino}methyl)phenyl]-N-methylmethanesulfonamide hydrochloride | MS m/z 634 [M + H]$^+$<br>$^1$H NMR (400 MHz, DMSO-$d_6$): δ ppm 0.85 (br s, 3H), 2.95 (m, 2H), 3.09 (s, 6H), 3.64 (s, 3H), 3.69 (s, 3H), 4.03 (m, 1H), 5.09 (m, 2H), 6.72-6.83 (m, 3H), 6.91 (br s, 1H), 7.16-7.32 (br s, 6H), 7.60 (br s, 1H), 7.98 (br s, 1H), 8.24 (br s, 1H), 9.80 (br s, 1H), 10.29 (br s, 1H).<br>N-(2-(((3,4-dimethoxyphenethyl)amino)methyl)phenyl)-N-methylmethanesulfonamide (Preparation 367). |
| 130 | N-[2-({[6-(2-ethyl-5-fluoro-4-hydroxyphenyl)-1H-pyrazolo[4,3-c]pyridin-4-yl](2-{4-[(methylsulfonyl)amino]phenyl}ethyl)amino}methyl)phenyl]-N-methylmethanesulfonamide hydrochloride | MS m/z 667 [M + H]$^+$<br>$^1$H NMR (400 MHz, DMSO-$d_6$): δ ppm 0.94-1.06 (m, 3H), 1.75-1.88 (m, 4H), 2.66 (s, 3H), 2.71-2.81 (m, 2H), 2.95-3.05 (s, 6H), 4.01 (m, 2H), 5.09 (m, 2H), 6.90-6.98 (m, 2H), 7.09-7.11 (m, 2H), 7.19-7.21 (m, 2H), 7.29-7.37 (m, 3H), 7.42-7.60 (m, 1H), 9.61 (s, 1H).<br>N-methyl-N-(2-(((4-(methylsulfonamido)phenethyl)amino)methyl) phenyl)methanesulfonamide (Preparation 369). |

Example 131

N-[2-({[6-(2-Ethyl-5-fluoro-4-hydroxyphenyl)-1H-pyrazolo[4,3-c]pyridin-4-yl]amino}methyl)phenyl]-N-methylmethanesulfonamide To a stirring solution of 4-nitrophenyl {2-[methyl(methylsulfonyl)amino]benzyl}carbamate (Preparation 166, 2.02 g, 5.32 mmol) and triethylamine (2.12 mL, 15.33 mmol) in anhydrous DMF (20 mL) was added 6-(2-ethyl-5-fluoro-4-{[2-(trimethylsilyl)ethoxy]methoxy}phenyl)-1-(tetrahydro-2H-pyran-2-yl)-1H-pyrazolo[4,3-c]pyridine 5-oxide (Prepa- The following compounds of the Examples below (Examples 132-136) were prepared according to the method described for Example 131 above using 6-(2-ethyl-5-fluoro-4-{[2-(trimethylsilyl)ethoxy]methoxy}phenyl)-1-(tetrahydro-2H-pyran-2-yl)-1H-pyrazolo[4,3-c]pyridine 5-oxide (Preparation 332) or 6-(2-ethyl-4-((2-(trimethylsilyl)ethoxy)methoxy)phenyl)-1-((2-(trimethylsilyl)ethoxy)methyl)-1H-pyrazolo[4,3-c]pyridine 5-oxide (Preparation 333) and the appropriate aminocarbamate. The compounds were isolated as their hydrochloride salts. Purification was carried out according to the Purification Method (PM) described or one of the following below:

Purification Method K: Trituration with pentane-ether.

| Ex | Name | MS Data/PM/Aminocarbamate |
|---|---|---|
| 132 | N-[2-({[6-(2-ethyl-5-fluoro-4-hydroxyphenyl)-1H-pyrazolo[4,3-c]pyridin-4-yl]amino}methyl)-4-methylphenyl]-N-methylmethanesulfonamide hydrochloride | MS m/z 484 [M + H]$^+$<br>$^1$H NMR (400 MHz, DMSO-d$_6$): δ ppm 1.00 (s, 3H), 2.30 (m, 5H), 3.14 (s, 6H), 4.77 (m, 2H), 6.97 (s, 2H), 7.21 (d, 2H), 7.33 (d, 1H), 7.45 s, 1H), 8.68 (s, 1H), 9.94 (s, 1H), 10.33 (s, 1H), 12.17 (s, 1H), 14.16 (s, 1H).<br>PM K.<br>4-nitrophenyl {5-methyl-2-[methyl(methylsulfonyl)amino]benzyl}carbamate (Preparation 165). |
| 133 | N-[4-chloro-2-({[6-(2-ethyl-5-fluoro-4-hydroxyphenyl)-1H-pyrazolo[4,3-c]pyridin-4-yl]amino}methyl)phenyl]-N-methylmethanesulfonamide hydrochloride | MS m/z 504 [M + H]$^+$<br>$^1$H NMR (400 MHz, DMSO-d$_6$): δ ppm 0.87 (t, 3H), 3.01 (s, 3H), 3.24 (s, 3H), 4.85-5.07 (br s, 4H), 6.87 (s, 1H), 6.93 (d, 1H), 7.13 (d, 1H), 7.45 (d, 1H), 7.53-7.59 (m, 2H), 8.48 (s, 1H), 9.96 (br s, 1H), 10.34 (br s, 1H), 12.32 (br s, 1H), 14.15 (br s, 1H).<br>4-nitrophenyl{5-chloro-2-[methyl(methylsulfonyl)amino]benzyl}carbamate (Preparation 156) |
| 134 | N-[2-({[6-(2-ethyl-5-fluoro-4-hydroxyphenyl)-1H-pyrazolo[4,3-c]pyridin-4-yl]amino}methyl)-3-fluorophenyl]-N-methylmethanesulfonamide hydrochloride | MS m/z 488 [M + H]$^+$<br>$^1$H NMR (400 MHz, DMSO-d$_6$): δ ppm 1.05 (t, 3H), 2.49 (s, 2H), 3.05 (s, 3H), 3.21 (s, 3H), 4.94 (s, 2H), 6.98 (t, 2H), 7.27 (d, 1H), 7.36 (t, 1H), 7.52 (m, 2H), 8.72 (s, 1H), 10.38 (s, 1H), 12.56 (s, 1H).<br>4-nitrophenyl{2-[ethyl(methylsulfonyl)amino]benzyl}carbamate (Preparation 162). |
| 135 | N-[2-({[6-(2-ethyl-5-fluoro-4-hydroxyphenyl)-1H-pyrazolo[4,3-c]pyridin-4-yl]amino}methyl)phenyl]-N-methylethanesulfonamide hydrochloride | MS m/z 488 [M + H]$^+$<br>$^1$H NMR (400 MHz, DMSO-d$_6$): δ ppm 0.98 (m, 3H), 1.25 (m, 3H), 2.39-2.41 (m, 1H), 2.53 (s, 1H), 3.20 (m, 1H), 5.08-5.10 (m, 2H), 6.99 (m, 2H), 7.27 (s, 1H), 7.43-7.47 (m, 3H), 7.61 (m, 1H), 8.65 (br s, 1H), 10.01 (s, 1H), 10.32 (br s, 1H), 12.15 (br s, 1H), 13.01 (br s, 1H), 14.22 (br s, 1H).<br>4-nitrophenyl{2-[(ethylsulfonyl)(methyl)amino]benzyl}carbamate (Preparation 159). |
| 136 | N-ethyl-N-[2-({[6-(2-ethyl-5-fluoro-4-hydroxyphenyl)-1H-pyrazolo[4,3-c]pyridin-4-yl]amino}methyl)phenyl]ethanesulfonamide hydrochloride | MS m/z 498 [M + H]$^+$<br>$^1$H NMR (400 MHz, DMSO-d$_6$): δ ppm 1.04 (m, 5H), 1.24 (m, 1H), 2.32 (m, 1H), 3.08 (m, 1H), 3.61-3.70 (m, 2H), 4.94 (m, 2H), 7.00 (m, 2H), 7.28 (m, 1H), 7.39-7.56 (m, 4H), 8.30-8.61 (m, 2H), 9.95 (br s, 1H), 10.31 (br s, 1H), 12.00 (br s, 1H), 13.00 (br s, 1H), 14.15 (br s, 1H).<br>4-nitrophenyl[ethyl(ethylsulfonyl)amino]benyl}-carbamate (Preparation 157). |

Example 137

N-[2-({[6-(2-Ethyl-5-fluoro-4-hydroxyphenyl)-1H-pyrazolo[4,3-c]pyridin-4-yl]amino}methyl)phenyl]-N-propylmethanesulfonamide To 6-(2-ethyl-5-fluoro-4-((2-(trimethylsilyl)ethoxy)methoxy)phenyl)-1-((2-(trimethylsilyl)ethoxy)methyl)-1H-pyrazolo[4,3-c]pyridin-4-yl trifluoromethanesulfonate (Preparation 331, 200 mg, 0.30 mmol) and N-(2-(aminomethyl)phenyl)-N-propylmethanesulfonamide trifluoroacetate (Preparation 349, 172 mg, 0.71 mmol) in DMF (5 mL) was added triethylamine (0.19 mL, 1.4 mmol) and the reaction was heated 10 to 110° C. for 2 hours. The reaction was cooled and partitioned between EtOAc and water. The organic layer was collected, washed with water, dried over magnesium sulfate and concentrated in vacuo. The residue was purified using silica gel column chromatography eluting with 1:1 EtOAc:Heptanes. The residue was dissolved in MeOH (5 mL) and cHCl (1.5 mL) was added and the reaction heated to 60° C. for 18 hours. The reaction was cooled, concentrated in vacuo and purified using preparative HPLC to afford the title compound as the free parent. Rt=2.85 minutes; MS m/z 498 [M+H]$^+$ The following compounds of the Examples below (Examples 138-144) were prepared according to the method described for Example 137 above using 6-(2-ethyl-5-fluoro-4-((2-(trimethylsilyl)ethoxy)methoxy)phenyl)-1-((2-(trimethylsilyl)ethoxy)methyl)-1H-pyrazolo-[4,3-c]pyridin-4-yl trifluoromethanesulfonate (Preparation 331) and the appropriate amine. Deprotection was carried out as described or using TFA/TES in place of cHCl. Purification was carried out according to the Purification Method (PM) described or one of the following below. The compounds were all isolated as free parents.

Purification Method L: The reaction mixture was quenched by the addition of saturated aqueous NaHCO$_3$ solution and extracted into DCM. The organic layer was collected, dried over sodium sulfate and concentrated in vacuo. The residue was purified using preparative HPLC.

| Ex | Name | MS Data/PM/Amine |
|---|---|---|
| 138 | N-ethyl-N-[2-({[6-(2-ethyl-5-fluoro-4-hydroxyphenyl)-1H-pyrazolo[4,3-c]pyridin- | MS m/z 484 [M + H]$^+$<br>Rt = 2.75 min<br>N-[2-(aminomethyl)phenyl]-N- |

| Ex | Name | MS Data/PM/Amine |
|---|---|---|
|  | 4-yl]amino}methyl)phenyl]methanesulfonamide | ethylmethanesulfonamide hydrochloride (Preparation 188). |
| 139 | N-butyl-N-[2-({[6-(2-ethyl-5-fluoro-4-hydroxyphenyl)-1H-pyrazolo[4,3-c]pyridin-4-yl]amino}methyl)phenyl]methanesulfonamide | MS m/z 512 [M + H]+<br>Rt = 2.98 min<br>N-(2-(aminomethyl)phenyl)-N-butylmethanesulfonamide trifluoroacetate (Preparation 350). |
| 140 | N-[2-({[6-(2-ethyl-5-fluoro-4-hydroxyphenyl)-1H-pyrazolo[4,3-c]pyridin-4-yl][2-(morpholin-4-yl)ethyl]amino}-methyl)phenyl]-N-methylmethanesulfonamide | MS m/z 583 [M + H]+<br>Rt = 1.98 min<br>N-methyl-N-(2-(((2-morpholinoethyl)amino)methyl)phenyl)methanesulfonamide (Preparation 353). |
| 141 | N-butyl-N-(2-(((6-(2-ethyl-5-fluoro-4-(I1-oxidanyl)phenyl)-1I2-pyrazolo[4,5-c]pyridin-4-yl)(methyl)amino)methyl)phenyl)methanesulfonamide | MS m/z 526 [M + H]+<br>Rt = 3.00 min<br>N-butyl-N-(2-((methylamino)methyl)phenyl)-methanesulfonamide (Preparation 354). |
| 142 | N-ethyl-N-[2-({[6-(2-ethyl-5-fluoro-4-hydroxyphenyl)-1H-pyrazolo[4,3-c]pyridin-4-yl](methyl)amino}methyl)-4-methylphenyl]methanesulfonamide | MS m/z 512 [M + H]+<br>Rt = 2.03 min<br>N-ethyl-N-(4-methyl-2-((methylamino)methyl)phenyl)methanesulfonamide (Preparation 355). |
| 143 | N-[2-({ethyl[6-(2-ethyl-5-fluoro-4-hydroxyphenyl)-1H-pyrazolo[4,3-c]pyridin-4-yl]amino}methyl)-4-methylphenyl]-N-methyl-methanesulfonamide | MS m/z 512 [M + H]+<br>Rt = 2.89 min<br>N-(2-((ethylamino)methyl)-4-methylphenyl)-N-methylmethanesulfonamide (Preparation 356).<br>PM L. |
| 144 | N-[2-({[6-(2-ethyl-5-fluoro-4-hydroxyphenyl)-1H-pyrazolo[4,3-c]pyridin-4-yl](propyl)amino}methyl)-4-methylphenyl]-N-methylmethanesulfonamide | MS m/z 526 [M + H]+<br>Rt = 3.04 min<br>N-methyl-N-(4-methyl-2-((propylamino)methyl)phenyl)methanesulfonamide (Preparation 357).<br>PM L. |

Example 145

N-Ethyl-N-[2-({[6-(2-ethyl-5-fluoro-4-hydroxyphenyl)-1H-pyrazolo[4,3-c]pyridin-4-yl](methyl)amino}methyl)phenyl]methanesulfonamide hydrochloride To a solution of 6-(2-ethyl-5-fluoro-4-((2-(trimethylsilyl)ethoxy)methoxy)phenyl)-1-(tetrahydro-2H-pyran-2-yl)-1H-pyrazolo[4,3-c]pyridin-4-yl trifluoromethanesulfonate (Preparation 330, 400 mg, 0.64 mmol) and N-ethyl-N-(2-((methyl-amino)methyl)phenyl)methanesulfonamide (Preparation 358, 234 mg, 0.96 mmol) in toluene (8 mL) was added cesium carbonate (420 mg, 1.29 mmol) and the mixture was degassed with nitrogen for 5 minutes. Pd(OAc)$_2$ (16 mg, 0.064 mmol) and BINAP (60 mg, 0.096 mmol) were added and the reaction was heated to 140° C. under microwave irradiation for 30 minutes. The reaction was partitioned between water and ethyl acetate, the organic layer collected, washed with brine, dried over sodium sulfate, and concentrated in vacuo. The residue was purified using silica gel column chromatography eluting with 36% EtOAc in hexanes. The residue (147 mg, 0.22 mmol) was dissolved in MeOH (10 mL) and cHCl (10 mL) was added with heating to 65° C. for 4 hours. The reaction was concentrated in vacuo and triturated with pentane-ether to afford the title compound as the hydrochloride salt (125 mg, 34%). $^1$H NMR (400 MHz, DMSO-d$_6$): δ ppm 1.00-1.13 (m, 6H), 2.56 (m, 2H), 3.07 (s, 3H), 3.43 (s, 3H), 3.66 (m, 2H), 5.19 (br s, 2H), 6.82 (s, 1H), 6.88 (d, 1H), 7.09 (d, 1H), 7.23 (t, 3H), 7.33 (t, 1H), 7.39 (t, 1H), 7.53 (d, 1H), 8.16 (s, 1H), 10.31 (br s, 1H), 11.95 (br s, 1H), 14.16 (br s, 1H). MS m/z 496 [M−H]−

Example 146

N-[2-({[6-(2-Ethyl-5-fluoro-4-hydroxyphenyl)-1H-pyrazolo[4,3-c]pyridin-4-yl](methyl)amino}methyl)phenyl]-N-methylmethanesulfonamide hydrochloride The title compound was prepared according to the method described for Example 145 using 6-(2-ethyl-5-fluoro-4-((2-(trimethylsilyl)ethoxy)methoxy)phenyl)-1-(tetrahydro-2H-pyran-2-yl)-1H-pyrazolo[4,3-c]pyridin-4-yl trifluoromethanesulfonate (Preparation 330), N-methyl-N-(2-((methylamino)methyl)phenyl)methanesulfonamide (Preparation 359). The residue was triturated with pentane-ether and further purified by Preparative TLC to afford the title compound as the hydrochloride salt (60 mg, 59%). $^1$H NMR (400 MHz, DMSO-d$_6$): δ ppm 0.91 (m, 3H), 2.54 (m, 2H), 3.09 (s, 3H), 3.16 (s, 3H), 3.37 (s, 3H), 5.10 (s, 2H), 6.67 (s, 1H), 6.79 (d, 1H), 7.01 (d, 1H), 7.09 (d, 1H), 7.28 (t, 1H), 7.34 (t, 1H), 7.55 (d, 1H), 8.06 (s, 1H), 9.74 (s, 1H), 13.08 (s, 1H). MS m/z 482 [M−H]−

Example 147

N-[2-({[6-(2-Ethyl-5-fluoro-4-hydroxyphenyl)-1H-pyrazolo[4,3-c]pyridin-4-yl]amino}methyl)phenyl]-N-(2-hydroxyethyl)methanesulfonamide To a solution of N-(2-(benzyloxy)ethyl)-N-(2-(((6-(2-ethyl-5-fluoro-4-((2-(trimethylsilyl)ethoxy)methoxy)phenyl)-1-((2-(trimethylsilyl)ethoxy)methyl)-1H-pyrazolo[4,3-c]pyridin-4-yl)amino)methyl)phenyl)methanesulfonamide (Preparation 327, 79 mg, 0.09 mmol) in 1:1 MeOH:EtOH (10 mL) was added ammonium formate (1 mg, 0.09 mmol) followed by palladium hydroxide (4 mg). The reaction was heated to 70° C. for 18 hours before cooling and filtering thought celite. The filtrate was concentrated in vacuo and partitioned between EtOAc and water. The organic layer was collected, washed with water and brine, dried over sodium sulfate and concentrated in vacuo. The residue was dissolved in DCM (3 mL) and TFA (141 µL, 1.84 mmol) followed by triethylsilane (21.5 µL, 0.18 mmol) were added. The reaction was heated to 70° C. for 72 hours before cooling and quenching with saturated aqueous NaHCO$_3$ solution. The reaction was extracted into EtOAc, and the organic layer was collected, dried over sodium sulfate and concentrated in vacuo. The residue was triturated with DCM to afford the title compound (16 mg, 43%). $^1$H NMR (400 MHz, CDCl$_3$): δ ppm 0.90 (t, 3H), 2.25-2.40 (m, 2H), 3.18 (s, 3H), 3.25 (m, 2H), 3.75-3.80 (m, 1H), 3.83-3.95 (m, 1H), 4.75 (m, 1H), 5.30 (m, 1H), 6.70 (s, 1H), 6.80 (m, 1H), 6.95 (m, 1H), 7.40 (m, 2H), 7.50 (m, 1H), 7.63 (m, 1H), 8.28 (s, 1H). MS m/z 500 [M+H]$^+$ Example 148

N-{2-[({6-[5-Fluoro-4-hydroxy-2-(2,2,2-trifluoroethyl)phenyl]-1H-pyrazolo[4,3-c]pyridin-4-yl}amino)methyl]phenyl}-N-methylmethanesulfonamide To a solution of 6-(5-fluoro-4-methoxy-2-(2,2,2-trifluoroethyl)phenyl)-1-((2-(trimethylsilyl)ethoxy)methyl)-1H-pyrazolo[4,3-c]pyridine 5-oxide (Preparation 334, 100 mg, 0.21 mmol) in DCM (1 mL) was added N-[2-(aminomethyl)phenyl]-N-methylmethanesulfonamide (WO20101058846A1, 60 mg, 0.28 mmol) followed by PyBrop (130 mg, 0.28 mmol) and DIPEA (0.14 mL, 0.81 mmol). The reaction was stirred at room temperature for 18 hours. The reaction was poured into saturated aqueous NaHCO$_3$ solution and extracted with DCM three times. The organic layers were collected, dried over sodium sulfate and concentrated in vacuo. The residue was purified using silica gel column chromatography eluting with 1:1 EtOAc in hexanes. The residue was dissolved in DCM (0.6 mL) and TFA (0.2 mL) followed by TES (0.05 mL) were added at 0° C. The reaction was stirred at room temperature for 18 hours before being quenched with saturated aqueous NaHCO$_3$ solution. The mixture was extracted into DCM, the organic layer collected, dried over sodium sulfate and concentrated in vacuo. The residue was purified using silica gel column chromatography eluting with 60% EtOAc in heptanes. The residue was dissolved in DCM (1 mL) and BBr$_3$ (0.72 mL) was added at 0° C. The reaction was stirred at room temperature for 18 hours before concentrating in vacuo and purifying by preparative HPLC to afford the title compound. MS m/z 524 [M+H]$^+$ Rt=2.39 minutes.

Example 149

N-(2-{[({6-[5-Fluoro-4-hydroxy-2-(2,2,2-trifluoroethyl)phenyl]-1H-pyrazolo[4,3-c]pyridin-4-yl}(methyl)amino]methyl})phenyl)-N-methylmethanesulfonamide The title compound was prepared according to the method described for Example 148 using N-methyl-N-(2-((methylamino)methyl)phenyl)methanesulfonamide (Preparation 359). MS m/z 538 [M+H]$^+$ Rt=2.52 minutes.

Example 150

N-{2-[({6-[5-Fluoro-4-hydroxy-2-(2,2,2-trifluoroethyl)phenyl]-1H-pyrazolo[4,3-c]pyridin-4-yl}amino)methyl]-4-methylphenyl}-N-methylmethanesulfonamide The title compound was prepared according to the method described for Example 148 using the free base of N-[2-(aminomethyl)-4-methylphenyl]-N-methylmethanesulfonamide hydrochloride (Preparation 189). MS m/z 538 [M+H]$^+$ Rt=2.47 minutes.

Library Protocol 2

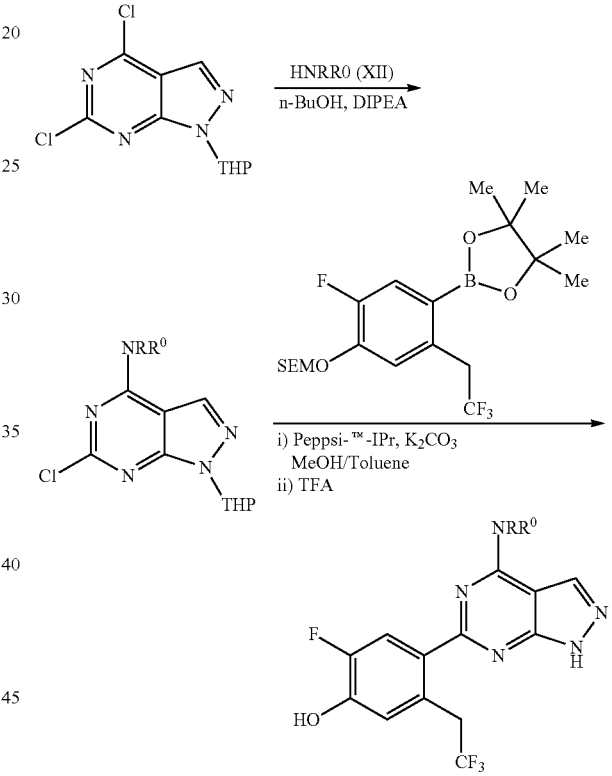

To a 0.2M solution of amines of formula (XII) (1 mL, 200 umol) in nBuOH was added a 0.2M solution of 4,6-dichloro-1-(tetrahydro-2H-pyran-2-yl)-1H-pyrazolo[3,4-d]pyrimidine (WO20131014567A1, 1 mL, 200 umol) followed by DIPEA (120 uL, 700 umol). The reaction was heated to 80° C. for 16 hours before concentrating in vacuo. The residue was dissolved in 1:1 MeOH:toluene (1.5 mL). To the solution was added potassium carbonate (62 mg, 450 umol), Peppsi™-IPr (3 mg, 4.5 umol) and (2-{[2-fluoro-4-(4,4,5,5-tetramethyl-1,3,2-dioxaborolan-2-yl)-5-(2,2,2-trifluoroethyl)phenoxy]methoxy}ethyl)(trimethyl)silane (Preparation 150, 400 mmol). The reaction was heated to 100° C. under microwave irradiation for 25 minutes before concentrating in vacuo. The residue was dissolved in EtOAc (5 mL) and washed with water (3 mL) and brine (3 mL). The organic extract was dried over sodium sulfate and concentrated in vacuo. The residue was dissolved in TFA (1 mL) and stirred at room temperature for 16 hours. The reaction was concentrated in vacuo and azeotroped with toluene. The residue was dissolved in MeOH and ethylenediamine (35 uL, 500 umol) was added with stirring at room temperature for 18 hours. The reaction was concentrated in vacuo, dissolved in DMSO (1 mL) and purified using preparative HPLC as described below:

LCMS:

A: 0.05% formic acid in water; B: MeCN; Column: RESTEK C18, 30×2.1 mm×3 µm; Gradient: From 98% [A] and 2% [B] to 90% [A] and 10% [B] in 1 min, further to 98% [B] in 2 min and finally back to initial condition in 2.90 min, 1.5 mL/min flow rate.

Preparative HPLC:

Method A: Gemini NXC18 (100×20 mm×5µ); Acetonitrile-water (20 mM $NH_4CO_3$); Flow rate 20 mL/min; Gradient time 10 mins for 10-75% organic elution.

Method B: reprosil Gold C18 (250×20 mm×5µ); Acetonitrile-water (20 mM $NH_4CO_3$); Flow rate 20 mL/min; Gradient time 18 mins for 10-70% organic elution.

The compounds of the Examples in the table below (Examples 151-154) were prepared and purified from 4,6-dichloro-1-(tetrahydro-2H-pyran-2-yl)-1H-pyrazolo[3,4-d]pyrimidine (WO20131014567A1), (2-{[2-fluoro-4-(4,4,5,5-tetramethyl-1,3,2-dioxaborolan-2-yl)-5-(2,2,2-trifluoroethyl)phenoxy]methoxy}ethyl)(trimethyl)silane (Preparation 150) and the appropriate amine according to Library Protocol 2.

| Ex | Name | MS Data/Amine |
|---|---|---|
| 151 | 4-{4-[(cyclopropylmethyl)-amino]-1H-pyrazolo[3,4-d]pyrimidin-6-yl}-2-fluoro-5-(2,2,2-trifluoroethyl)phenol | MS m/z 382 [M + H]$^+$<br>Rt = 1.53 minutes<br>Cyclopropylmethylamine |
| 152 | 4-{4-[(2-cyclopropylethyl)amino]-1H-pyrazolo[3,4-d]pyrimidin-6-yl}-2-fluoro-5-(2,2,2-trifluoroethyl)phenol | MS m/z 396 [M + H]$^+$<br>Rt = 1.57 minutes<br>Cyclopropylethylamine |
| 153 | 2-fluoro-4-{4-[(2-methylpropyl)amino]-1H-pyrazolo[3,4-d]pyrimidin-6-yl}-5-(2,2,2-trifluoroethyl)phenol | MS m/z 384 [M + H]$^+$<br>Rt = 1.56 minutes<br>Isobutylamine |
| 154 | 4-[4-(butylamino)-1H-pyrazolo[3,4-d]pyrimidin-6-yl]-2-fluoro-5-(2,2,2-trifluoroethyl)phenol | MS m/z 384 [M + H]$^+$<br>Rt = 1.57 minutes<br>Butylamine |

Example 155

N-[2-({[6-(2-Ethyl-5-fluoro-4-hydroxyphenyl-1H-pyrazolo[3,4-d]pyrimidin-4-yl]amino}methyl)phenyl]-N-methylmethanesulfonamide hydrochloride The title compound was prepared according to the method described for Example 125 using N-(2-(((6-chloro-1-(tetrahydro-2H-pyran-2-yl)-1H-pyrazolo[3,4-d]pyrimidin-4-yl)amino)methyl)phenyl)-N-methylmethanesulfonamide (Preparation 312) and (2-{[2-fluoro-4-(4,4,5,5-tetramethyl-1,3,2-dioxaborolan-2-yl)-5-ethyl-phenoxy]methoxy}ethyl)(trimethyl) silane (WO20131014567A1). SPhos was used as the ligand and the final residue was triturated with pentane/ether to afford the hydrochloride salt. $^1$H NMR (400 MHz, DMSO-d$_6$): δ ppm 0.91 (t, 3H), 2.66 (m, 2H), 3.06 (s, 3H), 3.13 (s, 3H), 4.82 (br s, 1H), 5.06 (br s, 1H), 6.86 (d, 1H), 7.33-7.46 (m, 4H), 7.55 (d, 1H), 8.55 (br s, 1H), 10.33 (br s, 1H), 14.56 (br s, 1H). MS m/z 471 [M+H]$^+$ Example 156

N-(2-(((6-(2-Ethyl-4-hydroxy-6-methylphenyl-1H-pyrazolo[4,3-c]pyridin-4-yl)amino)methyl)phenyl)-N-methylmethanesulfonamide The title compound was prepared according to the method described for Preparation 299 pyrimidines using 2-(4-(benzyloxy)-2-ethyl-6-methylphenyl)-4,4,5,5-tetramethyl-1,3,2-dioxaborolane (Preparation 342) followed by treating the residue with TFA at reflux. The reaction was concentrated in vacuo and partitioned between EtOAc and saturated aqueous sodium bicarbonate solution. The organic extracts were washed with brine, dried over sodium sulfate and concentrated in vacuo. The residue was purified by preparative HPLC. $^1$H NMR (400 MHz, DMSO-d$_6$): δ ppm 0.63-0.82 (m, 3H), 1.86 (m, 5H), 2.91 (s, 3H), 2.94 (s, 3H), 4.37 (br m, 1H), 4.85 (br m, 1H), 6.36 (br m, 3H), 7.20 (m, 2H), 7.33 (m, 2H), 8.17 (m, 1H), 9.03 (m, 1H), 12.88 (br s, 1H). MS m/z 466 [M+H]$^+$ Example 157

N-[2-({[6-(2-Ethyl-5-fluoro-4-hydroxyphenyl)-3-(1H-imidazol-2-yl)-1H-pyrazolo[4,3-c]pyridin-4-yl]amino}methyl)phenyl]-N-methylmethanesulfonamide A solution of N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)phenyl]-N-methylmethanesulfonamide (Preparation 79, 200 mg, 0.22 mmol) and 2-bromo-1-[[2-(trimethylsilyl)ethoxy]methyl]-1H-imidazole (J. Org. Chem. (2010) 75 (15) 4911-4920, 62.102 mg, 0.22 mmol) in toluene (2 mL) was degassed with nitrogen for 5 minutes. Bis(tributyltin) (0.27 mL, 0.54 mmol) and copper (I) iodide (8.53 mg, 0.045 mmol) were added followed by Pd(PPh$_3$)$_4$ (25.88 mg, 0.022 mmol) and the reaction was heated to 100° C. for 6.5 hours. The reaction was cooled, concentrated in vacuo and purified using silica gel column chromatography eluting with 15% EtOAc in hexanes. The residue (80 mg, 0.086 mmol) was treated with TFA (2 mL) and the solution stirred at room temperature for 30 minutes. The reaction was concentrated in vacuo, dissolved in MeOH (5 mL) and cooled in ice water. Ethylene diamine was added dropwise until the solution was basic, with stirring for 15 minutes. The solution was concentrated in vacuo and purified using silica gel column chromatography eluting with 60% EtOAc in hexanes to afford the title compound (25 mg, 54%). $^1$H NMR (400 MHz, DMSO-d$_6$): δ ppm 0.91 (t, 3H), 2.43 (m, 2H), 3.06 (s, 3H), 3.10 (s, 3H), 4.70 (br m, 1H), 5.00 (br m, 1H), 6.58 (m, 1H), 6.77 (m, 1H), 7.05 (m, 1H), 7.10 (s, 1H), 7.26-7.31 (m, 3H), 7.47 (m, 2H), 9.74 (s, 1H), 10.89 (t, 1H), 12.93 (s, 1H), 13.29 (s, 1H). MS m/z 536 [M+H]$^+$ Example 158

N-[2-({[3-(4,5-Dimethyl-1H-imidazol-2-yl)-6-(2-ethyl-5-fluoro-4-hydroxyphenyl-1H-pyrazolo[4,3-c]pyridin-4-yl]amino}methyl)phenyl]-N-methylmethanesulfonamide The title compound was prepared according to the method described by Example 157 using N-[2-({[6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-yl]amino}methyl)phenyl]-N-methylmethanesulfonamide (Preparation 79) and 2-bromo- 4,5-dimethyl-1-((2-(trimethylsilyl)ethoxy)methyl)-1H-imidazole (Preparation 386) at 115° C. under microwave irradiation for 30 minutes. $^1$H NMR (400 MHz, DMSO-d$_6$): δ ppm 0.97 (t, 3H), 2.56 (m, 2H), 3.04 (s, 3H), 3.10 (s, 3H), 4.60 (br m, 1H), 5.00 (br m, 1H), 6.55 (s, 1H), 6.79 (m, 1H), 7.08 (m, 1H), 7.35 (m, 2H), 7.49 (m, 1H), 7.51 (m, 1H), 9.74 (s, 1H), 10.95 (t, 1H), 12.40 (s, 1H), 13/15 (s, 1H). MS m/z 564 [M+H]$^+$ Example 159

N-[2-({[6-(2-Ethyl-5-fluoro-4-hydroxyphenyl)-3-(4-methyl-1H-imidazol-2-yl)-1H-pyrazolo[4,3-c]pyridin-4-yl]amino}methyl)phenyl]-N-methylmethanesulfonamide The title compound was prepared according to the method described by Example 157 using N-[2-({[6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-yl]amino}methyl)phenyl]-N-methylmethanesulfonamide (Preparation 79) and 2-iodo-5-methyl-1H-imidazole at 115° C. under microwave irradiation for 30 minutes. Following deprotection the residue was purified using preparative HPLC. $^1$H NMR (400 MHz, DMSO-d$_6$): δ ppm 0.95 (t, 1.5H), 0.99 (t, 1.5H), 1.99 (s, 1.5H), 2.32 (s, 1.5H), 3.05 (m, 3H), 3.10 (m, 3H), 4.66 (br m, 1H), 4.99 (br m, 1H), 6.56 (m, 1H), 6.77-6.90 (m, 2H), 7.01-7.09 (m, 1H), 7.27-7.36 (m, 2H), 7.46-7.61 (m, 2H), 9.74 (br s, 1H), 10.95 (m, 1H), 12.55 (s, 0.5H), 12.69 (s, 0.5H), 13.22 (br s, 1H). MS m/z 550 [M+H]$^+$ Example 160 Intermediate 2-Fluoro-4-(4-((2-(methylthio)ethyl)amino)-3-(4,5,6,7-tetrahydro-1H-imidazo[4,5-c]pyridin-2-yl)-1H-pyrazolo[4,3-c]pyridin-6-yl)-5-(2,2,2-trifluoroethyl)phenol The title compound was prepared according to the method described by Example 157 using 6-(5-fluoro-2-(2,2,2-trifluoroethyl)-4-((2-(trimethylsilyl)ethoxy)-methoxy)phenyl)-3-iodo-N-(2-(methylthio)ethyl)-1-((2-(trimethylsilyl)ethoxy)methyl)-1H-pyrazolo[4,3-c]pyridin-4-amine (Preparation 379) and tert-butyl 2-iodo-6,7-dihydro-1H-imidazo[4,5-c]pyridine-5(4H)-carboxylate (WO20131014567A1). MS m/z 522 [M+H]$^+$ Example 161

4-[3-(5-Benzyl-4,5,6,7-tetrahydro-1H-imidazo[4,5-c]pyridin-2-yl)-4-{[2-(methylsulfanyl)-ethyl]amino}-1H-pyrazolo[4,3-c]pyridin-6-yl]-2-fluoro-5-(2,2,2-trifluoroethyl)phenol To a suspension of anhydrous magnesium sulfate (40 mg, 0.33 mmol) and 2-fluoro-4-(4-((2-(methylthio)ethyl)amino)-3-(4,5,6,7-tetrahydro-1H-imidazo[4,5-c]pyridin-2-yl)-1H-pyrazolo[4,3-c]pyridin-6-yl)-5-(2,2,2-trifluoroethyl)phenol (Example 161, 44 mg, 0.08 mmol) in methanol (2.5 mL) was added a solution of benzaldehyde (0.017 mL, 0.17 mmol) in methanol (2.5 mL). The reaction was stirred for 1 hour at 55° C. before cooling to room temperature and adding sodium cyanoborohydride (10.6 mg, 0.17 mmol). The reaction was stirred at room temperature for 18 hours. The reaction was filtered and concentrated in vacuo. The residue was partitioned between 20% IPA in DCM and water. The organic layer was collected, dried over sodium sulfate and concentrated in vacuo. The residue was purified by preparative TLC to afford the title compound (20 mg, 39%). $^1$H NMR (400 MHz, DMSO-d$_6$): δ ppm 1.90 (s, 1.5H), 1.98 (s, 1.5H), 2.66-2.88 (m, 6H), 3.47 (m, 2H), 3.64-3.72 (m, 4H), 4.03-4.11 (m, 2H), 6.62 (s, 1H), 7.01 (m, 1H), 7.27-7.38 (m, 6H), 10.11 (s, 1H), 10.68 (t, 0.5H), 10.75 (t, 0.5H), 12.46 (s, 0.5H), 12.58 (s, 0.5H), 13.23 (s, 1H). MS m/z 612 [M+H]$^+$ Example 162

N-[2-({[6-(2-Ethyl-5-fluoro-4-hydroxyphenyl)-3-(1H-pyrazol-1-yl)-1H-pyrazolo[4,3-c]pyridin-4-yl]amino}methyl)phenyl]-N-methylmethanesulfonamide To a solution of N-[2-({[6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-yl]amino}methyl)phenyl]-N-methylmethanesulfonamide (Preparation 79, 250 mg, 0.29 mmol) in DMSO (0.5 mL) was added pyrazole (19.88 mg, 0.29 mmol), PEG (500 mg), cesium carbonate (133 mg, 0.41 mmol), cuprous oxide (1.25 mg, 0.01 mmol) and 4,7-dimethoxy-1,10-phenanthroline (5.61 mg, 0.023 mmol) and the reaction was heated to 110° C. for 18 hours. The reaction was cooled, diluted with EtOAc and washed with water and brine. The organic layer was dried over sodium sulfate and concentrated in vacuo. The residue was purified using silica gel column chromatography eluting with 27% EtOAc in hexanes. The residue (77 mg, 0.097 mmol) was treated with TFA (2.5 mL) and stirred at room temperature for 30 minutes. The reaction was concentrated in vacuo, dissolved in MeOH (5 mL) and cooled in ice water. Ethylene diamine was added dropwise until the solution was basic, with stirring for 15 minutes. The solution was concentrated in vacuo and purified using silica gel column chromatography eluting with 6% MeOH in DCM to afford the title compound (32 mg, 62%).
$^1$H NMR (400 MHz, DMSO-ds): δ ppm 0.93 (t, 3H), 2.49 (m, 2H), 3.05 (s, 3H), 3.07 (s, 3H), 4.67 (br m, 1H), 5.00 (br m, 1H), 6.60 (s, 1H), 6.66 (m, 1H), 6.80 (m, 1H), 7.05 (m, 1H), 7.31 (m, 2H), 7.45 (m, 2H), 7.91 (s, 1H), 8.54 (s, 1H), 9.61 (t, 1H), 9.76 (s, 1H), 13.11 (s, 1H). MS m/z 536 [M+H]$^+$ Example 163

N-{2-[({6-[5-Fluoro-4-hydroxy-2-(2,2,2-trifluoroethyl)phenyl]-3-(1H-pyrazol-1-yl)-1H-pyrazolo[4,3-c]pyridin-4-yl}amino)methyl]phenyl}-N-methylmethanesulfonamide The title compound was prepared according to the method described for Example 162 using N-methyl-N-(2-{[(6-[5-fluoro-2-(2,2,2-trifluoroethyl)-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl)amino]-methyl}phenyl)methanesulfonamide (Preparation 105) and pyrazole. Following deprotection the residue was purified using silica gel column chromatography eluting with 45% EtOAc in hexanes. $^1$H NMR (400 MHz, DMSO-d$_6$): δ ppm 3.06 (m, 6H), 3.40 (m, 2H), 4.64 (br m, 1H), 4.93 (br m, 1H), 6.66 (m, 2H), 6.94 (m, 1H), 7.19-7.22 (m, 1H), 7.28-7.34 (m, 2H), 7.41-7.50 (m, 2H), 7.93 (s, 1H), 8.57 (s, 1H), 9.71 (t, 1H), 10.11 (brs, 1H), 13.21 (brs, 1H). MS m/z 590 [M+H]$^+$

Example 164

N-{2-[({6-[5-Fluoro-4-hydroxy-2-(2,2,2-trifluoro-ethyl)phenyl]-3-(5-methyl-4H-1,2,4-triazol-3-yl)-1H-pyrazolo[4,3-c]pyridin-4-yl}amino)methyl]phenyl}-N-methylmethanesulfonamide To a solution of acetimidamide hydrochloride (33 mg, 0.35 mmol) in 2-methoxyethanol (3 mL) was added DIPEA (0.087 mL, 0.50 mmol) followed by N-(2-(((6-(5-fluoro-2-(2,2,2-trifluoroethyl)-4-((2-(trimethylsilyl)ethoxy)methoxy)phenyl)-3-(hydrazinecarbonyl)-1-((2-(tri-methylsilyl)ethoxy)methyl)-1H-pyrazolo[4,3-c]pyridin-4-yl)amino)methyl)phenyl)-N-methyl-methanesulfonamide (Preparation 374, 120 mg, 0.143 mmol). The reaction was stirred at 85° C. for 18 hours. The reaction was quenched with water and extracted with DCM. The organic extracts were collected, dried over sodium sulfate and concentrated in vacuo. The residue was purified using silica gel column chromatography eluting with 27% EtOAc in DCM. The residue (100 mg, 0.12 mmol) was treated with TFA (2 mL) and stirred at room temperature for 30 minutes. The reaction was concentrated in vacuo, dissolved in MeOH (5 mL) and cooled in ice water. Ethylene diamine was added dropwise until the solution was basic, with stirring for 15 minutes. The solution was concentrated in vacuo and purified using preparative TLC to afford the title compound (40 mg, 54%). $^1$H NMR (400 MHz, DMSO-$d_6$): δ ppm 1.75 (s, 3H), 3.04-3.12 (m, 6H), 3.68 (m, 2H), 4.70 (br m, 1H), 5.00 (br m, 1H), 6.67 (m, 1H), 6.97 (m, 1H), 7.20-7.22 (m, 1H), 7.25-7.29 (m, 2H), 7.34 (m, 2H), 7.85 (m, 1H), 10.08-10.25 (m, 1H), 13.36 (s, 0.5H), 13.71 (s, 0.5H), 14.02 (s, 0.5H), 14.52 (s, 0.5H). MS m/z 605 [M+H]$^+$

Example 165

N-[2-({[6-(2-Ethyl-5-fluoro-4-hydroxyphenyl)-3-(5-methyl-4H-1,2,4-triazol-3-yl)-1H-pyrazolo[4,3-c]pyridin-4-yl]amino}methyl)phenyl]-N-methylmethanesulfonamide To a solution of 6-[5-fluoro-2-ethyl-4-{[2-(trimethylsilyl)ethoxy]methoxy}phenyl]-4-({2-[methyl(methylsulfonyl)amino]benzyl}amino)-1-{[2-(trimethylsilyl)ethoxy]methyl}-1H-pyrazolo[4,3-c]pyridine-3-carboxylic acid (Preparation 373, 180 mg, 0.23 mmol) in THF (12 mL) was added hydrazine hydrochloride (39.82 mg, 0.58 mmol), BOP (257 mg, 0.58 mmol) and DIPEA (0.122 mL, 0.70 mmol). The reaction was stirred at room temperature for 18 hours. The reaction was quenched with water, extracted into DCM, the organic extracts collected, dried over sodium sulfate and concentrated in vacuo. The residue was purified by silica gel column chromatography eluting with 8% MeOH in DCM. The residue was added to a solution of acetimidamide hydrochloride (30 mg, 0.32 mmol) and DIPEA (0.08 mL, 0.44 mmol) in 2-methoxyethanol (3 mL) and the reaction was heated to 85° C. for 18 hours. The reaction was cooled and quenched by the addition of water and extracted into DCM. The organic layer was collected, washed with brine, dried over sodium sulfate and concentrated in vacuo. The residue was purified by preparative TLC. The residue was treated with TFA (2 mL) and stirred at room temperature for 30 minutes. The reaction was concentrated in vacuo, dissolved in MeOH (5 mL) and cooled in ice water. Ethylene diamine was added dropwise until the solution was basic, with stirring for 15 minutes. The solution was concentrated in vacuo and purified using preparative TLC to afford the title compound (30 mg, 88%). $^1$H NMR (400 MHz, DMSO-$d_6$): δ ppm 0.97 (t, 3H), 2.20 (s, 3H), 2.56 (m, 2H), 3.04 (s, 3H), 3.12 (s, 3H), 4.65 (br m, 1H), 5.00 (br m, 1H), 6.66 (m, 1H), 6.83 (m, 1H), 7.02 (m, 1H), 7.33 (m, 2H), 7.51-7.57 (m, 2H), 9.78 (m, 1H), 10.13 (m, 1H), 13.27 (s, 0.5H), 13.62 (s, 0.5H), 13.99 (s, 0.5H), 14.49 (s, 0.5H). MS m/z 549 [M−H]$^-$

Example 166

N-{2-[({6-[5-Fluoro-4-hydroxy-2-(2,2,2-trifluoro-ethyl)phenyl]-3-[5-(6-methylpyridin-3-yl)-4H-1,2,4-triazol-3-yl]-1H-pyrazolo[4,3-c]pyridin-4-yl}amino)methyl]phenyl}-N-methylmethanesulfonamide To a solution of N-(2-(((6-(5-fluoro-4-methoxy-2-(2,2,2-trifluoroethyl)phenyl)-3-(hydrazinecarbonyl)-1-((2-(trimethylsilyl)ethoxy)methyl)-1H-pyrazolo[4,3-c]pyridin-4-yl)amino)methyl)phenyl)-N-methylmethanesulfonamide (Preparation 376, 160 mg, 0.22 mmol) in n-butanol (2 mL) was added 5-cyano-2-methyl pyridine (65 mg, 0.55 mmol) and potassium carbonate (16 mg, 0.12 mmol). The reaction mixture was heated to 150° C. under microwave irradiation for 50 minutes. The reaction was cooled and concentrated in vacuo. The residue was partitioned between water and ethyl acetate. The organic extracts were washed with brine, dried over sodium sulfate and concentrated in vacuo. The residue was purified by silica gel column chromatography eluting with 15% MeOH in DCM followed by preparative TLC. The residue was treated with boron tribromide (0.047 mL 0.47 mmol) and the reaction stirred at room temperature for 30 minutes. The reaction was concentrated in vacuo and partitioned between saturated aqueous NaHCO$_3$ and EtOAc. The organic extracts were dried over sodium sulfate, concentrated in vacuo and purified by preparative TLC to afford the title compound (19 mg, 41%). $^1$H NMR (400 MHz, DMSO-$d_6$): δ ppm 1.22 (s, 3H), 3.03 (s, 3H), 3.07 (s, 3H), 3.71 (m, 2H), 4.75 (br m, 1H), 5.05 (br m, 1H), 6.78 (s, 1H), 6.96 (m, 1H), 7.22-7.38 (m, 4H), 7.40 (m, 2H), 7.75 (m, 1H), 8.93 (m, 1H), 10.01 (br m, 1H), 13.80 (br m, 1H). MS m/z 682 [M+H]$^+$

Example 167

4-(5-{6-[5-Fluoro-4-hydroxy-2-(2,2,2-trifluoroethyl)phenyl]-4-({5-hydroxy-2-[methyl(methylsulfonyl)amino]benzyl}amino)-1H-pyrazolo[3,4-d]pyrimidin-3-yl}-4H-1,2,4-triazol-3-yl)piperidine-1-carboxamide To a solution of N-(2-(((6-(5-fluoro-4-methoxy-2-(2,2,2-trifluoroethyl)phenyl)-3-(5-(piperidin-4-yl)-4H-1,2,4-triazol-3-yl)-1H-pyrazolo[3,4-d]pyrimidin-4-yl)amino)methyl)-4-methoxyphenyl)-N-methylmethanesulfonamide (Preparation 371, 70 mg, 0.097 mmol) in DCM (12 mL) was added triethylamine (0.02 mL, 0.146 mmol) and trimethylsilylisocyanate (0.013 mL, 0.097 mmol). The reaction was quenched with water, and the organic extracts were dried over sodium sulfate and concentrated in vacuo. The residue was dissolved in DCM (10 mL) and boron tribromide (0.041 mL, 0.41 mmol) was added at 0° C. and stirred for 3 hours. The reaction was quenched with saturated aqueous sodium bicarbonate solution followed by extraction with 20% IPA in DCM. The organic extracts were collected, dried over sodium sulfate and concentrated in vacuo. The residue was purified by preparative TLC eluting with 10% MeOH in DCM to afford the title compound (34 mg, 78%). $^1$H NMR (400 MHz, DMSO-d$_6$): δ ppm 1.42 (m, 2H), 1.75 (m, 2H), 2.67-2.75 (m, 2H), 3.01 (s, 3H), 3.08 (s, 3H), 3.17 (m, 1H), 3.89 (m, 2H), 4.34 (m, 2H), 4.69 (m, 1H), 4.99 (m, 1H), 5.93 (br s, 2H), 6.76 (m, 1H), 6.86 (m, 1H), 6.99 (m, 1H), 7.36 (m, 1H), 7.75 (m, 1H), 9.66 (br s, 1H), 10.38-10.50 (m, 2H), 13.72 (br s, 0.5H), 14.05 (br s, 0.5H), 14.20 (br s, 0.5H), 14.72 (br s, 0.5H). MS m/z 734 [M+H]$^+$

Example 168

N-(2-{[(6-[5-Fluoro-4-hydroxy-2-(2,2,2-trifluoroethyl)phenyl]-3-{5-[1-(pyrrolidin-1-ylacetyl)piperidin-4-yl]-4H-1,2,4-triazol-3-yl}-1H-pyrazolo[3,4-d]pyrimidin-4-yl)amino]methyl}phenyl)-N-methylmethanesulfonamide To a solution of N-(2-(((6-(5-fluoro-4-methoxy-2-(2,2,2-trifluoroethyl)phenyl)-3-(5-(piperidin-4-yl)-4H-1,2,4-triazol-3-yl)-1H-pyrazolo[3,4-d]pyrimidin-4-yl)amino)methyl)-phenyl)-N-methylmethanesulfonamide (Preparation 372, 90 mg, 0.13 mmol) and 2-(pyrrolidin-1-yl)acetic acid (21 mg, 0.13 mmol) in DCM (10 mL) was added DIPEA (0.065 mL, 0.39 mmol) followed by BOP (58 mg, 0.13 mmol). The reaction was allowed to stir at room temperature for 18 hours. The reaction was concentrated in vacuo and partitioned between 20% IPA in DCM and water. The organic extracts were washed with brine, dried and concentrated in vacuo. The residue was purified by silica gel column chromatography eluting with 12% MeOH in DCM. The residue was dissolved in DCM and treated with boron tribromide (0.083 mL, 0.87 mmol) at 0° C. The reaction was stirred at room temperature for 18 hours before the addition of another aliquot of boron tribromide (0.25 mL) and further stirring for 3 hours. The reaction was quenched by the addition of saturated aqueous sodium bicarbonate solution and extracted with 20% IPA in DCM. The organic extract was separated, dried over sodium sulfate and concentrated in vacuo. The residue was purified by silica gel column chromatography eluting with 15% MeOH in DCM to afford the title compound (41 mg, 42%).

$^1$H NMR (400 MHz, DMSO-d$_6$): δ ppm 1.33 (m, 1H), 1.48 (m, 1H), 1.71-1.90 (m, 6H), 2.59-2.70 (m, 3H), 2.97 (m, 1H), 3.06 (m, 4H), 3.13 (s, 3H), 3.31 (m, 2H), 3.90 (m, 1H), 4.08 (m, 1H), 4.19 (m, 1H), 4.31 (m, 2H), 4.79 (br m, 1H), 5.12 (br m, 1H), 6.99 (m, 1H), 7.35-7.59 (m, 4H), 7.73 (m, 1H), 10.44 (m, 2H), 13.93 (br s, 1H), 14.55 (br s, 1H). MS m/z 786 [M+H]$^+$

Example 169

N-{2-[({6-[5-Fluoro-4-hydroxy-2-(2,2,2-trifluoroethyl)phenyl]-3-(4,5,6,7-tetrahydro-1H-imidazo[4,5-c]pyridin-2-yl)-1H-pyrazolo[3,4-d]pyrimidin-4-yl}amino)methyl]-4-hydroxyphenyl}-N-methylmethanesulfonamide The title compound was prepared according to the method described for Example 29 using N-(2-(((6-(5-fluoro-4-methoxy-2-(2,2,2-trifluoroethyl)phenyl)-3-(4,5,6,7-tetrahydro-1H-imidazo[4,5-c]pyridin-2-yl)-1H-pyrazolo[3,4-d]pyrimidin-4-yl)amino)methyl)-4-methoxyphenyl)-N-methylmethanesulfonamide (Preparation 370). $^1$H NMR (400 MHz, DMSO-d$_6$): δ ppm 2.32-2.67 (m, 2H), 2.91 (m, 2H), 3.02 (s, 3H), 3.10 (s, 3H), 3.32 (m, 2H), 4.34 (m, 2H), 4.67 (m, 1H), 5.00 (m, 1H), 6.72 (m, 1H), 6.74 (m, 1H), 6.98 (m, 1H), 7.33 (m, 1H), 7.72 (m, 1H), 9.65 (m, 1H), 11.26-11.33 (m, 1H), 12.62 (m, 1H), 13.59 (m, 1H). MS m/z 662 [M+H]$^+$

Example 170

N-{2-[({3-(5-Acetyl-4,5,6,7-tetrahydro-1H-imidazo[4,5-c]pyridin-2-yl)-6-[5-fluoro-4-hydroxy-2-(2,2,2-trifluoroethyl)phenyl]-1H-pyrazolo[3,4-d]pyrimidin-4-yl}amino)methyl]-4-hydroxyphenyl}-N-methylmethanesulfonamide To a solution of N-(2-(((6-(5-fluoro-4-methoxy-2-(2,2,2-trifluoroethyl)phenyl)-3-(4,5,6,7-tetrahydro-1H-imidazo[4,5-c]pyridin-2-yl)-1H-pyrazolo[3,4-d]pyrimidin-4-yl)amino)methyl)-4-methoxyphenyl)-N-methylmethanesulfonamide (Preparation 370, 200 mg, 0.29 mmol) and DIPEA (0.096 ml, 0.58 mmol) in DCM (35 mL) at 0° C. was added acetyl chloride (0.021 mL, 0.29 mmol) and the reaction stirred at room temperature for 2 hours. The reaction was concentrated in vacuo and partitioned between EtOAc and water. The organic phase was dried, concentrated in vacuo and purified by silica gel column chromatography eluting with 5% MeOH in DCM. The residue was dissolved in DCM (10 mL) and treated with boron tribromide (0.083 mL, 0.87 mmol) at 0° C. The reaction was stirred at room temperature for 18 hours before the addition of another aliquot of boron tribromide (0.25 mL) with further stirring for 3 hours. The reaction was quenched by the addition of saturated aqueous sodium bicarbonate solution and extracted with 20% IPA in DCM. The organic extract was separated, dried over sodium sulfate and concentrated in vacuo. The residue was purified by preparative TLC eluting with 10% MeOH in DCM to afford the title compound (25 mg, 38%). $^1$H NMR (400 MHz, DMSO-d$_6$): δ ppm (tautomers?) 2.50 (m, 3H), 2.62 (m, 2H), 3.02 (s, 3H), 3.15 (s, 3H), 3.70 (m, 3H), 4.35 (m, 4H), 4.54 (m, 1H), 5.00 (m, 1H), 6.71-7.00 (m, 3H), 7.35 (m, 1H), 7.70 (m, 1H), 9.60 (m, 1H), 10.37 (m, 1H), 11.54-11.67 (m, 1H), 13.65 (s, 1H). MS m/z 704 [M+H]$^+$

Example 171

N-[2-(Dimethylamino)ethyl]-2-{6-[5-fluoro-4-hydroxy-2-(2,2,2-trifluoroethyl)phenyl]-4-({5-hydroxy-2-[methyl(methylsulfonyl)amino]benzyl}amino)-1H-pyrazolo[3,4-d]pyrimidin-3-yl}-1,4,6,7-tetrahydro-5H-imidazo[4,5-c]pyridine-5-carboxamide To a solution of N-(2-(((6-(5-fluoro-4-methoxy-2-(2,2,2-trifluoroethyl)phenyl)-3-(4,5,6,7-tetrahydro-1H-imidazo[4,5-c]pyridin-2-yl)-1H-pyrazolo[3,4-d]pyrimidin-4-yl)-amino)methyl)-4-methoxyphenyl)-N-methylmethanesulfonamide (Preparation 370, 80 mg, 0.116 mmol) in DCM (5 mL), was added boron tribromide (0.077 mL, 0.81 mmol) at 0° C. and stirred for 2 hours. Another aliquot of boron tribromide (7 eq) was added and the reaction mixture was stirred at room temperature for a further 2 hours. The reaction was quenched by the addition of saturated aqueous sodium bicarbonate solution and extracted with 20% IPA in DCM. The organic extract was separated, dried over sodium sulfate and concentrated in vacuo. The residue was purified by preparative TLC. The residue was dissolved in THF (1 mL) and added to a solution of N,N-dimethylamine (6 mL) in THF (1.5 mL) and bromoethylisocyanate (0.02 mL, 0.18 mmol) that had stirred at 0° C. for 10 minutes. The reaction was stirred at room temperature for 18 hours. The reaction was concentrated in vacuo and purified using preparative TLC to afford the title compound (15 mg, 21%). 25 minute HPLC QC (Sunfire C18 (150×4.6 mm×5 u), mobile phase A=MeCN, mobile phase B=10 mM ammonium acetate in water Rt=2.59 minutes. MS m/z 776 [M+H]$^+$ Example 172 Intermediate Racemic 2-Fluoro-4-(4-((3-hydroxy-2-methylpropyl)amino)-3-(4,5,6,7-tetrahydro-1H-imidazo[4,5-c]pyridin-2-yl)-1H-pyrazolo[3,4-d]pyrimidin-6-yl)-5-(2,2,2-trifluoroethyl)phenol The title compound was prepared according to the method described for Example 157 using tert-butyl 2-iodo-6,7-dihydro-1H-imidazo[4,5-c]pyridine-5(4H)-carboxylate (WO20131014567A1) and racemic 3-((6-(5-fluoro-2-(2,2,2-trifluoroethyl)-4-((2-(trimethylsilyl)ethoxy)-methoxy)phenyl)-3-iodo-1-((2-(trimethylsilyl)ethoxy)methyl)-1H-pyrazolo[3,4-d]pyrimidin-4-yl)amino)-2-methylpropan-1-ol (Preparation 380). MS m/z 521 [M+H]$^+$ Example 173

4-(3-(5-Benzyl-4,5,6,7-tetrahydro-1H-imidazo[4,5-c]pyridin-2-yl)-4-((3-hydroxy-2-methylpropyl)amino)-1H-pyrazolo[3,4-d]pyrimidin-6-yl)-2-fluoro-5-(2,2,2-trifluoroethyl)phenol The title compound was prepared according to the method described for Example 161 using racemic 2-fluoro-4-(4-((3-hydroxy-2-methylpropyl)amino)-3-(4,5,6,7-tetrahydro-1H-imidazo[4,5-c]pyridin-2-yl)-1H-pyrazolo[3,4-d]pyrimidin-6-yl)-5-(2,2,2-trifluoroethyl)phenol (Example 172). The residue was purified by preparative HPLC. 10 minute HPLC QC (Gemini NX-C18 (50×4.6 mm×3 u), mobile phase A=0.05% formic acid in water, mobile phase B=MeCN Rt=4.20 minutes MS m/z 611 [M+H]$^+$ Example 174 Intermediate 6-(5-Fluoro-4-hydroxy-2-(2,2,2-trifluoroethyl)phenyl)-4-((5-hydroxy-2-(N-methyl methylsulfonamido)benzyl)amino)-1H-pyrazolo[3,4-d]pyrimidine-3-carboxylic acid The title compound was prepared according to the method described for Preparation 11 using N-(2-(((6-(5-fluoro-4-hydroxy-2-(2,2,2-trifluoroethyl)phenyl)-3-iodo-1H-pyrazolo[3,4-d]pyrimidin-4-yl)amino)methyl)-4-hydroxyphenyl)-N-methylmethanesulfonamide (Preparation 271). MS m/z 585 [M+H]$^+$ Preparation 1

6-(2-Ethyl-5-fluoro-4-{[2-(trimethylsilyl)ethoxy]methoxy}phenyl)-N-methyl-4-({2-[methyl(sulfamoyl)amino]benzyl}amino)-1-{[2-(trimethylsilyl)ethoxy]methyl}-1H-pyrazolo[4,3-c]pyridine-3-carboxamide To a solution of 6-(2-ethyl-5-fluoro-4-{[2-(trimethylsilyl)ethoxy]methoxy}phenyl)-N-methyl-4-{[2-(methylamino)benzyl]amino}-1-{[2-(trimethylsilyl)ethoxy]methyl}-1H-pyrazolo[4,3-c]pyridine-3-carboxamide (Preparation 14, 500 mg, 0.705 mmol) in THF (2 mL) was added NaH (28.2 mg, 0.70 mmol) at 0° C. followed by dropwise addition of sulfamoyl chloride (97 mg, 0.84 mmol). The reaction was allowed to warm to room temperature for 1 hour. The reaction was quenched with water and extracted with ethyl acetate. The organic extracts were separated, dried over sodium sulfate and concentrated in vacuo. The residue was purified by silica gel column chromatography eluting with 40% EtOAc in Hexanes to afford the title compound as an off-white solid (350 mg, 62%). $^1$H NMR (400 MHz, DMSO-d$_6$): δ ppm −0.11 (s, 9H), −0.02 (s, 9H), 0.80 (t, 2H), 0.84-0.91 (m, 5H), 2.59 (m, 2H), 2.83 (s, 3H), 3.01 (s, 3H), 3.57 (t, 2H), 3.75 (t, 2H), 4.75 (br s, 1H), 5.00 (br s, 1H), 5.29 (s, 2H), 5.72 (s, 2H), 6.96 (s, 1H), 7.04 (s, 1H), 7.13 (m, 1H), 7.22-7.43 (m, 4H), 8.85 (m, 1H), 9.68 (m, 1H). MS m/z 788 [M+H]$^+$ Preparation 2

6-[5-Fluoro-2-(2,2,2-trifluoroethyl)-4-{[2-(trimethylsilyl)ethoxy]methoxy}phenyl]-4-{[2-(methyl{[3-(morpholin-4-yl)propyl]sulfonyl]amino)benzyl}amino)-1-{[2-(trimethylsilyl)ethoxy]methyl}-1H-pyrazolo[4,3-c]pyridine-3-carboxamide To a solution of 4-[(2-{[(3-chloropropyl)sulfonyl](methyl)amino}benzyl)amino]-6-[5-fluoro-2-(2,2,2-trifluoroethyl)-4-{[2-(trimethylsilyl)ethoxy]methoxy}phenyl]-1-{[2-(tri-methylsilyl)ethoxy]-methyl}-1H-pyrazolo[4,3-c]pyridine-3-carboxamide (Preparation 4, 290 mg, 0.32 mmol) in EtOH (2 mL) was added morpholine (0.5 mL) and the reaction was heated to 110° C. under microwave irradiation for 75 minutes. The reaction was cooled, concentrated in vacuo and partitioned between EtOAc and water. The organic layer was collected, dried over sodium sulfate and concentrated in vacuo. The residue was purified using preparative TLC to afford the title compound (70 mg, 80%). MS m/z 940 [M+H]$^+$ Preparation 3

6-(5-Fluoro-2-(2,2,2-trifluoroethyl)-4-((2-trimethylsilyl)ethoxy)methoxy)phenyl)-N-methyl-4-((2-(N-methyl-1H-pyrazole-4-sulfonamido)benzyl)amino)-1-((2-(trimethylsilyl)ethoxy)methyl)-1H-pyrazolo[4,3-c]pyridine-3-carboxamide To a solution of 6-(5-fluoro-2-(2,2,2-trifluoroethyl)-4-fluoro-4-{[2-(trimethyl-silyl)ethoxy]-methoxy}phenyl)-N-methyl-4-{[2-(methylamino)benzyl]amino}-1-{[2-(trimethylsilyl)ethoxy]-methyl}-1H-pyrazolo[4,3-c]pyridine-3-carboxamide (Preparation 17, 150 mg, 0.19 mmol) in THF (10 mL) was added 1H-pyrazole-4-sulfonylchloride (0.03 mL, 0.19 mmol) at 0° C. The reaction mixture was allowed to stir at room temperature for 18 hours. The reaction was concentrated in vacuo and purified using silica gel column chromatography to afford the title compound (76 mg, 43%). $^1$H NMR (400 MHz, DMSO-d$_6$): δ ppm −0.11 (s, 9H), −0.03 (s, 9H), 0.79-0.89 (m, 4H), 2.86 (d, 3H), 2.99 (s, 3H), 3.57 (t, 2H), 3.76 (m, 4H), 4.80 (br m, 1H), 4.97 (br m, 1H), 5.30 (s, 2H), 5.73 (s, 2H), 6.70 (m, 1H), 7.09 (s, 1H), 7.18-7.71 (m, 5H), 7.71 (s, 1H), 8.29 (s, 1H), 8.90 (m, 1H), 9.84 (m, 1H), 13.75 (s, 1H). MS m/z 893 [M+H]$^+$ The following Preparations (Preparations 4-10) were prepared according to the method described for Preparation 3 using either 6-[5-fluoro-2-(2,2,2-trifluoroethyl)-4-{[2-(trimethylsilyl)-ethoxy]methoxy}phenyl]-4-{[2-(methylamino)benzyl]amino}-1-{[2-(trimethylsilyl)ethoxy]-methyl}-1H-pyrazolo[4,3-c]pyridine-3-carboxamide (Preparation 16) or 6-(5-fluoro-2-(2,2,2-trifluoroethyl)-4-fluoro-4-{[2-(trimethylsilyl)ethoxy]methoxy}phenyl)-N-methyl-4-{[2-(methylamino)benzyl]amino}-1-{[2-(trimethylsilyl)ethoxy]methyl}-1H-pyrazolo[4,3-c]pyridine-3-carboxamide (Preparation 17) and the appropriate sulfonyl chloride as described below:

| Preparation Number | Name | Data |
|---|---|---|
| 4 | 4-[(2-{[(3-chloropropyl)sulfonyl]-(methyl)amino}benzyl)amino]-6-[5-fluoro-2-(2,2,2-trifluoroethyl)-4-{[2-(trimethylsilyl)ethoxy]methoxy}phenyl]-1-{[2-(trimethylsilyl)-ethoxy]methyl}-1H-pyrazolo[4,3-c]pyridine-3-carboxamide | MS m/z 889 [M + H]$^+$<br>Using 3-chloropropanesulfonyl chloride. |
| 5 | 6-[5-fluoro-2-(2,2,2-trifluoroethyl)-4-{[2-(trimethylsilyl)ethoxy]-methoxy}phenyl]-4-{[2-(methyl{[6-(morpholin-4-yl)pyridin-3-yl]sulfonyl}amino)benzyl]amino}-1-{[2-(trimethylsilyl)ethoxy]methyl}-1H-pyrazolo[4,3-c]pyridine-3-carboxamide | MS m/z 975 [M + H]$^+$<br>$^1$H NMR (400 MHz, DMSO-d$_6$): δ ppm −0.11 (s, 9H), −0.03 (s, 9H), 0.80-0.89 (m, 4H), 2.99 (s, 3H), 3.56-3.84 (m, 14H), 4.78 (m, 1H), 4.93 (m, 1H), 5.30 (s, 2H), 5.73 (s, 2H), 6.80 (d, 1H), 6.90 (d, 1H), 7.10 (s, 1H), 7.19-7.33 (m, 3H), 7.42 (m, 1H), 7.63 (m, 1H), 7.98 (s, 1H), 8.27 (m, 2H), 9.83 (m, 1H).<br>Using 6-morpholin-4-yl-pyridine-3-sulfonyl chloride. |
| 6 | 6-[5-fluoro-2-(2,2,2-trifluoroethyl)-4-{[2-(trimethylsilyl)ethoxy]-methoxy}phenyl]-N-methyl-4-[(2-{methyl[(6-methylpyridin-3-yl)sulfonyl]amino}benzyl)amino]-1-{[2-(trimethylsilyl)ethoxy]methyl}-1H-pyrazolo[4,3-c]pyridine-3-carboxamide | MS m/z 918 [M + H]$^+$<br>Using 6-methylpyridine-3-sulfonyl chloride. |
| 7 | 6-[5-fluoro-2-(2,2,2-trifluoroethyl)-4-{[2-(trimethylsilyl)ethoxy]-methoxy}phenyl]-4-[(2-{methyl[(6-methylpyridin-3-yl)sulfonyl]amino}-benzyl)amino]-1-{[2-(trimethylsilyl)ethoxy]methyl}-1H-pyrazolo[4,3-c]pyridine-3-carboxamide | MS m/z 904 [M + H]$^+$<br>Using 6-methylpyridine-3-sulfonyl chloride. |
| 8 | 4-((2-(N,1-dimethyl-1H-imidazole-4-sulfonamido)benzyl)amino)-6-(5-fluoro-2-(2,2,2-trifluoroethyl)-4-((2-(trimethylsilyl)ethoxy)methoxy)phenyl)-N-methyl-1-((2-(trimethylsilyl)-ethoxy)methyl)-1H-pyrazolo[4,3-c]pyridine-3-carboxamide | MS m/z 907 [M + H]$^+$<br>Using 1-methyl-1H-imidazole-4-sulfonylchloride. |
| 9 | 6-[5-fluoro-2-(2,2,2-trifluoroethyl)-4-{[2-(trimethylsilyl)ethoxy]-methoxy}phenyl]-4-[(2-{[(2-methoxyethyl)sulfonyl](methyl)amino}benzyl)amino]-N-methyl-1-{[2-(trimethylsilyl)ethoxy]methyl}-1H-pyrazolo-[4,3-c]pyridine-3-carboxamide | MS m/z 885 [M + H]$^+$<br>Using 2-methoxyethanesulfonyl chloride. |
| 10 | 6-[5-fluoro-2-(2,2,2-trifluoroethyl)-4-{[2-(trimethylsilyl)ethoxy]-methoxy}phenyl]-4-({2-[methyl-l(pyridin-3-ylsulfonyl)amino]benzyl}amino)-1-{[2-(trimethylsilyl)-ethoxy]methyl}-1H-pyrazolo[4,3-c]pyridine-3-carboxamide | Using pyridine-3-sulfonyl chloride.<br>Taken directly on to the next step. |

Preparation 11

6-[5-Fluoro-2-(2,2,2-trifluoroethyl)-4-{[2-(trimethylsilyl)ethoxy]methoxy}phenyl]-4-({5-methoxy-2-[methyl(methylsulfonyl)amino]benzyl}amino)-1-{[2-(trimethylsilyl)ethoxy]methyl}-1H-pyrazolo[4,3-c]pyridine-3-carboxylic acid To a solution of N-(2-{[(6-[5-fluoro-2-(2,2,2-trifluoroethyl)-4-{[2-(trimethylsilyl)ethoxy]-methoxy}phenyl]-3-iodo-1-{[2-(trimethylsilyl)ethoxy]methyl}-1H-pyrazolo[4,3-c]pyridin-4-yl)-amino]methyl}-4-methoxyphenyl)-N-methylmethanesulfonamide (Preparation 85, 250 mg, 0.26 mmol) in MeOH (4 mL) was added molybdenum hexacarbonyl (84.91 mg, 0.32 mmol), DBU (0.119 mL, 0.80 mmol) and Pd(OAc)$_2$ (4 mg, 0.02 mmol). The reaction was heated to 125° C. for 15 minutes under microwave irradiation. The reaction was cooled, diluted with EtOAc and filtered through celite. The filtrate was concentrated in vacuo and purified using silica gel column chromatography eluting with 10% MeOH in DCM to afford the title compound (100 mg, 51%). MS m/z 858 [M+H]$^+$

Preparation 12

6-[5-Fluoro-2-(2,2,2-trifluoroethyl)-4-{[2-(trimethylsilyl)ethoxy]methoxy}phenyl]-4-({2-[methyl(methylsulfonyl)amino]benzyl}amino)-1-{[2-(trimethylsilyl)ethoxy]methyl}-1H-pyrazolo[4,3-c]pyridine-3-carboxylic acid The title compound was prepared according to the method described for Preparation 11 using N-methyl-N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridin-4-yl)amino]-methyl}phenyl)methanesulfonamide (Preparation 105). MS m/z 829 [M+H]$^+$

Preparation 13

6-(5-Fluoro-2-(2,2,2-trifluoroethyl)-4-((2-(trimethylsilyl)ethoxy)methoxy)phenyl)-N-methyl-1-((2-(trimethylsilyl)ethoxy)methyl)-4-((2-(1,3,3-trimethylureido)benzyl)amino)-1H-pyrazolo[4,3-c]pyridine-3-carboxamide To a solution of 6-(5-fluoro-2-(2,2,2-trifluoroethyl)-4-fluoro-4-{[2-(trimethylsilyl)ethoxy]-methoxy}phenyl)-N-methyl-4-{[2-(methylamino)benzyl]amino}-1-{[2-(trimethylsilyl)ethoxy]methyl}-1H-pyrazolo[4,3-c]pyridine-3-carboxamide (Preparation 17, 50 mg, 0.06 mmol) in THF (5 mL) was added sodium hydride (1.88 mg, 0.08 mmol) at 0° C. After stirring for 2 minutes, dimethylsulfamoyl chloride (15 mg, 0.11 mmol) was added and the reaction was stirred for 1 hour. The reaction was partitioned between EtOAc and water, the organic layer was collected, dried over sodium sulfate and concentrated in vacuo. The residue was dissolved in DMF (1 mL) and treated with cesium carbonate (64 mg, 0.19 mmol) followed by methyl iodide (27 mg, 0.19 mmol). The reaction was stirred at room temperature for 18 hours before quenching with ammonium chloride and extraction with EtOAc. The organic layer was collected and purified using preparative TLC to afford the title compound (45 mg, 78%). MS m/z 870 [M+H]$^+$

Preparation 14

6-(2-Ethyl-5-fluoro-4-{[2-(trimethylsilyl)ethoxy]methoxy}phenyl)-N-methyl-4-{[2-(methyl-amino)benzyl]amino}-1-{[2-(trimethylsilyl)ethoxy]methyl}-1H-pyrazolo[4,3-c]pyridine-3-carboxamide To a solution of benzyl [2-({[6-(2-ethyl-5-fluoro-4-{[2-(trimethylsilyl)-ethoxy]methoxy}phenyl)-3-(methylcarbamoyl)-1-{[2-(trimethylsilyl)ethoxy]methyl}-1H-pyrazolo[4,3-c]pyridin-4-yl]amino}-methyl)phenyl] methylcarbamate (Preparation 18, 775 mg, 0.91 mmol) in EtOH (25 mL) was added 10% Pd/C (100 mg) and the reaction was hydrogenated at room temperature at 30 psi for 1 hour. The reaction was filtered, the filtrate was concentrated in vacuo and the residue was purified by silica gel column chromatography eluting with 15% EtOAc in hexanes to afford the title compound (530 mg, 81%). $^1$H NMR (400 MHz, DMSO-d$_6$): δ ppm −0.11 (s, 9H), −0.01 (s, 9H), 0.81 (t, 2H), 0.88 (t, 2H), 1.00 (t, 2H), 2.38 (s, 3H), 2.69 (m, 2H), 2.82 (s, 3H), 3.56 (t, 2H), 3.77 (t, 2H), 4.59 (m, 2H), 5.33 (s, 2H), 5.71 (s, 2H), 6.02 (m, 1H), 6.44 (m, 1H), 6.55 (m, 1H), 6.98 (s, 1H), 7.04-7.19 (m, 2H), 7.22 (m, 1H), 8.84 (m, 1H), 9.69 (m, 1H). MS m/z 709 [M+H]$^+$

Preparation 15

6-[5-Fluoro-4-hydroxy-2-(2,2,2-trifluoroethyl)phenyl]-4-[({2-[methyl(methylsulfonyl)amino]-pyridin-3-yl}methyl)amino]-1-(tetrahydro-2H-pyran-2-yl)-1H-pyrazolo[4,3-c]pyridine-3-carboxamide The title compound was prepared according to the method described for Preparation 14 using 6-[4-(benzyloxy)-5-fluoro-2-(2,2,2-trifluoroethyl)phenyl]-4-[({2-[methyl(methylsulfonyl)amino]pyridin-3-yl}methyl)amino]-1-(tetrahydro-2H-pyran-2-yl)-1H-pyrazolo[4,3-c]pyridine-3-carboxamide (Preparation 22). The residue was purified by silica gel column chromatography eluting with 25% EtOAc in DCM. $^1$H NMR (400 MHz, DMSO-d$_6$): δ ppm 1.58 (m, 2H), 1.74 (m, 1H), 1.93-2.10 (m, 3H), 3.10 (s, 1H), 3.12 (s, 3H), 3.61 (m, 1H), 3.74 (m, 2H), 3.90 (m, 1H), 4.82 (m, 2H), 5.88 (m, 1H), 6.95 (d, 1H), 7.03 (s, 1H), 7.25 (d, 1H), 7.36 (m, 1H), 7.81 (m, 1H), 7.97 (br s, 1H), 8.19 (br s, 1H), 8.41 (m, 1H), 9.82 (t, 1H), 10.15 (s, 1H). MS m/z 652 [M+H]$^+$

Preparation 16

6-[5-Fluoro-2-(2,2,2-trifluoroethyl)-4-{[2-(trimethylsilyl)ethoxy]methoxy})phenyl]-4-{[2-(methyl-amino)benzyl]amino}-1-{[2-(trimethylsilyl)ethoxy]methyl}-1H-pyrazolo[4,3-c]pyridine-3-carboxamide The title compound was prepared according to the method described for Preparation 14 using benzyl (2-{[(3-carbamoyl-6-[5-fluoro-2-(2,2,2-trifluoroethyl)-4-{[2-(trimethylsilyl)-ethoxy]methoxy}phenyl]-1-{[2-(trimethylsilyl)ethoxy]methyl}-1H-pyrazolo[4,3-c]pyridin-4-yl)-amino]methyl}phenyl)methylcarbamate (Preparation 23). The residue was purified by silica gel column chromatography eluting with 30% EtOAc in hexanes. MS m/z 749 [M+H]$^+$

Preparation 17

6-(5-Fluoro-2-(2,2,2-trifluoroethyl)-4-fluoro-4-{[2-(trimethylsilyl)ethoxy]methoxy}phenyl)-N-methyl-4-{[2-(methylamino)benzyl]amino}-1-{[2-(trimethylsilyl)ethoxy]methyl}-1H-pyrazolo[4,3-c]pyridine-3-carboxamide The title compound was prepared according to the method described for Preparation 14 using benzyl [2-({[6-(5-fluoro- 2-(2,2,2-trifluoroethyl)-4-{[2-(trimethylsilyl)ethoxy]methoxy}-phenyl)-3-(methylcarbamoyl)-1-{[2-(trimethylsilyl)ethoxy]methyl}-1H-pyrazolo[4,3-c]pyridin-4-yl]amino}methyl)phenyl]methylcarbamate (Preparation 19). $^1$H NMR (400 MHz, DMSO-d$_6$): δ ppm −0.11 (s, 9H), −0.01 (s, 9H), 0.81 (t, 2H), 0.89 (t, 2H), 2.50 (s, 3H), 2.84 (d, 3H), 3.58 (t, 2H), 3.76 (t, 2H), 3.95 (q, 2H), 4.58 (d, 2H), 5.33 (s, 2H), 5.73 (s, 2H), 5.74 (br s, 1H), 6.45-6.54 (m, 2H), 7.05-7.11 (m, 3H), 7.35-7.39 (m, 2H), 8.87 (m, 1H), 9.73 (m, 1H). MS m/z 763 [M+H]$^+$ Preparation 18

Benzyl [2-({[6-(2-ethyl-5-fluoro-4-{[2-(trimethylsilyl)ethoxy]methoxy}phenyl-3-(methylcarbamoyl)-1-{[2-(trimethylsilyl)ethoxy]methyl}-1H-pyrazolo[4,3-c]pyridin-4-yl]amino}methyl)phenyl]methylcarbamate To a solution of benzyl [2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)phenyl]methylcarbamate (Preparation 91, 1 g, 1 mmol) in methylamine/THF (10 mL) was added DBU (0.49 mL, 3.23 mmol), Pd(OAc)$_2$ (17 mg, 0.08 mmol) followed by molybdenum hexacarbonyl (0.29 mg, 1.09 mmol). The reaction was heated to 100° C. under microwave irradiation for 10 minutes. The reaction was cooled, concentrated in vacuo and diluted with EtOAc. The mixture was filtered through celite, the filtrate concentrated in vacuo and purified using silica gel column chromatography eluting with 47% EtOAc in hexanes to afford the title compound (775 mg, 84%). $^1$H NMR (400 MHz, DMSO-d$_6$): δ ppm −0.10 (s, 9H), −0.01 (s, 9H), 0.79 (t, 2H), 0.90 (m, 5H), 2.57 (m, 2H), 2.83 (d, 3H), 3.08 (s, 1H), 3.59 (t, 2H), 3.74 (t, 2H), 4.53 (m, 1H), 4.71 (m, 1H), 4.88 (m, 1H), 5.00 (m, 1H), 5.27 (s, 1H), 5.75 (s, 2H), 6.98 (s, 1H), 7.08-7.42 (m, 11H), 8.83 (m, 1H), 9.67 (m, 1H). MS m/z 843 [M+H]$^+$ Preparation 19

Benzyl [2-({[6-(5-fluoro-2-(2,2,2-trifluoroethyl)-4-{[2-(trimethylsilyl)ethoxy]methoxy}phenyl)-3-(methylcarbamoyl)-1-{[2-(trimethylsilyl)ethoxy]methyl}-1H-pyrazolo[4,3-c]pyridin-4-yl]amino}methyl)phenyl]methylcarbamate A solution of 6-[5-fluoro-2-(2,2,2-trifluoroethyl)-4-{[2-(trimethylsilyl)-ethoxy]methoxy}phenyl]-N-methyl-1-{[2-(trimethylsilyl)ethoxy]methyl}-1H-pyrazolo[4,3-c]pyridine-3-carboxamide-5-oxide (Preparation 117, 3.2 g, 4.96 mmol) in DMF (100 mL) was treated with benzyl methyl [2-({[(4-nitrophenoxy)carbonyl]amino}-methyl)phenyl]carbamate (Preparation 178, 2.68 g, 6.16 mmol) and triethylamine (0.68 mL, 4.96 mmol) and heated at 80° C. for 16 hours. Further benzyl methyl[2-({[(4-nitrophenoxy)carbonyl]amino}methyl)phenyl]carbamate (1.24 eq) and triethylamine (1 eq) were added and the reaction allowed to continue for 6 hours. The reaction was cooled, concentrated in vacuo and purified using silica gel column chromatography to afford the title compound as an oil (4.2 g, 94%). MS m/z 897 [M+H]$^+$ Preparation 20

6-(2-Ethyl-5-fluoro-4-{[2-(trimethylsilyl)ethoxy]methoxy}phenyl)-4-({2-[methyl(methylsulfonyl)amino]benzyl}amino)-N-(6-methylpyridin-3-yl)-1-{[2-(trimethylsilyl)ethoxy]methyl}-1H-pyrazolo[4,3-c]pyridine-3-carboxamide The title compound was prepared according to the method described for Preparation 18 using N-[2-({[6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-yl]amino}methyl)phenyl]-N-methylmethanesulfonamide (Preparation 79) and 6-methylpyridin-3-amine with DBU at 100° C. for 10 minutes under microwave irradiation. The reaction was cooled, concentrated in vacuo and purified using silica gel column chromatography eluting with 7% heptanes in EtOAc. MS m/z 864 [M+H]$^+$ Preparation 21

6-[5-Fluoro-2-(2,2,2-trifluoroethyl)-4-{[2-(trimethylsilyl)ethoxy]methoxy}phenyl]-4-({4-methoxy-2-[methyl(methylsulfonyl)amino]benzyl}amino)-1-{[2-(trimethylsilyl)ethoxy]methyl}-1H-pyrazolo[4,3-c]pyridine-3-carboxamide To a solution of N-(2-{[(6-[5-fluoro-2-(2,2,2-trifluoroethyl)-4-{[2-(trimethylsilyl)-ethoxy]-methoxy}phenyl]-3-iodo-1-{[2-(trimethylsilyl)ethoxy]methyl}-1H-pyrazolo[4,3-c]pyridin-4-yl)-amino]methyl}-5-methoxyphenyl)-N-methylmethanesulfonamide (Preparation 89, 350 mg, 0.37 mmol) in MeOH (2 mL) was added DBU (0.16 mL, 1.19 mmol), palladium acetate (5.86 mg, 0.03 mmol) and molybdenum hexacarbonyl (99 mg, 0.37 mmol) and the reaction was heated to 100° C. for 10 minutes under microwave irradiation. The reaction was cooled, concentrated in vacuo and purified directly using silica gel column chromatography eluting with 12% MeOH in DCM. The resulting residue was dissolved in anhydrous THF (5 mL) and NMM (0.033 mL, 0.30 mmol) was added followed by isobutylchloroformate (0.04 mL, 0.30 mmol) at −20° C. The reaction was stirred for 2 hours at this temperature before the addition of aqueous ammonia (0.5 mL) with further stirring for 1 hour. The reaction was partitioned between EtOAc and water, the organic layer collected, washed with brine, dried over sodium sulfate and concentrated in vacuo. The residue was purified using silica gel column chromatography eluting with 42% EtOAc in hexanes to afford the title compound (102 mg, 32% over 2 steps). MS m/z 857 [M+H]$^+$ The following Preparations (Preparations 22-26) were prepared according to the method described for Preparation 21 using the appropriate iodo intermediate as described below:

| Preparation Number | Name | Data |
|---|---|---|
| 22 | 6-[4-(benzyloxy)-5-fluoro-2-(2,2,2-trifluoroethyl)phenyl]-4-[({2-[methyl(methylsulfonyl)amino]pyridin-3-yl}methyl)amino]-1-(tetrahydro-2H-pyran-2-yl)-1H-pyrazolo[4,3-c]pyridine-3-carboxamide | MS m/z 742 [M + H]$^+$<br>Using N-{3-[({6-[4-(benzyloxy)-5-fluoro-2-(2,2,2-trifluoroethyl)phenyl]-3-iodo-1-(tetrahydro-2H-pyran-2-yl)-1H-pyrazolo[4,3-c]pyridin-4-yl}amino)methyl]pyridin-2-yl}-N-methylmethanesulfonamide (Preparation 93). |
| 23 | Benzyl (2-{[(3-carbamoyl-6-[5-fluoro-2-(2,2,2-trifluoroethyl)-4-{[2-(trimethylsilyl)ethoxy]methoxy}phenyl]-1-{[2-(trimethylsilyl)ethoxy]methyl}-1H-pyrazolo[4,3-c]pyridin-4-yl)amino]methyl}phenyl)methylcarbamate | MS m/z 883 [M + H]$^+$<br>Using benzyl (2-{[(6-[5-fluoro-2-(2,2,2-trifluoroethyl)-4-{[2-(trimethylsilyl)ethoxy]methoxy}phenyl]-3-iodo-1-{[2-(trimethylsilyl)-ethoxy]methyl}-1H-pyrazolo[4,3-c]pyridin-4-yl)amino]methyl}phenyl)methylcarbamate (Preparation 92). |
| 24 | 6-[5-fluoro-4-methoxy-2-(2,2,2-trifluoroethyl)phenyl]-4-({5-methoxy-2-[methyl(phenylsulfonyl)-amino]benzyl}amino)-1-{[2-(trimethylsilyl)ethoxy]methyl}-1H-pyrazolo[4,3-c]pyridine-3-carboxamide | MS m/z 803 [M + H]$^+$<br>Using N-(2-{[(6-[5-fluoro-2-(2,2,2-trifluoroethyl)-4-{[2-(trimethylsilyl)ethoxy]methoxy}pheny.l]-3-iodo-1-{[2-(trimethylsilyl)-ethoxy]methyl}-1H-pyrazolo[4,3-c]pyridin-4-yl)amino]methyl}-5-methoxyphenyl)-N-methylmethanesulfonamide (Preparation 108). |
| 25 | N-ethyl-N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)-ethoxy]methyl}-1H-pyrazolo[4,3-c]pyridin-4-yl)amino]methyl}-4-methoxyphenyl)benzenesulfonamide | MS m/z 933 [M + H]$^+$<br>Using N-ethyl-N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridin-4-yl)amino]methyl}-4-methoxyphenyl)benzenesulfonamide (Preparation 90). |
| 26 | 6-(2-cyclopropyl-5-fluoro-4-methoxyphenyl)-4-({2-[methyl(methylsulfonyl)amino]benzyl}amino)-1-{[2-(trimethylsilyl)-ethoxy]methyl}-1H-pyrazolo[4,3-c]pyridine-3-carboxamide | MS m/z 669 [M + H]$^+$<br>Using N-[2-({[6-(2-cyclopropyl-5-fluoro-4-methoxyphenyl)-3-iodo-1-{[2-(trimethylsilyl)-ethoxy]methyl}-1H-pyrazolo[4,3-c]pyridin-4-yl]amino}methyl)phenyl]-N-methylmethanesulfonamide (Preparation 109). |

Preparation 27

6-(4-(Benzyloxy)-5-fluoro-2-(2,2,2-trifluoroethyl)phenyl)-N-(tert-butyl)-4-((2-(N-methylmethylsulfonamido)benzyl)amino)-1-(tetrahydro-2H-pyran-2-yl)-1H-pyrazolo[4,3-c]pyridine-3-carboxamide To a solution of N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)phenyl)-N-methyl-methanesulfonamide (Preparation 60, 5.8 g, 7.04 mmol) in THF (15 mL) was added molybdenum hexacarbonyl (1.872 g, 7.04 mmol), DBU (3.15 mL) and Pd(OAc)$_2$ (111 mg, 0.15 mmol), and t-butyl amine (6 mL). The reaction was heated in a sealed tube to 100° C. for 45 minutes. The reaction was cooled, filtered and concentrated in vacuo. The residue was purified using silica gel column chromatography eluting with 29% EtOAc in hexanes to afford the title compound (4 g, 71%). $^1$H NMR (400 MHz, DMSO-d$_6$): 5 ppm 1.45 (s, 9H), 1.67-1.73 (m, 2H), 1.91-2.02 (m, 2H), 2.44 (m, 2H), 3.05 (s, 3H), 3.10 (s, 3H), 3.66-3.95 (m, 4H), 4.78-4.86 (m, 2H), 5.21 (s, 2H), 5.86 (m, 1H), 7.04 (s, 1H), 7.27-7.50 (m, 11H), 7.73 (s, 1H), 9.66 (t, 1H). MS m/z 797 [M+H]$^+$ The following Preparations (Preparations 28-38) were prepared according to the method described for Preparation 27 using the appropriate iodo intermediate as described below:

| Preparation Number | Name | Data |
|---|---|---|
| 28 | 6-(4-benzyloxy)-5-fluoro-2-(2,2,2-trifluoroethyl)phenyl-N-(tert-butyl)-4-((5-methyl-2-(N-methylmethylsulfonamido)benzyl)amino)-1-(tetrahydro-2H-pyran-2-yl)-1H-pyrazolo[4,3-c]pyridine-3-carboxamide | MS m/z 811 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridine-4-yl)amino)methyl)-4-methylphenyl)-N-methylmethanesulfonamide (Preparation 94). |

-continued

| Preparation Number | Name | Data |
|---|---|---|
| 29 | 6-(4-(benzyloxy)-5-fluoro-2-(2,2,2-trifluoroethyl)phenyl)-N-(tert-butyl)-4-((5-methoxy-2-(N-methylmethylsulfonamido)benzyl)amino)-1-(tetrahydro-2H-pyran-2-yl)-1H-pyrazolo[4,3-c]pyridine-3-carboxamide | MS m/z 826 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-4-methoxyphenyl)-N-methylmethanesulfonamide (Preparation 103). |
| 30 | 6-(4-(benzyloxy)-5-fluoro-2-(2,2,2-trifluoroethyl)phenyl)-N-(tert-butyl)-4-((5-chloro-2-(N-methylmethylsulfonamido)benzyl)amino)-1-(tetrahydro-2H-pyran-2-yl)-1H-pyrazolo[4,3-c]pyridine-3-carboxamide | MS m/z 831 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-4-chlorophenyl)-N-methylmethanesulfonamide (Preparation 101). |
| 31 | 6-(4-(benzyloxy)-5-fluoro-2-(2,2,2-trifluoroethyl)phenyl)-N-(tert-butyl)-4-((2-(N-ethylmethylsulfonamido)-5-methylbenzyl)amino)-1-(tetrahydro-2H-pyran-2-yl)-1H-pyrazolo[4,3-c]pyridine-3-carboxamide | MS m/z 825 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-4-methylphenyl)-N-ethylmethanesulfonamide (Preparation 104). |
| 32 | 6-(4-benzyloxy)-5-fluoro-2-(2,2,2-trifluoroethyl)phenyl-N-(tert-butyl)-4-((2-(N-ethylethylsulfonamido)benzyl)amino)-1-(tetrahydro-2H-pyran-2-yl)-1H-pyrazolo[4,3-c]pyridine-3-carboxamide | MS m/z 825 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridine-4-yl)amino)methyl)phenyl)-N-ethylethanesulfonamide (Preparation 95). |
| 33 | 6-(4-(benzyloxy)-5-fluoro-2-(2,2,2-trifluoroethyl)phenyl)-N-(tert-butyl)-4-(((2-(N-ethylmethylsulfonamido)-5-methylpyridin-3-yl)methyl)amino)-1-(tetrahydro-2H-pyran-2-yl)-1H-pyrazolo[4,3-c]pyridine-3-carboxamide | MS m/z 826 [M + H]$^+$<br>Using N-(3-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-5-methylpyridin-2-yl)-N-ethylmethanesulfonamide (Preparation 100). |
| 34 | 6-(4-(benzyloxy)-5-fluoro-2-(2,2,2-trifluoroethyl)phenyl)-N-(tert-butyl)-4-((2-(N-ethylmethylsulfonamido)-5-fluorobenzyl)amino)-1-(tetrahydro-2H-pyran-2-yl)-1H-pyrazolo[4,3-c]pyridine-3-carboxamide | MS m/z 829 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-4-fluorophenyl)-N-ethylmethanesulfonamide (Preparation 96). |
| 35 | 6-(4-(benzyloxy)-5-fluoro-2-(2,2,2-trifluoroethyl)phenyl)-N-(tert-butyl)-4-((2-(N-ethylmethylsulfonamido)-5-chlorobenzyl)amino)-1-(tetrahydro-2H-pyran-2-yl)-1H-pyrazolo[4,3-c]pyridine-3-carboxamide | MS m/z 845 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-4-chlorophenyl)-N-ethylmethanesulfonamide (Preparation 97). |
| 36 | 6-(4-(benzyloxy)-5-fluoro-2-(2,2,2-trifluoroethyl)phenyl)-N-(tert-butyl)-4-((2-(N-ethylmethylsulfonamido)benzyl)amino)-1-(tetrahydro-2H-pyran-2-yl)-1H-pyrazolo[4,3-c]pyridine-3-carboxamide | MS m/z 811 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)phenyl)-N-ethylmethanesulfonamide (Preparation 102). |
| 37 | 6-(4-(benzyloxy)-5-fluoro-2-(2,2,2-trifluoroethyl)phenyl)-N-(tert-butyl)-4-((2-(N-methylethylsulfonamido)benzyl)amino)-1-(tetrahydro-2H-pyran-2-yl)-1H-pyrazolo[4,3-c]pyridine-3-carboxamide | MS m/z 811 [M + H]$^+$<br>Using N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)phenyl)-N-methylethanesulfonamide (Preparation 98). |

-continued

| Preparation Number | Name | Data |
|---|---|---|
| 38 | 6-(4-(benzyloxy)-5-fluoro-2-(2,2,2-trifluoroethyl)phenyl)-N-(tert-butyl)-4-(((5-methyl-2-(N-methylmethylsulfonamido)pyridin-3-yl)methyl)amino)-1-(tetrahydro-2H-pyran-2-yl)-1H-pyrazolo[4,3-c]pyridine-3-carboxamide | MS m/z 812 [M + H]$^+$<br>Using N-(3-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-5-methylpyridin-2-yl)-N-methylmethanesulfonamide (Preparation 99). |

Preparation 39

6-[5-Fluoro-4-methoxy-2-(2,2,2-trifluoroethyl)phenyl]-N-methyl-4-[({3-[methyl(phenylsulfonyl)amino]pyrazin-2-yl}methyl)amino]-1-{[2-(trimethylsilyl)ethoxy]methyl}-1H-pyrazolo[4,3-c]pyridine-3-carboxamide To a solution of 4-chloro-6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide (Preparation 118, 150 mg, 0.27 mmol) in n-Butanol (4 mL) was added N-[3-(aminomethyl)pyrazin-2-yl]-N-methylbenzenesulfonamide (Preparation 219, 114 mg, 0.41 mmol) and DIPEA (0.17 mL 0.96 mmol). The reaction was heated to 90° C. in a sealed tube for 18 hours. The reaction was quenched by the addition of water and extracted with EtOAc. The organic layer was collected, dried over sodium sulfate and concentrated in vacuo. The residue was purified by silica gel column chromatography eluting with 30-50% EtOAc in hexanes to afford the title compound as a yellow solid (110 mg, 51%). MS m/z 789 [M+H]$^+$ The following Preparations (Preparations 40-59) were prepared according to the method described for Preparation 39 using the appropriate chloropyridine and the appropriate amine as described below:

| Preparation Number | Name | Data |
|---|---|---|
| 40 | 4-[({3-[ethyl(methylsulfonyl)amino]pyrazin-2-yl}methyl)amino]-6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide | MS m/z 741 [M + H]$^+$<br>Using 4-chloro-6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide (Preparation 118) and N-[3-(aminomethyl)pyrazin-2-yl]-N-ethylmethanesulfonamide (Preparation 221). |
| 41 | N-ethyl-4-[({3-[ethyl(methylsulfonyl)amino]pyrazin-2-yl}methyl)amino]-6-[5-fluoro-4-methoxy-2-(2,2,2-trifluoroethyl)phenyl]-1-{[2-(trimethylsilyl)ethoxy]methyl}-1H-pyrazolo[4,3-c]pyridine-3-carboxamide | MS m/z 755 [M + H]$^+$<br>Using 4-chloro-6-[5-fluoro-4-methoxy-2-(2,2,2-trifluoroethyl)phenyl]-N-ethyl-1-{[2-(trimethylsilyl)ethoxy]methyl}-1H-pyrazolo[4,3-c]pyridine-3-carboxamide (Preparation 119) and N-[3-(aminomethyl)pyrazin-2-yl]-N-ethylmethanesulfonamide (Preparation 221). |
| 42 | 6-[5-fluoro-4-methoxy-2-(2,2,2-trifluoroethyl)phenyl]-N-methyl-4-[({4-[methyl(methylsulfonyl)amino]pyridin-3-yl}methyl)amino]-1-{[2-(trimethylsilyl)ethoxy]methyl}-1H-pyrazolo[4,3-c]pyridine-3-carboxamide | MS m/z 726 [M + H]$^+$<br>Using 4-chloro-6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide (Preparation 118) and N-[3-(aminomethyl)pyridin-4-yl]methanesulfonamide (Preparation 197). |
| 43 | 6-[5-fluoro-2-(2,2,2-trifluoroethyl)-4-{[2-(trimethylsilyl)-ethoxy]methoxy}phenyl]-N-methyl-4-[({3-[methyl(methylsulfonyl)amino]pyridin-2-yl}methyl)amino]-1-{[2-(trimethylsilyl)ethoxy]methyl}-1H-pyrazolo[4,3-c]pyridine-3-carboxamide | MS m/z 842 [M + H]$^+$<br>Using 4-chloro-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 122) and N-(2-(aminomethyl)pyridine-3-yl)-N-methylmethane sulphonamide (WO2008/129380A1). |
| 44 | 6-[5-fluoro-2-(2,2,2-trifluoroethyl)-4-{[2-(trimethylsilyl)-ethoxy]methoxy}phenyl]-N-methyl-4-[({5-methyl-2- | MS m/z 856 [M + H]$^+$<br>Using 4-chloro-6-[5-fluoro-2-(2,2,2-trifluoroethyl)-4-{[2-(trimethylsilyl)ethoxy]methoxy}phenyl]-N-methyl-1-{[2- |

-continued

| Preparation Number | Name | Data |
|---|---|---|
| | [methyl(methylsulfonyl)amino]pyridin-3-yl}methyl)amino]-1-{[2-(trimethylsilyl)ethoxy]methyl}-1H-pyrazolo[4,3-c]pyridine-3-carboxamide | (trimethylsilyl)ethoxy]methyl}-1H-pyrazolo[4,3-c]pyridine-3-carboxamide (Preparation 122) and N-[3-(aminomethyl)-5-methylpyridin-2-yl]-N-methylmethanesulfonamide (Preparation 198). |
| 45 | 6-[5-fluoro-2-(2,2,2-trifluoroethyl)-4-{[2-(trimethylsilyl)-ethoxy]methoxy}phenyl]-N-methyl-4-({2-[methyl(pyridin-3-ylsulfonyl)amino]benzyl}amino)-1-{[2-(trimethylsilyl)ethoxy]methyl}-1H-pyrazolo[4,3-c]pyridine-3-carboxamide | MS m/z 904 [M + H]+<br>Using 4-chloro-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 122) and N-[2-(aminomethyl)phenyl]-N-methylpyridine-3-sulfonamide hydrochloride (Preparation 220). |
| 46 | 6-[5-fluoro-2-(2,2,2-trifluoroethyl)-4-{[2-(trimethylsilyl)-ethoxy]methoxy}phenyl]-4-({5-methoxy-2-[methyl(methylsulfonyl)amino]benzyl}amino)-N-methyl-1-{[2-(trimethylsilyl)ethoxy]methyl}-1H-pyrazolo[4,3-c]pyridine-3-carboxamide | MS m/z 871 [M + H]+<br>Using 4-chloro-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 122) and N-[2-(aminomethyl)-4-methoxyphenyl]-N-(methylsulfonyl)methanesulfonamide hydrochloride (Preparation 191). |
| 47 | 6-[5-fluoro-4-methoxy-2-(2,2,2-trifluoroethyl)phenyl]-N-methyl-4-[({3-[methyl(methylsulfonyl)amino]pyrazin-2-yl}methyl)amino]-1-{[2-(trimethylsilyl)ethoxy]methyl}-1H-pyrazolo[4,3-c]pyridine-3-carboxamide | MS m/z 727 [M + H]+<br>Using 4-chloro-6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide (Preparation 118) and N-(3-(aminomethyl)pyrazin-2-yl)-N-methylmethanesulfonamide (WO2008/129380A1). |
| 48 | 4-[({2-[ethyl(methyl-sulfonyl)amino]pyridin-3-yl}methyl)amino]-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide | MS m/z 856 [M + H]+<br>Using 4-chloro-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 122) and N-[3-(aminomethyl)pyridin-2-yl]-N-ethylmethanesulfonamide (Preparation 218). |
| 49 | 6-[5-fluoro-2-(2,2,2-trifluoroethyl)-4-{[2-(trimethylsilyl)-ethoxy]methoxy}phenyl]-N-methyl-4-{[2-(sulfamoylmethyl)-benzyl]amino}-1-{[2-(trimethylsilyl)ethoxy]methyl}-1H-pyrazolo[4,3-c]pyridine-3-carboxamide | MS m/z 826 [M + H]+<br>Using 4-chloro-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 122) and 1-[2-(aminomethyl)phenyl]methanesulfonamide hydrochloride (Preparation 199). |
| 50 | N-tert-butyl-4-[({5-chloro-2-[ethyl(methylsulfonyl)amino]pyridin-3-yl}methyl)amino]-6-[5-fluoro-2-(2,2,2-trifluoroethyl)-4-{[2-(trimethylsilyl)ethoxy]methoxy}phenyl]-1-{[2-(trimethyl-silyl)ethoxy]methyl}-1H-pyrazolo[4,3-c]pyridine-3-carboxamide | MS m/z 932 [M + H]+<br>Using N-tert-butyl-4-chloro-6-[5-fluoro-2-(2,2,2-trifluoroethyl)-4-{[2-(trimethylsilyl)ethoxy]methoxy}phenyl]-1-{[2-(trimethylsilyl)ethoxy]methyl}-1H-pyrazolo[4,3-c]pyridine-3-carboxamide (Preparation 120) and N-[3-(aminomethyl)-5-chloropyridin-2-yl]-N-ethylmethanesulfonamide hydrochloride (Preparation 201). |
| 51 | N-tert-butyl-4-[({5-chloro-2-[methyl(methylsulfonyl)amino]pyridin-3-yl}methyl)amino]-6-[5-fluoro-2-(2,2,2-trifluoroethyl)-4-{[2-(trimethylsilyl)ethoxy]methoxy}phenyl]-1-{[2-(trimethylsilyl)ethoxy]methyl}- | MS m/z 918 [M + H]+<br>Using N-tert-butyl-4-chloro-6-[5-fluoro-2-(2,2,2-trifluoroethyl)-4-{[2-(trimethylsilyl)ethoxy]methoxy}phenyl]-1-{[2-(trimethylsilyl)ethoxy]methyl}-1H-pyrazolo[4,3-c]pyridine-3-carboxamide (Preparation 120) and N-[3-(aminomethyl)-5-chloropyridin-2-yl]-N- |

-continued

| Preparation Number | Name | Data |
|---|---|---|
| | 1H-pyrazolo[4,3-c]pyridine-3-carboxamide | methylmethanesulfonamide hydrochloride (Preparation 202). |
| 52 | N-(2,4-dimethoxybenzyl)-4-[({2-[ethyl(methylsulfonyl)amino]pyridin-3-yl}methyl)amino]-6-[5-fluoro-4-methoxy-2-(2,2,2-trifluoroethyl)phenyl]-1-{[2-(trimethylsilyl)ethoxy]methyl}-1H-pyrazolo[4,3-c]pyridine-3-carboxamide | MS m/z 876 [M + H]$^+$<br>Using 4-chloro-N-(2,4-dimethoxybenzyl)-6-[5-fluoro-4-methoxy-2-(2,2,2-trifluoroethyl)phenyl]-1-{[2-(trimethylsilyl)ethoxy]methyl}-1H-pyrazolo[4,3-c]pyridine-3-carboxamide (Preparation 121) and N-[3-(aminomethyl)pyridin-2-yl]-N-ethylmethane-sulfonamide (Preparation 218). |
| 53 | 6-[5-fluoro-4-methoxy-2-(2,2,2-trifluoroethyl)phenyl]-N-methyl-4-[({2-[methyl(methylsulfonyl)amino]pyridin-3-yl}methyl)-amino]-1-{[2-(trimethylsilyl)ethoxy]methyl}-1H-pyrazolo[4,3-c]pyridine-3-carboxamide | MS m/z 726 [M + H]$^+$<br>Using 4-chloro-6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide (Preparation 118) and N-[3-(aminomethyl)pyridin-2-yl]-N-methylmethanesulfonamide (Preparation 217). |
| 54 | 6-[5-fluoro-4-methoxy-2-(2,2,2-trifluoroethyl)phenyl]-4-({5-methoxy-2-[methyl(pyridin-3-ylsulfonyl)amino]benzyl}amino)-N-methyl-1-{[2-(trimethylsilyl)ethoxy]methyl}-1H-pyrazolo[4,3-c]pyridine-3-carboxamide | MS m/z 818 [M + H]$^+$<br>Using 4-chloro-6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide (Preparation 118) and N-[2-(aminomethyl)-4-methoxyphenyl]-N-methylpyridine-3-sulfonamide (Preparation 212). |
| 55 | 6-((4-benzyloxy)-5-fluoro-2-(2,2,2-trifluoroethyl)phenyl)-N-(tert-butyl)-4-(((5-fluoro-2-(N-methylmethylsulfonamido)pyridin-3-yl)methyl)amino)-1-(tetrahydro-2H-pyran-2-yl)-1H-pyrazolo[4,3-c]pyridine-3-carboxamide | MS m/z 816 [M + H]$^+$<br>Using 6-(4-(benzyloxy)-5-fluoro-2-(2,2,2-trifluoroethyl)phenyl)-N-(tert-butyl)-4-chloro-1-(tetrahydro-2H-pyran-2-yl)-1H-pyrazolo[4,3-c]pyridine-3-carboxamide (Preparation 123) and N-[3-(aminomethyl)-5-fluoropyridin-2-yl]-N-methylmethanesulfonamide hydrochloride (Preparation 203). |
| 56 | 6-((4-benzyloxy)-5-fluoro-2-(2,2,2-trifluoroethyl)phenyl)-N-(tert-butyl)-4-(((5-fluoro-2-(N-ethylmethylsulfonamido)pyridin-3-yl)methyl)amino)-1-(tetrahydro-2H-pyran-2-yl)-1H-pyrazolo[4,3-c]pyridine-3-carboxamide | MS m/z 830 [M + H]$^+$<br>Using 6-(4-(benzyloxy)-5-fluoro-2-(2,2,2-trifluoroethyl)phenyl)-N-(tert-butyl)-4-chloro-1-(tetrahydro-2H-pyran-2-yl)-1H-pyrazolo[4,3-c]pyridine-3-carboxamide (Preparation 123) and N-[3-(aminomethyl)-5-fluoropyridin-2-yl]-N-ethylmethanesulfonamide hydrochloride (Preparation 204). |
| 57 | 6-((4-benzyloxy)-5-fluoro-2-(2,2,2-trifluoroethyl)phenyl)-N-(tert-butyl)-4-(((3-(N-ethylmethylsulfonamido)pyrazin-2-yl)methyl)amino)-1-(tetrahydro-2H-pyran-2-yl)-1H-pyrazolo[4,3-c]pyridine-3-carboxamide | MS m/z 813 [M + H]$^+$<br>Using 6-(4-(benzyloxy)-5-fluoro-2-(2,2,2-trifluoroethyl)phenyl)-N-(tert-butyl)-4-chloro-1-(tetrahydro-2H-pyran-2-yl)-1H-pyrazolo[4,3-c]pyridine-3-carboxamide (Preparation 123) and N-[3-(aminomethyl)pyrazin-2-yl]-N-ethylmethanesulfonamide (Preparation 221). |
| 58 | 6-(5-fluoro-2-(2,2,2-trifluoroethyl)-4-((2-(trimethylsilyl)ethoxy)methoxy)phenyl)-N-methyl-4-((2-(N-methyl-2-oxooxazolidine-3-sulfonamido)benzyl)amino)-1-((2-(trimethylsilyl)ethoxy)methyl)-1H-pyrazolo[4,3-c]pyridine-3-carboxamide | MS m/z 813 [M + H]$^+$<br>Using 4-chloro-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 122) and tert-butyl 2-(N-methyl-2-oxooxazolidine-3-sulfonamido)benzyl-carbamate hydrochloride (Preparation 208). |

| Preparation Number | Name | Data |
|---|---|---|
| 59 | 6-(4-(benzyloxy)-5-fluoro-2-(2,2,2-trifluoroethyl)phenyl)-N-(tert-butyl)-4-((5-fluoro-2-(N-methylmethylsulfonamido)benzyl)amino)-1-(tetrahydro-2H-pyran-2-yl)-1H-pyrazolo[4,3-c]pyridine-3-carboxamide | MS m/z 814 [M + H]$^+$<br>Using 6-(4-(benzyloxy)-5-fluoro-2-(2,2,2-trifluoroethyl)phenyl)-N-(tert-butyl)-4-chloro-1-(tetrahydro-2H-pyran-2-yl)-1H-pyrazolo[4,3-c]pyridine-3-carboxamide (Preparation 123) and N-[2-(aminomethyl)-4-fluorophenyl]-N-methylmethanesulfonamide hydrochloride (Preparation 186). |

Preparation 60

N-(2-(((6-(4-(Benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)phenyl)-N-methylmethanesulfonamide To a solution of 6-[4-(benzyloxy)-5-fluoro-2-(2,2,2-trifluoroethyl)phenyl]-3-iodo-1-(tetrahydro-2H-pyran-2-yl)-1H-pyrazolo[4,3-c]pyridine 5-oxide (Preparation 112, 110 mg, 0.18 mmol) in DMF (5 mL) was added 4-nitrophenyl {2-[methyl(methylsulfonyl)amino]benzyl}carbamate (Preparation 166, 82 mg, 0.22 mmol) followed by triethylamine (0.06 mL, 0.438 mmol). The reaction was heated to 100° C. for 16 hours. Further 4-nitrophenyl {2-[methyl(methylsulfonyl)amino]benzyl}carbamate (1.2 eq) and triethylamine (2.5 eq) were added and the reaction continued at 100° C. for 18 hours. The reaction was cooled, concentrated in vacuo and partitioned between ice-water and EtOAc. The organic layer was collected, washed with saturated aqueous potassium carbonate solution, brine, dried over sodium sulfate and concentrated in vacuo. The residue was purified using silica gel column chromatography eluting with 49% EtOAc in hexanes to afford the title compound (120 mg, 83%). $^1$H NMR (400 MHz, DMSO-d$_6$): δ ppm 1.50-1.75 (m, 3H), 1.89 (m, 2H), 2.32 (m, 1H), 3.05 (s, 3H), 3.06 (s, 3H), 3.53 (m, 1H), 3.70-3.73 (m, 2H), 3.87 (m, 1H), 4.74 (m, 1H), 4.92 (m, 1H), 5.21 (s, 2H), 5.78 (m, 1H), 6.82 (t, 1H), 7.11 (s, 1H), 7.27-7.50 (m, 11H). MS m/z 824 [M+H]$^+$

Preparation 61

N-(4-Chloro-2-{[(6-[5-fluoro-2-(2,2,2-trifluoroethyl)-4-{[2-(trimethylsilyl)ethoxy]methoxy)}phenyl]-3-iodo-1-{[2-(trimethylsilyl)ethoxy]methyl}-1H-pyrazolo[4,3-c]pyridin-4-yl)amino]methyl}phenyl)-N-methylmethanesulfonamide A solution of 6-[5-fluoro-2-(2,2,2-trifluoroethyl)-4-{[2-(trimethylsilyl)ethoxy]-methoxy}phenyl]-3-iodo-1-{[2-(trimethylsilyl)ethoxy]methyl}-1H-pyrazolo[4,3-c]pyridine 5-oxide (Preparation 114, 650 mg, 0.91 mmol) in DMF was treated with 4-nitrophenyl {5-chloro-2-[methyl(methylsulfonyl)amino]benzyl}carbamate (Preparation 156, 564.76 mg, 1.36 mmol) and triethylamine (0.31 mL, 2.27 mmol) and the reaction was heated to 90° C. for 16 hours. Further 4-nitrophenyl {5-chloro-2-[methyl(methylsulfonyl)amino]benzyl}carbamate (1.5 eq) and TEA (1.5 eq) were added and the reaction was heated to 90° C. for a further 4 hours. The reaction was cooled and concentrated in vacuo. The residue was purified by silica gel column chromatography eluting with 30% EtOAc in hexanes to afford the title compound (365 mg, 42%). MS m/z 944 [M$^{35}$Cl+H]$^+$ The following Preparations (Preparations 62-105) were prepared according to the method described for Preparation 61 using 6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridine 5-oxide (Preparation 114) or 6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridine 5-oxide (Preparation 113) or 6-[4-(benzyloxy)-5-fluoro-2-(2,2,2-trifluoroethyl)phenyl]-3-iodo-1-(tetrahydro-2H-pyran-2-yl)-1H-pyrazolo[4,3-c]pyridine 5-oxide (Preparation 112) and the appropriate aminocarbamate.

| Preparation Number | Name | Data |
|---|---|---|
| 62 | N-ethyl-N-(2-{[(6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridin-4-yl)amino]-methyl}phenyl)ethanesulfonamide | MS m/z 938 [M + H]$^+$<br>Using 4-nitrophenyl {2-[ethyl(ethylsulfonyl)amino]benzyl}carbamate (Preparation 157). |
| 63 | N-ethyl-N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)phenyl]ethanesulfonamide | MS m/z 884 [M + H]$^+$<br>Using 4-nitrophenyl {2-[ethyl(ethylsulfonyl)amino]benzyl}carbamate (Preparation 157). |

| Preparation Number | Name | Data |
|---|---|---|
| 64 | N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)phenyl]-N-methylethanesulfonamide | MS m/z 870 [M + H]+<br>Using 4-nitrophenyl {2-[(ethylsulfonyl)(methyl)amino]benzyl}carbamate (Preparation 159). |
| 65 | 4-(2-{[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}-ethyl)phenol | MS m/z 779 [M + H]+<br>Using 4-nitrophenyl [2-(4-hydroxyphenyl)ethyl]carbamate (Preparation 158). |
| 66 | 6-(2-ethyl-5-fluoro-4-{[2-(trimethylsilyl)ethoxy]methoxy}phenyl)-3-iodo-N-(2-methylpropyl)-1-{[2-(trimethylsilyl)ethoxy]methyl}-1H-pyrazolo[4,3-c]pyridin-4-amine | MS m/z 715 [M + H]+<br>Using 4-nitrophenyl (2-methylpropyl)carbamate (Preparation 160). |
| 67 | N-[4-chloro-2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}-methyl)phenyl]-N-methylmethane sulfonamide | MS m/z 890 [M + H]+<br>Using 4-nitrophenyl {5-chloro-2-[methyl(methylsulfonyl)amino]benzyl}carbamate (Preparation 156). |
| 68 | N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}-methyl)-4-fluorophenyl]-N-methyl-methane sulfonamide | MS m/z 874 [M + H]+<br>Using 4-nitrophenyl {5-fluoro-2-[methyl(methylsulfonyl)amino]benzyl}carbamate (Preparation 161). |
| 69 | N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)-3-fluorophenyl]-N-methylmethane sulfonamide | MS m/z 874 [M + H]+<br>Using 4-nitrophenyl {2-fluoro-6-[methyl(methylsulfonyl)amino]benzyl}carbamate (Preparation 162). |
| 70 | N-ethyl-N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)phenyl]methane sulfon-amide | MS m/z 870 [M + H]+<br>Using 4-nitrophenyl {2-[ethyl(methylsulfonyl)amino]benzyl}carbamate (Preparation 163). |
| 71 | N-(cyclopentylmethyl)-6-(2-ethyl-5-fluoro-4-{[2-(trimethylsilyl)ethoxy]-methoxy}phenyl)-3-iodo-1-{[2-(trimethylsilyl)ethoxy]methyl}-1H-pyrazolo[4,3-c]pyridin-4-amine | MS m/z 743 [M$^{129}$I + H]+<br>Using 4-nitrobenzyl (cyclopentylmethyl)carbamate (Preparation 164). |
| 72 | 6-(5-fluoro-2-(2,2,2-trifluoroethyl)-4-((2-(trimethylsilyl)ethoxy)methoxy)phenyl)-N-methyl-4-((5-methyl-2-(N-methylmethylsulfonamido)benzyl)amino)-1-((2-(trimethylsilyl)ethoxy)methyl)-1H-pyrazolo[4,3-c]pyridine-3-carboxamide | MS m/z 924 [M + H]+<br>Using 4-nitrophenyl {5-methyl-2-[methyl(methylsulfonyl)amino]benzyl}carbamate (Preparation 165). |
| 73 | N-ethyl-N-(2-{[(6-[5-fluoro-2-(2,2,2-trifluoroethyl)-4-{[2-(trimethylsilyl)ethoxy]-methoxy}phenyl]-3-iodo-1-{[2-(trimethylsilyl)ethoxy]methyl}-1H-pyrazolo[4,3-c]pyridin-4-yl)amino]-methyl}phenyl)methane sulfonamide | MS m/z 924 [M + H]+<br>Using 4-nitrophenyl {2-[ethyl(methylsulfonyl)amino]benzyl}carbamate (Preparation 163). |

| Preparation Number | Name | Data |
|---|---|---|
| 74 | N-(2-{[(6-[5-fluoro-2-(2,2,2-trifluoroethyl)-4-{[2-(trimethylsilyl)ethoxy]methoxy}-phenyl]-3-iodo-1-{[2-(trimethylsilyl)-ethoxy]methyl}-1H-pyrazolo[4,3-c]pyridin-4-yl)amino]-methyl}phenyl)-N-methylethane sulfonamide | MS m/z 924 [M + H]$^+$<br>Using 4-nitrophenyl {2-[(ethylsulfonyl)(methyl)amino]benzyl}carbamate (Preparation 159). |
| 75 | N-(4-fluoro-2-{[(6-[5-fluoro-2-(2,2,2-trifluoroethyl)-4-{[2-(trimethylsilyl)-ethoxy]methoxy}phenyl]-3-iodo-1-{[2-(tri-methylsilyl)ethoxy]methyl}-1H-pyrazolo-[4,3-c]pyridin-4-yl)amino]methyl}phenyl)-N-methylmethanesulfonamide | MS m/z 928 [M + H]$^+$<br>Using 4-nitrophenyl {5-fluoro-2-[methyl(methylsulfonyl)amino]benzyl}carbamate (Preparation 161). |
| 76 | N-(3-fluoro-2-{[(6-[5-fluoro-2-(2,2,2-trifluoroethyl)-4-{[2-(trimethylsilyl)-ethoxy]methoxy}phenyl]-3-iodo-1-{[2-(trimethylsilyl)ethoxy]methyl}-1H-pyrazolo[4,3-c]pyridin-4-yl)amino]-methyl}-phenyl)-N-methylmethanesulfonamide | MS m/z 928 [M + H]$^+$<br>Using 4-nitrophenyl {2-fluoro-6-[methyl(methylsulfonyl)amino]benzyl}carbamate (Preparation 162). |
| 77 | N-(cyclopentylmethyl)-6-[5-fluoro-2-(2,2,2-trifluoroethyl)-4-{[2-(trimethyl-silyl)ethoxy]methoxy}phenyl]-3-iodo-1-{[2-(trimethylsilyl)ethoxy]methyl}-1H-pyrazolo[4,3-c]pyridin-4-amine | MS m/z 795 [M + H]$^+$<br>Using 4-nitrobenzyl (cyclopentylmethyl)carbamate (Preparation 164). |
| 78 | 6-[5-fluoro-2-(2,2,2-trifluoroethyl)-4-{[2-(trimethylsilyl)ethoxy]methoxy}phenyl]-3-iodo-N-(2-methylpropyl)-1-{[2-(trimethylsilyl)ethoxy]methyl}-1H-pyrazolo[4,3-c]pyridin-4-amine | MS m/z 771 [M$^{129}$I + H]$^+$<br>Using 4-nitrophenyl (2-methylpropyl)carbamate (Preparation 160). |
| 79 | N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}-methyl)phenyl]-N-methylmethanesulfonamide | MS m/z 856 [M + H]$^+$<br>Using 4-nitrophenyl {2-[methyl(methylsulfonyl)amino]benzyl}carbamate (Preparation 166). |
| 80 | N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}-methyl)-4-methylphenyl]-N-methyl-methanesulfonamide | MS m/z 870 [M + H]$^+$<br>Using 4-nitrophenyl {5-methyl-2-[methyl(methylsulfonyl)amino]benzyl}carbamate (Preparation 165). |
| 81 | N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}-methyl)phenyl]-N-methylbenzene sulfonamide | MS m/z 918 [M + H]$^+$<br>Using 4-nitrophenyl {2-[methyl(phenylsulfonyl)amino]benzyl}carbamate (Preparation 167). |
| 82 | N-[4-(2-{[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}-ethyl)phenyl]benzenesulfonamide | MS m/z 918 [M + H]$^+$<br>4-nitrophenyl (2-{4-[(phenylsulfonyl)amino]phenyl}ethyl)carbamate (Preparation 168) |
| 83 | N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4- | MS m/z 886 [M + H]$^+$<br>4-nitrophenyl {2-[bis(methylsulfonyl)amino]-5-methoxybenzyl}carbamate (Preparation 169). |

-continued

| Preparation Number | Name | Data |
|---|---|---|
| | yl]amino}-methyl)-4-methoxyphenyl]-N-methylmethanesulfon amide | |
| 84 | Racemic N-[2-(1-{[6-(2-ethyl-5-fluoro-4-{[2-(trimethylsilyl)ethoxy]-methoxy}phenyl)-3-iodo-1-{[2-(trimethyl-silyl)ethoxy]methyl}-1H-pyrazolo[4,3-c]pyridin-4-yl]amino}ethyl)phenyl]-N-methylmethanesulfonamide | MS m/z 870 [M + H]$^+$<br>Racemic 4-nitrophenyl (1-{2-[methyl(methylsulfonyl)amino]phenyl}ethyl)carbamate (Preparation 170). |
| 85 | N-(2-{[(6-[5-fluoro-2-(2,2,2-trifluoroethyl)-4-{[2-(trimethylsilyl)ethoxy]-methoxy}-phenyl]-3-iodo-1-{[2-(trimethylsilyl)ethoxy]methyl}-1H-pyrazolo[4,3-c]pyridin-4-yl]amino]methyl}-4-methoxyphenyl)-N-methylmethane-sulfonamide | MS m/z 940 [M + H]$^+$<br>4-nitrophenyl {2-[bis(methylsulfonyl)amino]-5-methoxybenzyl}carbamate (Preparation 169). |
| 86 | N-(2-{[(6-[5-fluoro-2-(2,2,2-trifluoroethyl)-4-{[2-(trimethylsilyl)ethoxy]-methoxy}-phenyl]-3-iodo-1-{[2-(trimethylsilyl)-ethoxy]methyl}-1H-pyrazolo[4,3-c]pyridin-4-yl)amino]methyl}phenyl)-N-methylbenzenesulfonamide | MS m/z 972 [M + H]$^+$<br>Using 4-nitrophenyl {2-[methyl(phenylsulfonyl)amino]benzyl}carbamate (Preparation 167). |
| 87 | N-(2-{[(6-[5-fluoro-2-(2,2,2-trifluoroethyl)-4-{[2-(trimethyl-silyl)ethoxy]methoxy}-phenyl]-3-iodo-1-{[2-(trimethylsilyl)-ethoxy]methyl}-1H-pyrazolo[4,3-c]pyridin-4-yl)amino]methyl}phenyl)-N-[2-(tetra-hydro-2H-pyran-2-yloxy)ethyl]methane-sulfonamide | MS m/z 1024 [M + H]$^+$<br>Using 4-nitrobenzyl (2-{(methylsulfonyl)[2-(tetrahydro-2H-pyran-2-yloxy)ethyl]amino}benzyl)carbamate (Preparation 171). |
| 88 | N-[2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}methyl)-5-methoxyphenyl]-N-methylmethanesulfon amide | MS m/z 886 [M + H]$^+$<br>Using 4-nitrophenyl {4-methoxy-2-[methyl(methylsulfonyl)amino]benzyl}carbamate (Preparation 172). |
| 89 | N-(2-{[(6-[5-fluoro-2-(2,2,2-trifluoroethyl)-4-{[2-(trimethylsilyl)ethoxy]-methoxy}phenyl]-3-iodo-1-{[2-(trimethyl-silyl)ethoxy]methyl}-1H-pyrazolo[4,3-c]pyridin-4-yl)amino]methyl}-5-methoxy-phenyl)-N-methylmethanesulfonamide | MS m/z 940 [M + H]$^+$<br>Using 4-nitrophenyl {4-methoxy-2-[methyl(methylsulfonyl)amino]benzyl}carbamate (Preparation 172). |
| 90 | N-ethyl-N-(2-{[(6-[5-fluoro-2-(2,2,2-trifluoroethyl)-4-{[2-(trimethylsilyl)-ethoxy]methoxy}phenyl]-3-iodo-1-{[2-(trimethylsilyl)ethoxy]methyl}-1H-pyrazolo[4,3-c]pyridin-4-yl)amino]-methyl}-4-methoxyphenyl)benzenesulfonamide | MS m/z 1016 [M + H]$^+$<br>Using 4-nitrophenyl {2-[ethyl(phenylsulfonyl)amino]-5-methoxybenzyl}carbamate (Preparation 176). |
| 91 | benzyl [2-({[6-(2-ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridin-4-yl]amino}-methyl)phenyl]methylcarbamate | MS m/z 912 [M + H]$^+$<br>Using benzyl methyl[2-({[(4-nitrophenoxy)carbonyl]amino}methyl)phenyl]carbamate (Preparation 178). |
| 92 | benzyl (2-{[(6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H- | MS m/z 966 [M + H]$^+$<br>Using benzyl methyl[2-({[(4-nitrophenoxy)carbonyl]amino}methyl)phenyl]carbamate (Preparation 178). |

-continued

| Preparation Number | Name | Data |
|---|---|---|
|  | pyrazolo[4,3-c]pyridin-4-yl)amino]-methyl}-phenyl)methylcarbamate | |
| 93 | N-{3-[({6-[4-(benzyloxy)-5-fluoro-2-(2,2,2-trifluoroethyl)phenyl]-3-iodo-1-(tetrahydro-2H-pyran-2-yl)-1H-pyrazolo-[4,3-c]pyridin-4-yl}amino)-methyl]pyridin-2-yl}-N-methylmethanesulfonamide | MS m/z 825 [M + H]$^+$<br>Using 4-nitrophenyl ({2-[methyl(methylsulfonyl)amino]pyridin-3-yl}methyl)carbamate (Preparation 177). |
| 94 | N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridine-4-yl)amino)methyl)-4-methylphenyl)-N-methylmethane-sulfonamide | MS m/z 838 [M + H]$^+$<br>Using 4-nitrophenyl {5-methyl-2-[methyl(methylsulfonyl)amino]benzyl}carbamate (Preparation 165). |
| 95 | N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo-[4,3-c]pyridine-4-yl)amino)methyl)-phenyl)-N-ethylethanesulfonamide | MS m/z 852 [M + H]$^+$<br>Using 4-nitrophenyl {2-[ethyl(ethylsulfonyl)amino]benzyl}carbamate (Preparation 157). |
| 96 | N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-4-fluorophenyl)-N-ethylmethanesulfonamide | MS m/z 856 [M + H]$^+$<br>Using 4-nitrophenyl {2-[ethyl(methylsulfonyl)amino]-5-fluorobenzyl}carbamate (Preparation 179). |
| 97 | N-(2-(((6-(4-(benzyloxy)-5-chloro-2-(2,2,2-trifluoroethyl)phenyl)-3-iodo-1-(tetrahydro-2H-pyran-2-yl)-1H-pyrazolo[4,3-c]pyridin-4-yl)amino)methyl)-4-fluorophenyl)-N-ethylmethanesulfonamide | MS m/z 871 [M + H]$^+$<br>Using 4-nitrophenyl {2-[ethyl(methylsulfonyl)amino]-5-chlorobenzyl}carbamate (Preparation 180). |
| 98 | N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-phenyl)-N-methylethanesulfonamide | MS m/z 838 [M + H]$^+$<br>Using 4-nitrophenyl {2-[(ethylsulfonyl)(methyl)amino]benzyl} carbamate (Preparation 159). |
| 99 | N-(3-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-5-methylpyridin-2-yl)-N-methylmethane-sulfonamide | MS m/z 839 [M + H]+<br>Using 4-nitrobenzyl ((5-methyl-2-(N-methylmethylsulfonamido)pyridin-3-yl)methyl)carbamate (Preparation 181). |
| 100 | N-(3-(((6-(4-(benzyloxy)-5-fluoro-2-(2,2,2-trifluoroethyl)phenyl)-3-iodo-1-(tetrahydro-2H-pyran-2-yl)-1H-pyrazolo[-4,3-c]pyridin-4-yl)amino)-methyl)-5-methylpyridin-2-yl)-N-ethylmethane-sulfonamide | MS m/z 853 [M + H]$^+$<br>Using 4-nitrophenyl ((2-(N-ethylmethylsulfonamido)-5-methylpyridin-3-yl)methyl)carbamate (Preparation 182). |
| 101 | N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)methyl)-4-chlorophenyl)-N-methylmethane-sulfonamide | MS m/z 858 [M + H]$^+$<br>Using 4-nitrophenyl {5-chloro-2-[methyl(methylsulfonyl)amino]benzyl}carbamate (Preparation 156). |
| 102 | N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)-methyl)-phenyl)-N-ethylmethane-sulfonamide | MS m/z 838 [M + H]$^+$<br>Using 4-nitrophenyl {2-[ethyl(methylsulfonyl)amino]benzyl}carbamate (Preparation 163). |

-continued

| Preparation Number | Name | Data |
|---|---|---|
| 103 | N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo[4,3-c]pyridin-4-yl)amino)-methyl)-4-methoxyphenyl)-N-methylmethanesulfonamide | MS m/z 854 [M + H]$^+$<br>Using 4-nitrophenyl {2-[bis(methylsulfonyl)amino]-5-methoxybenzyl}carbamate (Preparation 169). |
| 104 | N-(2-(((6-(4-(benzyloxy)-5-fluoro-2-(2,2,2-trifluoroethyl)phenyl)-3-iodo-1-(tetrahydro-2H-pyran-2-yl)-1H-pyrazolo-[4,3-c]pyridin-4-yl)amino)-methyl)-4-methyl-phenyl)-N-ethylmethanesulfonamide | MS m/z 852 [M + H]$^+$<br>Using 4-nitrophenyl {2-[ethyl(methylsulfonyl)amino]-5-methylbenzyl}carbamate (Preparation 183). |
| 105 | N-methyl-N-(2-{[(6-[5-fluoro-2-(2,2,2-trifluoroethyl)-4-{[2-(trimethylsilyl)-ethoxy]methoxy}phenyl]-3-iodo-1-{[2-(trimethylsilyl)ethoxy]methyl}-1H-pyrazolo[4,3-c]pyridin-4-yl)amino]-methyl}-phenyl)methane sulfonamide | MS m/z 910 [M + H]$^+$<br>Using 4-nitrophenyl {2-[methyl(methylsulfonyl)amino]benzyl}carbamate (Preparation 166). |

The following Preparations (Preparations 106-109) were prepared according to the method described for Preparation 61 using 6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridine 5-oxide (Preparation 111) or 6-(2-cyclopropyl-5-fluoro-4-methoxyphenyl)-3-iodo-1-{[2-(trimethylsilyl)ethoxy]methyl}-1H-pyrazolo[4,3-c]pyridine 5-oxide (Preparation 115) and the appropriate aminocarbamate.

| Preparation Number | Name | Data |
|---|---|---|
| 106 | N-(2-{[(6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridin-4-yl)amino]-methyl}phenyl)-3-methoxy-N-methylbenzenesulfonamide | MS m/z 886 [M + H]$^+$<br>Using 4-nitrophenyl (2-{[(3-methoxyphenyl)sulfonyl](methyl)amino}benzyl)carbamate (Preparation 173). |
| 107 | N-ethyl-N-(2-{[(6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridin-4-yl)amino]-methyl}-4-methoxyphenyl)-methanesulfonamide | MS m/z 838 [M + H]$^+$<br>Using 4-nitrophenyl {2-[ethyl(methylsulfonyl)amino]-5-methoxybenzyl}carbamate (Preparation 174). |
| 108 | N-(2-{[(6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridin-4-yl)amino]-methyl}-4-methoxyphenyl)-N-methylbenzenesulfonamide | MS m/z 886 [M + H]$^+$<br>Using 4-nitrophenyl {5-methoxy-2-[methyl(phenylsulfonyl)amino]benzyl}carbamate (Preparation 175). |
| 109 | N-[2-({[6-(2-cyclopropyl-5-fluoro-4-methoxyphenyl)-3-iodo-1-{[2-(trimethylsilyl)ethoxy]methyl}-1H-pyrazolo[4,3-c]pyridin-4-yl]amino}methyl)phenyl]-N-methylmethanesulfonamide | MS m/z 752 [M + H]+<br>Using 4-nitrophenyl{2-[methyl(methylsulfonyl)amino]benzyl}carbamate (Preparation 166). |

Preparation 110

6-(2-Cyclopropyl-5-fluoro-4-methoxyphenyl)-N-methyl-4-[({2-[methyl(methylsulfonyl)-amino]pyridin-3-yl}methyl)amino]-1-{[2-(trimethylsilyl)ethoxy]methyl}-1H-pyrazolo[4,3-c]pyridine-3-carboxamide The title compound was prepared according to the method described for Preparation 61 using 6-(2-cyclopropyl-5-fluoro-4-methoxyphenyl)-N-methyl-1-{[2-(trimethylsilyl)ethoxy]-methyl}-1H-pyrazolo[4,3-c]pyridine-3-carboxamide 5-oxide (Preparation 116) and 4-nitrophenyl ({2-[methyl(methylsulfonyl)amino]pyridin-3-yl}methyl)carbamate (Preparation 177). MS m/z 684 [M+H]$^+$

Preparation 111

6-[5-Fluoro-4-methoxy-2-(2,2,2-trifluoroethyl)phenyl]-3-iodo-1-{[2-(trimethylsilyl)ethoxy]methyl}-1H-pyrazolo[4,3-c]pyridine 5-oxide To a stirred solution of 6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridine (Preparation 131, 5.50 g, 9.45 mmol) in dry DCM (550 mL) at 0° C., was added mCPBA (1.79 g, 10.40 mmol) portionwise followed by stirring at room temperature for 16 hours. The reaction was quenched with saturated aqueous sodium bicarbonate solution and saturated aqueous sodium bisulphite solution, the organic extracts separated, dried and purified by silica gel column chromatography eluting with EtOAc to afford the title compound (3.40 g, 50%). $^1$H NMR (400 MHz, DMSO-d$_6$): δ ppm −0.12 (s, 9H), 0.783 (m, 2H), 3.46-3.75 (m, 4H), 3.92 (s, 3H), 5.77 (m, 2H), 7.25 (d, 1H), 7.36 (d, 1H), 8.13 (s, 1H), 8.63 (s, 1H). MS m/z 598 [M+H]$^+$

Preparation 112

6-[4-(Benzyloxy)-5-fluoro-2-(2,2,2-trifluoroethyl)phenyl]-3-iodo-1-(tetrahydro-2H-pyran-2-yl)-1H-pyrazolo[4,3-c]pyridine 5-oxide To a stirred solution of 6-[4-(benzyloxy)-5-fluoro-2-(2,2,2-trifluoroethyl)phenyl]-3-iodo-1-(tetrahydro-2H-pyran-2-yl)-1H-pyrazolo[4,3-c]pyridine (Preparation 132, 17.7 g, 29 mmol) in anhydrous DCM (900 mL) at 0° C. was added mCPBA (7.51 g, 43.5 mmol) and the reaction was stirred warming to room temperature for 18 hours. The reaction was quenched by the addition of saturated sodium sulphite solution (600 mL) followed by saturated aqueous sodium bicarbonate solution (600 mL). The organic layer was collected, washed with water (3×50 mL), brine (2×50 mL), dried over sodium sulfate and concentrated in vacuo. The residue was purified using silica gel column chromatography eluting with 56-80% EtOAc in hexanes to afford the title compound (13 g, 71%). $^1$H NMR (400 MHz, DMSO-d$_6$): δ ppm 1.55-1.67 (m, 3H), 1.98 (m, 2H), 2.33 (m, 1H), 3.51 (m, 1H), 3.68 (m, 2H), 3.88 (m, 1H), 5.28 (s, 2H), 5.90 (m, 1H), 7.30-7.51 (m, 7H), 8.60 (s, 1H), 8.80 (s, 1H).

The following Preparations (Preparations 113-117) were prepared according to the method described for Preparation 111 using the appropriate pyrrolopyridine as described below:

| Preparation Number | Name | Data |
|---|---|---|
| 113 | 6-[5-fluoro-4-methoxy-2-(2,2,2-trifluoroethyl)-phenyl]-3-iodo-1-{[2-(trimethylsilyl)-ethoxy]methyl}-1H-pyrazolo[4,3-c]pyridine 5-oxide | MS m/z 598 [M + H]$^+$<br>$^1$H NMR (400 MHz, DMSO-d$_6$): δ ppm −0.147 (s, 9H), −0.02 (s, 9H), 0.78 (t, 2H), 0.92 (t, 2H), 0.97 (t, 2H), 2.31-2.49 (br m, 2H), 3.55 (br t, 2H), 3.78 (t, 2H), 5.35 (s, 1H), 5.74 (s, 2H), 7.14 (d, 1H), 7.24 (d, 2H), 8.05 (s, 1H), 8.59 (s, 1H).<br>Using 6-(2-ethyl-5-fluoro-4-{[2-(trimethylsilyl)ethoxy]-methoxy}phenyl)-3-iodo-1-{[2-(trimethylsilyl)ethoxy]-methyl}-1H-pyrazolo[4,3-c]pyridine (Preparation 144). |
| 114 | 6-[5-fluoro-2-(2,2,2-trifluoroethyl)-4-{[2-(trimethylsilyl)ethoxy]methoxy}phenyl]-3-iodo-1-{[2-(trimethyl-silyl)ethoxy]methyl}-1H-pyrazolo[4,3-c]pyridine 5-oxide | $^1$H NMR (400 MHz, DMSO-d$_6$): δ ppm −0.11 (s, 9H), 0.00 (s, 9H), 0.78 (t, 2H), 0.89 (t, 2H), 3.52 (m, 3H), 3.60-3.75 (m, 3H), 5.37 (m, 2H), 5.71 (m, 2H), 7.31 (d, 1H), 7.42 (d, 1H), 8.14 (s, 1H), 8.64 (s, 1H).<br>Using 6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridine (Preparation 135). |
| 115 | 6-(2-cyclopropyl-5-fluoro-4-methoxyphenyl)-3-iodo-1-{[2-(trimethylsilyl)ethoxy]-methyl}-1H-pyrazolo-[4,3-c]pyridine 5-oxide | $^1$H NMR (400 MHz, DMSO-d$_6$): δ ppm −0.11 (s, 9H), 0.64 (m, 4H), 0.81 (t, 2H), 1.71 (m, 1H), 3.55 (t, 2H), 3.89 (s, 3H), 5.74 (s, 2H), 6.78 (d, 1H), 7.14 (d, 1H), 8.06 (s, 1H), 8.59 (s, 1H).<br>Using 6-(2-cyclopropyl-5-fluoro-4-methoxyphenyl)-3-iodo-1-{[2-(trimethylsilyl)ethoxy]methyl}-1H-pyrazolo[4,3-c]pyridine (Preparation 136). |
| 116 | 6-(2-cyclopropyl-5-fluoro-4-methoxyphenyl)-3-iodo-1-{[2-(trimethyl-silyl)ethoxy]-methyl}-1H-pyrazolo-[4,3-c]pyridine 5-oxide | MS m/z 487 [M + H]$^+$<br>$^1$H NMR (400 MHz, DMSO-d$_6$): δ ppm −0.10 (s, 9H), 0.64 (m, 4H), 0.83 (t, 2H), 1.74 (m, 1H), 2.83 (d, 3H), 3.58 (t, 2H), 3.89 (s, 3H), 5.80 (s, 2H), 6.77 (d, 1H), 7.13 (d, 1H), 8.14 (s, 1H), 8.64 (m, 1H), 8.95 (s, 1H).<br>Using 6-(2-cyclopropyl-5-fluoro-4-methoxyphenyl)-N-methyl-1-{[2- |

| Preparation Number | Name | Data |
|---|---|---|
| 117 | 6-[5-fluoro-2-(2,2,2-tri-fluoro-ethyl)-4-{[2-(tri-methylsilyl)-ethoxy]-methoxy}phenyl]-N-methyl-1-{[2-(trimethylsilyl)-ethoxy]methyl}-1H-pyrazolo[4,3-c]pyridine-3-carboxamide-5-oxide | (trimethylsilyl)ethoxy]methyl}-1H-pyrazolo[4,3-c]pyridine-3-carboxamide (Preparation 128). MS m/z 645 [M + H]$^+$ Using 6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 130). |

Preparation 118

4-Chloro-6-[5-fluoro-4-methoxy-2-(2,2,2-trifluoro-ethyl)phenyl]-N-methyl-1-{[2-(trimethylsilyl)ethoxy]methyl}-1H-pyrazolo[4,3-c]pyridine-3-carboxamide Step 1

To a solution of 6-[5-fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide (Preparation 125, 2 g, 3.90 mmol) in anhydrous DCM (30 mL) was added mCPBA (1.2 g, 4.29 mmol) at 0° C. and the reaction was stirred at room temperature for 18 hours. The reaction was quenched by the addition of saturated aqueous sodium bisulfite and sodium bicarbonate solutions and extracted into DCM. The organic layer was collected, dried over sodium sulfate and concentrated in vacuo. The residue was purified using silica gel column chromatography eluting with 15% MeOH in DCM to afford the intermediate N-oxide.

Step 2

This intermediate was dissolved in DMF (20 mL) and oxalyl chloride (2.43 mL, 28.38 mmol) was added at 0° C. with stirring for 1 hour. The reaction was quenched by the addition of water and extracted into EtOAc. The organic layer was collected, dried over sodium sulfate and concentrated in vacuo. The residue was purified using silica gel column chromatography eluting with 17% EtOAc in DCM to afford the title compound (400 mg, 26%). $^1$H NMR (400 MHz, DMSO-d$_6$): δ ppm −0.11 (s, 9H), 0.82 (m, 2H), 2.85 (d, 3H), 3.57 (t, 2H), 3.92 (s, 3H), 4.10 (q, 2H), 5.85 (s, 2H), 7.37 (d, 1H), 7.49 (d, 1H), 8.11 (s, 1H), 8.69 (m, 1H). MS m/z 547 [M$^{35}$Cl+H]$^+$ Preparation 119

4-Chloro-6-[5-fluoro-4-methoxy-2-(2,2,2-trifluoro-ethyl)phenyl]-N-ethyl-1-{[2-(trimethylsilyl)ethoxy]methyl}-1H-pyrazolo[4,3-c]pyridine-3-carboxamide The title compound was prepared according to the method described for Preparation 118 using N-ethyl-6-[5-fluoro-4-methoxy-2-(2,2,2-trifluoroethyl)phenyl]-1-{[2-(trimethylsilyl)ethoxy]methyl}-1H-pyrazolo[4,3-c]pyridine-3-carboxamide (Preparation 129).

MS m/z 561 [M+H]$^+$

Preparation 120

N-tert-Butyl-4-chloro-6-{5-fluoro-2-(2,2,2-trifluoro-ethyl)-4-{[2-(trimethylsilyl)ethoxy}-methoxy}phenyl]-1-{[2-(trimethylsilyl)ethoxy]methyl}-1H-pyrazolo[4,3-c]pyridine-3-carboxamide The title compound may be prepared according to the method described for Preparation 118, Step 1 using N-tert-butyl-6-[5-fluoro-2-(2,2,2-trifluoroethyl)-4-{[2-(trimethyl-silyl)ethoxy]methoxy}phenyl]-1-{[2-(trimethylsilyl)ethoxy]methyl}-1H-pyrazolo[4,3-c]pyridine-3-carboxamide (Preparation 127). The N-oxide intermediate (1.3 g, 1.94 mmol) was dissolved in DCM (150 mL) with triethylamine (0.35 mL, 2.52 mmol) and POCl$_3$ (0.23 mL, 2.52 mmol) was added at 0° C. The reaction was stirred for 1 hour at 10° C. before quenching with saturated aqueous sodium bicarbonate solution and extraction with DCM. The organic layer was collected, dried over sodium sulfate and concentrated in vacuo. The residue was purified using silica gel column chromatography eluting with 15% EtOAc in DCM to afford a yellow oil (530 mg, 39%). $^1$H NMR (400 MHz, DMSO-d$_6$): δ ppm −0.08 (s, 9H), −0.01 (s, 9H), 0.84 (t, 2H), 0.90 (t, 2H), 1.41 (s, 9H), 3.58 (t, 2H), 3.77 (t, 2H), 4.07 (m, 2H), 5.37 (s, 2H), 5.84 (s, 2H), 7.46 (m, 2H), 8.08 (s, 1H), 8.33 (s, 1H). MS m/z 705 [M+H]$^+$ Preparation 121

4-Chloro-N-(2,4-dimethoxybenzyl)-6-[5-fluoro-4-methoxy-2-(2,2,2-trifluoroethyl)-phenyl]-1-{[2-(trimethylsilyl)ethoxy]methyl}-1H-pyrazolo[4,3-c]pyridine-3-carboxamide The title compound may be prepared according to the method described for Preparation 118 using N-(2,4-dimethoxybenzyl)-6-[5-fluoro-4-methoxy-2-(2,2,2-trifluoroethyl)phenyl]-1-{[2-(trimethylsilyl)-ethoxy]methyl}-1H-pyrazolo[4,3-c]pyridine-3-carboxamide (Preparation 126). $^1$H NMR (400 MHz, DMSO-d$_6$): δ ppm −0.10 (s, 9H), 0.85 (t, 2H), 3.58 (t, 2H), 3.75 (s, 3H), 3.81 (s, 3H), 3.92 (s, 3H), 4.09 (q, 2H), 4.43 (m, 2H), 5.85 (s, 2H), 6.50 (m, 1H), 6.58 (s, 1H), 7.24 (d, 1H), 7.35 (d, 1H), 7.49 (d, 1H), 8.11 (s, 1H), 8.97 (m, 1H). MS m/z 683 [M+H]$^+$

Preparation 122

4-Chloro-6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide The title compound may be prepared according to the method described for Preparation 118 using 6-[5-fluoro-2-(2,2,2-trifluoroethyl)-4-{[2-(trimethylsilyl)ethoxy]methoxy}phenyl]-N-methyl-1-{[2-(trimethylsilyl)ethoxy]methyl}-1H-pyrazolo[4,3-c]pyridine-3-carboxamide (Preparation 130). The N-oxide intermediate (800 mg, 1.24 mmol) was dissolved in DCM (7 mL) and a solution of POCl$_3$ (0.148 mL, 1.6 mmol) in DCM (3 mL) was added dropwise at 0° C. The reaction was stirred for 30 minutes before the addition of water and extraction into DCM. The organic layer was collected, dried over sodium sulfate and concentrated in vacuo. The residue was purified using silica gel column chromatography eluting with 14% EtOAc in DCM to afford the title compound as a yellow solid (600 mg, 73%).
$^1$H NMR (400 MHz, DMSO-d$_6$): δ ppm −0.11 (s, 9H), −0.01 (s, 9H), 0.82 (t, 2H), 0.90 (t, 3H), 2.85 (d, 3H), 3.57 (t, 2H), 3.77 (t, 2H), 5.37 (s, 2H), 5.85 (s, 2H), 7.43-7.51 (m, 2H), 8.11 (s, 1H), 8.67 (m, 1H). MS m/z 629 [M+H]$^+$

Preparation 123

6-(4-(Benzyloxy)-5-fluoro-2-(2,2,2-trifluoroethyl)phenyl)-N-(tert-butyl)-4-chloro-1-(tetrahydro-2H-pyran-2-yl)-1H-pyrazolo[4,3-c]pyridine-3-carboxamide To a solution of 6-(4-(benzyloxy)-5-fluoro-2-(2,2,2-trifluoroethyl)phenyl)-N-(tert-butyl)-1-(tetrahydro-2H-pyran-2-yl)-1H-pyrazolo[4,3-c]pyridine-3-carboxamide (Preparation 124, 3.80 g, 6.5 mmol) in anhydrous DCM (250 mL) was added mCPBA (1.68 g, 9.75 mol) at 0° C. and the reaction was stirred at room temperature for 18 hours. The reaction was quenched by the addition of saturated aqueous sodium sulphite solution and saturated aqueous sodium bicarbonate solution and extracted into EtOAc. The organic layer was collected, dried over sodium sulfate and concentrated in vacuo. The residue was purified using silica gel column chromatography eluting with EtOAc to afford the intermediate N-oxide, that was dissolved in DCM (300 mL). To the solution was added triethylamine (1.07 mL, 7.74 mmol) followed by POCl$_3$ (0.62 mL, 6.71 mmol) at 0° C. The reaction was stirred at 10° C. for 1 hour before the addition of ice-water. The reaction was extracted into DCM, the organic layer was collected, dried over sodium sulfate and concentrated in vacuo to afford the title compound as the desired chloro isomer confirmed by nOe irradiation of the remaining pyridyl proton.
$^1$H NMR (400 MHz, DMSO-d$_6$): δ ppm 1.41 (s, 9H), 1.56-1.80 (m, 3H), 1.95-2.04 (m, 2H), 2.37 (m, 1H), 3.76 (m, 1H), 3.91-4.18 (m, 3H), 5.27 (s, 2H), 6.01 (m, 1H), 7.34-7.55 (m, 7H), 8.03 (s, 1H), 8.38 (br s, 1H). MS m/z 619 [M+H]$^+$

Preparation 124

6-(4-(Benzyloxy)-5-fluoro-2-(2,2,2-trifluoroethyl)phenyl)-N-(tert-butyl)-1-(tetrahydro-2H-pyran-2-yl)-1H-pyrazolo[4,3-c]pyridine-3-carboxamide To a solution of 6-[4-(benzyloxy)-5-fluoro-2-(2,2,2-trifluoroethyl)phenyl]-3-iodo-1-(tetrahydro-2H-pyran-2-yl)-1H-pyrazolo[4,3-c]pyridine (Preparation 132, 8 g, 13 mmol) in THF (30 mL) and tert-butylamine (16 mL) was added molybdenum hexacarbonyl (3.48 g, 13 mmol), DBU (5.86 mL, 39.25 mmol) and Pd(OAc)$_2$ (180 mg, 1.3 mmol). The reaction was heated in a sealed tube at 100° C. for 1 hour. The reaction was cooled, concentrated in vacuo and purified using silica gel column chromatography to afford the title compound. $^1$H NMR (400 MHz, DMSO-d$_6$): δ ppm 1.46 (s, 9H), 1.60-1.74 (m, 4H), 1.97-2.01 (m, 2H), 3.76-3.82 (m, 1H), 3.94-4.22 (m, 3H), 5.27 (s, 2H), 6.03 (m, 1H), 7.36-7.52 (m, 7H), 7.60 (m, 1H), 8.01 (m, 1H), 9.41 (s, 1H). MS m/z 585 [M+H]$^+$

Preparation 125

6-[5-Fluoro-4-methoxy-2-(2,2,2-trifluoroethyl)phenyl]-N-methyl-1-{[2-(trimethylsilyl)ethoxy]methyl}-1H-pyrazolo[4,3-c]pyridine-3-carboxamide To a solution of 6-[5-fluoro-4-methoxy-2-(2,2,2-trifluoroethyl)phenyl]-3-iodo-1-{([2-(trimethylsilyl)ethoxy]methyl}-1H-pyrazolo[4,3-c]pyridine (Preparation 131, 3.4 g, 5.85 mmol) and 2M methylamine in THF (30 mL) was added palladium acetate (92 mg, 0.41 mmol), DBU (2.62 mL, 17.54 mmol) and molybdenum hexacarbonyl (1.55 g, 5.85 mmol). The reaction was heated in a sealed tube at 100° C. for 60 minutes before concentrating in vacuo. The residue was diluted with EtOAc, filtered through celite and concentrated in vacuo. The residue was purified using silica gel column chromatography eluting with 30% EtOAc in hexanes to afford the title compound as a yellow solid (2 g, 67%). $^1$H NMR (400 MHz, DMSO-d$_6$): δ ppm −0.15 (s, 9H), 0.80 (t, 2H), 2.85 (d, 3H), 3.56 (t, 2H), 3.92 (s, 3H), 4.18 (q, 2H), 5.87 (s, 2H), 7.33 (d, 1H), 7.41 (d, 1H), 8.07 (s, 1H), 8.66 (m, 1H), 9.45 (s, 1H). MS m/z 513 [M+H]$^+$ The following Preparations (Preparations 126-129) were prepared according to the method described for Preparation 125 using the appropriate pyrrolopyridine and amine as described below:

| Preparation Number | Name | Data |
|---|---|---|
| 126 | N-(2,4-dimethoxybenzyl)-6-[5-fluoro-4-methoxy-2-(2,2,2-trifluoroethyl)phenyl]-1-{[2-(trimethylsilyl)ethoxy]methyl}-1H-pyrazolo[4,3-c]pyridine-3-carboxamide | MS m/z 649 [M + H]$^+$ Using 6-[5-fluoro-4-methoxy-2-(2,2,2-trifluoroethyl)phenyl]-3-iodo-1-{[2-(trimethylsilyl)ethoxy]methyl}-1H-pyrazolo[4,3-c]pyridine (Preparation 131) and 2,4-dimethoxybenzylamine. |

| Preparation Number | Name | Data |
|---|---|---|
| 127 | N-tert-butyl-6-[5-fluoro-2-(2,2,2-trifluoroethyl)-4-{[2-(trimethylsilyl)-ethoxy]methoxy}phenyl]-1-{[2-(trimethylsilyl)-ethoxy]methyl}-1H-pyrazolo[4,3-c]pyridine-3-carboxamide | MS m/z 671 [M + H]$^+$<br>$^1$H NMR (400 MHz, DMSO-d$_6$): δ ppm −0.13 (s, 9H), −0.01 (s, 9H), 0.81 (t, 2H), 0.91 (t, 2H), 1.45 (s, 9H), 3.58 (t, 2H), 3.80 (t, 2H), 4.03 (m, 2H), 5.36 (s, 2H), 6.02 (s, 2H), 7.43 (m, 2H), 7.66 (s, 1H), 8.08 (s, 1H).<br>Using 6-[5-fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridine (Preparation 135) and tert-butylamine. |
| 128 | 6-(2-cyclopropyl-5-fluoro-4-methoxyphenyl)-N-methyl-1-{[2-(trimethylsilyl)ethoxy]methyl}-1H-pyrazolo[4,3-c]pyridine-3-carboxamide | Taken on directly to the next step.<br>Using 6-(2-cyclopropyl-5-fluoro-4-methoxyphenyl)-3-iodo-1-{[2-(trimethylsilyl)-ethoxy]methyl}-1H-pyrazolo[4,3-c]pyridine (Preparation 136) and methylamine. |
| 129 | N-ethyl-6-[5-fluoro-4-methoxy-2-(2,2,2-trifluoroethyl)phenyl]-1-{[2-(trimethylsilyl)ethoxy]methyl}-1H-pyrazolo[4,3-c]pyridine-3-carboxamide | $^1$H NMR (400 MHz, DMSO-d$_6$): δ ppm −0.14 (s, 9H), 0.80 (t, 2H), 1.17 (t, 3H), 3.37 (m, 2H), 3.56 (t, 2H), 3.89 (s, 3H), 4.18 (m, 2H), 5.87 (s, 2H), 7.33 (d, 1H), 7.44 (d, 1H), 8.08 (s, 1H), 8.72 (m, 1H), 9.45 (s, 1H).<br>Using 6-[5-fluoro-4-methoxy-2-(2,2,2-trifluoroethyl)phenyl]-3-iodo-1-{[2-(trimethylsilyl)-ethoxy]methyl}-1H-pyrazolo[4,3-c]pyridine (Preparation 131) with ethylamine. |

Preparation 130

6-[5-Fluoro-2-(2,2,2-trifluoroethyl)-4-{[2-(trimethylsilyl)ethoxy]methyl}phenyl]-N-methyl-1-{[2-(trimethylsilyl)ethoxy]methyl}-1H-pyrazolo[4,3-c]pyridine-3-carboxamide The title compound may be prepared according to the method described for Preparation 18 using 6-[5-fluoro-2-(2,2,2-trifluoroethyl)-4-{[2-(trimethylsilyl)ethoxy]-methoxy}phenyl]-3-iodo-1-{[2-(trimethylsilyl)ethoxy]methyl}-1H-pyrazolo[4,3-c]pyridine (Preparation 135) with methylamine. $^1$H NMR (400 MHz, DMSO-d$_6$): δ ppm −0.15 (s, 9H), −0.01 (s, 9H), 0.80 (t, 2H), 0.91 (t, 2H), 2.85 (d, 3H), 3.58 (t, 2H), 3.78 (t, 2H), 4.10 (q, 2H), 5.36 (s, 2H), 5.87 (s, 2H), 7.43 (m, 2H), 8.08 (s, 1H), 8.64 (m, 1H), 9.46 (s, 1H). MS m/z 629 [M+H]$^+$ Preparation 131

6-[5-Fluoro-4-methoxy-2-(2,2,2-trifluoroethyl)phenyl]-3-iodo-1-{[2-(trimethylsilyl)ethoxy]methyl}-1H-pyrazolo[4,3-c]pyridine To a suspension of NaH (0.59 g, 24.93 mmol) in dry DMF (100 mL) at 0° C. was added a solution of 6-[5-fluoro-4-methoxy-2-(2,2,2-trifluoroethyl)phenyl]-3-iodo-1H-pyrazolo[4,3-c]pyridine (Preparation 137, 7.50 g, 16.62 mmol) in DMF (100 mL). The reaction was stirred for 30 minutes before the addition of SEM-chloride (4.42 mL, 24.93 mmol) drop-wise. The reaction was stirred for 1 hour before being quenched with ice-water and extracted into EtOAc. The organic layer was washed with water, brine, dried over sodium sulfate and concentrated in vacuo. The crude residue was purified using silica gel column chromatography to afford the title compound as a yellow liquid (5.50 g, 47%). $^1$H NMR (400 MHz, DMSO-d$_6$): δ ppm −0.15 (s, 9H), 0.76 (m, 2H), 3.51 (m, 2H), 3.91 (s, 3H), 4.11 (q, 2H), 5.81 (s, 2H), 7.33 (d, 1H), 7.42 (d, 1H), 7.99 (s, 1H), 8.85 (s, 1H). MS m/z 582 [M+H]$^+$ Preparation 132

6-[4-(Benzyloxy)-5-fluoro-2-(2,2,2-trifluoroethyl)phenyl]-3-iodo-1-(tetrahydro-2H-pyran-2-yl)-1H-pyrazolo[4,3-c]pyridine To a solution of 2-fluoro-4-[3-iodo-1-(tetrahydro-2H-pyran-2-yl)-1H-pyrazolo[4,3-c]pyridin-6-yl]-5-(2,2,2-trifluoroethyl)phenol (Preparation 133, 21.8 g, 41.8 mmol) in acetone (200 mL) was treated with benzyl bromide (7.5 mL, 62.7 mmol) and potassium carbonate (14.4 g, 104 mmol) and the reaction was heated to reflux. The reaction was cooled, filtered, the filtrate collected and concentrated in vacuo. The residue was taken up in EtOAc, washed with water, brine, dried over sodium sulfate and concentrated in vacuo. The residue was purified using silica gel column chromatography eluting with 18% EtOAc in hexane to afford the title compound (23 g, 90%).
$^1$H NMR (400 MHz, DMSO-d$_6$): δ ppm 1.57-1.71 (m, 3H), 2.01 (m, 2H), 2.37 (m, 1H), 3.74 (m, 1H), 3.91 (m, 1H), 4.03 (m, 1H), 4.16 (m, 1H), 5.27 (s, 2H), 5.97 (m, 1H), 7.34-7.51 (m, 7H), 7.95 (s, 1H), 8.83 (s, 1H). MS m/z 612 [M+H]$^+$ Preparation 133

2-Fluoro-4-[3-iodo-1-(tetrahydro-2H-pyran-2-yl)-1H-pyrazolo[4,3-c]pyridin-6-yl]-5-(2,2,2-trifluoroethyl)phenol To a solution of 2-fluoro-4-(3-iodo-1H-pyrazolo[4,3-c]pyridin-6-yl)-5-(2,2,2-trifluoroethyl)phenol (Preparation 134, 40.8 g, 93 mmol) in DMF (500 mL) was added dihydropyran (17 mL, 187 mmol) and PTSA (7.10 g, 37 mmol) and the reaction was heated to 80° C. for 18 hours. Additional dihydropyran (2 eq) and PTSA (0.4 eq) were added and the reaction continued at this temperature for a further 2 hours followed by cooling to room temperature for 18 hours. The reaction was quenched by the addition of saturated aqueous sodium bicarbonate solution dropwise, and concentrated in vacuo. The aqueous residue was extracted into EtOAc, washed with water, brine, dried over sodium sulfate and concentrated in vacuo. The residue was purified using silica gel column chromatography eluting with 17-20% EtOAc in hexanes to afford the title compound as a yellow solid (22 g, 45%). $^1$H NMR (400 MHz, DMSO-d$_6$): δ ppm 1.44-1.70 (m, 3H), 2.02 (m, 2H), 2.37 (m, 1H), 3.75 (m, 1H), 3.88-4.06 (m, 2H), 4.15 (m, 1H), 5.97 (m, 1H), 7.10 (d, 1H), 7.40 (d, 1H), 7.91 (s, 1H), 8.81 (s, 1H), 10.31 (s, 1H). MS m/z 522 [M+H]$^+$ Preparation 134

2-Fluoro-4-(3-iodo-1H-pyrazolo[4,3-c]pyridin-6-yl)-5-(2,2,2-trifluoroethyl)phenol A solution of 6-[5-fluoro-4-methoxy-2-(2,2,2-trifluoroethyl)phenyl]-3-iodo-1H-pyrazolo[4,3-c]pyridine (Preparation 137, 44 g, 97 mmol) in DCM (350 mL) was treated with boron tribromide (46 mL, 488 mmol) at 0° C., and the reaction was allowed to stir warming to room temperature over 5 hours. The reaction was concentrated in vacuo and treated with saturated aqueous sodium bicarbonate solution. The resulting precipitate was filtered and dried under vacuum to afford the title compound as a white solid (41 g, 97%). $^1$H NMR (400 MHz, DMSO-d$_6$): δ ppm 4.00 (q, 2H), 7.09 (d, 1H), 7.37 (d, 1H), 7.58 (s, 1H), 8.81 (s, 1H), 10.26 (s, 1H), 13.95 (s, 1H). MS m/z 438 [M+H]$^+$ Preparation 135

6-[5-Fluoro-2-(2,2,2-trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridine The title compound was prepared according to the method described for Preparation 131 using 6-[4-{[tert-butyl(dimethyl)silyl]oxy}-5-fluoro-2-(2,2,2-trifluoroethyl)phenyl]-3-iodo-1H-pyrazolo[4,3-c]pyridine (Preparation 138). The reaction conditions cause deprotection of the TBDMS ether and subsequent re-protection with SEM-chloride. $^1$H NMR (400 MHz, DMSO-d$_6$): δ ppm −0.14 (s, 9H), −0.03 (s, 9H), 0.78 (t, 2H), 0.90 (t, 2H), 3.56 (t, 2H), 3.77 (t, 2H), 4.09 (m, 2H), 5.36 (s, 2H), 5.81 (s, 2H), 7.42 (m, 2H), 8.01 (s, 1H), 8.86 (s, 1H). MS m/z 698 [M+H]$^+$ Preparation 136

6-(2-Cyclopropyl-5-fluoro-4-methoxyphenyl)-3-iodo-1-{[2-(trimethylsilyl)ethoxy]methyl}-1H-pyrazolo[4,3-c]pyridine The title compound was prepared according to the method described for Preparation 131 using 6-(2-cyclopropyl-5-fluoro-4-methoxyphenyl)-3-iodo-1H-pyrazolo[4,3-c]pyridine (Preparation 139). Taken on to the next step without further purification.

Preparation 137

6-[5-Fluoro-4-methoxy-2-(2,2,2-trifluoroethyl)phenyl]-3-iodo-1H-pyrazolo[4,3-c]pyridine To a solution of 6-[5-fluoro-4-methoxy-2-(2,2,2-trifluoroethyl)phenyl]-1H-pyrazolo[4,3-c]pyridine (Preparation 140, 11.20 g, 34.43 mmol) in DMF (200 mL) at 0° C. was added N-iodosuccinimide (9.29 g, 41.32 mmol). The reaction was stirred at room temperature for 16 hours. The reaction was diluted with ethyl acetate, washed with saturated aqueous sodium bicarbonate solution and saturated aqueous sodium thiosulfate solution. The organic extracts were separated, washed with brine, dried over sodium sulfate and concentrated in vacuo. The residue was purified by silica gel column chromatography eluting with 22% EtOAc in hexanes to afford the title compound as a white solid (7.50 g, 48%). $^1$H NMR (400 MHz, DMSO-d$_6$): δ ppm 3.91 (s, 3H), 4.11 (q, 2H), 7.32 (d, 1H), 7.46 (d, 1H), 7.62 (s, 1H), 8.83 (s, 1H), 13.90 (br s, 1H). MS m/z 452 [M+H]$^+$ Preparation 138

6-[4-{[tert-Butyl(dimethyl)silyl]oxy}-5-fluoro-2-(2,2,2-trifluoroethyl)phenyl]-3-iodo-1H-pyrazolo[4,3-c]pyridine The title compound was prepared according to the method described for Preparation 137 using 6-[4-{[tert-butyl(dimethyl)silyl]oxy}-5-fluoro-2-(2,2,2-trifluoroethyl)phenyl]-1H-pyrazolo-[4,3-c]pyridine (Preparation 141). $^1$H NMR (400 MHz, DMSO-d$_6$): δ ppm 0.24 (s, 6H), 0.99 (s, 9H), 4.08 (m, 2H), 7.16 (d, 1H), 7.46 (d, 1H), 7.65 (s, 1H), 8.83 (s, 1H), 13.99 (br s, 1H). MS m/z 552 [M+H]$^+$ Preparation 139

6-(2-Cyclopropyl-5-fluoro-4-methoxyphenyl)-3-iodo-1H-pyrazolo[4,3-c]pyridine

The title compound was prepared according to the method described for Preparation 137 using 6-(2-cyclopropyl-5-fluoro-4-methoxyphenyl)-1H-pyrazolo[4,3-c]pyridine (Preparation 143). The residue was triturated with pentane and ether. $^1$H NMR (400 MHz, DMSO-d$_6$): δ ppm 0.69 (m, 2H), 0.80 (m, 2H), 2.09 (m, 1H), 3.88 (s, 3H), 6.73 (d, 1H), 7.30 (d, 1H), 7.65 (s, 1H), 8.83 (s, 1H), 13.88 (s, 1H).

Preparation 140

6-[5-Fluoro-4-methoxy-2-(2,2,2-trifluoroethyl)phenyl]-1H-pyrazolo[4,3-c]pyridine To a solution of 6-[5-fluoro-4-methoxy-2-(2,2,2-trifluoroethyl)phenyl]-1-(tetrahydro-2H-pyran-2-yl)-1H-pyrazolo[4,3-c]pyridine (Preparation 145, 14.50 g, 35.41 mmol) in dioxane (150 mL) was added 4M HCl in dioxane (60 mL). The reaction was stirred at room temperature for 16 hours before concentrating in vacuo. The residue was partitioned between EtOAc and saturated aqueous sodium bicarbonate solution. The organic layer was collected, washed with brine, dried over sodium sulfate and concentrated in vacuo to afford the title compound that was used directly in the next reaction (11.20 g, 97%). MS m/z 326 [M+H]$^+$

Preparation 141

6-[4-{[tert-Butyl(dimethyl)silyl]oxy}-5-fluoro-2-(2,2,2-trifluoroethyl)phenyl]-1H-pyrazolo[4,3-c]pyridine To a solution of 2-fluoro-4-(1H-pyrazolo[4,3-c]sulfate-6-yl)-5-(2,2,2-trifluoroethyl)phenol (Preparation 142, 13 g, 41.76 mmol) and 2,6 lutidine (7.29 mL, 62.65 mmol) in anhydrous THF (500 mL) at 0° C. was added TBDMS-triflate (11.52 mL, 50.12 mmol) and the reaction was stirred at room temperature for 18 hours. The reaction was concentrated in vacuo and partitioned between water and ethyl acetate. The organic layer was collected, washed with brine, dried over sodium sulfate and concentrated in vacuo. The residue was purified by silica gel column chromatography eluting with 20% EtOAc in hexanes to afford the title compound as a white solid (11 g, 62%). $^1$H NMR (400 MHz, DMSO-d$_6$): δ ppm 0.24 (s, 6H), 0.99 (s, 9H), 4.09 (m, 2H), 7.17 (d, 1H), 7.45 (d, 1H), 7.63 (s, 1H), 8.33 (s, 1H), 9.15 (s, 1H), 13.57 (br s, 1H).

Preparation 142

2-Fluoro-4-(1H-pyrazolo[4,3-c]pyridin-6-yl)-5-(2,2,2-trifluoroethyl)phenol

6-[5-fluoro-2-(2,2,2-trifluoroethyl)-4-{[2-(trimethylsilyl)ethoxy]methoxy}phenyl]-1-(tetrahydro-2H-pyran-2-yl)-1H-pyrazolo[4,3-c]pyridine (Preparation 146, 24 g, 45.66 mmol) was dissolved in TFA (48 mL) at 0° C. and stirred for 1 hour. The reaction was concentrated in vacuo and taken up in MeOH. Ethylene diamine (2.4 mL) was added at 0° C. and the reaction stirred for 20 minutes. The reaction was concentrated in vacuo and partitioned between IPA:DCM (1:9) and water. The organic extract was dried with sodium sulfate and concentrated in vacuo. The residue was purified by silica gel column chromatography to afford the title compound as an off-white solid (13 g, 91%). $^1$H NMR (400 M$_3$Hz, DMSO-d$_6$): δ ppm 3.98 (m, 2H), 7.08 (d, 1H), 7.33 (d, 1H), 7.57 (s, 1H), 8.32 (s, 1H), 9.14 (s, 1H), 10.21 (brs, 1H), 13.52 (brs, 1H).

Preparation 143

6-(2-Cyclopropyl-5-fluoro-4-methoxyphenyl)-1H-pyrazolo[4,3-c]pyridine

To a solution of 6-(2-cyclopropyl-5-fluoro-4-methoxyphenyl)-1-(tetrahydro-2H-pyran-2-yl)-1H-pyrazolo[4,3-c]pyridine (Preparation 148, 5 g, 13.61 mmol) in MeOH (25 mL) was added concentrated HCl (3.5 mL) at 0° C. and the reaction was stirred for 16 hours. The reaction was concentrated in vacuo and partitioned between saturated aqueous NaHCO$_3$ solution and 25% IPA in DCM. The organic layer was collected, dried over sodium sulfate and concentrated in vacuo to afford the title compound as a white solid (3.3 g, 85%). $^1$H NMR (400 MHz, DMSO-d$_6$): δ ppm 0.71 (m, 2H), 0.81 (m, 2H), 2.12 (m, 1H), 3.88 (s, 3H), 6.71 (d, 1H), 7.30 (d, 1H), 7.66 (s, 1H), 8.32 (s, 1H), 9.16 (s, 1H), 13.46 (s, 1H). MS m/z 284 [M+H]$^+$

Preparation 144

6-(2-Ethyl-5-fluoro-4-{[2-(trimethylsilyl)ethoxy]methoxy}phenyl)-3-iodo-1-{[2-(trimethylsilyl)ethoxy]methyl}-1H-pyrazolo[4,3-c]pyridine The title compound was prepared according to the methods described by Preparations 142, 141, 137 and 131 using 6-[2-ethyl-5-fluoro-4-{[2-(trimethylsilyl)ethoxy]methoxy}phenyl]-1-(tetrahydro-2H-pyran-2-yl)-1H-pyrazolo[4,3-c]pyridine (Preparation 147). $^1$H NMR (400 MHz, DMSO-d$_6$): δ ppm −0.13 (s, 9H), −0.01 (s, 9H), 0.79 (t, 2H), 0.91 (t, 2H), 0.99 (t, 2H), 2.66 (q, 2H), 3.55 (t, 2H), 3.78 (t, 2H), 5.35 (s, 2H), 5.80 (s, 2H), 7.22 (m, 2H), 7.88 (s, 1H), 8.84 (s, 1H).

Preparation 145

6-[5-Fluoro-4-methoxy-2-(2,2,2-trifluoroethyl)phenyl]-1-(tetrahydro-2H-pyran-2-yl)-1H-pyrazolo[4,3-c]pyridine A solution of palladium acetate (0.47 g, 2.10 mmol) and S-Phos (0.86 g, 2.10 mmol) in ethanol (75 mL) was heated at 50° C. for 45 minutes after purging with nitrogen (Solution A). Meanwhile a solution of 6-chloro-1-(tetrahydro-2H-pyran-2-yl)-1H-pyrazolo[4,3-c]pyridine (Preparation 149, 10 g, 42.07 mmol) in ethanol (75 mL) was treated with 2-[5-fluoro-4-methoxy-2-(2,2,2-trifluoroethyl)phenyl]-4,4,5,5-tetramethyl-1,3,2-dioxaborolane (WO20131014567A1, 21.08 g, 63.10 mmol) and an aqueous solution of potassium phosphate (17.86 g, 84.14 mmol) in water (50 mL) followed by purging with nitrogen for 10 minutes (Solution B). Solution A was added to Solution B and the reaction heated to 80° C. for 18 hours before cooling and concentrating in vacuo. The residue was partitioned between ethyl acetate and water, the organic extracts collected, washed with brine, dried over sodium sulfate and concentrated in vacuo. The residue was purified using silica gel column chromatography eluting with 15% EtOAc in hexanes to afford the title compound as a yellow liquid (14.10 g, 82%). $^1$H NMR (400 MHz, DMSO-ds): δ ppm 1.58 (m, 2H), 1.73 (m, 1H), 1.99 (m, 2H), 2.42 (m, 1H), 3.78 (m, 1H), 3.92 (m, 4H), 4.09 (m, 1H), 4.26 (m, 1H), 5.98 (d, 1H), 7.33 (d, 1H), 7.48 (d, 1H), 7.92 (s, 1H), 8.37 (s, 1H), 9.15 (s, 1H). MS m/z 410 [M+H]$^+$

Preparation 146

6-[5-Fluoro-2-(2,2,2-trifluoroethyl)-4-{[2-(trimethylsilyl)ethoxy]methoxy}phenyl]-1-(tetrahydro-2H-pyran-2-yl)-1H-pyrazolo[4,3-c]pyridine The title compound was prepared according to the method described for Preparation 145 using 6-chloro-1-(tetrahydro-2H-pyran-2-yl)-1H-pyrazolo[4,3-c]pyridine (Preparation 149) and (2-{[2-fluoro-4-(4,4,5,5-tetramethyl-1,3,2-dioxaborolan-2-yl)-5-(2,2,2-trifluoroethyl)phenoxy]methyl}ethyl)(trimethyl)silane (Preparation 150). The residue was purified using silica gel column chromatography eluting with 9% EtOAc in hexanes (19 g, 86%). $^1$H NMR (400 MHz, DMSO-d$_6$): δ ppm −0.02 (s, 9H), 0.91 (m, 2H), 1.58 (m, 2H), 1.73 (m, 1H), 2.05 (m, 2H), 2.41 (m, 1H), 3.73 (m, 2H), 3.92-4.21 (m, 2H), 5.35 (s, 2H), 5.98 (m, 1H), 7.40 (d, 1H), 7.50 (d, 1H), 7.93 (s, 1H), 8.38 (s, 1H), 9.16 (s, 1H).

Preparation 147

6-[2-Ethyl-5-fluoro-4-{[2-(trimethylsilyl)ethoxy]methoxy}phenyl]-1-(tetrahydro-2H-pyran-2-yl)-1H-pyrazolo[4,3-c]pyridine The title compound was prepared according the method described for Preparation 145 using (2-{[2-fluoro-4-(4,4,5,5-tetramethyl-1,3,2-dioxaborolan-2-yl)-5-ethyl-phenoxy]methoxy}ethyl)(trimethyl)silane (WO20131014567A1) and 6-chloro-1-(tetrahydro-2H-pyran-2-yl)-1H-pyrazolo[4,3-c]pyridine (Preparation 149). The residue was purified using silica gel column chromatography eluting with 30% EtOAc in hexanes (34 g, 85%). $^1$H NMR (400 MHz, DMSO-$d_6$): δ ppm 0.01 (s, 9H), 0.92 (m, 2H), 1.05 (m, 3H), 1.58 (m, 2H), 1.73 (m, 1H), 2.03 (m, 2H), 2.41 (m, 1H), 2.65 (m, 2H), 3.72-3.92 (m, 4H), 5.34 (s, 2H), 5.93 (m, 1H), 7.21-7.28 (m, 2H), 7.80 (s, 1H), 8.36 (s, 1H), 9.14 (s, 1H). MS m/z 526 [M+H]$^+$

Preparation 148

6-(2-Cyclopropyl-5-fluoro-4-methoxyphenyl)-1-(tetrahydro-2H-pyran-2-yl)-1H-pyrazolo[4,3-c]pyridine The title compound was prepared according the method described for Preparation 145 using 2-(2-cyclopropyl-5-fluoro-4-methoxyphenyl)-4,4,5,5-tetramethyl-1,3,2-dioxaborolane (Preparation 151) and 6-chloro-1-(tetrahydro-2H-pyran-2-yl)-1H-pyrazolo[4,3-c]pyridine (Preparation 149). $^1$H NMR (400 MHz, DMSO-$d_6$): δ ppm 0.65-0.85 (m, 4H), 1.58 (m, 2H), 1.71 (m, 1H), 2.01 (m, 2H), 2.11 (m, 1H), 2.40 (m, 1H), 3.31 (s, 3H), 3.74 (m, 1H), 3.90 (m, 1H), 5.94 (m, 1H), 6.74 (d, 1H), 7.31 (d, 1H), 7.91 (s, 1H), 8.35 (s, 1H), 9.15 (s, 1H). MS m/z 368 [M+H]$^+$

Preparation 149

6-Chloro-1-(tetrahydro-2H-pyran-2-yl)-1H-pyrazolo[4,3-c]pyridine

To a solution of 6-chloro-1H-pyrazolo[4,3-c]pyridine (75 g, 488.37 mmol) in DCM (2 L) was added dihydropyran (66.98 mL, 732.56 mmol) followed by para-toluenesulfonic acid (18.58 g, 97.67 mmol) and the reaction was heated to reflux for 18 hours. Further para-toluenesulfonic acid (0.1 eq) and dihydropyran (0.75 eq) were added and the reaction continued heating at reflux for 6 hours. The reaction was cooled and quenched with saturated aqueous sodium bicarbonate solution. The organic layer was collected, washed with brine, dried over sodium sulfate and concentrated in vacuo. The residue was purified using silica gel column chromatography eluting with 17% EtOAc in hexanes followed by trituration with ether to afford the title compound as a pale yellow solid (83 g, 72%). $^1$H NMR (400 MHz, DMSO-$d_6$): δ ppm 1.59 (m, 2H), 1.71 (m, 1H), 2.02 (m, 2H), 2.29 (m, 1H), 3.74 (m, 1H), 3.89 (m, 1H), 5.91 (m, 1H), 7.93 (s, 1H), 8.38 (s, 1H), 8.94 (s, 1H).

Preparation 150

(2-{[2-Fluoro-4-(4,4,5,5-tetramethyl-1,3,2-dioxaborolan-2-yl)-5-(2,2,2-trifluoroethyl)phenoxy]methoxy}ethyl)(trimethyl)silane To a solution of (2-{[4-bromo-2-fluoro-5-(2,2,2-trifluoroethyl)phenoxy]methoxy}ethyl)-(trimethyl)silane (Preparation 152, 34 g, 84.31 mmol), in dry 1,4-dioxane (1 L) was added bis(pinacolonato)diboron (21.41 g, 84.31 mmol) followed by KOAc (24.82 g, 252.95 mmol). The reaction mixture was purged with nitrogen for 20 minutes before the addition of Pd(dppf)$_2$Cl$_2$ (6.886 g, 8.432 mmol) followed by further degassing for 20 minutes. The reaction was heated to reflux for 18 hours before cooling to room temperature and concentrating in vacuo. The residue was suspended in EtOAc and filtered through a bed of Celite. The filtrate was washed with water, dried over sodium sulfate and concentrated in vacuo. The residue was purified using silica gel column chromatography eluting with 10% EtOAc in hexanes to afford the title compound as an oil (31 g, 82%). $^1$H NMR (400 MHz, DMSO-$d_6$): δ ppm −0.05 (s, 9H), 0.87 (m, 2H), 1.32 (s, 12H), 3.74 (m, 2H), 3.92 (m, 2H), 5.32 (s, 2H), 7.29 (d, 1H), 7.42 (d, 1H).

Preparation 151

2-(2-Cyclopropyl-5-fluoro-4-methoxyphenyl)-4,4,5,5-tetramethyl-1,3,2-dioxaborolane The title compound was prepared according to the method described for Preparation 150 using 1-bromo-2-cyclopropyl-5-fluoro-4-methoxybenzene (Preparation 154). Taken on to the next step as is.

Preparation 152

(2-{[4-Bromo-2-fluoro-5-(2,2,2-trifluoroethyl)phenoxy]methoxy}ethyl)(trimethyl)silane To a solution of 4-bromo-2-fluoro-5-(2,2,2-trifluoroethyl)phenol (Preparation 153, 25 g, 91.57 mmol) in DCM (200 mL) was added DIPEA (17.54 mL, 100.73 mmol) at room temperature followed by SEM-Cl (17.86 mL, 100 mmol) drop-wise at 0° C. and the reaction was stirred at room temperature for 4 hours. The reaction was partitioned between DCM and water, the organic layer was collected, washed with brine, dried over sodium sulfate and concentrated in vacuo to afford the title compound as an oil (34 g, 92%). $^1$H NMR (400 MHz, DMSO-$d_6$): δ ppm −0.03 (s, 9H), 0.87 (m, 2H), 3.70-3.79 (m, 4H), 5.29 (s, 2H), 7.42 (d, 1H), 7.70 (d, 1H).

Preparation 153

4-Bromo-2-fluoro-5-(2,2,2-trifluoroethyl)phenol

To a solution of 1-bromo-5-fluoro-4-methoxy-2-(2,2,2-trifluoroethyl)benzene (WO20131014567A1, 30 g, 104.51 mmol) in DCM (800 mL) at 0° C. was added boron tribromide (130.91 g, 522 mmol) drop-wise and the reaction was stirred at room temperature for 16 hours. The reaction was quenched by the addition of saturated aqueous NaHCO$_3$ solution and extracted into DCM. The organic layer was collected, washed with brine, dried over sodium sulfate and concentrated in vacuo to afford the title compound as a white solid that was taken directly on to the next step (22 g, 77%).

Preparation 154

1-Bromo-2-cyclopropyl-5-fluoro-4-methoxybenzene

To a solution of 4-cyclopropyl-1-fluoro-2-methoxybenzene (Preparation 155, 8.7 g, 41 mmol) in DMF (250 mL) at 0° C. was added NBS (7.40 g, 41 mmol) and the reaction was stirred at room temperature for 3 hours. The reaction was partitioned between EtOAc and brine, the organic layer was collected, dried over sodium sulfate and concentrated in vacuo. The residue was purified using silica gel column chromatography eluting with hexanes to afford the title compound as a colorless oil (9.5 g, 92%). $^1$H NMR (400 MHz, DMSO-$d_6$): δ ppm 0.73 (m, 2H), 0.96 (m, 2H), 2.01 (m, 1H), 3.82 (s, 3H), 6.72 (d, 1H), 7.50 (d, 1H).

Preparation 155

4-Cyclopropyl-1-fluoro-2-methoxybenzene

To a solution of 5-bromo-2-fluoroanisole (10 g, 48.77 mmol) in toluene (100 mL) was added water (10 mL), cyclopropyl boronic acid (5.44 g, 63 mmol), tricyclohexylphosphine (1.37 g, 4.87 mmol) and potassium phosphate (36.3 g, 170 mmol). The reaction was degassed with nitrogen before the addition of Pd(OAc)$_2$ (547 mg, 2.44 mmol) followed by heating to 100° C. for 3 hours. The reaction was cooled and partitioned between EtOAc and brine. The organic layer was collected, concentrated in vacuo and purified using silica gel column chromatography to afford the title compound as a colorless oil (9.7 g, quant).

$^1$H NMR (400 MHz, DMSO-$d_6$): δ ppm 0.65 (m, 2H), 0.92 (m, 2H), 1.88 (m, 1H), 3.81 (s, 3H), 6.61 (m, 1H), 6.82 (m, 1H), 7.06 (m, 1H).

Preparation 156

4-Nitrophenyl {5-chloro-2-[methyl(methylsulfonyl)amino]benzyl}carbamate

To a solution of N-[2-(aminomethyl)-4-chlorophenyl]-N-methylmethanesulfonamide hydrochloride (Preparation 211, 3.20 g, 11.39 mmol) and sodium carbonate (3.62 g, 34.18 mmol) in DCM (50 mL) at 0° C., was added 4-nitrophenyl-chloroformate (2.52 g, 12.53 mmol) and the reaction was stirred at room temperature for 18 hours. The reaction was concentrated in vacuo and the residue purified by silica gel column chromatography eluting with 55-100% EtOAc in hexanes to afford the title compound as a pale yellow solid (2.20 g, 46%). $^1$H NMR (400 MHz, DMSO-$d_6$): δ ppm 3.08 (s, 3H), 3.17 (s, 3H), 4.32 (br m, 1H), 4.52 (br m, 1H), 7.40-7.61 (m, 5H), 8.25 (m, 2H).

The following Preparations (Preparations 157-183) were prepared according to the method described for Preparation 156 using the appropriate amine as described below, and taken directly on to the next step;

| Preparation Number | Name | Data/SM |
|---|---|---|
| 157 | 4-nitrophenyl {2-[ethyl(ethylsulfonyl)amino]benzyl}carbamate | N-[2-(aminomethyl)phenyl]-N-ethylethanesulfonamide hydrochloride (Preparation 184). |
| 158 | 4-nitrophenyl [2-(4-hydroxyphenyl)ethyl]carbamate | 2-(4-hydroxyphenyl)ethanamine. |
| 159 | 4-nitrophenyl {2-[(ethylsulfonyl)(methyl)amino]benzyl}carbamate | N-[2-(aminomethyl)phenyl]-N-methylethanesulfonamide hydrochloride (Preparation 185). |
| 160 | 4-nitrophenyl (2-methylpropyl)carbamate | 2-methylpropylamine. |
| 161 | 4-nitrophenyl {5-fluoro-2-[methyl(methylsulfonyl)amino]benzyl}carbamate | N-[2-(aminomethyl)-4-fluorophenyl]-N-methylmethanesulfonamide hydrochloride (Preparation 186). |
| 162 | 4-nitrophenyl {2-fluoro-6-[methyl(methylsulfonyl)amino]benzyl}carbamate | N-[2-(aminomethyl)-3-fluorophenyl]-N-methylmethanesulfonamide hydrochloride (Preparation 187). |
| 163 | 4-nitrophenyl {2-[ethyl(methylsulfonyl)amino]benzyl}carbamate | N-[2-(aminomethyl)phenyl]-N-ethylmethanesulfonamide hydrochloride (Preparation 188). |
| 164 | 4-nitrobenzyl (cyclopentylmethyl)carbamate | 1-cyclopentylmethanamine |
| 165 | 4-nitrophenyl {5-methyl-2-[methyl(methylsulfonyl)amino]benzyl}carbamate | N-[2-(aminomethyl)-4-methylphenyl]-N-methylmethanesulfonamide hydrochloride (Preparation 189). |
| 166 | 4-nitrophenyl {2-[methyl-(methylsulfonyl)amino]benzyl}carbamate | N-[2-(aminomethyl)phenyl]-N-methylmethanesulfonamide (WO2010/058846A1). |
| 167 | 4-nitrophenyl {2-[methyl(phenylsulfonyl)amino]benzyl}carbamate | N-[2-(aminomethyl)phenyl]-N-methylbenzenesulfonamide hydrochloride (Preparation 190). |
| 168 | 4-nitrophenyl (2-{4-[(phenylsulfonyl)amino]phenyl}172ulph)carbamate | N-[4-(2-aminoethyl)phenyl]benzenesulfonamide (Preparation 210). |
| 169 | 4-nitrophenyl {2-[bis(methylsulfonyl)amino]-5-methoxybenzyl}carbamate | N-[2-(aminomethyl)-4-methoxyphenyl]-N-(methylsulfonyl)methanesulfonamide hydrochloride (Preparation 191). |
| 170 | Racemic 4-nitrophenyl (1-{2-[methyl(methylsulfonyl)amino]phenyl}ethyl)carbamate | Racemic N-[2-(1-aminoethyl)phenyl]-N-methylmethanesulfonamide (Preparation 209). |
| 171 | 4-nitrobenzyl (2-{(methylsulfonyl)[2-(tetrahydro-2H-pyran-2-yloxy)ethyl]amino}benzyl)carbamate | N-[2-(aminomethyl)phenyl]-N-[2-(tetrahydro-2H-pyran-2-yloxy)ethyl]methanesulfonamide (Preparation 216) |
| 172 | 4-nitrophenyl {4-methoxy-2-[methyl(methylsulfonyl)amino]benzyl}carbamate | N-[2-(aminomethyl)-5-methoxyphenyl]-N-methylmethanesulfonamide hydrochloride (Preparation 192). |

-continued

| Preparation Number | Name | Data/SM |
|---|---|---|
| 173 | 4-nitrophenyl (2-{[(3-methoxyphenyl)sulfonyl](methyl)amino}benzyl)carbamate | N-[2-(aminomethyl)phenyl]-3-methoxy-N-methylbenzenesulfonamide hydrochloride (Preparation 193). |
| 174 | 4-nitrophenyl {2-[ethyl(methylsulfonyl)amino]-5-methoxybenzyl}carbamate | N-[2-(aminomethyl)-4-methoxyphenyl]-N-ethylmethanesulfonamide hydrochloride (Preparation 194). |
| 175 | 4-nitrophenyl {5-methoxy-2-[methyl(phenylsulfonyl)amino]benzyl}carbamate | N-[2-(aminomethyl)-4-methoxyphenyl]-N-methylbenzenesulfonamide hydrochloride (Preparation 195). |
| 176 | 4-nitrophenyl {2-[ethyl(phenylsulfonyl)amino]-5-methoxybenzyl}carbamate | N-[2-(aminomethyl)-4-methoxyphenyl]-N-ethylbenzenesulfonamide hydrochloride (Preparation 196). |
| 177 | 4-nitrophenyl ({2-[methyl(methylsulfonyl)amino]pyridin-3-yl}methyl)carbamate | N-[3-(aminomethyl)pyridin-2-yl]-N-methylmethanesulfonamide (Preparation 217) |
| 178 | benzyl methyl[2-({[(4-nitrophenoxy)carbonyl]amino}methyl)phenyl]carbamate | Benzyl [2-(aminomethyl)phenyl]methylcarbamate hydrochloride (Preparation 249). |
| 179 | 4-nitrophenyl {2-[ethyl(methylsulfonyl)amino]-5-fluorobenzyl}carbamate | N-[2-(aminomethyl)-4-fluorophenyl]-N-ethylmethanesulfonamide (Preparation 205). |
| 180 | 4-nitrophenyl {2-[ethyl(methylsulfonyl)amino]-5-chlorobenzyl}carbamate | N-[2-(aminomethyl)-4-chlorophenyl]-N-ethylmethanesulfonamide (Preparation 206). |
| 181 | 4-nitrobenzyl ((5-methyl-2-(N-methylmethylsulfonamido)pyridin-3-yl)methyl)carbamate | N-[3-(aminomethyl)-5-methylpyridin-2-yl]-N-methylmethanesulfonamide hydrochloride (Preparation 198). |
| 182 | 4-nitrophenyl ((2-(N-ethylmethylsulfonamido)-5-methylpyridin-3-yl)methyl)carbamate | N-[3-(aminomethyl)-5-methylpyridin-2-yl]-N-ethylmethanesulfonamide hydrochloride (Preparation 207). |
| 183 | 4-nitrophenyl {2-[ethyl(methylsulfonyl)amino]-5-methylbenzyl}carbamate | N-[2-(aminomethyl)-4-methylphenyl]-N-ethylmethanesulfonamide hydrochloride (Preparation 200). |

The following Preparations (Preparations 184-207) were prepared according to the methods described in the three steps below:
1) Preparation 236
2) Preparation 213
3) Preparation 211
using the appropriate alkyl halide as described below:

| Preparation Number | Name | Data/SM |
|---|---|---|
| 184 | N-[2-(aminomethyl)phenyl]-N-ethylethanesulfonamide hydrochloride | $^1$H NMR (400 MHz, DMSO-$d_6$): δ ppm 3.06 (s, 3H), 3.22 (s, 3H), 4.09 (b s, 1H), 4.21 (b s, 1H), 7.47-7.52 (m, 2H), 7.62-7.63 (m, 2H), 8.23 (b s, 1H). Using N-(2-cyanophenyl)-N-(ethylsulfonyl)ethanesulfonamide (Preparation 241) and ethyl iodide. |
| 185 | N-[2-(aminomethyl)phenyl]-N-methylethanesulfonamide hydrochloride | MS m/z 229 [M + H]$^+$ $^1$H NMR (400 MHz, DMSO-$d_6$): δ ppm 1.26 (t, 3H), 3.06-3.56 (br m, 4H), 4.03-4.19 (br m, 2H), 7.42-7.49 (m, 2H), 7.60 (m, 1H), 7.68 (m, 1H), 8.48 (br s, 3H). Using N-(2-cyanophenyl)-N-(ethylsulfonyl)ethanesulfonamide (Preparation 241) and methyl iodide. |
| 186 | N-[2-(aminomethyl)-4-fluorophenyl]-N-methylmethanesulfonamide hydrochloride | MS m/z 233 [M + H]$^+$ $^1$H NMR (400 MHz, DMSO-$d_6$): δ ppm 3.06 (s, 3H), 3.56 (s, 3H), 4.02 (br s, 1H), 4.20 (br s, 1H), 7.32-7.37 (m, 1H), 7.56-7.59 (m, 1H), 7.68-7.71 (m, 1H), 8.49 (br s, 2H). Using N-(4-fluoro-2-cyanophenyl)-N-(methylsulfonyl)-methanesulfonamide (Preparation 239) and methyl iodide. |
| 187 | N-[2-(aminomethyl)-3-fluorophenyl]-N- | MS m/z 233 [M + H]$^+$ $^1$H NMR (400 MHz, DMSO-$d_6$): δ ppm 3.06 (s, |

| Preparation Number | Name | Data/SM |
|---|---|---|
| | methylmethanesulfonamide hydrochloride | 3H), 3.27 (s, 3H), 4.05 (br s, 1H), 4.20 (br s, 1H), 7.36-7.41 (t, 1H), 7.52-7.62 (m, 2H), 8.38 (br s, 2H).<br>Using N-(3-fluoro-2-cyanophenyl)-N-(methylsulfonyl)methanesulfonamide (Preparation 240) and methyl iodide. |
| 188 | N-[2-(aminomethyl)phenyl]-N-ethylmethanesulfonamide hydrochloride | MS m/z 229 [M + H]$^+$<br>$^1$H NMR (400 MHz, DMSO-d$_6$): δ ppm 1.26 (t, 3H), 3.13 (m, 1H), 3.24 (s, 3H), 3.39 (m, 1H), 4.03 (br s, 1H), 4.19 (br s, 1H), 7.44-7.49 (m, 2H), 7.59-7.70 (m, 2H), 8.48 (br s, 2H).<br>Using N-(2-cyanophenyl)-N-(methylsulfonyl)methanesulfonamide (Preparation 238) and ethyl iodide. |
| 189 | N-[2-(aminomethyl)-4-methylphenyl]-N-methylmethanesulfonamide hydrochloride | MS m/z 229 [M + H]$^+$<br>$^1$H NMR (400 MHz, DMSO-d$_6$): δ ppm 2.34 (s, 3H), 3.03 (s, 3H), 3.19 (s, 3H), 3.98 (br s, 1H), 4.17 (br s, 1H), 7.29-7.31 (d, 1H), 7.47-7.51 (m, 2H), 8.33 (br s, 2H).<br>Using N-(4-methyl-2-cyanophenyl)-N-(methylsulfonyl)methanesulfonamide (Preparation 242) and methyl iodide. |
| 190 | N-[2-(aminomethyl)phenyl]-N-methylbenzenesulfonamide hydrochloride | MS m/z 277 [M + H]$^+$<br>$^1$H NMR (400 MHz, DMSO-d$_6$): δ ppm 3.10 (s, 3H), 4.20 (br m, 1H), 4.40 (br m, 1H), 6.51 (m, 1H), 7.16 (m, 1H), 7.33 (m, 3H), 7.64 (m, 4H), 7.77 (m, 1H).<br>Using N-(2-cyanophenyl)-N-(phenylsulfonyl)benzenesulfonamide (Preparation 243) and methyl iodide. |
| 191 | N-[2-(aminomethyl)-4-methoxyphenyl]-N-(methylsulfonyl)methanesulfonamide hydrochloride | $^1$H NMR (400 MHz, DMSO-d$_6$): δ ppm 3.05 (s, 3H), 3.18 (s, 3H), 3.80 (s, 3H), 3.99 (m, 1H), 4.18 (m, 1H), 7.02 (dd, 1H), 7.26 (d, 1H), 7.54 (d, 1H), 8.43 (br s, 3H).<br>Using N-(2-cyano-4-methoxyphenyl)-N-(methylsulfonyl)methanesulfonamide (Preparation 244). |
| 192 | N-[2-(aminomethyl)-5-methylphenyl]-N-methylmethane-sulfonamide hydrochloride | MS m/z 245 [M + H]$^+$<br>$^1$H NMR (400 MHz, DMSO-d$_6$): δ ppm 3.07 (s, 3H), 3.22 (s, 3H), 3.81 (s, 3H), 3.93 (br m, 1H), 4.13 (br m, 1H), 7.07 (dd, 1H), 7.17 (d, 1H), 7.58 (d, 1H), 8.24 (br s, 3H).<br>Using N-(2-cyano-5-methoxyphenyl)-N-methylmethanesulfonamide (Preparation 224). |
| 193 | N-[2-(aminomethyl)phenyl]-3-methoxy-N-methylbenzenesulfonamide hydrochloride | MS m/z 307 [M + H]$^+$<br>$^1$H NMR (400 MHz, DMSO-d$_6$): δ ppm 3.37 (s, 3H), 3.78 (s, 3H), 4.11 (m, 1H), 4.31 (m, 1H), 6.61 (m, 1H), 6.99 (m, 1H), 7.17 (d, 1H), 7.28-7.35 (m, 2H), 7.42-7.46 (m, 1H), 7.56 (t, 1H), 7.73 (m, 1H), 8.53 (br s, 3H).<br>Using N-(2-cyanophenyl)-3-methoxy-N-methylbenzenesulfonamide (Preparation 225). |
| 194 | N-[2-(aminomethyl)-4-methoxyphenyl]-N-ethylmethane-sulfonamide hydrochloride | MS m/z 259 [M + H]$^+$<br>$^1$H NMR (400 MHz, DMSO-d$_6$): δ ppm 0.99 (t, 3H), 3.02 (3.46 (m, 1H), 3.71 (m, 1H), 3.81 (s, 3H), 4.09 (m, 2H), 7.02 (dd, 1H), 7.30 (d, 1H), 7.50 (d, 1H), 8.40 (br s, 3H).<br>N-(2-cyano-4-methoxyphenyl)-N-(methylsulfonyl)-methanesulfonamide (Preparation 244) and ethyl iodide. |
| 195 | N-[2-(aminomethyl)-4-methoxyphenyl]-N-methylbenzenesulfonamide hydrochloride | MS m/z 307 [M + H]$^+$<br>$^1$H NMR (400 MHz, DMSO-d$_6$): δ ppm 3.11 (s, 3H), 3.54 (s, 3H), 4.06 (m, 1H), 4.30 (m, 1H), 6.45 (d, 1H), 6.82 (m, 1H), 7.30 (d, 1H), 7.58-7.75 (m, 4H), 7.77 (m, 1H), 8.41 (br s, 3H).<br>N-(4-methoxy-2-cyanophenyl)-N-(phenylsulfonyl)benzenesulfonamide (Preparation 246) and methyl iodide. |
| 196 | N-[2-(aminomethyl)-4-methoxyphenyl]-N-ethylbenzene-sulfonamide hydrochloride | MS m/z 321 [M + H]$^+$<br>$^1$H NMR (400 MHz, DMSO-d$_6$): δ ppm 0.96 (t, 3H), 3.20 (m, 1H), 3.78 (s, 3H), 3.86 (m, 1H), 4.15 (m, 2H), 6.47 (d, 1H), 6.85 (m, 1H), 7.31 (s, 1H), 7.61 (m, 4H), 7.76 (m, 1H), 8.40 (br s, 3H).<br>N-(4-methoxy-2-cyanophenyl)-N-(phenylsulfonyl)benzenesulfonamide (Preparation 246) and ethyl iodide. |

-continued

| Preparation Number | Name | Data/SM |
|---|---|---|
| 197 | N-(3-(aminomethyl)pyridin-4-yl)-N-methylmethanesulfonamide | MS m/z 216 [M + H]⁺<br>Using N-(3-cyanopyridin-4-yl)methanesulfonamide (Preparation 248) and methyl iodide. |
| 198 | N-[3-(aminomethyl)-5-methylpyridin-2-yl]-N-methylmethanesulfonamide hydrochloride | $^1$H NMR (400 MHz, DMSO-$d_6$): δ ppm 2.36 (s, 3H), 3.09 (s, 3H), 3.18 (s, 3H), 7.90 (d, 1H), 8.26 (br s, 3H), 8.39 (d, 1H).<br>MS m/z 230 [M + H]⁺<br>Using N-(3-cyano-5-methylpyridin-2-yl)-N-(methylsulfonyl)methanesulfonamide (Preparation 245) and methyl iodide. |
| 199 | 1-[2-(aminomethyl)phenyl]methanesulfonamide hydrochloride | MS m/z 201 [M + H]⁺<br>$^1$H NMR (400 MHz, DMSO-$d_6$): δ ppm 4.18 (br m, 2H), 4.48 (s, 2H), 7.00 (s, 2H), 7.43 (m, 3H), 7.53 (m, 1H), 8.23 (br s, 3H).<br>Using Steps 2 and 3 only with (2-cyanophenyl)methanesulfonamide. |
| 200 | N-[2-(aminomethyl)-4-methylphenyl]-N-ethylmethaneulfonamide hydrochloride | MS m/z 243 [M + H]⁺<br>$^1$H NMR (400 MHz, DMSO-$d_6$): δ ppm 0.98 (t, 3H), 2.50 (s, 3H), 3.03 (s, 3H), 3.49 (m, 1H), 3.70 (m, 1H), 4.09 (m, 2H), 7.29 (m, 1H), 7.45 (d, 1H), 7.51 (s, 1H), 8.42 (br s, 3H).<br>MS m/z 243 [M + H]⁺<br>Using N-(4-methyl-2-cyanophenyl)-N-(methylsulfonyl)-methanesulfonamide (Preparation 242) and ethyl iodide. |
| 201 | N-[3-(aminomethyl)-5-chloropyridin-2-yl]-N-ethylmethane-sulfonamide hydrochloride | MS m/z 264 [M + H]⁺<br>$^1$H NMR (400 MHz, DMSO-$d_6$): δ ppm 0.99 (t, 3H), 3.07 (s, 3H), 3.70 (q, 2H), 4.17 (m, 2H), 8.31 (s, 1H), 8.44 (br s, 3H), 8.67 (s, 1H).<br>Using steps 2 and 3 only with N-(5-chloro-3-cyanopyridin-2-yl)-N-ethylmethanesulfonamide (Preparation 232). |
| 202 | N-[3-(aminomethyl)-5-chloropyridin-2-yl]-N-methylmethanesulfonamide hydrochloride | MS m/z 250 [M + H]<br>$^1$H NMR (400 MHz, DMSO-$d_6$): δ ppm 2.98 (s, 3H), 3.29 (s, 3H), 4.39 (m, 2H), 8.46 (s, 1H), 8.57 (m, 1H), 8.70 (br s, 3H).<br>Using steps 2 and 3 only with N-(5-chloro-3-cyanopyridin-2-yl)-N-methylmethanesulfonamide (Preparation 233). |
| 203 | N-[3-(aminomethyl)-5-fluoropyridin-2-yl]-N-methylmethanesulfonamide hydrochloride | $^1$H NMR (400 MHz, DMSO-$d_6$): δ ppm 3.07 (s, 3H), 3.19 (s, 3H), 4.18 (br s, 2H), 8.10 (dd, 1H), 8.40 (br s, 3H), 8.60 (d, 1H).<br>Using steps 2 and 3 only with N-(5-fluoro-3-cyanopyridin-2-yl)-N-methylmethanesulfonamide (Preparation 231). |
| 204 | N-[3-(aminomethyl)-5-fluoropyridin-2-yl]-N-ethylmethane-sulfonamide hydrochloride | MS m/z 250 [M + H]<br>Using steps 2 and 3 only with N-(5-fluoro-3-cyanopyridin-2-yl)-N-ethylmethanesulfonamide (Preparation 235). Taken on directly to the next step. |
| 205 | N-[2-(aminomethyl)-4-fluorophenyl]-N-ethylmethanesulfonamide | MS m/z 247 [M + H]<br>$^1$H NMR (400 MHz, DMSO-$d_6$): δ ppm 0.98 (t, 3H), 3.07 (s, 3H), 3.48 (m, 1H), 3.64 (m, 1H), 3.71-3.83 (q, 2H), 7.13 (m, 1H), 7.44 (m, 2H).<br>Using N-(4-fluoro-2-cyanophenyl)-N-(methylsulfonyl)-methanesulfonamide (Preparation 239), ethyl iodide and washing with saturated aqueous sodium bicarbonate solution. |
| 206 | N-[2-(aminomethyl)-4-chlorophenyl]-N-ethylmethanesulfonamide hydrochloride | MS m/z 263 [M + H]<br>$^1$H NMR (400 MHz, DMSO-$d_6$): δ ppm 1.00 (t, 3H), 3.55 (m, 1H), 3.75 (m, 1H), 4.03-4.20 (m, 2H), 7.55 (dd, 1H), 7.62 (m, 1H), 7.83 (d, 1H), 8.54 (br s, 3H).<br>Using N-(4-chloro-2-cyanophenyl)-N-methylmethanesulfonamide (Preparation 237). |
| 207 | N-[3-(aminomethyl)-5-methylpyridin-2-yl]-N-ethylmethanesulfonamide hydrochloride | MS m/z 244 [M + H]<br>$^1$H NMR (400 MHz, DMSO-$d_6$): δ ppm 0.95 (t, 3H), 2.49 (s, 3H), 3.59 (s, 3H), 3.65 (q, 2H), 4.10 (m, 2H), 8.07 (d, 1H), 8.40 (d, 1H), 8.71 (br s, 3H).<br>Using N-(3-cyano-5-methylpyridin-2-yl)-N-(methylsulfonyl)methanesulfonamide (Preparation 245) and ethyl iodide. |

Preparation 208 tert-Butyl 2-(N-methyl-2-oxooxazolidine-3-sulfonamido)benzylcarbamate hydrochloride To a suspension of tert-butyl (2-((2-oxooxazolidine)-3-sulfonamido)benzyl)carbamate (Preparation 251, 2.5 g, 6.73 mmol) and anhydrous potassium carbonate (2.32 g, 16.82 mmol) in acetone (300 mL) was added methyl iodide (2.39 g, 16.83 mmol) and the reaction heated to reflux for 18 hours. The reaction was cooled and concentrated in vacuo. The residue was partitioned between water and DCM, the organic layer was collected, washed with brine and concentrated in vacuo. The residue was purified using silica gel column chromatography eluting with 35% EtOAc in hexanes before being treated with 4M HCl in dioxane (7 mL) and stirring at room temperature for 18 hours. The reaction was concentrated in vacuo and triturated with ether/pentane to afford the title compound as the hydrochloride salt (1.60 g, 68% over 2 steps). $^1$H NMR (400 MHz, DMSO-$d_6$): δ ppm 3.36 (s, 3H), 3.56 (m, 1H), 3.98 (m, 1H), 4.08 (m, 1H), 4.19 (m, 1H), 4.44 (m, 2H), 7.52-7.68 (m, 4H), 8.36 (br s, 3H). MS m/z 285 [M+H]$^+$

Preparation 209

Racemic N-[2-(1-Aminoethyl)phenyl]-N-methyl-methanesulfonamide

To a solution of N-(2-acetylphenyl)-N-methylmethanesulfonamide (Preparation 246, 10 g, 43.99 mmol) in EtOH (150 mL) was added triethylamine (7.93 mL, 57 mmol) and hydroxylamine hydrochloride (3.98 g, 57 mmol) and the reaction was heated to 80° C. for 18 hours. The reaction was cooled, diluted with EtOAc, washed with brine, dried over sodium sulfate and concentrated in vacuo. The residue was dissolved in MeOH (50 mL) and ammonium formate (2.15 g, 34 mmol) and activated zinc dust (2.25 g, 34 mmol) were added. The reaction was heated to reflux for 18 hours. The reaction was filtered through celite and concentrated in vacuo. The residue was purified using silica gel column chromatography eluting with 12% MeOH in DCM to afford the title compound as a colorless oil (1.2 g, 77%). $^1$H NMR (400 MHz, DMSO-$d_6$): δ ppm 1.48 (d, 3H), 3.16 (s, 3H), 3.22 (s, 3H), 4.76 (m, 1H), 7.40-7.80 (m, 4H), 8.32 (s, 1H). MS m/z 229 [M+H]$^+$

Preparation 210

N-[4-(2-Aminoethyl)phenyl]benzenesulfonamide

To a solution of 2-(2-aminoethyl)aniline (30 g, 220 mmol) in DCM (700 mL) at 0° C. was added triethylamine (36.8 mL, 264 mmol) followed by tert-butyldicarbonate (52.9 g, 242 mmol) and the reaction was allowed to warm to room temperature stirring for 2 hours. The reaction was added to water (500 mL), the organic layer collected, washed with brine, dried over sodium sulfate and concentrated in vacuo to afford a yellow oil. The oil was dissolved in DCM (400 mL) and pyridine (20 mL), and benzenesulfonyl chloride (26.1 mL, 203 mmol) was added. The reaction was stirred at room temperature for 48 hours. Further benzenesulfonyl chloride (6.51 mL, 0.3 eq) was added and the reaction continued for 24 hours. The reaction was washed with 1M aqueous HCl solution (500 mL), concentrated aqueous ammonia solution (400 mL), brine (500 mL), dried over sodium sulfate and concentrated in vacuo. The residue was recrystallised from EtOAc/Ether to afford a white solid. The solid was dissolved in dioxane (200 mL), 4M HCl in dioxane (282 mL) was added and the reaction was stirred at room temperature for 18 hours. The reaction was concentrated in vacuo and the residue suspended in hot MeOH (150 mL). 7M ammonia in MeOH (150 mL) was added and the solution cooled. The resulting precipitate was collected and purified further using silica gel column chromatography eluting with 0.4% NH$_3$ in 10-15% MeOH in DCM to afford the title compound as a yellow solid (16.8 g, 26% over three steps).

$^1$H NMR (400 MHz, DMSO-$d_6$): δ ppm 2.64 (t, 2H), 2.82 (t, 2H), 6.95-7.05 (m, 4H), 7.50-7.60 (m, 3H), 7.53 (m, 2H). MS m/z 275 [M–H]$^-$

Preparation 211

N-[2-(Aminomethyl)-4-chlorophenyl]-N-methyl-methanesulfonamide hydrochloride To a solution of tert-butyl {5-chloro-2-[methyl(methylsulfonyl)-amino]benzyl}carbamate (Preparation 213, 8.2 g, 23 mmol) in MeOH (100 mL) was added 4M HCl in dioxane (100 mL) at 0° C. and the reaction was stirred at room temperature for 5 hours. The reaction was concentrated in vacuo and triturated with a 1:1 mixture of MeCN:ether to afford the title compound as the hydrochloride salt (8.00 g, 100%). $^1$H NMR (400 MHz, DMSO-$d_6$): δ ppm 3.07 (s, 3H), 3.20 (s, 3H), 4.05 (br m, 1H), 4.20 (br m, 1H), 7.58 (m, 1H), 7.66 (m, 1H), 7.73 (m, 1H), 8.32 (br s, 3H). MS m/z 249 [M+H]

Preparation 212

N-[2-(Aminomethyl)-4-methoxyphenyl]-N-methyl-pyridine-3-sulfonamide dihydrochloride The title compound was prepared according to the method described for Preparation 211 using tert-butyl {5-methoxy-2-[methyl(pyridin-3-ylsulfonyl)amino]benzyl}carbamate (Preparation 214). MS m/z 308 [M+H]$^+$

Preparation 213 tert-Butyl {5-chloro-2-[methyl(methylsulfonyl)amino]benzyl}carbamate

To a solution of N-(4-chloro-2-cyanophenyl)-N-methyl-methanesulfonamide (Preparation 236, 6.20 g, 25.40 mmol) in MeOH (150 mL) was added di-tert-butyl dicarbonate (11.71 mL, 50.82 mmol) and NiCl$_2$.6H$_2$O (1.20 g, 5.08 mmol). The reaction was cooled to 0° C. and NaBH$_4$ (9.61 g, 254 mmol) was added portion-wise. The reaction was stirred at room temperature for 6 hours before being quenched by the addition of diethylenetriamine with stirring for 30 minutes. The reaction was concentrated in vacuo and partitioned between EtOAc and saturated aqueous sodium bicarbonate. The organic layer was collected, dried over sodium sulfate and concentrated in vacuo. The residue was purified by silica gel column chromatography to afford the title compound (8.20 g, 93%). 1H NMR (400 MHz, DMSO-$d_6$): 3.06 (s, 3H), 3.21 (s, 3H), 4.01-4.19 (m, 2H), 7.54-7.57 (q, 1H), 7.65-7.68 (d, 1H), 7.82-7.83 (d, 1H) MS m/z 349 [M+H]$^+$ and 249 [M-Boc+H]$^+$

Preparation 214 tert-Butyl {5-methoxy-2-[methyl(pyridin-3-ylsulfonyl)amino]benzyl}carbamate

To a solution of tert-butyl [5-methoxy-2-(methylamino)benzyl]carbamate (Preparation 215, 3.8 g, 10 mmol) in THF (20 mL) was added NaH (373 mg, 15 mmol) at 0° C. and the reaction was stirred for 15 minutes before the addition of pyridine-3-sulfonyl chloride (1.36 mL, 11 mmol) dropwise. The reaction was stirred at room temperature for 18 hours before being quenched with water and extracted into EtOAc. The organic layer was collected, washed with water, brine, dried over sodium sulfate and concentrated in vacuo. The residue was purified using silica gel column chromatography eluting with 55% EtOAc in hexanes to afford the title compound (3.3 g, 78%). MS m/z 407 [M−H]−

Preparation 215 tert-Butyl [5-methoxy-2-(methylamino)benzyl]carbamate

The title compound was prepared according to the method described for Preparation 213 using 5-methoxy-2-(methylamino)benzonitrile (Preparation 250). $^1$H NMR (400 MHz, DMSO-$d_6$): δ ppm 1.37 (s, 9H), 2.66 (d, 3H), 3.63 (s, 3H), 3.95 (m, 2H), 4.77 (br s, 1H), 6.45 (d, 1H), 6.63 (br s, 1H), 6.69 (dd, 1H), 7.23 (br t, 1H). MS m/z 267 [M+H]+

Preparation 216

N-[2-(Aminomethyl)phenyl]-N-[2-(tetrahydro-2H-pyran-2-yloxy)ethyl]methanesulfonamide To a solution of N-(2-cyanophenyl)-N-[2-(tetrahydro-2H-pyran-2-yloxy)ethyl]methanesulfonamide (Preparation 222, 8 g, 25 mmol) in MeOH (100 mL) was added NiCl$_2$.6H$_2$O (1.17 g, 5 mmol) followed by sodium borohydride (6.53 g, 172 mmol) at 0° C. The reaction was stirred at room temperature for 4 hours before being quenched by the addition of diethylenetetramine. The reaction was concentrated in vacuo and purified using silica gel column chromatography eluting with 10% MeOH in DCM to afford the title compound (4.9 g, 60%). Taken on directly to the next step.

Preparation 217

N-[3-(Aminomethyl)pyridin-2-yl]-N-methylmethanesulfonamide

To a solution of N-(3-cyanopyridin-2-yl)-N-methylmethanesulfonamide (Preparation 230, 10 g, 47 mmol) in methanolic ammonia (100 mL) was added Raney Nickel (2 g) and the reaction was hydrogenated at 40 psi at room temperature for 18 hours. The reaction was filtered through celite, concentrated in vacuo and purified using silica gel column chromatography eluting with 10% MeOH in DCM to afford the title compound (7.5 g, 74%). $^1$H NMR (400 MHz, DMSO-$d_6$): δ ppm 3.13 (s, 6H), 3.82 (br s, 2H), 7.44 (m, 1H), 8.03 (m, 1H), 8.37 (m, 1H).

Preparation 218

N-[3-(Aminomethyl)pyridin-2-yl]-N-ethylmethanesulfonamide

The title compound was prepared according to the method described for Preparation 217 using N-(3-cyanopyridin-2-yl)-N-methylmethanesulfonamide (Preparation 234). $^1$H NMR (400 MHz, DMSO-$d_6$): δ ppm 0.94 (t, 3H), 3.06 (s, 3H), 3.63 (q, 2H), 3.86 (br s, 2H), 7.46 (m, 1H), 8.06 (m, 1H), 8.41 (m, 1H). MS m/z 230 [M+H]

Preparation 219

N-[3-(Aminomethyl)pyrazin-2-yl]-N-methylbenzenesulfonamide

A solution of N-(3-cyanopyrazin-2-yl)-N-methylbenzenesulfonamide (Preparation 228, 7.2 g, 32 mmol) in AcOH (100 mL) was purged under nitrogen for 15 minutes followed by the addition of 10% Pd—C (1.4 g) and hydrogenated under at 40 psi hydrogen in a Parr-shaker for 18 hours. The reaction was filtered through celite, concentrated in vacuo, neutralized with 1N NaOH and extracted with DCM. The organic layer was collected, dried over sodium sulfate, concentrated in vacuo and purified by silica gel column chromatography eluting with 10% MeOH in DCM to afford the title compound as a yellow solid (4.1 g, 46%). $^1$H NMR (400 MHz, DMSO-$d_6$): δ ppm 3.06 (s, 3H), 4.04 (s, 2H), 7.17 (m, 4H), 7.33 (m, 1H), 8.34 (d, 1H), 8.64 (d, 1H). MS m/z 279 [M+H]+

Preparation 220

N-[2-(Aminomethyl)phenyl]-N-methylpyridine-3-sulfonamide hydrochloride

To a solution of tert-butyl {2-[(pyridin-3-ylsulfonyl)amino]benzyl}carbamate (Preparation 227, 4.57 g, 12 mmol) in acetone (100 mL) was added potassium carbonate (5.20 g, 38 mmol) followed by methyl iodide (1.56 mL, 25 mmol). The reaction was heated to reflux for 2 hours. The reaction was evaporated to dryness and partitioned between water & ethyl acetate. The organic phase was washed with brine, dried over sodium sulfate, evaporated and purified by silica gel column chromatography eluting with 52% EtOAc in hexanes. The residue was dissolved in MeOH (25 mL) and 4M HCl in dioxane (25 mL) was added with stirring at room temperature for 4 hours. The reaction was concentrated in vacuo and triturated with MeCN-ether to afford the title compound as the hydrochloride salt (4.2 g, 100%). $^1$H NMR (400 MHz, DMSO-$d_6$): δ ppm 3.19 (s, 3H), 4.14 (m, 1H), 4.32 (m, 1H), 6.65 (d, 1H), 7.31 (t, 1H), 7.47 (t, 1H), 7.67-7.72 (m, 2H), 7.99 (m, 1H), 8.36 (br s, 3H), 8.71 (m, 1H), 8.95 (m, 1H),

Preparation 221

N-[3-(Aminomethyl)pyrazin-2-yl]-N-ethylmethanesulfonamide

The title compound was prepared according to the method described for Preparation 219 using N-(3-cyanopyrazin-2-yl)-N-ethylmethanesulfonamide (Preparation 229). $^1$H NMR (400 MHz, DMSO-$d_6$): δ ppm 1.00 (t, 3H), 1.86 (br s, 2H), 3.13 (s, 3H), 3.68 (q, 2H), 3.95 (s, 2H). MS m/z 231 [M+H]+

Preparation 222

N-(2-Cyanophenyl)-N-[2-(tetrahydro-2H-pyran-2-yloxy)ethyl]methanesulfonamide To a suspension of N-(2-cyanophenyl)methanesulfonamide (Preparation 223, 7 g, 25 mmol) and polymer bound triphenylphosphine (14 g, 53 mmol) in anhydrous THF (100 mL) was added DEAD (8.42 mL, 53 mmol) followed by 2-(tetrahydro-pyran-2-yloxy)ethanol (7.82 g, 146 mmol) drop-wise at 0° C. The reaction was stirred at room temperature for 5 hours before filtering through celite. The filtrate was concentrated in vacuo and purified using silica gel column chromatography eluting with 30-35% EtOAc in hexanes to afford the title compound (8 g, 69%). $^1$H NMR (400 MHz, MeOD): δ ppm 1.42-1.62 (m, 6H), 3.14 (s, 3H), 3.40-3.55 (m, 2H), 3.70-4.00 (m, 5H), 7.53 (m, 1H), 7.69 (m, 1H), 7.72-7.81 (m, 2H).

Preparation 223

N-(2-Cyanophenyl)-N-methylmethanesulfonamide

To a solution of N-(2-cyanophenyl)-N-(methylsulfonyl)methanesulfonamide (Preparation 238, 300 g, 1.09 mol) in THF (2 L) was added 40% aqueous sodium hydroxide (2 L), benzyl triethylammonium chloride (24.91 g, 0.100 mol), and iodomethane (81.68 mL, 1.31 mol.) The reaction was stirred at room temperature for 18 hours. The reaction was diluted with EtOAc and partitioned with brine. The organic layer was collected, dried over sodium sulfate and concentrated in vacuo. The residue was triturated in pentane-ether to afford the title compound (208 g, 90%). $^1$H NMR (400 MHz, CDCl$_3$): δ ppm 3.11 (s, 3H), 3.38 (s, 3H), 7.43-7.47 (t, 1H), 7.52-7.55 (m, 1H), 7.63-7.71 (m, 2H); MS m/z 211[M−H]$^-$ Preparation 224

N-(2-Cyano-5-methoxyphenyl)-N-methylmethanesulfonamide

To a stirred solution of 4-methoxy-2-(methylamino)benzonitrile (Preparation 226, 11 g, 68 mmol) in THF at −78° C., 1M LiHMDS in THF (108.5 mL) was added drop wise. The solution was stirred for 30 minutes followed by the addition of methanesulfonyl chloride (7.92 mL, 102 mmol). The reaction was stirred for 1 hour before quenching with saturated aqueous ammonium chloride solution and extracting into EtOAc. The organic layer was collected, dried over sodium sulfate and concentrated in vacuo. The residue was purified by silica gel column chromatography eluting with 40% EtOAc in hexanes to afford the title compound as a white solid (12 g, 73%). $^1$H NMR (400 MHz, DMSO-d$_6$): δ ppm 3.13 (s, 3H), 3.26 (s, 3H), 3.88 (s, 3H), 7.11 (dd, 1H), 7.28 (d, 1H), 7.83 (d, 1H).

Preparation 225

N-(2-Cyanophenyl)-3-methoxy-N-methylbenzenesulfonamide

The title compound was prepared according to the method described for Preparation 224 using 2-(methylamino)benzonitrile and 3-methoxybenzenesulfonyl chloride. Taken on directly to the next step. MS m/z 303 [M+H]$^+$ Preparation 226

4-Methoxy-2-(methylamino)benzonitrile

To a solution of 2-fluoro-4-methoxybenzonitrile (1 g, 6.61 mmol) in MeCN (10 mL) was added 40% aqueous methylamine (20 mL) and the reaction heated to 60° C. in a sealed tube. The reaction was cooled, concentrated in vacuo and purified using silica gel column chromatography eluting with 60% EtOAc in hexanes to afford the title compound as a white solid (600 mg, 56%). $^1$H NMR (400 MHz, DMSO-d$_6$): δ ppm 2.76 (d, 3H), 3.78 (s, 3H), 6.12 (m, 2H), 6.22 (m, 1H), 7.37 (m, 1H). MS m/z 163 [M+H]$^+$ Preparation 227 tert-Butyl {2-[(pyridin-3-ylsulfonyl)amino]benzyl}carbamate

To a solution of (2-amino-benzyl)-carbamic acid tert butyl ester (3.2 g, 14 mmol) in pyridine (25 mL) was added pyridine-3-sulfonylchloride (1.75 mL, 14 mmol) at 0° C. The reaction was stirred at room temperature for 4 hours before concentrating in vacuo. The residue was partitioned between EtOAc and water, the organic layer was collected, dried over sodium sulfate and concentrated in vacuo. The residue was purified using silica gel column chromatography eluting with 65% EtOAc in hexanes to afford the title compound (4.5 g, 87%). $^1$H NMR (400 MHz, DMSO-d$_6$): δ ppm 1.38 (s, 9H), 4.07 (m, 2H), 6.80 (d, 1H), 7.13 (m, 1H), 7.21 (m, 2H), 7.32 (m, 1H), 7.62 (m, 1H), 8.05 (m, 1H), 8.78-8.83 (m, 2H), 9.92 (s, 1H). MS m/z 364 [M+H]$^+$ Preparation 228

N-(3-Cyanopyrazin-2-yl)-N-methylbenzenesulfonamide

To a solution of 2-chloro-3-cyanopyrazine (5 g, 35.94 mmol) and Cs$_2$CO$_3$ (16.27 g, 50 mmol) in acetonitrile (75 mL) was added N-methylbenzenesulfonamide (7.37 g, 43 mmol) and the reaction heated to 80° C. for 3 hours. The reaction mixture was concentrated in vacuo and the residue partitioned between water and EtOAc. The organic layer was collected, dried, concentrated in vacuo and purified by silica gel column chromatography eluting with 50% EtOAc in hexanes to afford the title compound (7.2 g, 73%). $^1$H NMR (400 MHz, DMSO-d$_6$): δ ppm 3.12 (s, 3H), 7.64 (m, 4H), 7.76 (m, 1H), 8.80 (d, 1H), 8.85 (d, 1H).

Preparation 229

N-(3-Cyanopyrazin-2-yl)-N-ethylmethanesulfonamide

The title compound was prepared according to the method described for Preparation 228 using N-ethylmethanesulfonamide. $^1$H NMR (400 MHz, DMSO-d$_6$): δ ppm 1.09 (t, 3H), 3.20 (s, 3H), 3.83 (q, 2H), 8.89 (d, 1H), 8.97 (d, 1H).

Preparation 230

N-(3-Cyanopyridin-2-yl)-N-methylmethanesulfonamide

To a solution of 2-chloronicotinonitrile (10 g, 71.9 mmol) in MeCN (200 mL) was added cesium carbonate (32.5 g, 99 mmol) followed by N-methylmethanesulfonamide (9.42 g, 86 mmol) and the reaction was heated to 80° C. for 3 hours. The reaction was cooled, concentrated in vacuo and partitioned between EtOAc and water. The organic layer was collected, dried over sodium sulfate and concentrated in vacuo. The residue was purified using silica gel column chromatography eluting with 50% EtOAc in hexanes to afford the title compound (12.9 g, 85%). $^1$H NMR (400 MHz, DMSO-d$_6$): δ ppm 3.21 (s, 3H), 3.28 (s, 3H), 7.62 (m, 1H), 8.45 (d, 1H), 8.77 (d, 1H). MS m/z 212 [M+H]$^+$ The following Preparations (Preparations 231-235) were prepared according to the method described for Preparation 230 using the appropriate chloropyridine and sulfonamide as described below, and taken directly on to the next step:

| Preparation Number | Name | Data/SM |
|---|---|---|
| 231 | N-(5-fluoro-3-cyanopyridin-2-yl)-N-methylmethanesulfonamide | MS m/z 230 [M + H]$^+$<br>Using N-methylmethanesulfonamide and 2-chloro-5-fluoronicotinonitrile. |
| 232 | N-(5-chloro-3-cyanopyridin-2-yl)-N-ethylmethanesulfonamide | MS m/z 260 [M + H]$^+$<br>$^1$H NMR (400 MHz, DMSO-d$_6$): δ ppm 1.17 (t, 3H), 3.10 (s, 3H), 3.87 (q, 2H), 8.02 (s, 1H), 8.62 (s, 1H).<br>Using N-ethylmethanesulfonamide and 2,5-dichloronictinonitrile. |
| 233 | N-(5-chloro-3-cyanopyridin-2-yl)-N-methylmethanesulfonamide | MS m/z 246 [M + H]$^+$<br>$^1$H NMR (400 MHz, DMSO-d$_6$): δ ppm 3.21 (s, 3H), 3.27 (s, 3H), 8.73 (d, 1H), 8.86 (d, 1H).<br>Using N-methylmethanesulfonamide and 2,5-dichloronictinonitrile. |
| 234 | N-(3-cyanopyridin-2-yl)-N-ethylmethanesulfonamide | MS m/z 226 [M + H]$^+$<br>$^1$H NMR (400 MHz, DMSO-d$_6$): δ ppm 1.05 (t, 3H), 3.17 (s, 3H), 3.77 (q, 2H), 7.67 (m, 1H), 8.49 (m, 1H), 8.84 (m, 1H).<br>Using 2-chloronicotinonitrile and N-ethylmethanesulfonamide. |
| 235 | N-(5-fluoro-3-cyanopyridin-2-yl)-N-ethylmethanesulfonamide | MS m/z 244 [M + H]$^+$<br>Using N-ethylmethanesulfonamide and 2-chloro-5-fluoronicotinonitrile. |

Preparation 236

N-(4-Chloro-2-cyanophenyl)-N-methylmethanesulfonamide

A solution of N-(4-chloro-2-cyanophenyl)-N-(methylsulfonyl)methanesulfonamide (Preparation 237, 8.00 g, 25.91 mmol) in THF (100 mL) and 40% aqueous NaOH solution (100 mL) was cooled to 0° C. Benzyltriethylammonium chloride (0.59 g, 2.591 mmol) and MeI (5.64 mL, 90.68 mmol) were added and the reaction was stirred for 18 hours. The reaction was partitioned between EtOAc and water and concentrated in vacuo. The residue was purified by silica gel column chromatography eluting with 30% EtOAc in hexanes to afford the title compound as a yellow solid (6.20 g, 97%). $^1$H NMR (400 MHz, DMSO-d$_6$): δ ppm 3.14 (s, 3H), 3.26 (s, 3H), 7.78 (d, 1H), 7.88 (dd, 1H), 8.13 (d, 1H).

Preparation 237

N-(4-Chloro-2-cyanophenyl)-N-(methylsulfonyl)methanesulfonamide

To a solution of 2-amino-5-chloro-benzonitrile (5.00 g, 32.77 mmol) in pyridine (100 mL) at 0° C. was added methanesulphonylchloride (10.21 mL, 131.07 mmol) and the reaction stirred at room temperature for 18 hours. The reaction was concentrated in vacuo and partitioned between 2N HCl and EtOAc. The organic layer was collected, washed with brine, dried over sodium sulfate and concentrated in vacuo. The residue was triturated with 1:1 acetonitrile:ether to afford the title compound (8.00 g, 79%).

$^1$H NMR (400 MHz, DMSO-d$_6$): δ ppm 3.61 (s, 6H), 7.90 (d, 1H), 7.98 (dd, 1H), 8.31 (d, 1H).

The following Preparations (Preparations 238-246) were prepared according to the method described for Preparation 237 using the appropriate aniline as described below:

| Preparation Number | Name | Data/SM |
|---|---|---|
| 238 | N-(2-cyanophenyl)-N-(methylsulfonyl)methanesulfonamide | $^1$H NMR (400 MHz, DMSO-d$_6$): δ ppm 1.10 (t, 3H), 3.12 (s, 3H), 3.67-3.73 (q, 2H), 7.59 (t, 1H), 7.73-7.75 (d, 1H), 7.82 (t, 1H), 7.93 (d, 1H).<br>Using 2-aminobenzonitrile. |
| 239 | N-(4-fluoro-2-cyanophenyl)-N-(methylsulfonyl)methanesulfonamide | $^1$H NMR (400 MHz, DMSO-d$_6$): δ ppm 3.61 (s, 6H), 7.70-7.80 (m, 1H), 7.93-7.96 (m, 1H), 8.11-8.14 (m, 1H).<br>Using 2-amino-5-fluorobenzonitrile. |
| 240 | N-(3-fluoro-2-cyanophenyl)-N-(methylsulfonyl)methanesulfonamide | $^1$H NMR (400 MHz, DMSO-d$_6$): δ ppm 3.10 (s, 3H), 3.20 (s, 3H), 7.54-7.58 (m, 1H), 7.63-7.65 (m, 1H), 7.83-7.89 (m, 1H).<br>Using 2-amino-6-fluorobenzonitrile. |
| 241 | N-(2-cyanophenyl)-N-(ethylsulfonyl)ethanesulfonamide | Taken on directly to the next step as crude.<br>Using 2-aminobenzonitrile. |
| 242 | N-(4-methyl-2-cyanophenyl)-N-(methylsulfonyl)methanesulfonamide | $^1$H NMR (400 MHz, DMSO-d$_6$): δ ppm 2.44 (s, 3H), 3.50 (s, 6H), 7.35-7.37 (d, 1H), 7.48-7.50 (d, 1H), 7.59 (s, 1H).<br>Using 2-amino-5-methylbenzonitrile. |
| 243 | N-(2-cyanophenyl)-N-(phenylsulfonyl)benzenesulfonamide | MS m/z 399 [M + H]$^+$<br>$^1$H NMR (400 MHz, DMSO-d$_6$): δ ppm 7.18 (m, 1H), 7.65-7.88 (m, 12H), 8.02 (m, 1H). |

| Preparation Number | Name | Data/SM |
|---|---|---|
| 244 | N-(2-cyano-4-methoxyphenyl)-N-(methylsulfonyl)methanesulfonamide | Using 2-aminobenzonitrile and benzenesulfonyl chloride.<br>$^1$H NMR (400 MHz, DMSO-d$_6$): δ ppm 3.57 (s, 6H), 3.87 (s, 3H), 7.37 (dd, 1H), 7.65 (d, 1H), 7.75 (d, 1H).<br>Using 2-amino-4-methoxybenzonitrile and methanesulfonyl chloride. |
| 245 | N-(3-cyano-5-methyl-pyridin-2-yl)-N-(methylsulfonyl)methanesulfonamide | Taken directly on to the next step.<br>Using 2-amino-5-methylpyridine-3-carbonitrile and methanesulfonyl chloride. |
| 246 | N-(4-methoxy-2-cyanophenyl)-N-(phenylsulfonyl)benzenesulfonamide | Taken directly on to the next step.<br>Using 2-amino-5-methylpyridine-3-carbonitrile and methanesulfonyl chloride. |

Preparation 247

N-(2-Acetylphenyl)-N-methylmethanesulfonamide

To a solution of N-[2-(aminomethyl)phenyl]-N-methylmethanesulfonamide (Preparation 252, 10.5 g, 49 mmol) in acetone (250 mL) was added potassium carbonate (13.59 g, 98.47 mmol) and methyl iodide (6.13 mL, 98.47 mmol) at 0° C. followed by heating to 60° C. for 4 hours. The reaction was cooled and concentrated in vacuo. The residue was partitioned between EtOAc and water, the organic layer was collected, washed with brine, dried and concentrated in vacuo. The residue was purified using silica gel column chromatography eluting with 40% EtOAc in hexanes to afford the title compound (10 g, 89%). $^1$H NMR (400 MHz, DMSO-d$_6$): δ ppm 2.54 (s, 3H), 2.97 (s, 3H), 3.29 (s, 3H), 7.46 (m, 1H), 7.60-7.64 (m, 3H). MS m/z 228 [M+H]$^+$

Preparation 248

N-[3-(Aminomethyl)pyridin-4-yl]methanesulfonamide

The title compound was prepared according to the method described for Preparation 247 using 3-cyano-4-aminopyridine. $^1$H NMR (400 MHz, DMSO-d$_6$): δ ppm 2.92 (s, 3H), 7.31 (d, 1H), 7.99 (d, 1H), 8.66 (s, 1H), 13.14 (br s, 1H). MS m/z 198 [M+H]$^+$

Preparation 249

Benzyl [2-(aminomethyl)phenyl]methylcarbamate hydrochloride

To a solution of tert-butyl [2-(methylamino)benzyl]carbamate (WO2004/046107A1, 1.7 g, 7.2 mmol) in THF (25 mL) at 0° C. was added NaH (0.25 g, 10.8 mmol) followed by Cbz-chloride (1.22 g, 7.2 mmol) and catalytic DMAP (9 mg, 0.72 mmol). The reaction was heated to reflux for 2 hours before cooling, quenching with water and extracting into EtOAc. The organic extracts were dried over sodium sulfate, concentrated in vacuo and purified by silica gel column chromatography. The residue was dissolved in MeOH (10 mL) and 20% HCl in dioxane (10 mL) was added with stirring at room temperature for 18 hours. The reaction was concentrated in vacuo, and triturated with pentane and ether to afford the title compound as the hydrochloride salt (1.2 g, 91%). MS m/z 271 [M+H]$^+$

Preparation 250

5-Methoxy-2-(methylamino)benzonitrile

To a solution of 2-amino-5-methoxybenzonitrile (10 g, 67 mmol) in DMF (100 mL) was added tBuOK (9.46 g, 84 mmol) followed by dimethyl oxalate (11.95 g, 101 mmol) at 0° C. and the reaction was heated to 120° C. for 4 hours. The reaction was cooled, quenched by the addition of ice-water and extracted into EtOAc. The organic layer was collected, washed with brine, dried over sodium sulfate and concentrated in vacuo. The residue was purified using silica gel column chromatography to afford the title compound (2.9 g, 27%). $^1$H NMR (400 MHz, DMSO-d$_6$): δ ppm 2.72 (s, 3H), 3.67 (s, 3H), 5.77 (br s, 1H), 6.67 (d, 1H), 7.06 (d, 1H), 7.11 (dd, 1H).

Preparation 251 tert-Butyl 2-(2-oxooxazolidine-3-sulfonamido)benzylcarbamate

To a solution of chlorosulfonyl isocyanate (2 g, 8.99 mmol) in dry DCM (20 mL) at 0° C. was added bromoethanol (0.60 mL, 8.19 mmol) and the reaction was stirred at room temperature for 10 minutes. Triethylamine (2.74 mL, 19.79 mmol) in DCM was added followed by (2-aminobenzyl)-carbamic acid tert-butyl ester (1.9 g, 8.19 mmol) and the reaction stirred at room temperature for 18 hours. The reaction was quenched with water, extracted into DCM, the organic layer was collected, dried over sodium sulfate and concentrated in vacuo. The residue was purified using silica gel column chromatography eluting with 20% EtOAc in hexanes to afford the title compound (2.5 g, 75%). $^1$H NMR (400 MHz, DMSO-d$_6$): δ ppm 1.43 (s, 9H), 3.81 (t, 2H), 4.25 (m, 2H), 4.36 (t, 2H), 7.23-7.37 (m, 5H), 10.42 (br s, 1H).

Preparation 252

N-[2-(Aminomethyl)phenyl]-N-methylmethanesulfonamide

To a solution of 1-(2-aminophenyl)ethanone (2 g, 14.8 mmol) in pyridine (20 mL) at 0° C. was added methanesulfonyl chloride (4.6 mL, 59 mmol) and the reaction was stirred at room temperature for 18 hours. The reaction was concentrated in vacuo and partitioned between 2N HCl and EtOAc. The organic layer was collected, washed with brine, dried over sodium sulfate and concentrated in vacuo to afford the title compound as a brown solid (1.6 g, 51%). $^1$H NMR (400 MHz, DMSO-$d_6$): δ ppm 2.65 (s, 3H), 3.18 (s, 3H), 7.23 (t, 1H), 7.58-7.67 (m, 2H), 8.07 (d, 1H). MS m/z 212 [M−H]$^−$ Preparation 253

4-(2-(N-Ethylphenylsulfonamido)-5-methoxybenzyl)amino)-6-(5-fluoro-4-methoxy-2-(2,2,2-trifluoroethyl)phenyl)-1-((2-(trimethylsilyl)ethoxy)methyl)-1H-pyrazolo[3,4-d]pyrimidine-3-carboxamide To a solution of 4-((2-(N-ethylphenylsulfonamido)-5-hydroxybenzyl)amino)-6-(5-fluoro-4-hydroxy-2-(2,2,2-trifluoroethyl)phenyl)-1H-pyrazolo[3,4-d]pyrimidine-3-carboxylic acid (Preparation 259, 300 mg, 0.36 mmol) in anhydrous THF (4 mL) was added NMM (0.06 mL, 0.58 mmol) and isobutylchloroformate (0.07 mL, 0.58 mmol) at −20° C. and the reaction was stirred at this temperature for 30 minutes. Aqueous ammonia (0.2 mL) was added and the reaction stirred at room temperature for 30 minutes. The reaction was diluted with water and extracted into EtOAc. The organic layer was collected, washed with brine, dried over sodium sulfate and concentrated in vacuo. The residue was purified using silica gel column chromatography eluting with 40% EtOAc in hexanes to afford the title compound (180 mg, 60%). MS m/z 818 [M+H]$^+$ Preparation 254

4-((2-(N-Methylphenylsulfonamido)-5-methoxybenzyl)amino)-6-(5-fluoro-4-methoxy-2-(2,2,2-trifluoroethyl)phenyl)-1-((2-(trimethylsilyl)ethoxy)methyl)-1H-pyrazolo[3,4-d]pyrimidine-3-carboxamide The title compound was prepared according to the method described for Preparation 253 using 4-((2-(N-methylphenylsulfonamido)-5-hydroxybenzyl)amino)-6-(5-fluoro-4-hydroxy-2-(2,2,2-trifluoroethyl)phenyl)-1H-pyrazolo[3,4-d]pyrimidine-3-carboxylic acid (Preparation 260). MS m/z 804 [M+H]$^+$ Preparation 255 tert-Butyl 6-(4-((tert-butoxycarbonyl)oxy)-5-fluoro-2-(2,2,2-trifluoroethyl)phenyl)-4-((2-(methylamino)benzyl)amino)-3-(methylcarbamoyl)-1H-pyrazolo[3,4-d]pyrimidine-1-carboxylate To a solution of (2-(((6-(5-fluoro-4-methoxy-2-(2,2,2-trifluoroethyl)phenyl)-3-(methylcarbamoyl)-1H-pyrazolo[3,4-d]pyrimidin-4-yl)amino)methyl)phenyl)(methyl)carbamate (Preparation 256, 80 mg, 0.13 mmol) in anhydrous THF was added boron tribromide (0.08 mL, 0.9 mmol) at 0° C. and the reaction was stirred at this temperature for 2 hours. Another aliquot of boron tribromide was added (7eq) and the reaction continued stirring for a further 2 hours. The reaction was concentrated in vacuo and dissolved in DCM. The solution was washed with saturated aqueous sodium bicarbonate solution, brine, dried over sodium sulfate and concentrated in vacuo. The residue was purified using preparative TLC. The residue was dissolved in anhydrous THF (5 mL). To this solution at 0° C. was added triethylamine (0.04 mL, 0.3 mmol) followed by ditertbutyldicarbonate (0.05 mL, 0.21 mmol) and catalytic DMAP (1 mg, 0.008 mmol). The reaction was stirred at room temperature for 1 hour before concentrating in vacuo. The residue was purified by preparative TLC to afford the title compound. MS m/z 704 [M+H]$^+$ Preparation 256 tert-Butyl 6-(5-fluoro-4-methoxy-2-(2,2,2-trifluoroethyl)phenyl)-4-((2-(methylamino)benzyl)amino)-3-(methylcarbamoyl)-1H-pyrazolo[3,4-d]pyrimidine-1-carboxylate To a solution of benzyl (2-(((6-(5-fluoro-4-methoxy-2-(2,2,2-trifluoroethyl)phenyl)-3-(methylcarbamoyl)-1H-pyrazolo[3,4-d]pyrimidin-4-yl)amino)methyl)phenyl)(methyl)carbamate (Preparation 257, 150 mg, 0.23 mmol) in anhydrous THF (5 mL) at 0° C. was added triethylamine (0.08 mL, 0.575 mmol) followed by ditertbutyldicarbonate (60 mg, 0.27 mmol) and a catalytic amount of DMAP. The reaction was stirred at room temperature for 18 hours. The reaction was partitioned between EtOAc and brine, the organic layer collected, dried over sodium sulfate and concentrated in vacuo. The residue was purified using silica gel column chromatography eluting with 32% EtOAc in hexanes. The residue was dissolved in ethanol (15 mL) and was hydrogenated at 30 psi for 1 hour over 10% palladium on carbon (10 mg). The reaction was filtered through celite, concentrated in vacuo and purified using silica gel column chromatography eluting with 32% EtOAc in hexanes to afford the title compound as a white solid (50 mg, 80%). MS m/z 618 [M+H]$^+$ Preparation 257

Benzyl (2-(((6-(5-fluoro-4-methoxy-2-(2,2,2-trifluoroethyl)phenyl)-3-(methylcarbamoyl)-1H-pyrazolo[3,4-d]pyrimidin-4-yl)amino)methyl)phenyl)(methyl)carbamate The title compound was prepared according to the method described for Preparation 18 using benzyl (2-(((6-(5-fluoro-4-methoxy-2-(2,2,2-trifluoroethyl)phenyl)-3-iodo-1H-pyrazolo[3,4-d]pyrimidin-4-yl)amino)methyl)phenyl)(methyl)carbamate (Preparation 284). $^1$H NMR (400 MHz, DMSO-$d_6$): δ ppm 2.82 (s, 3H), 3.17 (s, 3H), 3.88 (s, 3H), 4.26-4.39 (m, 2H), 4.65 (m, 1H), 4.79-4.90 (m, 2H), 5.03 (m, 1H), 7.09-7.42 (m, 10H), 7.70 (m, 1H), 8.83 (t, 1H), 9.90 (t, 1H), 14.07 (s, 1H).

The following Preparations (Preparations 258-261) were prepared according to the method described for Preparation 11 using the appropriate pyrazolopyrimidine as described below.

| Preparation Number | Name | Data/SM |
|---|---|---|
| 258 | 6-(2-ethyl-5-fluoro-4-((2-(trimethylsilyl)ethoxy)methoxy)phenyl)- | MS m/z 835 [M − H]$^−$ N-(2-(((6-(2-ethyl-5-fluoro-4-((2- |

| Preparation Number | Name | Data/SM |
|---|---|---|
| | 4-((2-(N-methylphenylsulfonamido)benzyl)amino)-1-((2-(trimethylsilyl)ethoxy)methyl)-1H-pyrazolo-[3,4-d]pyrimidine-3-carboxylic acid | (trimethylsilyl)ethoxy)methoxy)phenyl)-3-iodo-1-((2-(trimethylsilyl)ethoxy)methyl)-1H-pyrazolo[3,4-d]pyrimidin-4-yl)amino)-methyl)phenyl)-N-methylbenzenesulfonamide (Preparation 262). |
| 259 | 4-((2-(N-ethylphenylsulfonamido)-5-methoxybenzyl)amino)-6-(5-fluoro-4-methoxy-2-(2,2,2-trifluoroethyl)phenyl)-1-((2-(trimethylsilyl)ethoxy)methyl)-1H-pyrazolo[3,4-d]pyrimidine-3-carboxylic acid | MS m/z 819 [M − H]⁻ N-ethyl-N-(2-(((6-(5-fluoro-4-methoxy-2-(2,2,2-trifluoroethyl)phenyl)-3-iodo-1-((2-(trimethylsilyl)ethoxy)methyl)-1H-pyrazolo[3,4-d]pyrimidin-4-yl)amino)methyl)-4-methoxyphenyl)benzenesulfonamide (Preparation 266). |
| 260 | 6-(5-fluoro-4-methoxy-2-(2,2,2-trifluoroethyl)phenyl)-4-((5-methoxy-2-(N-methylphenylsulfonamido)benzyl)amino)-1-((2-(trimethylsilyl)ethoxy)methyl)-1H-pyrazolo[3,4-d]pyrimidine-3-carboxylic acid | MS m/z 805 [M + H]⁺ N-methyl-N-(2-(((6-(5-fluoro-4-methoxy-2-(2,2,2-trifluoroethyl)phenyl)-3-iodo-1-((2-(trimethylsilyl)ethoxy)methyl)-1H-pyrazolo[3,4-d]pyrimidin-4-yl)amino)methyl)-4-methoxyphenyl)benzenesulfonamide (Preparation 267). |
| 261 | 6-(5-fluoro-2-(2,2,2-trifluoro-ethyl)-4-((2-(trimethylsilyl)-ethoxy)methoxy)phenyl)-4-((2-(N-methylphenylsulfonamido)benzyl)amino)-1-((2-(trimethylsilyl)ethoxy)-methyl)-1H-pyrazolo[3,4-d]pyrimidine-3-carboxylic acid | MS m/z 889 [M − H]⁻ N-(2-(((6-(5-fluoro-2-(2,2,2-trifluoroethyl)-4-((2-(trimethylsilyl)ethoxy)methoxy)phenyl)-3-iodo-1-((2-(trimethylsilyl)ethoxy)methyl)-1H-pyrazolo[3,4-d]pyrimidin-4-yl)amino)methyl)phenyl)-N-methylbenzenesulfonamide (Preparation 264). |

Preparation 262

N-(2-(((6-(2-Ethyl-5-fluoro-4-((2-(trimethylsilyl)ethoxy)methoxy)phenyl)-3-iodo-1-((2-(trimethylsilyl)ethoxy)methyl)-1H-pyrazolo[3,4-d]pyrimidin-4-yl)amino)methyl)phenyl-N-methylbenzenesulfonamide To a suspension of NaH (0.163 g, 6.79 mmol) in dry DMF (50 mL) was added N-(2-(((6-(4-((tert-butyldimethylsilyl)oxy)-2-ethyl-5-fluorophenyl)-3-iodo-1H-pyrazolo[3,4-d]pyrimidin-4-yl)amino)methyl)phenyl)-N-methylbenzenesulfonamide (Preparation 274, 2.1 g, 2.71 mmol) at 0° C. and the reaction stirred for 15 minutes. SEMCl was then added (1.06 mL, 5.97 mmol) and the reaction allowed to warm to room temperature. The reaction was quenched with water, partioned between EtOAc and brine, the organic layer collected, dried over sodium sulfate and concentrated in vacuo. The residue was purified using silica gel column chromatography to afford the title compound (760 mg, 43%). $^1$H NMR (400 MHz, DMSO-d$_6$): δ ppm −0.10 (s, 9H), −0.05 (s, 9H), 0.89 (m, 4H), 1.03 (t, 3H), 2.88 (m, 2H), 3.09 (s, 3H), 3.57 (t, 2H), 3.73 (t, 2H), 4.93 (m, 1H), 5.16 (m, 1H), 5.31 (s, 2H), 5.61 (s, 2H), 6.54 (m, 1H), 7.10 (d, 1H), 7.17 (t, 1H), 7.30 (t, 1H), 7.42 (m, 1H), 7.46 (m, 1H), 7.62-7.67 (m, 4H), 7.76 (m, 1H), 7.95 (s, 1H). MS m/z 919 [M+H]⁺

The following Preparations (Preparations 263-268) were prepared according to the method described for Preparation 131 using either DMF or THF and the appropriate pyrazolopyrimidine as described below.

| Preparation Number | Name | Data/SM |
|---|---|---|
| 263 | N-ethyl-N-(2-(((6-(5-fluoro-2-(2,2,2-trifluoroethyl)-4-((2-(trimethylsilyl)ethoxy)methoxy)phenyl)-3-iodo-1-((2-(trimethylsilyl)ethoxy)methyl)-1H-pyrazolo-[3,4-d]pyrimidin-4-yl)amino)-methyl)phenyl)methanesulfonamide | MS m/z 925 [M + H]⁺ N-(2-(((6-(4-((tert-butyldimethylsilyl)oxy)-5-fluoro-2-(2,2,2-trifluoroethyl)phenyl)-3-iodo-1H-pyrazolo[3,4-d]pyrimidin-4-yl)amino)methyl)phenyl)-N-ethylmethanesulfonamide (Preparation 280). |
| 264 | N-(2-(((6-(5-fluoro-2-(2,2,2-trifluoroethyl)-4-((2-(trimethyl-silyl)ethoxy)methoxy)phenyl)-3-iodo-1-((2-(trimethylsilyl)ethoxy)methyl)- | MS m/z 973 [M + H]⁺ N-(2-(((6-(4-((tert-butyldimethylsilyl)oxy)-5-fluoro-2-(2,2,2-trifluoroethyl)phenyl)-3-iodo-1H-pyrazolo[3,4-d]pyrimidin-4-yl)amino)methyl)phenyl)-N-methylbenzenesulfonamide |

| Preparation Number | Name | Data/SM |
|---|---|---|
| | 1H-pyrazolo[3,4-d]pyrimidin-4-yl)amino)methyl)phenyl)-N-methylbenzenesulfonamide | (Preparation 278). |
| 265 | N-(2-(((6-(4-((tert-butyldimethylsilyl)oxy)-5-fluoro-2-(2,2,2-trifluoroethyl)phenyl)-3-iodo-1-((2-(trimethylsilyl)ethoxy)methyl)-1H-pyrazolo[3,4-d]pyrimidin-4-yl)amino)methyl)phenyl)-N-(2-((tert-butyldimethylsilyl)oxy)ethyl)methanesulfonamide | Taken on directly to the next step. N-(2-(((6-(4-((tert-butyldimethylsilyl)oxy)-5-fluoro-2-(2,2,2-trifluoroethyl)phenyl)-3-iodo-1H-pyrazolo[3,4-d]pyrimidin-4-yl)amino)methyl)phenyl)-N-(2-((tert-butyldimethylsilyl)oxy)ethyl)methanesulfonamide (Preparation 279). |
| 266 | N-ethyl-N-(2-(((6-(5-fluoro-4-methoxy-2-(2,2,2-trifluoroethyl)phenyl)-3-iodo-1-((2-(trimethylsilyl)ethoxy)methyl)-1H-pyrazolo[3,4-d]pyrimidin-4-yl)amino)methyl)-4-methoxyphenyl)benzenesulfonamide | MS m/z 901 [M + H]$^+$ N-ethyl-N-(2-(((6-(5-fluoro-4-methoxy-2-(2,2,2-trifluoroethyl)phenyl)-3-iodo-1H-pyrazolo[3,4-d]pyrimidin-4-yl)amino)methyl)-4-methoxyphenyl)benzenesulfonamide (Preparation 281). |
| 267 | N-methyl-N-(2-(((6-(5-fluoro-4-methoxy-2-(2,2,2-trifluoroethyl)phenyl)-3-iodo-1-((2-(trimethylsilyl)ethoxy)methyl)-1H-pyrazolo[3,4-d]pyrimidin-4-yl)amino)methyl)-4-methoxyphenyl)benzenesulfonamide | MS m/z 885 [M − H]$^-$ N-methyl-N-(2-(((6-(5-fluoro-4-methoxy-2-(2,2,2-trifluoroethyl)phenyl)-3-iodo-1H-pyrazolo[3,4-d]pyrimidin-4-yl)amino)methyl)-4-methoxyphenyl)benzenesulfonamide (Preparation 282). |
| 268 | N-(4-fluoro-2-(((6-(5-fluoro-4-methoxy-2-(2,2,2-trifluoroethyl)phenyl)-3-iodo-1-((2-(trimethylsilyl)ethoxy)methyl)-1H-pyrazolo[3,4-d]pyrimidin-4-yl)amino)methyl)phenyl)-N-methylmethanesulfonamide | MS m/z 813 [M + H]$^+$ N-(4-fluoro-2-(((6-(5-fluoro-4-methoxy-2-(2,2,2-trifluoroethyl)phenyl)-3-iodo-1H-pyrazolo[3,4-d]pyrimidin-4-yl)amino)methyl)phenyl)-N-methylmethanesulfonamide (Preparation 283). |

Preparation 269

6-(5-Fluoro-4-methoxy-2-(2,2,2-trifluoroethyl)phenyl)-4-((5-methoxy-2-(N-methylmethylsulfonamido)benzyl)amino)-1-((2-(trimethylsilyl)ethoxy)methyl)-1H-pyrazolo[3,4-d]pyrimidine-3-carboxylic acid The title compound was prepared according to the methods described for Preparations 262 and 258 using N-(2-(((6-(5-fluoro-4-methoxy-2-(2,2,2-trifluoro-ethyl)phenyl)-3-iodo-1H-pyrazolo[3,4-d]pyrimidin-4-yl)amino)methyl)-4-methoxyphenyl)-N-methylmethanesulfonamide (Preparation 273). MS m/z 743 [M+H]$^+$ Preparation 270

6-(5-Fluoro-4-methoxy-2-(2,2,2-trifluoroethyl)phenyl)-4-((2-(N-methylmethylsulfonamido)-benzyl)amino)-1-((2-(trimethylsilyl)ethoxy)methyl)-1H-pyrazolo[3,4-d]pyrimidine-3-carboxylic acid The title compound was prepared according to the methods described for Preparations 262 and 258 using N-(2-(((6-(5-fluoro-4-methoxy-2-(2,2,2-trifluoroethyl)phenyl)-3-iodo-1H-pyrazolo[3,4-d]pyrimidin-4-yl)amino)methyl)phenyl)-N-methylmethanesulfonamide (Preparation 275). MS m/z 713 [M+H]$^+$ Preparation 271

N-(2-((6-(5-Fluoro-4-hydroxy-2-(2,2,2-trifluoroethyl)phenyl)-3-iodo-1H-pyrazolo[3,4-d]pyrimidin-4-yl)amino)methyl)-4-hydroxyphenyl)-N-methylmethanesulfonamide To a solution of N-(2-(((6-(5-fluoro-4-methoxy-2-(2,2,2-trifluoroethyl)phenyl)-3-iodo-1H-pyrazolo[3,4-d]pyrimidin-4-yl)amino)methyl)-4-methoxyphenyl)-N-methylmethane sulfonamide (Preparation 273, 300 mg, 0.43 mmol) in DCM (10 mL) at 0° C. was added boron tribromide (0.28 mL, 3.02 mmol). The reaction was stirred at room temperature for 30 minutes before concentrating in vacuo. The residue was partitioned between ethyl acetate and water, the organic layer was collected, dried and concentrated in vacuo. The residue was purified using silica gel column chromatography eluting with 10% MeOH in DCM to afford the title compound as a white solid (250 mg, 87%). $^1$H NMR (400 MHz, DMSO-d$_6$): δ ppm 3.02 (s, 3H), 3.12 (s, 3H), 4.11-4.21 (m, 2H), 4.80 (m, 1H), 4.94 (m, 1H), 6.67 (m, 1H), 6.76 (m, 1H), 6.97 (m, 1H), 7.29-7.33 (m, 2H), 7.57 (m, 1H), 9.58 (s, 1H), 10.36 (s, 1H), 13.88 (s, 1H). MS m/z 667 [M+H]$^+$ The following Preparations (Preparations 272-284) were prepared according to the method described for Preparation 137 in an organic solvent such as DCM or DMF and using the appropriate pyrazolopyrimidine as described below.

| Preparation Number | Name | Data/SM |
|---|---|---|
| 272 | N-(2-(((6-(4-(benzyloxy)-2-ethyl-5-fluorophenyl)-3-iodo-1H-pyrazolo[3,4-d]pyrimidin-4-yl)amino)methyl)phenyl)-N-methylmethanesulfonamide | MS m/z 687 [M + H]+<br>N-(2-(((6-(4-(benzyloxy)-2-ethyl-5-fluorophenyl)-1H-pyrazolo[3,4-d]pyrimidin-4-yl)amino)methyl)phenyl)-N-methylmethanesulfonamide (Preparation 285). |
| 273 | N-(2-(((6-(5-fluoro-4-methoxy-2-(2,2,2-trifluoroethyl)phenyl)-3-iodo-1H-pyrazolo[3,4-d]pyrimidin-4-yl)amino)methyl)-4-methoxyphenyl)-N-methylmethanesulfonamide | MS m/z 695 [M + H]+<br>N-(2-(((6-(5-fluoro-4-methoxy-2-(2,2,2-trifluoroethyl)phenyl)-1H-pyrazolo[3,4-d]pyrimidin-4-yl)amino)methyl)-4-methoxyphenyl)-N-methylmethanesulfonamide (Preparation 286). |
| 274 | N-(2-(((6-(4-((tert-butyldimethylsilyl)oxy)-2-ethyl-5-fluoro-phenyl)-3-iodo-1H-pyrazolo[3,4-d]pyrimidin-4-yl)amino)-methyl)phenyl)-N-methylbenzenesulfonamide | MS m/z 773 [M + H]+<br>$^1$H NMR (400 MHz, DMSO-d$_6$): δ ppm 0.18 (s, 6H), 0.93 (t, 3H), 0.95 (s, 9H), 2.81 (q, 2H), 3.06 (s, 3H), 4.89 (m, 1H), 5.17 (m, 1H), 6.53 (d, 1H), 7.14 (d, 1H), 7.18 (m, 1H), 7.31 (m, 1H), 7.33-7.45 (m, 3H), 7.61-7.66 (m, 4H), 7.76 (m, 1H).<br>N-(2-(((6-(4-((tert-butyldimethylsilyl)oxy)-2-ethyl-5-fluorophenyl)-1H-pyrazolo[3,4-d]pyrimidin-4-yl)amino)methyl)phenyl)-N-methylbenzenesulfonamide (Preparation 294). |
| 275 | N-(2-(((6-(5-fluoro-4-methoxy-2-(2,2,2-trifluoroethyl)phenyl)-3-iodo-1H-pyrazolo[3,4-d]pyrimidin-4-yl)amino)-methyl)phenyl)-N-methyl-methanesulfonamide | MS m/z 665 [M + H]+<br>N-(2-(((6-(5-fluoro-4-methoxy-2-(2,2,2-trifluoroethyl)phenyl)-1H-pyrazolo[3,4-d]pyrimidin-4-yl)amino)methyl)phenyl)-N-methylmethanesulfonamide (Preparation 287). |
| 276 | N-(2-(((6-(4-(benzyloxy)-5-fluoro-2-(2,2,2-trifluoroethyl)phenyl)-3-iodo-1H-pyrazolo[3,4-d]pyrimidin-4-yl)amino)methyl)phenyl)-N-methylmethanesulfonamide | MS m/z 741 [M + H]+<br>N-(2-(((6-(4-(benzyloxy)-5-fluoro-2-(2,2,2-trifluoroethyl)phenyl)-1H-pyrazolo[3,4-d]pyrimidin-4-yl)amino)methyl)phenyl)-N-methylmethanesulfonamide (Preparation 288). |
| 277 | N-(3-(((6-(5-fluoro-4-methoxy-2-(2,2,2-trifluoroethyl)phenyl)-3-iodo-1H-pyrazolo[3,4-d]pyrimidin-4-yl)amino)-methyl)pyrazin-2-yl)-N-methylmethanesulfonamide | MS m/z 665 [M − H]−<br>N-(3-(((6-(5-fluoro-4-methoxy-2-(2,2,2-trifluoroethyl)phenyl)-1H-pyrazolo[3,4-d]pyrimidin-4-yl)amino)methyl)pyrazin-2-yl)-N-methylmethanesulfonamide (Preparation 289). |
| 278 | N-(2-(((6-(4-((tert-butyldimethylsilyl)oxy)-5-fluoro-2-(2,2,2-trifluoroethyl)phenyl)-3-iodo-1H-pyrazolo[3,4-d]pyrimidin-4-yl)amino)-methyl)phenyl)-N-methylbenzenesulfonamide | MS m/z 827 [M + H]+<br>N-(2-(((6-(4-((tert-butyldimethylsilyl)oxy)-5-fluoro-2-(2,2,2-trifluoroethyl)phenyl)-1H-pyrazolo[3,4-d]pyrimidin-4-yl)amino)methyl)phenyl)-N-methylbenzenesulfonamide (Preparation 295). |
| 279 | N-(2-(((6-(4-((tert-butyldimethylsilyl)oxy)-5-fluoro-2-(2,2,2-trifluoroethyl)phenyl)-3-iodo-1H-pyrazolo[3,4-d]pyrimidin-4-yl)amino)-methyl)phenyl)-N-(2-((tert-butyldimethyl-silyl)oxy)ethyl)methanesulfonamide | MS m/z 909 [M + H]+<br>N-(2-(((6-(4-((tert-butyldimethylsilyl)oxy)-5-fluoro-2-(2,2,2-trifluoroethyl)phenyl)-1H-pyrazolo[3,4-d]pyrimidin-4-yl)amino)methyl)phenyl)-N-(2-((tert-butyldimethylsilyl)oxy)ethyl)methanesulfonamide (Preparation 296). |
| 280 | N-(2-(((6-(4-((tert-butyldimethylsilyl)oxy)-5-fluoro-2-(2,2,2-trifluoroethyl)phenyl)-3-iodo-1H-pyrazolo[3,4-d]pyrimidin-4-yl)amino)methyl)phenyl)-N-ethylmethanesulfonamide | MS m/z 779 [M + H]+<br>N-(2-(((6-(4-((tert-butyldimethylsilyl)oxy)-5-fluoro-2-(2,2,2-trifluoroethyl)phenyl)-1H-pyrazolo[3,4-d]pyrimidin-4-yl)amino)methyl)phenyl)-N-ethylmethanesulfonamide (Preparation 297). |
| 281 | N-ethyl-N-(2-(((6-(5-fluoro-4-methoxy-2-(2,2,2-trifluoroethyl)phenyl)-3-iodo-1H-pyrazolo[3,4-d]pyrimidin-4-yl)amino)methyl)-4-methoxyphenyl)benzenesulfonamide | MS m/z 771 [M + H]+<br>N-ethyl-N-(2-(((6-(5-fluoro-4-methoxy-2-(2,2,2-trifluoroethyl)phenyl)-1H-pyrazolo[3,4-d]pyrimidin-4-yl)amino)methyl)-4-methoxyphenyl)benzenesulfonamide (Preparation 290). |

| Preparation Number | Name | Data/SM |
|---|---|---|
| 282 | N-methyl-N-(2-(((6-(5-fluoro-4-methoxy-2-(2,2,2-trifluoroethyl)phenyl)-3-iodo-1H-pyrazolo[3,4-d]pyrimidin-4-yl)amino)methyl)-4-methoxyphenyl)benzenesulfonamide | MS m/z 757 [M + H]+ N-methyl-N-(2-(((6-(5-fluoro-4-methoxy-2-(2,2,2-trifluoroethyl)phenyl)-1H-pyrazolo[3,4-d]pyrimidin-4-yl)amino)methyl)-4-methoxyphenyl)benzenesulfonamide (Preparation 291). |
| 283 | N-(4-fluoro-2-(((6-(5-fluoro-4-methoxy-2-(2,2,2-trifluoroethyl)phenyl)-3-iodo-1H-pyrazolo[3,4-d]pyrimidin-4-yl)amino)methyl)phenyl)-N-methylmethanesulfonamide | MS m/z 683 [M + H]+ N-(4-fluoro-2-(((6-(5-fluoro-4-methoxy-2-(2,2,2-trifluoroethyl)phenyl)-1H-pyrazolo[3,4-d]pyrimidin-4-yl)amino)methyl)phenyl)-N-methylmethanesulfonamide (Preparation 292). |
| 284 | Benzyl (2-(((6-(5-fluoro-4-methoxy-2-(2,2,2-trifluoroethyl)phenyl)-3-iodo-1H-pyrazolo[3,4-d]pyrimidin-4-yl)amino)methyl)phenyl)(methyl)carbamate | MS m/z 721 [M + H]+ Benzyl (2-(((6-(5-fluoro-4-methoxy-2-(2,2,2-trifluoroethyl)phenyl)-1H-pyrazolo[3,4-d]pyrimidin-4-yl)amino)methyl)phenyl)(methyl)carbamate (Preparation 293). |

The following Preparations (Preparations 285-293) were prepared according to the method described for Preparation 140 using either 4M HCl in dioxane or cHCl in MeOH with the appropriate pyrazolopyrimidine as described below.

| Preparation Number | Name | Data/SM |
|---|---|---|
| 285 | N-(2-(((6-(4-(benzyloxy)-2-ethyl-5-fluorophenyl)-1H-pyrazolo[3,4-d]pyrimidin-4-yl)amino)methyl)phenyl)-N-methylmethanesulfonamide | MS m/z 561 [M + H]+ N-(2-(((6-(4-(benzyloxy)-2-ethyl-5-fluorophenyl)-1-(tetrahydro-2H-pyran-2-yl)-1H-pyrazolo[3,4-d]pyrimidin-4-yl)amino)methyl)phenyl)-N-methylmethanesulfonamide (Preparation 299). |
| 286 | N-(2-(((6-(5-fluoro-4-methoxy-2-(2,2,2-trifluoroethyl)phenyl)-1H-pyrazolo[3,4-d]pyrimidin-4-yl)amino)methyl)-4-methoxyphenyl)-N-methylmethanesulfonamide | MS m/z 569 [M + H]+ N-(2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)-4-methoxyphenyl)-N-methylmethanesulfonamide (Preparation 300). |
| 287 | N-(2-(((6-(5-fluoro-4-methoxy-2-(2,2,2-trifluoroethyl)phenyl)-1H-pyrazolo[3,4-d]pyrimidin-4-yl)amino)methyl)phenyl)-N-methylmethanesulfonamide | MS m/z 539 [M + H]+ N-(2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)phenyl)-N-methylmethanesulfonamide (Preparation 302). |
| 288 | N-(2-(((6-(4-(benzyloxy)-5-fluoro-2-(2,2,2-trifluoroethyl)phenyl)-1H-pyrazolo[3,4-d]pyrimidin-4-yl)amino)methyl)phenyl)-N-methylmethanesulfonamide | MS m/z 615 [M + H]+ N-(2-(((6-(4-(benzyloxy)-5-fluoro-2-(2,2,2-trifluoroethyl)phenyl)-1-(tetrahydro-2H-pyran-2-yl)-1H-pyrazolo[3,4-d]pyrimidin-4-yl)amino)methyl)phenyl)-N-methylmethanesulfonamide (Preparation 303). |
| 289 | N-(3-(((6-(5-fluoro-4-methoxy-2-(2,2,2-trifluoroethyl)phenyl)-1H-pyrazolo[3,4-d]pyrimidin-4-yl)amino)methyl)pyrazin-2-yl)-N-methylmethanesulfonamide | MS m/z 541 [M + H]+ N-(3-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)pyrazin-2-yl)-N-methylmethanesulfonamide (Preparation 304). |
| 290 | N-ethyl-N-(2-(((6-(5-fluoro-4-methoxy-2-(2,2,2-trifluoroethyl)phenyl)-1H-pyrazolo[3,4-d]pyrimidin-4-yl)amino)methyl)-4-methoxy-phenyl)benzenesulfonamide | MS m/z 645 [M + H]+ N-ethyl-N-(2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)-4-methoxyphenyl)benzenesulfonamide (Preparation 308). |
| 291 | N-methyl-N-(2-(((6-(5-fluoro-4-methoxy-2-(2,2,2-trifluoroethyl)phenyl)-1H- | MS m/z 631 [M + H]+ N-methyl-N-(2-(((6-(5-fluoro-4-methoxy-2-(2,2,2-trifluoroethyl)phenyl)-1-(tetrahydro- |

| Preparation Number | Name | Data/SM |
|---|---|---|
| | pyrazolo[3,4-d]pyrimidin-4-yl)amino)methyl)-4-methoxyphenyl)benzenesulfonamide | 2H-pyran-2-yl)-1H-pyrazolo[3,4-d]pyrimidin-4-yl)amino)methyl)-4-methoxyphenyl)benzenesulfonamide (Preparation 309). |
| 292 | N-(4-fluoro-2-(((6-(5-fluoro-4-methoxy-2-(2,2,2-trifluoroethyl)phenyl)-1H-pyrazolo[3,4-d]pyrimidin-4-yl)amino)methyl)phenyl)-N-methylmethanesulfonamide | MS m/z 557 [M + H]$^+$ N-(4-fluoro-2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)phenyl)-N-methylmethanesulfonamide (Preparation 310). |
| 293 | Benzyl (2-(((6-(5-fluoro-4-methoxy-2-(2,2,2-trifluoroethyl)phenyl)-1H-pyrazolo[3,4-d]pyrimidin-4-yl)amino)methyl)phenyl)(methyl)carbamate | MS m/z 595 [M + H]$^+$ Benzyl (2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)phenyl)(methyl)carbamate (Preparation 311). |

Preparation 294

N-(2-(((6-(4-((tert-Butyldimethylsilyl)oxy)-2-ethyl-5-fluorophenyl-1H-pyrazolo[3,4-d]pyrimidin-4-yl)amino)methyl)phenyl)-N-methylbenzenesulfonamide N-(2-(((6-(2-ethyl-5-fluoro-4-((2-(trimethylsilyl)ethoxy)methoxy)phenyl)-1-(tetrahydro-2H-pyran-2-yl)-1H-pyrazolo[3,4-d]pyrimidin-4-yl)amino)methyl)phenyl)-N-methylbenzene sulfonamide (Preparation 301, 2.6 g, 3.48 mmol) was treated with TFA (5 mL) and the reaction stirred at room temperature for 30 minutes before concentrating in vacuo. The residue was diluted with methanol (20 mL), cooled in ice-water and treated with a drop-wise addition of ethylene diamine until the solution became basic. The solution was concentrated in vacuo and purified using silica gel column chromatography eluting with EtOAc. The residue (1.7 g, 3.19 mmol) was dissolved in anhydrous THF (10 mL) and 2,6 lutidine (0.55 mL, 4.78 mmol) was added followed by TBDMS-triflate (0.88 mL, 3.83 mmol) at 0° C. The reaction was stirred for 18 hours. The reaction was concentrated in vacuo and partitioned between water and ethyl acetate. The organic phase was washed with brine, dried over sodium sulfate, concentrated in vacuo and purified by silica gel column chromatography eluting with 20% EtOAc in hexanes to afford the title compound as a white solid (1.9 g, 92%). MS m/z 647 [M+H]$^+$ The following Preparations (Preparations 295-297) were prepared according to the method described for Preparation 294 using the appropriate pyrazolopyrimidine as described below.

| Preparation Number | Name | SM |
|---|---|---|
| 295 | N-(2-(((6-(4-((tert-butyldimethylsilyl)oxy)-5-fluoro-2-(2,2,2-trifluoro-ethyl)phenyl)-1H-pyrazolo[3,4-d]pyrimidin-4-yl)amino)methyl)phenyl)-N-methylbenzenesulfonamide | MS m/z 701 [M + H]$^+$ N-(2-(((6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidin-4-yl)amino)methyl)phenyl)-N-methylbenzenesulfonamide (Preparation 305). |
| 296 | N-(2-(((6-(4-((tert-butyldimethylsilyl)oxy)-5-fluoro-2-(2,2,2-trifluoro-ethyl)phenyl)-1H-pyrazolo[3,4-d]pyrimidin-4-yl)amino)methyl)phenyl)-N-(2-((tert-butyldimethyl-silyl)oxy)ethyl)methanesulfonamide | MS m/z 783 [M + H]$^+$ N-(2-(((6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidin-4-yl)amino)methyl)phenyl)-N-(2-((tetrahydro-2H-pyran-2-yl)oxy)ethyl)methanesulfonamide (Preparation 316). |
| 297 | N-(2-(((6-(4-((tert-butyl-dimethylsilyl)oxy)-5-fluoro-2-(2,2,2-trifluoro-ethyl)phenyl)-1H-pyrazolo[3,4-d]pyrimidin-4-yl)amino)methyl)phenyl)-N-ethylmethanesulfonamide | MS m/z 653 [M + H]$^+$ N-ethyl-N-(2-(((6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidin-4-yl)amino)methyl)phenyl)methanesulfonamide (Preparation 307). |

Preparation 298

4-Chloro-6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidine To a solution of 4-(benzyloxy)-6-(5-fluoro-2-(2,2,2-trifluoroethyl)-4-((2-(trimethyl-silyl)ethoxy)methoxy)phenyl)-1-(tetrahydro-2H-pyran-2-yl)-1H-pyrazolo[3,4-d]pyrimidine (Preparation 306, 12.5 g, 19.75 mmol) in THF (100 mL) was added 10% palladium on carbon (1.5 g) and the reaction was hydrogenated at 50 psi for 18 hours. The reaction was filtered and the filtrate was concentrated in vacuo. The residue was purified using silica gel column chromatography to afford a white solid. 5 g (9.22 mmol) was dissolved in DMF (50 mL) and cooled to 0° C. Oxalyl chloride (7.96 mL, 92 mmol) was added and the reaction stirred at room temperature for 6 hours. The reaction was quenched with water and extracted into EtOAc. The organic layer was collected, dried over sodium sulfate and concentrated in vacuo. The residue was purified using silica gel column chromatography to afford the title compound (1.2 g, 23%). MS m/z 561 [M+H]$^+$

Preparation 299

N-(2-(((6-(4-(Benzyloxy)-2-ethyl-5-fluorphenyl)-1-(tetrahydro-2H-pyran-2-yl)-1H-pyrazolo[3,4-d]pyrimidin-4-yl)amino)methyl)phenyl)-N-methylmethanesulfonamide A solution of palladium acetate (42 mg, 0.19 mmol) and S-Phos (77 mg, 0.19 mmol) in ethanol (10 mL) was heated at 50° C. for 45 minutes after purging with nitrogen (Solution A). Meanwhile a solution of N-(2-(((6-chloro-1-(tetrahydro-2H-pyran-2-yl)-1H-pyrazolo[3,4-d]pyrimidin-4-yl)amino)methyl)phenyl)-N-methylmethanesulfonamide (Preparation 312, 1.7 g, 3.77 mmol) in ethanol (30 mL) was treated with 2-(4-(benzyloxy)-2-ethyl-5-fluorophenyl)-4,4,5,5-tetramethyl-1,3,2-dioxaborolane (Preparation 323, 1.83 g, 5.13 mmol) and an aqueous solution of potassium phosphate (1.6 g, 7.54 mmol) in water (12 mL) This solution was purged with nitrogen for 10 minutes (Solution B). Solution A was added to Solution B and the mixture heated at 80° C. for 18 hours. The reaction was cooled, concentrated in vacuo. The resulting black solid was suspended in ethyl acetate filtered through celite. The filtrate was concentrated in vacuo, the residue was taken up in EtOAc, washed with water, brine, dried over sodium sulfate and concentrated in vacuo. The residue was purified by silica gel column chromatography eluting with 40% EtOAc in hexanes to afford the title compound as a fluffy white solid (1.58 g, 65%). $^1$H NMR (400 MHz, DMSO-ds): δ ppm 1.02 (m, 3H), 1.55 (m, 2H), 1.74 (m, 1H), 1.85 (m, 1H), 2.00 (m, 1H), 2.43 (m, 1H), 2.84 (m, 2H), 3.07 (s, 3H), 3.16 (s, 3H), 3.63 (m, 1H), 3.93 (m, 1H), 4.75 (br m, 1H), 5.00 (br m, 1H), 5.22 (s, 2H), 5.85 (m, 1H), 7.10 (m, 1H), 7.30-7.54 (m, 10H), 8.22 (s, 1H), MS m/z 645 [M+H]$^+$ The following Preparations (Preparations 300-311) were prepared according to the method described for Preparation 299 using the appropriate chloro-pyrazolopyrimidine and arylboronic ester as described below.

| Preparation Number | Name | Data | SM |
| --- | --- | --- | --- |
| 300 | N-(2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)-4-methoxyphenyl)-N-methylmethanesulfonamide | $^1$H NMR (400 MHz, DMSO-d$_6$): δ ppm 1.56 (m, 2H), 1.73 (m, 1H), 1.89 (m, 1H), 1.98-2.01 (m, 1H), 2.42-2.50 (m, 1H), 3.04 (s, 3H), 3.13 (s, 3H), 3.66 (m, 4H), 3.88 (s, 3H), 3.93 (m, 1H), 4.29-4.34 (m, 2H), 4.70 (m, 1H), 5.00 (m, 1H), 5.87 (m, 1H), 6.91 (m, 2H), 7.23 (d, 1H), 7.48 (d, 1H), 7.78 (m, 1H), 8.24 (s, 1H), 8.85 (t, 1H). | 2-[5-fluoro-4-methoxy-2-(2,2,2-trifluoroethyl)phenyl]-4,4,5,5-tetramethyl-1,3,2-dioxaborolane (WO2013/014567A1) and N-(2-(((6-chloro-1-(tetrahydro-2H-pyran-2-yl)-1H-pyrazolo[3,4-d]pyrimidin-4-yl)amino)methyl)-4-methoxyphenyl)-N-methylmethanesulfonamide (Preparation 314). |
| 301 | N-(2-(((6-(2-ethyl-5-fluoro-4-((2-(trimethylsilyl)ethoxy)methoxy)phenyl)-1-(tetrahydro-2H-pyran-2-yl)-1H-pyrazolo[3,4-d]pyrimidin-4-yl)amino)methyl)phenyl)-N-methylbenzenesulfonamide | MS m/z 747 [M + H]$^+$ | N-(2-(((6-chloro-1-(tetrahydro-2H-pyran-2-yl)-1H-pyrazolo[3,4-d]pyrimidin-4-yl)amino)methyl)phenyl)-N-methylbenzenesulfonamide (Preparation 313) and 2-[2-ethyl-5-fluoro-4-[[2-(trimethylsilyl)ethoxy]methoxy]phenyl]-4,4,5,5-tetramethyl-1,3,2-dioxaborolane (WO2013/014567A1). |
| 302 | N-(2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)phenyl)- | MS m/z 623 [M + H]$^+$ $^1$H NMR (400 MHz, DMSO-d$_6$): δ ppm 1.56 (m, 2H), 1.73 (m, 1H), 1.86 (m, 1H), 2.04 (m, 2H), 3.08 (s, 3H), 3.18 (s, 3H), 3.65 (m, 1H), | N-(2-(((6-chloro-1-(tetrahydro-2H-pyran-2-yl)-1H-pyrazolo[3,4-d]pyrimidin-4-yl)amino)methyl)phenyl)-N-methylmethanesulfonamide |

| Preparation Number | Name | Data | SM |
|---|---|---|---|
|  | N-methylmethanesulfonamide | 3.88 (s, 3H), 3.92-3.96 (m, 1H), 4.30-4.38 (m, 2H), 4.75 (br s, 1H), 5.00 (br s, 1H), 5.87 (m, 1H), 7.20 (m, 1H), 7.30-7.38 (m, 3H), 7.54 (m, 1H), 7.70-7.73 (m, 1H), 8.24 (s, 1H), 8.90 (t, 1H). | (Preparation 312) and 2-[5-fluoro-4-methoxy-2-(2,2,2-trifluoroethyl)phenyl]-4,4,5,5-tetramethyl-1,3,2-dioxaborolane (WO2013/014567A1). |
| 303 | N-(2-(((6-(4-(benzyloxy)-5-fluoro-2-(2,2,2-trifluoro-ethyl)phenyl)-1-(tetrahydro-2H-pyran-2-yl)-1H-pyrazolo[3,4-d]pyrimidin-4-yl)amino)methyl)phenyl)-N-methylmethanesulfonamide | $^1$H NMR (400 MHz, DMSO-$d_6$): δ ppm 1.56 (m, 2H), 1.74 (m, 1H), 1.89 (m, 1H), 2.00 (m, 2H), 3.07 (s, 3H), 3.16 (s, 3H), 3.67 (m, 1H), 3.93 (m, 1H), 4.22-4.37 (m, 2H), 4.80 (br m, 1H), 5.00 (br m, 1H), 5.23 (s, 2H), 5.86 (m, 1H), 7.29-7.55 (m, 10H), 7.73 (m, 1H), 8.24 (s, 1H), 8.89 (t, 1H). | N-(2-(((6-chloro-1-(tetrahydro-2H-pyran-2-yl)-1H-pyrazolo[3,4-d]pyrimidin-4-yl)amino)methyl)phenyl)-N-methylmethanesulfonamide (Preparation 312) and 2-(4-(benzyloxy)-5-fluoro-2-(2,2,2-trifluoroethyl)phenyl)-4,4,5,5-tetramethyl-1,3,2-dioxaborolane (Preparation 325). |
| 304 | N-(3-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)pyrazin-2-yl)-N-methyl-methanesulfonamide | MS m/z 625 [M + H]$^+$ $^1$H NMR (400 MHz, DMSO-$d_6$): δ ppm 1.56 (m, 2H), 1.65 (m, 1H), 1.89 (m, 1H), 2.00 (m, 1H), 2.49 (m, 1H), 3.13 (s, 3H), 3.18 (s, 3H), 3.66 (m, 1H), 3.88 (m, 4H), 4.25-4.30 (m, 2H), 5.03 (m, 2H), 5.85 (m, 1H), 7.19 (m, 1H), 7.58 (m, 1H), 8.29 (s, 1H), 8.53 (d, 1H), 8.60 (m, 1H), 9.03 (t, 1H). | N-(3-(((6-chloro-1-(tetrahydro-2H-pyran-2-yl)-1H-pyrazolo[3,4-d]pyrimidin-4-yl)amino)methyl)pyrazin-2-yl)-N-methylmethanesulfonamide (Preparation 315) and 2-[5-fluoro-4-methoxy-2-(2,2,2-trifluoroethyl)phenyl]-4,4,5,5-tetramethyl-1,3,2-dioxaborolane (WO2013/014567A1). |
| 305 | N-(2-(((6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidin-4-yl)amino)-methyl)phenyl)-N-methyl-benzenesulfonamide | MS m/z 801 [M + H]$^+$ | N-(2-(((6-chloro-1-(tetrahydro-2H-pyran-2-yl)-1H-pyrazolo[3,4-d]pyrimidin-4-yl)amino)methyl)phenyl)-N-methylbenzene-sulfonamide (Preparation 313) and (2-{[2-fluoro-4-(4,4,5,5-tetramethyl-1,3,2-dioxaborolan-2-yl)-5-(2,2,2-trifluoroethyl)-phenoxy]methoxy}ethyl)(trimethyl)silane (Preparation 150). |
| 306 | 4-(benzyloxy)-6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidine | MS m/z 634 [M + H]$^+$ $^1$H NMR (400 MHz, DMSO-$d_6$): δ ppm −0.01 (s, 9H), 0.89 (t, 2H), 1.583 (m, 2H), 1.75 (m, 1H), 1.92-2.05 (m, 2H), 2.44 (m, 1H), 3.67 (m, 1H), 3.77 (t, 2H), 4.01 (m, 1H), 4.34-4.47 (m, 2H), 5.39 (s, 2H), 5.70 (s, 2H), 5.95 (m, 1H), 7.36-7.54 (m, 6H), 8.01 (m, 1H), 8.34 (s, 1H). | 4-(benzyloxy)-6-chloro-1-(tetrahydro-2H-pyran-2-yl)-1H-pyrazolo[3,4-d]pyrimidine (Preparation 322) and (2-{[2-fluoro-4-(4,4,5,5-tetramethyl-1,3,2-dioxaborolan-2-yl)-5-(2,2,2-trifluoroethyl)-phenoxy]methoxy}ethyl)(trimethyl)silane (Preparation 150). |
| 307 | N-ethyl-N-(2-(((6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidin-4-yl)amino)- | MS m/z 753 [M + H]$^+$ $^1$H NMR (400 MHz, DMSO-$d_6$): δ ppm −0.05 (s, 9H), 0.80 (t, 2H), 1.00 (t, 3H), 1.56 (m, 2H), 1.75 (m, 1H), 1.98 (m, 1H), 2.04 (m, 1H), 2.49 (m, 1H), | N-(2-(((6-chloro-1-(tetrahydro-2H-pyran-2-yl)-1H-pyrazolo[3,4-d]pyrimidin-4-yl)amino)methyl)phenyl)-N-ethylmethane-sulfonamide (Preparation 317) |

| Preparation Number | Name | Data | SM |
|---|---|---|---|
| | methyl)phenyl)methane-sulfonamide | 3.06 (s, 3H), 3.54 (m, 1H), 3.57-3.76 (m, 4H), 3.93 (m, 1H), 4.20 (m, 2H), 4.85 (m, 1H), 5.00 (m, 1H), 5.32 (s, 2H), 5.87 (m, 1H), 7.29-7.39 (m, 4H), 7.52 (m, 1H), 7.66 (m, 1H), 8.26 (s, 1H), 8.91 (t, 1H). | and (2-{[2-fluoro-4-(4,4,5,5-tetramethyl-1,3,2-dioxaborolan-2-yl)-5-(2,2,2-trifluoroethyl)-phenoxy]methoxy}ethyl)(trimethyl)silane (Preparation 150). |
| 308 | N-ethyl-N-(2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)-4-methoxyphenyl)benzene-sulfonamide | MS m/z 729 [M + H]$^+$ $^1$H NMR (400 MHz, DMSO-d$_6$): δ ppm 0.93 (t, 3H), 1.57 (m, 2H), 1.75 (m, 1H), 1.90 (m, 1H), 2.01 (m, 1H), 2.43 (m, 1H), 3.21 (m, 1H), 3.63-3.68 (m, 4H), 3.79-3.96 (m, 4H), 4.05-4.35 (m, 2H), 4.81 (m, 1H), 4.99 (m, 1H), 5.90 (m, 1H), 6.50 (m, 1H), 6.75 (m, 1H), 6.90 (m, 1H), 7.25 (m, 1H), 7.60-7.80 (m, 6H), 8.30 (s, 1H), 8.85 (t, 1H). | N-(2-(((6-chloro-1-(tetrahydro-2H-pyran-2-yl)-1H-pyrazolo[3,4-d]pyrimidin-4-yl)amino)methyl)-4-methoxyphenyl)-N-ethylbenzenesulfonamide (Preparation 318) and 2-[5-fluoro-4-methoxy-2-(2,2,2-trifluoroethyl)phenyl]-4,4,5,5-tetramethyl-1,3,2-dioxaborolane (WO2013/014567A1). |
| 309 | N-methyl-N-(2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)-4-methoxyphenyl)benzene-sulfonamide | MS m/z 715 [M + H]$^+$ $^1$H NMR (400 MHz, DMSO-d$_6$): δ ppm 1.56 (m, 2H), 1.74 (m, 1H), 1.98 (m, 1H), 2.00 (m, 1H), 2.50 (m, 1H), 3.33 (s, 3H), 3.63-3.68 (m, 4H), 3.88-3.96 (m, 4H), 4.25-4.40 (m, 2H), 4.73 (m, 1H), 5.03 (m, 1H), 5.86 (m, 1H), 6.45 (m, 1H), 6.71 (m, 1H), 6.92 (m, 1H), 7.22 (m, 1H), 7.61-7.79 (m, 6H), 8.26 (s, 1H), 8.90 (t, 1H). | N-(2-(((6-chloro-1-(tetrahydro-2H-pyran-2-yl)-1H-pyrazolo[3,4-d]pyrimidin-4-yl)amino)methyl)-4-methoxyphenyl)-N-methylbenzenesulfonamide (Preparation 319) and 2-[5-fluoro-4-methoxy-2-(2,2,2-trifluoroethyl)phenyl]-4,4,5,5-tetramethyl-1,3,2-dioxaborolane (WO2013/014567A1). |
| 310 | N-(4-fluoro-2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)phenyl)-N-methylmethanesulfonamide | $^1$H NMR (400 MHz, DMSO-d$_6$): δ ppm 1.56 (m, 2H), 1.74 (m, 1H), 1.86 (m, 1H), 2.01 (m, 1H), 2.42 (m, 1H), 3.08 (s, 3H), 3.16 (s, 3H), 3.60 (m, 1H), 3.88 (s, 3H), 3.96 (m, 1H), 4.03-4.31 (m, 2H), 4.76 (m, 1H), 5.01 (m, 1H), 5.88 (m, 1H), 7.11-7.22 (m, 3H), 7.61-7.71 (m, 2H), 8.24 (s, 1H), 8.93 (t, 1H). | N-(2-(((6-chloro-1-(tetrahydro-2H-pyran-2-yl)-1H-pyrazolo[3,4-d]pyrimidin-4-yl)amino)methyl)-4-fluoro-phenyl)-N-methylmethanesulfonamide (Preparation 320) and 2-[5-fluoro-4-methoxy-2-(2,2,2-trifluoroethyl)-phenyl]-4,4,5,5-tetra-methyl-1,3,2-dioxa-borolane (WO2013/014567A1). |
| 311 | Benzyl (2-(((6-(5-fluoro-4-methoxy-2-(2,2,2-trifluoroethyl)phenyl)-1-(tetrahydro-2H-pyran-2-yl)-1H-pyrazolo[3,4-d]pyrimidin-4-yl)amino)methyl)phenyl)-(methyl)carbamate | $^1$H NMR (400 MHz, DMSO-d$_6$): δ ppm 1.56 (m, 2H), 1.73 (m, 1H), 1.85 (m, 1H), 2.01 (m, 1H), 2.42 (m, 1H), 3.18 (s, 3H), 3.69 (m, 1H), 3.87 (s, 3H), 3.93 (m, 1H), 4.27-4.50 (m, 2H), 4.57 (m, 1H), 4.75 (m, 1H), 4.93-5.03 (m, 2H), 5.86 (m, 1H), 7.12-7.39 (m, 10H), 7.71 (m, 1H), 8.22 (s, 1H), 8.85 (t, 1H). | benzyl (2-(((6-chloro-1-(tetrahydro-2H-pyran-2-yl)-1H-pyrazolo[3,4-d]pyrimidin-4-yl)amino)methyl)phenyl)(methyl)carbamate (Preparation 321) and 2-[5-fluoro-4-methoxy-2-(2,2,2-trifluoroethyl)phenyl]-4,4,5,5-tetramethyl-1,3,2-dioxaborolane (WO2013/014567A1). |

Preparation 312

N-(2-(((6-Chloro-1-(tetrahydro-2H-pyran-2-yl)-1H-pyrazolo[3,4-d]pyrimidin-4-yl)amino)methyl)phenyl)-N-methylmethanesulfonamide To a stirred solution of 4,6-dichloro-1-(tetrahydro-2H-pyran-2-yl)-1H-pyrazolo[3,4-d]pyrimidine (WO20131014567A1, 3 g, 10.99 mmol) in anhydrous n-butanol (12 mL), containing DIPEA (6.69 mL, 38.45 mmol) was added N-[2-(aminomethyl)phenyl]-N-methylmethane sulphonamide hydrochloride (WO20101058846A1, 2.76 g, 10.98 mmol) and the reaction was heated in a sealed tube at 90° C. for 16 hours. The reaction was concentrated in vacuo and the residue partitioned between water & ethyl acetate. The organic extracts were washed with brine, dried over sodium sulfate, concentrated in vacuo and triturated with pentane-ether to afford the title compound as an off white solid (3.5 g, 71%). $^1$H NMR (400 MHz, DMSO-$d_6$): δ ppm 1.17 (m, 2H), 1.70 (m, 1H), 1.81 (m, 1H), 1.98 (m, 1H), 2.36 (m, 1H), 3.09 (s, 3H), 3.25 (s, 3H), 3.66 (m, 1H), 3.94 (m, 1H), 4.60 (br m, 1H), 4.90 (br m, 1H), 5.72 (m, 1H), 7.33-7.42 (m, 3H), 7.56 (m, 1H), 8.22 (s, 1H), 9.26 (m, 1H).

The following Preparations (Preparations 313-321) were prepared according to the method described for Preparation 312 using 4,6-dichloro-1-(tetrahydro-2H-pyran-2-yl)-1H-pyrazolo[3,4-d]pyrimidine (WO20131014567A1) or other suitable pyrazolopyrimidine and benzylamine as described below.

| Preparation Number | Name | Data | SM |
|---|---|---|---|
| 313 | N-(2-(((6-chloro-1-(tetrahydro-2H-pyran-2-yl)-1H-pyrazolo[3,4-d]pyrimidin-4-yl)amino)methyl)phenyl)-N-methylbenzenesulfonamide | $^1$H NMR (400 MHz, DMSO-$d_6$): δ ppm 1.54 (m, 2H), 1.71 (m, 1H), 1.84 (m, 1H), 1.98 (m, 1H), 2.32 (m, 1H), 3.19 (s, 3H), 3.75 (m, 1H), 3.90 (m, 1H), 0.89 (br m, 1H), 5.00 (br m, 1H), 5.75 (m, 2H), 6.58 (m, 1H), 7.19 (t, 1H), 7.35 (t, 1H), 7.45 (m, 1H), 7.63-7.78 (m, 5H), 8.23 (s, 1H), 9.30 (m, 1H). | N-[2-(aminomethyl)phenyl]-N-methylbenzenesulfonamide hydrochloride (Preparation 190). |
| 314 | N-(2-(((6-chloro-1-(tetra-hydro-2H-pyran-2-yl)-1H-pyrazolo[3,4-d]pyrimidin-4-yl)amino)methyl)-4-methoxyphenyl)-N-methyl-methanesulfonamide | MS m/z 481 [M + H]$^+$ $^1$H NMR (400 MHz, DMSO-$d_6$): δ ppm 1.54 (m, 2H), 1.73 (m, 1H), 1.84 (m, 1H), 1.98 (m, 1H), 2.37 (m, 1H), 3.06 (s, 3H), 3.21 (s, 3H), 3.63-3.77 (m, 4H), 3.94 (m, 1H), 4.54 (m, 1H), 4.95 (m, 1H), 5.74 (m, 1H), 6.94 (m, 2H), 7.48 (m, 1H), 8.22 (s, 1H), 9.22 (t, 1H). | N-[2-(aminomethyl)-4-methoxyphenyl]-N-(methylsulfonyl)methanesulfonamide hydrochloride (Preparation 191). |
| 315 | N-(3-(((6-chloro-1-(tetrahydro-2H-pyran-2-yl)-1H-pyrazolo[3,4-d]pyrimidin-4-yl)amino)methyl)pyrazin-2-yl)-N-methylmethanesulfonamide | MS m/z 453 [M + H]$^+$ $^1$H NMR (400 MHz, DMSO-$d_6$): δ ppm 1.54 (m, 2H), 1.73 (m, 1H), 1.85 (m, 1H), 1.98 (m, 1H), 2.33 (m, 1H), 3.15 (s, 3H), 3.31 (s, 3H), 3.66 (m, 1H), 3.90 (m, 1H), 4.90 (m, 2H), 5.73 (m, 1H), 8.24 (s, 1H), 8.54 (m, 1H), 8.62 (m, 1H), 9.44 (t, 1H). | N-(3-(aminomethyl)pyrazin-2-yl)-N-methylmethanesulfonamide hydrochloride (WO2008/129380A1). |
| 316 | N-(2-(((6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidin-4-yl)amino)methyl)phenyl)-N-(2-((tetrahydro-2H-pyran-2-yl)oxy)ethyl)methane-sulfonamide | MS m/z 854 [M + H]$^+$ | 4-chloro-6-(5-fluoro-2-(2,2,2-trifluoroethyl)-4-((2-(trimethylsilyl)ethoxy)methoxy)phenyl)-1-(tetrahydro-2H-pyran-2-yl)-1H-pyrazolo[3,4-d]pyrimidine (Preparation 298) and N-[2-(aminomethyl)-phenyl]-N-[2-(tetra-hydro-2H-pyran-2-yloxy)ethyl]-methane-sulfonamide (Preparation 216). |
| 317 | N-(2-(((6-chloro-1-(tetra-hydro-2H-pyran-2-yl)-1H-pyrazolo[3,4-d]pyrimidin-4-yl)amino)methyl)phenyl)- | MS m/z 465 [M + H]$^+$ | N-[2-(aminomethyl)phenyl]-N-ethylmethanesulfonamide hydrochloride (Preparation 188). |

| Preparation Number | Name | Data | SM |
|---|---|---|---|
| 318 | N-ethylmethanesulfonamide N-(2-(((6-chloro-1-(tetrahydro-2H-pyran-2-yl)-1H-pyrazolo[3,4-d]pyrimidin-4-yl)amino)methyl)-4-methoxyphenyl)-N-ethylbenzenesulfonamide | MS m/z 557 [M + H]$^+$ | N-[2-(aminomethyl)-4-methoxyphenyl]-N-ethylbenzenesulfonamide hydrochloride (Preparation 196). |
| 319 | N-(2-(((6-chloro-1-(tetra-hydro-2H-pyran-2-yl)-1H-pyrazolo[3,4-d]pyrimidin-4-yl)amino)methyl)-4-methoxyphenyl)-N-methylbenzenesulfona | MS m/z 543 [M + H]$^+$ | N-[2-(aminomethyl)-4-methoxyphenyl]-N-methylbenzenesulfonamide hydrochloride (Preparation 195). |
| 320 | N-(2-(((6-chloro-1-(tetra-hydro-2H-pyran-2-yl)-1H-pyrazolo[3,4-d]pyrimidin-4-yl)amino)methyl)-4-fluorophenyl)-N-methylmethanesulfonamide | MS m/z 469 [M + H]$^+$ | N-[2-(aminomethyl)-4-fluorophenyl]-N-methyl-methanesulfonamide hydrochloride (Preparation 186). |
| 321 | benzyl (2-(((6-chloro-1-(tetra-hydro-2H-pyran-2-yl)-1H-pyrazolo[3,4-d]pyrimidin-4-yl)amino)methyl)phenyl)(methyl)carbamate | MS m/z 507 [M + H]$^+$ | Benzyl [2-(aminomethyl)phenyl]methylcarbamate hydrochloride (Preparation 249). |

Preparation 322

4-(Benzyloxy)-6-chloro-1-(tetrahydro-2H-pyran-2-yl)-1H-pyrazolo[3,4-d]pyrimidine To a suspension of NaH (0.48 g, 20.13 mmol) in THF (50 mL) at 0° C. was added benzyl alcohol (1.98 g, 18.30 mol) slowly. The mixture was allowed to stir for 45 minutes at 0° C. followed by the addition of 4,6-dichloro-1-(tetrahydro-2H-pyran-2-yl)-1H-pyrazolo[3,4-d]pyrimidine (WO20131014567A1, 5 g, 18.30 mmol). The reaction was stirred at room temperature for 2 hours before being quenched with brine. The solution was extracted into EtOAc, washed with brine, dried over sodium sulfate and concentrated in vacuo. The residue was purified by silica gel column chromatography to afford the title compound (3.4 g, 54%). $^1$H NMR (400 MHz, DMSO-d$_6$): δ ppm 1.56 (m, 2H), 1.74-1.78 (m, 1H), 1.87-1.91 (m, 1H), 1.98-2.02 (m, 1H), 2.33-2.43 (m, 1H), 3.71 (m, 1H), 3.92 (m, 1H), 5.62 (s, 2H), 5.86 (m, 1H), 7.38 (m, 3H), 7.55 (m, 2H), 8.37 (s, 1H). MS m/z 345 [M+H]$^+$ Preparation 323

2-(4-(Benzyloxy)-2-ethyl-5-fluorophenyl)-4,4,5,5-tetramethyl-1,3,2-dioxaborolane The title compound was prepared according to the method described for Preparation 150 using 1-(benzyloxy)-4-bromo-5-ethyl-2-fluorobenzene (Preparation 324). Taken on directly to the next step.

Preparation 324

1-(Benzyloxy)-4-bromo-5-ethyl-2-fluorobenzene

To a solution of 4-bromo-5-ethyl-2-fluorophenol (WO20131014567A1, 3 g, 13.69 mmol) in acetone (30 mL) was added benzyl bromide (2.57 g, 15.06 mmol) and the reaction heated to reflux with potassium carbonate (2.83 g, 20.54 mmol) for 18 hours. The reaction was filtered, concentrated in vacuo and purified using silica gel column chromatography eluting with 5% EtOAc in hexanes to afford the title compound as a colorless oil (3.20 g, 76%). $^1$H NMR (400 MHz, DMSO-ds): δ ppm 1.13 (t, 3H), 2.62 (q, 2H), 5.18 (s, 2H), 7.26-7.51 (m, 7H).

Preparation 325

2-(4-(Benzyloxy)-5-fluoro-2-(2,2,2-trifluoroethyl)phenyl)-4,4,5,5-tetramethyl-1,3,2-dioxaborolane The title compound was prepared according to the methods described for Preparations 323 and 324 using 4-bromo-2-fluoro-5-(2,2,2-trifluoroethyl)phenol (Preparation 326). Taken on directly to the next step.

Preparation 326

4-Bromo-2-fluoro-5-(2,2,2-trifluoroethyl)phenol

To a solution of 1-bromo-5-fluoro-4-methoxy-2-(2,2,2-trifluoroethyl)benzene (WO20131014567A1, 88.5 g, 308.31 mmol) at 0° C. in DCM (2000 mL), was added boron tribromide (204.56 mL, 2158.17 mmol) and the reaction was stirred at room temperature for 18 hours. The reaction was quenched by the addition of cold water dropwise at 0° C. The organic layer was separated, the aqueous extracts washed twice with DCM, the organic extracts combined, washed with brine, dried, concentrated in vacuo and triturated with pentane to afford the title compound as a white solid (78 g, 93%). $^1$H NMR (400 MHz, DMSO-d$_6$): δ ppm 3.66-3.74 (m, 2H), 7.10 (d, 1H), 7.52 (d, 1H), 10.50 (br s, 1H).

Preparation 327

N-(2-(Benzyloxy)ethyl)-N-(2-(((6-(2-ethyl-5-fluoro-4-((2-(trimethylsilyl)ethoxy)-methoxy)phenyl-1-((2-(trimethyl)ethoxymethyl)-1H-pyrazolo[4,3-c]pyridin-4-yl)amino)methyl)phenyl)methanesulfonamide A solution of 6-(2-ethyl-5-fluoro-4-((2-(trimethylsilyl)ethoxy)methoxy)phenyl)-1-((2-(trimethylsilyl)ethoxy)methyl)-1H-pyrazolo[4,3-c]pyridin-4-yl trifluoromethanesulfonate (Preparation 331, 100 mg, 0.15 mmol), N-(2-(aminomethyl)phenyl)-N-(2-(benzyloxy)ethyl)methanesulfonamide hydrochloride (Preparation 366, 64 mg, 0.225 mmol) and triethylamine (62 µL, 0.45 mmol) in DMF (2 mL) was heated to between 80-90° C. for 36 hours. The reaction was cooled and partitioned between EtOAc (50 mL) and water (50 mL). The organic layer was collected, further washed with water and brine, dried over sodium sulfate and concentrated in vacuo. The residue was purified using silica gel column chromatography eluting with EtOAc in heptanes to afford the title compound (51 mg, 40%). $^1$H NMR (400 MHz, CDCl$_3$): δ ppm 0.00 (s, 9H), 0.50 (s, 9H), 0.95 (m, 3H), 1.05 (m, 3H), 1.15 (m, 3H), 2.80 (m, 2H), 3.10 (s, 3H), 3.50 (m, 1H), 3.60 (m, 4H), 3.80 (m, 1H), 3.90 (m, 2H), 4.05-4.20 (m, 1H), 4.60 (m, 2H), 5.15 (m, 1H), 5.20 (s, 2H), 5.60 (s, 2H), 6.15 (m, 1H), 6.80 (s, 1H), 7.10-7.40 (m, 10H), 7.70 (m, 1H), 7.90 (s, 1H). MS m/z 851 [M+H]$^+$

Preparation 328

6-(2-Ethyl-4-((2-(trimethylsilyl)ethoxy)methoxy)phenyl)-1-((2-(trimethylsilyl)ethoxy)methyl)-1H-pyrazolo[4,3-c]pyridin-4-yl trifluoromethanesulfonate Triflic anhydride (0.21 mL, 1.25 mmol) was added dropwise to a solution of 6-(2-ethyl-4-((2-(trimethylsilyl)ethoxy)methoxy)phenyl)-1-((2-(trimethylsilyl)ethoxy)methyl)-1H-pyrazolo[4,3-c]pyridin-4-ol (Preparation 329, 495 mg, 0.96 mmol) and pyridine (0.34 mL, 4.2 mmol) in DCM (5 mL) at 0° C. The reaction was stirred at room temperature for 4 hours. The reaction was diluted with water (45 mL), acidified to pH=3 with citric acid and extracted with EtOAc (2×45 mL). The organic layers were combined, washed with a dilute solution of citric acid at pH=3 (45 mL), saturated aqueous NaHCO$_3$ solution, brine, dried over sodium sulfate and concentrated in vacuo to afford the title compound that was used directly in the next reaction.

Preparation 329

6-(2-Ethyl-4-((2-(trimethylsilyl)ethoxy)methoxy)phenyl)-1-((2-(trimethylsilyl)ethoxy)methyl)-1H-pyrazolo[4,3-c]pyridin-4-ol To a solution of 6-(2-ethyl-4-((2-(trimethylsilyl)ethoxy)methoxy)phenyl)-1-((2-(trimethylsilyl)ethoxy)methyl)-1H-pyrazolo[4,3-c]pyridine 5-oxide (Preparation 333, 8 g, 15.5 mmol) in THF (160 mL) was added TEA (3.13 g, 31 mmol) dropwise, followed by the addition of acetic anhydride (23.7 g, 232.5 mmol) dropwise at room temperature. The reaction was heated to 65° C. for 18 hours. The reaction was cooled and quenched by the addition of saturated aqueous NaHCO$_3$ solution (60 mL), and stirred for 10 hours. The reaction was diluted with water and extracted into EtOAc. The organic layer was collected, washed with brine, dried over sodium sulfate and concentrated in vacuo. The residue was purified using silica gel column chromatography to afford the title compound as an oil (5 g, 63%). $^1$H NMR (400 MHz, CDCl$_3$): δ ppm −0.06 (s, 9H), 0.0 (s, 9H), 0.84-0.88 (m, 2H), 0.94-0.98 (m, 2H), 1.12-1.16 (m, 3H), 2.62-2.64 (m, 2H), 3.55-3.59 (m, 2H), 3.75-3.79 (m, 2H), 5.26 (s, 2H), 5.57 (s, 2H), 6.42 (s, 1H), 6.92-6.96 (m, 1H), 6.99 (s, 1H), 7.21-7.25 (m, 1H), 8.14 (s, 1H), 9.15 (s, 1H). MS m/z 516 [M+H]$^+$

Preparation 330

6-(2-Ethyl-5-fluoro-4-((2-(trimethylsilyl)ethoxy)methoxy)phenyl)-1-(tetrahydro-2H-pyran-2-yl)-1H-pyrazolo[4,3-c]pyridin-4-yl trifluoromethanesulfonate The title compound was prepared according to the methods described for Preparations 328 and 329 using 6-(2-ethyl-5-fluoro-4-{[2-(trimethylsilyl)-ethoxy]methoxy}phenyl)-1-(tetrahydro-2H-pyran-2-yl)-1H-pyrazolo[4,3-c]pyridine 5-oxide (Preparation 332). $^1$H NMR (400 MHz, DMSO-d$_6$): δ ppm −0.01 (s, 9H), 0.91 (t, 2H), 1.04 (t, 3H), 1.59 (m, 2H), 1.71 (m, 1H), 2.30 (m, 2H), 2.37 (m, 2H), 2.70 (m, 2H), 3.78 (t, 3H), 3.90 (d, 1H), 5.36 (s, 2H), 6.05 (d, 1H), 7.25 (d, 1H), 7.35 (d, 1H), 8.10 (s, 1H), 8.52 (s, 1H).

Preparation 331

6-(2-Ethyl-5-fluoro-4-((2-(trimethylsilyl)ethoxy)methoxy)phenyl)-1-((2-(trimethylsilyl)ethoxy)methyl)-1H-pyrazolo[4,3-c]pyridin-4-yl trifluoromethanesulfonate The title compound was prepared according to the methods described for Preparations 328 and 329 using 6-(2-ethyl-5-fluoro-4-((2-(trimethylsilyl)-ethoxy)methoxy)phenyl)-1-((2-(trimethylsilyl)ethoxy)methyl)-1H-pyrazolo[4,3-c]pyridine 5-oxide (Preparation 335). Used directly in the next reaction.

Preparation 332

6-(2-Ethyl-5-fluoro-4-{[2-(trimethylsilyl)ethoxy]methoxy}phenyl)-1-(tetrahydro-2H-pyran-2-yl)-1H-pyrazolo[4,3-c]pyridine 5-oxide To a stirred solution of 6-[2-ethyl-5-fluoro-4-{[2-(trimethylsilyl)-ethoxy]-methoxy}phenyl]-1-(tetrahydro-2H-pyran-2-yl)-1H-pyrazolo[4,3-c]pyridine (Preparation 147, 24 g, 50.88 mmol) in anhydrous DCM (300 mL) was added mCPBA (33.52 g, 117 mmol) and the reaction was stirred at room temperature for 18 hours. The reaction was quenched with saturated aqueous NaHCO$_3$ solution and extracted into DCM. The organic layer was collected, washed with brine, dried over sodium sulfate and concentrated in vacuo. The residue was purified using silica gel column chromatography eluting with 10% heptanes in EtOAc to afford the title compound as a yellow solid (14.5 g, 58%). $^1$H NMR (400 MHz, DMSO-d$_6$): δ ppm 0.01 (s, 9H), 0.91-0.95 (t, 2H), 1.00-1.01 (t, 3H), 1.56 (s, 2H), 1.66-1.69 (m, 1H), 1.95. 1.98 (m, 2H), 2.28-2.36 (m, 3H), 3.69-3.80 (m, 3H), 3.71-3.80 (m, 3H), 3.86 (d, 1H), 5.34 (s, 2H), 5.94 (d, 1H), 7.16-7.23 (m, 2H), 7.94 (s, 1H), 8.20 (s, 1H), 8.91 (s, 1H). MS m/z 488 [M+H]$^+$

Preparation 333

6-(2-Ethyl-4-((2-(trimethylsilyl)ethoxy)methoxy)phenyl)-1-((2-(trimethylsilyl)ethoxy)methyl)-1H-pyrazolo[4,3-c]pyridine 5-oxide To a solution of 6-(2-ethyl-4-((2-(trimethylsilyl)ethoxy)methoxy)phenyl)-1-((2-(trimethylsilyl)-ethoxy)methyl)-1H-pyrazolo[4,3-c]pyridine (Preparation 336, 7 g, 14 mmol) in DCM (100 mL) was added m-CPBA (5.6 g, 28 mmol) at room temperature, and the reaction was stirred for 5 hours. The reaction was washed with 10% aqueous $NaHSO_3$ solution and saturated aqueous $NaHCO_3$ solution. The organic layer was separated, dried over sodium sulfate and concentrated in vacuo to afford the title compound (7 g, 97%). $^1$H NMR (400 MHz, $CDCl_3$): δ ppm 0.01 (s, 9H), 0.09 (s, 9H), 0.92-0.96 (m, 2H), 1.03-1.07 (m, 2H), 1.17-1.21 (m, 3H), 2.41-2.56 (m, 1H), 2.68-2.81 (m, 1H), 3.62-3.66 (m, 2H), 3.82-3.87 (m, 2H), 5.33 (s, 2H), 5.75 (s, 2H), 6.99-7.08 (m, 1H), 7.12 (m, 1H), 7.24 (d, 1H), 7.57 (d, 1H), 7.57 (d, 1H), 8.12 (s, 1H). MS m/z 516 [M+H]$^+$

Preparation 334

6-(5-Fluoro-4-methoxy-2-(2,2,2-trifluoroethyl)phenyl)-1-((2-(trimethylsilyl)ethoxy)methyl)-1H-pyrazolo[4,3-c]pyridine 5-oxide The title compound was prepared according to the method described for Preparation 111 using 6-(5-fluoro-4-methoxy-2-(2,2,2-trifluoroethyl)phenyl)-1-((2-(trimethylsilyl)ethoxy)-methyl)-1H-pyrazolo[4,3-c]pyridine (Preparation 337). MS m/z 472 [M+H]$^+$

Preparation 335

6-(2-Ethyl-5-fluoro-4-((2-(trimethylsilyl)ethoxy)methoxy)phenyl)-1-((2-(trimethylsilyl)ethoxy)methyl)-1H-pyrazolo[4,3-c]pyridine 5-oxide The title compound was prepared according to the method described for Preparation 111 using 6-(2-ethyl-5-fluoro-4-((2-(trimethylsilyl)ethoxy)methoxy)phenyl)-1-((2-(trimethylsilyl)-ethoxy)methyl)-1H-pyrazolo[4,3-c]pyridine (Preparation 338). MS m/z 534 [M+H]$^+$

Preparation 336

6-(2-Ethyl-4-((2-(trimethylsilyl)ethoxy)methoxy)phenyl)-1-((2-(trimethylsilyl)ethoxy)methyl)-1H-pyrazolo[4,3-c]pyridine To a solution of 6-chloro-1-((2-(trimethylsilyl)ethoxy)methyl)-1H-pyrazolo[4,3-c]pyridine (Preparation 340, 6.7 g, 23.67 mmol) in DMSO (120 mL) was added (2-((3-ethyl-4-(4,4,5,5-tetramethyl-1,3,2-dioxaborolan-2-yl)phenoxy)methoxy)ethyl)trimethylsilane (Preparation 343, 9.8 g, 26.03 mmol), potassium phosphate (18.88 g, 71.01 mmol) and water (12 mL) at room temperature. Pd(PPh$_3$)$_4$ (2.7 g, 2.3 mmol) was added, the reaction degassed under vacuum and refilled with nitrogen, and heated to 100° C. for 18 hours. The reaction was poured into ice water (200 mL) and extracted with EtOAc. The organic layer was washed with brine, dried over sodium sulfate and concentrated in vacuo. The residue was purified by silica gel column chromatography to afford the title compound as a yellow oil (6 g, 51%). Taken on directly to the next step.

Preparation 337

6-(5-Fluoro-4-methoxy-2-(2,2,2-trifluoroethyl)phenyl)-1-((2-(trimethylsilyl)ethoxy)methyl)-1H-pyrazolo[4,3-c]pyridine The title compound was prepared according to the method described for Preparation 336 using 2-[5-fluoro-4-methoxy-2-(2,2,2-trifluoroethyl)phenyl]-4,4,5,5-tetramethyl-1,3,2-dioxaborolane (WO20131014567A1) and 6-chloro-1-((2-(trimethylsilyl)ethoxy)methyl)-1H-pyrazolo[4,3-c]pyridine (Preparation 340). $^1$H NMR (400 MHz, $CDCl_3$): δ ppm 0.00 (s, 9H), 0.95 (m, 2H), 3.62 (m, 2H), 3.82 (q, 2H), 4.02 (s, 3H), 5.80 (s, 2H), 7.10 (m, 1H), 7.30 (m, 1H), 7.60 (s, 1H), 8.25 (s, 1H), 9.12 (s, 1H).

Preparation 338

6-(2-Ethyl-5-fluoro-4-((2-(trimethylsilyl)ethoxy)methoxy)phenyl)-1-((2-(trimethylsilyl)ethoxy)methyl)-1H-pyrazolo[4,3-c]pyridine The title compound was prepared according to the method described for Preparation 336 using (2-{[2-fluoro-4-(4,4,5,5-tetramethyl-1,3,2-dioxaborolan-2-yl)-5-ethylphenoxy]methoxy}ethyl)(trimethyl)-silane (WO20131014567A1) and 6-chloro-1-((2-(trimethylsilyl)ethoxy)methyl)-1H-pyrazolo[4,3-c]pyridine (Preparation 340). $^1$H NMR (400 MHz, $CDCl_3$): δ ppm 0.10 (s, 9H), 0.10 (s, 9H), 0.93-1.00 (m, 2H), 1.04-1.08 (m, 2H), 1.13-1.22 (m, 3H), 2.76 (q, 2H), 3.66 (m, 2H), 3.91 (m, 2H), 5.38 (s, 2H), 5.82 (s, 2H), 7.21-7.25 (m, 2H), 7.56 (s, 1H), 8.24 (s, 1H), 9.21 (s, 1H). MS m/z 518 [M+H]$^+$

Preparation 339

N-(2-(((6-Chloro-1-(tetrahydro-2H-pyran-2-yl)-1H-pyrazolo[4,3-c]pyridin-4-yl)amino)methyl)phenyl)-N-methylmethanesulfonamide The title compound was prepared according to the method described for Preparation 312 using 4,6-dichloro-1-(tetrahydro-2H-pyran-2-yl)-1H-pyrazolo[4,3-c]pyridine (Preparation 341) and N-[2-(aminomethyl)phenyl]-N-methylmethanesulfonamide (WO20101058846A1). $^1$H NMR (400 MHz, DMSO-d$_6$): δ ppm 1.55 (m, 2H), 1.69 (m, 1H), 1.88-2.00 (m, 2H), 2.29 (m, 1H), 3.04 (s, 1H), 3.27 (s, 3H), 3.69 (m, 1H), 3.85 (m, 1H), 4.55 (br m, 1H), 4.91 (br m, 1H), 5.67 (m, 1H), 6.91 (s, 1H), 7.32-7.52 (m, 4H), 8.24 (s, 1H), 8.29 (t, 1H). MS m/z 449 [M+H]$^+$

Preparation 340

6-Chloro-1-((2-(trimethylsilyl)ethoxy)methyl)-1H-pyrazolo[4,3-c]pyridine

To a solution of 6-chloro-1H-pyrazolo[4,3-c]pyridine (8.5 g, 55 mmol) in anhydrous THF (200 mL) was added NaH (60% dispersion in oil, 2.3 g, 58 mmol) at 0° C. After stirring at room temperature for 20 minutes, SEMCl (9.67 g, 58.06 mmol) was added dropwise at 0° C. The reaction was stirred at room temperature for 2 hours before quenching with water and extracting into EtOAc. The organic layer was separated, dried over Na$_2$SO$_4$ and concentrated in vacuo.

The residue was purified by silica gel column chromatography to afford the title compound as a yellow oil (14 g, 90%). Taken on directly to the next step.

Preparation 341

4,6-Dichloro-1-(tetrahydro-2H-pyran-2-yl)-1H-pyrazolo[4,3-c]pyridine

The title compound was prepared according to the method described for Preparation 149 using 4,6-dichloro-1H-pyrazolo[4,3-c]pyridine. $^1$H NMR (400 MHz, DMSO-d$_6$): δ ppm 1.58-1.61 (m, 3H), 1.97-2.03 (m, 2H), 2.31-2.34 (m, 1H), 3.76-3.80 (s, 1H), 3.84-3.91 (m, 1H), 5.92-5.95 (d, 1H), 8.07 (s, 1H), 8.46 (s, 1H). MS m/z 272 [M+H]$^+$ Preparation 342

2-((4-Benzyloxy)-2-ethyl-6-methylphenyl-4,4,5,5-tetramethyl-1,3,2-dioxaborolane

To a solution of 3-ethyl-4-iodo-5-methylphenol (J. Med. Chem. (2005), 48(2), 586-592, 500 mg, 1.90 mmol) in acetone (20 mL) was added benzylbromide (1.43 mL, 2.86 mmol) and potassium carbonate (658 mg, 4.77 mol). The reaction was heated to 70° C. for 18 hours. The reaction was cooled, filtered and concentrated in vacuo. The residue was dissolved in EtOAc and washed with water, brine, dried over sodium sulfate and concentrated in vacuo. The residue was purified by silica gel column chromatography eluting with hexanes. The residue was dissolved in anhydrous DMSO (1.6 mL) and bis(pinacolonato)diboron (1032 mg, 4.06 mmol) and KOAc (543 mg, 5.54 mmol) were added The reaction was purged under argon for 10 minutes before the addition of Pd(dppf)$_2$Cl$_2$ (135 mg, 0.18 mmol) followed by degassing for another 10 minutes and then heating to 80° C. for 18 hours. The reaction was cooled, concentrated in vacuo and suspended in EtOAc. The suspension was filtered through celite and the filtrate washed with water, dried over sodium sulfate and concentrated in vacuo. The residue was purified using silica gel column chromatography eluting with 5% EtOAc in hexanes to afford the title compound. $^1$H NMR (400 MHz, DMSO-d$_6$): δ ppm 1.10 (t, 3H), 1.30 (s, 12H), 2.28 (s, 3H), 2.60 (q, 2H), 5.06 (s, 2H), 6.63 (m, 2H), 7.31-7.44 (m, 5H).

Preparation 343

(2-((3-Ethyl-4-(4,4,5,5-tetramethyl-1,3,2-dioxaborolan-2-yl)phenoxy)methoxy)ethyl)trimethylsilane To a solution of (2-((4-bromo-3-ethylphenoxy)methoxy)ethyl)trimethylsilane (Preparation 344, 300 mg, 0.9 mmol) in dioxane (5 mL) was added bispinacolatodiboron (276 mg, 1.09 mmol), Pd(PPh$_3$)$_4$ (105 mg, 0.09 mmol) and potassium phosphate (384 mg, 1.81 mmol) and the reaction was heated to 80° C. for 18 hours. The reaction was cooled and partitioned between water and EtOAc, eluted though a phase separation cartridge and concentrated in vacuo. The residue was purified using silica gel column chromatography eluting with 0-50% DCM in heptanes to afford the title compound. Taken on directly to the next step.

Preparation 344

(2-((4-Bromo-3-ethylphenoxy)methoxy)ethyl)trimethylsilane

To a solution of 4-bromo-3-ethylphenol (9 g, 44.8 mmol) in DCM (100 mL) was added DIPEA (8.6 mL, 49.3 mmol) followed by SEMCl (8.73 mL, 49.3 mmol) and the reaction was stirred at room temperature for 18 hours. The reaction was washed with water, 1N aqueous HCl solution and saturated aqueous sodium hydrogen carbonate solution, brine, dried over sodium sulfate and concentrated in vacuo. The residue was purified using silica gel column chromatography eluting with 3% EtOAc in hexanes to afford the title compound. $^1$H NMR (400 MHz, CDCl$_3$): δ ppm 0.00 (s, 9H), 0.90 (m, 2H), 1.25 (m, 3H), 2.75 (m, 2H), 3.75 (m, 2H), 5.20 (s, 2H), 6.80 (m, 1H), 7.00 (d, 1H), 7.40 (d, 1H).

Preparation 345

6-(4-Methyl-1H-imidazol-1-yl)-1,2,3,4-tetrahydroisoquinoline hydrochloride

To a solution of 6-fluoro-3,4-dihydro-2H-isoquinolin-1-one (13 g, 79 mmol) in DMSO (150 mL) was added 4-methylimidazole (7.8 g, 95 mmol) followed by cesium carbonate (38 g, 118.5 mmol) and the reaction was heated to 125° C. for 18 hours. The reaction was cooled and extracted into chloroform/isopropanol (v:v 3:1, 500 mL) three times. The organic layers were combined, washed with brine, dried over sodium sulfate and concentrated in vacuo. A portion of the residue (9 g, 39.6 mmol) was dissolved in THF and cooled to 0° C. LiAlH$_4$ (3 g, 79.2 mmol) was added portionwise, and the reaction heated to 60° C. for 18 hours. The reaction was cooled and quenched by the addition of 10% NaOH solution (6 mL), before filtration and concentration in vacuo. The residue was purified by silica gel column chromatography eluting with 30-100% EtOAc in petroleum ether followed by the addition of 2N HCl in EtOAc. The resulting precipitate was filtered to afford the title compound as the hydrochloride salt (11.6 g, 42%). $^1$H NMR (400 MHz, DMSO-d$_6$): δ ppm 2.34 (s, 3H), 3.08 (m, 2H), 3.37 (m, 2H), 4.30 (m, 2H), 7.48 (m, 1H), 7.62-7.68 (m, 2H), 8.00 (s, 1H), 9.61 (s, 1H), 9.91 (br s, 2H).

Preparation 346

N-(2-(Pyrrolidin-1-yl)ethyl)-1,2,3,4-tetrahydroisoquinoline-7-sulfonamide

To a solution of 1,2,3,4-tetrahydro-2-(2,2,2-trufluoroacetyl)-7-isoquinoline sulfonyl chloride (400 mg, 1.2 mmol) in MeOH (5 mL) was added 2-(pyrrolidin-1-yl)ethanamine in excess and the reaction stirred at room temperature for 30 minutes. Water (1 mL) followed by potassium carbonate (150 mg, 1.4 mmol) were added and the reaction stirred at room temperature for 18 hours. The reaction was concentrated in vacuo and the residue dissolved in DCM. The suspension was filtered and the filtrate purified by silica gel column chromatography eluting with 10-100% (90:10:1 DCM:MeOH:NH$_3$) in DCM to afford the title compound (130 mg, 35%). MS m/z 310 [M+H]$^+$ Preparation 347

N-Benzyl-1,2,3,4-tetrahydroisoquinoline-5-carboxamide hydrochloride

To a solution of 2-(tert-butoxycarbonyl)-1,2,3,4-tetrahydroisoquinoline-5-carboxylic acid (200 mg, 0.721 mmol) and DIPEA (87 μL, 0.793 mmol) in DCM (10 mL) was added HBTU (301 mg, 0.793 mmol) followed by a solution of benzylamine (151 μL 0.865 mmol) in DCM (5 mL) and the reaction was stirred at room temperature for 72 hours.

The reaction was washed with water (1 mL), 1N HCl (aq) (1 mL) and 1N NaOH (aq) (1 mL). The organic layer was dried over sodium sulfate and concentrated in vacuo. The residue was dissolved in MeOH (5 mL) and 4N HCl in dioxane (3 mL) was added. The reaction was stirred at room temperature for 18 hours. The reaction was concentrated in vacuo and triturated with diethylether to afford the title compound as the hydrochloride salt (200 mg, quant.).

$^1$H NMR (400 MHz, DMSO-$d_6$): δ ppm 3.09 (t, 2H), 3.33 (m, 2H), 4.28 (t, 2H), 4.44 (d, 2H), 5.19 (s, 2H), 5.95 (d, 1H), 7.23-7.42 (m, 8H), 8.93 (t, 1H), 9.49 (br s, 2H).

Preparation 348

3-(Azetidin-3-yloxy)-4-chlorobenzonitrile hydrochloride

To a solution of 1-benzhydryl-3-azetidinyl methanesulfonate (44.6 g, 0.147 mol) and 2-chloro-5-cyanophenol (22.6 g, 0.147 mol) in MeCN (600 mL) was added $Cs_2CO_3$ (62.3 g, 0.19 mol). The reaction was stirred at 80° C. for 24 hours. The reaction was filtered, and the filtrate was concentrated in vacuo. The residue was purified by silica gel column chromatography eluting with 5-20% EtOAc in petroleum ether. The residue was dissolved in dichloroethane (550 mL) and potassium carbonate (66.4 g, 0.48 mmol) followed by ACE-Cl (20.5 g, 0.14 mmol) was added. The reaction was heated to reflux for 2 hours. The reaction was concentrated in vacuo and the residue was recrystallized with MeOH to afford the title compound as the hydrochloride salt (13.8 g, 59%). $^1$H NMR (400 MHz, MeOD): δ ppm 4.21-4.25 (m, 2H), 4.61-4.66 (m, 2H), 5.25-5.31 (m, 1H), 7.30 (s, 1H), 7.40-7.43 (d, 1H), 7.63-7.65 (d, 1H).

Preparation 349

N-(2-(Aminomethyl)phenyl)-N-propylmethanesulfonamide trifluoroacetate

To a solution of tert-butyl 2-(N-propylmethylsulfonamido)benzylcarbamate (Preparation 351, 265 mg, 0.77 mmol) in DCM (2 mL) was added TFA (0.5 mL) and the reaction stirred at room temperature for 1 hour. The reaction was diluted with DCM and washed with a 1:1 mixture of 880 $NH_3$ in water (20 mL). The organic layer was collected, dried over magnesium sulfate and concentrated in vacuo to afford the title compound as the trifluoroacetate salt (172 mg, 92%). $^1$H NMR (400 MHz, $CDCl_3$): δ ppm 0.89 (t, 3H), 1.41-1.55 (m, 2H), 2.96 (s, 3H), 3.39-3.46 (m, 1H), 3.62-3.69 (m, 1H), 3.83-3.87 (m, 1H), 4.10-4.20 (m, 1H), 7.19-7.22 (m, 1H), 7.28-7.32 (m, 1H), 7.36-7.40 (m, 1H), 7.57 (d, 1H).

Preparation 350

N-(2-(Aminomethyl)phenyl)-N-butylmethanesulfonamide trifluoroacetate

The title compound was prepared according to the method described by Preparation 349 using tert-butyl 2-(N-butylmethylsulfonamido)benzylcarbamate (Preparation 354) and isolated as the trifluoroacetate salt. $^1$H NMR (400 MHz, $CDCl_3$): δ ppm 0.87 (t, 3H), 1.26-1.52 (m, 4H), 2.95 (s, 3H), 3.41-3.48 (m, 1H), 3.67-3.75 (m, 1H), 3.83-3.86 (m, 1H), 4.10-4.14 (m, 1H), 7.19-7.21 (m, 1H), 7.28-7.32 (m, 1H), 7.37-7.41 (m, 1H), 7.58 (d, 1H).

Preparation 351 tert-Butyl 2-(N-propylmethylsulfonamido)benzylcarbamate

The title compound was prepared according to the method described by Preparation 213 using N-(2-cyanophenyl)-N-propylmethanesulfonamide (Preparation 352). Taken on directly to the next step.

Preparation 352

N-(2-Cyanophenyl)-N-propylmethanesulfonamide

To a solution of N-(2-cyanophenyl)methanesulfonamide (Preparation 223, 500 mg, 2.55 mmol) in NMP (10 mL) was added sodium hydride (148 mg, 3.83 mmol) and the reaction stirred for 30 minutes at room temperature. Propyl iodide (1.74 mL, 3.83 mmol) was added and the reaction was stirred at room temperature for 18 hours. The reaction was quenched by the addition of water and extracted into EtOAc. The organic layer was collected, washed with water, dried over sodium sulfate and concentrated in vacuo. The residue was purified using silica gel column chromatography eluting with 30% EtOAc in heptanes to afford the title compound (505 mg, 83%). $^1$H NMR (400 MHz, $CDCl_3$): δ ppm 0.94 (t, 3H), 1.48-1.60 (m, 2H), 3.11 (s, 3H), 3.71 (t, 2H), 7.46-7.54 (m, 2H), 7.65-7.69 (m, 1H), 7.72-7.74 (m, 1H).

Preparation 353

N-Methyl-N-(2-(((2-morpholinoethyl)amino)methyl)phenyl)methanesulfonamide

Sodium hydride (76 mg, 1.92 mmol) was added to a solution of tert-butyl 2-(N-methylmethylsulfonamido)benzylcarbamate (WO20101058846A1, 200 mg, 0.64 mmol) in NMP and the reaction was stirred at 0° C. for 30 minutes. 2-morpholinoethanamine (226 mg, 0.96 mL) was added and the reaction stirred at room temperature for 18 hours. The reaction was quenched by the addition of water and extracted into EtOAc. The organic layer was collected, dried and concentrated in vacuo. The residue was purified using silica gel column chromatography eluting with 100:10:1 DCM:MeOH:TEA. The residue was dissolved in DCM (2 mL) and TFA (1 mL) was added. The reaction was stirred at room temperature for 1 hour. The reaction was concentrated in vacuo to afford the title compound as the trifluoroacetate salt. MS m/z 328 [M+H]$^+$ The following Preparations (Preparations 354-359) were prepared according to the method described by Preparation 353 using the appropriate sulphonamide and alkyl halide as described below. The compounds were isolated according to the described experimental or by dissolving in DCM (20 mL) and washing with a 1:1 mixture of ammonium hydroxide:water. The organic layer was collected, dried over magnesium sulfate and concentrated in vacuo to afford the title compound that was used in the next reaction directly.

| Preparation Number | Name | SM | Data |
| --- | --- | --- | --- |
| 354 | N-butyl-N-(2-((methyl-amino)methyl)phenyl)methanesulfonamide | tert-butyl 2-(N-butylmethylsulfonamido)benzylcarbamate (Preparation 364) and methyl iodide. | $^1$H NMR (400 MHz, CDCl$_3$): δ ppm 0.88 (t, 3H), 1.27-1.58 (m, 4H), 2.50 (s, 3H), 2.95 (s, 3H), 3.44-3.50 (m, 1H), 3.67-3.76 (m, 2H), 3.95-4.00 (m, 1H), 7.20-7.23 (m, 1H), 7.28-7.32 (m, 1H), 7.34-7.38 (m, 1H), 7.61 (d, 1H). |
| 355 | N-ethyl-N-(4-methyl-2-((methylamino)methyl)phenyl)methanesulfonamide | tert-butyl 2-(N-ethylmethylsulfonamido)-5-methylbenzylcarbamate (Preparation 361) and methyl iodide. | Taken on directly to the next step. |
| 356 | N-(2-((ethylamino)methyl)-4-methylphenyl)N-methylmethanesulfonamide | tert-butyl 5-methyl-2-(N-methylmethylsulfonamido)benzylcarbamate (Preparation 360) and ethyl iodide. | $^1$H NMR (400 MHz, CDCl$_3$): δ ppm 1.21 (t, 3H), 2.32 (s, 3H), 2.82 (m, 2H), 2.99 (s, 3H), 3.21 (s, 3H), 3.95 (s, 2H), 7.07 (m, 2H), 7.40 (s, 1H). |
| 357 | N-methyl-N-(4-methyl-2-((propyl-amino)methyl)phenyl)methanesulfonamide | tert-butyl 5-methyl-2-(N-methylmethylsulfonamido)benzylcarbamate (Preparation 360) and propyl iodide. | $^1$H NMR (400 MHz, CDCl$_3$): δ ppm 0.95 (t, 3H), 1.60 (q, 2H), 2.83 (d, 3H), 2.31 (s, 3H), 2.95 (s, 3H), 3.20 (s, 3H), 3.95 (s, 2H), 7.07 (m, 2H), 7.40 (s, 1H). |
| 358 | N-ethyl-N-(2-((methylamino)methyl)phenyl)methanesulfonamide | tert-butyl 2-(N-ethylmethylsulfonamido)benzylcarbamate (Preparation 362) and methyl iodide. | Taken on directly to the next step. |
| 359 | N-methyl-N-(2-((methylamino)methyl)phenyl)methanesulfonamide | tert-butyl 2-(N-methylmethylsulfonamido)benzylcarbamate (Preparation 363) and methyl iodide. | Taken on directly to the next step. |

35

The following Preparations (Preparations 360-364) were prepared according to the methods described by Preparations 351 and 352 using the appropriate sulphonamide and alkyl halide as described below:

| Preparation Number | Name | SM | Data |
| --- | --- | --- | --- |
| 360 | tert-butyl 5-methyl-2-(N-methylmethylsulfonamido)benzylcarbamate | N-(2-cyano-4-methylphenyl)-methanesulfonamide (Preparation 365) and methyl iodide. | Taken on directly to the next step. |
| 361 | tert-butyl 2-(N-ethyl-methylsulfonamido)-5-methylbenzylcarbamate | N-(2-cyano-4-methylphenyl)-methanesulfonamide (Preparation 365) and ethyl iodide. | MS m/z 343 [M + H]$^+$ Taken on directly to the next step. |
| 362 | tert-butyl 2-(N-ethyl-methylsulfonamido)benzylcarbamate | N-(2-cyanophenyl)methanesulfonamide (Preparation 223) and ethyl iodide. | MS m/z 329 [M + H]$^+$ Taken on directly to the next step. |
| 363 | tert-butyl 2-(N-methylmethylsulfonamido)benzylcarbamate | N-(2-cyanophenyl)methanesulfonamide (Preparation 223) and methyl iodide. | MS m/z 315 [M + H]$^+$ Taken on directly to the next step. |
| 364 | tert-butyl 2-(N-butylmethylsulfonamido)benzylcarbamate | N-(2-cyanophenyl)methanesulfonamide (Preparation 223) and butyl iodide | $^1$H NMR (400 MHz, CDCl$_3$): δ ppm 0.87 (t, 3H), 1.26-1.55 (m, 13H), 2.94 (s, 3H), 3.39-3.46 (m, 1H), 3.71-3.78 (m, 1H), 4.30-4.35 (m, 1H), 4.56-4.61 (m, 1H), 5.35 (br s, 1H), 7.19-7.21)m, 1H), 7.30-7.39 (m, 2H), 7.60 (d, 1H). |

Preparation 365

N-(2-Cyano-4-methylphenyl)methanesulfonamide

The title compound was prepared according to the method described for Preparation 223 using methyl iodide and N-(4-methyl-2-cyanophenyl)-N-(methylsulfonyl)methanesulfonamide (Preparation 242). Taken on directly to the next step.

Preparation 366

N-(2-(Aminomethyl)phenyl)-N-(2-(benzyloxy)ethyl) methanesulfonamide hydrochloride The title compound was prepared according to the methods described for Preparations 222, 213 and 211 using 2-(benzyloxy)ethanol and N-(2-cyanophenyl)methanesulfonamide. MS m/z 335 [M+H]$^+$

Preparation 367

N-(2-(((3,4-Dimethoxyphenethyl)amino)methyl) phenyl)-N-methylmethanesulfonamide To a solution of 2-(3,4-dimethoxyphenyl)-N-(2-(N-methylmethylsulfonamido)benzyl)acetamide (Preparation 368, 800 mg, 2.03 mmol) in THF (15 mL) was added borane-dimethylsulfide (2M in THF, 2.55 mL, 5.10 mmol) and the reaction was heated to reflux for 2.5 hours. The reaction was cooled, concentrated in vacuo and the residue dissolved in methanol (12 mL). The solution was treated with 6N HCl (8 mL) and heated to reflux for 2 hours. The reaction was concentrated in vacuo and the residue basified with 3N NaOH solution. The aqueous layer was extracted into 10% MeOH/DCM, the organic extracts were washed with brine, dried over sodium sulfate and concentrated in vacuo. The residue was purified using silica gel column chromatography eluting with 7% MeOH in DCM to afford the title compound (390 mg, 51%). $^1$H NMR (400 MHz, DMSO-d$_6$): δ ppm 2.63-2.71 (m, 4H), 3.04 (s, 3H), 3.17 (s, 3H), 3.71 (s, 6H), 3.80 (br s, 2H), 6.68-6.83 (m, 3H), 7.28-7.51 (m, 4H). MS m/z 379 [M+H]$^+$

Preparation 368

2-(3,4-Dimethoxyphenyl)-N-(2-(N-methylmethylsulfonamido)benzyl)acetamide

To a solution of N-[2-(aminomethyl)phenyl]-N-methylmethanesulfonamide (WO 2010/058846A1, 1 g, 3.64 mmol) and 2-(3,4-dimethoxyphenyl)acetic acid (786 mg, 4.00 mmol) in THF (20 mL) was added propylphosphonic anhydride (2.9 g, 9.11 mmol) followed by DIPEA (2.21 mL, 12.68 mmol) and the reaction was stirred at room temperature for 14 hours. The reaction was concentrated in vacuo and the residue was partitioned between EtOAc and saturated aqueous sodium bicarbonate solution. The organic layer was collected, washed with brine, dried, concentrated in vacuo and purified using silica gel column chromatography eluting with 4% MeOH in DCM to afford the title compound as a white solid (540 mg, 38%). $^1$H NMR (400 MHz, DMSO-d$_6$): δ ppm 3.05 (s, 3H), 3.14 (s, 3H), 3.40 (s, 2H), 3.71 (s, 6H), 4.26 (br s, 1H), 4.46 (br s, 1H), 6.77-6.88 (m, 3H), 7.26-7.34 (m, 3H), 7.45-7.47 (m, 1H), 8.34 (t, 1H). MS m/z 393 [M+H]$^+$

Preparation 369

N-Methyl-N-(2-(((4-(methylsulfonamido)phenethyl) amino)methyl) phenyl)methanesulfonamide The title compound was prepared according to the methods described for Preparations 368 and 367 using 2-(4-(methylsulfonamido)phenyl)acetic acid. $^1$H NMR (400 MHz, DMSO-d$_6$): δ ppm 2.66-2.73 (m, 4H), 2.92 (s, 3H), 3.04 (s, 3H), 3.13 (s, 3H), 3.80 (br s, 2H), 7.09-7.17 (m, 4H), 7.29-7.34 (m, 2H), 7.42-7.49 (m, 2H), 9.52 (br s, 1H). MS m/z 412 [M+H]$^+$

Preparation 370

N-(2-(((6-(5-Fluoro-4-methoxy-2-(2,2,2-trifluoroethyl)phenyl)-3-(4,5,6,7-tetrahydro-1H-imidazo[4,5-c]pyridin-2-yl)-1H-pyrazolo[3,4-d]pyrimidin-4-yl) amino)methyl)-4-methoxyphenyl)-N-methylmethanesulfonamide The title compound was prepared according to the method described for Example 157 using N-(2-(((6-(5-fluoro-4-methoxy-2-(2,2,2-trifluoroethyl)phenyl)-3-iodo-1H-pyrazolo[3,4-d]pyrimidin-4-yl)amino)methyl)-4-methoxyphenyl)-N-methylmethanesulfonamide (Preparation 273) and tert-butyl 2-iodo-6,7-dihydro-1H-imidazo[4,5-c]pyridine-5 (4H)-carboxylate (WO20131014567A1) using HCl in dioxane for the deprotection step. MS m/z 690 [M+H]$^+$

Preparation 371

N-(2-(((6-(5-Fluoro-4-methoxy-2-(2,2,2-trifluoroethyl)phenyl)-3-(5-(piperidin-4-yl)-4H-1,2,4-triazol-3-yl)-1H-pyrazolo[3,4-d]pyrimidin-4-yl)amino) methyl)-4-methoxyphenyl)-N-methylmethanesulfonamide To a solution of N-(2-(((6-(5-fluoro-4-methoxy-2-(2,2,2-trifluoroethyl)phenyl)-3-(hydrazinecarbonyl)-1-((2-(trimethylsilyl)ethoxy)methyl)-1H-pyrazolo[3,4-d]pyrimidin-4-yl)amino)methyl)-4-methoxyphenyl)-N-methylmethanesulfonamide (Preparation 375, 450 mg, 0.59 mol) in butanol (2 mL) was added tert-butyl 4-cyanopiperidine-1-carboxylate (624 mg, 2.97 mmol) and the reaction was heated to 150° C. under microwave irradiation for 50 minutes. The reaction was cooled, filtered and concentrated in vacuo. The residue was purified using preparative HPLC. The residue was treated with TFA (2 mL) and stirred at room temperature for 30 minutes. The reaction was concentrated in vacuo, dissolved in MeOH (5 mL) and cooled in ice water. Ethylene diamine was added dropwise until the solution was basic, with stirring for 1 hour. The solution was concentrated in vacuo and extracted into 20% IPA in DCM. The organic layer was washed with water, dried over sodium sulfate and concentrated in vacuo to afford the title compound that was used directly in the next reaction. MS m/z 719 [M+H]$^+$

Preparation 372

N-(2-(((6-(5-Fluoro-4-methoxy-2-(2,2,2-trifluoroethyl)phenyl)-3-(5-(piperidin-4-yl)-4H-1,2,4-triazol-3-yl)-1H-pyrazolo[3,4-d]pyrimidin-4-yl)amino) methyl)phenyl)-N-methylmethanesulfonamide The title compound was prepared according to the method described by Preparation 371 using N-(2-(((3-cyano-6-(5- fluoro-4-methoxy-2-(2,2,2-trifluoro-ethyl)phenyl)-1-((2-(trimethylsilyl)ethoxy)methyl)-1H-pyrazolo[3,4-d]pyrimidin-4-yl)amino)methyl)phenyl)-N-methylmethanesulfonamide (Preparation 377) and tert-butyl 4-(hydrazinecarbonyl)piperidine-1-carboxylate in the presence of potassium carbonate. MS m/z 689 [M+H]$^+$ Preparation 373

6-[5-Fluoro-2-ethyl-4-{[2-(trimethylsilyl)ethoxy]methoxyphenyl]-4-(2-[methyl(methylsulfonyl)amino]benzyl}amino)-1-{[2-(trimethylsilyl)ethoxy]methyl}-1H-pyrazolo[4,3-c]pyridine-3-carboxylic acid The title compound may be prepared according to the method described for Preparation 11 using N-[2-({[6-(2-ethyl-5-fluoro-4-{[2-(trimethylsilyl)ethoxy]methoxy}phenyl)-3-iodo-1-{[2-(trimethylsilyl)-ethoxy]methyl}-1H-pyrazolo[4,3-c]pyridin-4-yl]-amino}methyl)phenyl]-N-methylmethanesulfonamide (Preparation 79). Taken on directly to the next step.

Preparation 374

N-(2-(((6-(5-Fluoro-2-(2,2,2-trifluoroethyl)-4-((2-(trimethylsilyl)ethoxy)methoxy)phenyl)-3-(hydrazinecarbonyl)-1-((2-(trimethylsilyl)ethoxy)methyl-1H-pyrazolo[4,3-c]pyridin-4-yl)amino)methyl)phenyl)-N-methylmethanesulfonamide To a solution of 6-[5-fluoro-2-(2,2,2-trifluoroethyl)-4-{[2-(trimethylsilyl)ethoxy]methoxy}phenyl]-4-({2-[methyl(methylsulfonyl)amino]benzyl}amino)-1-{[2-(trimethylsilyl)ethoxy]methyl}-1H-pyrazolo[4,3-c]pyridine-3-carboxylic acid (Preparation 12, 0.55 g, 0.66 mmol) in MeOH/Toluene (15 mL) was added 2M trimethylsilyldiazomethane in THF (0.997 mL, 1.99 mmol) dropwise at 0° C. The reaction was stirred for 2 hours at room temperature. The reaction was concentrated in vacuo and the residue was purified using silica gel column chromatography eluting with 8% MeOH in DCM. The residue was dissolved in MeOH (5 mL) and hydrazine monohydrate (40.12 mg, 0.80 mmol) was added. The reaction was heated to reflux for 18 hours. The reaction was concentrated in vacuo and the residue was purified using neutral alumina column chromatography eluting with 50% EtOAc in hexanes to afford the title compound (297 mg, 66%). MS m/z 842 [M+H]$^+$ Preparation 375

N-(2-(((6-(5-Fluoro-4-methoxy-2-(2,2,2-trifluoroethyl)phenyl)-3-(hydrazinecarbonyl)-1-((2-(trimethylsilyl)ethoxy)methyl)-1H-pyrazolo[3,4-d]pyrimidin-4-yl)amino)methyl)-4-methoxyphenyl)-N-methylmethanesulfonamide The title compound was prepared according to the method described by Preparation 374 using 6-(5-fluoro-4-methoxy-2-(2,2,2-trifluoroethyl)phenyl)-4-((5-methoxy-2-(N-methylmethylsulfonamido)benzyl)amino)-1-((2-(trimethylsilyl)ethoxy)-methyl)-1H-pyrazolo[3,4-d]pyrimidine-3-carboxylic acid (Preparation 269). MS m/z 757 [M+H]$^+$ Preparation 376

N-(2-(((6-(5-Fluoro-4-methoxy-2-(2,2,2-trifluoroethyl)phenyl)-3-(hydrazinocarbonyl)-1-((2-(trimethylsilyl)ethoxy)methyl)-1H-pyrazolo[4,3-c]pyridin-4-yl)amino)methyl)phenyl)-N-methylmethanesulfonamide The - was prepared according to the methods described for Preparations 11 and 374 using N-(2-(((6-(5-fluoro-4-methoxy-2-(2,2,2-tri-fluoroethyl)phenyl)-3-iodo-1-((2-(trimethylsilyl)ethoxy)methyl)-1H-pyrazolo[4,3-c]pyridin-4-yl)amino)methyl)phenyl)-N-methyl-methanesulfonamide (Preparation 378). $^1$H NMR (400 MHz, DMSO-d$_6$): δ ppm −0.11 (s, 9H), 0.83 (m, 2H), 1.23 (br s, 2H), 3.05 (s, 3H), 3.11 (s, 3H), 3.57 (m, 2H), 3.77 (m, 2H), 3.86 (s, 3H), 4.68 (m, 2H), 4.80 (br m, 1H), 4.90 (br m, 1H), 5.72 (s, 2H), 7.08 (s, 1H), 7.20-7.51 (m, 6H), 9.68 (t, 1H), 10.17 (m, 1H). MS m/z 726 [M+H]$^+$ Preparation 377

N-(2-(((3-Cyano-6-(5-fluoro-4-methoxy-2-(2,2,2-trifluoroethyl)phenyl)-1-((2-(trimethylsilyl)ethoxy)methyl)-1H-pyrazolo[3,4-d]pyrimidin-4-yl)amino)methyl)phenyl)-N-methylmethanesulfonamide To a solution of N-(2-(((6-(5-fluoro-4-methoxy-2-(2,2,2-trifluoroethyl)phenyl)-3-iodo-1-((2-(trimethylsilyl)ethoxy)methyl)-1H-pyrazolo[4,3-c]pyridin-4-yl)amino)methyl)-phenyl)-N-methylmethanesulfonamide (Preparation 378, 1.2 g, 1.51 mmol) in DMF (10 mL), was added zinc cyanide (0.19 g, 1.66 mmol) and Pd(PPh$_3$)$_4$ (0.05 mg, 0.04 mmol). The reaction was degassed with nitrogen and heated to 120° C. under microwave irradiation for 20 minutes. The reaction was quenched with water and extracted into ethyl acetate. The organic extracts were dried over sodium sulfate and concentrated in vacuo. The residue was purified by silica gel column chromatography eluting with 48% EtOAc in hexanes to afford the title compound (610 mg, 58%). $^1$H NMR (400 MHz, DMSO-d$_6$): δ ppm −0.07 (s, 9H), 0.86 (t, 2H), 3.08 (s, 3H), 3.17 (s, 3H), 3.65 (t, 2H), 3.88 (s, 3H), 4.22 (m, 2H), 4.89 (br m, 1H), 5.00 (br m, 1H), 5.75 (s, 2H), 7.24-7.41 (m, 4H), 7.55-7.59 (m, 2H), 8.29 (t, 1H). MS m/z 694 [M+H]$^+$ Preparation 378

N-(2-(((6-(5-Fluoro-4-methoxy-2-(2,2,2-trifluoroethyl)phenyl)-3-iodo-1-((2-(trimethylsilyl)ethoxy)methyl)-1H-pyrazolo[4,3-c]pyridin-4-yl)amino)methyl)phenyl)-N-methylmethanesulfonamide The title compound was prepared according to the method described for Preparation 61 using 6-[5-fluoro-4-methoxy-2-(2,2,2-trifluoroethyl)phenyl]-3-iodo-1-{([2-(trimethylsilyl)ethoxy]-methyl}-1H-pyrazolo[4,3-c]pyridine (Preparation 111) and 4-nitrophenyl {2-[methyl(methylsulfonyl)amino]benzyl}carbamate (Preparation 166). MS m/z 794 [M+H]$^+$ Preparation 379

6-(5-Fluoro-2-(2,2,2-trifluoroethyl)-4-((2-(trimethylsilyl)ethoxy)methoxy)phenyl)-3-iodo-N-(2-(methylthio)ethyl)-1-((2-(trimethylsilyl)ethoxy)methyl)-1H-pyrazolo[4,3-c]pyridin-4-amine The title compound was prepared according to the method described for Preparation 61 using 6-[5-fluoro-2-(2,2,2- trifluoroethyl)-4-{[2-(trimethylsilyl)ethoxy]methoxy}phenyl]-3-iodo-1-{[2-(trimethylsilyl)ethoxy]methyl}-1H-pyrazolo[4,3-c]pyridine 5-oxide (Preparation 114) and 4-nitrophenyl (2-(methylthio)ethyl)carbamate (Preparation 385). MS m/z 787 [M+H]+

Preparation 380

Racemic 3-((6-(5-Fluoro-2-(2,2,2-trifluoroethyl)-4-((2-(trimethylsilyl)ethoxy)methoxy)phenyl)-3-iodo-1-((2-(trimethylsilyl)ethoxy)methyl)-1H-pyrazolo[3,4-d]pyrimidin-4-yl)amino)-2-methylpropan-1-ol The title compound was prepared according to the method described for Preparation 131 using racemic N-(3-((tert-butyldimethylsilyl)oxy)-2-methylpropyl)-6-(4-((tert-butyldimethylsilyl)-oxy)-5-fluoro-2-(2,2,2-trifluoroethyl)phenyl)-3-iodo-1H-pyrazolo[3,4-d]pyrimidin-4-amine (Preparation 381). MS m/z 786 [M+H]+

Preparation 381

Racemic N-(3-((tert-Butyldimethylsilyl)oxy)-2-methylpropyl)-6-(4-((tert-butyldimethylsilyl)oxy)-5-fluoro-2-(2,2,2-ethyl)phenyl)-3-iodo-1H-pyrazolo[3,4-d]pyrimidin-4-amine The title compound was prepared according to the method described for Preparation 137 using racemic N-(3-((tert-butyldimethylsilyl)oxy)-2-methylpropyl)-6-(4-((tert-butyldimethylsilyl)oxy)-5-fluoro-2-(2,2,2-trifluoroethyl)phenyl)-1H-pyrazolo[3,4-d]pyrimidin-4-amine (Preparation 382). $^1$H NMR (400 MHz, DMSO-$d_6$): δ ppm −0.01 (s, 6H), 0.22 (s, 6H), 0.79 (m, 9H), 0.98 (m, 12H), 2.04 (m, 1H), 3.48 (m, 1H), 3.56 (m, 2H), 3.68 (m, 1H), 4.45 (m, 2H), 6.71 (m, 1H), 7.13 (m, 1H), 7.81 (m, 1H), 13.88 (s, 1H). MS m/z 754 [M+H]+

Preparation 382

Racemic N-(3-((tert-Butyldimethylsilyl)oxy)-2-methylpropyl)-6-(4-((tert-butyldimethylsilyl)oxy)-5-fluoro-2-trifluoroethyl)phenyl)-1H-pyrazolo[3,4-d]pyrimidin-4-amine The title compound was prepared according to the methods described by Preparations 142 and 141 using racemic 3-((6-(5-fluoro-2-(2,2,2-trifluoroethyl)-4-((2-(trimethylsilyl)-ethoxy)methoxy)phenyl)-1-(tetrahydro-2H-pyran-2-yl)-1H-pyrazolo[3,4-d]pyrimidin-4-yl)amino)-2-methylpropan-1-ol (Preparation 383). MS m/z 626 [M−H]−

Preparation 383

Racemic 3-((6-(5-Fluoro-2-(2,2,2-trifluoroethyl-4-((2-(trimethylsilyl)ethoxy)methoxy)phenyl)-1-(tetrahydro-2H-pyran-2-yl)-1H-pyrazolo[3,4-d]pyrimidin-4-yl)amino)-2-methylpropan-1-ol The title compound was prepared according to the method described for Preparation 299 using racemic 3-((6-chloro-1-(tetrahydro-2H-pyran-2-yl)-1H-pyrazolo[3,4-d]pyrimidin-4-yl)amino)-2-methylprop-an-1-ol (Preparation 384) and (2-{[2-fluoro-4-(4,4,5,5-tetramethyl-1,3,2-dioxaborolan-2-yl)-5-(2,2,2-trifluoroethyl)phenoxy]-methoxy}ethyl)(trimethyl)silane (Preparation 150). MS m/z 614 [M+H]+

Preparation 384

Racemic 3-((6-Chloro-1-(tetrahydro-2H-pyran-2-yl)-1H-pyrazolo[3,4-d]pyrimidin-4-yl)amino)-2-methylpropan-1-ol The title compound was prepared according to the method described by Preparation 299 using racemic 3-amino-2-methylpropan-1-ol. MS m/z 326 [M+H]+

Preparation 385

4-Nitrophenyl (2-(methylthio)ethyl)carbamate

The title compound was prepared according to the method described for Preparation 156 using 2-(methylthio)ethanamine. Taken on directly to the next step.

Preparation 386

2-Bromo-4,5-dimethyl-1-((2-(trimethylsilyl)ethoxy)methyl)-1H-imidazole

To solution of 4,5-dimethyl-1-((2-(trimethylsilyl)ethoxy)methyl)-1H-imidazole (Preparation 387, 270 mg, 1.19 mmol) in anhydrous THF (3 mL) at −78° C., was added butyllithium (0.54 mL, 1.31 mmol) dropwise. The reaction was kept at −78° C. for 15 minutes before the addition of carbon tetrabromide (474 mg, 1.43 mmol) in THF (2 mL). The reaction was warmed to room temperature before quenching with ammonium chloride and extracting into EtOAc. The organic layer was collected, washed with water, brine, dried over sodium sulfate and concentrated in vacuo. The residue was purified by silica gel column chromatography eluting with 3% MeOH in DCM to afford the title compound as a colorless oil (220 mg, 60%). $^1$H NMR (400 MHz, DMSO-$d_6$): δ ppm −0.01 (s, 9H), 0.87 (t, 2H), 2.01 (s, 3H), 2.14 (s, 3H), 3.51 (t, 2H), 5.18 (s, 2H).

Preparation 387

4,5-Dimethyl-1-((2-(trimethylsilyl)ethoxymethyl)-1H-imidazole

A suspension of NaH (124 mg, 3.12 mmol) in DMF (3 mL) was added a solution of 4,5-dimethyl-1H-imidazole (200 mg, 2.08 mmol) in DMF (2 mL) at 0° C. The suspension was stirred for 15 minutes before the dropwise addition of SEM chloride (0.44 mL, 2.49 mmol). The reaction was stirred at room temperature for 1 hour, then partitioned between ethyl acetate and water. The combined organic extracts were washed with brine, dried over sodium sulfate and concentrated in vacuo. The residue was purified by silica gel column chromatography eluting with 5% MeOH in DCM to afford the title compound as a colorless oil (270 mg, 57%). $^1$H NMR (400 MHz, DMSO-$d_6$): δ ppm −0.01 (s, 9H), 0.82 (t, 2H), 2.01 (s, 3H), 2.09 (s, 3H), 3.43 (t, 2H), 5.18 (s, 2H), 7.52 (s, 1H).

Biological Evaluation

JAK Caliper Enzyme Assay at 1 mM ATP

Test article was solubilized in dimethyl sulfoxide (DMSO) to a stock concentration of 30 mM. An 11-point half log dilution series was created in DMSO with a top concentration of 600 μM. The test compound plate also contained positive control wells containing a known inhibitor to define 100% inhibition and negative control wells containing DMSO to define no inhibition. The compound plates were diluted 1 to 60 resulting in a top final assay compound concentration of 10 µM and a 2% DMSO concentration.

Test article and assay controls were added to a 384-well plate. Reaction mixtures contained 20 mM HEPES, pH 7.4, 10 mM magnesium chloride, 0.01% bovine serum albumin (BSA), 0.0005% Tween 20, 1 mM ATP and 1 µM peptide substrate. The JAK1 and TYK2 assays contained 1 µM of the IRStide peptide (5FAM-KKSRGDYMTMQID) and the JAK2 and JAK3 assays contained 1 µM of the JAKtide peptide (FITC-KGGEEEEYFELVKK). The assays were initiated by the addition of 20 nM JAK1, 1 nM JAK2, 1 nM JAK3 or 1 nM TYK2 enzyme and were incubated at room temperature for three hours for JAK1, 60 minutes for JAK2, 75 minutes for JAK3 or 135 minutes for TYK2. Enzyme concentrations and incubation times were optimized for each new enzyme preps and were modified slightly over time to ensure 20%-30% phosphorylation. The assays were stopped with a final concentration of 10 mM EDTA, 0.1% Coating Reagent and 100 mM HEPES, pH=7.4. The assay plates were placed on a Caliper Life Science Lab Chip 3000 (LC3000) instrument, and each well was sampled using appropriate separation conditions to measure the unphosphorylated and phosphorylated peptide.

A549 Cell Assay: Inhibition of pSTAT3

An assay measuring the efficacy of JAK inhibitors on the functional response of recombinant human interferon γ (rhIFNγ) stimulated STAT-3 phosphorylation in the A549 human epithelial cell line.

Method

A549 cells (ATCC #CCL-185), were plated at 30,000 cells/well in 96 well flat bottomed tissue culture plates (BD#353072) in 200 µL of growth medium (DMEM, Pfizer media prep, with 10% Fetal Bovine Serum, Sigma #F4135, 2 mM L-Glutamine, Pfizer media prep, 100 U/mL penicillin, Pfizer media prep, and 200 µg/ml streptomycin, Pfizer media prep), and cultured at 37° C., 5% $CO_2$ incubator for 18 hours. Growth medium was removed by vacuum aspiration (V&P Scientific #vp187 bp-60), and 90 µL of pre-warmed assay medium (DMEM with 0.2% BSA, Miltenyi #130-091-376) was added to each well and incubated for 15 minutes at 37° C. 10 µL of vehicle control or test compound (final concentration range of 0.3 nM to 10 µM with 0.1% DMSO) was added to the cells. Plates were incubated at 37° C. for 1 hour. After compound incubation, 10 µL of 220 ng/mL recombinant human IFNγ (R&D Systems #285-IF, final rhIFNγ concentration of 20 ng/mL) was added to the cells and plates were incubated for 30 minutes at 37° C. Wells containing A549 cells, medium with 0.1% DMSO and no rhIFNγ were used as background controls. After rhIFNγ stimulation, media was aspirated from each well and 35 µL/well of iced-cold MSD lysis buffer containing protease and phosphatase inhibitors from Phospho-STAT3 Tyr705 assay kit (Meso-Scale Discovery #K150DID) was added to each well. Plates were incubated at 4° C. with shaking for 30 minutes. Cell lysates were assayed following the MSD Phospho-STAT3 Tyr705 assay kit protocol to detect pSTAT3.

Data were collected and transformed into percent inhibition and calculated using the following formula:

$$\% \text{ Inhibition} = \left(1 - \left(\frac{\text{Compound } pSTAT3 - \text{Basal } pSTAT3}{\text{No Compound Control } pSTAT3 - \text{Basal } pSTAT3}\right)\right) * 100$$

Data were graphically displayed as percent inhibition using GraphPad Prism 4.0, and $IC_{50}$ curves were fitted using a point to point analysis.

Human T Cell Assay: Inhibition of pSTAT5

An assay measuring the efficacy of JAK inhibitors on the functional response of recombinant human interleukin-2 (rhIL-2) stimulated STAT5 phosphorylation in isolated human T cells.

Method:

Human whole blood from individual donors was collected from the phlebotomy unit on-site. Peripheral venous blood (30-60 mL) from healthy volunteers of either sex was used as the source of T cells. T cell isolation from venous whole blood is routinely performed in a class II microbiological safety cabinet. Each sample was collected into between 3 and 6 10 mL Sodium Heparin Vacutainer tubes (BD #367874). The blood was poured into sterile 50 mL conicals (Corning #430828) and incubated with the T cell Rosette Sep Cocktail (Stemcell Technologies #15061) at 50 µL/mL antibody/blood ratio for 20 min. with shaking at room temperature. The blood/antibody mixture was then diluted 1:2 with PBS (Pfizer media prep)/2% FBS (Sigma #F4135) and 30 mL of the mixture was layered onto 15 mL Ficoll-Hypaque (GE Healthcare #17-1440-03) in 50 mL conical tubes. The tubes were then centrifuged at 1200×g for 20 min. at room temperature with no brake. Following centrifugation the T cells formed a buffy coat between the Ficoll-Hypaque and plasma layers. The plasma above the buffy coats was removed to within 5 mm of the buffy coat using a sterile Pasteur pipette. The buffy coats were then collected into fresh sterile 50 mL conical tubes containing 25 mL PBS/2% FBS (2 buffy coats per 50 mL conical). PBS/2% FBS was added to the buffy coat cells such that the final volume in the tube was 50 mL. The tubes were then centrifuged at 200×g for 15 min. at room temperature. The supernatant was discarded and the pellet re-suspended in 10-20 mL of DMEM (Pfizer media prep) Assay media/0.2% BSA (Miltenyi #130-091-376). A differential cell count was performed using a haemacytometer and cells were diluted to $1.1 \times 10^6$ T cells/ml in DMEM/0.2% BSA media. Compounds (10 mM-0.3 µM) were diluted with Hanks Balanced Salt Solution (HBSS) (Sigma #H6648) at 1:100 dilution. Immediately following cell isolation and compound dilution, 90 µl/well of T cells (~$1 \times 10^6$/ml) in assay medium (DMEM+0.2% BSA) was added to the VWR Deep well V bottom plate (#3906-520-300). 10 µl/well of compound (final concentration range of 10 µM-0.3 nM with 0.1% DMSO) or 0.1% DMSO in HBSS as controls was added to the appropriate wells. Plates were incubated for 1 hour at 37° C., 5% $CO_2$ incubator. 10 µl of 3.3 µg/mL rhIL-2 (R&D Systems #202-IL) was added to the cells (300 ng/ml final assay concentration). Wells containing T cells, medium with 0.1% DMSO and no rhIL-2 were used as background controls. Plates were incubated for 15 min at 37° C. After rhIL-2 stimulation, 800 µL of cold PBS/0.1% BSA was added and the plates were centrifuged at 1400 rpm for 5 min at 4° C. Supernatant was aspirated and 100 µL of ice-cold MSD lysis buffer containing protease and phosphatase inhibitors from Phospho-STAT5a/b Tyr694 assay kit (Meso-Scale Discovery #K150IGD) was added to the cell pellet. Plates were shaken for 30 min. at 4° C. and then frozen overnight. The following day, cell lysates were assayed using the MSD ELISA kit protocol for detection of pSTAT5.

Data were collected and transformed into percent inhibition and calculated using the following formula:

$$\% \text{ Inhibition} = \left(1 - \left(\frac{\text{Compound } pSTAT5 - \text{Basal } pSTAT5}{\text{No Compound Control } pSTAT5 - \text{Basal } pSTAT5}\right)\right) * 100$$

Data were graphically displayed as percent inhibition using GraphPad Prism 4.0, and $IC_{50}$ curves were fitted using a point to point analysis.

TABLE 1

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | | | | | A549 cell assay: Inhibition of pSTAT3 $IC_{50}$ (nM) | Human T cell assay: Inhibition of pSTAT5 $IC_{50}$ (nM) |
| | | JAK1 $IC_{50}$ (nM) | JAK2 $IC_{50}$ (nM) | JAK3 $IC_{50}$ (nM) | TYK2 $IC_{50}$ (nM) | | |
| 125 | 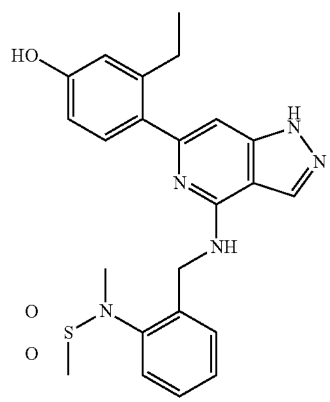 | 0.2 | 1.0 | 4.4 | 5.6 | | |
| 126 | 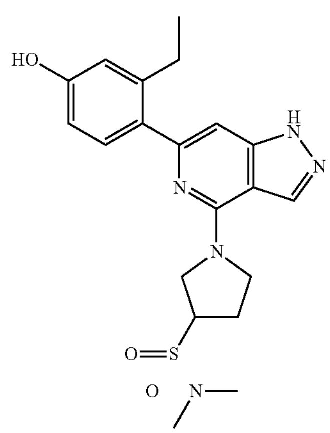 | 8.1 | 23.5 | 35.1 | 668.3 | | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 127 | | 6.0 | 14.9 | 53.3 | 624.9 | | |
| 131 | | <0.5 | 2.1 | 10.2 | 4.7 | 7.4 | 24.3 |
| 124 | | 87.6 | 182.6 | 156.7 | 4234.5 | | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 123 | | 3.3 | 4.5 | 9.5 | 82.1 | | |
| 128 | | 3.6 | 12.6 | 30.5 | 514.3 | | |
| 132 | | 19.0 | 31.4 | 18.4 | 1293.1 | 256.5 | 206.4 |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 111 | 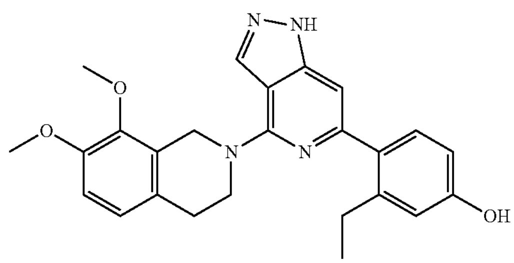 [SMILES: CCc1cc(O)ccc1-c1cc2[nH]ncc2c(N2CCc3ccc(OC)c(OC)c3C2)n1] | 13.8 | 52.4 | 193.6 | 1540.2 | | |
| 112 | 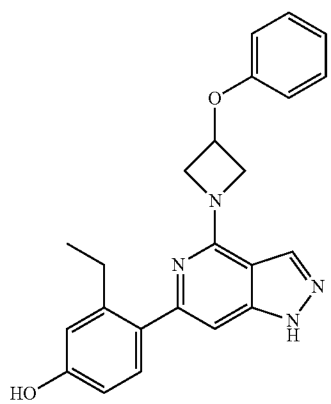 [SMILES: CCc1cc(O)ccc1-c1cc2[nH]ncc2c(N2CC(Oc3ccccc3)C2)n1] | 12.1 | 82.9 | 67.5 | 5170.8 | | |
| 113 | 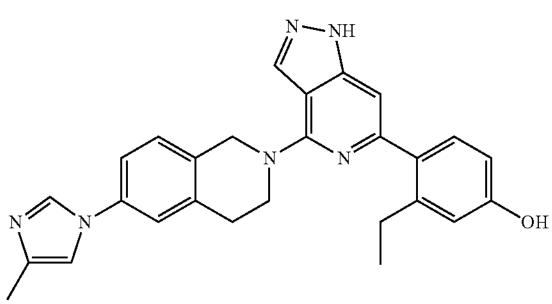 [SMILES: CCc1cc(O)ccc1-c1cc2[nH]ncc2c(N2CCc3cc(-n4cnc(C)c4)ccc3C2)n1] | 10.7 | 26.3 | 42.4 | 723.1 | | |
| 114 | 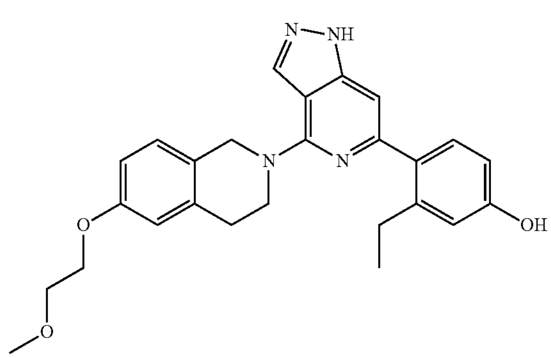 [SMILES: CCc1cc(O)ccc1-c1cc2[nH]ncc2c(N2CCc3cc(OCCOC)ccc3C2)n1] | 10.1 | 25.9 | 56.2 | 289.2 | | |

TABLE 1-continued

Data for JAK Caliper™ Kinase assays at 1 mM ATP and Cell Based assays

| Ex. | Structure | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
|---|---|---|---|---|---|---|---|
| 115 | 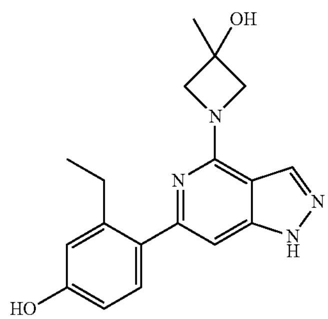 [SMILES: CCc1cc(O)ccc1-c1cc2[nH]ncc2c(N2CC(C)(O)C2)n1] | 4.3 | 10.1 | 16.8 | 229.0 | | |
| 116 | 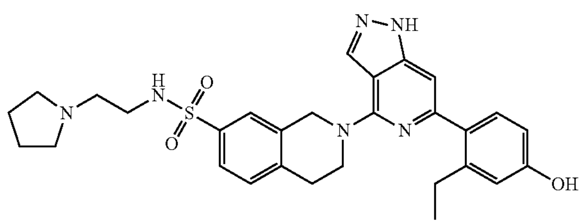 [SMILES: CCc1cc(O)ccc1-c1cc2[nH]ncc2c(N2CCc3ccc(S(=O)(=O)NCCN4CCCC4)cc3C2)n1] | 3.8 | 10.1 | 23.3 | 162.7 | | |
| 117 | 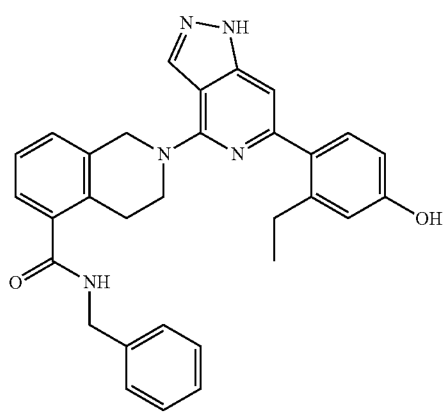 [SMILES: CCc1cc(O)ccc1-c1cc2[nH]ncc2c(N2CCc3c(cccc3C(=O)NCc3ccccc3)C2)n1] | 7.2 | 5.0 | 41.6 | 425.0 | | |
| 118 | 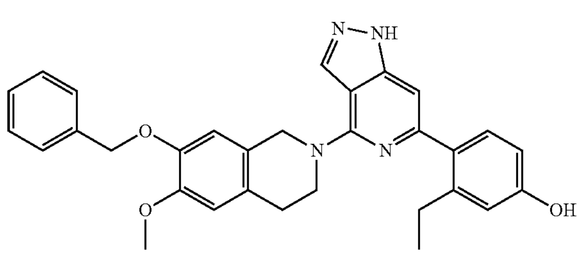 [SMILES: CCc1cc(O)ccc1-c1cc2[nH]ncc2c(N2CCc3cc(OC)c(OCc4ccccc4)cc3C2)n1] | 67.4 | 118.9 | 339.6 | 2730.0 | | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 119 | 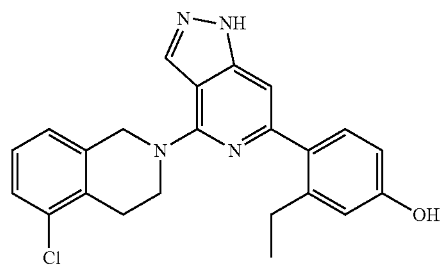 [SMILES: CCc1cc(O)ccc1-c1cc2[nH]ncc2c(N2CCc3c(Cl)cccc3C2)n1] | 39.4 | 46.5 | 111.0 | 561.1 | | |
| 120 | 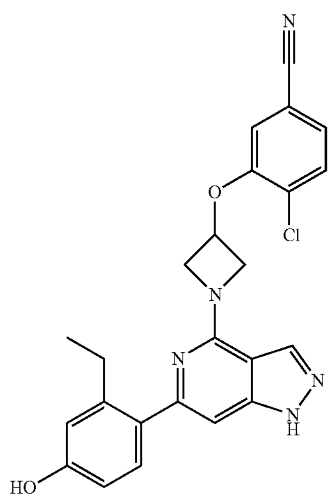 [SMILES: CCc1cc(O)ccc1-c1cc2[nH]ncc2c(N2CC(Oc3cc(C#N)ccc3Cl)C2)n1] | 10.8 | 127.8 | 89.2 | 3320.1 | | |
| 121 | 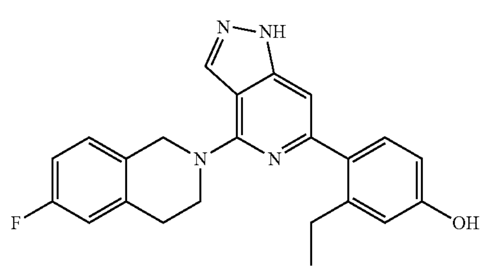 [SMILES: CCc1cc(O)ccc1-c1cc2[nH]ncc2c(N2CCc3cc(F)ccc3C2)n1] | 9.7 | 16.9 | 40.8 | 302.1 | | |
| 122 | 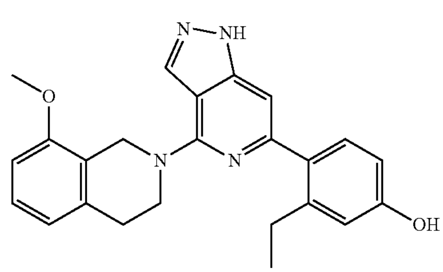 [SMILES: CCc1cc(O)ccc1-c1cc2[nH]ncc2c(N2CCc3cccc(OC)c3C2)n1] | 14.9 | 25.1 | 78.1 | 478.4 | | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 137 | 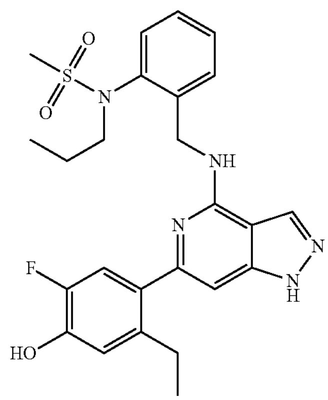 [SMILES: CCCN(c1ccccc1CNc1nc(-c2cc(F)c(O)cc2CC)cc2[nH]ncc12)S(C)(=O)=O] | <0.1 | 0.3 | 3.3 | 45.4 | | |
| 138 | 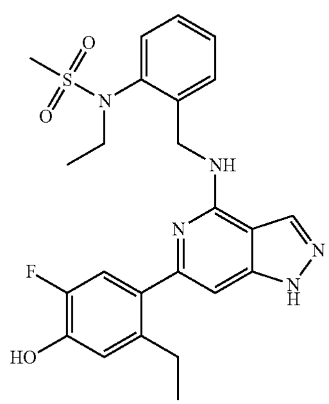 [SMILES: CCc1cc(O)c(F)cc1-c1cc2[nH]ncc2c(NCc2ccccc2N(CC)S(C)(=O)=O)n1] | 0.6 | 2.6 | 14.2 | 4.8 | 5.4 | |
| 139 | 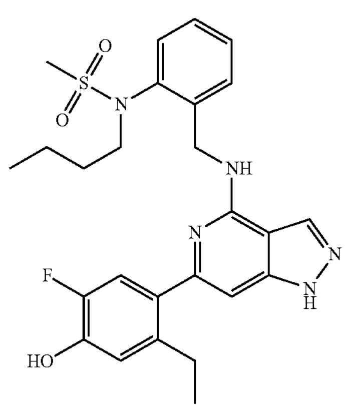 [SMILES: CCCCN(c1ccccc1CNc1nc(-c2cc(F)c(O)cc2CC)cc2[nH]ncc12)S(C)(=O)=O] | 8.5 | 16.7 | 27.5 | 1992.6 | | |

TABLE 1-continued
Data for JAK Caliper ™ Kinase assays at 1 mM ATP and Cell Based assays
| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 133 | 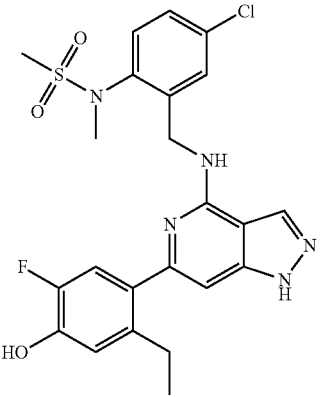 [SMILES: CCc1cc(O)c(F)cc1-c1cc2[nH]ncc2c(NCc2cc(Cl)ccc2N(C)S(C)(=O)=O)n1] | 1.2 | 5.9 | 30.5 | 249.3 | 10.1 | 34.7 |
| 135 | 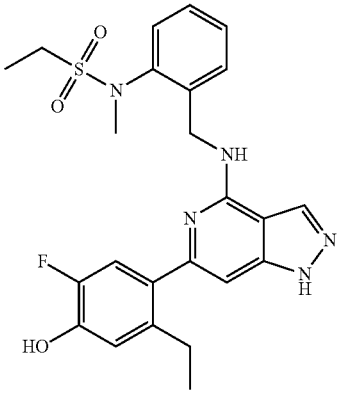 [SMILES: CCc1cc(O)c(F)cc1-c1cc2[nH]ncc2c(NCc2ccccc2N(C)S(=O)(=O)CC)n1] | 0.7 | 3.4 | 17.3 | 8.4 | 3.3 | |
| 145 | 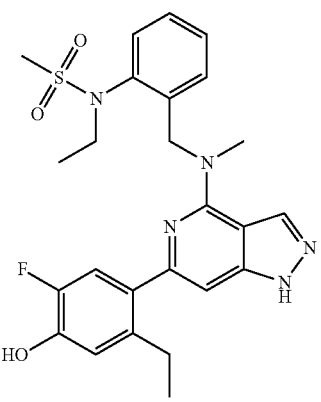 [SMILES: CCc1cc(O)c(F)cc1-c1cc2[nH]ncc2c(N(C)Cc2ccccc2N(CC)S(C)(=O)=O)n1] | 1.0 | 4.5 | 16.2 | 15.8 | 15.7 | 157.3 |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 141 | 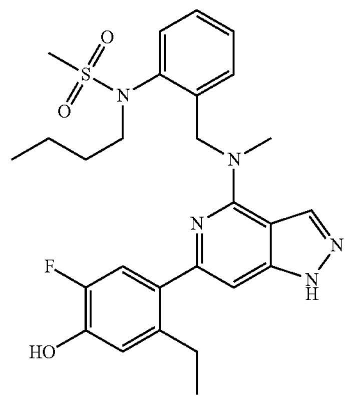 [SMILES: CCCCN(c1ccccc1CN(C)c1nc(-c2cc(F)c(O)cc2CC)cc2[nH]ncc12)S(C)(=O)=O] | 19.5 | 43.2 | 61.6 | 7069.4 | | |
| 140 | 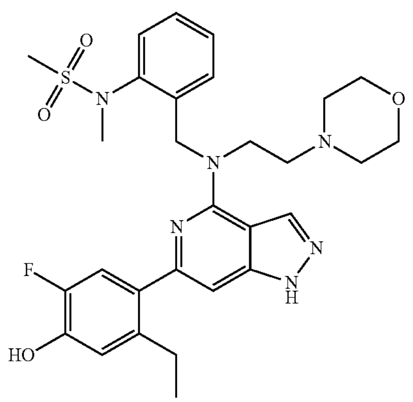 [SMILES: CCc1cc(O)c(F)cc1-c1cc2[nH]ncc2c(N(CCN2CCOCC2)Cc2ccccc2N(C)S(C)(=O)=O)n1] | 18.1 | 53.5 | 131.1 | 1410.3 | | |
| 147 | 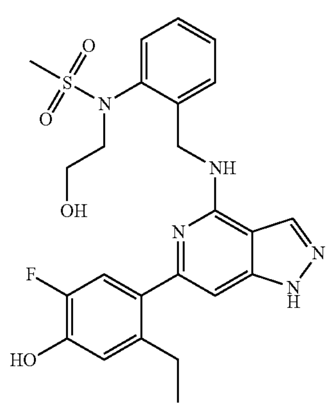 [SMILES: CCc1cc(O)c(F)cc1-c1cc2[nH]ncc2c(NCc2ccccc2N(CCO)S(C)(=O)=O)n1] | 1.1 | 4.7 | 18.5 | 49.4 | | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 142 | | 3.4 | 7.9 | 27.9 | 885.1 | | |
| 143 | | 40.4 | 43.6 | 121.9 | 4663.2 | | |
| 144 | | 55.3 | 70.7 | 185.9 | 8734.3 | | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 146 | 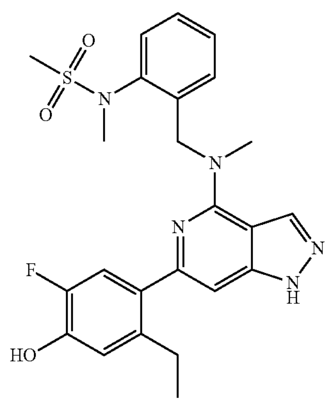 [SMILES: CCc1cc(O)c(F)cc1-c1cc2[nH]ncc2c(N(C)Cc2ccccc2N(C)S(C)(=O)=O)n1] | 0.9 | 5.1 | 19.1 | 49.9 | 7.6 | 62.3 |
| 148 | 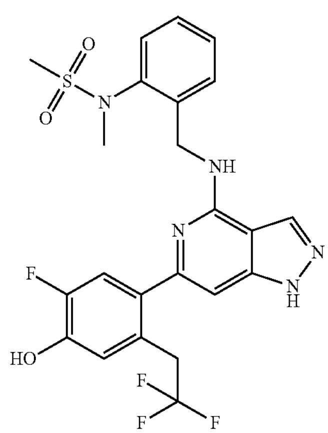 [SMILES: CN(c1ccccc1CNc1nc(-c2cc(F)c(O)cc2CC(F)(F)F)cc2[nH]ncc12)S(C)(=O)=O] | 1.8 | 6.3 | 22.8 | 145.6 | 14.9 | |
| 149 | 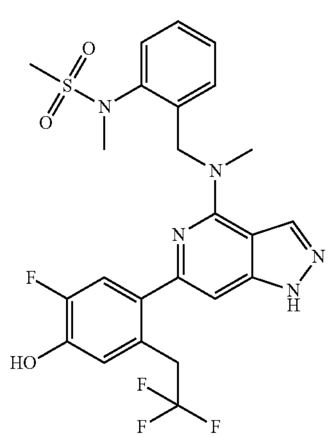 [SMILES: CN(Cc1ccccc1N(C)S(C)(=O)=O)c1nc(-c2cc(F)c(O)cc2CC(F)(F)F)cc2[nH]ncc12] | 2.7 | 14.5 | 22.7 | 763.5 | | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 150 | 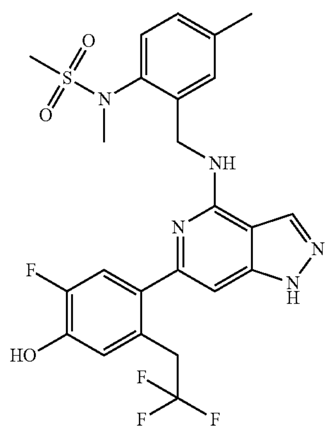 [SMILES: Cc1ccc(N(C)S(C)(=O)=O)c(CNc2nc(-c3cc(F)c(O)cc3CC(F)(F)F)cc3[nH]ncc23)c1] | 21.6 | 48.9 | 77.8 | 4156.1 | | |
| 19 | 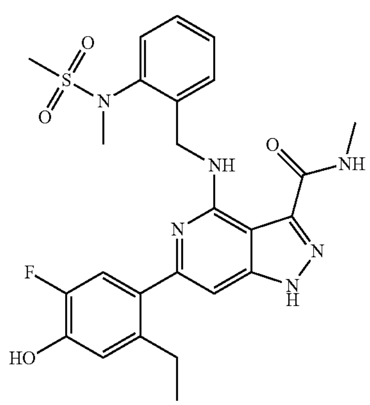 | 0.9 | 5.9 | 30.9 | 4.8 | 11.9 | 20.2 |
| 134 | 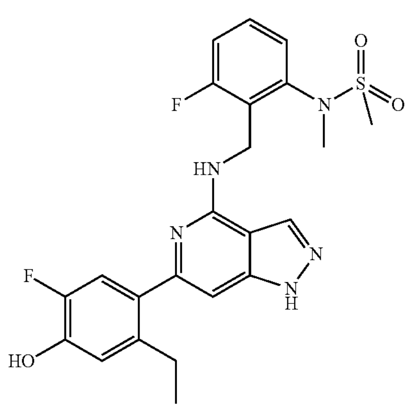 [SMILES: CCc1cc(O)c(F)cc1-c1cc2[nH]ncc2c(NCc2c(F)cccc2N(C)S(C)(=O)=O)n1] | <0.5 | 1.7 | 7.6 | 20.3 | | 258.6 |

TABLE 1-continued

Data for JAK Caliper ™ Kinase assays at 1 mM ATP and Cell Based assays

| | | Caliper ™ Assays at 1 mM ATP | | | | Cell Based Assays | |
| --- | --- | --- | --- | --- | --- | --- | --- |
| | | | | | | A549 cell assay: Inhibition | Human T cell assay: Inhibition |
| Ex. | Structure | JAK1 IC$_{50}$ (nM) | JAK2 IC$_{50}$ (nM) | JAK3 IC$_{50}$ (nM) | TYK2 IC$_{50}$ (nM) | of pSTAT3 IC$_{50}$ (nM) | of pSTAT5 IC$_{50}$ (nM) |
| 136 | | 0.8 | 4.3 | 22.4 | 8.7 | 13.3 | |
| 155 | | 1.2 | 5.0 | 15.5 | 61.0 | 30.1 | |
| 129 | | 11.6 | 43.7 | 180.1 | 56.6 | 62.4 | |

TABLE 1-continued
Data for JAK Caliper ™ Kinase assays at 1 mM ATP and Cell Based assays
| Ex. | Structure | Caliper ™ Assays at 1 mM ATP | | | | Cell Based Assays | |
|---|---|---|---|---|---|---|---|
| | | JAK1 $IC_{50}$ (nM) | JAK2 $IC_{50}$ (nM) | JAK3 $IC_{50}$ (nM) | TYK2 $IC_{50}$ (nM) | A549 cell assay: Inhibition of pSTAT3 $IC_{50}$ (nM) | Human T cell assay: Inhibition of pSTAT5 $IC_{50}$ (nM) |
| 130 | 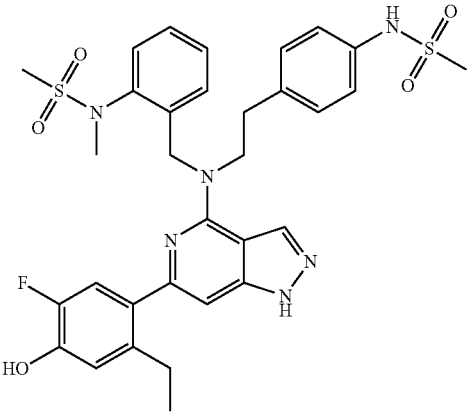 [SMILES: CCc1cc(O)c(F)cc1-c1cc2[nH]ncc2c(N(CCc2ccc(NS(C)(=O)=O)cc2)Cc2ccccc2N(C)S(C)(=O)=O)n1] | 43.8 | 154.9 | 1358.2 | 194.1 | 728.6 | |
| 5 | 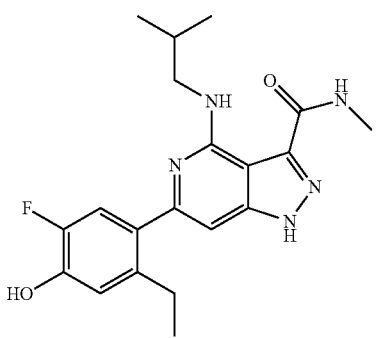 [SMILES: CCc1cc(O)c(F)cc1-c1cc2[nH]nc(C(=O)NC)c2c(NCC(C)C)n1] | 2.1 | 7.5 | 31.9 | 7.0 | 1.7 | |
| 20 | 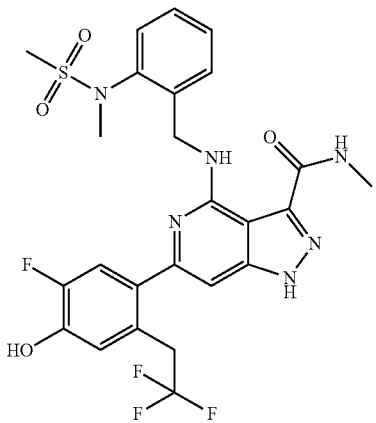 [SMILES: CNC(=O)c1n[nH]c2cc(-c3cc(F)c(O)cc3CC(F)(F)F)nc(NCc3ccccc3N(C)S(C)(=O)=O)c12] | 3.6 | 16.6 | 95.3 | 20.9 | 18.8 | 31.9 |

TABLE 1-continued
Data for JAK Caliper ™ Kinase assays at 1 mM ATP and Cell Based assays
| Ex. | Structure | Caliper ™ Assays at 1 mM ATP | | | | Cell Based Assays | |
|---|---|---|---|---|---|---|---|
| | | | | | | A549 cell assay: Inhibition of pSTAT3 | Human T cell assay: Inhibition of pSTAT5 |
| | | JAK1 IC$_{50}$ (nM) | JAK2 IC$_{50}$ (nM) | JAK3 IC$_{50}$ (nM) | TYK2 IC$_{50}$ (nM) | IC$_{50}$ (nM) | IC$_{50}$ (nM) |
| 3 | 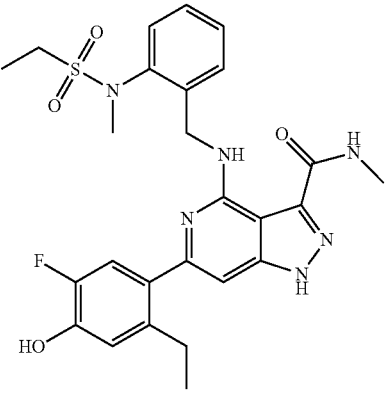 [SMILES: CCc1cc(O)c(F)cc1-c1cc2[nH]nc(C(=O)NC)c2c(NCc2ccccc2N(C)S(=O)(=O)CC)n1] | 1.9 | 9.6 | 47.5 | 6.8 | 16.2 | |
| 6 | 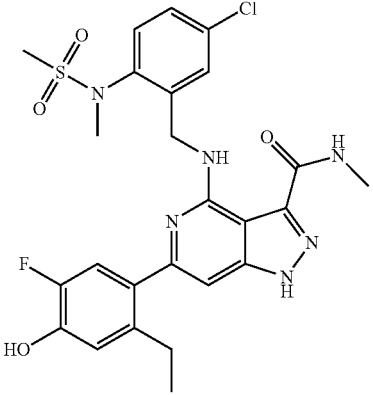 | 3.1 | 15.8 | 84.9 | 15.3 | 23.4 | |
| 8 | 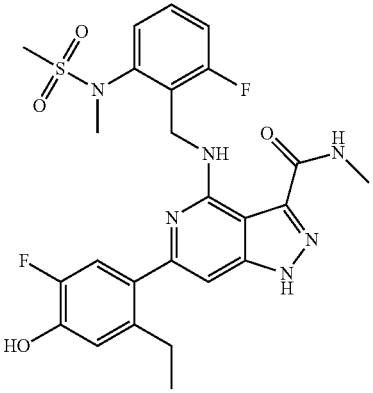 [SMILES: CCc1cc(O)c(F)cc1-c1cc2[nH]nc(C(=O)NC)c2c(NCc2c(F)cccc2N(C)S(C)(=O)=O)n1] | 1.7 | 7.5 | 33.8 | 5.7 | 6.4 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 7 | 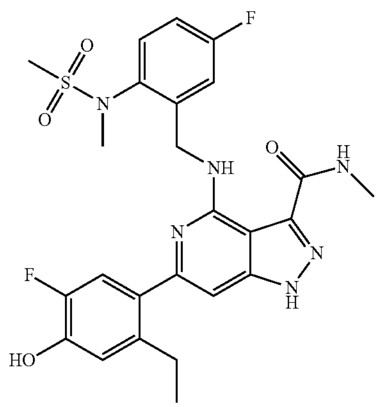 [SMILES: CCc1cc(O)c(F)cc1-c1cc2[nH]nc(C(=O)NC)c2c(NCc2cc(F)ccc2N(C)S(C)(=O)=O)n1] | 1.7 | 9.2 | 49.0 | 6.5 | 5.7 | |
| 21 | 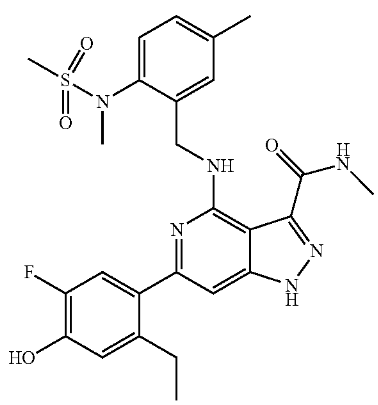 [SMILES: CCc1cc(O)c(F)cc1-c1cc2[nH]nc(C(=O)NC)c2c(NCc2cc(C)ccc2N(C)S(C)(=O)=O)n1] | 2.7 | 13.2 | 67.9 | 11.4 | 35.6 | |
| 9 | 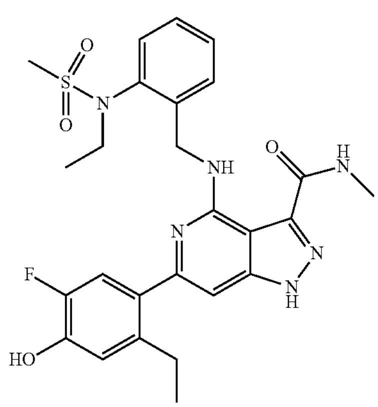 [SMILES: CCc1cc(O)c(F)cc1-c1cc2[nH]nc(C(=O)NC)c2c(NCc2ccccc2N(CC)S(C)(=O)=O)n1] | 1.7 | 10.8 | 60.0 | 7.2 | 14.9 | |

TABLE 1-continued

Data for JAK Caliper™ Kinase assays at 1 mM ATP and Cell Based assays

| | | Caliper™ Assays at 1 mM ATP | | | | Cell Based Assays | |
|---|---|---|---|---|---|---|---|
| | | | | | | A549 cell assay: Inhibition | Human T cell assay: Inhibition |
| Ex. | Structure | JAK1 IC$_{50}$ (nM) | JAK2 IC$_{50}$ (nM) | JAK3 IC$_{50}$ (nM) | TYK2 IC$_{50}$ (nM) | of pSTAT3 IC$_{50}$ (nM) | of pSTAT5 IC$_{50}$ (nM) |
| 2 | | 3.4 | 17.0 | 84.5 | 12.1 | 46.8 | |
| 10 | | 4.7 | 19.0 | 93.1 | 17.9 | 26 | |
| 11 | | 8.7 | 36.9 | 206.6 | 229.4 | 72.4 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | | | | | A549 cell assay: Inhibition | Human T cell assay: Inhibition |
| | | JAK1 $IC_{50}$ (nM) | JAK2 $IC_{50}$ (nM) | JAK3 $IC_{50}$ (nM) | TYK2 $IC_{50}$ (nM) | of pSTAT3 $IC_{50}$ (nM) | of pSTAT5 $IC_{50}$ (nM) |
| 14 | | 4.2 | 20.5 | 99.7 | 43.2 | 20.7 | |
| 1 | | 8.0 | 38.1 | 176.8 | 36.5 | 67.4 | |
| 15 | | 13.6 | 55.0 | 342.4 | 618.3 | 92.4 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 93 | 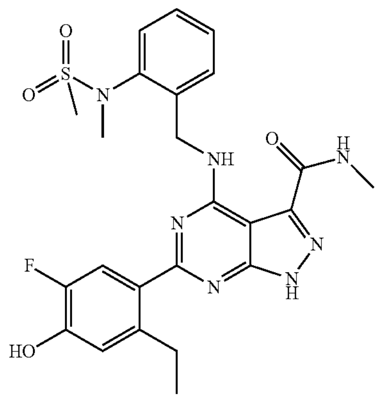 [SMILES: CCc1cc(O)c(F)cc1-c1nc(NCc2ccccc2N(C)S(C)(=O)=O)c2c(C(=O)NC)n[nH]c2n1] | 2.0 | 8.4 | 27.4 | 13.9 | 31.9 | 40.4 |
| 16 | 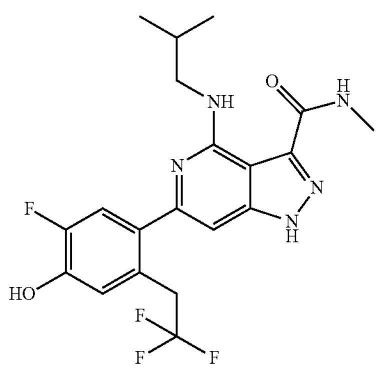 [SMILES: CNC(=O)c1n[nH]c2cc(-c3cc(F)c(O)cc3CC(F)(F)F)nc(NCC(C)C)c12] | 6.3 | 23.0 | 130.8 | 66.0 | 65.1 | |
| 18 | 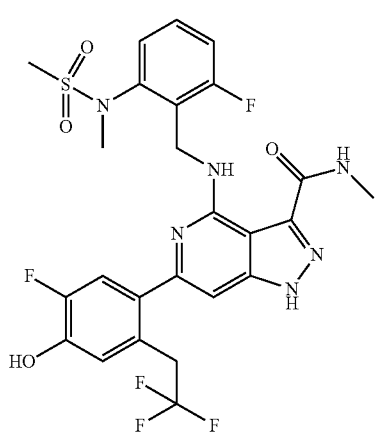 [SMILES: CNC(=O)c1n[nH]c2cc(-c3cc(F)c(O)cc3CC(F)(F)F)nc(NCc3c(F)cccc3N(C)S(C)(=O)=O)c12] | 4.0 | 17.4 | 73.0 | 31.0 | 97 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | | | | | A549 cell assay: Inhibition of pSTAT3 $IC_{50}$ (nM) | Human T cell assay: Inhibition of pSTAT5 $IC_{50}$ (nM) |
| | | JAK1 $IC_{50}$ (nM) | JAK2 $IC_{50}$ (nM) | JAK3 $IC_{50}$ (nM) | TYK2 $IC_{50}$ (nM) | | |
| 17 | 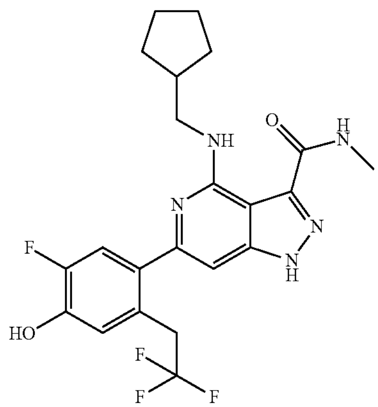 [SMILES: CNC(=O)c1n[nH]c2cc(-c3cc(F)c(O)cc3CC(F)(F)F)nc(NCC3CCCC3)c12] | 18.5 | 52.9 | 255.7 | 142.4 | 173.9 | |
| 13 | 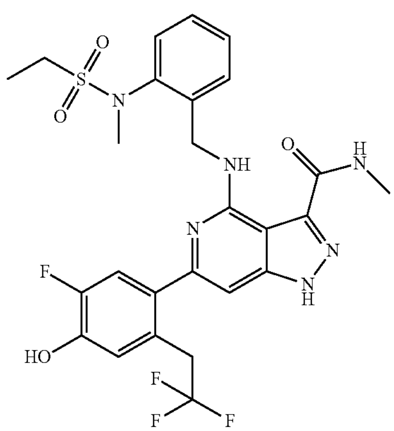 [SMILES: CCS(=O)(=O)N(C)c1ccccc1CNc1nc(-c2cc(F)c(O)cc2CC(F)(F)F)cc2[nH]nc(C(=O)NC)c12] | 5.3 | 26.6 | 118.0 | 35.7 | 96.7 | |
| 12 | 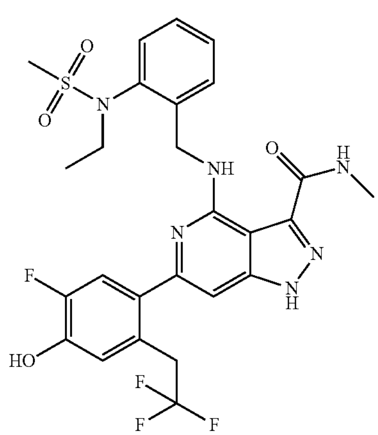 [SMILES: CCN(c1ccccc1CNc1nc(-c2cc(F)c(O)cc2CC(F)(F)F)cc2[nH]nc(C(=O)NC)c12)S(C)(=O)=O] | 6.4 | 31.5 | 120.6 | 24.8 | 44.9 | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 $IC_{50}$ (nM) | JAK2 $IC_{50}$ (nM) | JAK3 $IC_{50}$ (nM) | TYK2 $IC_{50}$ (nM) | A549 cell assay: Inhibition of pSTAT3 $IC_{50}$ (nM) | Human T cell assay: Inhibition of pSTAT5 $IC_{50}$ (nM) |
| 4 | 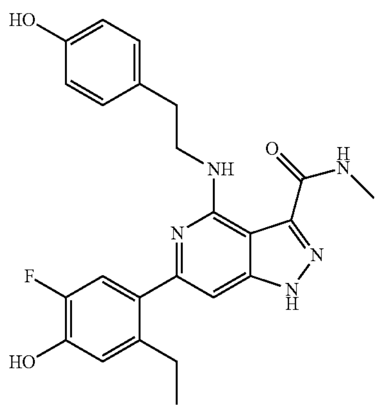 [SMILES: CCc1cc(O)c(F)cc1-c1cc2[nH]nc(C(=O)NC)c2c(NCCc2ccc(O)cc2)n1] | 1.7 | 6.2 | 26.6 | 15.3 | 29.7 | |
| 56 | 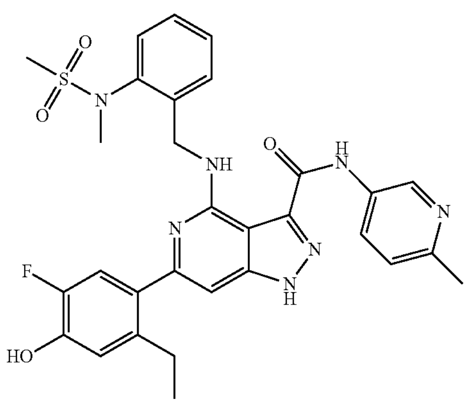 [SMILES: CCc1cc(O)c(F)cc1-c1cc2[nH]nc(C(=O)Nc3ccc(C)nc3)c2c(NCc2ccccc2N(C)S(C)(=O)=O)n1] | 6.6 | 26.1 | 134.8 | 19.9 | 276.9 | 53.4 |
| 31 | 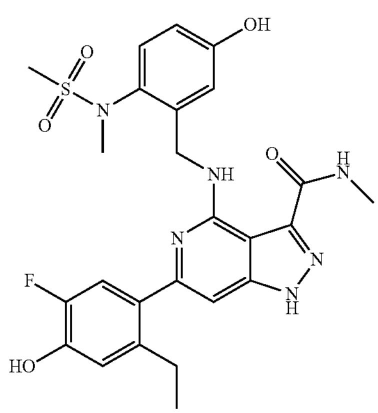 [SMILES: CCc1cc(O)c(F)cc1-c1cc2[nH]nc(C(=O)NC)c2c(NCc2cc(O)ccc2N(C)S(C)(=O)=O)n1] | 1.3 | 7.0 | 33.0 | 4.6 | 74 | 48.2 |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 22 | 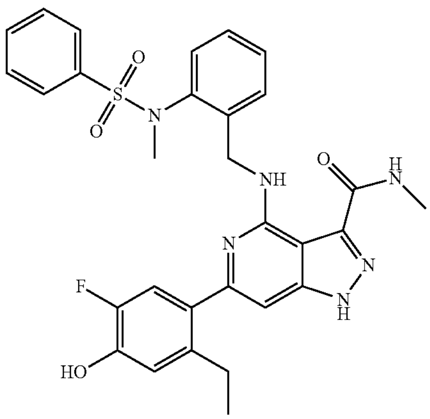 [SMILES: CCc1cc(O)c(F)cc1-c1cc2[nH]nc(C(=O)NC)c2c(NCc2ccccc2N(C)S(=O)(=O)c2ccccc2)n1] | 17.5 | 81.3 | 359.0 | 59.1 | 52.8 | |
| 23 | 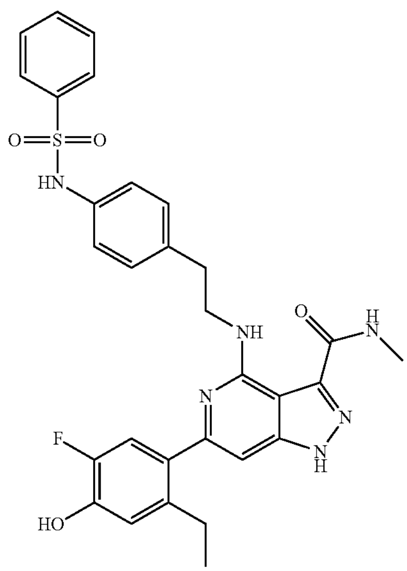 [SMILES: CCc1cc(O)c(F)cc1-c1cc2[nH]nc(C(=O)NC)c2c(NCCc2ccc(NS(=O)(=O)c3ccccc3)cc2)n1] | 5.8 | 25.7 | 110.7 | 83.2 | 51.4 | |
| 165 | 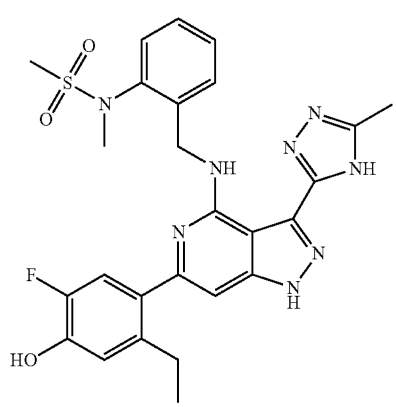 [SMILES: CCc1cc(O)c(F)cc1-c1cc2[nH]nc(-c3nnc(C)[nH]3)c2c(NCc2ccccc2N(C)S(C)(=O)=O)n1] | 3.5 | 16.9 | 78.0 | 14.6 | 566.7 | 91.3 |

TABLE 1-continued

Data for JAK Caliper ™ Kinase assays at 1 mM ATP and Cell Based assays

| Ex. | Structure | | Caliper ™ Assays at 1 mM ATP | | | | Cell Based Assays | |
|---|---|---|---|---|---|---|---|---|
| | | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 38 | Chiral | | 4.0 | 25.0 | 121.8 | 17.8 | 30.8 | |
| 39 | Chiral | | 32.3 | 48.2 | 278.5 | 320.3 | 60.9 | |
| 162 | 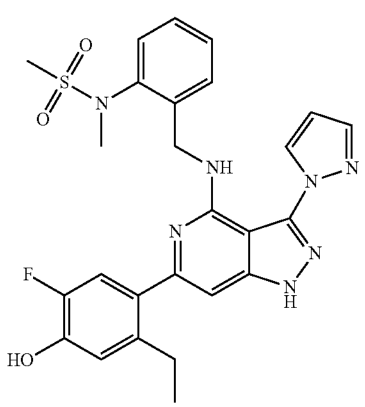 [SMILES: CCc1cc(O)c(F)cc1-c1cc2[nH]nc(-n3cccn3)c2c(NCc2ccccc2N(C)S(C)(=O)=O)n1] | | 4.1 | 23.6 | 90.6 | 15.4 | 20 | |

TABLE 1-continued

Data for JAK Caliper ™ Kinase assays at 1 mM ATP and Cell Based assays

| Ex. | Structure | Caliper ™ Assays at 1 mM ATP ||||  Cell Based Assays ||
|---|---|---|---|---|---|---|---|
|  |  | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 157 | 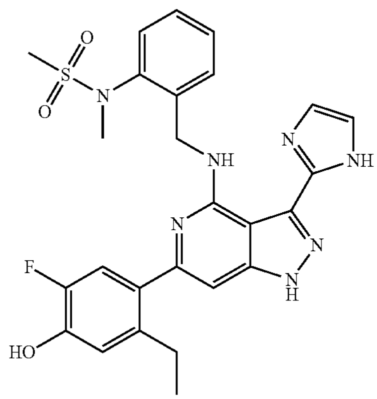 [SMILES: CCc1cc(O)c(F)cc1-c1cc2[nH]nc(-c3ncc[nH]3)c2c(NCc2ccccc2N(C)S(C)(=O)=O)n1] | 3.4 | 15.0 | 76.5 | 11.7 | 26.2 |  |
| 94 | 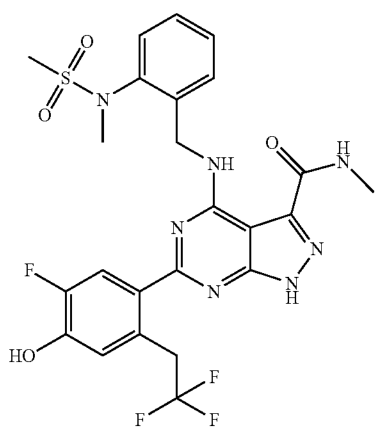 [SMILES: CNC(=O)c1n[nH]c2nc(-c3cc(F)c(O)cc3CC(F)(F)F)nc(NCc3ccccc3N(C)S(C)(=O)=O)c12] | 5.4 | 27.7 | 71.2 | 503.4 | 125.5 |  |
| 158 | 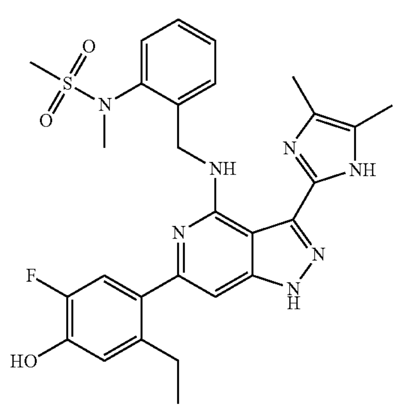 [SMILES: CCc1cc(O)c(F)cc1-c1cc2[nH]nc(-c3nc(C)c(C)[nH]3)c2c(NCc2ccccc2N(C)S(C)(=O)=O)n1] | 5.3 | 27.8 | 114.0 | 33.3 | 31.3 |  |

TABLE 1-continued
Data for JAK Caliper ™ Kinase assays at 1 mM ATP and Cell Based assays
| | | Caliper ™ Assays at 1 mM ATP | | | | Cell Based Assays | |
|---|---|---|---|---|---|---|---|
| | | | | | | A549 cell assay: Inhibition of pSTAT3 | Human T cell assay: Inhibition of pSTAT5 |
| Ex. | Structure | JAK1 IC$_{50}$ (nM) | JAK2 IC$_{50}$ (nM) | JAK3 IC$_{50}$ (nM) | TYK2 IC$_{50}$ (nM) | IC$_{50}$ (nM) | IC$_{50}$ (nM) |
| 159 | 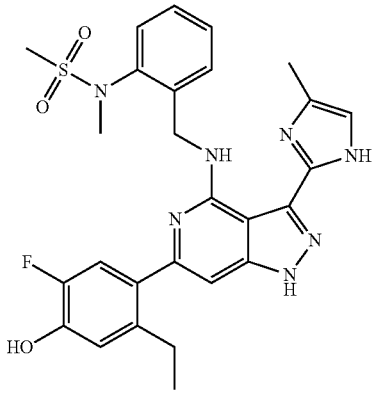 [SMILES: CCc1cc(O)c(F)cc1-c1cc2[nH]nc(-c3nc(C)c[nH]3)c2c(NCc2ccccc2N(C)S(C)(=O)=O)n1] | 4.3 | 18.5 | 83.3 | 16.1 | 18.7 | |
| 163 | 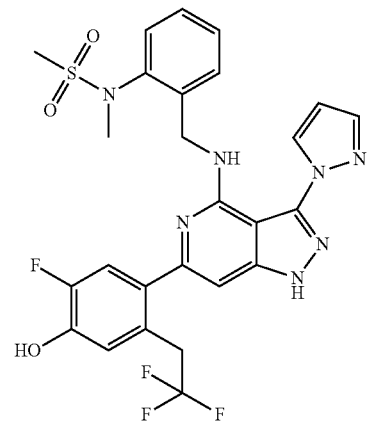 [SMILES: CN(c1ccccc1CNc1nc(-c2cc(F)c(O)cc2CC(F)(F)F)cc2[nH]nc(-n3cccn3)c12)S(C)(=O)=O] | 32.9 | 150.2 | 491.0 | 355.9 | 98.6 | |
| 76 | 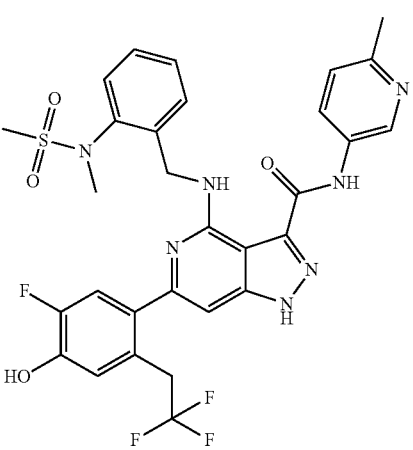 [SMILES: Cc1ccc(NC(=O)c2n[nH]c3cc(-c4cc(F)c(O)cc4CC(F)(F)F)nc(NCc4ccccc4N(C)S(C)(=O)=O)c23)cn1] | 29.6 | 112.9 | 475.0 | 315.5 | 324.8 | 120.7 |

TABLE 1-continued
Data for JAK Caliper ™ Kinase assays at 1 mM ATP and Cell Based assays
| | | Caliper ™ Assays at 1 mM ATP | | | | Cell Based Assays | |
|---|---|---|---|---|---|---|---|
| | | | | | | A549 cell assay: Inhibition | Human T cell assay: Inhibition |
| Ex. | Structure | JAK1 IC$_{50}$ (nM) | JAK2 IC$_{50}$ (nM) | JAK3 IC$_{50}$ (nM) | TYK2 IC$_{50}$ (nM) | of pSTAT3 IC$_{50}$ (nM) | of pSTAT5 IC$_{50}$ (nM) |
| 171 | 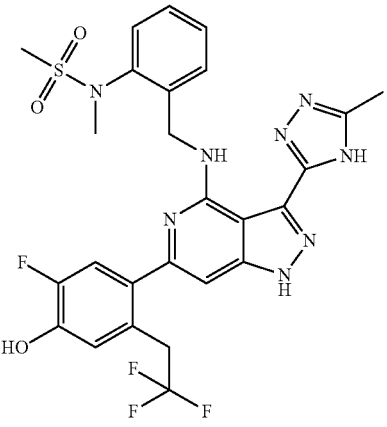 [SMILES: Cc1nnc(-c2n[nH]c3cc(-c4cc(F)c(O)cc4CC(F)(F)F)nc(NCc4ccccc4N(C)S(C)(=O)=O)c23)[nH]1] | 27.5 | 128.9 | 428.9 | 150.2 | 1575.2 | 1090.4 |
| 92 | 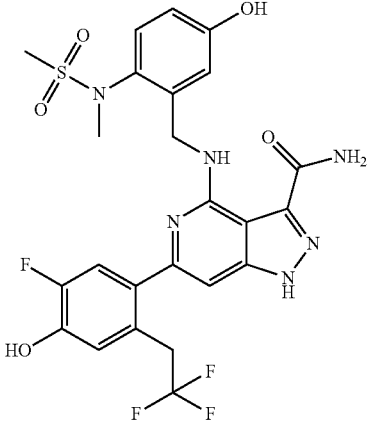 [SMILES: CN(c1ccc(O)cc1CNc1nc(-c2cc(F)c(O)cc2CC(F)(F)F)cc2[nH]nc(C(N)=O)c12)S(C)(=O)=O] | 2.1 | 13.5 | 45.7 | 14.5 | 398.2 | 343.4 |
| 77 | 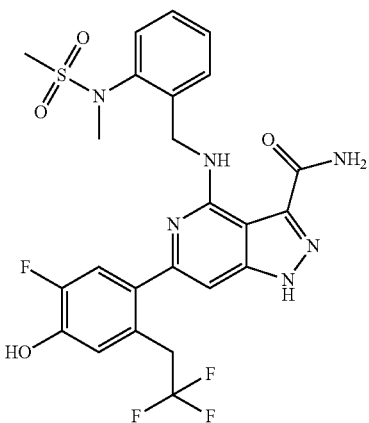 [SMILES: CN(c1ccccc1CNc1nc(-c2cc(F)c(O)cc2CC(F)(F)F)cc2[nH]nc(C(N)=O)c12)S(C)(=O)=O] | 3.3 | 15.1 | 63.6 | 27.1 | 32.9 | 59.9 |

TABLE 1-continued
Data for JAK Caliper ™ Kinase assays at 1 mM ATP and Cell Based assays
| Ex. | Structure | Caliper ™ Assays at 1 mM ATP | | | | Cell Based Assays | |
|---|---|---|---|---|---|---|---|
| | | | | | | A549 cell assay: Inhibition of pSTAT3 IC$_{50}$ (nM) | Human T cell assay: Inhibition of pSTAT5 IC$_{50}$ (nM) |
| | | JAK1 IC$_{50}$ (nM) | JAK2 IC$_{50}$ (nM) | JAK3 IC$_{50}$ (nM) | TYK2 IC$_{50}$ (nM) | | |
| 166 | 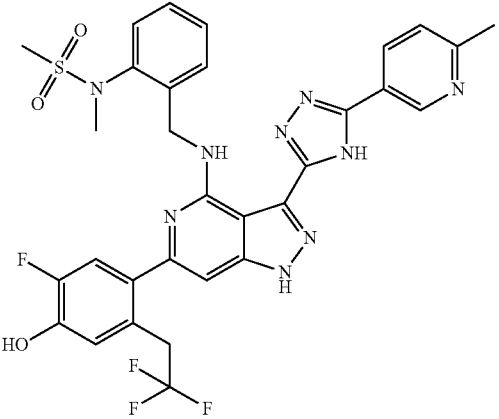 [SMILES: Cc1ccc(-c2nnc(-c3n[nH]c4cc(-c5cc(F)c(O)cc5CC(F)(F)F)nc(NCc5ccccc5N(C)S(C)(=O)=O)c34)[nH]2)cn1] | 20.9 | 97.4 | 322.5 | 126.5 | 697.3 | 590.8 |
| 164 | 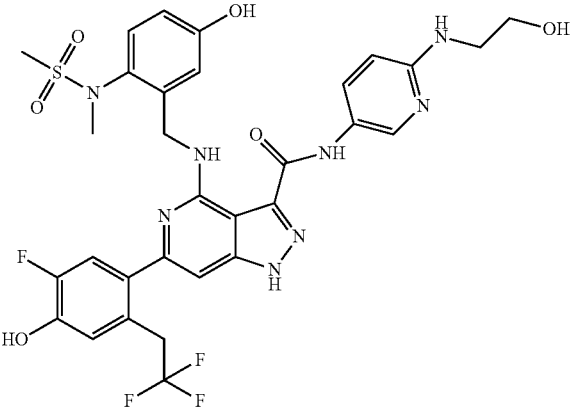 [SMILES: CN(c1ccc(O)cc1CNc1nc(-c2cc(F)c(O)cc2CC(F)(F)F)cc2[nH]nc(C(=O)Nc3ccc(NCCO)nc3)c12)S(C)(=O)=O] | 4.5 | 22.2 | 91.0 | 24.2 | 3022.5 | 3897.0 |
| 98 | 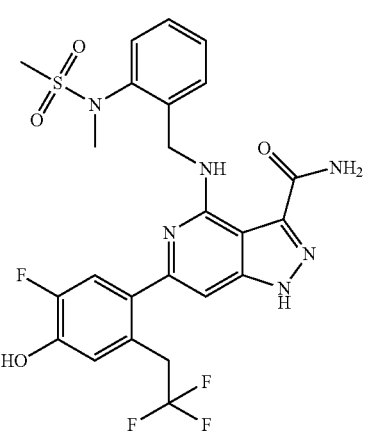 [SMILES: CN(c1ccccc1CNc1nc(-c2cc(F)c(O)cc2CC(F)(F)F)cc2[nH]nc(C(N)=O)c12)S(C)(=O)=O] | 4.9 | 18.3 | 39.6 | 600.3 | 723.6 | 324.5 |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 170 | 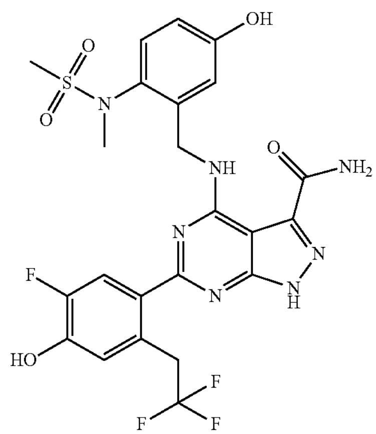 [SMILES: CN(c1ccc(O)cc1CNc1nc(-c2cc(F)c(O)cc2CC(F)(F)F)nc2[nH]nc(C(N)=O)c12)S(C)(=O)=O] | 3.2 | 12.7 | 38.0 | 373.4 | 1356.3 | 767.2 |
| 169 | 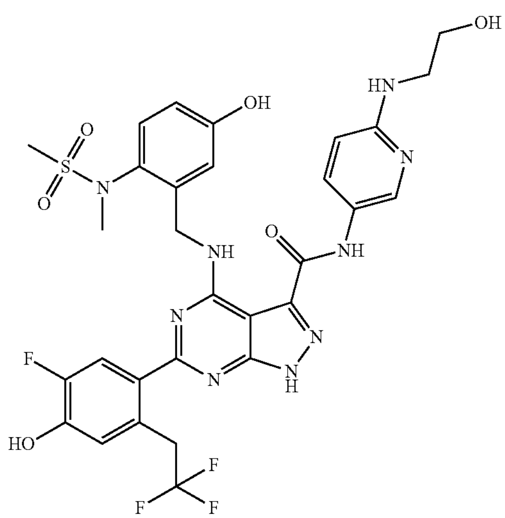 [SMILES: CN(c1ccc(O)cc1CNc1nc(-c2cc(F)c(O)cc2CC(F)(F)F)nc2[nH]nc(C(=O)Nc3ccc(NCCO)nc3)c12)S(C)(=O)=O] | 10.5 | 22.9 | 59.8 | 305.7 | >10000 | |
| 109 | 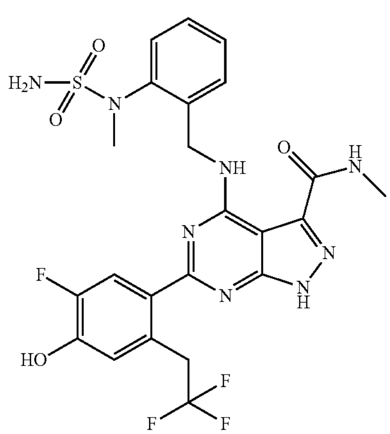 [SMILES: CNC(=O)c1n[nH]c2nc(-c3cc(F)c(O)cc3CC(F)(F)F)nc(NCc3ccccc3N(C)S(N)(=O)=O)c12] | 6.4 | 31.2 | 107.3 | 674.2 | | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 73 | 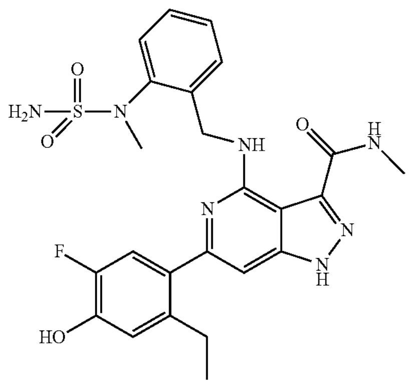 [SMILES: CCc1cc(O)c(F)cc1-c1cc2[nH]nc(C(=O)NC)c2c(NCc2ccccc2N(C)S(N)(=O)=O)n1] | 5.4 | 18.8 | 80.9 | 33.9 | 35.6 | |
| 167 | 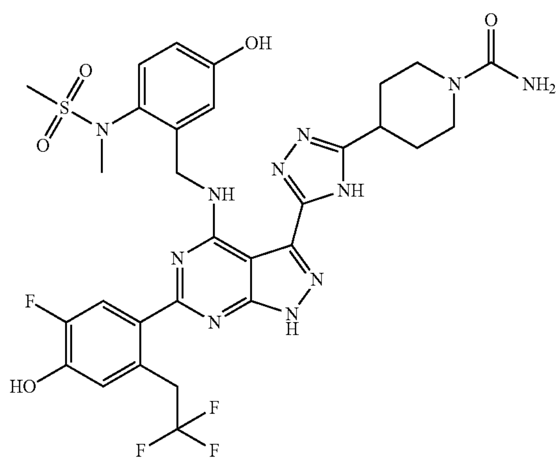 [SMILES: CN(c1ccc(O)cc1CNc1nc(-c2cc(F)c(O)cc2CC(F)(F)F)nc2[nH]nc(-c3nnc(C4CCN(C(N)=O)CC4)[nH]3)c12)S(C)(=O)=O] | 4.1 | 16.0 | 47.4 | 310.0 | >10000 | |
| 168 | 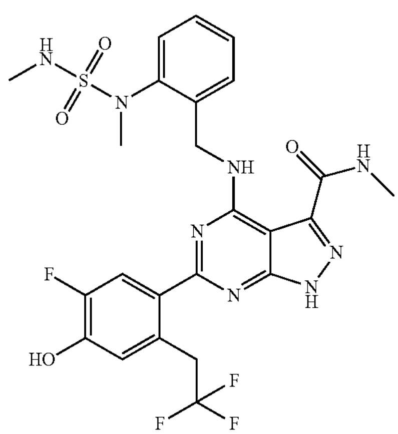 | 15.7 | 59.5 | 121.7 | 1156.7 | 1327.4 | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 161 | 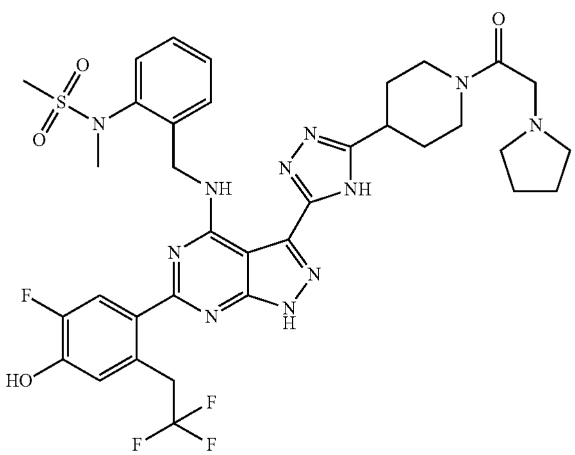 [SMILES: CN(c1ccccc1CNc1nc(-c2cc(F)c(O)cc2CC(F)(F)F)nc2[nH]nc(-c3nnc(C4CCN(C(=O)CN5CCCC5)CC4)[nH]3)c12)S(C)(=O)=O] | 16.8 | 54.3 | 157.6 | 2260.9 | >10000 | |
| 102 | 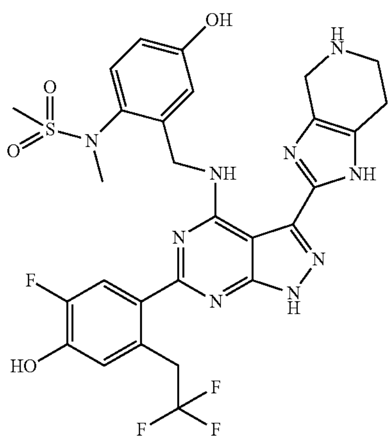 [SMILES: CN(c1ccc(O)cc1CNc1nc(-c2cc(F)c(O)cc2CC(F)(F)F)nc2[nH]nc(-c3nc4c([nH]3)CCNC4)c12)S(C)(=O)=O] | 5.6 | 35.3 | 110.6 | 68.6 | 3357.9 | |
| 105 | 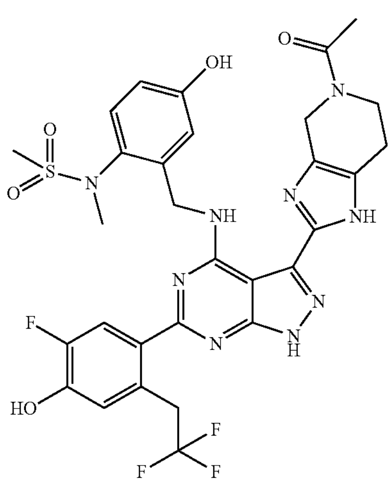 [SMILES: CC(=O)N1CCc2[nH]c(-c3n[nH]c4nc(-c5cc(F)c(O)cc5CC(F)(F)F)nc(NCc5cc(O)ccc5N(C)S(C)(=O)=O)c34)nc2C1] | 3.2 | 14.4 | 51.2 | 14.0 | 7023.2 | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 110 | | 5.4 | 26.9 | 120.4 | 35.0 | >10000 | |
| 74 | | 14.7 | 68.7 | 208.9 | 215.7 | | |
| 50 | | 1.7 | 10.7 | 47.4 | 10.5 | 320.8 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | | | | | A549 cell assay: Inhibition of pSTAT3 $IC_{50}$ (nM) | Human T cell assay: Inhibition of pSTAT5 $IC_{50}$ (nM) |
| | | JAK1 $IC_{50}$ (nM) | JAK2 $IC_{50}$ (nM) | JAK3 $IC_{50}$ (nM) | TYK2 $IC_{50}$ (nM) | | |
| 106 | | 41.2 | 283.2 | 210.6 | 6111.8 | 2517.2 | |
| 51 | | 3.5 | 20.8 | 66.9 | 226.4 | 182.5 | |
| 40 | | 4.6 | 23.1 | 130.3 | 18.1 | 50 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 173 | | 9.3 | 50.3 | 133.9 | 180.1 | 220.3 | |
| 26 | | 19.9 | 91.1 | 293.3 | 217.5 | 124.5 | |

TABLE 1-continued
Data for JAK Caliper ™ Kinase assays at 1 mM ATP and Cell Based assays
| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 107 | 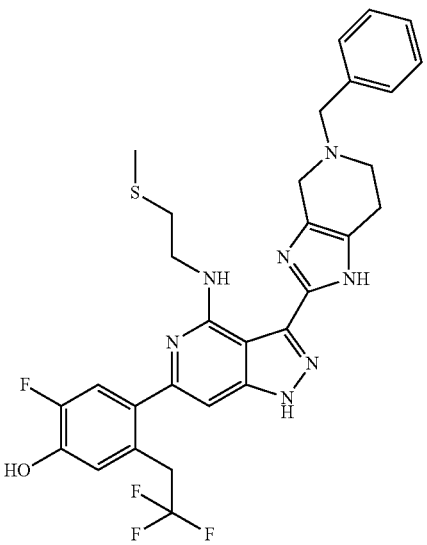 [SMILES: CSCCNc1nc(-c2cc(F)c(O)cc2CC(F)(F)F)cc2[nH]nc(-c3nc4c([nH]3)CCN(Cc3ccccc3)C4)c12] | 50.0 | 196.3 | 589.0 | 172.5 | 898.7 | |
| 95 | 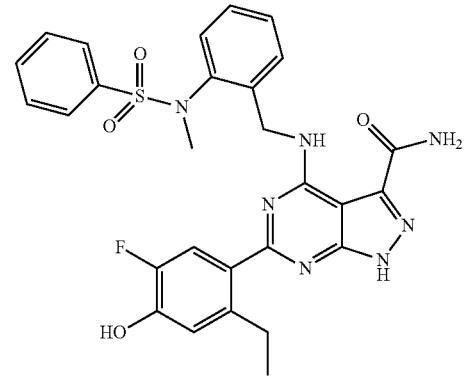 [SMILES: CCc1cc(O)c(F)cc1-c1nc(NCc2ccccc2N(C)S(=O)(=O)c2ccccc2)c2c(C(N)=O)n[nH]c2n1] | 6.7 | 27.0 | 82.4 | 89.3 | 59.9 | |
| 108 | 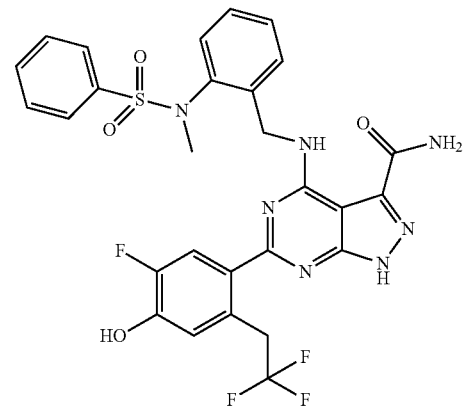 [SMILES: CN(c1ccccc1CNc1nc(-c2cc(F)c(O)cc2CC(F)(F)F)nc2[nH]nc(C(N)=O)c12)S(=O)(=O)c1ccccc1] | 50.5 | 123.5 | 197.7 | 5692.8 | 1504.2 | |

TABLE 1-continued
Data for JAK Caliper ™ Kinase assays at 1 mM ATP and Cell Based assays
| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 100 | 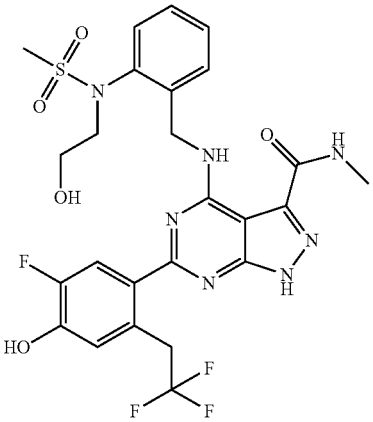 [SMILES: CNC(=O)c1n[nH]c2nc(-c3cc(F)c(O)cc3CC(F)(F)F)nc(NCc3ccccc3N(CCO)S(C)(=O)=O)c12] | 8.7 | 32.3 | 61.9 | 1149.1 | 6880.8 | |
| 152 | 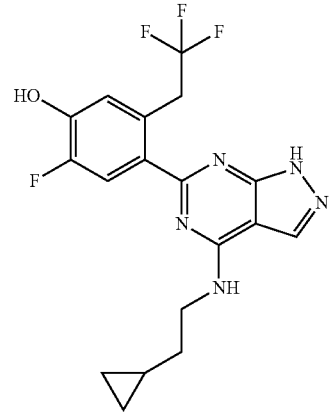 [SMILES: Oc1cc(CC(F)(F)F)c(-c2nc(NCCC3CC3)c3cn[nH]c3n2)cc1F] | 41.6 | 228.0 | 156.7 | 3673.3 | 133.2 | |
| 151 | 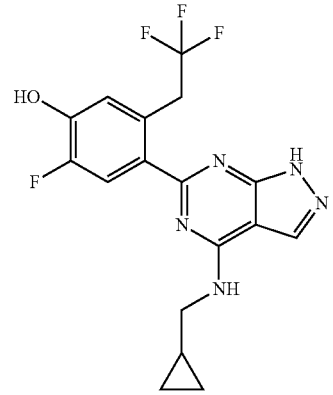 [SMILES: Oc1cc(CC(F)(F)F)c(-c2nc(NCC3CC3)c3cn[nH]c3n2)cc1F] | 33.9 | 168.9 | 124.7 | 2976.2 | 133.4 | |

TABLE 1-continued

Data for JAK Caliper ™ Kinase assays at 1 mM ATP and Cell Based assays

| Ex. | Structure | Caliper ™ Assays at 1 mM ATP ||||Cell Based Assays ||
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 154 | 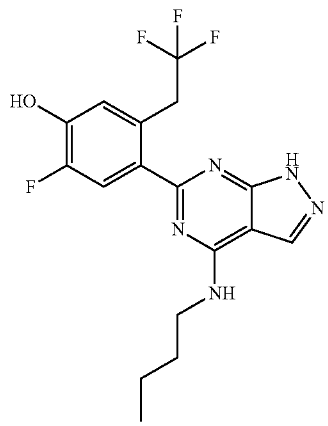 [SMILES: CCCCNc1nc(-c2cc(F)c(O)cc2CC(F)(F)F)nc2[nH]ncc12] | 77.6 | 301.6 | 228.0 | 5136.3 | | |
| 153 | 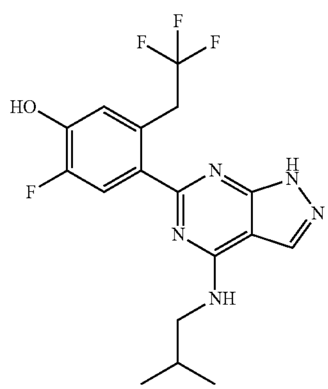 [SMILES: CC(C)CNc1nc(-c2cc(F)c(O)cc2CC(F)(F)F)nc2[nH]ncc12] | 74.0 | 241.2 | 207.0 | 7458.4 | | |
| 24 | 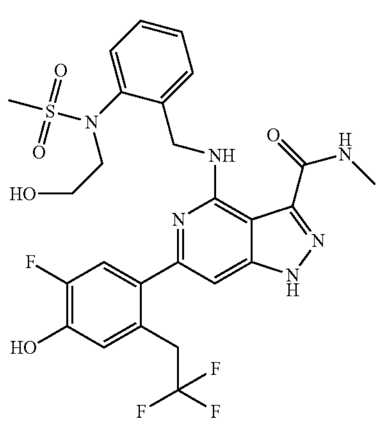 | 2.9 | 16.5 | 69.6 | 29.9 | 226.4 | |

TABLE 1-continued
Data for JAK Caliper ™ Kinase assays at 1 mM ATP and Cell Based assays
| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 27 | 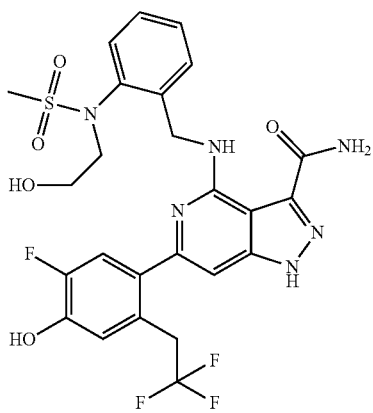 [SMILES: CS(=O)(=O)N(CCO)c1ccccc1CNc1nc(-c2cc(F)c(O)cc2CC(F)(F)F)cc2[nH]nc(C(N)=O)c12] | 2.9 | 14.7 | 53.5 | 48.8 | 873.6 | |
| 101 | 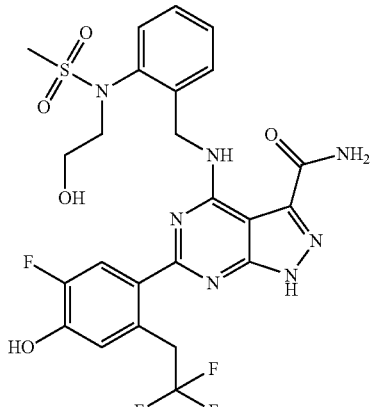 | 10.5 | 41.3 | 51.1 | 1956.2 | >10000 | |
| 29 | 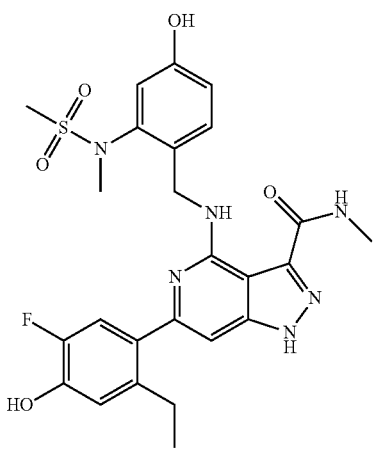 [SMILES: CCc1cc(O)c(F)cc1-c1cc2[nH]nc(C(=O)NC)c2c(NCc2ccc(O)cc2N(C)S(C)(=O)=O)n1] | 1.5 | 8.5 | 33.2 | 19.0 | 86.9 | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 30 | 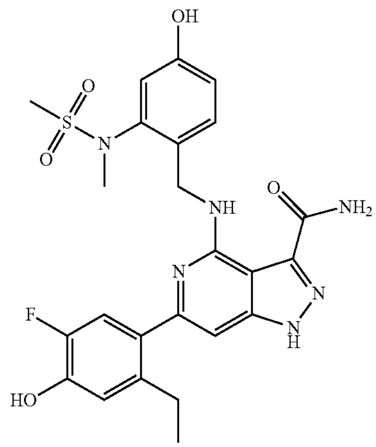 [SMILES: CCc1cc(O)c(F)cc1-c1cc2[nH]nc(C(N)=O)c2c(NCc2ccc(O)cc2N(C)S(C)(=O)=O)n1] | 1.0 | 5.8 | 23.3 | 29.0 | 163.5 | |
| 99 | 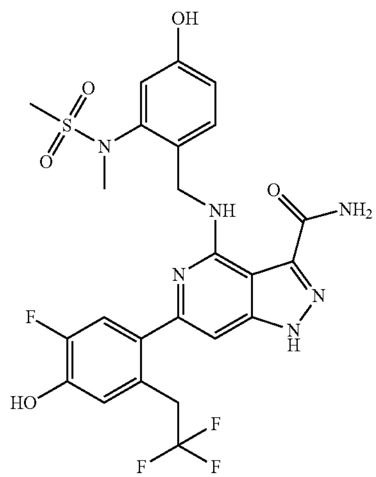 [SMILES: CN(c1cc(O)ccc1CNc1nc(-c2cc(F)c(O)cc2CC(F)(F)F)cc2[nH]nc(C(N)=O)c12)S(C)(=O)=O] | 6.8 | 26.9 | 62.4 | 425.6 | 2465.9 | |
| 33 | 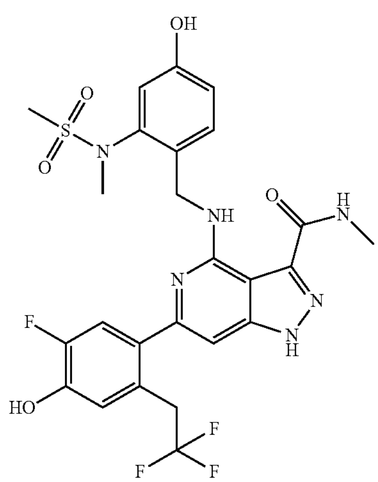 [SMILES: CNC(=O)c1n[nH]c2cc(-c3cc(F)c(O)cc3CC(F)(F)F)nc(NCc3ccc(O)cc3N(C)S(C)(=O)=O)c12] | 5.7 | 25.0 | 75.2 | 281.9 | 490.1 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 103 | | 5.0 | 31.0 | 92.6 | 349.0 | 235 | |
| 32 | | 60.4 | 276.8 | 839.2 | 373.4 | 627.5 | |
| 90 | | 2.7 | 18.1 | 77.1 | 23.2 | 30.4 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 34 | 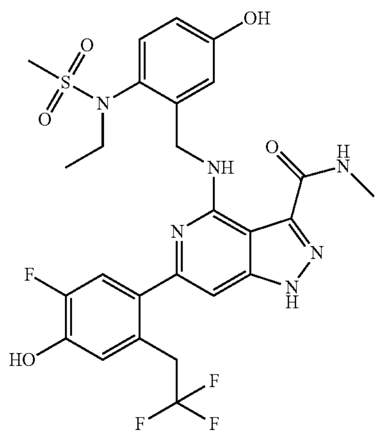 [SMILES: CCN(c1ccc(O)cc1CNc1nc(-c2cc(F)c(O)cc2CC(F)(F)F)cc2[nH]nc(C(=O)NC)c12)S(C)(=O)=O] | 5.1 | 27.8 | 98.4 | 24.6 | 300.6 | |
| 41 | 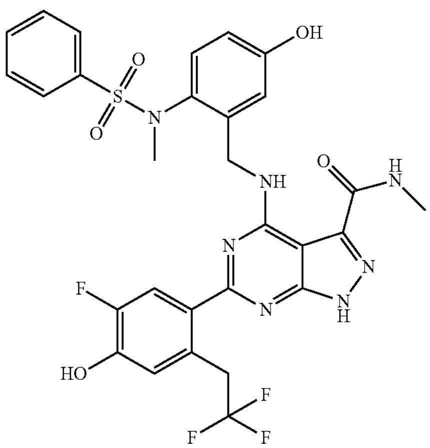 [SMILES: CNC(=O)c1n[nH]c2nc(-c3cc(F)c(O)cc3CC(F)(F)F)nc(NCc3cc(O)ccc3N(C)S(=O)(=O)c3ccccc3)c12] | 27.4 | 142.0 | 383.2 | 1188.3 | 1185.0 | |
| 48 | 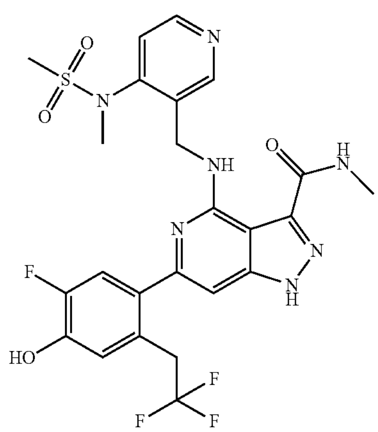 | 67.6 | 188.4 | 148.5 | 6329.8 | >10000 | |

TABLE 1-continued
Data for JAK Caliper™ Kinase assays at 1 mM ATP and Cell Based assays
| Ex. | Structure | Caliper™ Assays at 1 mM ATP | | | | Cell Based Assays | |
|---|---|---|---|---|---|---|---|
| | | JAK1 $IC_{50}$ (nM) | JAK2 $IC_{50}$ (nM) | JAK3 $IC_{50}$ (nM) | TYK2 $IC_{50}$ (nM) | A549 cell assay: Inhibition of pSTAT3 $IC_{50}$ (nM) | Human T cell assay: Inhibition of pSTAT5 $IC_{50}$ (nM) |
| 75 | 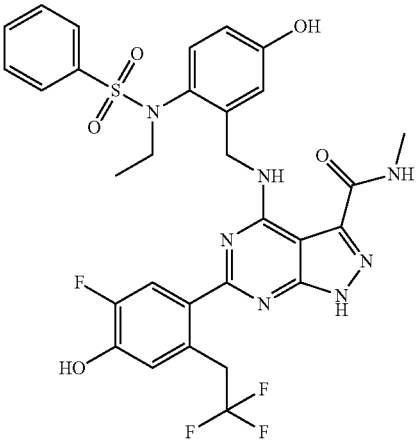 [SMILES: CCN(c1ccc(O)cc1CNc1nc(-c2cc(F)c(O)cc2CC(F)(F)F)nc2[nH]nc(C(=O)NC)c12)S(=O)(=O)c1ccccc1] | 61.1 | 320.9 | 755.3 | 1935.5 | 1345.1 | |
| 35 | 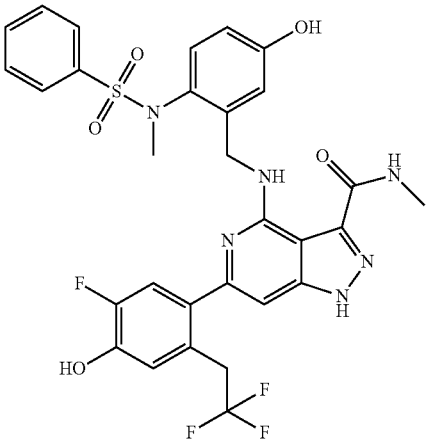 [SMILES: CNC(=O)c1n[nH]c2cc(-c3cc(F)c(O)cc3CC(F)(F)F)nc(NCc3cc(O)ccc3N(C)S(=O)(=O)c3ccccc3)c12] | 39.9 | 249.0 | 816.9 | 256.4 | 437.4 | |
| 96 | 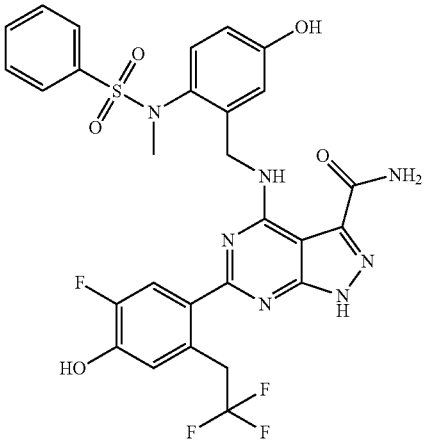 [SMILES: CN(c1ccc(O)cc1CNc1nc(-c2cc(F)c(O)cc2CC(F)(F)F)nc2[nH]nc(C(N)=O)c12)S(=O)(=O)c1ccccc1] | 30.5 | 122.6 | 247.5 | 1734.4 | 2871.2 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | | | | | A549 cell assay: Inhibition | Human T cell assay: Inhibition |
| | | JAK1 IC$_{50}$ (nM) | JAK2 IC$_{50}$ (nM) | JAK3 IC$_{50}$ (nM) | TYK2 IC$_{50}$ (nM) | of pSTAT3 IC$_{50}$ (nM) | of pSTAT5 IC$_{50}$ (nM) |
| 97 | 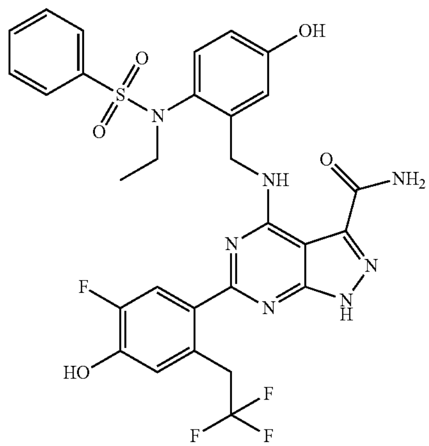 [SMILES: CCN(c1ccc(O)cc1CNc1nc(-c2cc(F)c(O)cc2CC(F)(F)F)nc2[nH]nc(C(N)=O)c12)S(=O)(=O)c1ccccc1] | 55.1 | 204.6 | 414.6 | 2193.5 | 2073.3 | |
| 36 | 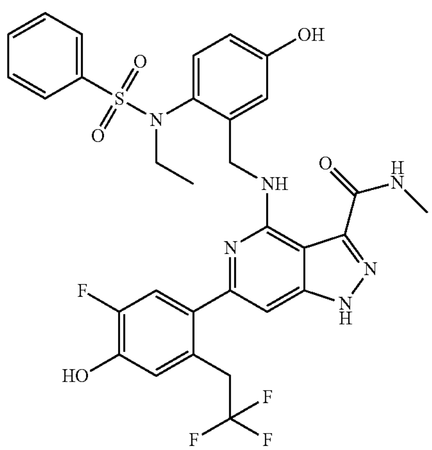 [SMILES: CCN(c1ccc(O)cc1CNc1nc(-c2cc(F)c(O)cc2CC(F)(F)F)cc2[nH]nc(C(=O)NC)c12)S(=O)(=O)c1ccccc1] | 75.0 | 401.0 | 1226.6 | 364.4 | 433.1 | |
| 68 | 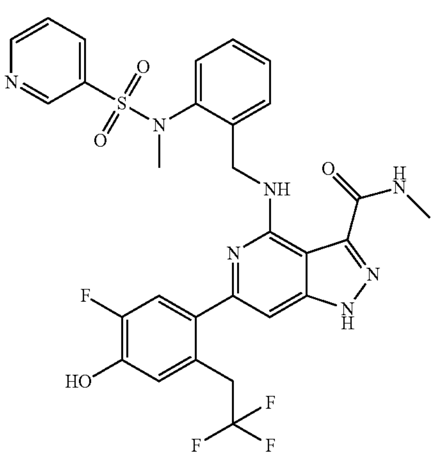 [SMILES: CNC(=O)c1n[nH]c2cc(-c3cc(F)c(O)cc3CC(F)(F)F)nc(NCc3ccccc3N(C)S(=O)(=O)c3cccnc3)c12] | 14.2 | 72.7 | 252.8 | 72.3 | 43.9 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 42 | 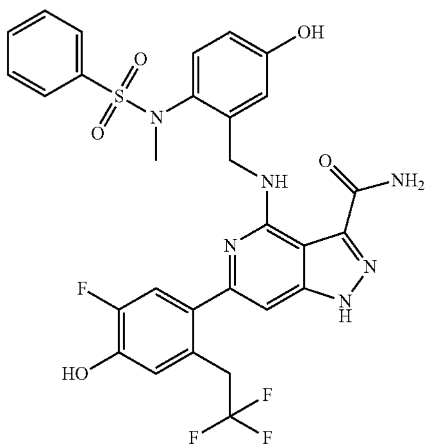 [SMILES: CN(c1ccc(O)cc1CNc1nc(-c2cc(F)c(O)cc2CC(F)(F)F)cc2[nH]nc(C(N)=O)c12)S(=O)(=O)c1ccccc1] | 25.3 | 158.4 | 534.0 | 233.3 | 645 | |
| 43 | 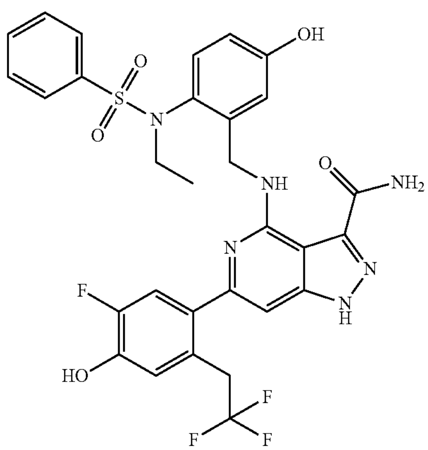 [SMILES: CCN(c1ccc(O)cc1CNc1nc(-c2cc(F)c(O)cc2CC(F)(F)F)cc2[nH]nc(C(N)=O)c12)S(=O)(=O)c1ccccc1] | 55.1 | 302.0 | 1068.7 | 438.7 | 763.5 | |
| 45 | 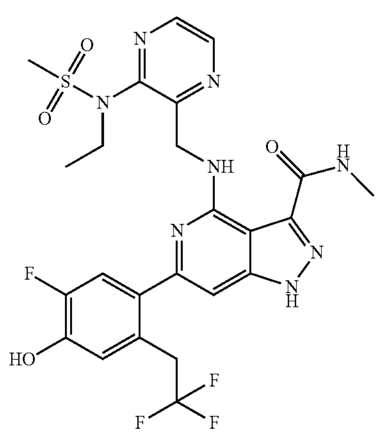 | 4.0 | 18.9 | 68.7 | 148.5 | 46.5 | |

TABLE 1-continued
Data for JAK Caliper ™ Kinase assays at 1 mM ATP and Cell Based assays
| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 57 | 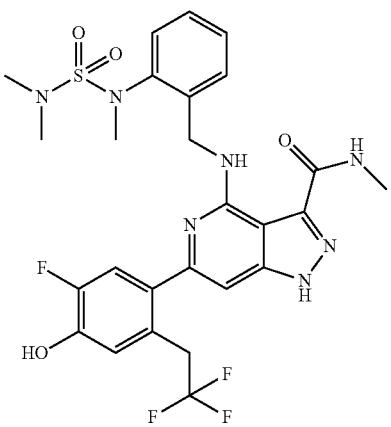 | 21.1 | 93.4 | 408.7 | 148.7 | 60.4 | |
| 46 | 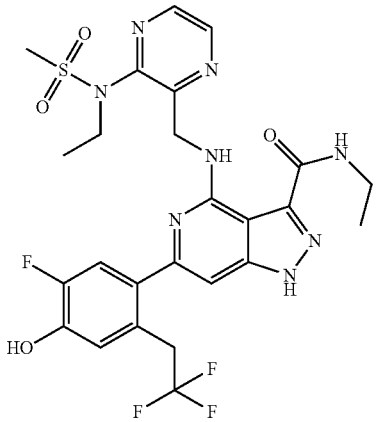 [SMILES: CCNC(=O)c1n[nH]c2cc(-c3cc(F)c(O)cc3CC(F)(F)F)nc(NCc3nccnc3N(CC)S(C)(=O)=O)c12] | 32.9 | 101.0 | 179.0 | 1032.8 | 103.4 | |
| 44 | 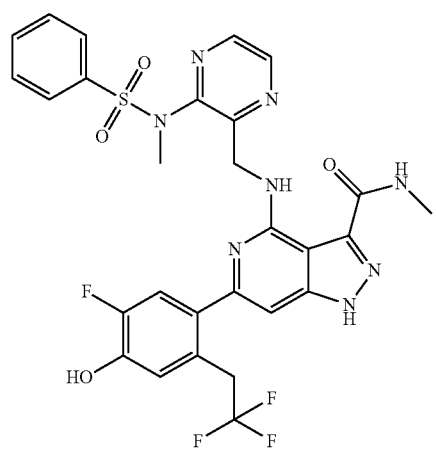 [SMILES: CNC(=O)c1n[nH]c2cc(-c3cc(F)c(O)cc3CC(F)(F)F)nc(NCc3nccnc3N(C)S(=O)(=O)c3ccccc3)c12] | 25.8 | 85.2 | 292.6 | 999.0 | 59.7 | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 58 | 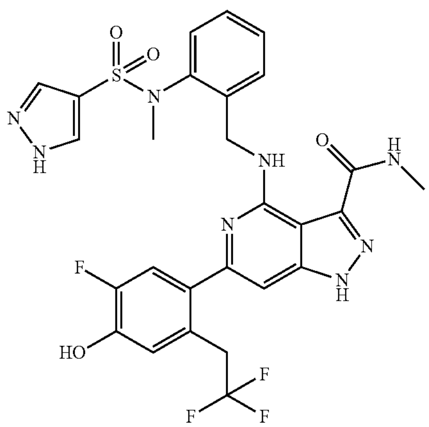 [SMILES: CNC(=O)c1n[nH]c2cc(-c3cc(F)c(O)cc3CC(F)(F)F)nc(NCc3ccccc3N(C)S(=O)(=O)c3cn[nH]c3)c12] | 10.3 | 54.4 | 236.5 | 67.5 | 173.7 | |
| 59 | 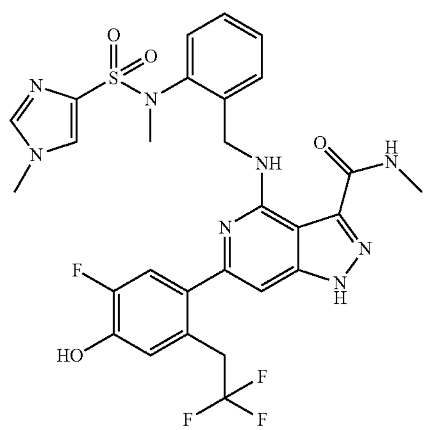 [SMILES: CNC(=O)c1n[nH]c2cc(-c3cc(F)c(O)cc3CC(F)(F)F)nc(NCc3ccccc3N(C)S(=O)(=O)c3cn(C)cn3)c12] | 5.3 | 23.5 | 112.4 | 22.6 | 290.5 | |
| 53 | 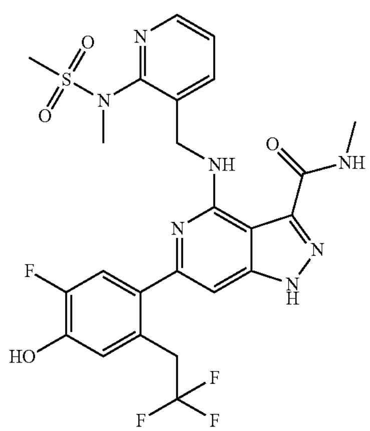 [SMILES: CNC(=O)c1n[nH]c2cc(-c3cc(F)c(O)cc3CC(F)(F)F)nc(NCc3cccnc3N(C)S(C)(=O)=O)c12] | 9.7 | 33.1 | 102.3 | 242.9 | 21.3 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 88 | 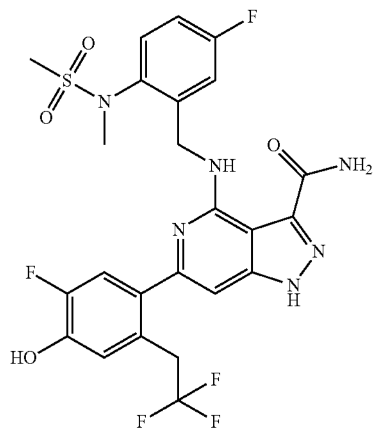 [SMILES: CN(c1ccc(F)cc1CNc1nc(-c2cc(F)c(O)cc2CC(F)(F)F)cc2[nH]nc(C(N)=O)c12)S(C)(=O)=O] | 6.6 | 41.1 | 139.7 | 127.3 | 31.5 | |
| 52 | 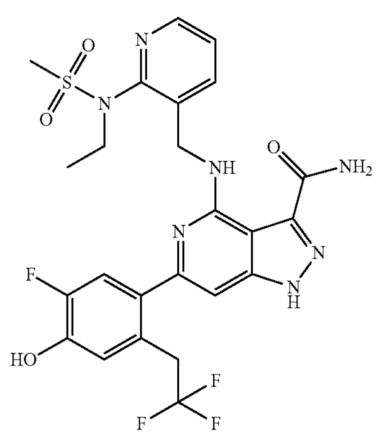 [SMILES: CCN(c1ncccc1CNc1nc(-c2cc(F)c(O)cc2CC(F)(F)F)cc2[nH]nc(C(N)=O)c12)S(C)(=O)=O] | 2.9 | 15.0 | 46.3 | 109.2 | 74.3 | |
| 62 | 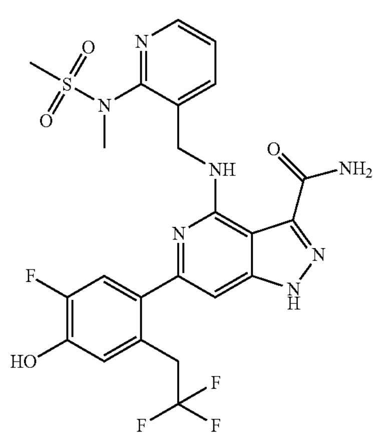 [SMILES: CN(c1ncccc1CNc1nc(-c2cc(F)c(O)cc2CC(F)(F)F)cc2[nH]nc(C(N)=O)c12)S(C)(=O)=O] | 2.9 | 14.4 | 39.5 | 278.0 | 71.8 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 $IC_{50}$ (nM) | JAK2 $IC_{50}$ (nM) | JAK3 $IC_{50}$ (nM) | TYK2 $IC_{50}$ (nM) | A549 cell assay: Inhibition of pSTAT3 $IC_{50}$ (nM) | Human T cell assay: Inhibition of pSTAT5 $IC_{50}$ (nM) |
| 63 | | 5.0 | 22.5 | 82.1 | 107.0 | 14.6 | |
| 104 | | 10.4 | 66.1 | 112.7 | 1377.4 | 292.2 | |
| 54 | | 6.1 | 32.9 | 122.7 | 25.9 | 134.6 | |

TABLE 1-continued

Data for JAK Caliper™ Kinase assays at 1 mM ATP and Cell Based assays

| | | Caliper™ Assays at 1 mM ATP | | | | Cell Based Assays | |
|---|---|---|---|---|---|---|---|
| | | | | | | A549 cell assay: Inhibition of pSTAT3 $IC_{50}$ (nM) | Human T cell assay: Inhibition of pSTAT5 $IC_{50}$ (nM) |
| Ex. | Structure | JAK1 $IC_{50}$ (nM) | JAK2 $IC_{50}$ (nM) | JAK3 $IC_{50}$ (nM) | TYK2 $IC_{50}$ (nM) | | |
| 64 | | 3.3 | 11.1 | 36.9 | 153.1 | 212.7 | |
| 55 | | 2.1 | 13.7 | 54.0 | 45.9 | 155.6 | |
| 37 | | 5.0 | 19.7 | 52.0 | 169.0 | 47.4 | |

TABLE 1-continued

Data for JAK Caliper ™ Kinase assays at 1 mM ATP and Cell Based assays

| Ex. | Structure | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
|---|---|---|---|---|---|---|---|
| 60 | 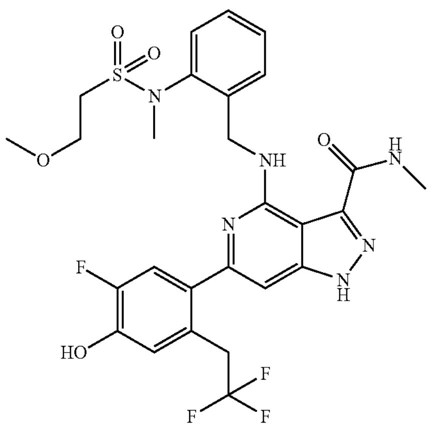 | 6.6 | 29.2 | 115.2 | 56.5 | 34.4 | |
| 47 | 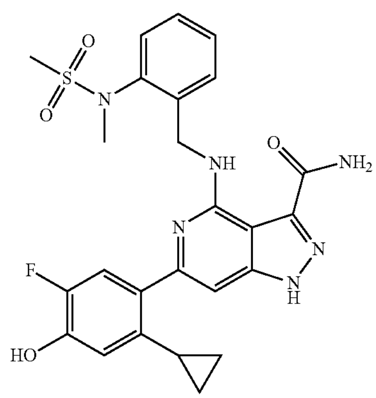 [SMILES: CN(c1ccccc1CNc1nc(-c2cc(F)c(O)cc2C2CC2)cc2[nH]nc(C(N)=O)c12)S(C)(=O)=O] | 10.6 | 28.4 | 54.3 | 320.2 | 281.9 | |
| 65 | 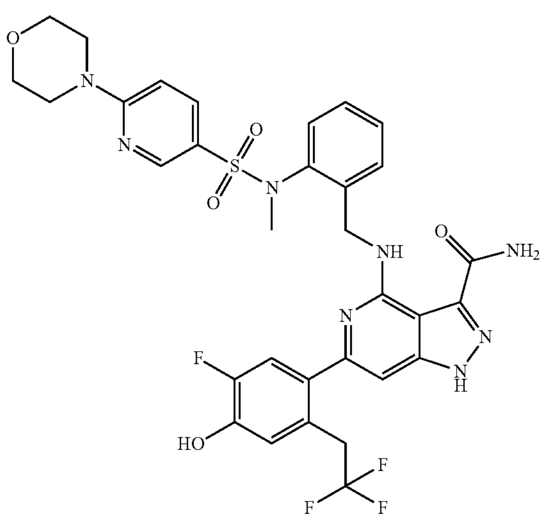 [SMILES: CN(c1ccccc1CNc1nc(-c2cc(F)c(O)cc2CC(F)(F)F)cc2[nH]nc(C(N)=O)c12)S(=O)(=O)c1ccc(N2CCOCC2)nc1] | 23.3 | 83.8 | 283.3 | 125.8 | 160.9 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | | | | | A549 cell assay: Inhibition | Human T cell assay: Inhibition |
| | | JAK1 IC$_{50}$ (nM) | JAK2 IC$_{50}$ (nM) | JAK3 IC$_{50}$ (nM) | TYK2 IC$_{50}$ (nM) | of pSTAT3 IC$_{50}$ (nM) | of pSTAT5 IC$_{50}$ (nM) |
| 69 | 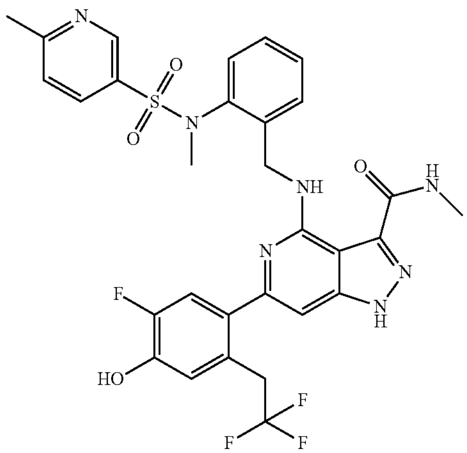 | 16.2 | 63.7 | 256.8 | 66.8 | 91.6 | |
| 61 | 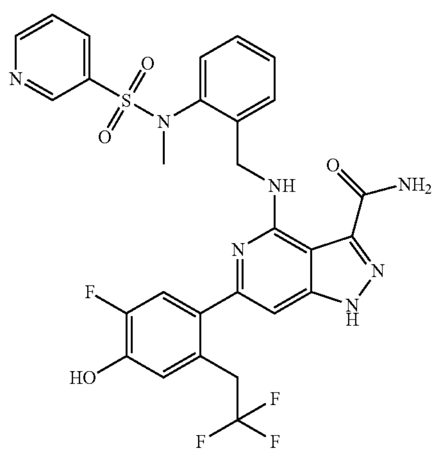 [SMILES: CN(c1ccccc1CNc1nc(-c2cc(F)c(O)cc2CC(F)(F)F)cc2[nH]nc(C(N)=O)c12)S(=O)(=O)c1cccnc1] | 7.3 | 30.2 | 110.5 | 52.3 | 71.2 | |
| 70 | 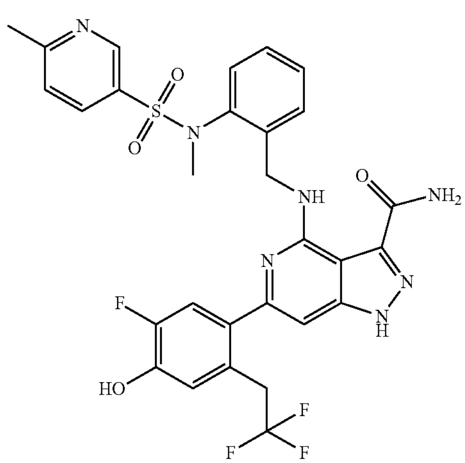 [SMILES: Cc1ccc(S(=O)(=O)N(C)c2ccccc2CNc2nc(-c3cc(F)c(O)cc3CC(F)(F)F)cc3[nH]nc(C(N)=O)c23)cn1] | 12.0 | 52.4 | 207.9 | 79.4 | 46.2 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | | | | | A549 cell assay: Inhibition | Human T cell assay: Inhibition |
| | | JAK1 $IC_{50}$ (nM) | JAK2 $IC_{50}$ (nM) | JAK3 $IC_{50}$ (nM) | TYK2 $IC_{50}$ (nM) | of pSTAT3 $IC_{50}$ (nM) | of pSTAT5 $IC_{50}$ (nM) |
| 89 | | 14.6 | 57.1 | 211.6 | 916.9 | 46.3 | |
| 67 | | 16.3 | 48.2 | 72.8 | 2028.3 | 104.1 | |

TABLE 1-continued

Data for JAK Caliper™ Kinase assays at 1 mM ATP and Cell Based assays

| Ex. | Structure | Caliper™ Assays at 1 mM ATP ||||  Cell Based Assays ||
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 66 | 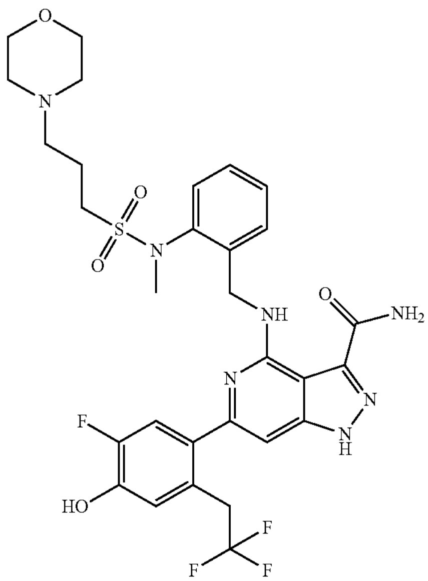 [SMILES: CN(c1ccccc1CNc1nc(-c2cc(F)c(O)cc2CC(F)(F)F)cc2[nH]nc(C(N)=O)c12)S(=O)(=O)CCCN1CCOCC1] | 3.5 | 14.8 | 60.0 | 81.3 | 221.2 | |
| 86 | 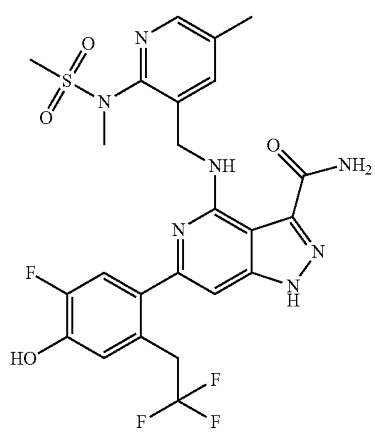 [SMILES: Cc1cnc(N(C)S(C)(=O)=O)c(CNc2nc(-c3cc(F)c(O)cc3CC(F)(F)F)cc3[nH]nc(C(N)=O)c23)c1] | 38.4 | 110.3 | 81.7 | 4819.5 | 425 | |
| 49 | 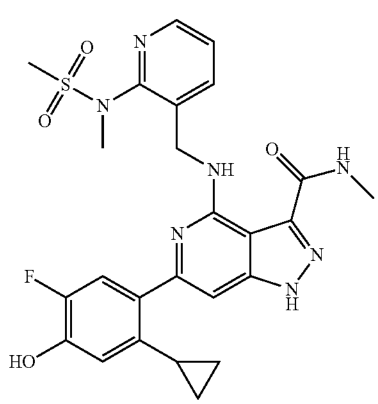 [SMILES: CNC(=O)c1n[nH]c2cc(-c3cc(F)c(O)cc3C3CC3)nc(NCc3cccnc3N(C)S(C)(=O)=O)c12] | 78.0 | 181.1 | 248.0 | 3603.3 | 385.3 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 $IC_{50}$ (nM) | JAK2 $IC_{50}$ (nM) | JAK3 $IC_{50}$ (nM) | TYK2 $IC_{50}$ (nM) | A549 cell assay: Inhibition of pSTAT3 $IC_{50}$ (nM) | Human T cell assay: Inhibition of pSTAT5 $IC_{50}$ (nM) |
| 87 | | 30.6 | 87.8 | 133.4 | 2486.5 | 213.2 | |
| 84 | | 27.6 | 142.3 | 537.3 | 880.1 | 32.9 | |
| 83 | | 12.1 | 63.3 | 201.2 | 139.1 | 30 | |

TABLE 1-continued

Data for JAK Caliper ™ Kinase assays at 1 mM ATP and Cell Based assays

| Ex. | Structure | Caliper ™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 91 | 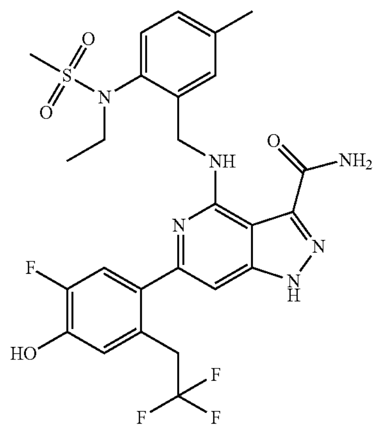 [SMILES: CCN(c1ccc(C)cc1CNc1nc(-c2cc(F)c(O)cc2CC(F)(F)F)cc2[nH]nc(C(N)=O)c12)S(C)(=O)=O] | 28.7 | 127.7 | 462.5 | 865.2 | 26.3 | |
| 71 | 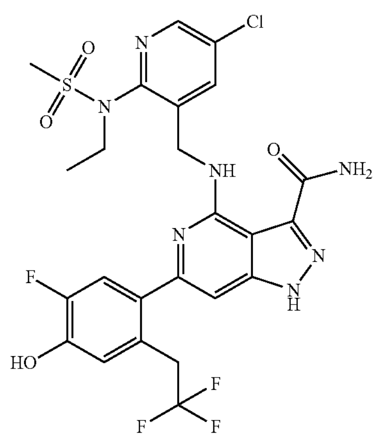 | 44.1 | 156.5 | 359.0 | 2753.5 | 110.1 | |
| 72 | 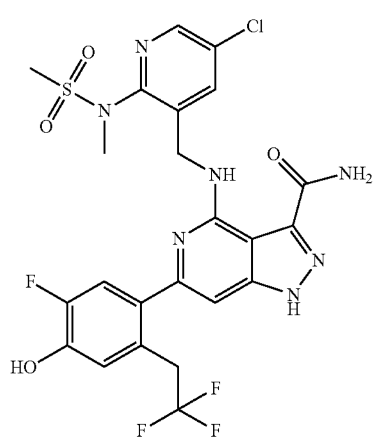 | 44.8 | 134.9 | 197.9 | 3445.7 | 94.1 | |

TABLE 1-continued

Data for JAK Caliper ™ Kinase assays at 1 mM ATP and Cell Based assays

| Ex. | Structure | Caliper ™ Assays at 1 mM ATP ||||  Cell Based Assays ||
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 156 | 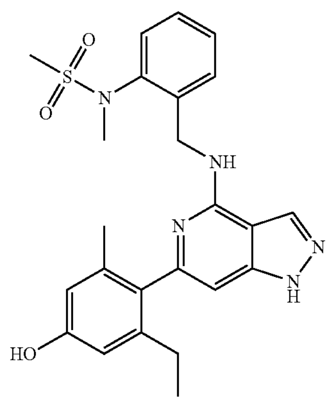 [SMILES: CCc1cc(O)cc(C)c1-c1cc2[nH]ncc2c(NCc2ccccc2N(C)S(C)(=O)=O)n1] | 25.5 | 120.4 | 176.8 | 9995.0 | 72.4 | |
| 85 | 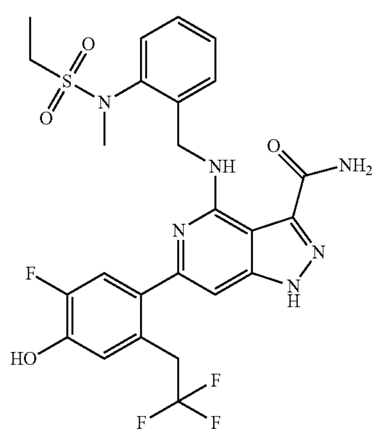 [SMILES: CCS(=O)(=O)N(C)c1ccccc1CNc1nc(-c2cc(F)c(O)cc2CC(F)(F)F)cc2[nH]nc(C(N)=O)c12] | 7.8 | 47.2 | 155.9 | 81.4 | 12.9 | |
| 78 | 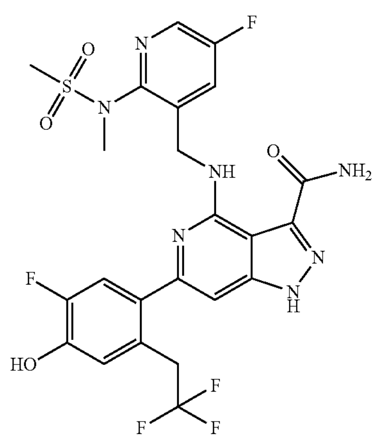 [SMILES: CN(c1ncc(F)cc1CNc1nc(-c2cc(F)c(O)cc2CC(F)(F)F)cc2[nH]nc(C(N)=O)c12)S(C)(=O)=O] | 5.9 | 39.4 | 89.9 | 930.1 | 27.2 | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | JAK1 IC$_{50}$ (nM) | JAK2 IC$_{50}$ (nM) | JAK3 IC$_{50}$ (nM) | TYK2 IC$_{50}$ (nM) | A549 cell assay: Inhibition of pSTAT3 IC$_{50}$ (nM) | Human T cell assay: Inhibition of pSTAT5 IC$_{50}$ (nM) |
| 79 | | 10.7 | 59.1 | 175.0 | 698.4 | 30.7 | |
| 80 | | 2.9 | 16.2 | 49.2 | 167.4 | 197 | |
| 82 | | 13.7 | 83.9 | 313.1 | 121.2 | 20.9 | |

TABLE 1-continued

Data for JAK Caliper™ Kinase assays at 1 mM ATP and Cell Based assays

| Ex. | Structure | Caliper™ Assays at 1 mM ATP | | | | Cell Based Assays | |
|---|---|---|---|---|---|---|---|
| | | | | | | A549 cell assay: Inhibition | Human T cell assay: Inhibition |
| | | JAK1 IC$_{50}$ (nM) | JAK2 IC$_{50}$ (nM) | JAK3 IC$_{50}$ (nM) | TYK2 IC$_{50}$ (nM) | of pSTAT3 IC$_{50}$ (nM) | of pSTAT5 IC$_{50}$ (nM) |
| 81 | 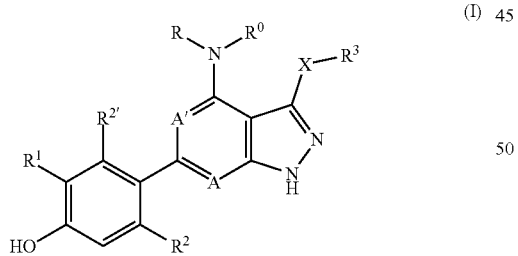 | 4.7 | 27.1 | 102.8 | 297.5 | | |

The invention claimed is:

1. A method of treating a disease or condition selected from inflammation, neuroinflammation, arthritis, rheumatoid arthritis, spondyloarthropathies, systemic lupus erythematous arthritis, osteoarthritis, gouty arthritis, pulmonary sarcoisosis, silicosis, inflammatory bowel disease, Crohn's disease, ulcerative colitis, nephritis, retinitis, autoimmune disease, fibrosis, polymyositis, eczema, psoriasis, and atopic dermatitis, comprising administering to the subject a therapeutically effective amount of a compound having the structure:

(I)

or a pharmaceutically acceptable salt thereof, or a pharmaceutically acceptable solvate of said compound or pharmaceutically acceptable salt, wherein:

A and A' are independently C or N, where C may be unsubstituted or substituted by halo or $C_1$-$C_6$ alkyl;

R and $R^0$ are independently selected from the group consisting of H, $C_1$-$C_6$ alkyl, hydroxy($C_1$-$C_6$ alkyl), phenyl($C_1$-$C_6$ alkyl), and —(CH$_2$)$_n$—W, where W is $C_3$-$C_8$ cycloalkyl, phenyl, naphthyl, 5- or 6-membered heteroaryl or heterocyclic containing 1-3 N, S and/or O atoms, —SO$_2$—R', —NHSO$_2$—R', —NR"SO$_2$—R' and SR', where R' and R" are independently $C_1$-$C_6$ alkyl or $C_3$-$C_8$ cycloalkyl, amino, $C_1$-$C_6$ alkylamino, di($C_1$-$C_6$ alkyl)amino, phenyl, heteroaryl, or heterocyclic; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —SO$_2$—R', —CONR'R", NR'COR", —NR'CONR'R", —NR'CO$_2$R", —(CH$_2$)$_n$—SO$_2$—R', —NHSO$_2$—R', —NR"SO$_2$—R' or SR' where R' and R" are independently $C_1$-$C_6$ alkyl, $C_3$-$C_8$ cycloalkyl, phenyl, amino, hydroxyalkylamino, heterocyclic, or —(CH$_2$)$_n$—W', where W' is hydroxy, $C_3$-$C_8$ cycloalkyl, phenyl, naphthyl, heterocyclic, or 5- or 6-membered heteroaryl containing 1-3 N, S and/or O atoms;

or, R and $R^0$ and the N atom to which they are bonded together form a monocyclic or bicyclic heterocyclic ring which may be unsubstituted or substituted by (a) halo, hydroxy, heteroaryl, $C_1$-$C_6$ alkyl, $C_1$-$C_6$ alkoxy, ($C_1$-$C_6$ alkoxy)$C_1$-$C_6$ alkoxy, aryl($C_1$-$C_6$ alkoxy), aryloxy, amino, aminoacyl, $C_1$-$C_6$ alkylaminoacyl, arylalkylaminoacyl, di($C_1$-$C_6$ alkyl)aminoacyl, —SO$_2$—R', —SO$_2$—NR"—(CH$_2$)$_n$—W, —NHSO$_2$—R', —NR"SO$_2$—R' or SR' where R' and R" is independently amino, $C_1$-$C_6$ alkylamino, di($C_1$-$C_6$ alkyl)amino, $C_1$-$C_6$ alkyl or $C_3$-$C_8$ cycloalkyl, or (b) —(CH$_2$)$_n$—W, where W is $C_3$-$C_8$ cycloalkyl, phenyl, naphthyl, heterocyclic, 5- or 6-membered heteroaryl containing 1-3 N atoms, —SO$_2$—R', —NHSO$_2$—R', —NR"SO$_2$—R' or SR', where R' and R" is independently alkyl or cycloalkyl; wherein each of said phenyl, aryl, or heteroaryl may be unsubstituted or substituted by halo, $C_1$-$C_6$ alkyl, $C_1$-$C_6$ alkoxy, cyano, or hydroxy;

$R^1$ is H, halo or cyano;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

X is a bond, —CO—, —CONH—, —SO$_2$—, —SONH—, or —(CH$_2$)$_m$—;

$R^3$ is H, $C_1$-$C_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—$R^4$ and/or 1-4 substituents each independently selected from $R^5$; with the proviso that when X is —CO— or —SO$_2$—, $R^3$ is not H;

Y is a bond, —(CH$_2$)$_m$— or —O—;

$R^4$ is (a) H, $C_1$-$C_6$ alkyl, $C_3$-$C_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; (b) phenyl or naphthyl, said phenyl and naphthyl being optionally substituted with 1-5 substituents selected from $C_1$-$C_6$ alkyl, $C_3$-$C_8$ cycloalkyl, halo, cyano, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; or (c) a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, cyano, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$;

$R^5$ is $C_1$-$C_6$ alkyl, $C_3$-$C_8$ cycloalkyl, halo, cyano, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ or —NR$^6$SO$_2$NR$^7$R$^8$;

$R^6$ is H, $C_1$-$C_6$ alkyl or $C_3$-$C_8$ cycloalkyl, said $C_1$-$C_6$ alkyl is optionally substituted by —NR$^7$R$^8$ or a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, hydroxy and cyano;

$R^7$ and $R^8$ are each independently H, $C_1$-$C_6$ alkyl or $C_3$-$C_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said $C_1$-$C_6$ alkyl is optionally substituted by $C_3$-$C_8$ cycloalkyl, halo, hydroxy, amino, ($C_1$-$C_6$ alkyl)amino or di($C_1$-$C_6$ alkyl)amino and said heterocyclic ring being optionally substituted by one or more $C_1$-$C_6$ alkyl or $C_3$-$C_8$ cycloalkyl groups;

$R^9$ is $C_1$-$C_6$ alkyl or $C_3$-$C_8$ cycloalkyl; and, m and n are independently 0, 1, 2 or 3.

2. The method of claim 1, wherein the compound has the structure:

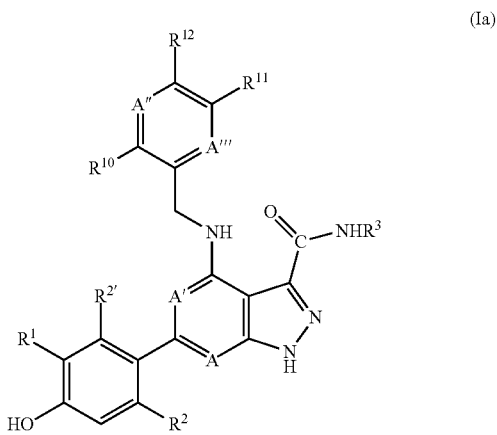

(Ia)

or a pharmaceutically acceptable salt thereof, or a pharmaceutically acceptable solvate of said compound or pharmaceutically acceptable salt, wherein:

A, A" and A''' are independently C or N, where C may be unsubstituted or substituted by halo or $C_1$-$C_6$ alkyl;

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^3$ is H, $C_1$-$C_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—$R^4$ and/or 1-4 substituents each independently selected from $R^5$;

Y is a bond, —(CH$_2$)$_m$— or —O—;

$R^4$ is (a) H, $C_1$-$C_6$ alkyl, $C_3$-$C_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; (b) phenyl or naphthyl, said phenyl and naphthyl being optionally substituted with 1-5 substituents selected from $C_1$-$C_6$ alkyl, $C_3$-$C_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; or (c) a 3 to 8-membered saturated or partially unsaturated monocyclic heteroaryl, containing 1 or 2 heteroatoms selected from O and N, said heteroaryl being optionally substituted by 1-5 substituents selected from $C_1$-$C_6$ alkyl, $C_3$-$C_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR⁷R⁸, —NR⁶SO₂R⁹, —SO₂NR⁷R⁸, —NR⁶CONR⁷R⁸, —NR⁶COOR⁹ and —NR⁶SO₂NR⁷R⁸;

R⁵ is C₁-C₆ alkyl, C₃-C₈ cycloalkyl, halo, —CN, —OR⁶, —NR⁷R⁸, —SR⁶, —SOR⁹, —SO₂R⁹, —COR⁶, —OCOR⁶, —COOR⁶, —NR⁶COR⁶, —CONR⁷R⁸, —NR⁶SO₂R⁹, —SO₂NR⁷R⁸, —NR⁶CONR⁷R⁸, —NR⁶COOR⁹ or —NR⁶SO₂NR⁷R⁸;

R⁶ is H, C₁-C₆ alkyl or C₃-C₈ cycloalkyl, said C₁-C₆ alkyl is optionally substituted by —NR⁷R⁸ or a 3 to 8-membered saturated or partially unsaturated monocyclic heteroaryl, containing 1 or 2 heteroatoms selected from O and N, said heteroaryl being optionally substituted by 1-5 substituents selected from C₁-C₆ alkyl, C₃-C₈ cycloalkyl, halo, hydroxy and cyano;

R⁷ and R⁸ are each independently H, C₁-C₆ alkyl or C₃-C₈ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said C₁-C₆ alkyl is optionally substituted by C₃-C₈ cycloalkyl, halo, hydroxy, amino, (C₁-C₆ alkyl)amino or di(C₁-C₆ alkyl)amino and said heterocyclic ring being optionally substituted by one or more C₁-C₆ alkyl or C₃-C₈ cycloalkyl groups;

R⁹ is C₁-C₆ alkyl or C₃-C₈ cycloalkyl;

R¹⁰ is —NHSO₂—R', —NR"SO₂—R' or SR' where R' and R" are independently hydrogen, C₁-C₆ alkyl, C₃-C₈ cycloalkyl, phenyl, amino, C₁-C₆ alkylamino, di(C₁-C₆ alkyl)amino, heterocyclic, —(CH₂)ₙ—W', where W' is hydroxy, C₃-C₈ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, C₁-C₆ alkyl, C₁-C₆ alkoxy, aryloxy, —SO₂—R', —NHSO₂—R', —NR"SO₂—R' or SR' where R' and R" are independently phenyl, C₁-C₆ alkyl or C₃-C₈ cycloalkyl;

R¹¹ and R¹² are each independently H, hydroxy, halo, cyano, C₁-C₆ alkyl or C₃-C₈ cycloalkyl; and, m and n are independently 0, 1, 2, or 3.

3. The method of claim 1, wherein the compound has the structure:

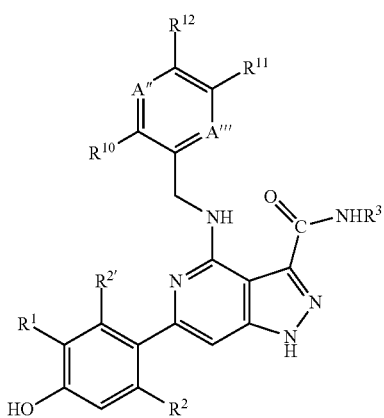

(Ib)

or a pharmaceutically acceptable salt thereof, or a pharmaceutically acceptable solvate of said compound or pharmaceutically acceptable salt, wherein:

A" and A'" are independently C or N, where C may be unsubstituted or substituted by halo or C₁-C₆ alkyl;

R¹ is H, cyano or halo;

R² and R²' are independently H, C₁-C₆ alkyl, cyano, C₁-C₆ alkoxy, C₁-C₆ alkylthio, or C₃-C₈ cycloalkyl where alkyl, alkoxy, or cycloalkyl is optionally substituted by one or more fluorine atoms;

R³ is H, C₁-C₄ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—R⁴ and/or 1-4 substituents each independently selected from R⁵;

Y is a bond, —(CH₂)ₘ— or —O—;

R⁴ is (a) H, C₁-C₆ alkyl, C₃-C₈ cycloalkyl, halo, oxo, —OR⁶, —NR⁷R⁸, —SR⁶, —SOR⁹, —SO₂R⁹, —COR⁶, —OCOR⁶, —COOR⁶, —NR⁶COR⁶, —CONR⁷R⁸, —NR⁶SO₂R⁹, —SO₂NR⁷R⁸, —NR⁶CONR⁷R⁸, —NR⁶COOR⁹ and —NR⁶SO₂NR⁷R⁸; (b) phenyl or naphthyl, said phenyl and naphthyl being optionally substituted with 1-5 substituents selected from C₁-C₆ alkyl, C₃-C₈ cycloalkyl, halo, —CN, —OR⁶, —NR⁷R⁸, —SR⁶, —SOR⁹, —SO₂R⁹, —COR⁶, —OCOR⁶, —COOR⁶, —NR⁶COR⁶, —CONR⁷R⁸, —NR⁶SO₂R⁹, —SO₂NR⁷R⁸, —NR⁶CONR⁷R⁸, —NR⁶COOR⁹ and —NR⁶SO₂NR⁷R⁸; or (c) a 3 to 8-membered saturated or partially unsaturated monocyclic heteroaryl, containing 1 or 2 heteroatoms selected from O and N, said heteroaryl being optionally substituted by 1-5 substituents selected from C₁-C₆ alkyl, C₃-C₈ cycloalkyl, halo, oxo, —OR⁶, —NR⁷R⁸, —SR⁶, —SOR⁹, —SO₂R⁹, —COR⁶, —OCOR⁶, —COOR⁶, —NR⁶COR⁶, —CONR⁷R⁸, —NR⁶SO₂R⁹, —SO₂NR⁷R⁸, —NR⁶CONR⁷R⁸, —NR⁶COOR⁹ and —NR⁶SO₂NR⁷R⁸;

R⁵ is C₁-C₆ alkyl, C₃-C₈ cycloalkyl, halo, —CN, —OR⁶, —NR⁷R⁸, —SR⁶, —SOR⁹, —SO₂R⁹, —COR⁶, —OCOR⁶, —COOR⁶, —NR⁶COR⁶, —CONR⁷R⁸, —NR⁶SO₂R⁹, —SO₂NR⁷R⁸, —NR⁶CONR⁷R⁸, —NR⁶COOR⁹ or —NR⁶SO₂NR⁷R⁸;

R⁶ is H, C₁-C₆ alkyl or C₃-C₈ cycloalkyl, said C₁-C₆ alkyl is optionally substituted by —NR⁷R⁸ or a 3 to 8-membered saturated or partially unsaturated monocyclic heteroaryl, containing 1 or 2 heteroatoms selected from O and N, said heteroaryl being optionally substituted by 1-5 substituents selected from C₁-C₆ alkyl, C₃-C₈ cycloalkyl, halo, hydroxy and cyano;

R⁷ and R⁸ are each independently H, C₁-C₆ alkyl or C₃-C₈ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said C₁-C₆ alkyl is optionally substituted by C₃-C₈ cycloalkyl, halo, hydroxy, amino, (C₁-C₆ alkyl)amino or di(C₁-C₆ alkyl)amino and said heterocyclic ring being optionally substituted by one or more C₁-C₆ alkyl or C₃-C₈ cycloalkyl groups;

R$^9$ is C$_1$-C$_6$ alkyl or C$_3$-C$_8$ cycloalkyl;

R$^{10}$ is —NHSO$_2$—R', —NR"SO$_2$—R' or SR' where R' and R" are independently hydrogen, C$_1$-C$_6$ alkyl, C$_3$-C$_8$ cycloalkyl, phenyl, amino, C$_1$-C$_6$ alkylamino, di(C$_1$-C$_6$ alkyl)amino, heterocyclic, —(CH$_2$)$_n$—W', where W' is hydroxy, C$_3$-C$_8$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, hydroxy, C$_1$-C$_6$ alkyl, C$_1$-C$_6$ alkoxy, aryloxy, —SO$_2$—R', —NHSO$_2$—R', —NR"SO$_2$—R' or SR' where R' and R" are independently phenyl, C$_1$-C$_6$ alkyl or C$_3$-C$_8$ cycloalkyl;

R$^{11}$ and R$^{12}$ are each independently H, hydroxy, halo, cyano, C$_1$-C$_6$ alkyl or C$_3$-C$_8$ cycloalkyl; and, m and n are independently 0, 1, 2 or 3.

4. The method of claim 1, wherein the compound has the structure:

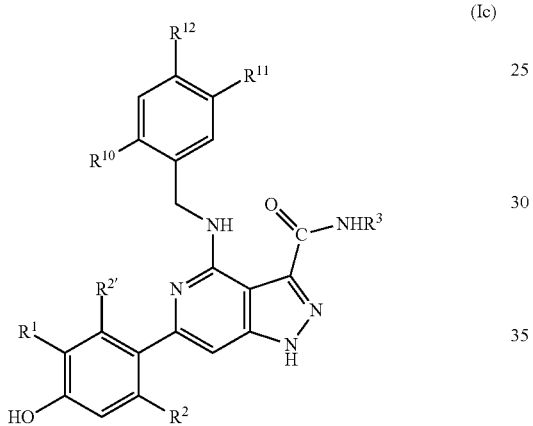

(Ic)

or a pharmaceutically acceptable salt thereof, or a pharmaceutically acceptable solvate of said compound or pharmaceutically acceptable salt, wherein:

R$^1$ is H, cyano or halo;

R$^2$ and R$^{2'}$ are independently H, C$_1$-C$_6$ alkyl, cyano, C$_1$-C$_6$ alkoxy, C$_1$-C$_6$ alkylthio, or C$_3$-C$_8$ cycloalkyl where alkyl, alkoxy, or cycloalkyl is optionally substituted by one or more fluorine atoms;

R$^3$ is H, C$_1$-C$_4$ alkyl, phenyl, naphthyl, 6-membered heteroaryl or heterocyclic containing 1-3 N atoms, a 5-membered heteroaryl or heterocyclic containing either (a) 1-4 N atoms or (b) 1 O or S atom and 0-3 N atoms, a 10-membered bicyclic heteroaryl or heterocyclic containing 1-4 N atoms, a 9-membered bicyclic heteroaryl or heterocyclic containing either (a) 1-4 N atoms or (b) 1 O or S atom and 0-3 N atoms, or an 8-membered bicyclic heteroaryl or heterocyclic containing (a) 1-4 N atoms or (b) 1 O or S atom and 1-3 N atoms or (c) 2 O or S atoms and 0-2 N atoms; wherein each of said phenyl, naphthyl, heteroaryl or heterocyclic is optionally substituted by alkyl, 1 substituent —Y—R$^4$ and/or 1-4 substituents each independently selected from R$^5$;

Y is a bond, —(CH$_2$)$_m$— or —O—;

R$^4$ is (a) H, C$_1$-C$_6$ alkyl, C$_3$-C$_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; (b) phenyl or naphthyl, said phenyl and naphthyl being optionally substituted with 1-5 substituents selected from C$_1$-C$_6$ alkyl, C$_3$-C$_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; or (c) a 3 to 8-membered saturated or partially unsaturated monocyclic heteroaryl, containing 1 or 2 heteroatoms selected from O and N, said heteroaryl being optionally substituted by 1-5 substituents selected from C$_1$-C$_6$ alkyl, C$_3$-C$_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$;

R$^5$ is C$_1$-C$_6$ alkyl, C$_3$-C$_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ or —NR$^6$SO$_2$NR$^7$R$^8$;

R$^6$ is H, C$_1$-C$_6$ alkyl or C$_3$-C$_8$ cycloalkyl, said C$_1$-C$_6$ alkyl is optionally substituted by —NR$^7$R$^8$ or a 3 to 8-membered saturated or partially unsaturated monocyclic heteroaryl, containing 1 or 2 heteroatoms selected from O and N, said heteroaryl being optionally substituted by 1-5 substituents selected from C$_1$-C$_6$ alkyl, C$_3$-C$_8$ cycloalkyl, halo, hydroxy and cyano;

R$^7$ and R$^8$ are each independently H, C$_1$-C$_6$ alkyl or C$_3$-C$_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said C$_1$-C$_6$ alkyl is optionally substituted by C$_3$-C$_8$ cycloalkyl, halo, hydroxy, amino, (C$_1$-C$_6$ alkyl)amino or di(C$_1$-C$_6$ alkyl)amino and said heterocyclic ring being optionally substituted by one or more C$_1$-C$_6$ alkyl or C$_3$-C$_8$ cycloalkyl groups;

R$^9$ is C$_1$-C$_6$ alkyl or C$_3$-C$_8$ cycloalkyl;

R$^{10}$ is —NHSO$_2$—R', —NR"SO$_2$—R' or SR' where R' and R" are independently hydrogen, C$_1$-C$_6$ alkyl, C$_3$-C$_8$ cycloalkyl, phenyl, amino, C$_1$-C$_6$ alkylamino, di(C$_1$-C$_6$ alkyl)amino, heterocyclic, —(CH$_2$)$_n$—W', where W' is hydroxy, C$_3$-C$_8$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, C$_1$-C$_6$ alkyl, C$_1$-C$_6$ alkoxy, aryloxy, —SO$_2$—R', —NHSO$_2$—R', —NR"SO$_2$—R' or SR' where R' and R" are independently phenyl, C$_1$-C$_6$ alkyl or C$_3$-C$_8$ cycloalkyl;

R$^{11}$ and R$^{12}$ are each independently H, hydroxy, halo, cyano, C$_1$-C$_6$ alkyl or C$_3$-C$_8$ cycloalkyl; and, m and n are independently 0, 1, 2 or 3.

5. The method of claim 1 wherein the compound has the structure:

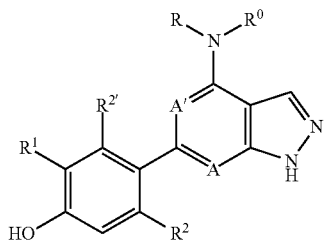

(Id)

or a pharmaceutically acceptable salt thereof, or a pharmaceutically acceptable solvate of said compound or pharmaceutically acceptable salt, wherein:

A and A' are independently C or N, where C may be unsubstituted or substituted by $C_1$-$C_6$ alkyl;

R and $R^0$ are independently selected from the group consisting of H, $C_1$-$C_6$ alkyl, hydroxy($C_1$-$C_6$ alkyl), phenyl($C_1$-$C_6$ alkyl), and —$(CH_2)_n$—W, where W is $C_3$-$C_8$ cycloalkyl, phenyl, naphthyl, 5- or 6-membered heteroaryl or heterocyclic containing 1-3 N, S and/or O atoms, —$SO_2$—R', —$NHSO_2$—R', —NR"$SO_2$—R' and SR', where R' and R" are independently $C_1$-$C_6$ alkyl or $C_3$-$C_8$ cycloalkyl, amino, $C_1$-$C_6$ alkylamino, di($C_1$-$C_6$ alkyl)amino, phenyl, heteroaryl, or heterocyclic; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —CONR'R", NR'COR", —NR'CONR'R", —NR'$CO_2$R", —$(CH_2)_n$—$SO_2$—R', —$NHSO_2$—R', —NR"$SO_2$—R' or SR' where R' and R" are independently $C_1$-$C_6$ alkyl, $C_3$-$C_8$ cycloalkyl, phenyl, amino, hydroxyalkylamino, heterocyclic, or —$(CH_2)_n$—W', where W' is hydroxy, $C_3$-$C_8$ cycloalkyl, phenyl, naphthyl, heterocyclic, or 5- or 6-membered heteroaryl containing 1-3 N, S and/or O atoms;

or, R and $R^0$ and the N atom to which they are bonded together form a monocyclic or bicyclic heterocyclic ring which may be unsubstituted or substituted by (a) halo, hydroxy, heteroaryl, $C_1$-$C_6$ alkyl, $C_1$-$C_6$ alkoxy, ($C_1$-$C_6$ alkoxy)$C_1$-$C_6$ alkoxy, aryl($C_1$-$C_6$ alkoxy), aryloxy, amino, aminoacyl, $C_1$-$C_6$ alkylaminoacyl, arylalkylaminoacyl, di($C_1$-$C_6$ alkyl)aminoacyl, —$SO_2$—R', —$SO_2$—NR"—$(CH_2)_n$—W, —$NHSO_2$—R', —NR"$SO_2$—R' or SR' where R' and R" is independently amino, $C_1$-$C_6$ alkylamino, di($C_1$-$C_6$ alkyl)amino, $C_1$-$C_6$ alkyl or $C_3$-$C_8$ cycloalkyl, or (b) —$(CH_2)_n$—W, where W is $C_3$-$C_8$ cycloalkyl, phenyl, naphthyl, heterocyclic, 5- or 6-membered heteroaryl containing 1-3 N atoms, —$SO_2$—R', —$NHSO_2$—R', —NR"$SO_2$—R' or SR', where R' and R" is independently alkyl or cycloalkyl; wherein each of said phenyl, aryl, or heteroaryl may be unsubstituted or substituted by halo, $C_1$-$C_6$ alkyl, $C_1$-$C_6$ alkoxy, cyano, or hydroxy;

$R^1$ is halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms; and, n is 0, 1, 2 or 3.

6. The method of claim 1 wherein the compound has the structure:

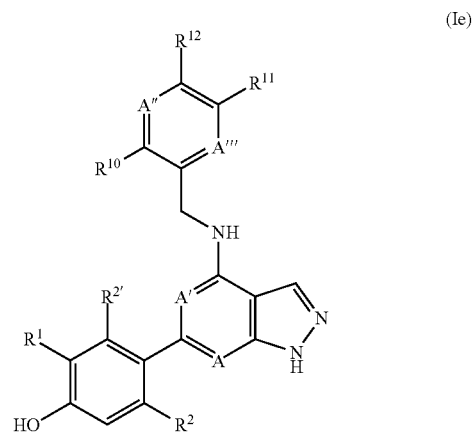

(Ie)

wherein:

A, A', A" and A''' are independently C or N, where C may be unsubstituted or substituted by halo or $C_1$-$C_6$ alkyl;

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^{10}$ is —$NHSO_2$—R', —NR"$SO_2$—R' or SR' where R' and R" is independently $C_1$-$C_6$ alkyl or $C_3$-$C_8$ cycloalkyl; and $R^{11}$ and $R^{12}$ are each independently H, hydroxy, halo, cyano, $C_1$-$C_6$ alkyl or $C_3$-$C_8$ cycloalkyl.

7. The method of claim 1 wherein the compound has the structure:

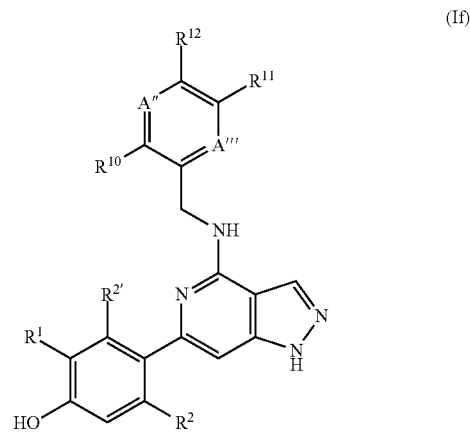

(If)

or a pharmaceutically acceptable salt thereof, or a pharmaceutically acceptable solvate of said compound or pharmaceutically acceptable salt, wherein:

A" and A''' are independently C or N, where C may be unsubstituted or substituted by halo or $C_1$-$C_6$ alkyl;

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^{10}$ is —$NHSO_2$—R', —NR"$SO_2$—R' or SR' where R' and R" are independently hydrogen, $C_1$-$C_6$ alkyl, $C_3$-$C_8$ cycloalkyl, phenyl, amino, $C_1$-$C_6$ alkylamino, di($C_1$-$C_6$ alkyl)amino, heterocyclic, —$(CH_2)_n$—W', where W' is hydroxy, $C_3$-$C_8$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyanohydroxy, $C_1$-$C_6$ alkyl, $C_1$-$C_6$ alkoxy, aryloxy, —$SO_2$—R', —$NHSO_2$—R', —NR"$SO_2$—R' or SR' where R' and R" are independently phenyl, $C_1$-$C_6$ alkyl or $C_3$-$C_8$ cycloalkyl;

$R^{11}$ and $R^{12}$ are each independently H, hydroxy, halo, cyano, $C_1$-$C_6$ alkyl or $C_3$-$C_8$ cycloalkyl; and, m and n are independently 0, 1, 2 or 3.

8. The method of claim 1 wherein the compound has the structure:

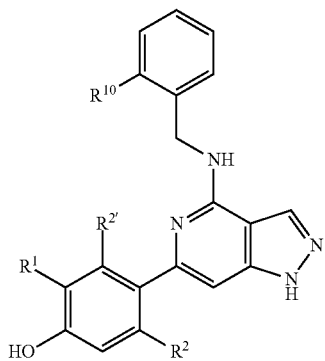

(Ig)

or a pharmaceutically acceptable salt thereof, or a pharmaceutically acceptable solvate of said compound or pharmaceutically acceptable salt, wherein:

$R^1$ is H, cyano or halo;

$R^2$ and $R^{2'}$ are independently H, $C_1$-$C_6$ alkyl, cyano, $C_1$-$C_6$ alkoxy, $C_1$-$C_6$ alkylthio, or $C_3$-$C_8$ cycloalkyl where alkyl, alkoxy, or cycloalkyl is optionally substituted by one or more fluorine atoms;

$R^{10}$ is —$NHSO_2$—R', —NR"$SO_2$—R' or SR' where R' and R" are independently hydrogen, $C_1$-$C_6$ alkyl, $C_3$-$C_8$ cycloalkyl, phenyl, amino, $C_1$-$C_6$ alkylamino, di($C_1$-$C_6$ alkyl)amino, heterocyclic, —$(CH_2)_n$—W', where W' is hydroxy, $C_3$-$C_8$ cycloalkyl, phenyl, naphthyl, heterocyclic, 5- or 6-membered heteroaryl containing 1-3 N and/or O atoms; wherein each of said alkyl, cycloalkyl, heterocyclic, phenyl, naphthyl or heteroaryl may be unsubstituted or substituted by phenyl, heteroaryl, heterocyclic, halo, cyano, hydroxy, $C_1$-$C_6$ alkyl, $C_1$-$C_6$ alkoxy, aryloxy, —$SO_2$—R', —$NHSO_2$—R', —NR"$SO_2$—R' or SR' where R' and R" are independently phenyl, $C_1$-$C_6$ alkyl or $C_3$-$C_8$ cycloalkyl; and, n is 0, 1, 2 or 3.

9. The method of claim 1 wherein the compound is selected from the group consisting of:

4-({2-[ethyl(ethylsulfonyl)amino]benzyl}amino)-6-[5-fluoro-4-hydroxy-2-(2,2,2-trifluoroethyl)-phenyl]-N-methyl-1H-pyrazolo[4,3-c]pyridine-3-carboxamide;

4-({2-[ethyl(ethylsulfonyl)amino]benzyl}amino)-6-(2-ethyl-5-fluoro-4-hydroxyphenyl)-N-methyl-1H-pyrazolo[4,3-c]pyridine-3-carboxamide;

6-(2-ethyl-5-fluoro-4-hydroxyphenyl)-4-({2-[(ethylsulfonyl)(methyl)amino]benzyl}amino)-N-methyl-1H-pyrazolo[4,3-c]pyridine-3-carboxamide;

6-(2-ethyl-5-fluoro-4-hydroxyphenyl)-4-{[2-(4-hydroxyphenyl)ethyl]amino}-N-methyl-1H-pyrazolo[4,3-c]pyridine-3-carboxamide;

6-(2-ethyl-5-fluoro-4-hydroxyphenyl)-N-methyl-4-[(2-methylpropyl)amino]-1H-pyrazolo[4,3-c]pyridine-3-carboxamide;

4-({5-chloro-2-[methyl(methylsulfonyl)amino]benzyl}amino)-6-(2-ethyl-5-fluoro-4-hydroxyphenyl)-N-methyl-1H-pyrazolo[4,3-c]pyridine-3-carboxamide;

6-(2-ethyl-5-fluoro-4-hydroxyphenyl)-4-({5-fluoro-2-[methyl(methylsulfonyl)amino]benzyl}amino)-N-methyl-1H-pyrazolo[4,3-c]pyridine-3-carboxamide;

6-(2-ethyl-5-fluoro-4-hydroxyphenyl)-4-({2-fluoro-6-[methyl(methylsulfonyl)amino]benzyl}amino)-N-methyl-1H-pyrazolo[4,3-c]pyridine-3-carboxamide;

6-(2-ethyl-5-fluoro-4-hydroxyphenyl)-4-({2-[ethyl(methylsulfonyl)amino]benzyl}amino)-N-methyl-1H-pyrazolo[4,3-c]pyridine-3-carboxamide;

4-[(cyclopentylmethyl)amino]-6-(2-ethyl-5-fluoro-4-hydroxyphenyl)-N-methyl-1H-pyrazolo[4,3-c]pyridine-3-carboxamide;

6-[5-fluoro-4-hydroxy-2-(2,2,2-trifluoroethyl)phenyl]-N-methyl-4-({5-methyl-2-[methyl(methylsul-fonyl)amino]benzyl}amino)-1H-pyrazolo[4,3-c]pyridine-3-carboxamide;

4-({2-[ethyl(methylsulfonyl)amino]benzyl}amino)-6-[5-fluoro-4-hydroxy-2-(2,2,2-trifluoro-ethyl)phenyl]-N-methyl-1H-pyrazolo[4,3-c]pyridine-3-carboxamide;

4-({2-[(ethylsulfonyl)(methyl)amino]benzyl}amino)-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-4-({5-fluoro-2-[methyl(methylsulfon-yl)amino]benzyl}amino)-N-methyl-1H-pyrazolo[4,3-c]pyridine-3-carboxamide;

4-({5-chloro-2-[methyl(methylsulfonyl)amino]benzyl}amino)-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-N-methyl-4-[(2-methylpropyl)amino]-1H-pyrazolo[4,3-c]pyridine-3-carboxamide;

4-[(cyclopentylmethyl)amino]-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-4-({2-fluoro-6-[methyl(methylsulfonyl)-amino]benzyl}amino)-N-methyl-1H-pyrazolo[4,3-c]pyridine-3-carboxamide;

6-(2-ethyl-5-fluoro-4-hydroxyphenyl)-N-methyl-4-({2-[methyl(methylsulfonyl)amino]benzyl}-amino)-1H-pyrazolo[4,3-c]pyridine-3-carboxamide;

6-[5-fluoro-4-hydroxy-2-(2,2,2-trifluoroethyl)phenyl]-N-methyl-4-({2-[methyl(methylsulfonyl)-amino]benzyl}amino)-1H-pyrazolo[4,3-c]pyridine-3-carboxamide;

6-(2-ethyl-5-fluoro-4-hydroxyphenyl)-N-methyl-4-({5-methyl-2-[methyl(methylsulfonyl)amino]-benzyl}amino)-1H-pyrazolo[4,3-c]pyridine-3-carboxamide;

6-(2-ethyl-5-fluoro-4-hydroxyphenyl)-N-methyl-4-({2-[methyl(phenylsulfonyl)-amino]benzyl}am-ino)-1H-pyrazolo[4,3-c]pyridine-3-carboxamide;

6-(2-ethyl-5-fluoro-4-hydroxyphenyl)-N-methyl-4-[(2-{4-[(phenylsulfonyl)amino]-phenyl}ethyl)-amino]-1H-pyrazolo[4,3-c]pyridine-3-carboxamide;

6-[5-fluoro-4-hydroxy-2-(2,2,2-trifluoroethyl)phenyl]-4-({2-[(2-hydroxyethyl)(methylsulfonyl)-amino]benzyl}amino)-N-methyl-1H-pyrazolo[4,3-c]pyridine-3-carboxamide;

6-[5-fluoro-4-hydroxy-2-(2,2,2-trifluoroethyl)phenyl]-4-({2-[methyl(phenylsulfonyl)amino]benzyl}-amino)-1H-pyrazolo[4,3-c]pyridine-3-carboxamide;

6-[5-fluoro-4-hydroxy-2-(2,2,2-trifluoroethyl)phenyl]-4-({2-[(2-hydroxyethyl)(methylsulfonyl)-amino]benzyl}amino)-1H-pyrazolo[4,3-c]pyridine-3-carboxamide;

6-(2-ethyl-5-fluoro-4-hydroxyphenyl)-4-({4-hydroxy-2-[methyl(methylsulfonyl)amino]benzyl}-amino)-N-methyl-1H-pyrazolo[4,3-c]pyridine-3-carboxamide;

6-(2-ethyl-5-fluoro-4-hydroxyphenyl)-4-({4-hydroxy-2-[methyl(methylsulfonyl)amino]benzyl}-amino)-1H-pyrazolo[4,3-c]pyridine-3-carboxamide;

6-(2-ethyl-5-fluoro-4-hydroxyphenyl)-4-({5-hydroxy-2-[methyl(methylsulfonyl)amino]benzyl}-amino)-N-methyl-1H-pyrazolo[4,3-c]pyridine-3-carboxamide;

6-[5-fluoro-4-hydroxy-2-(2,2,2-trifluoroethyl)phenyl]-4-[(2-{[(3-hydroxyphenyl)sulfonyl](methyl)-amino}benzyl)amino]-N-methyl-1H-pyrazolo[4,3-c]pyridine-3-carboxamide;

6-[5-fluoro-4-hydroxy-2-(2,2,2-trifluoroethyl)phenyl]-4-({4-hydroxy-2-[methyl(methylsulfonyl)-amino]benzyl}amino)-N-methyl-1H-pyrazolo[4,3-c]pyridine-3-carboxamide;

4-({2-[ethyl(methylsulfonyl)amino]-5-hydroxybenzyl}amino)-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-4-({5-hydroxy-2-[methyl(phenylsulfonyl)-amino]benzyl}amino)-N-methyl-1H-pyrazolo[4,3-c]pyridine-3-carboxamide;

4-({2-[ethyl(phenylsulfonyl)amino]-5-hydroxybenzyl}amino)-6-[5-fluoro-4-hydroxy-2-(2,2,2-trifluoroethyl)phenyl]-N-methyl-1H-pyrazolo[4,3-c]pyridine-3-carboxamide;

6-(2-cyclopropyl-5-fluoro-4-hydroxyphenyl)-N-methyl-4-({2-[methyl(methylsulfonyl)amino]-benzyl}amino)-1H-pyrazolo[4,3-c]pyridine-3-carboxamide;

6-(2-ethyl-5-fluoro-4-hydroxyphenyl)-N-methyl-4-{[(1R)-1-{2-[methyl(methylsulfonyl)amino]-phenyl}ethyl]amino}-1H-pyrazolo[4,3-c]pyridine-3-carboxamide;

6-(2-ethyl-5-fluoro-4-hydroxyphenyl)-N-methyl-4-{[(1S)-1-{2-[methyl(methylsulfonyl)-amino]phenyl}ethyl]amino}-1H-pyrazolo[4,3-c]pyridine-3-carboxamide;

6-(2-ethyl-5-fluoro-4-hydroxyphenyl)-4-({2-[methyl(phenylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-4-({4-hydroxy-2-[methyl(methylsulfonyl)-amino]benzyl}amino)-1H-pyrazolo[4,3-c]pyridine-3-carboxamide;

6-[5-fluoro-4-hydroxy-2-(2,2,2-trifluoroethyl)phenyl]-4-({5-hydroxy-2-[methyl(phenylsulfonyl)-amino]benzyl}amino)-1H-pyrazolo[4,3-c]pyridine-3-carboxamide;

4-({2-[ethyl(phenylsulfonyl)amino]-5-hydroxybenzyl}amino)-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-N-methyl-4-[({3-[methyl(phenylsulfonyl)-amino]pyrazin-2-yl}methyl)amino]-1H-pyrazolo[4,3-c]pyridine-3-carboxamide;

4-[({3-[ethyl(methylsulfonyl)amino]pyrazin-2-yl}methyl)amino]-6-[5-fluoro-4-hydroxy-2-(2,2,2-trifluoroethyl)phenyl]-N-methyl-1H-pyrazolo[4,3-c]pyridine-3-carboxamide;

N-ethyl-4-[({3-[ethyl(methylsulfonyl)amino]pyrazin-2-yl}methyl)amino]-6-[5-fluoro-4-hydroxy-2-(2,2,2-trifluoroethyl)phenyl]-1H-pyrazolo[4,3-c]pyridine-3-carboxamide;

6-(2-cyclopropyl-5-fluoro-4-hydroxyphenyl)-4-({2-[methyl(methylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-N-methyl-4-[({4-[methyl(methylsulfonyl)-amino]pyridin-3-yl}methyl)amino]-1H-pyrazolo[4,3-c]pyridine-3-carboxamide;

6-(2-cyclopropyl-5-fluoro-4-hydroxyphenyl)-N-methyl-4-[({2-[methyl(methylsulfonyl)amino]-pyridin-3-yl}methyl)amino]-1H-pyrazolo[4,3-c]pyridine-3-carboxamide;

6-[5-fluoro-4-hydroxy-2-(2,2,2-trifluoroethyl)phenyl]-4-({5-methoxy-2-[methyl(methylsulfonyl)-amino]benzyl}amino)-N-methyl-1H-pyrazolo[4,3-c]pyridine-3-carboxamide;

6-[5-fluoro-4-hydroxy-2-(2,2,2-trifluoroethyl)phenyl]-N-methyl-4-[({3-[methyl(methylsulfonyl)am-ino]pyrazin-2-yl}methyl)amino]-1H-pyrazolo[4,3-c]pyridine-3-carboxamide;

4-[({2-[ethyl(methylsulfonyl)amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,22-trifluoroethyl)phenyl]-N-methyl-4-[({2-[methyl(methylsulfonyl)-amino]pyridin-3-yl}methyl)amino]-1H-pyrazolo[4,3-c]pyridine-3-carboxamide;

6-[5-fluoro-4-hydroxy-2-(2,2,2-trifluoroethyl)phenyl]-4-({5-hydroxy-2-[methyl(pyridin-3-ylsulfonyl)amino]benzyl}amino)-N-methyl-1H-pyrazolo[4,3-c]pyridine-3-carboxamide;

6-[5-fluoro-4-hydroxy-2-(2,2,2-trifluoroethyl)phenyl]-N-methyl-4-[({3-[methyl(methylsulfonyl)-amino]pyridin-2-yl}methyl)amino]-1H-pyrazolo[4,3-c]pyridine-3-carboxamide;

6-(2-ethyl-5-fluoro-4-hydroxyphenyl)-4-({2-[methyl(methylsulfonyl)amino]benzyl}amino)-N-(6-methylpyridin-3-yl)-1H-pyrazolo[4,3-c]pyridine-3-carboxamide;

6-(5-fluoro-4-hydroxy-2-(2,2,2-trifluoroethyl)phenyl)-N-methyl-4-((1,3,3-trimethylureido)benzyl)-amino)-1H-pyrazolo[4,3-c]pyridine-3-carboxamide;

6-(5-fluoro-4-hydroxy-2-(2,2,2-trifluoroethyl)phenyl)-N-methyl-4-((2-(N-methyl-1H-pyrazole-4-sulfonamido)benzyl)amino)-1H-pyrazolo[4,3-c]pyridine-3-carboxamide;

4-((2-N,1-dimethyl-1H-imidazole-4-sulfonamido)benzyl)amido)-6-(5-fluoro-4-hydroxy-2-(2,2,2-trifluoroethyl)phenyl)-N-methyl-1H-pyrazolo[4,3-c]pyridine-3-carboxamide;

6-[5-fluoro-4-hydroxy-2-(2,2,2-trifluoroethyl)phenyl]-4-[(2-{[(2-methoxyethyl)sulfonyl]-(methyl)amino}benzyl)amino]-N-methyl-1H-pyrazolo[4,3-c]pyridine-3-carboxamide;

6-[5-fluoro-4-hydroxy-2-(2,2,2-trifluoroethyl)phenyl]-4-({2-[methyl(pyridin-3-ylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-4-[({2-[methyl(methylsulfonyl)amino]pyridin-3-yl}methyl)amino]-1H-pyrazolo[4,3-c]pyridine-3-carboxamide;

4-[({2-[ethyl(methylsulfonyl)amino]pyridin-3-yl}methyl)amino]-6-[5-fluoro-4-hydroxy-2-(2,2,2-trifluoroethyl)phenyl]-N-methyl-1H-pyrazolo[4,3-c]pyridine-3-carboxamide;

6-[5-fluoro-4-hydroxy-2-(2,2,2-trifluoroethyl)phenyl]-N-methyl-4-{[2-(sulfamoylmethyl)benzyl]-amino}-1H-pyrazolo[4,3-c]pyridine-3-carboxamide;

6-[5-fluoro-4-hydroxy-2-(2,2,2-trifluoroethyl)phenyl]-4-{[2-(methyl{[6-(morpholin-4-yl)pyridin-3-yl]sulfonyl}amino)benzyl]amino}-1H-pyrazolo[4,3-c]pyridine-3-carboxamide;

6-[5-fluoro-4-hydroxy-2-(2,2,2-trifluoroethyl)phenyl]-4-{[2-(methyl{[3-(morpholin-4-yl)propyl]sulfonyl}amino)benzyl]amino}-1H-pyrazolo[4,3-c]pyridine-3-carboxamide;

6-[5-fluoro-4-hydroxy-2-(2,2,2-trifluoroethyl)phenyl]-N-methyl-4-[({5-methyl-2-[methyl(methyl-sulfonyl)amino]pyridin-3-yl}methyl)amino]-1H-pyrazolo[4,3-c]pyridine-3-carboxamide;

6-[5-fluoro-4-hydroxy-2-(2,2,2-trifluoroethyl)phenyl]-N-methyl-4-({2-[methyl(pyridin-3-ylsulfonyl)amino]benzyl}amino)-1H-pyrazolo[4,3-c]pyridine-3-carboxamide;

6-[5-fluoro-4-hydroxy-2-(2,2,2-trifluoroethyl)phenyl]-N-methyl-4-[(2-{methyl[(6-methylpyridin-3-yl)sulfonyl]amino}benzyl)amino]-1H-pyrazolo[4,3-c]pyridine-3-carboxamide;

6-[5-fluoro-4-hydroxy-2-(2,2,2-trifluoroethyl)phenyl]-4-[(2-{methyl[(6-methylpyridin-3-yl)sulfonyl]amino}benzyl)amino]-1H-pyrazolo[4,3-c]pyridine-3-carboxamide;

4-[({5-chloro-2-[ethyl(methylsulfonyl)amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide;

4-[({5-chloro-2-[methyl(methylsulfonyl)amino]pyridin-3-yl}methyl)amino]-6-[5-fluoro-4-hydroxy-2-(2,2,2-trifluoroethyl)phenyl]-1H-pyrazolo[4,3-c]pyridine-3-carboxamide;

6-(2-ethyl-5-fluoro-4-hydroxyphenyl)-N-methyl-4-({2-[methyl(sulfamoyl)amino]benzyl}amino)-1H-pyrazolo[4,3-c]pyridine-3-carboxamide;

6-(5-fluoro-4-hydroxy-2-(2,2,2-trifluoroethyl)phenyl)-4-((N-(2-hydroxyethyl)sulfamoyl)(methyl)-aminobenzyl)amino)-N-methyl-1H-pyrazolo[4,3-c]pyridine-3-carboxamide;

6-[5-fluoro-4-hydroxy-2-(2,2,22-trifluoroethyl)phenyl]-N-{6-[(2-hydroxyethyl)amino]pyridin-3-yl}-4-({5-hydroxy-2-[methyl(methylsulfonyl)amino]benzyl}amino)-1H-pyrazolo[4,3-c]pyridine-3-carboxamide;

6-[5-fluoro-4-hydroxy-2-(2,2,22-trifluoroethyl)phenyl]-4-({2-[methyl(methylsulfonyl)amino]benzyl}amino)-N-(6-methylpyridin-3-yl)-1H-pyrazolo[4,3-c]pyridine-3-carboxamide;

6-[5-fluoro-4-hydroxy-2-(2,2,2-trifluoroethyl)phenyl]-4-({2-[methyl(methylsulfonyl)-amino]benzyl}amino)-1H-pyrazolo[4,3-c]pyridine-3-carboxamide;

6-[5-fluoro-4-hydroxy-2-(2,2,22-trifluoroethyl)phenyl]-4-[({5-fluoro-2-[methyl(methylsulfonyl)-amino]pyridin-3-yl}methyl)amino]-1H-pyrazolo[4,3-c]pyridine-3-carboxamide;

4-[({2-[ethyl(methylsulfonyl)amino]-5-fluoropyridin-3-yl}methyl)amino]-6-[5-fluoro-4-hydroxy-2-(2,2,2-trifluoroethyl)phenyl]-1H-pyrazolo[4,3-c]pyridine-3-carboxamide;

4-[({3-[ethyl(methylsulfonyl)amino]pyrazin-2-yl}methyl)amino]-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,22-trifluoroethyl)phenyl]-4-({5-methyl-2-[methyl(methylsulfonyl)-amino]benzyl}amino)-1H-pyrazolo[4,3-c]pyridine-3-carboxamide;

4-((2-(N-ethylethylsulfonamido)benzyl)amino)-6-(5-fluoro-4-hydroxy-2-(2,2,2-trifluoroethyl)phenyl)-1H-pyrazolo[4,3-c]pyridine-3-carboxamide;

4-((2-(N-ethylmethylsulfonamido)-5-fluorobenzyl)amino)-6-(5-fluoro-4-hydroxy-2-(2,2,2-trifluoro-ethyl)phenyl)-1H-pyrazolo[4,3-c]pyridine-3-carboxamide;

4-((5-chloro-2-(N-ethylmethylsulfonamido)benzyl)amino)-6-(5-fluoro-4-hydroxy-2-(2,2,2-trifluoro-ethyl)phenyl)-1H-pyrazolo[4,3-c]pyridine-3-carboxamide;

6-(5-fluoro-4-hydroxy-2-(2,2,2-trifluoroethyl)phenyl)-4-((2-(N-methylethyl-sulfonamido)benzyl)-amino)-1H-pyrazolo[4,3-c]pyridine-3-carboxamide;

6-(5-fluoro-4-hydroxy-2-(2,2,2-trifluoroethyl)phenyl)-4-(((5-methyl-2-(N-methylmethylsulfonam-ido)pyridin-3-yl)methyl)amino)-1H-pyrazolo[4,3-c]pyridine-3-carboxamide;

4-[({2-[ethyl(methylsulfonyl)amino]-5-methylpyridin-3-yl}methyl)amino]-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-4-({5-fluoro-2-[methyl(methylsulfonyl)-amino]benzyl}amino)-1H-pyrazolo[4,3-c]pyridine-3-carboxamide;

4-({5-chloro-2-[methyl(methylsulfonyl)amino]benzyl}amino)-6-[5-fluoro-4-hydroxy-2-(2,2,2-trifluoroethyl)phenyl]-1H-pyrazolo[4,3-c]pyridine-3-carboxamide;

4-({2-[ethyl(methylsulfonyl)amino]benzyl}amino)-6-[5-fluoro-4-hydroxy-2-(2,2,2-trifluoroethyl)-phenyl]-1H-pyrazolo[4,3-c]pyridine-3-carboxamide;

4-({2-[ethyl(methylsulfonyl)amino]-5-methylbenzyl}amino)-6-[5-fluoro-4-hydroxy-2-(2,2,2-trifluoroethyl)phenyl]-1H-pyrazolo[4,3-c]pyridine-3-carboxamide;

6-[5-fluoro-4-hydroxy-2-(2,2,2-trifluoroethyl)phenyl]-4-({5-hydroxy-2-[methyl(methylsulfonyl)-amino]benzyl}amino)-1H-pyrazolo[4,3-c]pyridine-3-carboxamide;

6-(2-ethyl-5-fluoro-4-hydroxyphenyl)-N-methyl-4-((2-(N-methylmethylsulfonamido)benzyl)-amino)-1H-pyrazolo[3,4-d]pyrimidine-3-carboxamide;

6-(5-fluoro-4-hydroxy-2-(2,2,2-trifluoroethyl)phenyl)-N-methyl-4-((2-(N-methylmethylsulfon-amido)benzyl)amino)-1H-pyrazolo[3,4-d]pyrimidine-3-carboxamide;

6-(2-ethyl-5-fluoro-4-hydroxyphenyl)-4-((2-(N-methyl-phenylsulfonamido)benzyl)amino)-1H-pyrazolo[3,4-d]pyrimidine-3-carboxamide;

6-(5-fluoro-4-hydroxy-2-(2,2,2-trifluoroethyl)phenyl)-4-((2-(N-methylphenylsulfonamido)-benzyl)amino)-1H-pyrazolo[3,4-d]pyrimidine-3-carboxamide;

6-(5-fluoro-4-hydroxy-2-(2,2,2-trifluoroethyl)phenyl)-4-((5-hydroxy-2-(N-methylmethylsulfon-amido)benzyl)amino)-1H-pyrazolo[3,4-d]pyrimidine-3-carboxamide;
6-(5-fluoro-4-hydroxy-2-(2,2,2-trifluoroethyl)phenyl)-4-((2-(N-methylmethylsulfon-amido)benzyl)amino)-1H-pyrazolo[3,4-d]pyrimidine-3-carboxamide;
6-(5-fluoro-4-hydroxy-2-(2,2,2-trifluoroethyl)phenyl)-4-((5-hydroxy-2-(N-methylmethylsulfon-amido)benzyl)amino)-N-(6-((2-hydroxyethyl)amino)pyridin-3-yl)-1H-pyrazolo[3,4-d]pyrimidine-3-carboxamide;
6-(5-fluoro-4-hydroxy-2-(2,2,22-trifluoroethyl)phenyl)-N-methyl-4-(((3-(N-methylmethyl-sulfonamido)pyrazin-2-yl)methyl)amino)-1H-pyrazolo[3,4-d]pyrimidine-3-carboxamide;
6-(5-fluoro-4-hydroxy-2-(2,2,2-trifluoroethyl)phenyl)-4-((2-(N-(2-hydroxyethyl)methyl-sulfonamido)benzyl)amino)-1H-pyrazolo[3,4-d]pyrimidine-3-carboxamide;
6-(5-fluoro-4-hydroxy-2-(2,2,2-trifluoroethyl)phenyl)-4-((2-(N-(2-hydroxyethyl)methylsulfon-amido)benzyl)amino)-N-methyl-1H-pyrazolo[3,4-d]pyrimidine-3-carboxamide;
4-((2-(N-ethylmethylsulfonamido)benzyl)amino)-6-(5-fluoro-4-hydroxy-2-(2,2,2-trifluoroethyl)-phenyl)-N-methyl-1H-pyrazolo[3,4-d]pyrimidine-3-carboxamide;
4-((5-fluoro-2-(N-methylmethylsulfonamido)benzyl)amino)-6-(5-fluoro-4-hydroxy-2-(2,2,2-trifluoroethyl)phenyl)-N-methyl-1H-pyrazolo[3,4-d]pyrimidine-3-carboxamide;
4-((2-(N-ethylphenylsulfonamido)-5-hydroxybenzyl)amino)-6-(5-fluoro-4-hydroxy-2-(2,2,2-trifluoroethyl)phenyl)-N-methyl-1H-pyrazolo[3,4-d]pyrimidine-3-carboxamide;
4-((2-(N-methylphenylsulfonamido)-5-hydroxybenzyl)amino)-6-(5-fluoro-4-hydroxy-2-(2,2,2-trifluoroethyl)phenyl)-N-methyl-1H-pyrazolo[3,4-d]pyrimidine-3-carboxamide;
4-((2-(N-ethylphenylsulfonamido)-5-hydroxybenzyl)amino)-6-(5-fluoro-4-hydroxy-2-(2,2,2-trifluoroethyl)phenyl)-1H-pyrazolo[3,4-d]pyrimidine-3-carboxamide;
4-((2-(N-methylphenylsulfonamido)-5-hydroxybenzyl)amino)-6-(5-fluoro-4-hydroxy-2-(2,2,2-trifluoroethyl)phenyl)-1H-pyrazolo[3,4-d]pyrimidine-3-carboxamide;
6-(5-fluoro-4-hydroxy-2-(2,2,2-trifluoroethyl)phenyl)-N-methyl-4-((2-(methyl(sulfamoyl)amino)-benzyl)amino)-1H-pyrazolo[3,4-d]pyrimidine-3-carboxamide;
6-(5-fluoro-4-hydroxy-2-(2,2,2-trifluoroethyl)phenyl)-N-methyl-4-((2-(methyl(N-methylsulfamoyl)amino)benzyl)amino)-1H-pyrazolo[3,4-d]pyrimidine-3-carboxamide;
4-[4-(7,8-dimethoxy-3,4-dihydroisoquinolin-2(1H)-yl)-1H-pyrazolo[4,3-c]pyridin-6-yl]-3-ethylphenol formate;
3-ethyl-4-[4-(3-phenoxyazetidin-1-yl)-1H-pyrazolo[4,3-c]pyridin-6-yl]phenol formate;
3-ethyl-4-{4-[6-(4-methyl-1H-imidazol-1-yl)-3,4-dihydroisoquinolin-2(1H)-yl]-1H-pyrazolo[4,3-c]pyridin-6-yl}phenol formate;
3-ethyl-4-{4-[6-(2-methoxyethoxy)-3,4-dihydroisoquinolin-2(1H)-yl]-1H-pyrazolo[4,3-c]pyridin-6-yl}phenol formate;
1-[6-(2-ethyl-4-hydroxyphenyl)-1H-pyrazolo[4,3-c]pyridin-4-yl]-3-methylazetidin-3-ol formate;
2-[6-(2-ethyl-4-hydroxyphenyl)-1H-pyrazolo[4,3-c]pyridin-4-yl]-N-[2-(pyrrolidin-1-yl)ethyl]-1,2,3,4-tetrahydroisoquinoline-7-sulfonamide formate;

N-benzyl-2-[6-(2-ethyl-4-hydroxyphenyl)-1H-pyrazolo[4,3-c]pyridin-4-yl]-1,2,3,4-tetrahydroiso-quinoline-5-carboxamide formate;
4-{4-[7-(benzyloxy)-6-methoxy-3,4-dihydroisoquinolin-2(1H)-yl]-1H-pyrazolo[4,3-c]pyridin-6-yl}-3-ethyl-phenol formate;
4-[4-(5-chloro-3,4-dihydroisoquinolin-2(1H)-yl)-1H-pyrazolo[4,3-c]pyridin-6-yl]-3-ethylphenol formate;
4-chloro-3-({1-[6-(2-ethyl-4-hydroxyphenyl)-1H-pyrazolo[4,3-c]pyridin-4-yl]azetidin-3-yl}oxy)benzonitrile formate;
3-ethyl-4-[4-(6-fluoro-3,4-dihydroisoquinolin-2(1H)-yl)-1H-pyrazolo[4,3-c]pyridin-6-yl]phenol formate;
3-ethyl-4-[4-(8-methoxy-3,4-dihydroisoquinolin-2(1H)-yl)-1H-pyrazolo[4,3-c]pyridin-6-yl]phenol formate;
N-{2-[6-(2-ethyl-4-hydroxyphenyl)-1H-pyrazolo[4,3-c]pyridin-4-yl]-1,2,3,4-tetrahydroisoquinolin-5-yl}methanesulfonamide formate;
4-(4-{[2-(biphenyl-4-yl)ethyl]amino}-1H-pyrazolo[4,3-c]pyridin-6-yl)-3-ethylphenol formate;
N-[2-({[6-(2-ethyl-4-hydroxyphenyl)-1H-pyrazolo[4,3-c]pyridin-4-yl]amino}methyl)phenyl]-N-methylmethanesulfonamide hydrochloride;
1-[6-(2-ethyl-4-hydroxyphenyl)-1H-pyrazolo[4,3-c]pyridin-4-yl]-N, N-dimethylpyrrolidine-3-sulfon-amide (racemic);
N-[2-({[6-(2-ethyl-4-hydroxyphenyl)-1H-pyrazolo[4,3-c]pyridin-4-yl]amino}methyl)-3-methylphenyl]-N-methylmethanesulfonamide diethylamine salt;
3-ethyl-4-[4-(4-methoxypiperidin-1-yl)-1H-pyrazolo[4,3-c]pyridin-6-yl]phenol diethylamine salt;
N-[2-({[2-(3,4-dimethoxyphenyl)ethyl][6-(2-ethyl-5-fluoro-4-hydroxyphenyl)-1H-pyrazolo[4,3-c]pyridin-4-yl]amino}methyl)phenyl]-N-methylmethanesulfonamide hydrochloride;
N-[2-({[6-(2-ethyl-5-fluoro-4-hydroxyphenyl)-1H-pyrazolo[4,3-c]pyridin-4-yl](2-{4-[(methylsulfon-yl)amino]phenyl}ethyl)amino}methyl)phenyl]-N-methylmethanesulfonamide hydrochloride;
N-[2-({[6-(2-ethyl-5-fluoro-4-hydroxyphenyl)-1H-pyrazolo[4,3-c]pyridin-4-yl]amino}methyl)-phenyl]-N-methylmethanesulfonamide;
N-[2-({[6-(2-ethyl-5-fluoro-4-hydroxyphenyl)-1H-pyrazolo[4,3-c]pyridin-4-yl]amino}methyl)-4-methylphenyl]-N-methylmethanesulfonamide hydrochloride;
N-[4-chloro-2-({[6-(2-ethyl-5-fluoro-4-hydroxyphenyl)-1H-pyrazolo[4,3-c]pyridin-4-yl]amino}methyl)phenyl]-N-methylmethanesulfonamide hydrochloride;
N-[2-({[6-(2-ethyl-5-fluoro-4-hydroxyphenyl)-1H-pyrazolo[4,3-c]pyridin-4-yl]amino}methyl)-3-fluorophenyl]-N-methylmethanesulfonamide hydrochloride;
N-[2-({[6-(2-ethyl-5-fluoro-4-hydroxyphenyl)-1H-pyrazolo[4,3-c]pyridin-4-yl]amino}methyl)-phenyl]-N-methylethanesulfonamide hydrochloride;
N-ethyl-N-[2-({[6-(2-ethyl-5-fluoro-4-hydroxyphenyl)-1H-pyrazolo[4,3-c]pyridin-4-yl]amino}-methyl)phenyl]ethanesulfonamide hydrochloride;
N-[2-({[6-(2-ethyl-5-fluoro-4-hydroxyphenyl)-1H-pyrazolo[4,3-c]pyridin-4-yl]amino}methyl)phenyl]-N-propylmethanesulfonamide;
N-ethyl-N-[2-({[6-(2-ethyl-5-fluoro-4-hydroxyphenyl)-1H-pyrazolo[4,3-c]pyridin-4-yl]amino}-methyl)phenyl]methanesulfonamide;
N-butyl-N-[2-({[6-(2-ethyl-5-fluoro-4-hydroxyphenyl)-1H-pyrazolo[4,3-c]pyridin-4-yl]amino}-methyl)phenyl]methanesulfonamide;

N-[2-({[6-(2-ethyl-5-fluoro-4-hydroxyphenyl)-1H-pyrazolo[4,3-c]pyridin-4-yl][2-(morpholin-4-yl)ethyl]amino}methyl)phenyl]-N-methylmethanesulfonamide;

N-[2-({[6-(2-ethyl-5-fluoro-4-hydroxyphenyl)-1H-pyrazolo[4,3-c]pyridin-4-yl][2-(morpholin-4-yl)ethyl]amino}methyl)phenyl]-N-methylmethanesulfonamide;

N-ethyl-N-[2-({[6-(2-ethyl-5-fluoro-4-hydroxyphenyl)-1H-pyrazolo[4,3-c]pyridin-4-yl](methyl)amino}methyl)-4-methylphenyl]methanesulfonamide;

N-[2-({ethyl[6-(2-ethyl-5-fluoro-4-hydroxyphenyl)-1H-pyrazolo[4,3-c]pyridin-4-yl]amino}methyl)-4-methylphenyl]-N-methylmethanesulfonamide;

N-[2-({[6-(2-ethyl-5-fluoro-4-hydroxyphenyl)-1H-pyrazolo[4,3-c]pyridin-4-yl](propyl)amino}-methyl)-4-methylphenyl]-N-methylmethanesulfonamide;

N-ethyl-N-[2-({[6-(2-ethyl-5-fluoro-4-hydroxyphenyl)-1H-pyrazolo[4,3-c]pyridin-4-yl](methyl)amino}methyl)phenyl]methanesulfonamide hydrochloride;

N-[2-({[6-(2-ethyl-5-fluoro-4-hydroxyphenyl)-1H-pyrazolo[4,3-c]pyridin-4-yl](methyl)amino}-methyl)phenyl]-N-methylmethanesulfonamide hydrochloride;

N-[2-({[6-(2-ethyl-5-fluoro-4-hydroxyphenyl)-1H-pyrazolo[4,3-c]pyridin-4-yl]amino}methyl)phenyl]-N-(2-hydroxyethyl)methanesulfonamide;

N-{2-[({6-[5-fluoro-4-hydroxy-2-(2,2,2-trifluoroethyl)phenyl]-1H-pyrazolo[4,3-c]pyridin-4-yl}amino)methyl]phenyl}-N-methylmethanesulfonamide;

N-(2-{[{6-[5-fluoro-4-hydroxy-2-(2,2,2-trifluoroethyl)phenyl]-1H-pyrazolo[4,3-c]pyridin-4-yl}(methyl)amino]methyl}phenyl)-N-methylmethanesulfonamide;

N-{2-[({6-[5-fluoro-4-hydroxy-2-(2,2,2-trifluoroethyl)phenyl]-1H-pyrazolo[4,3-c]pyridin-4-yl}amino)methyl]-4-methylphenyl}-N-methylmethanesulfonamide;

4-{4-[(cyclopropylmethyl)amino]-1H-pyrazolo[3,4-d]pyrimidin-6-yl}-2-fluoro-5-(2,2,2-trifluoroethyl)phenol;

4-{4-[(2-cyclopropylethyl)amino]-1H-pyrazolo[3,4-d]pyrimidin-6-yl}-2-fluoro-5-(2,2,2-trifluoroethyl)phenol;

2-fluoro-4-{4-[(2-methylpropyl)amino]-1H-pyrazolo[3,4-d]pyrimidin-6-yl}-5-(2,2,2-trifluoro-ethyl)phenol;

4-[4-(butylamino)-1H-pyrazolo[3,4-d]pyrimidin-6-yl]-2-fluoro-5-(2,2,2-trifluoroethyl)phenol;

N-[2-({[6-(2-ethyl-5-fluoro-4-hydroxyphenyl)-1H-pyrazolo[3,4-d]pyrimidin-4-yl]amino}methyl)-phenyl]-N-methylmethanesulfonamide hydrochloride;

N-(2-(((6-(2-ethyl-4-hydroxy-6-methylphenyl)-1H-pyrazolo[4,3-c]pyridin-4-yl)amino)methyl)-phenyl)-N-methylmethanesulfonamide;

N-[2-({[6-(2-ethyl-5-fluoro-4-hydroxyphenyl)-3-(1H-imidazol-2-yl)-1H-pyrazolo[4,3-c]pyridin-4-yl]amino}methyl)phenyl]-N-methylmethanesulfonamide;

N-[2-({[3-(4,5-dimethyl-1H-imidazol-2-yl)-6-(2-ethyl-5-fluoro-4-hydroxyphenyl)-1H-pyrazolo[4,3-c]pyridin-4-yl]amino}methyl)phenyl]-N-methylmethanesulfonamide;

N-[2-({[6-(2-ethyl-5-fluoro-4-hydroxyphenyl)-3-(4-methyl-1H-imidazol-2-yl)-1H-pyrazolo[4,3-c]pyridin-4-yl]amino}methyl)phenyl]-N-methylmethanesulfonamide;

4-[3-(5-benzyl-4,5,6,7-tetrahydro-1H-imidazo[4,5-c]pyridin-2-yl)-4-{[2-(methylsulfanyl)ethyl]-amino}-1H-pyrazolo[4,3-c]pyridin-6-yl]-2-fluoro-5-(2,2,2-trifluoroethyl)phenol;

N-[2-({[6-(2-ethyl-5-fluoro-4-hydroxyphenyl)-3-(1H-pyrazol-1-yl)-1H-pyrazolo[4,3-c]pyridin-4-yl]amino}methyl)phenyl]-N-methylmethanesulfonamide;

N-{2-[({6-[5-fluoro-4-hydroxy-2-(2,2,2-trifluoroethyl)phenyl]-3-(1H-pyrazol-1-yl)-1H-pyrazolo[4,3-c]pyridin-4-yl}amino)methyl]phenyl}-N-methylmethanesulfonamide;

N-{2-[({6-[5-fluoro-4-hydroxy-2-(2,2,2-trifluoroethyl)phenyl]-3-(5-methyl-4H-1,2,4-triazol-3-yl)-1H-pyrazolo[4,3-c]pyridin-4-yl}amino)methyl]phenyl}-N-methylmethanesulfonamide;

N-[2-({[6-(2-ethyl-5-fluoro-4-hydroxyphenyl)-3-(5-methyl-4H-1,2,4-triazol-3-yl)-1H-pyrazolo[4,3-c]pyridin-4-yl]amino}methyl)phenyl]-N-methylmethanesulfonamide;

N-{2-[({6-[5-fluoro-4-hydroxy-2-(2,2,2-trifluoroethyl)phenyl]-3-[5-(6-methylpyridin-3-yl)-4H-1,2,4-triazol-3-yl]-1H-pyrazolo[4,3-c]pyridin-4-yl}amino)methyl]phenyl}-N-methylmethanesulfonamide;

4-(5-{6-[5-fluoro-4-hydroxy-2-(2,2,2-trifluoroethyl)phenyl]-4-({5-hydroxy-2-[methyl(methyl-sulfonyl)amino]benzyl}amino)-1H-pyrazolo[3,4-d]pyrimidin-3-yl}-4H-1,2,4-triazol-3-yl)piperidine-1-carboxamide;

N-(2-{[(6-[5-fluoro-4-hydroxy-2-(2,2,2-trifluoroethyl)phenyl]-3-{5-[1-(pyrrolidin-1-ylacetyl)piperid-in-4-yl]-4H-1,2,4-triazol-3-yl}-1H-pyrazolo[3,4-d]pyrimidin-4-yl)amino]methyl}phenyl)-N-methyl-methanesulfonamide;

N-{2-[({6-[5-fluoro-4-hydroxy-2-(2,2,2-trifluoroethyl)phenyl]-3-(4,5,6,7-tetrahydro-1H-imidazo[4,5-c]pyridin-2-yl)-1H-pyrazolo[3,4-d]pyrimidin-4-yl}amino)methyl]-4-hydroxyphenyl}-N-methylmethanesulfonamide;

N-{2-[({3-(5-acetyl-4,5,6,7-tetrahydro-1H-imidazo[4,5-c]pyridin-2-yl)-6-[5-fluoro-4-hydroxy-2-(2,2,2-trifluoroethyl)phenyl]-1H-pyrazolo[3,4-d]pyrimidin-4-yl}amino)methyl]-4-hydroxyphenyl}-N-methylmethanesulfonamide;

N-[2-(dimethylamino)ethyl]-2-{6-[5-fluoro-4-hydroxy-2-(2,2,2-trifluoroethyl)phenyl]-4-({5-hydroxy-2-[methyl(methylsulfonyl)amino]benzyl}amino)-1H-pyrazolo[3,4-d]pyrimidin-3-yl}-1,4,6,7-tetrahydro-5H-imidazo[4,5-c]pyridine-5-carboxamide; and 4-(3-(5-benzyl-4,5,6,7-tetrahydro-1H-imidazo[4,5-c]pyridin-2-yl)-4-((3-hydroxy-2-methylpropyl)-amino)-1H-pyrazolo[3,4-d]pyrimidin-6-yl)-2-fluoro-5-(2,2,2-trifluoroethyl)phenol.

* * * * *